United States Patent
Brige et al.

(10) Patent No.: US 9,265,834 B2
(45) Date of Patent: Feb. 23, 2016

(54) STABLE FORMULATIONS OF POLYPEPTIDES AND USES THEREOF

(71) Applicant: Ablynx N.V., Zwijnaarde (BE)

(72) Inventors: Ann Brige, Ertvelde (BE); Christine Labeur, Bruges (BE); Veronique De Brabandere, Ghent (BE); Marc Lauwereys, Haaltert (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

(21) Appl. No.: 13/964,469

(22) Filed: Aug. 12, 2013

(65) Prior Publication Data

US 2014/0178383 A1    Jun. 26, 2014

Related U.S. Application Data

(63) Continuation-in-part of application No. 13/393,636, filed as application No. PCT/EP2010/062975 on Sep. 3, 2010, now abandoned, application No. 13/964,469, which is a continuation-in-part of application No. 13/254,266, filed as application No. PCT/EP2010/052600 on Mar. 2, 2010.

(60) Provisional application No. 61/275,816, filed on Sep. 3, 2009, provisional application No. 61/284,502, filed on Dec. 18, 2009, provisional application No. 61/157,688, filed on Mar. 5, 2009.

(51) Int. Cl.

| A61K 47/34 | (2006.01) |
|---|---|
| A61K 47/22 | (2006.01) |
| A61K 47/26 | (2006.01) |
| A61K 39/395 | (2006.01) |
| C07K 16/18 | (2006.01) |
| C07K 16/24 | (2006.01) |
| C07K 16/28 | (2006.01) |
| A61K 9/00 | (2006.01) |
| A61K 47/12 | (2006.01) |
| A61K 47/18 | (2006.01) |

(52) U.S. Cl.
CPC ............... *A61K 47/26* (2013.01); *A61K 9/0019* (2013.01); *A61K 39/39591* (2013.01); *A61K 47/12* (2013.01); *A61K 47/183* (2013.01); *C07K 16/18* (2013.01); *C07K 16/244* (2013.01); *C07K 16/2866* (2013.01); *C07K 16/2875* (2013.01); *C07K 2317/22* (2013.01); *C07K 2317/31* (2013.01); *C07K 2317/35* (2013.01); *C07K 2317/569* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| 6,171,586 | B1 | 1/2001 | Lam et al. |
| 7,807,162 | B2 | 10/2010 | Silence |
| 8,188,233 | B2 | 5/2012 | Condra |
| 8,703,131 | B2 | 4/2014 | Beirnaert |
| 2003/0113316 | A1 | 6/2003 | Kaisheva et al. |
| 2003/0138417 | A1 | 7/2003 | Kaisheva et al. |
| 2003/0181527 | A1 | 9/2003 | Andersson et al. |
| 2003/0202972 | A1 | 10/2003 | Andya et al. |
| 2006/0088523 | A1 | 4/2006 | Andya et al. |
| 2006/0115470 | A1 | 6/2006 | Silence et al. |
| 2006/0149041 | A1 | 7/2006 | Silence |
| 2007/0086979 | A1 * | 4/2007 | Chevrier et al. ............. 424/85.1 |
| 2007/0172479 | A1 * | 7/2007 | Warne et al. ................ 424/145.1 |
| 2008/0292640 | A1 | 11/2008 | Solinger et al. |
| 2009/0226530 | A1 * | 9/2009 | Lassner et al. ................ 424/497 |
| 2010/0137213 | A1 * | 6/2010 | Fernandez et al. ............. 514/12 |
| 2011/0311515 | A1 | 12/2011 | Bouche et al. |
| 2012/0034212 | A1 | 2/2012 | Bowen et al. |
| 2012/0093839 | A1 * | 4/2012 | Brige et al. ................ 424/177.1 |
| 2012/0201812 | A1 | 8/2012 | Brige et al. |
| 2012/0244158 | A1 | 9/2012 | Brige et al. |

FOREIGN PATENT DOCUMENTS

| WO | WO 02/30463 A2 | 4/2002 |
| WO | WO 2004/041863 A2 | 5/2004 |
| WO | WO 2004/062551 A2 | 7/2004 |
| WO | WO 2005/044858 A1 | 5/2005 |
| WO | WO 2005/072772 A1 | 8/2005 |
| WO | WO 2006/020935 A2 | 2/2006 |

(Continued)

OTHER PUBLICATIONS

Chang et al, p. 1, first paragraph (Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25.).*

(Continued)

*Primary Examiner* — Brian J Gangle
*Assistant Examiner* — Andrea McCollum
(74) *Attorney, Agent, or Firm* — Wolf, Greenfield & Sacks, P.C.

(57) ABSTRACT

Formulations are provided that contain single variable domains with a good solubility and good stability under different storage, transportation and stress conditions. The formulations are useful as pharmaceutical formulation. The formulation comprises an aqueous carrier with a pH of 5.5 to 8.0, a buffer selected from the group consisting of histidine pH 6.0-6.5, hepes pH 7.0-8.0, MES pH 6.0, succinate pH 6.0-6.5 and acetate pH 5.5-6.0; an excipient; and/or a surfactant selected from polysorbate 80, polysorbate 20 and poloxamers. The formulation is further characterized that it has an inorganic salt concentration of 150 mM or lower.

25 Claims, 122 Drawing Sheets

(56) References Cited

FOREIGN PATENT DOCUMENTS

Figure 1A:
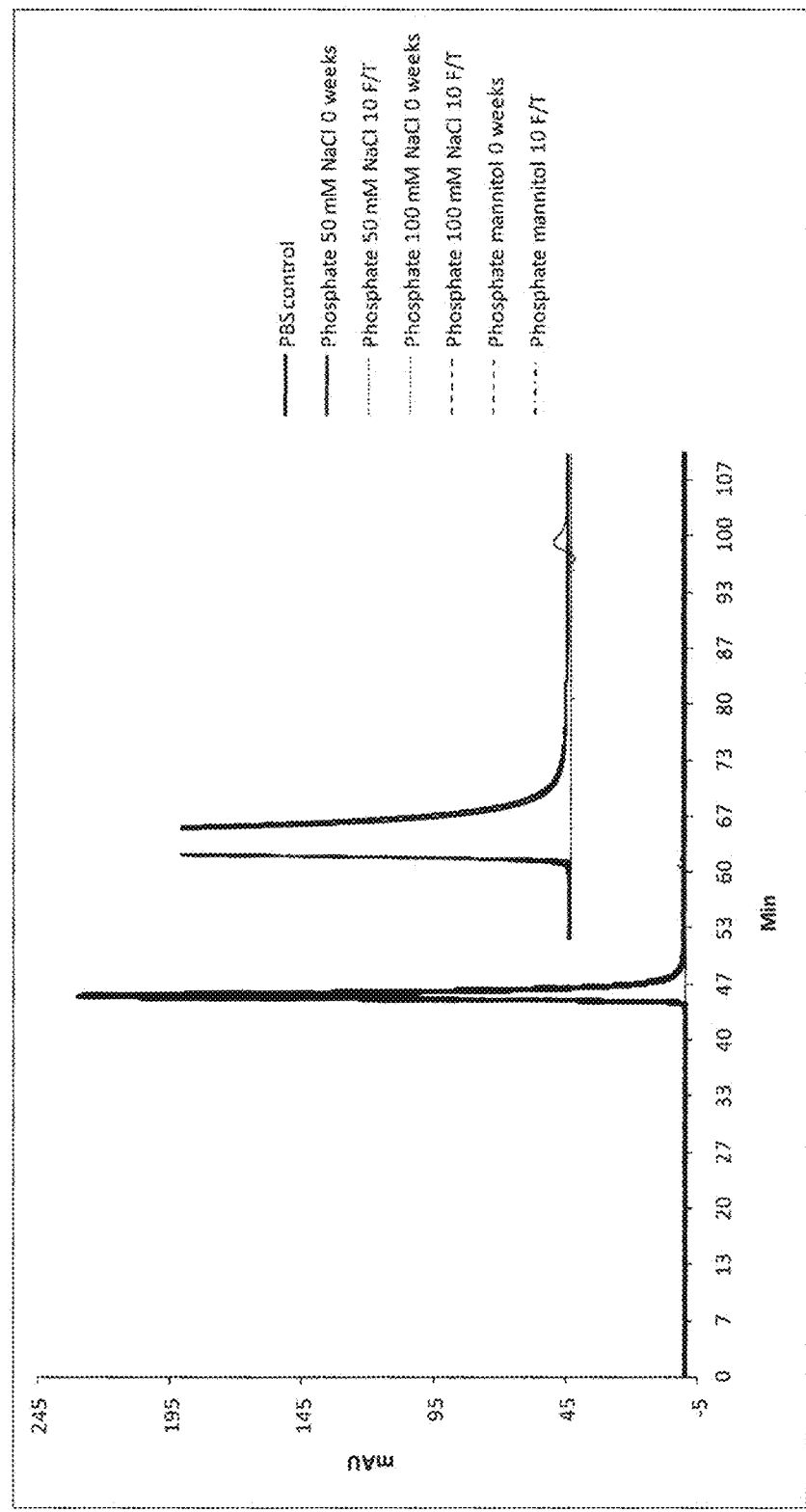

| WO | WO 2006/040153 A2 | 4/2006 |
|---|---|---|
| WO | WO 2006/074947 A2 | 7/2006 |
| WO | WO 2006/122825 A2 | 11/2006 |
| WO | WO 2007/002261 A2 | 1/2007 |
| WO | WO 2007/042289 A2 | 4/2007 |
| WO | WO 2007/0086797 A1 | 8/2007 |
| WO | WO 2007/092772 A2 | 8/2007 |
| WO | WO 2007/104529 A2 | 9/2007 |
| WO | WO 2008/020079 A1 | 2/2008 |
| WO | WO 2008/039761 A2 | 4/2008 |
| WO | WO 2008/049897 A1 | 5/2008 |
| WO | WO 2008/070721 A2 | 6/2008 |
| WO | WO 2008/071447 A2 | 6/2008 |
| WO | WO 2008/071685 A1 | 6/2008 |
| WO | WO 2008/074839 A2 | 6/2008 |
| WO | WO 2008/074840 A2 | 6/2008 |
| WO | WO 2008/074867 A2 | 6/2008 |
| WO | WO 2008/074868 A1 | 6/2008 |
| WO | WO 2008/077945 A2 | 7/2008 |
| WO | WO 2008/079290 A2 | 7/2008 |
| WO | WO 2008/101985 A2 | 8/2008 |
| WO | WO 2008/142164 A2 | 11/2008 |
| WO | WO 2008/142165 A1 | 11/2008 |
| WO | WO 2009/068625 A2 | 6/2009 |
| WO | WO 2009/068627 A2 | 6/2009 |
| WO | WO 2009/095235 A1 | 8/2009 |
| WO | WO 2009/099641 A2 | 8/2009 |
| WO | WO 2009/109635 A2 | 9/2009 |
| WO | WO 2009/115614 A2 | 9/2009 |
| WO | WO 2010/060768 A1 | 6/2010 |
| WO | WO 2010/077422 A2 | 7/2010 |

OTHER PUBLICATIONS

[No Author Listed] Mannitol, a polypol (or sugar alcohol). Polyols Information Source. Last accessed at http://www.polyol.org/fap/fap_mannitol.html on Oct. 30, 2009.

[No Author Listed] Scientific Discussion. EMEA 2005. 29 pages.

Barthelemy et al., Comprehensive analysis of the factors contributing to the stability and solubility of autonomous human VH domains. J Biol Chem. Feb. 8, 2008;283(6):3639-54. Epub Nov. 28, 2007.

Bork, Powers and pitfalls in sequence analysis: the 70% hurdle. Genome Res. Apr. 2000;10(4):398-400.

Bowie et al., Deciphering the message in protein sequences: tolerance to amino acid substitutions. Science. Mar. 16, 1990;247(4948):1306-10.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Cleland et al., The development of stable protein formulations: a close look at protein aggregation, deamidation, and oxidation. Crit Rev Ther Drug Carrier Syst. 1993;10(4):307-77.

Dottorini et al., Crystal structure of a human VH: requirements for maintaining a monomeric fragment. Biochemistry. Jan. 27, 2004;43(3):622-8. Epub Dec. 25, 2003.

Katayama et al., Effect of buffer species on the thermally induced aggregation of interferon-tau. J Pharm Sci. Jun. 2006;95(6):1212-26.

Labeur, Development of a high concentration Nanobody® formulation. Ablynx. Presentation. Sep. 9, 2009.

Lazar et al., Transforming growth factor alpha: mutation of aspartic acid 47 and leucine 48 results in different biological activities. Mol Cell Biol. Mar. 1988;8(3):1247-52.

Riechmann et al., Single domain antibodies: comparison of camel VH and camelised human VH domains. J Immunol Methods. Dec. 10, 1999;231(1-2):25-38.

Sepúlveda et al., Binders based on dimerised immunoglobulin VH domains. J Mol Biol. Oct. 17, 2003;333(2):355-65.

Spinelli et al., Domain swapping of a llama VHH domain builds a crystal-wide beta-sheet structure. FEBS Lett. Apr. 23, 2004;564(1-2):35-40. Epub Mar. 29, 2004.

* cited by examiner

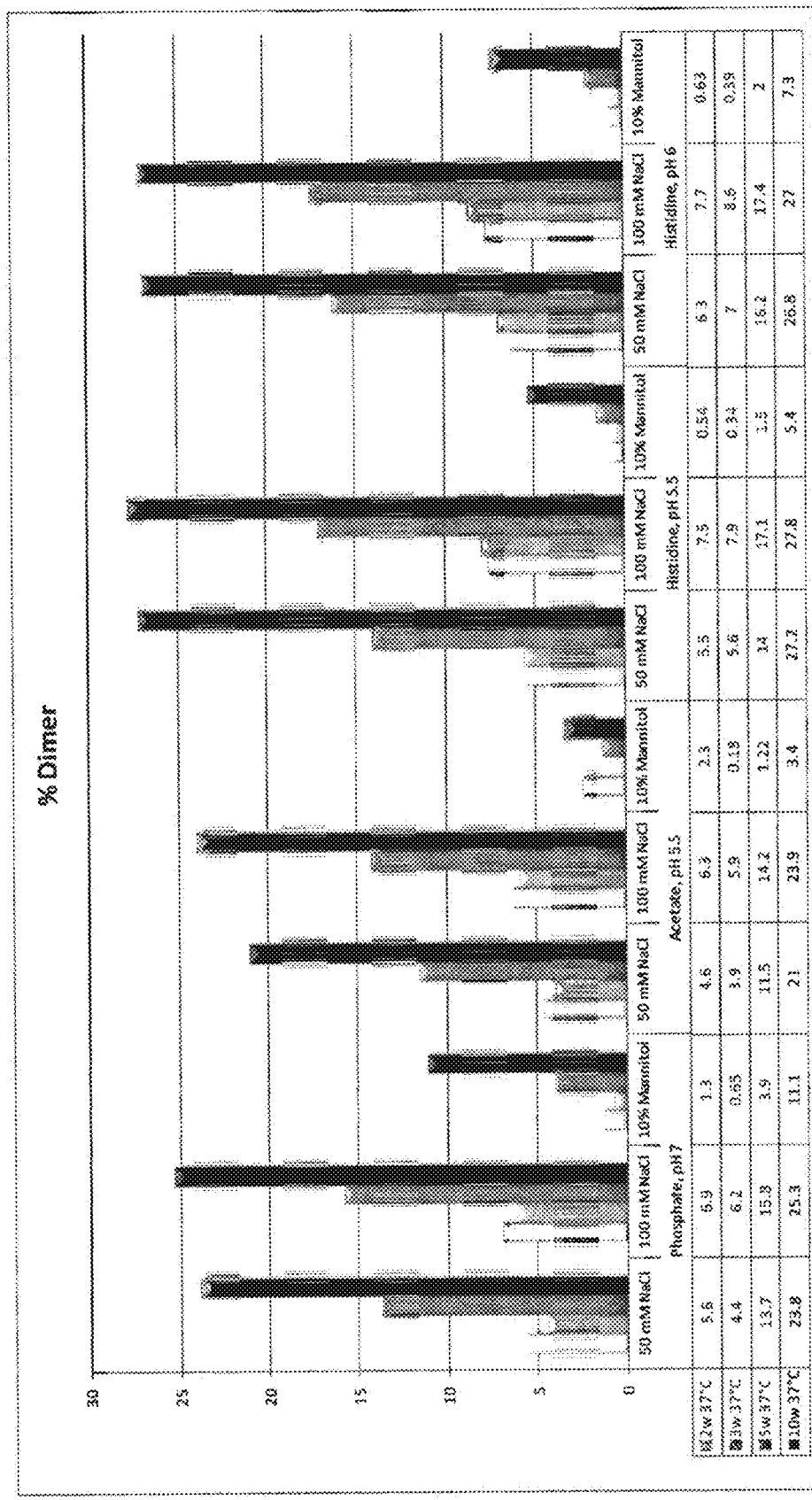

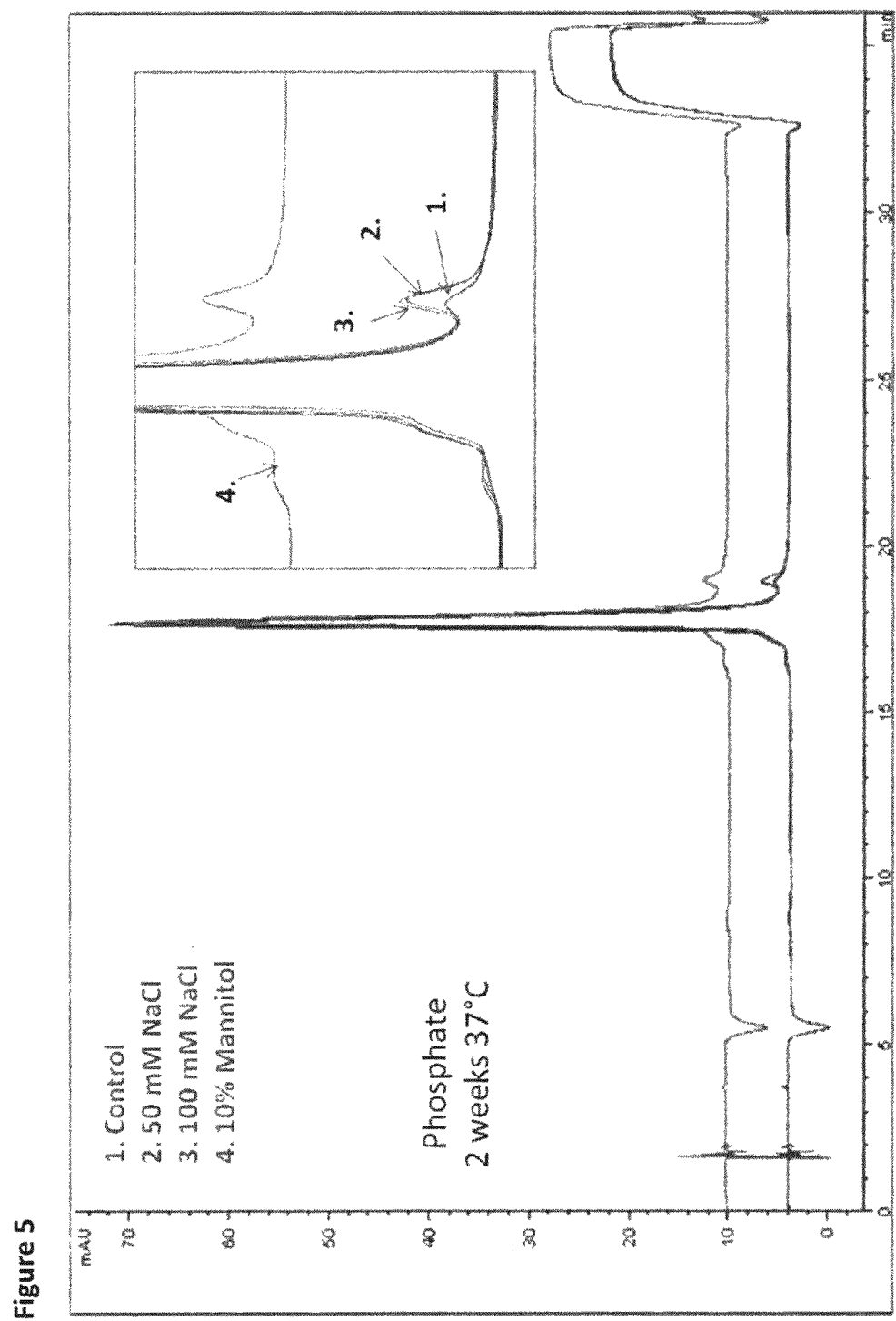

Samples:
1. RANKL008a diluted to 5 mg/ml without Tween80
2. RANKL008a diluted to 5 mg/ml with 0.01% Tween80
3. RANKL008a undiluted without Tween80
4. RANKL008a undiluted with 0.01% Tween80

| Diluted/undiluted | Without Tween80 | 0.01% Tween80 |
|---|---|---|
| Diluted to 5 mg/ml | Opaque (sample 1) | Clear (sample 2) |
| | More foam (sample 1) | Foam (sample 2) |
| Undiluted | Clear (sample 3) | Clear (sample 4) |
| | More foam (sample 3) | Foam (sample 4) |

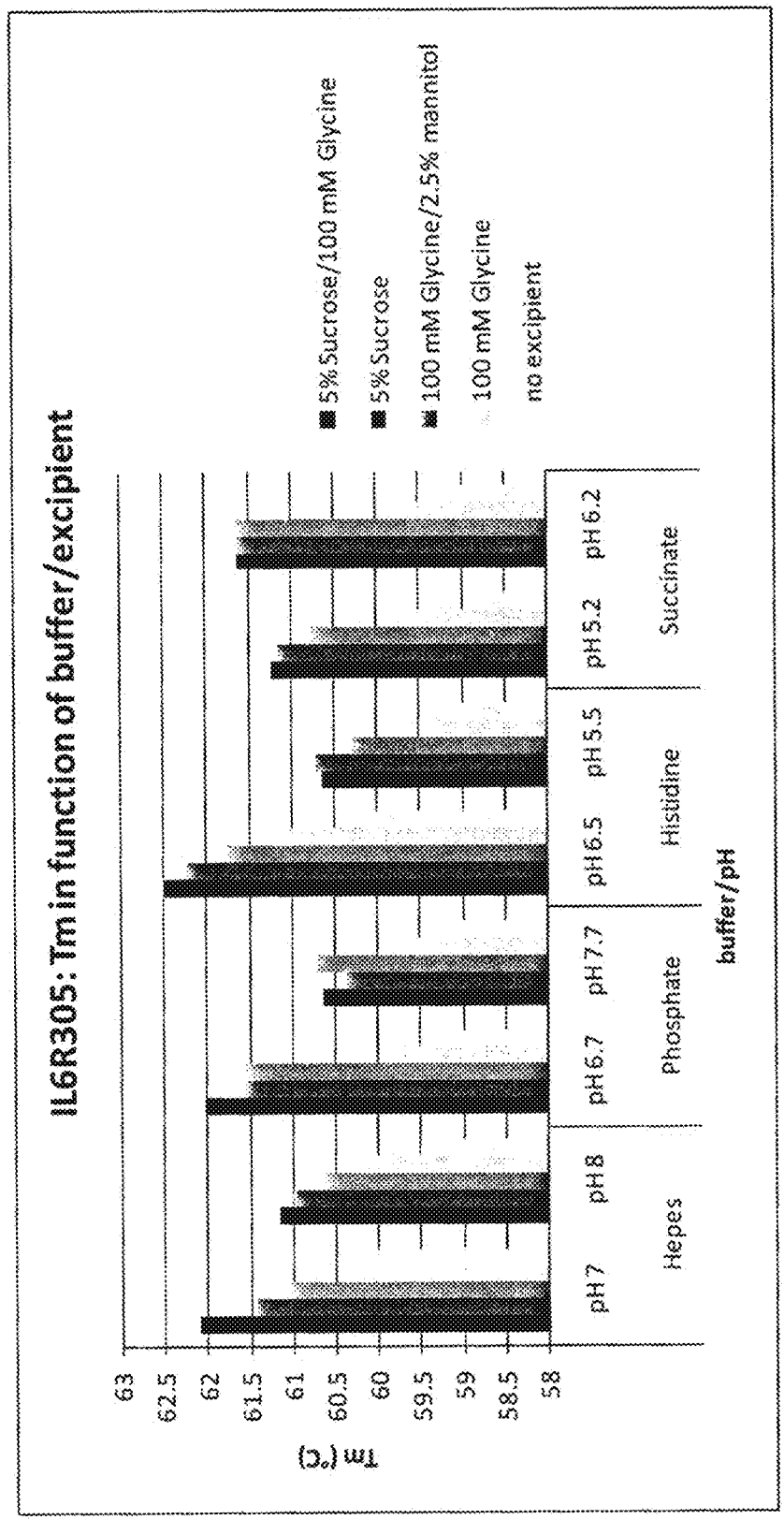

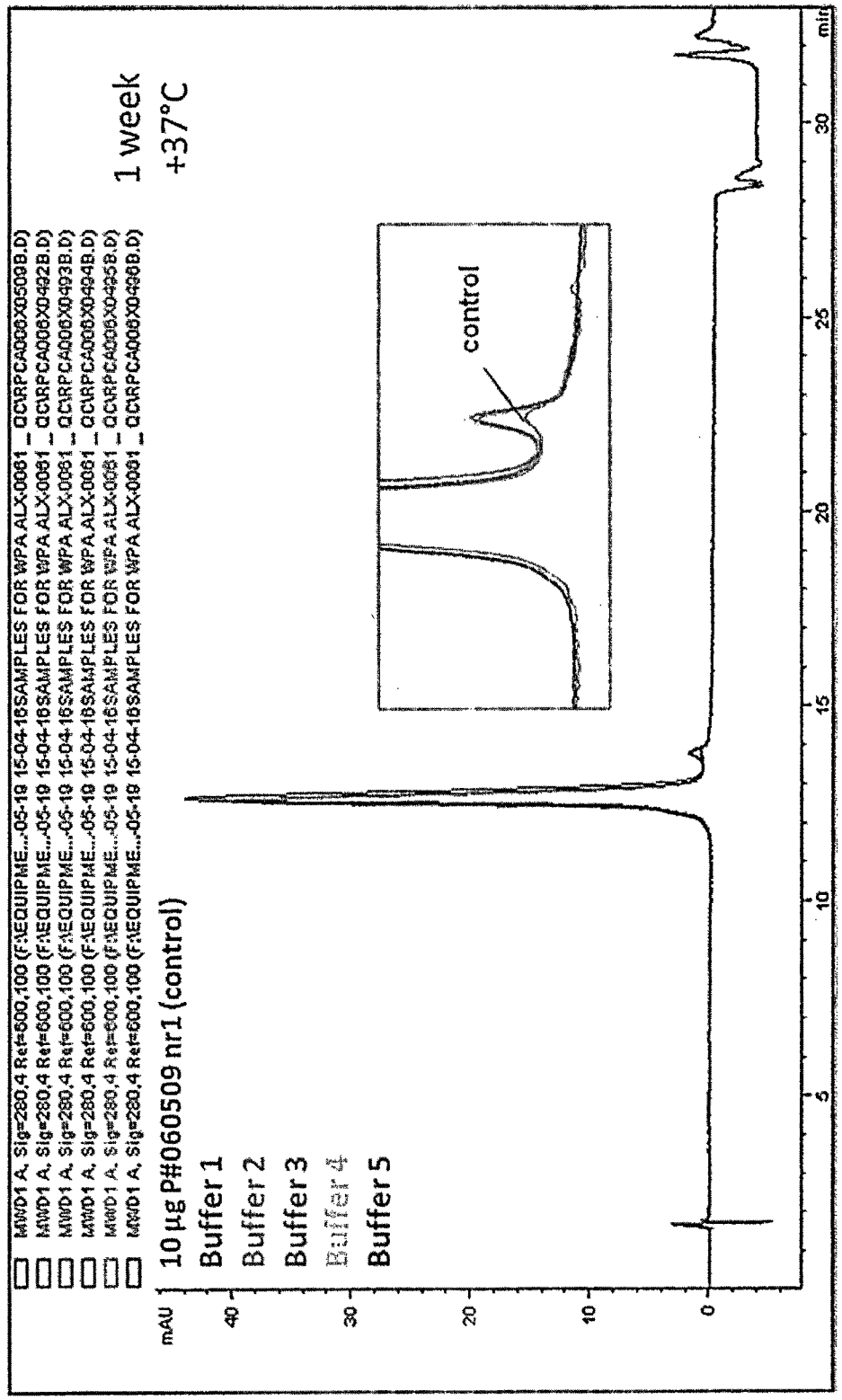

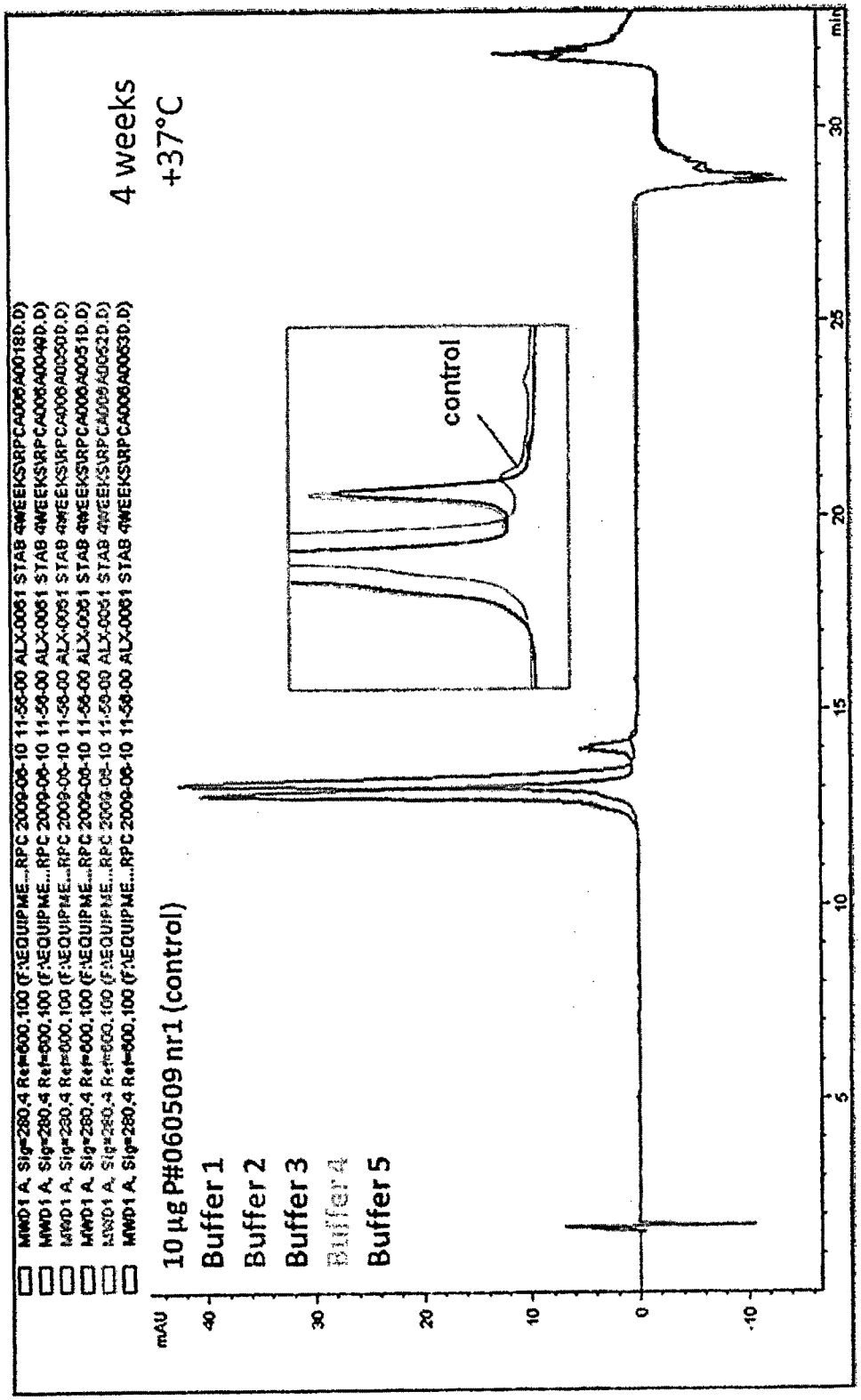

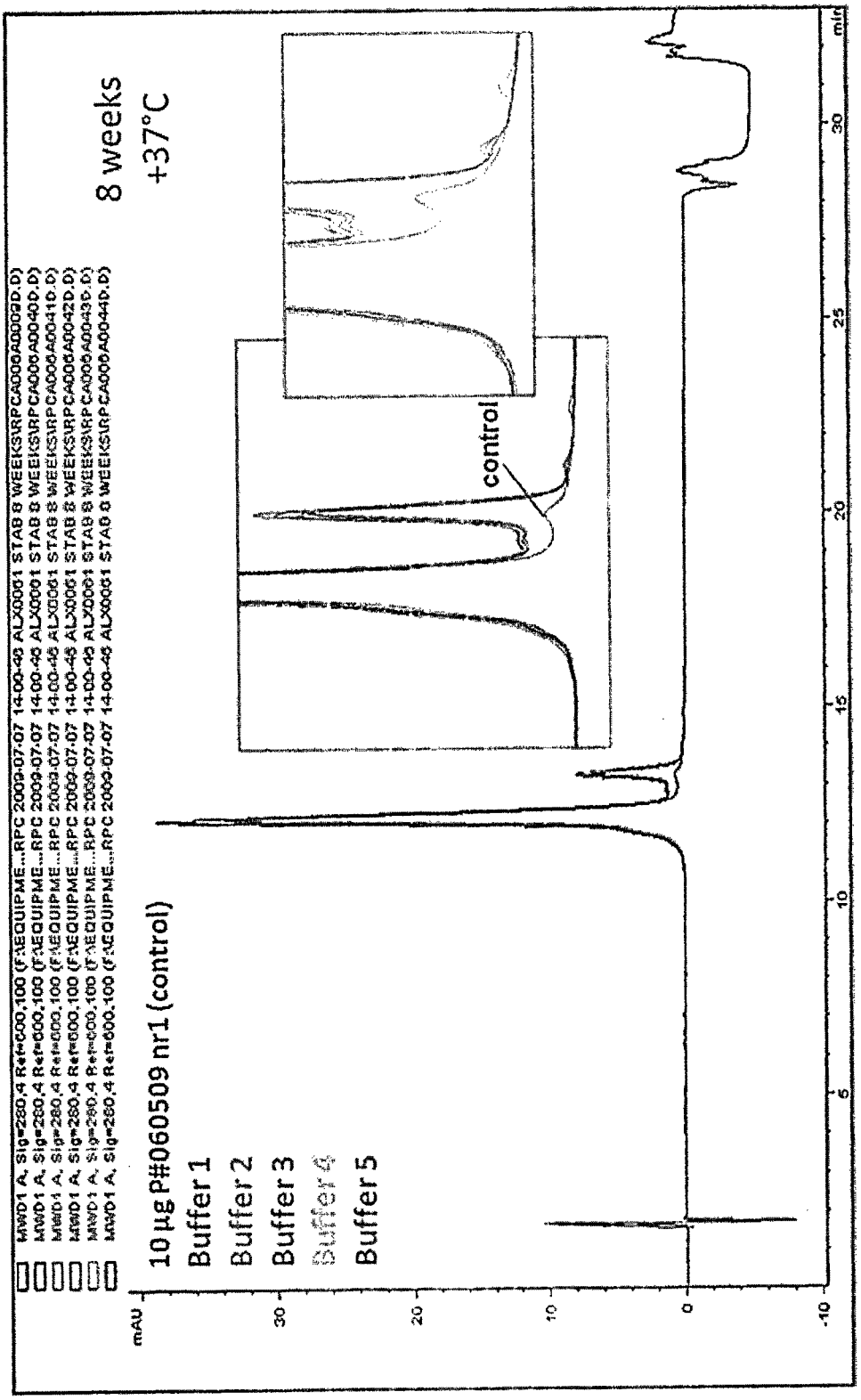

Figure 52

| Position | Human V$_H$3 | Hallmark Residues |
|---|---|---|
| 11 | L, V; predominantly L | L, M, S, V, W; preferably L |
| 37 | V, I, F; usually V | F$^{(1)}$, Y, H, I, L or V, preferably F$^{(1)}$ or Y |
| 44$^{(8)}$ | G | G$^{(2)}$, E$^{(3)}$, A, D, Q, R, S, L; preferably G$^{(2)}$, E$^{(3)}$ or Q; most preferably G$^{(2)}$ or E$^{(3)}$. |
| 45$^{(8)}$ | L | L$^{(2)}$, R$^{(3)}$, C, I, L, P, Q, V; preferably L$^{(2)}$ or R$^{(3)}$ |
| 47$^{(8)}$ | W, Y | W$^{(2)}$, L$^{(1)}$ or F$^{(1)}$, A, G, I, M, R, S, V or Y; preferably W$^{(2)}$, L$^{(1)}$, F$^{(1)}$ or R |
| 83 | R or K; usually R | R, K$^{(5)}$, N, E$^{(5)}$, G, I, M, Q or T; preferably K or R; most preferably K |
| 84 | A, T, D; predominantly A | P$^{(5)}$, A, L, R, S, T, D, V; preferably P |
| 103 | W | W$^{(4)}$, P$^{(6)}$, R$^{(6)}$, S; preferably W |
| 104 | G | G or D; preferably G |
| 108 | L, M or T; predominantly L | Q, L$^{(7)}$ or R; preferably Q or L$^{(7)}$ |

Notes:

(1) In particular, but not exclusively, in combination with KERE or KQRE at positions 43-46.

(2) Usually as GLEW at positions 44-47.

(3) Usually as KERE or KQRE at positions 43-46, e.g. as KEREL, KEREF, KQREL, KQREF or KEREG at positions 43-47. Alternatively, also sequences such as TERE (for example TEREL), KECE (for example KECEL or KECER), RERE (for example REREG), QERE (for example QEREG), KGRE (for example KGREG), KDRE (for example KDREV) are possible. Some other possible, but less preferred sequences include for example DECKL and NVCEL.

(4) With both GLEW at positions 44-47 and KERE or KQRE at positions 43-46.

(5) Often as KP or EP at positions 83-84 of naturally occurring V$_{HH}$ domains.

(6) In particular, but not exclusively, in combination with GLEW at positions 44-47.

(7) With the proviso that when positions 44-47 are GLEW, position 108 is always Q in (non-humanized) V$_{HH}$ sequences that also contain a W at 103.

(8) The GLEW group also contains GLEW-like sequences at positions 44-47, such as for example GVEW, EPEW, GLER, DQEW, DLEW, GIEW, ELEW, GPEW, EWLP, GPER, GLER and ELEW.

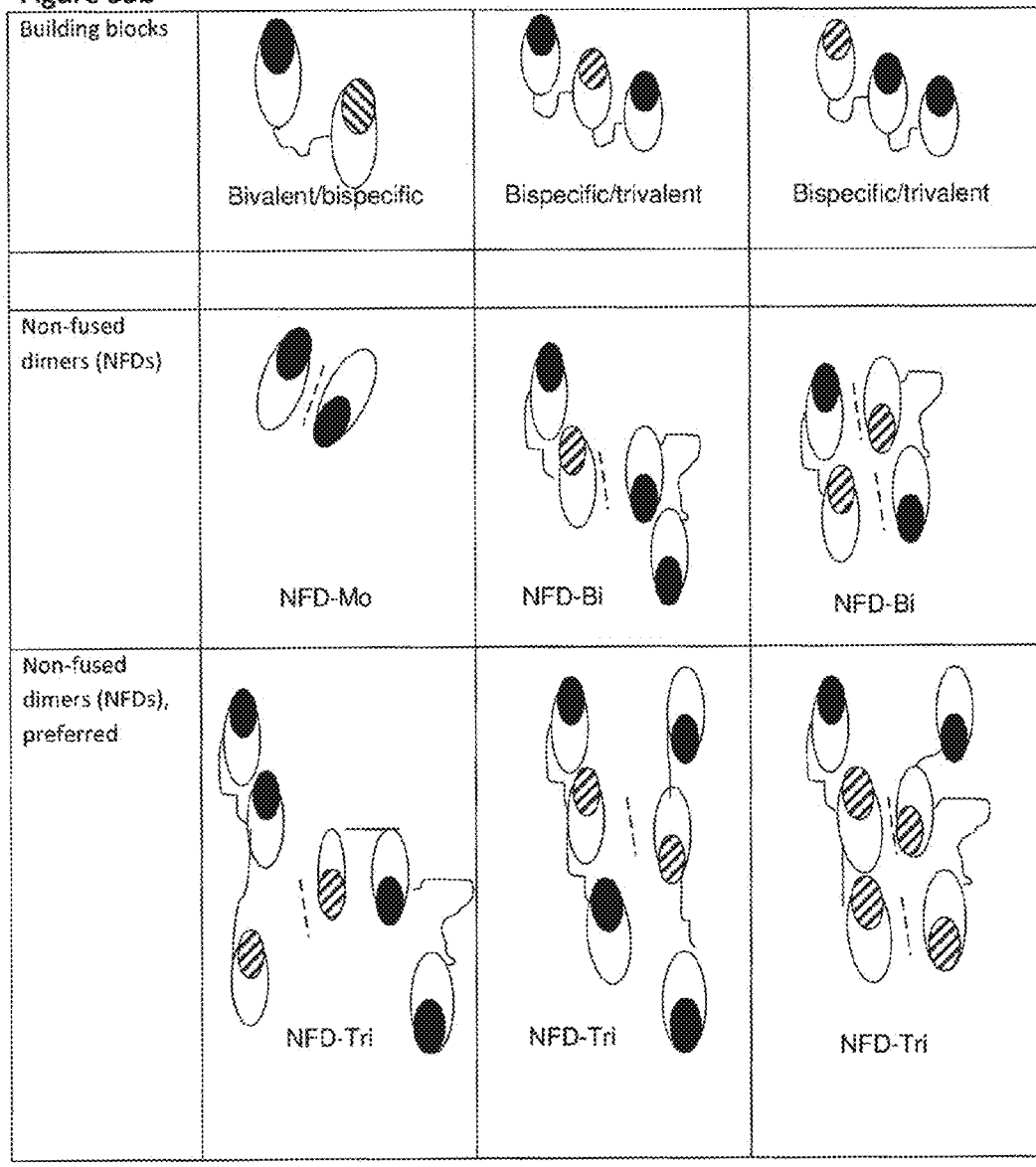
Figure 53b
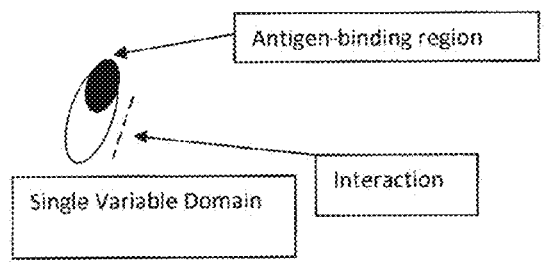

Figure 65
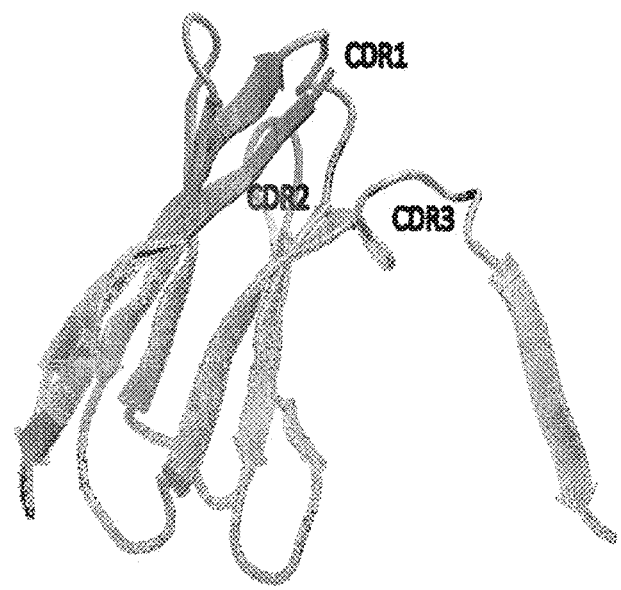
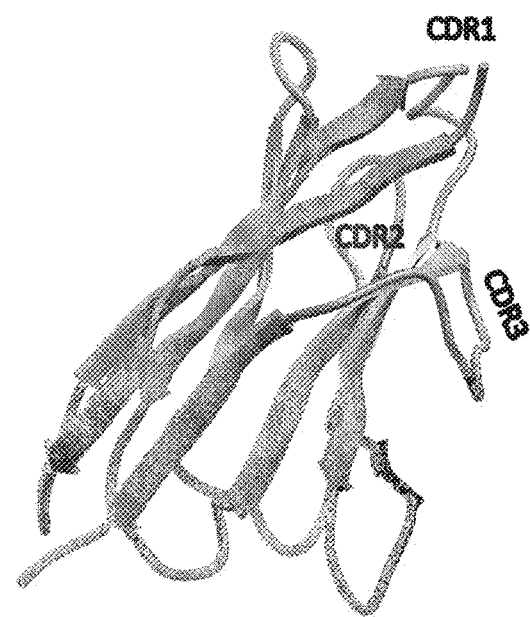

Figure 68
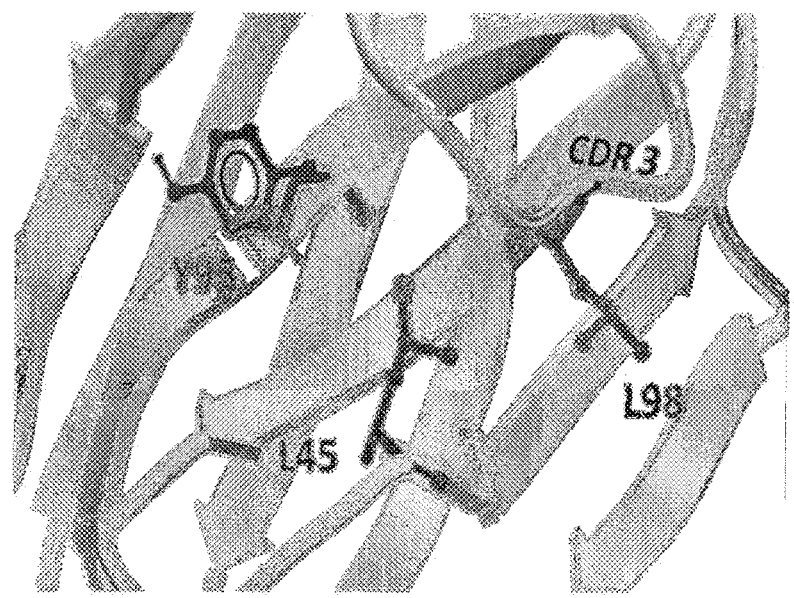
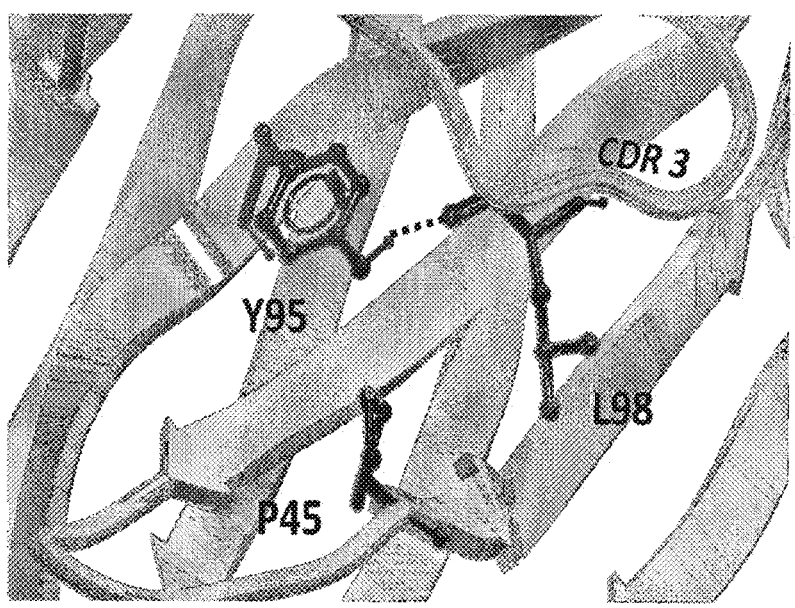

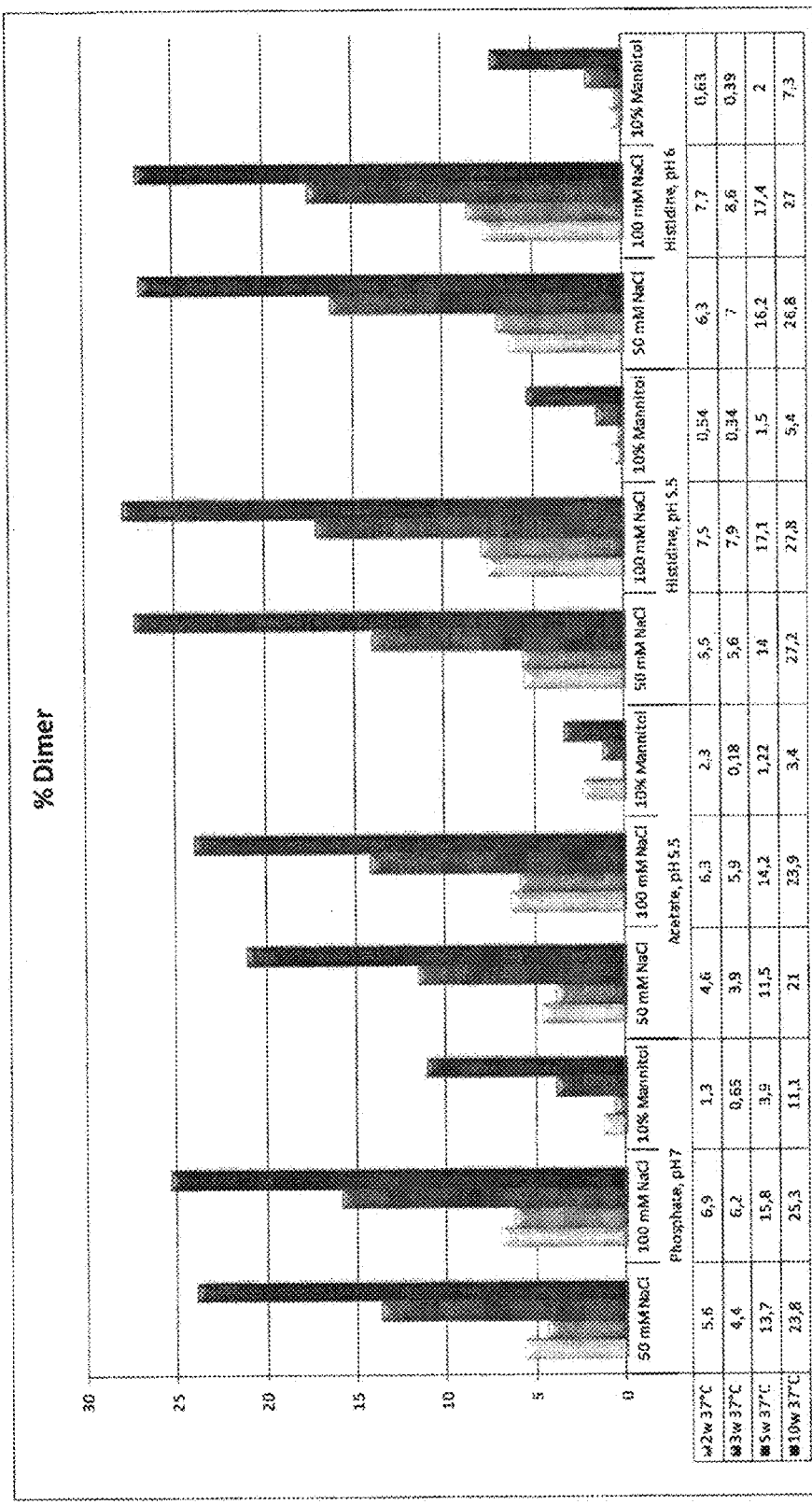

SEQUENCE LISTING

```
<160> NUMBER OF SEQ ID NOS: 20

<210> SEQ ID NO 1
<211> LENGTH: 245
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
```

```
            35                  40                  45
Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser Gly Gly Gly Ser Gly Gly
                115                 120                 125

Gly Ser Glu Val Gln Leu Val Glu Ser Gly Gly Gly Leu Val Gln Pro
130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
                195                 200                 205

Leu Tyr Leu Gln Met Asn Ser Leu Arg Pro Glu Asp Thr Ala Val Tyr
210                 215                 220

Tyr Cys Thr Ile Gly Gly Ser Leu Ser Arg Ser Ser Gln Gly Thr Leu
225                 230                 235                 240

Val Thr Val Ser Ser
                245

<210> SEQ ID NO 2
<211> LENGTH: 375
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Pro Gly Gly
 1                   5                  10                  15

Ser Leu Arg Leu Ser Cys Ala Ala Ser Gly Ser Val Phe Lys Ile Asn
                 20                  25                  30

Val Met Ala Trp Tyr Arg Gln Ala Pro Gly Lys Gly Arg Glu Leu Val
                 35                  40                  45

Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser Gly Gly Gly Ser Gly Gly
                115                 120                 125

Gly Ser Glu Val Gln Leu Val Glu Ser Gly Gly Gly Leu Val Gln Pro
130                 135                 140

Gly Gly Ser Leu Arg Leu Ser Cys Ala Ala Ser Gly Ser Val Phe Lys
```

```
            145                 150                 155                 160
        Ile Asn Val Met Ala Trp Tyr Arg Gln Ala Pro Gly Lys Gly Arg Glu
                        165                 170                 175

Leu Val Ala Gly Ile Ile Ser Gly Ser Thr Ser Tyr Ala Asp Ser
                        180                 185                 190

Val Lys Gly Arg Phe Thr Ile Ser Arg Asp Asn Ala Lys Asn Thr Leu
                        195                 200                 205

Tyr Leu Gln Met Asn Ser Leu Arg Pro Glu Asp Thr Ala Val Tyr Tyr
                        210                 215                 220

Cys Ala Phe Ile Thr Thr Glu Ser Asp Tyr Asp Leu Gly Arg Arg Tyr
        225                 230                 235                 240

Trp Gly Gln Gly Thr Leu Val Thr Val Ser Ser Gly Gly Gly Gly Ser
                        245                 250                 255

Gly Gly Gly Ser Glu Val Gln Leu Val Glu Ser Gly Gly Gly Leu Val
                        260                 265                 270

Gln Pro Gly Asn Ser Leu Arg Leu Ser Cys Ala Ala Ser Gly Phe Thr
                        275                 280                 285

Phe Ser Ser Phe Gly Met Ser Trp Val Arg Gln Ala Pro Gly Lys Gly
                        290                 295                 300

Leu Glu Trp Val Ser Ser Ile Ser Gly Ser Gly Ser Asp Thr Leu Tyr
        305                 310                 315                 320

Ala Asp Ser Val Lys Gly Arg Phe Thr Ile Ser Arg Asp Asn Ala Lys
                        325                 330                 335

Thr Thr Leu Tyr Leu Gln Met Asn Ser Leu Arg Pro Glu Asp Thr Ala
                        340                 345                 350

Val Tyr Tyr Cys Thr Ile Gly Gly Ser Leu Ser Arg Ser Ser Gln Gly
                        355                 360                 365

Thr Leu Val Thr Val Ser Ser
                        370                 375

<210> SEQ ID NO 3
<211> LENGTH: 375
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
                20                  25                  30

Val Met Ala Trp Tyr Arg Gln Ala Pro Gly Lys Gly Arg Glu Leu Val
                35                  40                  45

Ala Gly Ile Ile Ser Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser Gly Gly Gly Ser Gly Gly
                115                 120                 125

Gly Ser Glu Val Gln Leu Val Glu Ser Gly Gly Gly Leu Val Gln Pro
```

```
            130                 135                 140
Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
        210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
                260                 265                 270

Arg Leu Ser Cys Ala Ala Ser Gly Ser Val Phe Lys Ile Asn Val Met
            275                 280                 285

Ala Trp Tyr Arg Gln Ala Pro Gly Lys Gly Arg Glu Leu Val Ala Gly
        290                 295                 300

Ile Ile Ser Gly Gly Ser Thr Ser Tyr Ala Asp Ser Val Lys Gly Arg
305                 310                 315                 320

Phe Thr Ile Ser Arg Asp Asn Ala Lys Asn Thr Leu Tyr Leu Gln Met
                325                 330                 335

Asn Ser Leu Arg Pro Glu Asp Thr Ala Val Tyr Tyr Cys Ala Phe Ile
                340                 345                 350

Thr Thr Glu Ser Asp Tyr Asp Leu Gly Arg Arg Tyr Trp Gly Gln Gly
            355                 360                 365

Thr Leu Val Thr Val Ser Ser
        370                 375

<210> SEQ ID NO 4
<211> LENGTH: 385
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Pro Met Gly Trp Phe Arg Gln Ala Pro Gly Lys Gly Arg Glu Phe Val
            35                  40                  45

Ser Ser Ile Thr Gly Ser Gly Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser Gly Gly
```

```
              115                 120                 125
Gly Gly Ser Gly Gly Ser Glu Val Gln Leu Val Glu Ser Gly Gly
    130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
                165                 170                 175

Gly Lys Gly Leu Glu Trp Val Ser Ser Ile Ser Gly Ser Gly Ser Asp
                180                 185                 190

Thr Leu Tyr Ala Asp Ser Val Lys Gly Arg Phe Thr Ile Ser Arg Asp
            195                 200                 205

Asn Ala Lys Thr Thr Leu Tyr Leu Gln Met Asn Ser Leu Arg Pro Glu
        210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Gly Ser Thr Tyr Tyr Ala
305                 310                 315                 320

Asp Ser Val Lys Gly Arg Phe Thr Ile Ser Arg Asp Asn Ala Lys Asn
                325                 330                 335

Thr Leu Tyr Leu Gln Met Asn Ser Leu Arg Pro Glu Asp Thr Ala Val
            340                 345                 350

Tyr Tyr Cys Ala Ala Tyr Ile Arg Pro Asp Thr Tyr Leu Ser Arg Asp
        355                 360                 365

Tyr Arg Lys Tyr Asp Tyr Trp Gly Gln Gly Thr Leu Val Thr Val Ser
    370                 375                 380

Ser
385

<210> SEQ ID NO 5
<211> LENGTH: 386
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
```

-continued

```
                85                  90                  95
Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
            165                 170                 175

Lys Gly Leu Glu Trp Val Ser Ser Ile Ser Gly Ser Gly Ser Asp Thr
        180                 185                 190

Leu Tyr Ala Asp Ser Val Lys Gly Arg Phe Thr Ile Ser Arg Asp Asn
    195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
            245                 250                 255

Gly Ser Glu Val Gln Leu Leu Glu Ser Gly Gly Gly Leu Val Gln Pro
        260                 265                 270

Gly Gly Ser Leu Arg Leu Ser Cys Ala Ala Ser Gly Arg Thr Leu Ser
    275                 280                 285

Ser Tyr Ala Met Gly Trp Phe Arg Gln Ala Pro Gly Lys Gly Arg Glu
290                 295                 300

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
            325                 330                 335

Leu Tyr Leu Gln Met Asn Ser Leu Arg Pro Glu Asp Thr Ala Val Tyr
        340                 345                 350

Tyr Cys Ala Lys Asp Pro Ser Pro Tyr Tyr Arg Gly Ser Ala Tyr Leu
    355                 360                 365

Leu Ser Gly Ser Tyr Asp Ser Trp Gly Gln Gly Thr Leu Val Thr Val
370                 375                 380

Ser Ser
385

<210> SEQ ID NO 6
<211> LENGTH: 386
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Leu Glu Ser Gly Gly Gly Leu Val Gln Pro Gly Gly
1               5                  10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
```

```
                50                  55                  60
Arg Thr Tyr Tyr Ala Asp Ser Val Lys Gly Arg Phe Thr Ile Ser Arg
 65                  70                  75                  80

Asp Asn Ser Lys Lys Thr Leu Tyr Leu Gln Met Asn Ser Leu Arg Pro
                 85                  90                  95

Glu Asp Thr Ala Val Tyr Tyr Cys Gln Thr Ser Gly Ser Gly Ser Pro
                100                 105                 110

Asn Phe Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
        290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
        370                 375                 380

Ser Ser
385

<210> SEQ ID NO 7
<211> LENGTH: 259
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Tyr Asn
```

```
                    20                  25                  30
Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Met Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
        130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
                180                 185                 190

Asp Ser Val Glu Gly Arg Phe Thr Ile Ser Arg Asp Asn Ala Lys Arg
            195                 200                 205

Met Val Tyr Leu Gln Met Asn Ser Leu Arg Ala Glu Asp Thr Ala Val
        210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser
```

<210> SEQ ID NO 8
<211> LENGTH: 115
<212> TYPE: PRT
<213> ORGANISM: Artificial Sequence
<220> FEATURE:
<223> OTHER INFORMATION: Nanobody sequence

<400> SEQUENCE: 8

```
Glu Val Gln Leu Val Glu Ser Gly Gly Gly Leu Val Gln Pro Gly Asn
 1                   5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
                100                 105                 110

Val Ser Ser
        115
```

<210> SEQ ID NO 9
<211> LENGTH: 387
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Leu Val Gln Pro Gly Gly
1               5                  10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser Gly
        115                 120                 125

Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Ser Phe Gly Met Ser Trp Val Arg Gln Ala
                165                 170                 175

Pro Gly Lys Gly Leu Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Arg
225                 230                 235                 240

Ser Ser Gln Gly Thr Leu Val Thr Val Ser Ser Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Arg Leu Ser Cys Ala Ala Ser Gly Phe Thr
        275                 280                 285

Phe Ser Asp Tyr Asp Ile Gly Trp Phe Arg Gln Ala Pro Gly Lys Gly
    290                 295                 300

Arg Glu Gly Val Ser Gly Ile Ser Ser Asp Gly Asn Thr Tyr Tyr
305                 310                 315                 320

Ala Asp Ser Val Lys Gly Arg Phe Thr Ile Ser Arg Asp Asn Ala Lys
                325                 330                 335

Asn Thr Leu Tyr Leu Gln Met Asn Ser Leu Arg Pro Glu Asp Thr Ala
            340                 345                 350

Val Tyr Tyr Cys Ala Ala Glu Pro Pro Asp Ser Ser Trp Tyr Leu Asp
        355                 360                 365

Gly Ser Pro Glu Phe Phe Lys Tyr Trp Gly Gln Gly Thr Leu Val Thr
            370                 375                 380

Val Ser Ser
385

<210> SEQ ID NO 10
<211> LENGTH: 712
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser Asp
        115                 120                 125

Ala His Lys Ser Glu Val Ala His Arg Phe Lys Asp Leu Gly Glu Glu
    130                 135                 140

Asn Phe Lys Ala Leu Val Leu Ile Ala Phe Ala Gln Tyr Leu Gln Gln
145                 150                 155                 160

Cys Pro Phe Glu Asp His Val Lys Leu Val Asn Glu Val Thr Glu Phe
                165                 170                 175

Ala Lys Thr Cys Val Ala Asp Glu Ser Ala Glu Asn Cys Asp Lys Ser
            180                 185                 190

Leu His Thr Leu Phe Gly Asp Lys Leu Cys Thr Val Ala Thr Leu Arg
        195                 200                 205

Glu Thr Tyr Gly Glu Met Ala Asp Cys Cys Ala Lys Gln Glu Pro Glu
    210                 215                 220

Arg Asn Glu Cys Phe Leu Gln His Lys Asp Asp Asn Pro Asn Leu Pro
225                 230                 235                 240

Arg Leu Val Arg Pro Glu Val Asp Val Met Cys Thr Ala Phe His Asp
                245                 250                 255

Asn Glu Glu Thr Phe Leu Lys Lys Tyr Leu Tyr Glu Ile Ala Arg Arg
            260                 265                 270

His Pro Tyr Phe Tyr Ala Pro Glu Leu Leu Phe Phe Ala Lys Arg Tyr
        275                 280                 285

Lys Ala Ala Phe Thr Glu Cys Cys Gln Ala Ala Asp Lys Ala Ala Cys
    290                 295                 300

Leu Leu Pro Lys Leu Asp Glu Leu Arg Asp Glu Gly Lys Ala Ser Ser
305                 310                 315                 320

Ala Lys Gln Arg Leu Lys Cys Ala Ser Leu Gln Lys Phe Gly Glu Arg
                325                 330                 335

Ala Phe Lys Ala Trp Ala Val Ala Arg Leu Ser Gln Arg Phe Pro Lys
            340                 345                 350

Ala Glu Phe Ala Glu Val Ser Lys Leu Val Thr Asp Leu Thr Lys Val
            355                 360                 365

His Thr Glu Cys Cys His Gly Asp Leu Leu Glu Cys Ala Asp Asp Arg
            370                 375                 380

Ala Asp Leu Ala Lys Tyr Ile Cys Glu Asn Gln Asp Ser Ile Ser Ser
385                 390                 395                 400

Lys Leu Lys Glu Cys Cys Glu Lys Pro Leu Leu Glu Lys Ser His Cys
                405                 410                 415

Ile Ala Glu Val Glu Asn Asp Glu Met Pro Ala Asp Leu Pro Ser Leu
            420                 425                 430

Ala Ala Asp Phe Val Glu Ser Lys Asp Val Cys Lys Asn Tyr Ala Glu
            435                 440                 445

Ala Lys Asp Val Phe Leu Gly Met Phe Leu Tyr Glu Tyr Ala Arg Arg
450                 455                 460

His Pro Asp Tyr Ser Val Val Leu Leu Leu Arg Leu Ala Lys Thr Tyr
465                 470                 475                 480

Glu Thr Thr Leu Glu Lys Cys Cys Ala Ala Ala Asp Pro His Glu Cys
                485                 490                 495

Tyr Ala Lys Val Phe Asp Glu Phe Lys Pro Leu Val Glu Glu Pro Gln
            500                 505                 510

Asn Leu Ile Lys Gln Asn Cys Glu Leu Phe Glu Gln Leu Gly Glu Tyr
            515                 520                 525

Lys Phe Gln Asn Ala Leu Leu Val Arg Tyr Thr Lys Lys Val Pro Gln
530                 535                 540

Val Ser Thr Pro Thr Leu Val Glu Val Ser Arg Asn Leu Gly Lys Val
545                 550                 555                 560

Gly Ser Lys Cys Cys Lys His Pro Glu Ala Lys Arg Met Pro Cys Ala
                565                 570                 575

Glu Asp Tyr Leu Ser Val Val Leu Asn Gln Leu Cys Val Leu His Glu
            580                 585                 590

Lys Thr Pro Val Ser Asp Arg Val Thr Lys Cys Cys Thr Glu Ser Leu
            595                 600                 605

Val Asn Arg Arg Pro Cys Phe Ser Ala Leu Glu Val Asp Glu Thr Tyr
610                 615                 620

Val Pro Lys Glu Phe Asn Ala Glu Thr Phe Thr Phe His Ala Asp Ile
625                 630                 635                 640

Cys Thr Leu Ser Glu Lys Glu Arg Gln Ile Lys Lys Gln Thr Ala Leu
                645                 650                 655

Val Glu Leu Val Lys His Lys Pro Lys Ala Thr Lys Glu Gln Leu Lys
            660                 665                 670

Ala Val Met Asp Asp Phe Ala Ala Phe Val Glu Lys Cys Cys Lys Ala
            675                 680                 685

Asp Asp Lys Glu Thr Cys Phe Ala Glu Glu Gly Lys Lys Leu Val Ala
            690                 695                 700

Ala Ser Gln Ala Ala Leu Gly Leu
705                 710

<210> SEQ ID NO 11
<211> LENGTH: 251
<212> TYPE: PRT
<213> ORGANISM: Artificial Sequence
<220> FEATURE:

<223> OTHER INFORMATION: Nanobody sequence

<400> SEQUENCE: 11

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Asp Ile Gly Trp Phe Arg Gln Ala Pro Gly Lys Gly Arg Glu Gly Val
        35                  40                  45
Ser Gly Ile Ser Ser Asp Gly Asn Thr Tyr Tyr Ala Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Pro Glu Asp Thr Ala Val Tyr Tyr Cys
                85                  90                  95
Ala Ala Glu Pro Pro Asp Ser Ser Trp Tyr Leu Asp Gly Ser Pro Glu
            100                 105                 110
Phe Phe Lys Tyr Trp Gly Gln Gly Thr Leu Val Thr Val Ser Ser Gly
        115                 120                 125
Gly Gly Gly Ser Gly Gly Gly Ser Glu Val Gln Leu Val Glu Ser Gly
130                 135                 140
Gly Gly Leu Val Gln Pro Gly Asn Ser Leu Arg Leu Ser Cys Ala Ala
145                 150                 155                 160
Ser Gly Phe Thr Phe Ser Ser Phe Gly Met Ser Trp Val Arg Gln Ala
            165                 170                 175
Pro Gly Lys Gly Leu Glu Trp Val Ser Ser Ile Ser Gly Ser Gly Ser
        180                 185                 190
Asp Thr Leu Tyr Ala Asp Ser Val Lys Gly Arg Phe Thr Ile Ser Arg
    195                 200                 205
Asp Asn Ala Lys Thr Thr Leu Tyr Leu Gln Met Asn Ser Leu Arg Pro
210                 215                 220
Glu Asp Thr Ala Val Tyr Tyr Cys Thr Ile Gly Gly Ser Leu Ser Arg
225                 230                 235                 240
Ser Ser Gln Gly Thr Leu Val Thr Val Ser Ser
                245                 250
```

<210> SEQ ID NO 12
<211> LENGTH: 115
<212> TYPE: PRT
<213> ORGANISM: Artificial Sequence
<220> FEATURE:
<223> OTHER INFORMATION: Nanobody sequence

<400> SEQUENCE: 12

```
Ala Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Arg Ser Phe
            20                  25                  30
Gly Met Ser Trp Val Arg Gln Ala Pro Gly Lys Glu Pro Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Lys Pro Glu Asp Thr Ala Val Tyr Tyr Cys
                85                  90                  95
```

Thr Ile Gly Gly Ser Leu Ser Arg Ser Ser Gln Gly Thr Gln Val Thr
            100                 105                 110

Val Ser Ser
        115

<210> SEQ ID NO 13
<211> LENGTH: 214
<212> TYPE: PRT
<213> ORGANISM: Artificial Sequence
<220> FEATURE:
<223> OTHER INFORMATION: A3 domain of vWF

<400> SEQUENCE: 13

Asp Ile Ser Glu Pro Pro Leu His Asp Phe Tyr Cys Ser Arg Leu Leu
1               5                   10                  15

Asp Leu Val Phe Leu Leu Asp Gly Ser Ser Arg Leu Ser Glu Ala Glu
            20                  25                  30

Phe Glu Val Leu Lys Ala Phe Val Val Asp Met Met Glu Arg Leu Arg
        35                  40                  45

Ile Ser Gln Lys Trp Val Arg Val Ala Val Val Glu Tyr His Asp Gly
    50                  55                  60

Ser His Ala Tyr Ile Gly Leu Lys Asp Arg Lys Arg Pro Ser Glu Leu
65                  70                  75                  80

Arg Arg Ile Ala Ser Gln Val Lys Tyr Ala Gly Ser Gln Val Ala Ser
                85                  90                  95

Thr Ser Glu Val Leu Lys Tyr Thr Leu Phe Gln Ile Phe Ser Lys Ile
            100                 105                 110

Asp Arg Pro Glu Ala Ser Arg Ile Ala Leu Leu Leu Met Ala Ser Gln
        115                 120                 125

Glu Pro Gln Arg Met Ser Arg Asn Phe Val Arg Tyr Val Gln Gly Leu
    130                 135                 140

Lys Lys Lys Lys Val Ile Val Ile Pro Val Gly Ile Gly Pro His Ala
145                 150                 155                 160

Asn Leu Lys Gln Ile Arg Leu Ile Glu Lys Gln Ala Pro Glu Asn Lys
                165                 170                 175

Ala Phe Val Leu Ser Ser Val Asp Glu Leu Glu Gln Gln Arg Asp Glu
            180                 185                 190

Ile Val Ser Tyr Leu Cys Asp Leu Ala Pro Glu Ala Pro Pro Pro Thr
        195                 200                 205

His His His His His His
    210

<210> SEQ ID NO 14
<211> LENGTH: 17
<212> TYPE: PRT
<213> ORGANISM: Artificial Sequence
<220> FEATURE:
<223> OTHER INFORMATION: CDR3 and FR4 sequence

<400> SEQUENCE: 14

Gly Gly Ser Leu Ser Arg Ser Ser Gln Gly Thr Leu Val Thr Val Ser
1               5                   10                  15

Ser

<210> SEQ ID NO 15
<211> LENGTH: 115
<212> TYPE: PRT
<213> ORGANISM: Artificial Sequence

```
<220> FEATURE:
<223> OTHER INFORMATION: Nanobody sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: Nanobody sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 17
<211> LENGTH: 385
<212> TYPE: PRT
<213> ORGANISM: Artificial Sequence
<220> FEATURE:
<223> OTHER INFORMATION: Nanobody sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Pro Met Gly Trp Phe Arg Gln Ala Pro Gly Lys Gly Arg Glu Phe Val
35                  40                  45

Ser Ser Ile Thr Gly Ser Gly Ser Thr Tyr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Glu Val Gln Leu Val Glu Ser Gly Gly
130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
                165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Ser Thr Tyr Tyr Ala
305                 310                 315                 320

Asp Ser Val Lys Gly Arg Phe Thr Ile Ser Arg Asp Asn Ala Lys Asn
                325                 330                 335

Thr Leu Tyr Leu Gln Met Asn Ser Leu Arg Pro Glu Asp Thr Ala Val
            340                 345                 350

Tyr Tyr Cys Ala Ala Tyr Ile Arg Pro Asp Thr Tyr Leu Ser Arg Asp
        355                 360                 365

Tyr Arg Lys Tyr Asp Tyr Trp Gly Gln Gly Thr Leu Val Thr Val Ser
    370                 375                 380

Ser
385

<210> SEQ ID NO 18
<211> LENGTH: 245
<212> TYPE: PRT
<213> ORGANISM: Artificial Sequence
<220> FEATURE:
<223> OTHER INFORMATION: Nanobody sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
            165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser
            245

<210> SEQ ID NO 19
<211> LENGTH: 375
<212> TYPE: PRT
<213> ORGANISM: Artificial Sequence
<220> FEATURE:
<223> OTHER INFORMATION: Nanobody sequence

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
            115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Ser Val Phe Lys
145                 150                 155                 160

Ile Asn Val Met Ala Trp Tyr Arg Gln Ala Pro Gly Lys Gly Arg Glu
                165                 170                 175

Leu Val Ala Gly Ile Ile Ser Gly Gly Ser Thr Ser Tyr Ala Asp Ser
            180                 185                 190

Val Lys Gly Arg Phe Thr Ile Ser Arg Asp Asn Ala Lys Asn Thr Leu
    195                 200                 205

Tyr Leu Gln Met Asn Ser Leu Arg Pro Glu Asp Thr Ala Val Tyr Tyr
    210                 215                 220

Cys Ala Phe Ile Thr Thr Glu Ser Asp Tyr Asp Leu Gly Arg Arg Tyr
225                 230                 235                 240

Trp Gly Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Asn Ser Leu Arg Leu Ser Cys Ala Ala Ser Gly Phe Thr
    275                 280                 285

Phe Ser Ser Phe Gly Met Ser Trp Val Arg Gln Ala Pro Gly Lys Gly
    290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
    355                 360                 365

Thr Leu Val Thr Val Ser Ser
    370                 375

<210> SEQ ID NO 20
<211> LENGTH: 375
<212> TYPE: PRT
<213> ORGANISM: Artificial Sequence
<220> FEATURE:
<223> OTHER INFORMATION: Nanobody sequence

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

-continued

```
Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Ser Gly Gly Gly Ser Glu Val
            245                 250                 255

Gln Leu Val Glu Ser Gly Gly Gly Leu Val Gln Pro Gly Gly Ser Leu
            260                 265                 270

Arg Leu Ser Cys Ala Ala Ser Gly Ser Val Phe Lys Ile Asn Val Met
        275                 280                 285

Ala Trp Tyr Arg Gln Ala Pro Gly Lys Gly Arg Glu Leu Val Ala Gly
    290                 295                 300

Ile Ile Ser Gly Gly Ser Thr Ser Tyr Ala Asp Ser Val Lys Gly Arg
305                 310                 315                 320

Phe Thr Ile Ser Arg Asp Asn Ala Lys Asn Thr Leu Tyr Leu Gln Met
                325                 330                 335

Asn Ser Leu Arg Pro Glu Asp Thr Ala Val Tyr Tyr Cys Ala Phe Ile
            340                 345                 350

Thr Thr Glu Ser Asp Tyr Asp Leu Gly Arg Arg Tyr Trp Gly Gln Gly
        355                 360                 365

Thr Leu Val Thr Val Ser Ser
    370                 375
```

STABLE FORMULATIONS OF POLYPEPTIDES AND USES THEREOF

RELATED APPLICATIONS

This application is a continuation-in-part application of U.S. patent application Ser. No. 13/393,636, which is a national stage filing under 35 U.S.C. §371 of international application PCT/EP2010/062975, filed Sep. 3, 2010, which claims the benefit under 35 U.S.C. §119(e) of U.S. provisional application Ser. No. 61/275,816, filed Sep. 3, 2009 and U.S. provisional application Ser. No. 61/284,502, filed Dec. 18, 2009, the disclosures of which are incorporated by reference herein in their entireties.

This application is also a continuation-in-part application of U.S. patent application Ser. No. 13/254,266, which is a national stage filing under 35 U.S.C. §371 of international application PCT/EP2010/052600, filed Mar. 2, 2010, which was published under PCT Article 21(2) in English, and claims the benefit under 35 U.S.C. §119(e) of U.S. provisional application Ser. No. 61/157,688, filed Mar. 5, 2009, U.S. provisional application Ser. No. 61/275,816, filed Sep. 3, 2009, and of U.S. provisional application Ser. No. 61/284,502, filed Dec. 18, 2009, the disclosures of which are incorporated by reference herein in their entireties.

FIELD OF THE INVENTION

The present invention relates to formulations of single variable domains. More specifically the present invention provides formulations that contain single variable domains with a good solubility and good stability under different storage and stress conditions. The formulations of the invention are suitable for administration to human subjects.

The invention further relates to containers and pharmaceutical units comprising such formulations and to prophylactic and therapeutic uses of the formulations and pharmaceutical units of the invention.

Other aspects, embodiments, advantages and applications of the invention will become clear from the further description herein.

In a broad aspect the present invention generally relates to novel dimer-complexes (herein called "non-fused-dimers" or NFDs) comprising single variable domains such as e.g. Nanobodies®, methods of making these complexes and uses thereof. These non-covalently bound dimer-complexes consist of two identical monomers that each comprises one or more single variable domains (homodimers) or of two different monomers that each comprises on or more single variable domains (heterodimers). The subject NFDs have typically altered e.g. improved or decreased binding characteristics over their monomeric counterpart. The NFDs of the invention may further be engineered through linkage by a flexible peptide or cysteines in order to improve the stability.

This invention also describes conditions under which such NFDs are formed and conditions under which the formation of such dimers can be avoided. E.g., the present invention also provides methods for suppressing NFDs such as the dimerization of (human serum) albumin-binding Nanobodies® by adding to a formulation one or more excipients that increase the melting temperature of the singe variable domain such as e.g. by adding mannitol, other polyols or reducing sugars to a liquid formulation.

The present invention also provides formulations of single variable domains wherein the formation of NFDs is suppressed. The formulations of the invention are suitable for administration to human subjects. The invention further relates to containers and pharmaceutical units comprising such formulations and to prophylactic and therapeutic uses of the formulations and pharmaceutical units of the invention.

Other aspects, embodiments, advantages and applications of the invention will become clear from the further description herein.

BACKGROUND ART

Nanobodies (as further described herein) are characterized by formation of the antigen binding site by a single variable domain, which does not require interaction with a further domain (e.g. in the form of VH/VL interaction) for antigen recognition. Nanobodies have been described against a wide range of different targets (WO 04/062551, WO 05/044858, WO 06/040153, WO 06/122825, WO 07/104529, WO 08/020079, WO 08/074839, WO 08/071447, WO 08/074840, WO 08/074867, WO 08/077945, WO 08/101985, WO 08/142164, WO 09/068625, WO 08/142165, WO 09/068627) which could be ideal candidates for drug development. Nanobodies against IL-6R that can inhibit the IL-6/IL-6R interaction are described in WO 08/020079. Nanobodies against the p19 subunit of IL-23 that block the interaction of IL-23 with its receptor have been described in WO 09/068627. Nanobodies against RANKL that can inhibit osteoclast formation are described in WO 08/142164. The OPG/RANKL/RANK system has recently been discovered as pivotal regulatory factors in the pathogenesis of bone diseases and disorders like e.g. osteoporosis.

Proteins, such as therapeutic antibodies and Nanobodies, are often transported and/or stored for later use. It is important therefore that such proteins preserve the stability and biological activity of the protein under various conditions such as different temperature regimens and mechanical stress.

Certain prior liquid antibody preparations have shown short shelf lives and loss of biological activity of the antibodies resulting from chemical and/or physical instabilities during the transportation and storage. Chemical instability may be caused by deamidation, racemization, hydrolysis, oxidation, beta elimination or disulfide exchange, and physical instability may be caused by antibody denaturation, aggregation, precipitation or adsorption. Among those, aggregation, deamidation and oxidation are known to be the most common causes of the antibody degradation (Cleland et al., 1993, Critical Reviews in Therapeutic Drug Carrier Systems 10: 307-377). Little is known about drug formulation components that provide stable liquid formulations of Nanobodies.

There exists a need for stable liquid formulations of Nanobodies which show a good solubility of the Nanobody and which exhibit increases stability, low to undetectable levels of aggregation, low to undetectable levels of Nanobody degradation, and very little to no loss of biological activity of the Nanobody, even under different transportation and storage conditions.

The antigen binding sites of conventional antibodies are formed primarily by the hypervariable loops from both the heavy and the light chain variable domains. Functional antigen binding sites can however also be formed by heavy chain variable domains (VH) alone. In vivo, such binding sites have evolved in camels and camelids as part of heavy chain antibodies, which consist only of two heavy chains and lack light chains. Furthermore, analysis of the differences in amino acid sequence between the VHs of these camel heavy chain-only antibodies (also referred to as VHH) and VH domains from conventional human antibodies helped to design altered human VH domains (Lutz Riechmann and Serge Muyldermans, J. of Immunological Methods, Vol. 231, Issues 1 to 2, 1999, 25-38).

Similarly, it has been shown that by mutation studies of the interface residues as well as of the CDR3 on the VH of the anti-Her2 antibody 4D5 in parallel with the anti-hCG VHH H14, some mutations were found to promote autonomous VH domain behaviour (i.e. beneficial solubility and reversible refolding) (Barthelemy P A et al., 2008, J. of Biol. Chemistry, Vol 283, No 6, pp 3639-3654). It was also found that increasing the hydrophilicity of the former light chain interface by replacing exposed hydrophobic residues by more hydrophilic residues improves the autonomous VH domain behaviour. These engineered VHs were shown to be predominantly monomeric at high concentration, however low quantities of dimers and other aggregates of said engineered VHs were also found that presumably form relative weak interaction similar to those described in the art for VL-VH pair interactions. Similarly, a camelized VH, called cVH-E2, is claimed to form dimers in solution in a concentration dependent manner i.e. at concentrations above 7 mg/ml (but note that data has not been shown in study; Dottorini et al., Biochemistry, 2004, 43, 622-628). Below this concentration, the dimer likely dissociates into monomers and it remains unclear whether these dimers were active (i.e. binding antigen).

Furthermore, it has recently been reported that a truncated llama derived VHH (the first seven amino acids are cleaved off) with a very short CDR3 (only 6 residues) called VHH-R9 forms a domain swapped dimer in the crystal structure. Since VHH-R9 has been shown to be functional in solution (low Kd against hapten) and to consist of a monomer only, it is likely that dimerization occurred during the very slow crystallization process (4 to 5 weeks) and that elements such as N-terminal cleavage, high concentration conditions and short CDR3 could lead or contribute to the "condensation" phenomena (see in particular also conclusion part of Spinelli et al., FEBS Letter 564, 2004, 35-40). Sepulveda et al. (J. Mol. Biol. (2003) 333, 355-365) has found that spontaneous formation of VH dimers (VHD) is in many cases permissive, producing molecules with antigen binding specificity. However, based on the reported spontaneous formation (versus the dimers formed by PIA reported herein) and the lack of stability data on the non-fused dimers, it is likely that these are weakly interacting dimers similar to the ones described by Barthelemy (supra).

Taken together, the literature describes the formation of dimers of single variable domains and fragments thereof that a) are interacting primarily on relatively weak hydrophobic interaction (which are e.g. depending on the concentration, reversible), and/or b) occur in another occasion only in the crystallisation process (e.g. as a result of crystal packing forces). Moreover, it has been described that these dimers were not binding antigens anymore (as in Spinelli (supra)) or it is unclear whether these dimers were binding dimers (as in Dottorini (supra) and Barthelemy (supra)).

It has been found (see e.g. WO 09/109635) that stable dimer-complexes can be formed in solution with polypeptides comprising at least one single variable VHH domain. These dimer-complexes are also herein referred to as non-fused-dimers.

SUMMARY OF THE INVENTION

The present invention provides improved formulations (also referred to as "formulation(s) of the invention") of polypeptides comprising one or more single variable domains that show good solubility of the single variable domains and retain increased stability of the single variable domains under a variety of different transportation, storage and in-use conditions. The present invention is based on the finding that the presence in the formulation of certain buffers, certain excipients and/or certain surfactants may increase the solubility, the melting temperature and/or the stability of the single variable domains present in the formulation.

The present invention provides solubility data for formulations with polypeptides comprising one or more single variable domains (also referred to as "polypeptide(s) of the invention") up to 150 mg/mL and higher. The invention further shows that such formulations can be transported, manipulated through various administration devices and retain activity, purity and potency under different stress conditions: mechanical stress conditions; storage of the formulation at various stress conditions such as different freeze/thaw cycles, at 2-8° C., at 25±5° C. and at elevated temperature.

The formulation of the present invention comprises an aqueous carrier with a pH of 5.5 to 8.0 and a polypeptide comprising one or more single variable domains at a concentration of 1 mg/ml to 200 mg/ml, said formulation being formulated for administration to a human subject and said formulation further comprising one or more components selected from:
  a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
  b) An excipient at a concentration of 1% to 20% (w:v);
  c) A surfactant at a concentration of 0.001% to 1% selected from TWEEN (polysorbate) 80, TWEEN (polysorbate) 20 and poloxamers;
wherein said formulation has an inorganic salt concentration of 150 mM or lower.

In a preferred aspect, the formulation of the invention comprises at least two of the above components, such as e.g. at least the components in a) and b), at least the components in a) and c) or at least the components in b) and c). Preferably, the formulation of the invention comprises the components in a), b) and c).

The present inventors observed that formulations that have 150 mM or less of inorganic salt show a much better stability of the single variable domains contained in the formulation. Inorganic salts frequently used in pharmaceutical formulation are NaCl and KCl. The single variable domains present in formulations containing 150 mM or less of inorganic salt have shown increased stability (e.g. less tendency to form aggregates, dimers and/or pyroglutamate, or to loose potency) at different stress storage conditions (such as e.g. during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), an improved melting temperature and/or an increased solubility. Preferably, the formulation contains 100 mM or less of inorganic salt, more preferably even 50 mM or less of inorganic salt. Most preferably the formulation does not contain any inorganic salt.

The polypeptide (also referred to as "polypeptide of the invention") comprising one or more single variable domains for use in the formulation of the invention may be therapeutic or prophylactic, and may be useful in the prevention, treatment and/or management of one or more diseases and/or disorders. In one specific aspect, the polypeptide has at least two single variable domains. In another specific aspect, the polypeptide has at least three single variable domains. Preferred polypeptides of the invention and single variable domains used in the polypeptide of the invention are described in WO 08/142164, WO 08/020079 and WO 09/068627. Particularly preferred polypeptides of the invention may be selected from SEQ ID NO's: 1 to 6.

The polypeptide of the invention may be present in the formulation of the present invention at a concentration of about 1 to 200 mg/mL or more, preferably about 5 to 100 mg/mL or more, more preferably about 5 to 50 mg/mL or more, most preferably about 5 to 30 mg/mL or more, such as around 5 mg/mL, around 10 mg/mL, around 20 mg/mL, around 30 mg/mL, around 40 mg/mL, around 50 mg/mL, around 60 mg/mL, around 70 mg/mL, around 80 mg/mL, around 90 mg/mL, around 100 mg/mL, around 150 mg/mL or even more.

In an aspect of the invention, the formulation is homogeneous. In another aspect, the formulation of the invention is sterile. In addition to the polypeptide of the invention, the formulation of the present invention comprises at least an aqueous carrier (e.g. distilled water, MILLI-Q water or WFI) and a buffer.

The pH of the formulation of the invention should be in the range of 5.5 to 8.0, preferably the pH is around 6.0 to 7.5, more preferably around 6.2 to 7.5 or around 6.2 to 7.0. Most preferably the pH is in the range of 6.5 to 7.0, such as e.g. pH 6.5. These pH ranges have shown to provide an increased melting temperature to the polypeptides present in the formulation of the invention.

Preferred buffers for use in the formulation of the invention are hepes pH 7.0-8.0, histidine pH 6.0-6.5, MES pH 6.0, succinate pH 6.0-6.5 or acetate pH 5.5-6.0, preferably hepes pH 7.0 or histidine pH 6.0-6.5, most preferably histidine pH 6.0, 6.2 or 6.5. Formulations comprising one of these buffers have shown a very good solubility (as defined herein) of the polypeptides of the invention, an improved melting temperature of the polypeptides present in the formulation and increased stability (e.g. less tendency to form aggregates, dimers and/or pyroglutamate, or to lose potency) at different stress storage conditions (such as e.g. during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)). The buffer is preferably at a concentration of about 10 to 20 mM, such as 10 mM or 15 mM. In a specific aspect, the formulation of the invention comprises a histidine buffer pH 6.5 at a concentration of 15 mM or a histidine buffer pH 6.0 at a concentration of 10 mM.

Accordingly, the present invention provides stable formulations of polypeptides comprising one or more single variable domains, said formulations comprising an aqueous carrier, the polypeptide at a concentration from about 1 to 200 mg/mL or more, preferably about 5 to 100 mg/mL or more, more preferably about 5 to 50 mg/mL or more, most preferably about 5 to 30 mg/mL or more, such as around 5 mg/mL, around 10 mg/mL, around 20 mg/mL, around 30 mg/mL, around 40 mg/mL, around 50 mg/mL, around 60 mg/mL, around 70 mg/mL, around 80 mg/mL, around 90 mg/mL, around 100 mg/mL, around 150 mg/mL or even more, and a buffer such as a histidine buffer with a pH ranging from 6.0 to 7.0 at a concentration of about 10 to 20 mM.

Preferably the formulation of the invention is isotonic or slightly hypotonic and/or has an osmolality of about 290±60 mOsm/kg, such as about 240 or higher, 250 or higher or 260 or higher. Isotonicity of the formulation can be further adjusted by the addition of one or more excipients and/or tonifiers.

Preferred excipients/tonifiers for use in the formulation of the present invention are saccharides and/or polyols. Accordingly, in another aspect, the formulation of the invention comprises a saccharide and/or polyol. Formulations comprising one or more saccharides and/or polyols have shown increased stability (e.g. less tendency to form aggregates, dimers and/or pyroglutamate, or to loose potency) at different stress storage conditions (such as e.g. during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more) and during mechanical stress conditions) and/or an improved melting temperature of the polypeptides present in the formulation. In a specific aspect of the invention, the excipient present in the formulation of the invention is a non-reducing sugar. In another specific aspect, the excipient present in the formulation of the invention is a disaccharide. In another specific aspect, the excipient present in the formulation of the invention is selected from sucrose, trehalose, sorbitol and mannitol. The saccharide and/or polyol is preferably present in the formulation of the invention at a concentration of about 1% to 20%, preferably about 2.5% to 15%, more preferably about 5% to 10%, such as around 5%, around 7.5%, around 8% or around 10%.

Accordingly, the present invention provides stable formulations of polypeptides comprising one or more single variable domains, said formulations comprising an aqueous carrier, the polypeptide at a concentration from about 1 to 200 mg/mL or more, preferably about 5 to 100 mg/mL or more, more preferably about 5 to 50 mg/mL or more, most preferably about 5 to 30 mg/mL or more, such as around 5 mg/mL, around 10 mg/mL, around 20 mg/mL, around 30 mg/mL, around 40 mg/mL, around 50 mg/mL, around 60 mg/mL, around 70 mg/mL, around 80 mg/mL, around 90 mg/mL, around 100 mg/mL, around 150 mg/mL or even more, and a saccharide and/or polyol at a concentration of about 1% to 20%, preferably about 2.5% to 15%, more preferably about 5% to 10%, such as around 5%, around 7.5%, around 8% or around 10%.

In another specific aspect, the formulation of the invention may comprise one or more surfactants (e.g., TWEEN (polysorbate) 20, TWEEN (polysorbate) 80 or a poloxamer). Formulations comprising a surfactant have shown a very good solubility (as defined herein) of the polypeptides of the invention and/or increased stability under mechanical stress. The surfactant may be present at a concentration in the range of about 0.001% to 1% (preferably between about 0.001% to 0.1%, or about 0.01% to 0.1% such as around 0.001%, around 0.005%, around 0.01%, around 0.02%, around 0.05%, around 0.08%, around 0.1%, around 0.5%, or around 1% of the formulation, preferably around 0.01%).

Accordingly, the present invention provides stable formulations of polypeptides comprising one or more single variable domains, said formulations comprising an aqueous carrier, the polypeptide at a concentration from about 1 to 200 mg/mL or more, preferably about 5 to 100 mg/mL or more, more preferably about 5 to 50 mg/mL or more, most preferably about 5 to 30 mg/mL or more, such as around 5 mg/mL, around 10 mg/mL, around 20 mg/mL, around 30 mg/mL, around 40 mg/mL, around 50 mg/mL, around 60 mg/mL, around 70 mg/mL, around 80 mg/mL, around 90 mg/mL, around 100 mg/mL, around 150 mg/mL or even more, and a surfactant (e.g., TWEEN (polysorbate) 20, TWEEN (polysorbate) 80 or a poloxamer) at a concentration in the range of about 0.001% to 1% (preferably between about 0.001% to 0.1%, or about 0.01% to 0.1% such as around 0.001%, around 0.005%, around 0.01%, around 0.02%, around 0.05%, around 0.08%, around 0.1%, around 0.5%, or around 1% of the formulation, preferably around 0.01%).

A preferred formulation of the invention may comprise:
a) A histidine pH 6.5 buffer at a concentration of 10 mM to 100 mM, such as 10 mM to 20 mM;
b) Sucrose at a concentration of 1% to 10%; and
c) TWEEN (polysorbate) 80 at a concentration of 0.001% to 1%.

Another preferred formulation of the invention may comprise:
a) A histidine pH 6.5 buffer at a concentration of 15 mM;
b) Sucrose at a concentration of 8%; and
c) TWEEN (polysorbate) 80 at a concentration of 0.01%.

Another preferred formulation of the invention may comprise:
a) A histidine pH 6.0 buffer at a concentration of 10 mM to 100 mM, such as 10 mM to 20 mM;
b) Sucrose at a concentration of 1% to 10%; and
c) TWEEN (polysorbate) 80 at a concentration of 0.001% to 1%.

Another preferred formulation of the invention may comprise:
a) A histidine pH 6.0 buffer at a concentration of 10 mM;
b) Sucrose at a concentration of 10%; and
c) TWEEN (polysorbate) 80 at a concentration of 0.005%.

The present invention provides formulations of a polypeptide comprising one or more single variable domains which exhibit high solubility of the polypeptide, little to no aggregation of the polypeptide and high stability during long periods of storage.

In one aspect, the components present in the formulations of the invention have been selected such that the polypeptides of the invention have a solubility of at least 20 mg/mL, at least 50 mg/mL, preferably at least 90 mg/mL, at least 120 mg/mL, at least 150 mg/mL or even 200 mg/mL or more.

In another aspect, the components present in the formulations of the invention have been selected such that the polypeptide present in the formulation of the invention has a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

In yet another aspect, the formulation of the present invention exhibits stability under various stress conditions such as:
multiple (up to 10) freeze/thaw cycles;
storage at a temperature of 2-8° C. up to at least 2 weeks (preferably at least 3 weeks, at least 5 weeks, at least 8 weeks, at least 10 weeks, at least 3 months, at least 6 months, at least 1 year, 1.5 year or even 2 years or more);
storage at a temperature of 25±5° C. up to at least 2 weeks (preferably at least 3 weeks, at least 5 weeks, at least 8 weeks, at least 10 weeks, at least 3 months, at least 1 year, 1.5 year or even 2 years or more);
storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more); and/or
mechanical stress.

Mechanical stress as used in the present invention can be any form of external force applied on the formulation that may affect the stability of the polypeptide present in the formulation. Without being limiting, the mechanical stress applied to the solution can be shear stress, stir stress, shake stress, rotation stress, etc. Preferably the formulation of the invention is stable under one or more of the following forms of mechanical stress:
shaking the formulation during 10 s to 1 min;
pushing the formulation through a needle (25 G, preferably 26 G, more preferably 27 G, even more preferably 28 G, most preferably 29 G or more) with a syringe (the syringe used can be any commercially available syringe, such as e.g. a 1 mL, 2 mL, 3 mL, 4 mL, 5 ml, 10 mL up to 50 mL syringe);
rotating for two days at 10 rpm; and/or
stirring for 1 hour at room temperature and/or 4-48 hours (such as 4-8 hours, 12 hours, 24 hours or even 48 hours) at 4° C. at at least 10 rpm (such as 50 rpm, 100 rpm or more).

Preferably, the formulations of the present invention are stable under more than one (such as two, three, four, five, six or seven) of the above stress conditions, most preferably under all of the above stress conditions.

Accordingly, the polypeptide of the invention present in the formulation of the invention:
is stable after multiple (up to 10) freeze/thaw cycles, said stability as determined by OD320/OD280 measurement, SE-HPLC, RP-HPLC, IEX-HPLC, potency assay (such as BIACORE or ELISA) and/or SDS-PAGE;
is stable during storage at a temperature of 2-8° C. up to at least 2 weeks (preferably at least 3 weeks, at least 5 weeks, at least 8 weeks, at least 10 weeks, at least 3 months, at least 6 months, at least 1 year, 1.5 year or even 2 years or more), said stability as determined by OD320/OD280 measurement, SE-HPLC, RP-HPLC, IEX-HPLC, potency assay (such as BIACORE or ELISA) and/or SDS-PAGE;
is stable during storage at a temperature of 25±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more), said stability as determined by OD320/OD280 measurement, SE-HPLC, RP-HPLC, IEX-HPLC, potency assay (such as BIACORE or ELISA) and/or SDS-PAGE;
is stable during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more), said stability as determined by OD320/OD280 measurement, SE-HPLC, RP-HPLC, IEX-HPLC, potency assay (such as BIACORE or ELISA) and/or SDS-PAGE;
is stable when shaking the formulation during 10 s to 1 min;
is stable when pushing the formulation through a needle (25 G, preferably 26 G, more preferably 27 G, even more preferably 28 G, most preferably 29 G or more) with a syringe (the syringe used can be any commercially available syringe, such as e.g. a 1 mL, 2 mL, 3 mL, 4 mL, 5 mL, 10 mL, 20 mL, 30 mL, 40 mL up to 50 mL syringe);
is stable when rotating for two days at 10 rpm; and/or
is stable when stirring for 1 hour at room temperature and/or 4-48 hours (such as 4-8 hours, 12 hours, 24 hours or even 48 hours) at 4° C. at at least 10 rpm (such as 50 rpm, 100 rpm or more).

The stability of the formulations of the present invention can be demonstrated by the fact that less than 10% of the polypeptides forms pyroglutamate at the N-terminal glutamic acid (e.g. as assessed by RP-HPLC) and/or less than 10% of the polypeptides forms dimers (e.g. as assessed by SE-HPLC) during storage under one or more of the above stress conditions. Preferably less than 10% of the polypeptides forms pyroglutamate at the N-terminal glutamic acid (e.g. as assessed by RP-HPLC) and less than 10% of the polypeptides forms dimers (e.g. as assessed by SE-HPLC) during storage under one or more of the above stress conditions.

In a specific aspect, less than 10% of the polypeptides present in the formulation of the invention forms pyroglutamate at the N-terminal glutamic acid (e.g. as assessed by RP-HPLC) during storage at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more). In another specific aspect, less than 10% of the polypeptides forms dimers (e.g. as assessed by SE-HPLC) during storage at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more). In yet another specific aspect, less than 10% of the polypeptides present in the formulation of the invention forms pyroglutamate at the N-terminal glutamic acid (e.g. as assessed by RP-HPLC) during storage at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more) and less than 10% of the polypeptides forms dimers (e.g. as assessed by SE-HPLC) during storage at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more).

Apart from this and/or in addition, the stability of the formulations of the present invention can be demonstrated by the fact that it shows only low to undetectable levels of aggregation and/or particulate formation (e.g. as assessed by SE-HPLC, subvisible particle counting, analytical ultracentrifugation, dynamic light scattering, OD320/OD280 ratio measurement and/or elastic light scattering) even during storage under one ore more of the above stress conditions. In a specific aspect, the formulations of the present invention show only low to undetectable levels of aggregation and/or particulate formation (e.g. as assessed by SE-HPLC, subvisible particle counting, analytical ultracentrifugation, dynamic light scattering and/or OD320/OD280 measurement) at a temperature of 37±5° C. and/or 5±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more).

Apart from this and/or in addition, the stability of the formulations of the present invention can be demonstrated by the fact that it shows only low to undetectable levels of fragmentation and/or degradation of the polypeptides (e.g. as assessed by SDS-PAGE, SE-HPLC, RP-HPLC and/or IEX-HPLC) even during storage under one or more of the above stress conditions. In a specific aspect, the formulations of the present invention show only low to undetectable levels of fragmentation and/or degradation of the polypeptides (e.g. as assessed by SDS-PAGE, SE-HPLC, RP-HPLC and/or IEX-HPLC) at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more).

Apart from this and/or in addition, the stability of the formulations of the present invention can be demonstrated by the fact that it shows very little to no loss of the biological activities of the polypeptide of the invention (e.g. as assessed by ELISA and/or BIACORE) even during storage under one or more of the above stress conditions. In a specific aspect, the formulations of the present invention show very little to no loss of the biological activities of the polypeptide of the invention (e.g. as assessed by ELISA and/or BIACORE) at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more).

More specifically, in the formulations of the present invention at least 80% (preferably at least 90%, more preferably at least 95% or even at least 99%) of the polypeptides retain their binding activity to at least one (preferably to all) of their targets (e.g. as assessed by ELISA and/or BIACORE) after storage under one or more of the above stress conditions compared to the binding activity prior to storage.

In a specific aspect, at least 80% (preferably at least 90%, more preferably at least 95% or even at least 99%) of the polypeptides retains their binding activity (e.g. as assessed by ELISA and/or BIACORE) to at least one (preferably to all) of their targets after storage at 37±5° C. for up to at least 2 weeks (preferably at least 3 weeks, at least 5 weeks, at least 2 months, at least 6 months, at least 1 year, 1.5 year or even 2 years or more) compared to the binding activity prior to storage.

Accordingly the present invention provides stable formulations of polypeptides comprising one or more single variable domains, wherein:

less than 10% of the polypeptides forms pyroglutamate at the N-terminal glutamic acid (e.g. as assessed by RP-HPLC) during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

less than 10% of the polypeptides forms dimers (e.g. as assessed by SE-HPLC) during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

at least 80% of the polypeptides retain its binding activity (e.g. as assessed by ELISA and/or BIACORE) to at least one (preferably to all) of its targets after storage at 37±5° C. up to 2 weeks (preferably at least 3 weeks, at least 5 weeks, at least 2 months, at least 6 months, at least 1 year, 1.5 year or even 2 years or more) compared to the binding activity prior to storage; and/or the polypeptide is stable under mechanical stress.

In a preferred aspect, the formulation of the invention is a pharmaceutical formulation.

The present invention further provides methods for preparing the stable formulations of the invention. The methods of the invention may comprise the steps of concentrating a polypeptide comprising one or more single variable domains and exchanging it with the preferred buffer and/or excipient.

Also provided are containers, kits and pharmaceutical unit dosages comprising the formulations of the invention for use by, e.g., a healthcare professional. In specific embodiments, the kits or pharmaceutical unit dosages comprising the stable formulations of the invention are formulated for parenteral administration (e.g., intradermally, intramuscularly, intraperitoneally, intravenously and/or subcutaneously) of the polypeptide of the invention to a human subject. The formulations, containers, pharmaceutical unit dosages and/or kits can be used in prophylaxis and/or therapy. In a specific aspect, the formulations, containers, pharmaceutical unit dosages and/or kits are used for the prevention and/or treatment of one ore more diseases and/or disorders such as bone diseases and/or disorders (such as e.g. osteoporosis, cancer-related bone diseases, and/or bone loss associated with autoimmunity and/or viral infection) or autoimmune diseases (such as e.g. rheumatoid arthritis).

The present invention provides methods and formulations that avoid the formation of dimer-complexes of single variable domains. In one aspect the present invention provides a formulation (also referred to herein as "formulation of the invention"), such as a pharmaceutical formulation, comprising i) a polypeptide that comprises at least one single variable domain, and ii) an excipient, preferably selected from a polyol, a non-reducing sugar and/or a dissaccharide. Preferred excipients for use in the formulation of the invention include sorbitol, mannitol, xylitol, ribitol, trehalose, sucrose and/or erythritol. The excipient is preferably present at a concentration of 1% to 20%, 2.5% to 15%, preferably 5% to 10%, such as 5%, 7.5%, 8% or 10%.

The present inventors have shown that the addition of such an excipient in a formulation can drastically reduce the formation of non-fused dimers of single variable domains. The formulation of the invention is therefore particularly suitable for use with polypeptides comprising at least one single variable domain, wherein said single variable domain is susceptible to dimerization.

As indicated in the background art, it has been found (see e.g. WO 09/109635) that stable dimer-complexes can be formed in solution for polypeptides comprising at least one single variable VHH domain, preferably for polypeptides comprising at least one single variable VHH domain that forms dimers using the methods described herein (i.e. process-induced association, introduction of CDR3/framework region 4 destabilizing residues and/or storage at high temperature and high concentration), more preferably for polypeptides comprising at least one single variable VHH domain with sequences SEQ ID NO: 7 to 12 and 17-20 and/or variants thereof, e.g. single variable VHH domain with sequences that are 70% and more identical to SEQ ID NO: 7 to 12 and 17-20. Some of these stable dimer-complexes (also herein referred to as non-fused-dimers or NFDs; non-fused-dimer or NFD) can retain binding functionality to at least 50% or can even have increased binding affinity compared to their monomeric building blocks, others have decreased or no binding functionality anymore. These NFDs are much more stable compared to the 'transient' concentration-dependent dimers described e.g. in Barthelemy (supra) and are once formed stable in a wide range of concentrations. These NFDs may be formed by swapping framework 4 region between the monomeric building blocks whereby both said monomeric building blocks interlock (see experimental part of the crystal structure of polypeptide B NFD). These dimers are typically formed upon process-induced association (PIA) using methods described herein and/or storage at relative high temperature over weeks (such as e.g. 37° C. over 4 weeks) and high concentration (such as e.g. higher than 50 mg/ml, e.g. 65 mg/ml).

As indicated above, the invention teaches methods and formulations that avoid the formation of such dimer-complexes in i) e.g. an up-scaled production or purification process of said polypeptides comprising single variable domain(s) under non-stress condition (i.e. condition that do not favour unfolding of immunoglobulins), ii) by an adequate formulation with excipients increasing the melting temperature of the single variable domain(s), e.g. by having mannitol in the formulation and/or iii) by increasing the stability of the CDR3 and/or framework 4 region conformation.

Accordingly, in one aspect, the present invention relates to a formulation that comprises a polypeptide comprising one or more single variable domains, said formulation being formulated for administration to a human subject, and further comprising an excipient at a concentration of 1% to 20% (w:v). Preferred excipients for use in the formulation of the present invention are saccharides and/or polyols. Accordingly, in another aspect, the formulation of the invention comprises a saccharide and/or polyol. Formulations comprising one or more saccharides and/or polyols have shown increased stability (i.e. less tendency to form dimmers and/or oligomers and/or or to lose potency) at different stress storage conditions (such as e.g. during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) and/or an improved melting temperature of the polypeptides present in the formulation. In a specific aspect of the invention, the excipient present in the formulation of the invention is a non-reducing sugar. In another specific aspect, the excipient present in the formulation of the invention is a disaccharide. In another specific aspect, the excipient present in the formulation of the invention is selected from sucrose, trehalose, sorbitol and mannitol. The saccharide and/or polyol is preferably present in the formulation of the invention at a concentration of about 1% to 20%, preferably about 2.5% to 15%, more preferably about 5% to 10%, such as around 5%, around 7.5%, around 8% or around 10%.

The stability of the formulations of the present invention can be demonstrated by the fact that they show only low to undetectable levels of dimer and/or oligomer formation (e.g. as assessed by SE-HPLC) even during storage under one or more stress conditions, such as at a temperature of 37±5° C. and/or 5±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more). The stability of the formulations of the present invention can also be demonstrated by the fact that they show very little to no loss of the biological activities (e.g. as assessed by ELISA and/or BIACORE) even during storage under one or more stress conditions, such as at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more).

More specifically, in the formulations of the present invention at least 80% (preferably at least 90%, more preferably at least 95% or even at least 99%) of the polypeptides retains its binding activity to at least one (preferably to all) of its targets (e.g. as assessed by ELISA and/or BIACORE) after storage under one or more of the above stress conditions compared to the binding activity prior to storage. In a specific aspect, at least 80% (preferably at least 90%, more preferably at least 95% or even at least 99%) of the polypeptides retains its binding activity (e.g. as assessed by ELISA and/or BIA-CORE) to at least one (preferably to all) of its targets after storage at 37±5° C. for up to at least 2 weeks (preferably at least 3 weeks, at least 5 weeks, at least 2 months, at least 6 months, at least 1 year, 1.5 year or even 2 years or more) compared to the binding activity prior to storage.

Accordingly the present invention provides stable formulations of polypeptides comprising one or more single variable domains, wherein:
  less than 10% of the polypeptides forms dimers (e.g. as assessed by SE-HPLC) during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

at least 80% of the polypeptides retain its binding activity (e.g. as assessed by ELISA and/or BIACORE) to at least one (preferably to all) of its targets after storage at 37±5° C. up to 2 weeks (preferably at least 3 weeks, at least 5 weeks, at least 2 months, at least 6 months, at least 1 year, 1.5 year or even 2 years or more) compared to the binding activity prior to storage; and/or The present invention further provides methods for preparing the stable formulations of the invention. The methods of the invention may comprise the steps of concentrating a polypeptide comprising one or more single variable domains and exchanging it with the preferred buffer and/or excipient.

Also provided are containers, kits and pharmaceutical unit dosages comprising the formulations of the invention for use by, e.g., a healthcare professional. In specific embodiments, the kits or pharmaceutical unit dosages comprising the stable formulations of the invention are formulated for parenteral administration (e.g., intradermally, intramuscularly, intraperitoneally, intravenously and/or subcutaneously) of the polypeptide of the invention to a human subject. The formulations, containers, pharmaceutical unit dosages and/or kits can be used in prophylaxis and/or therapy. In a specific aspect, the formulations, containers, pharmaceutical unit dosages and/or kits are used for the prevention and/or treatment of one or more diseases and/or disorders such as vascular diseases and/or disorders (such as e.g. acute coronary syndrome (ACS), myocardial infarction, thrombotic thrombocytopenic purpura (TTP) or Moschcowitz syndrome, vascular surgery, stroke), bone diseases and/or disorders (such as e.g. osteoporosis, cancer-related bone diseases, and/or bone loss associated with autoimmunity and/or viral infection) or autoimmune diseases (such as e.g. rheumatoid arthritis).

FIGURE LEGENDS

Figure 1:
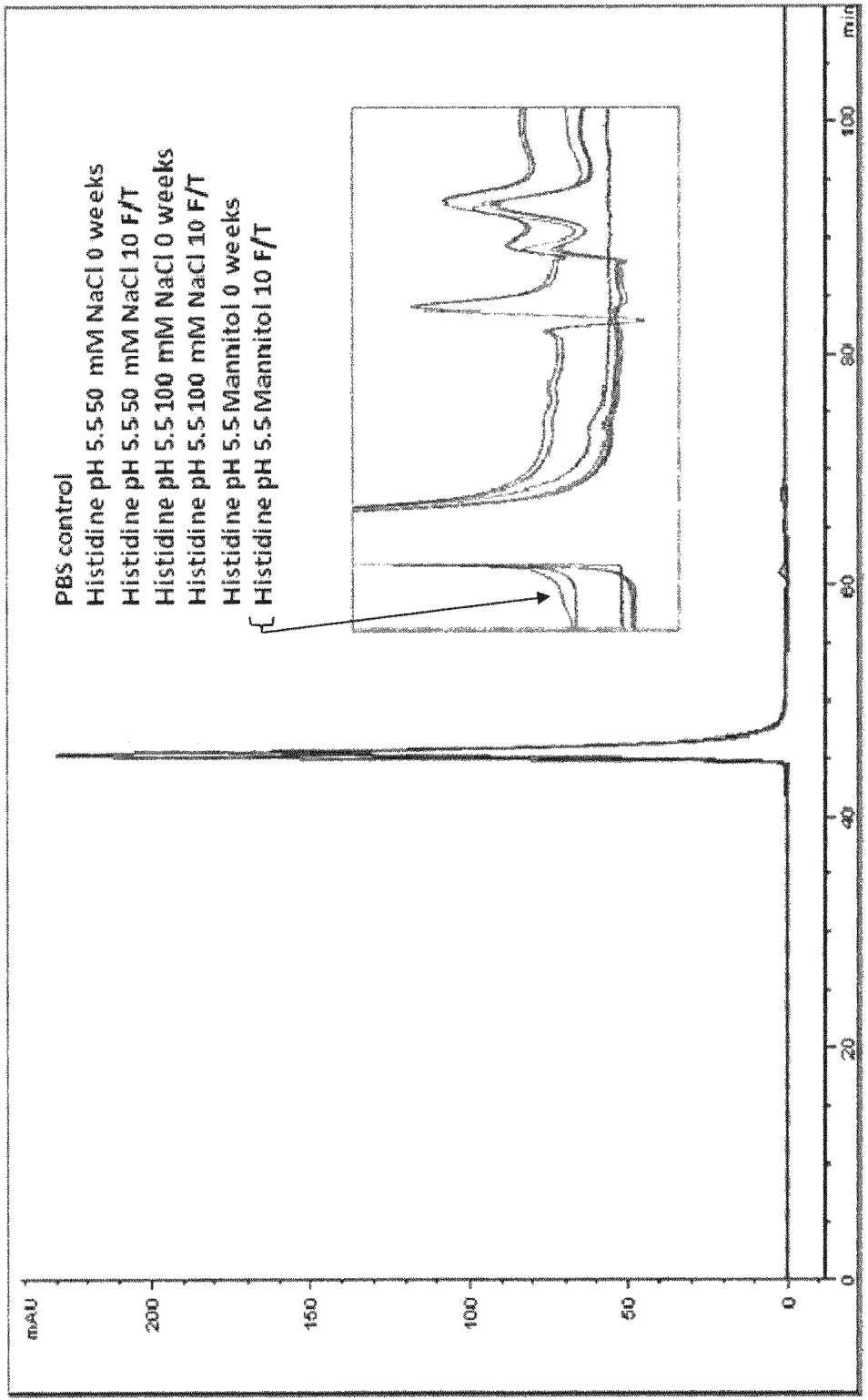

FIG. 1. The 280 nm SE-HPLC chromatograms of RANKL008a formulated in phosphate (A), or histidine (B) buffers with either 50 mM NaCl, 100 mM NaCl or 10% mannitol, before and after 10 freeze/thaw cycles. A zoom on the main peak is shown as inset.

Figure 2:
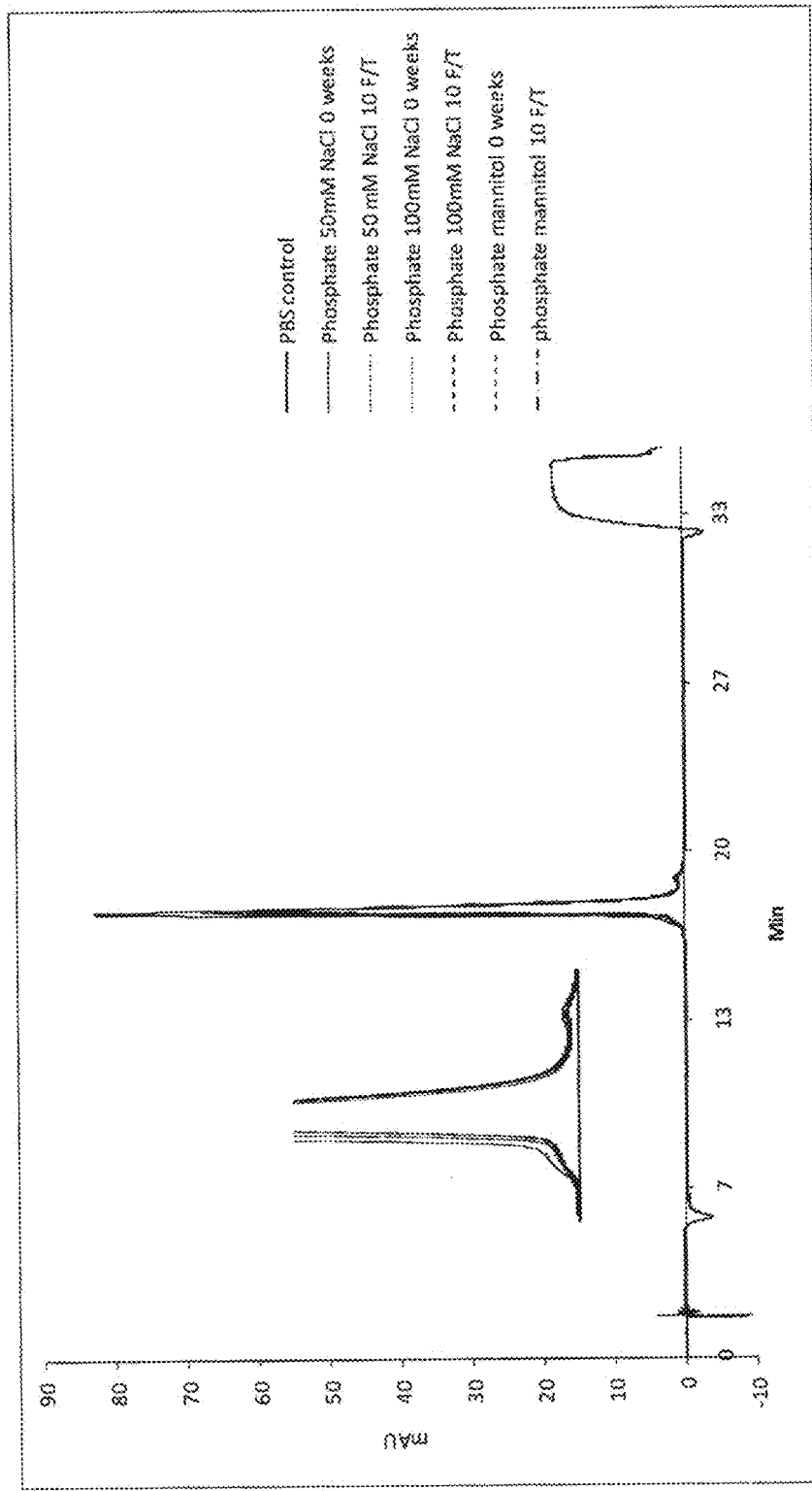

FIG. 2. The 280 nm RP-HPLC chromatograms of RANKL008a formulated in phosphate buffers with either 50 mM NaCl, 100 mM NaCl or 10% mannitol, before and after 10 freeze/thaw cycles. A zoom on the main peak is shown as inset.

Figure 3:
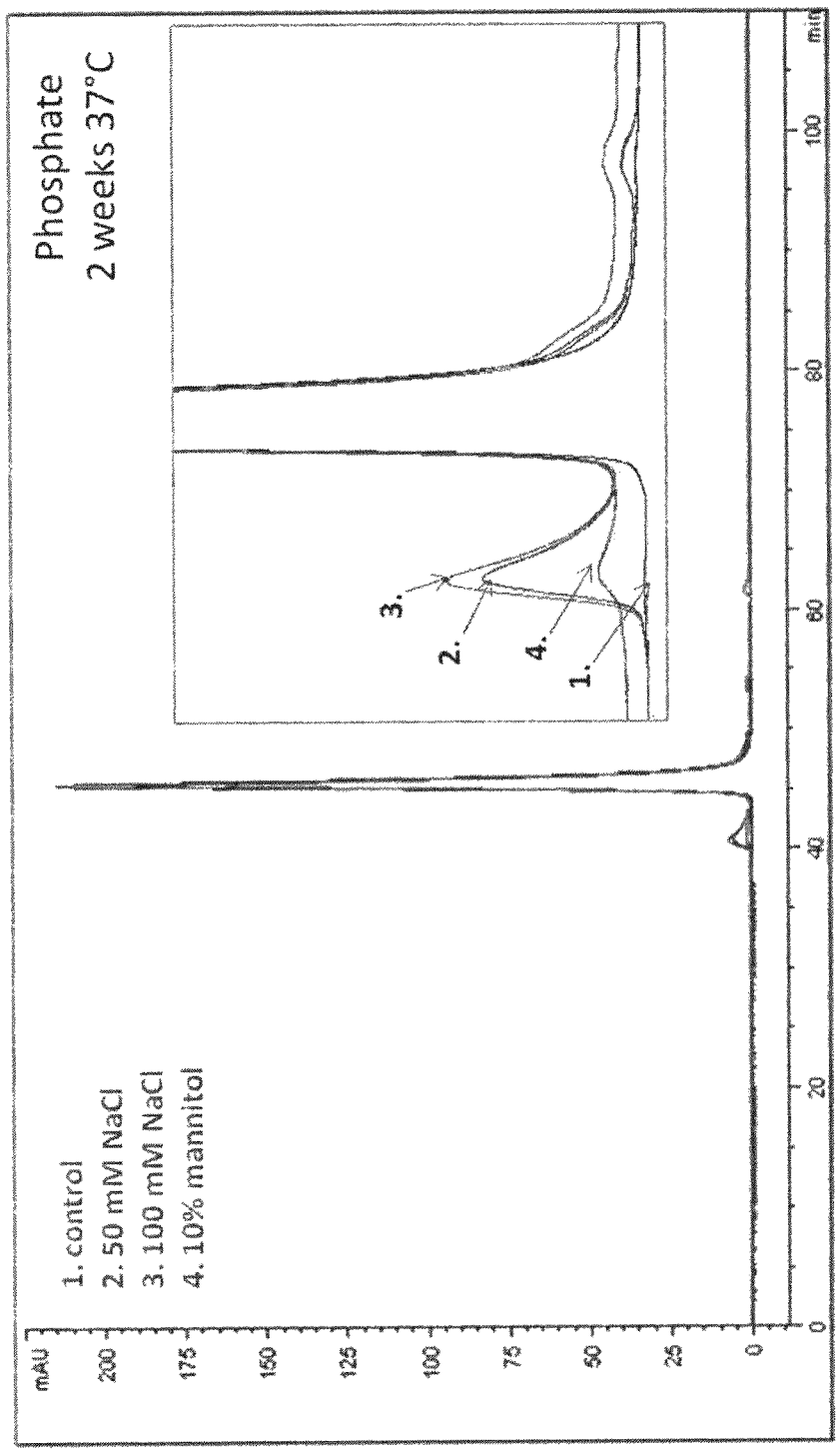

FIG. 3. The 280 nm SE-HPLC chromatograms of RANKL008a formulated in phosphate buffer with either 50 mM NaCl, 100 mM NaCl or 10% mannitol, after incubation for 2 weeks at 37° C. A zoom on the main peak is shown as inset.

Figure 4:
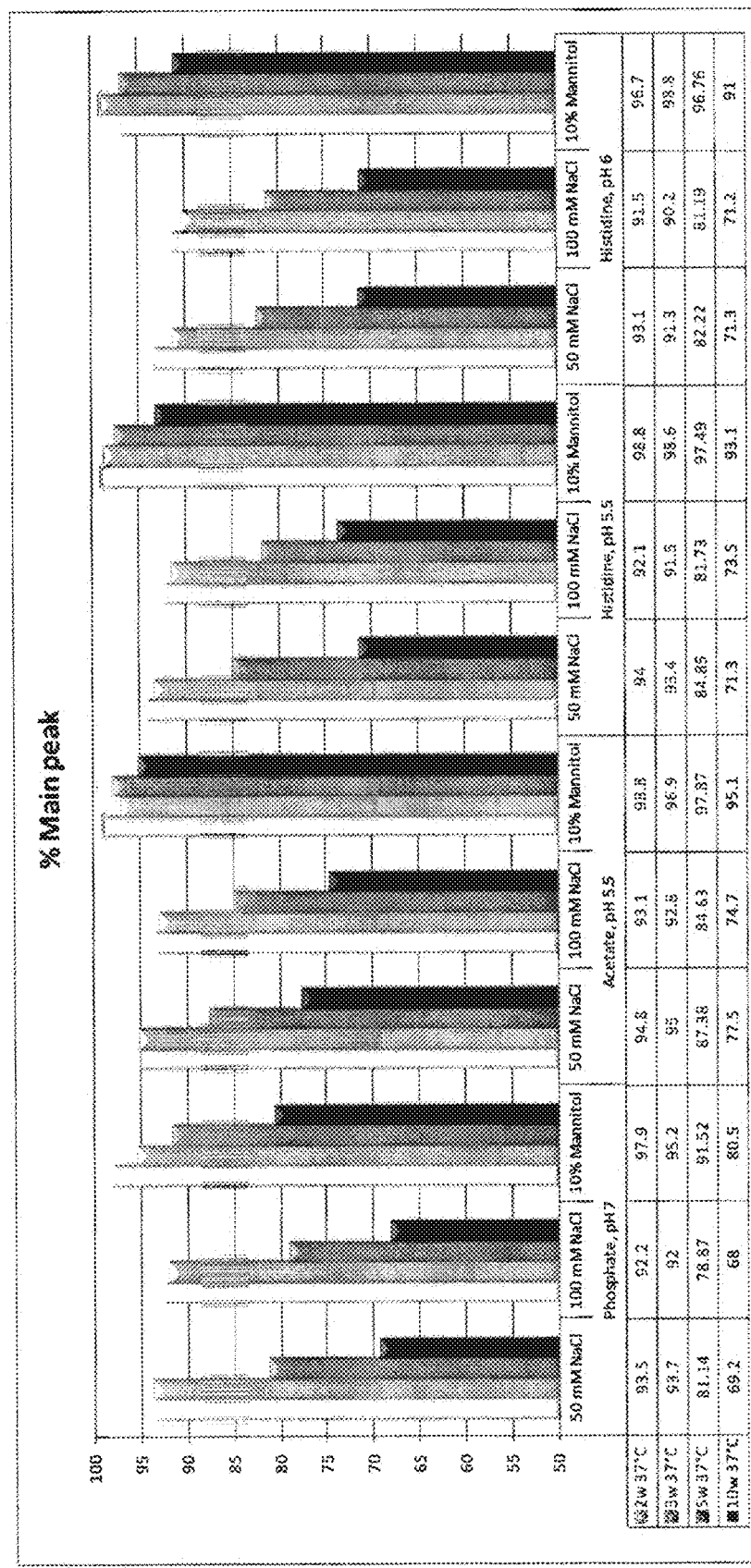

FIG. 4. Figure demonstrating the time-dependent decrease (A) and increase (B) of the surface area of, respectively, the main peak (A) and % dimers (B) observed in SE-HPLC analysis of RANKL008a formulated in different buffers and stored up to 10 weeks at 37° C.

FIG. 5. The 280 nm RP-HPLC chromatograms of RANKL008a formulated in phosphate buffer with either 50 mM NaCl, 100 mM NaCl or 10% mannitol, after incubation for 2 weeks at 37° C. A zoom on the main peak is shown as inset.

Figure 6:
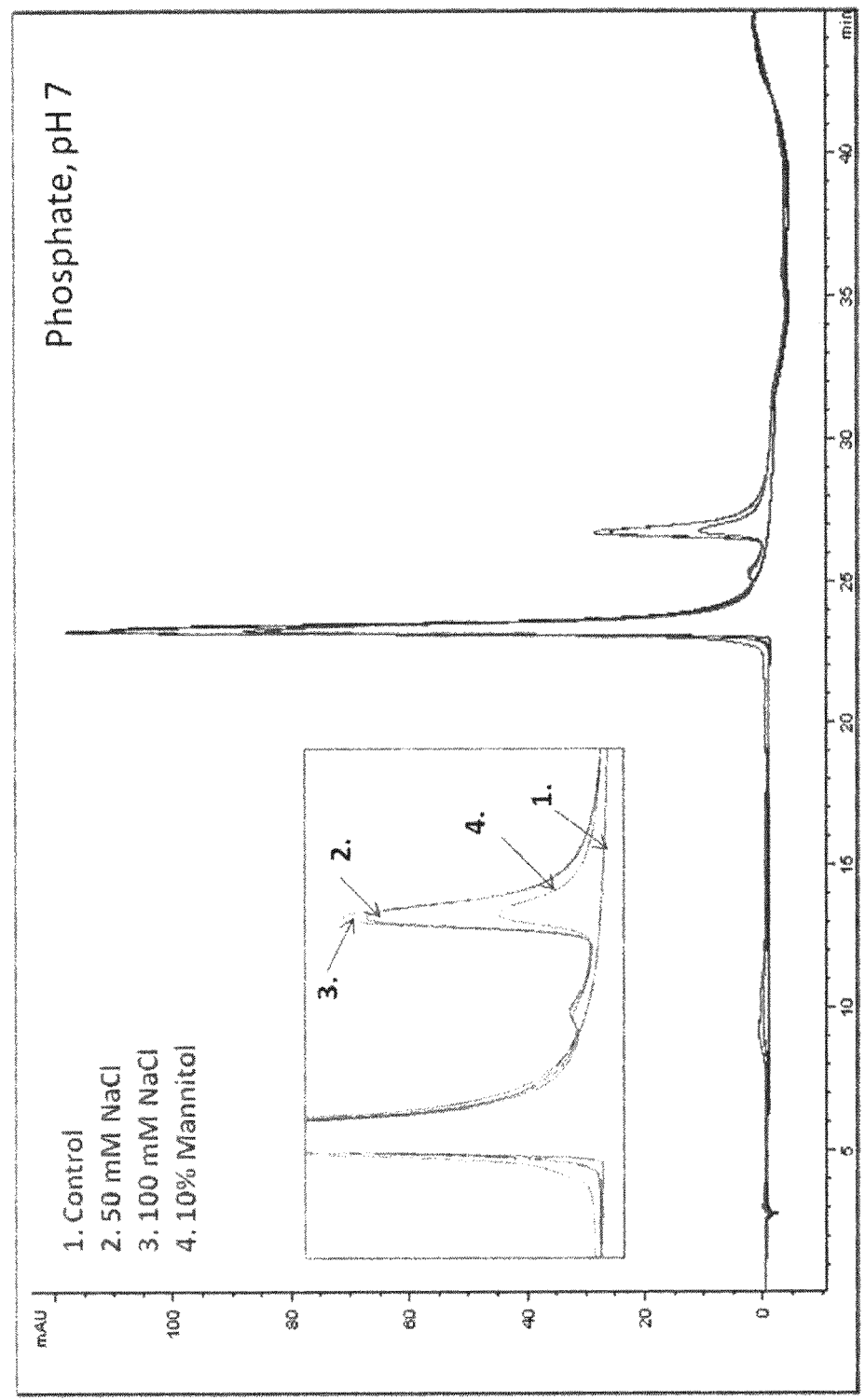

FIG. 6. Overlay of the 280 nm IEX-HPLC chromatograms of RANKL008a formulated in phosphate buffer with either 50 mM NaCl, 100 mM NaCl or 10% mannitol, after incubation for 2 weeks at 37° C. A zoom on the main peak and postpeaks is shown as inset.

Figure 7:
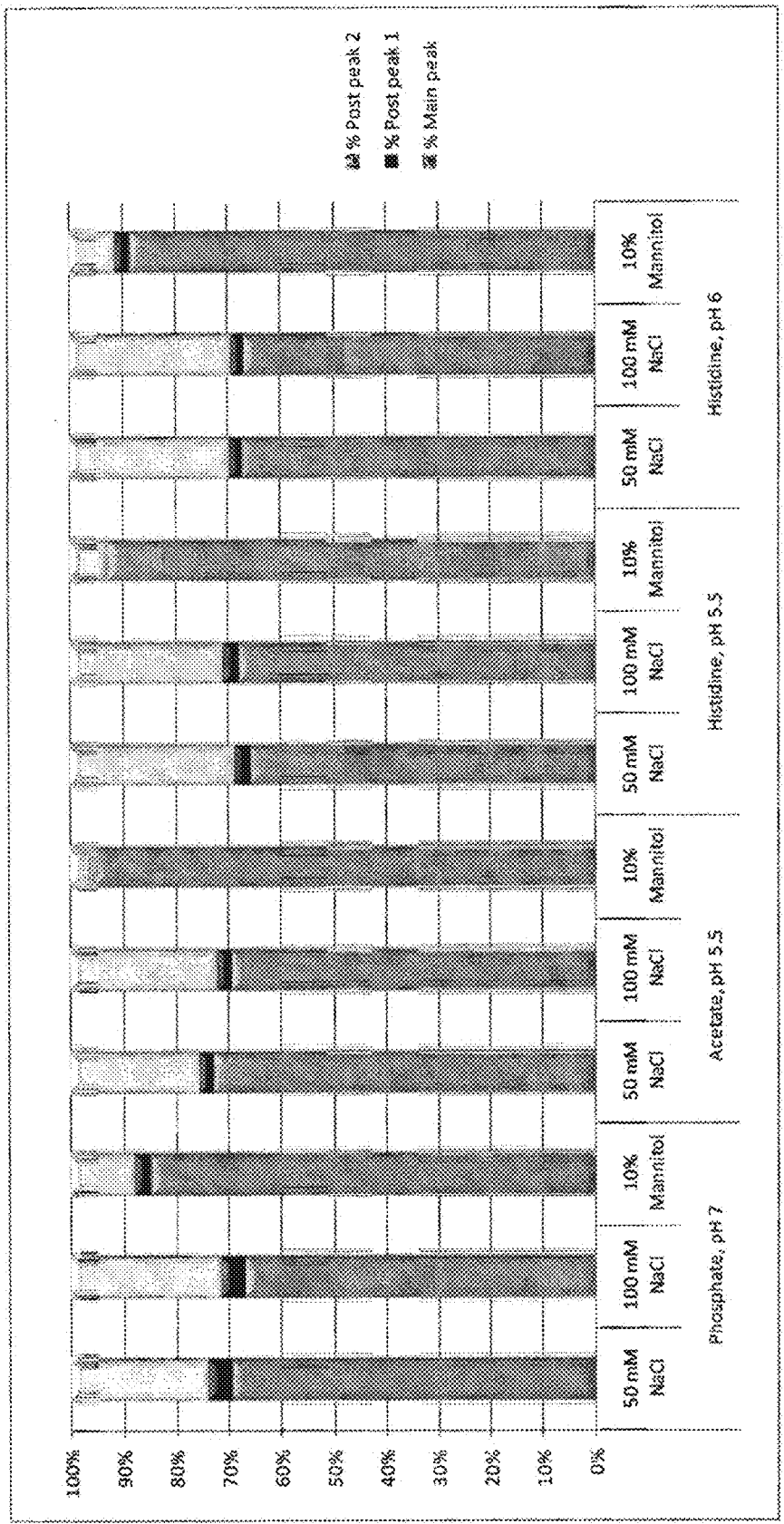

FIG. 7. Relative amounts (%) of the main peak and the two postpeaks observed in the IEX-HPLC chromatograms of the stability samples after storage for 10 weeks at 37° C.

Figure 8:
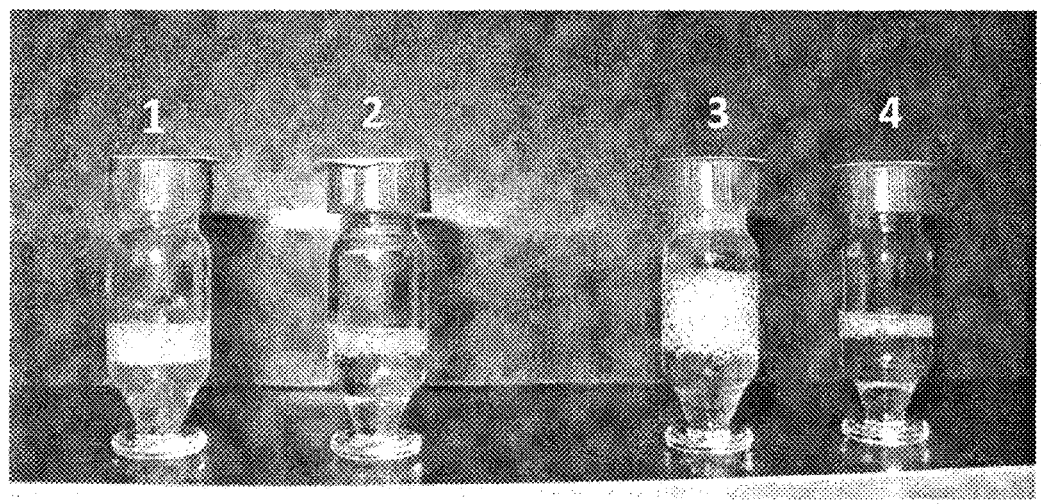

FIG. 8. Picture and visual observation of the vials after shaking. The RANKL008a sample, diluted (to 5 mg/mL) and undiluted with or without 0.01% TWEEN (polysorbate) 80 was shaken strongly (10 s-1 min).

Figure 9:
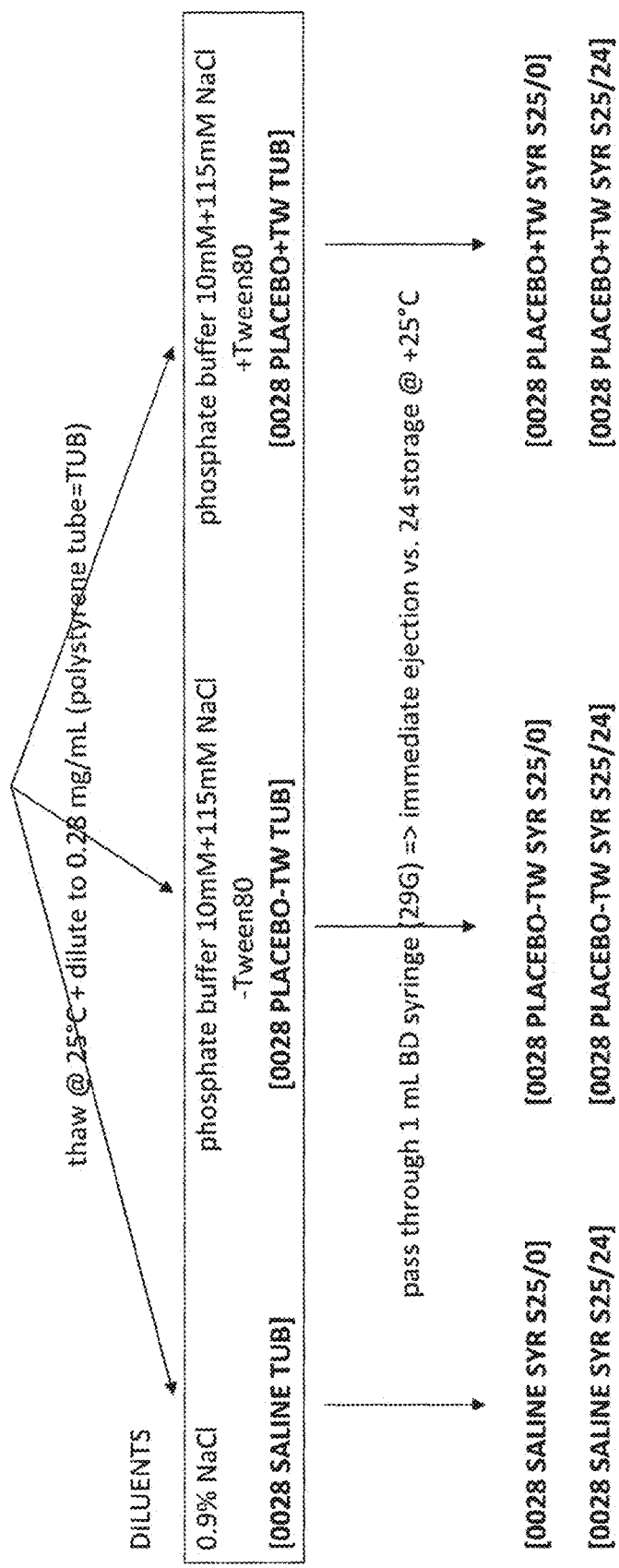

FIG. 9. Overview of dilutions and steps made in syringeability study as described in Example 1.6.

Figure 10:
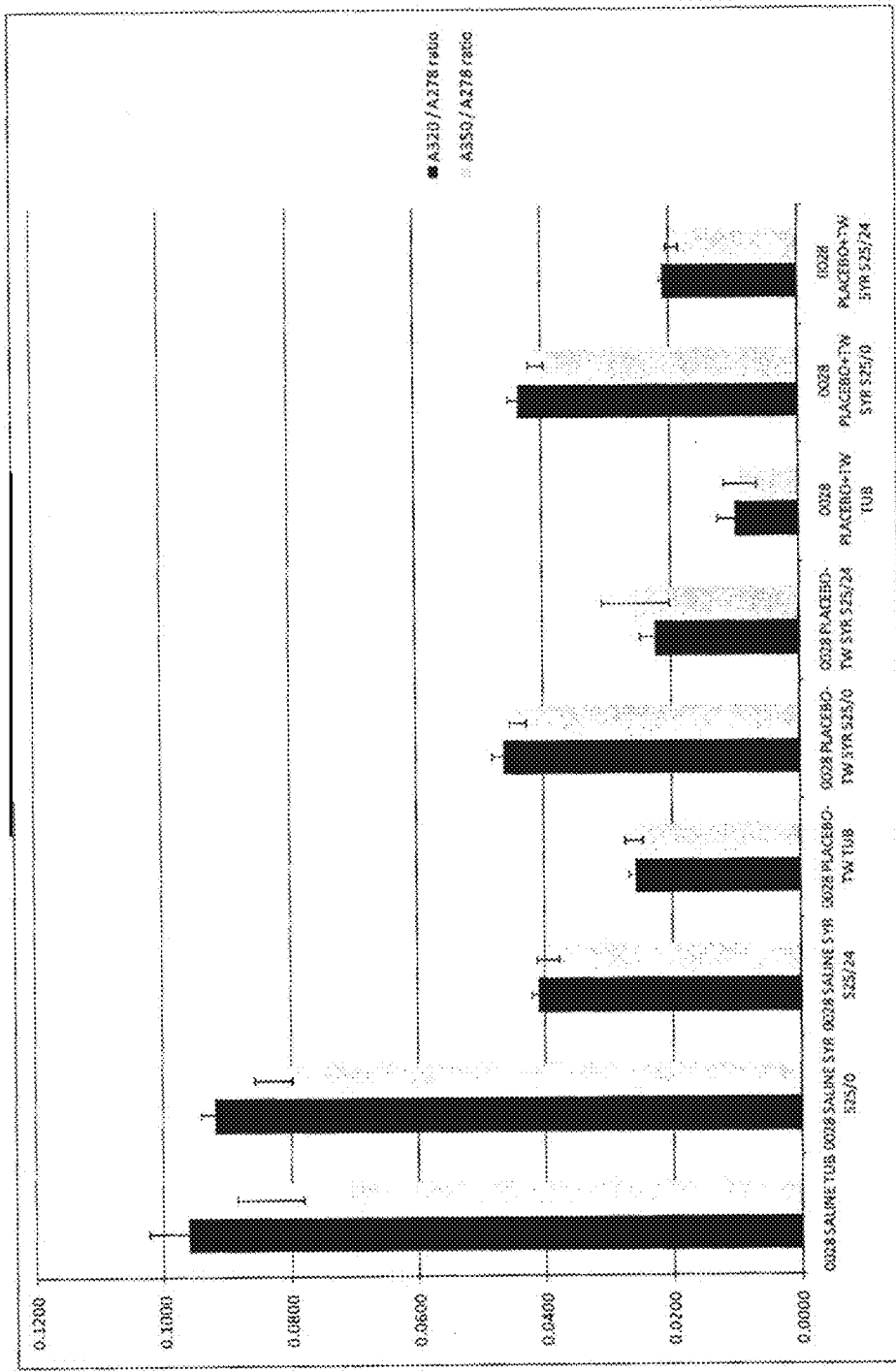

FIG. 10. OD 320/278 and OD 350/278 ratios (n=3) after passage/storage of RANKL008a in syringes with different diluents as described in Example 1.6.

Figure 11:
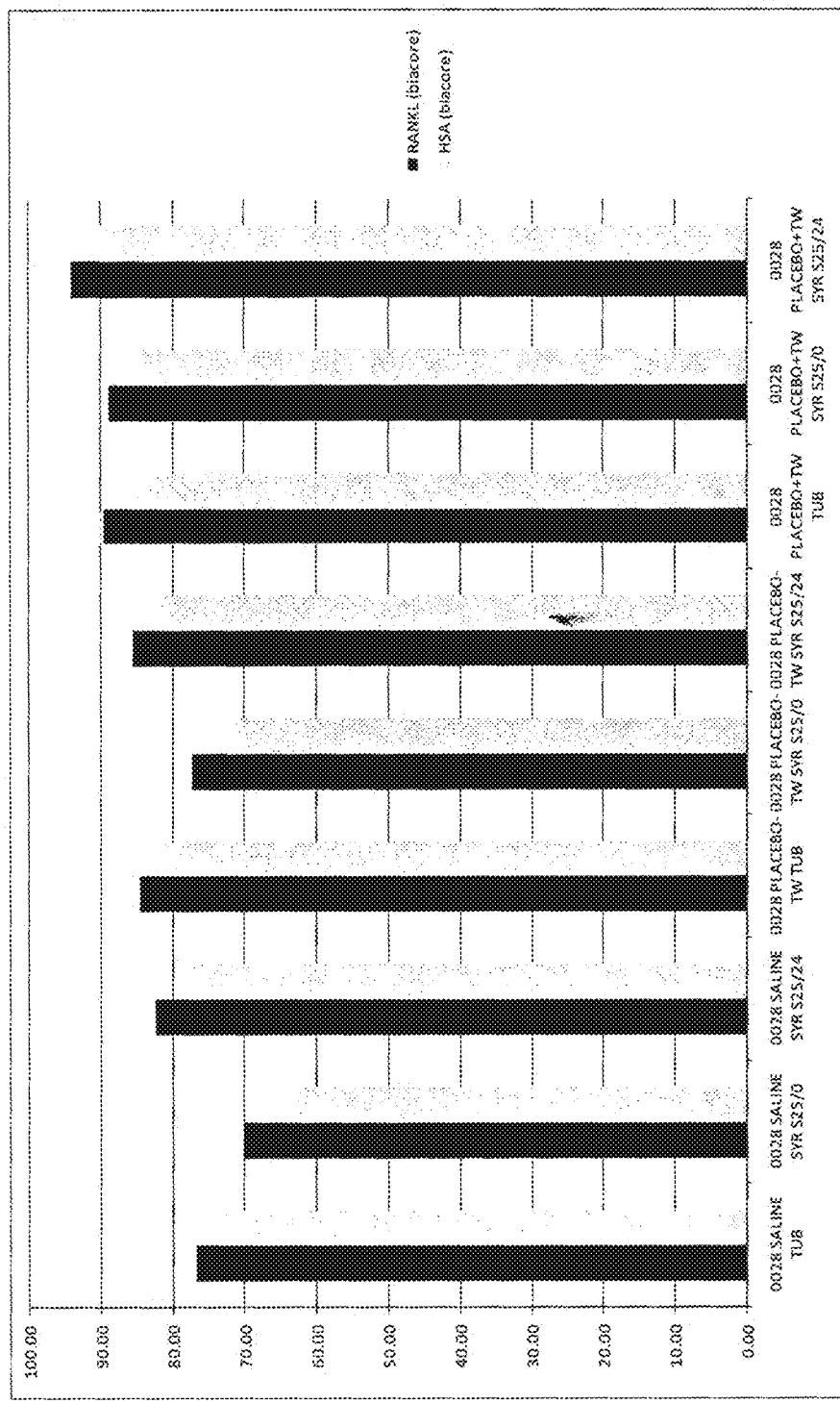

FIG. 11. Relative HSA and RANKL potency of RANKL008a after dilution in different diluents and passage/storage in syringes as described in Example 1.6.

Figure 12:
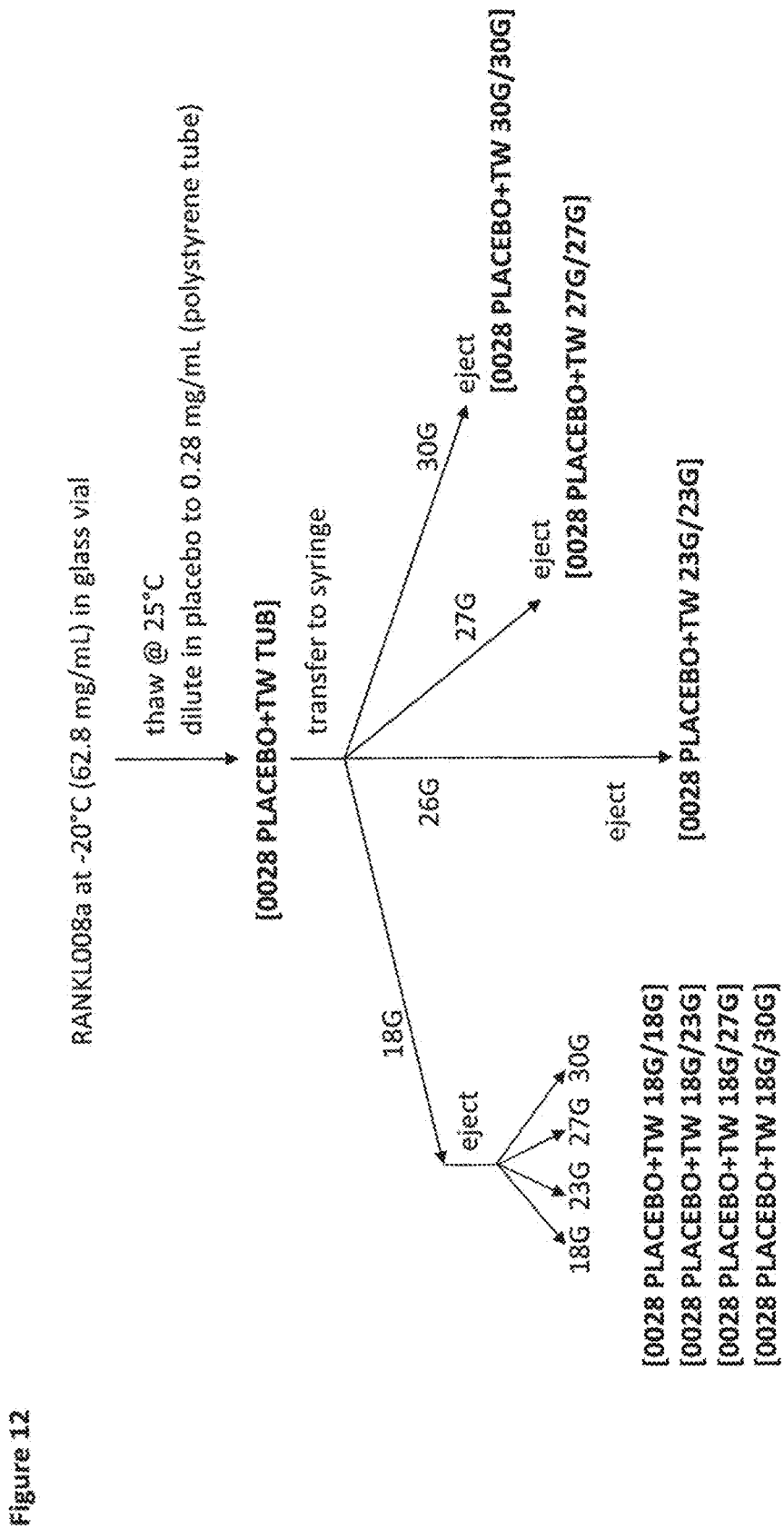

FIG. 12. Overview of needle/gauge size study with diluted RANKL008a as described in Example 1.7.

Figure 13:
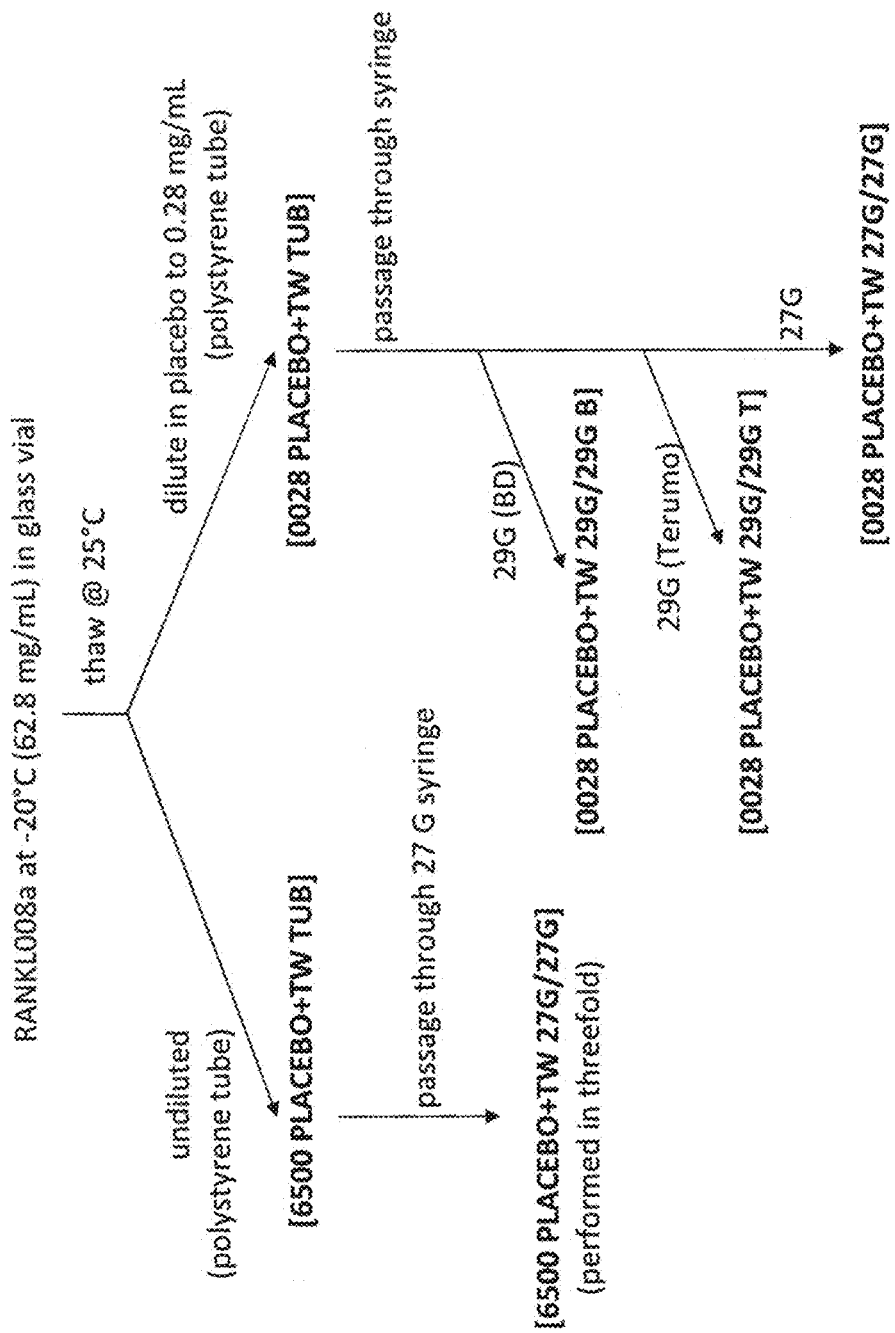

FIG. 13. Overview of further needle/gauge size study with diluted and undiluted RANKL008a as described in Example 1.7.

Figure 14:
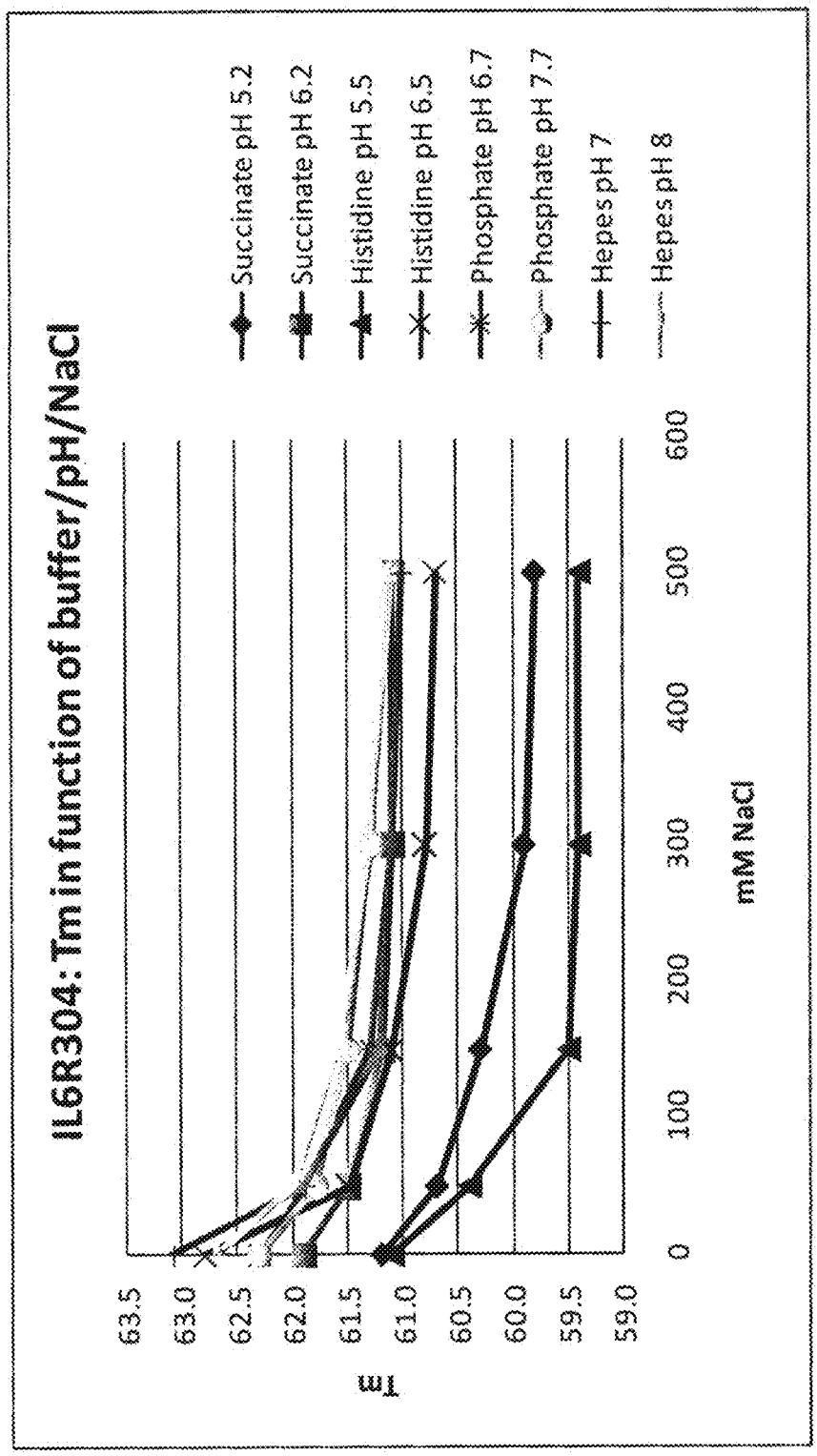
Figure 14:
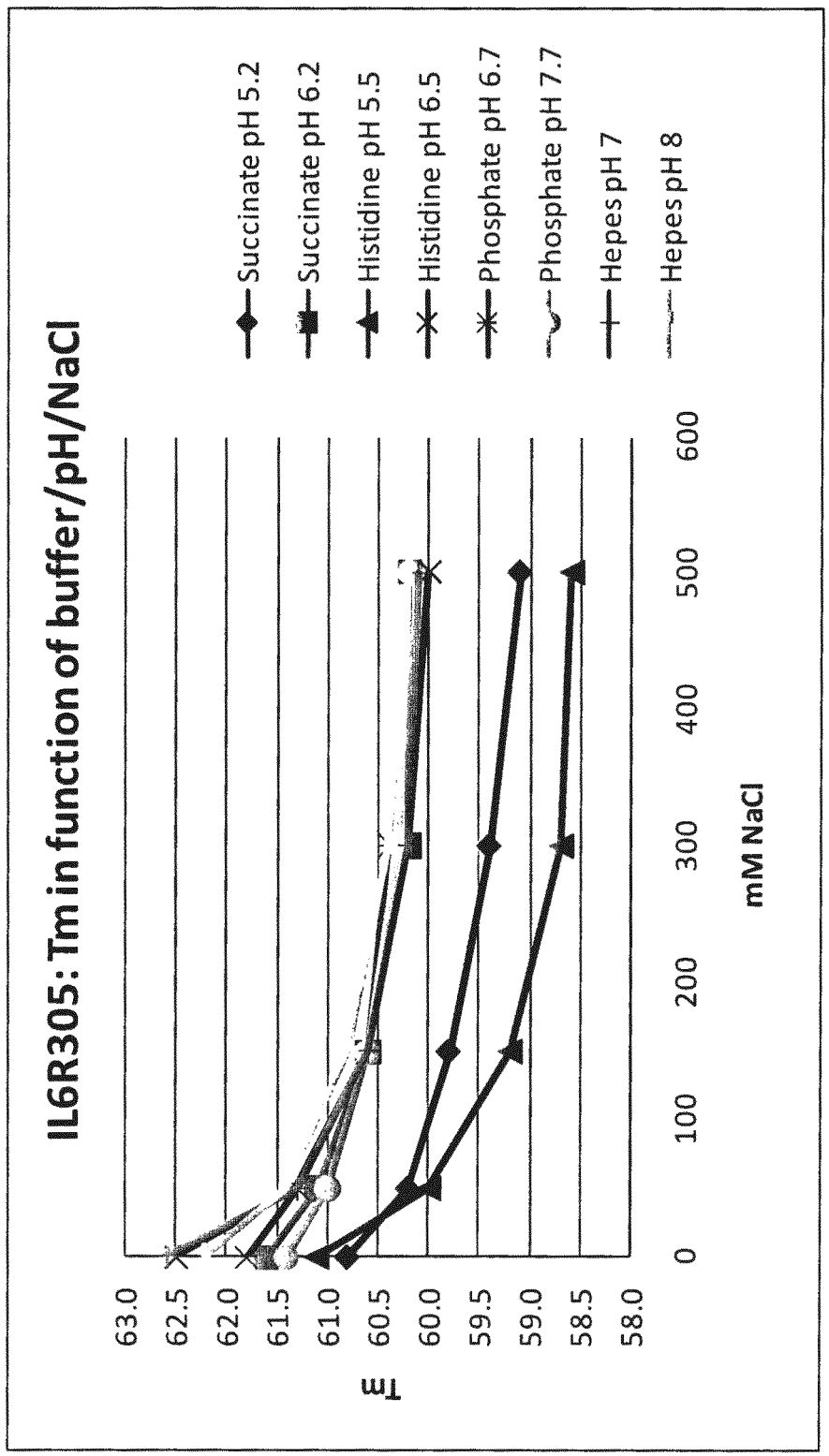
Figure 14:
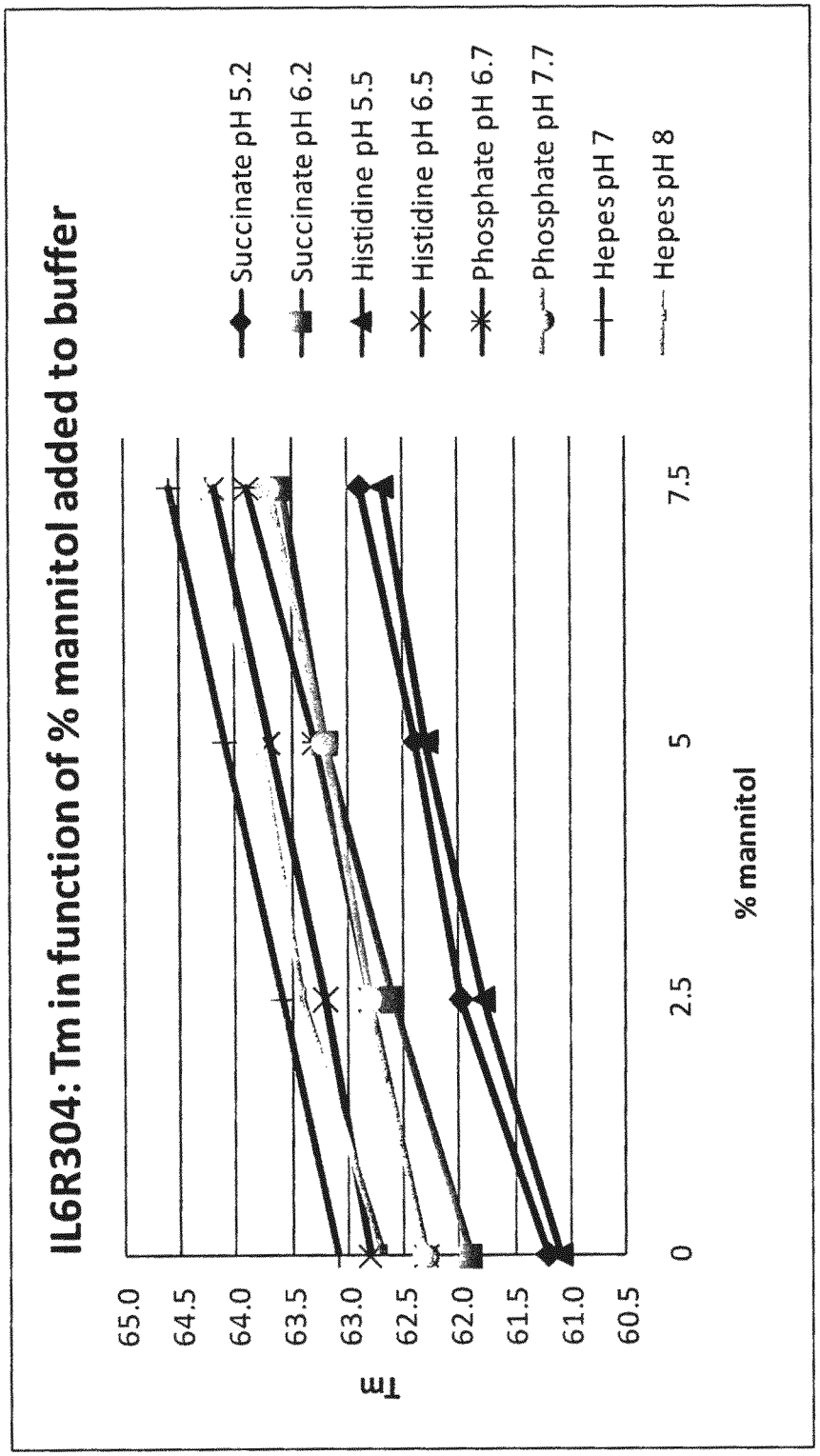
Figure 14:
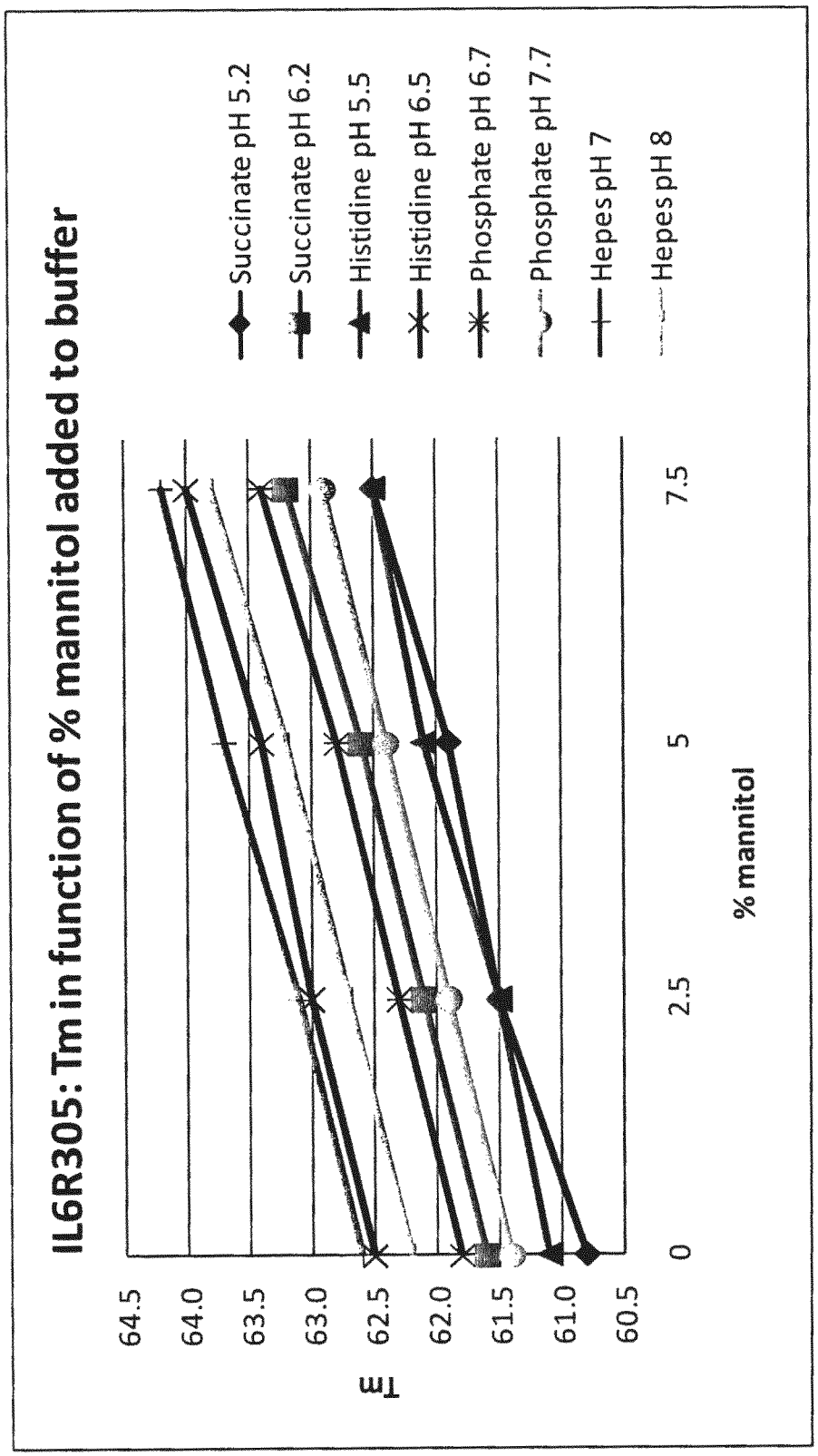
Figure 14:
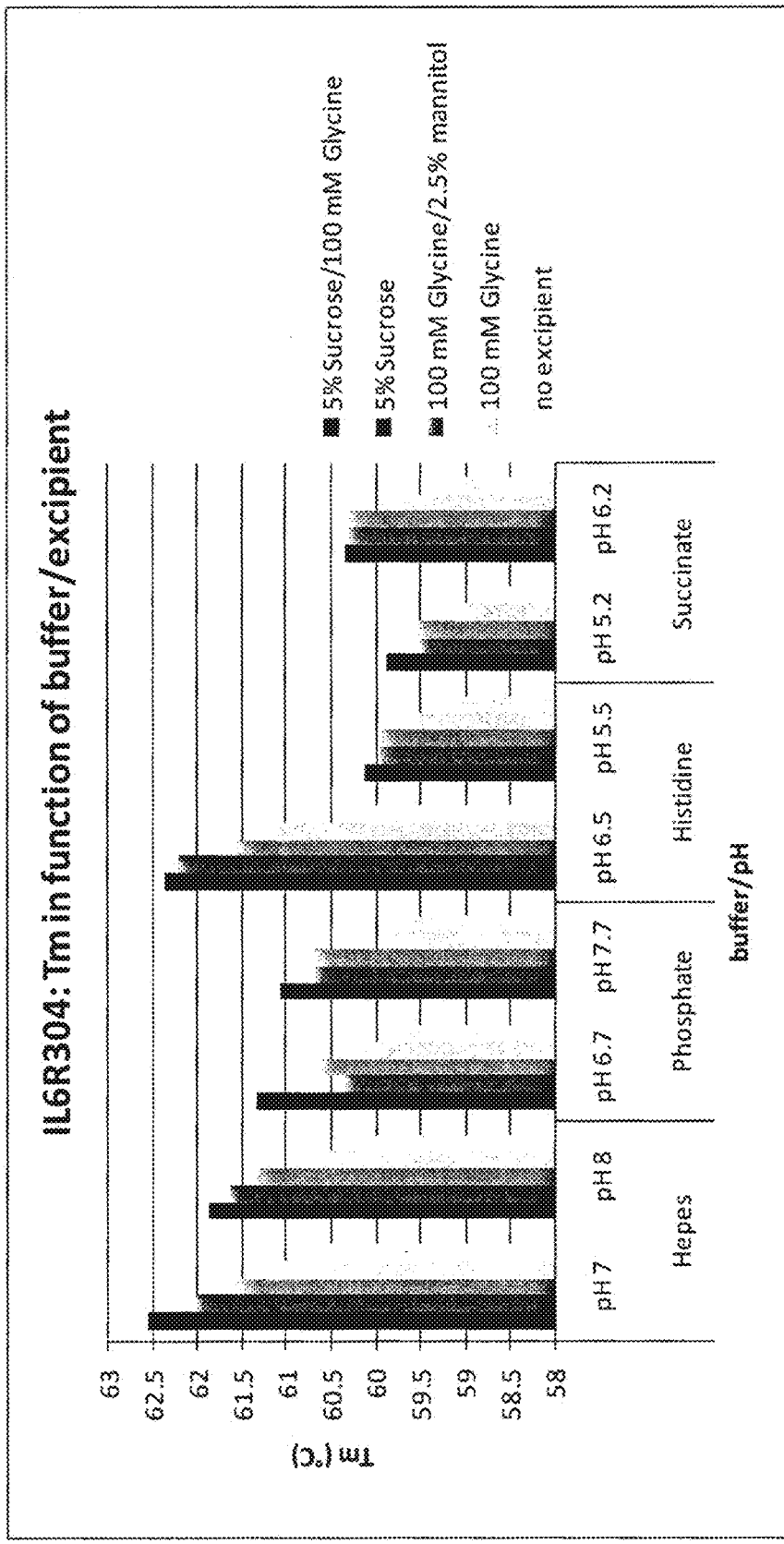

FIG. 14. Overview of the results obtained for thermal stability testing of IL6R304 (A, C, E) and IL6R305 (B, D, F) and in function of NaCl concentration (A, B), mannitol added (C, D) and buffer/excipient (E, F).

Figure 15:
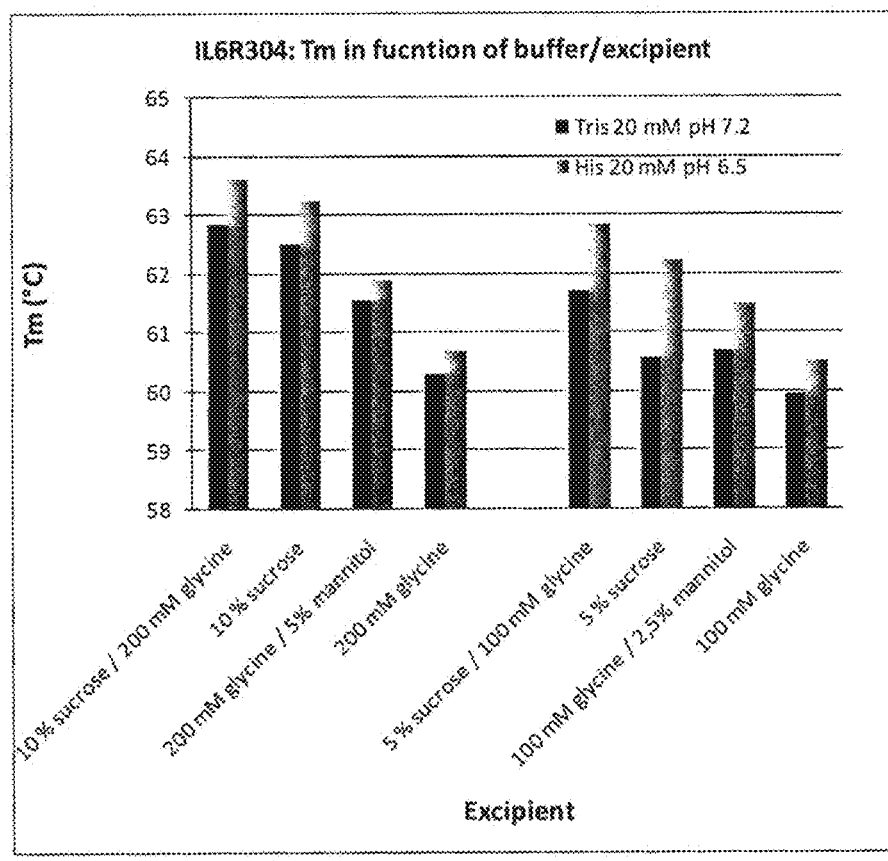
Figure 15:
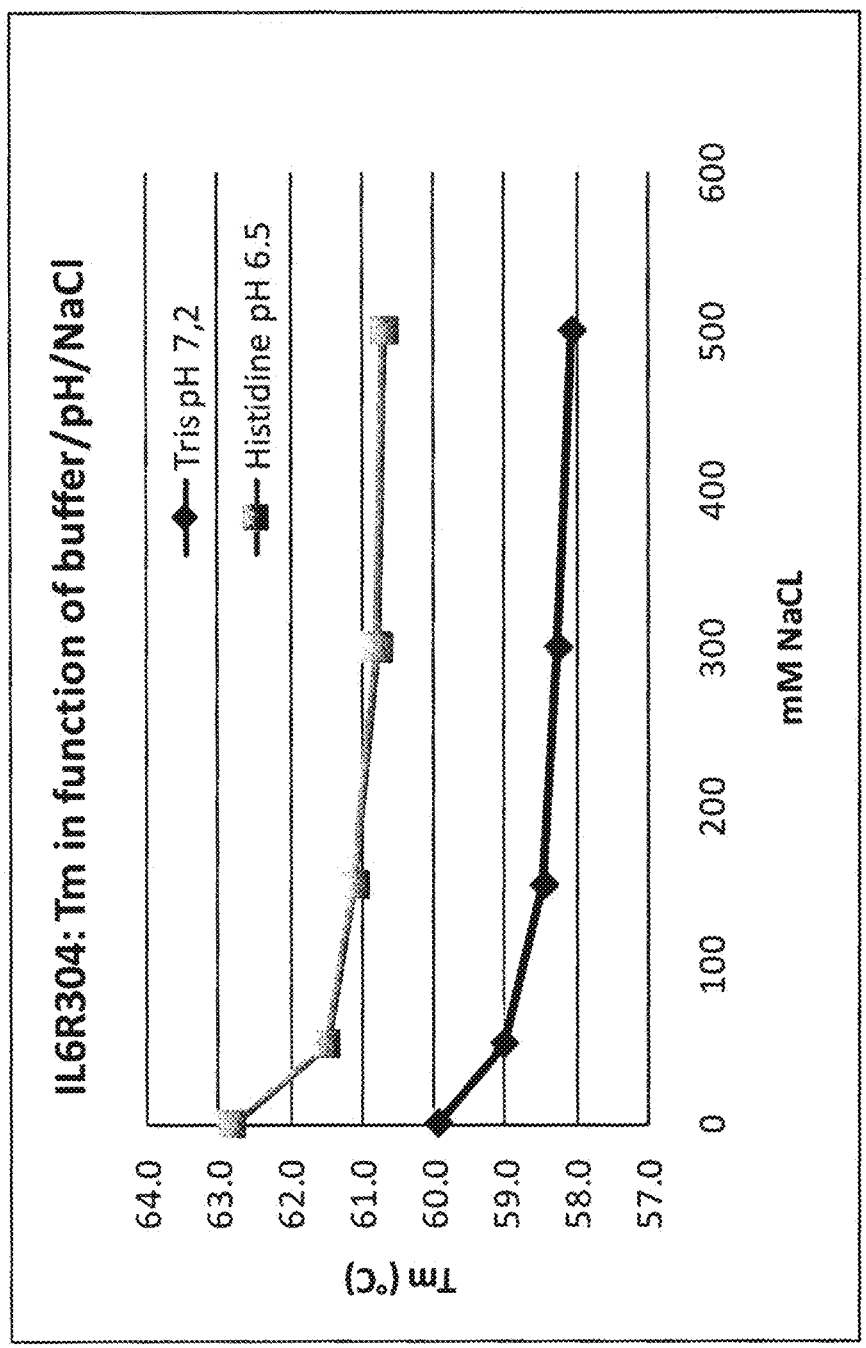
Figure 15:
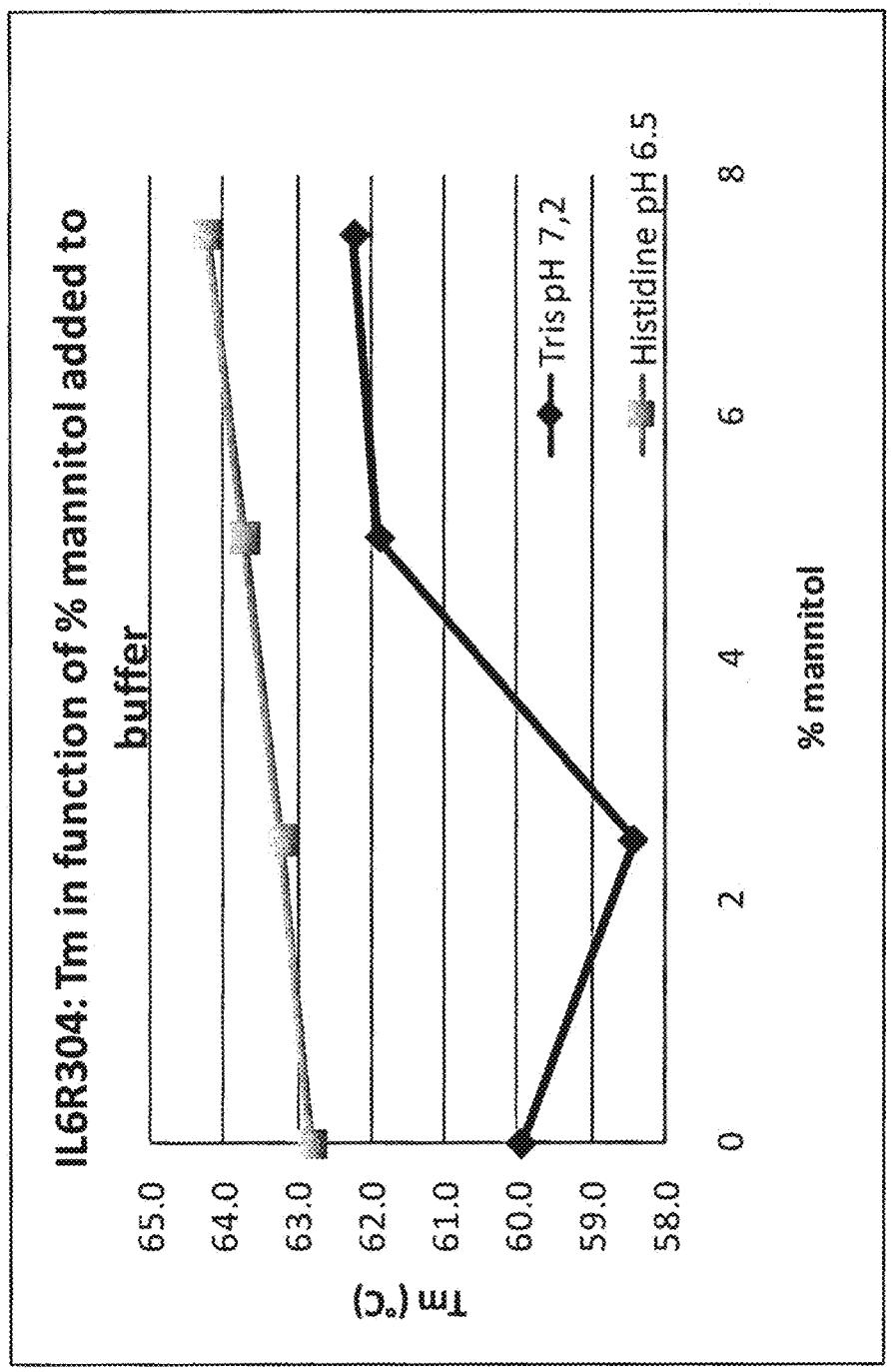

FIG. 15. Overview of the results obtained in thermal stability testing of IL6R304 in Tris buffer pH 7.2 or Histidine pH 6.5, with sucrose, glycine or mannitol added as excipient.

Figure 16:
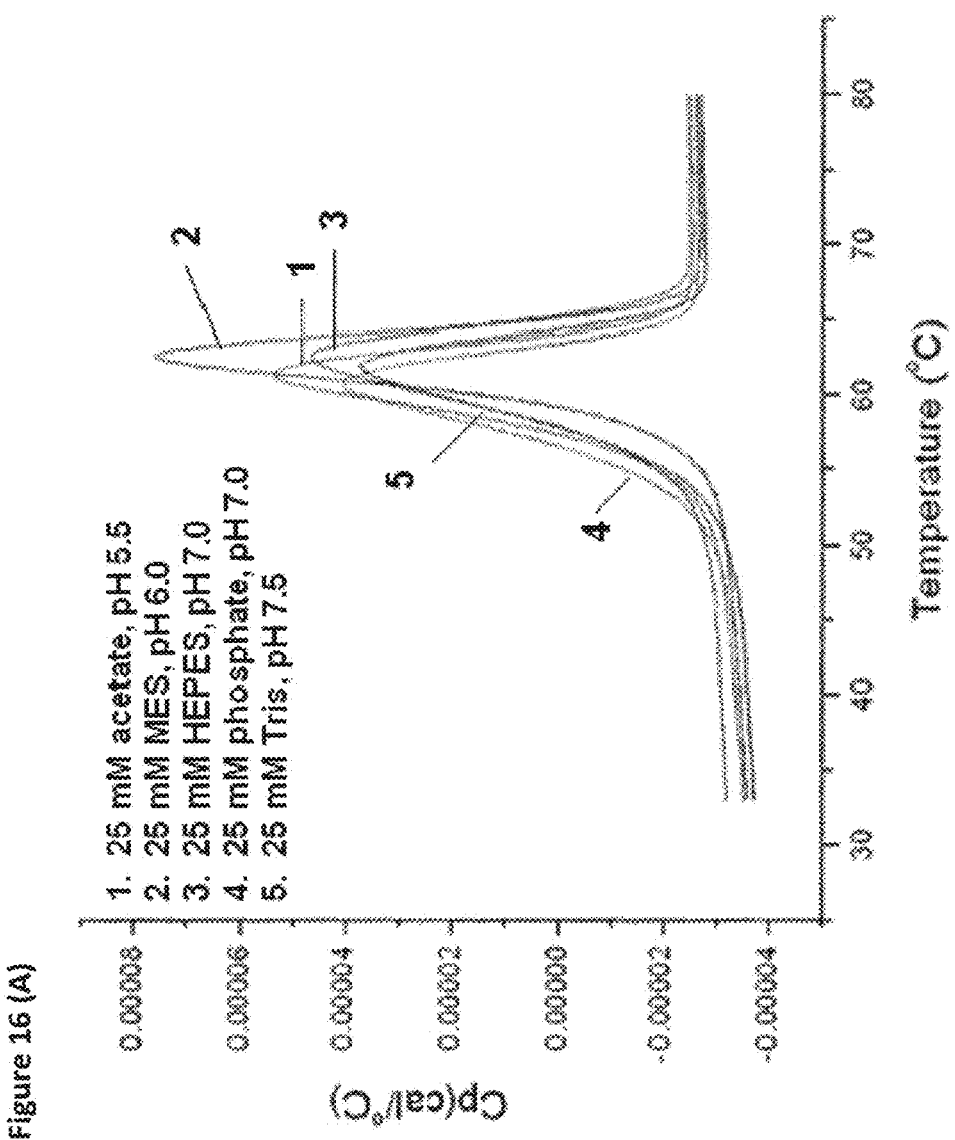
Figure 16:
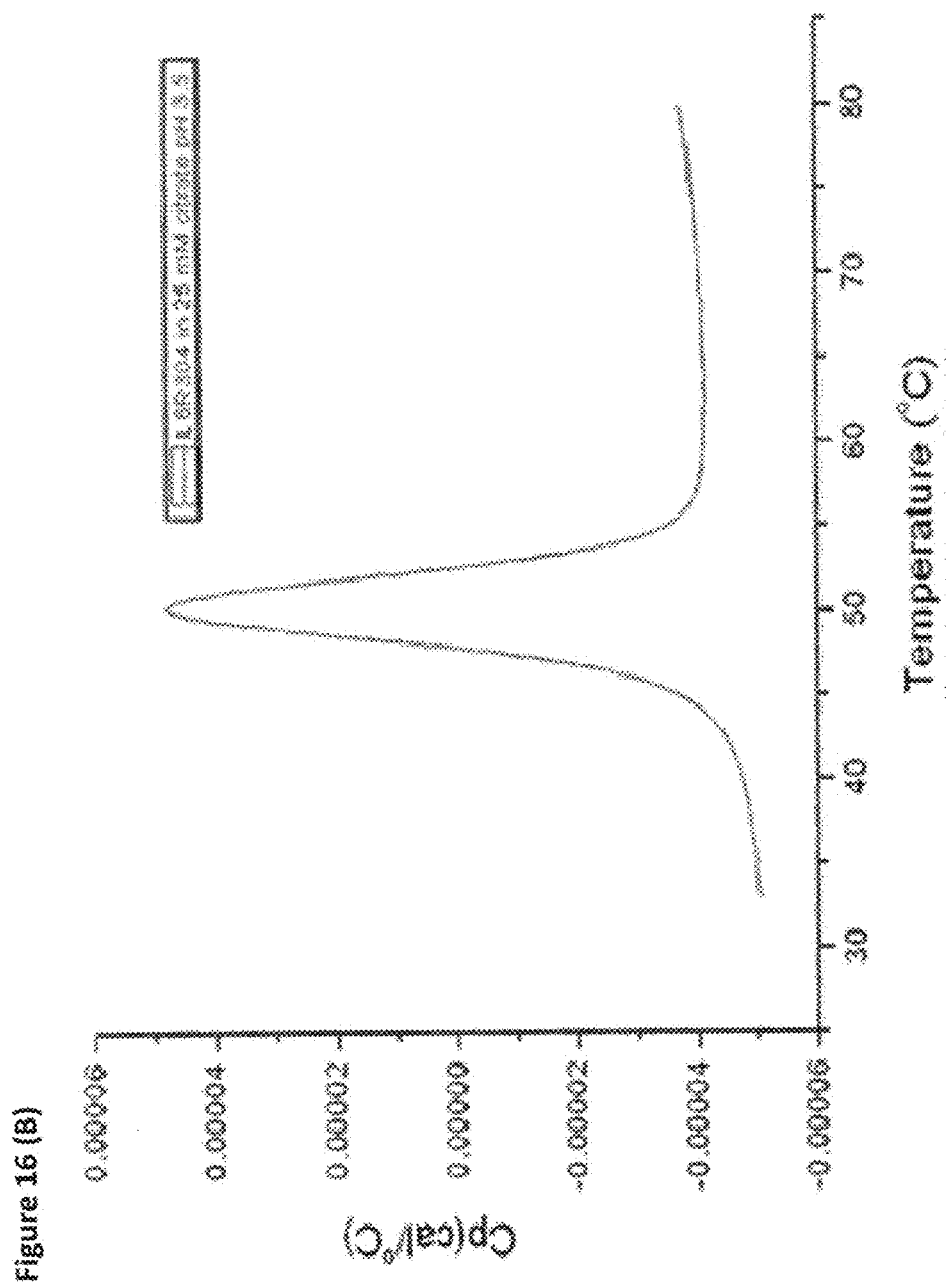

FIG. 16. Thermograms (obtained after subtracting the base-lines) of IL6R304 in the buffers as indicated in the graph.

Figure 17:
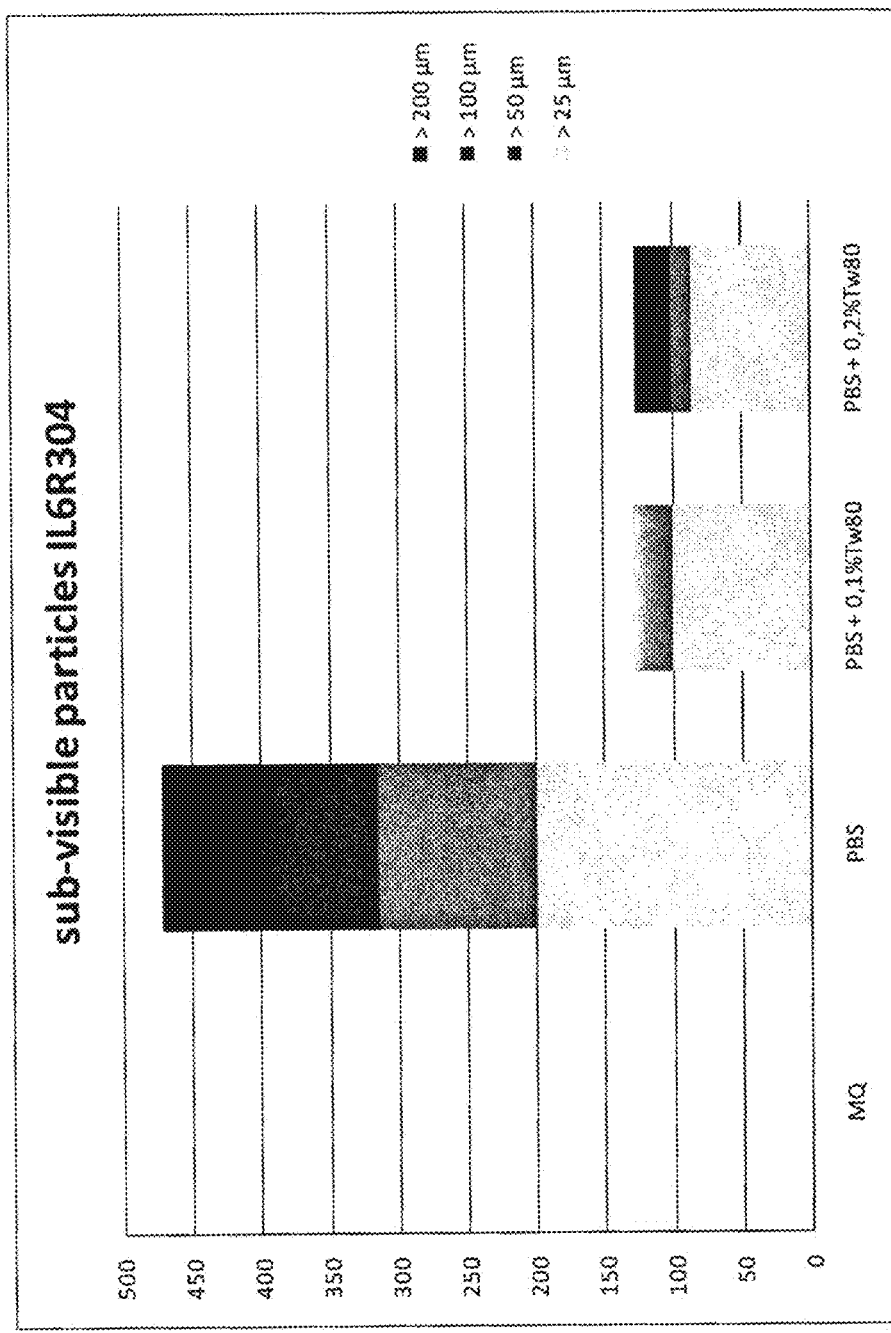
Figure 17:
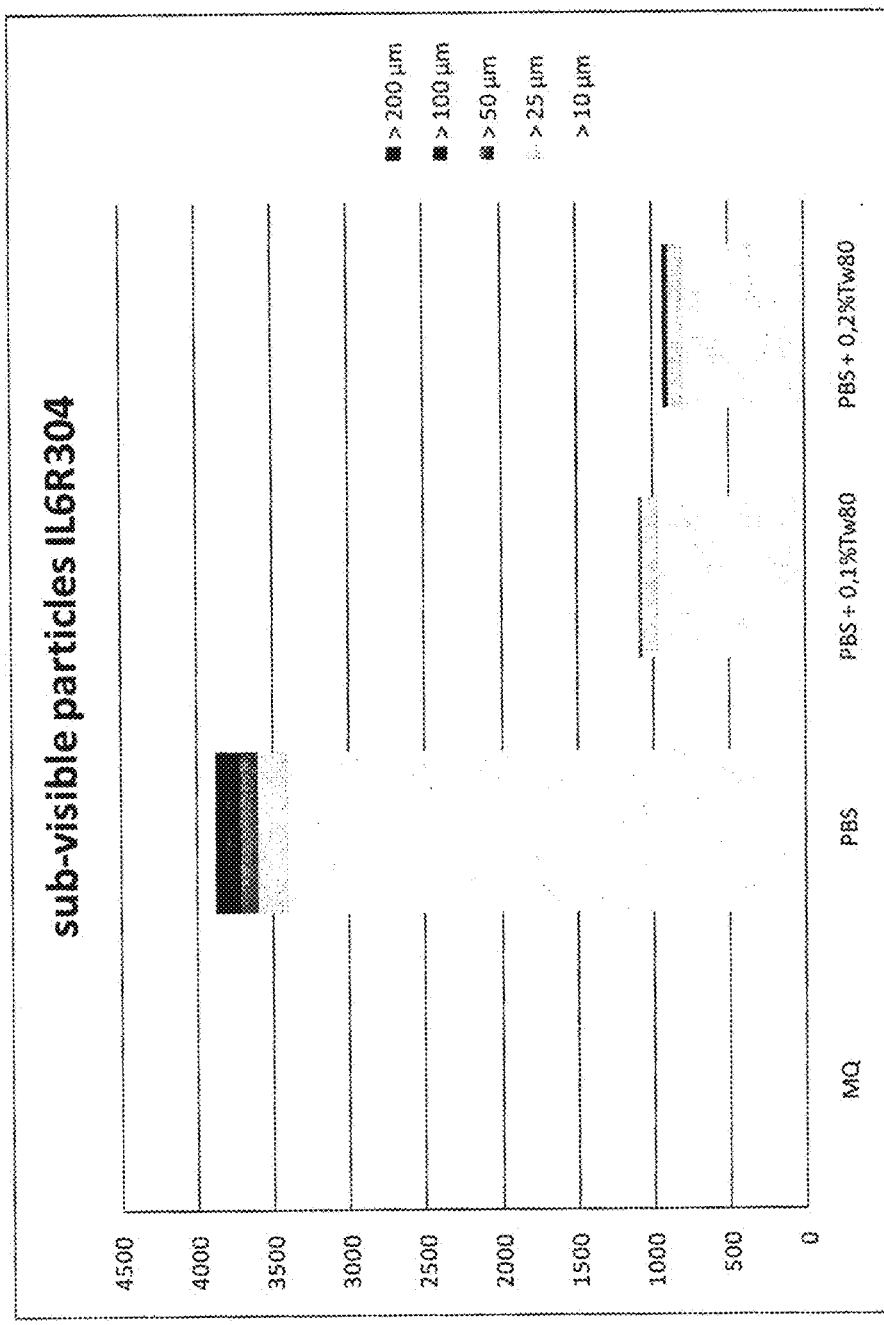

FIG. 17. PAMAS analysis of IL6R304 formulated in PBS compared to IL6R304 formulated in PBS+0.01% or 0.02% TWEEN (polysorbate) 80. Counts of particles: >10 μm, >25 μm, >50 μm, >100 μm and >200 μm.

Figure 18:
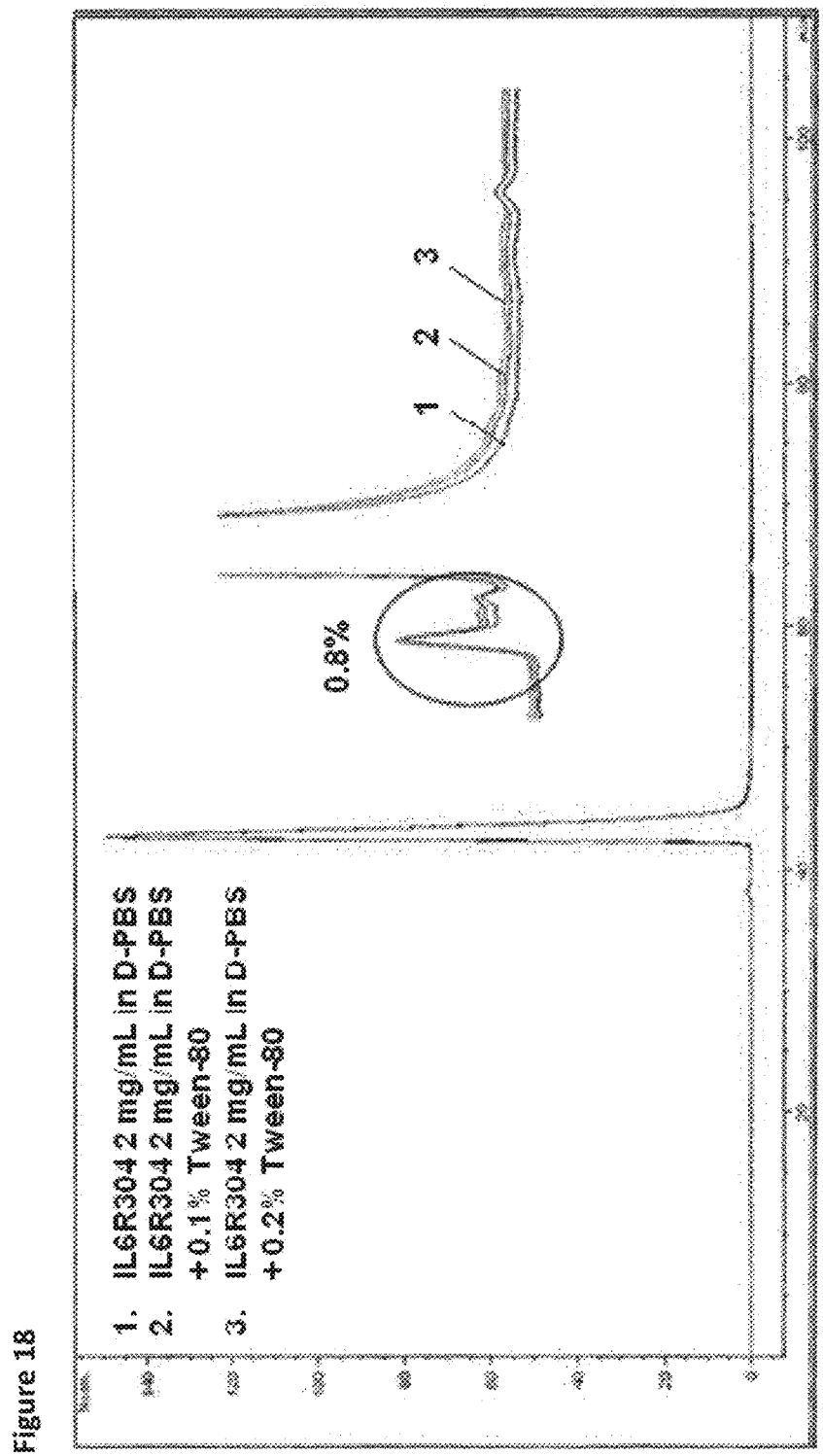

FIG. 18. SE-HPLC for the IL6R304 molecule in the presence of different concentrations of TWEEN (polysorbate) 80.

Figure 19:
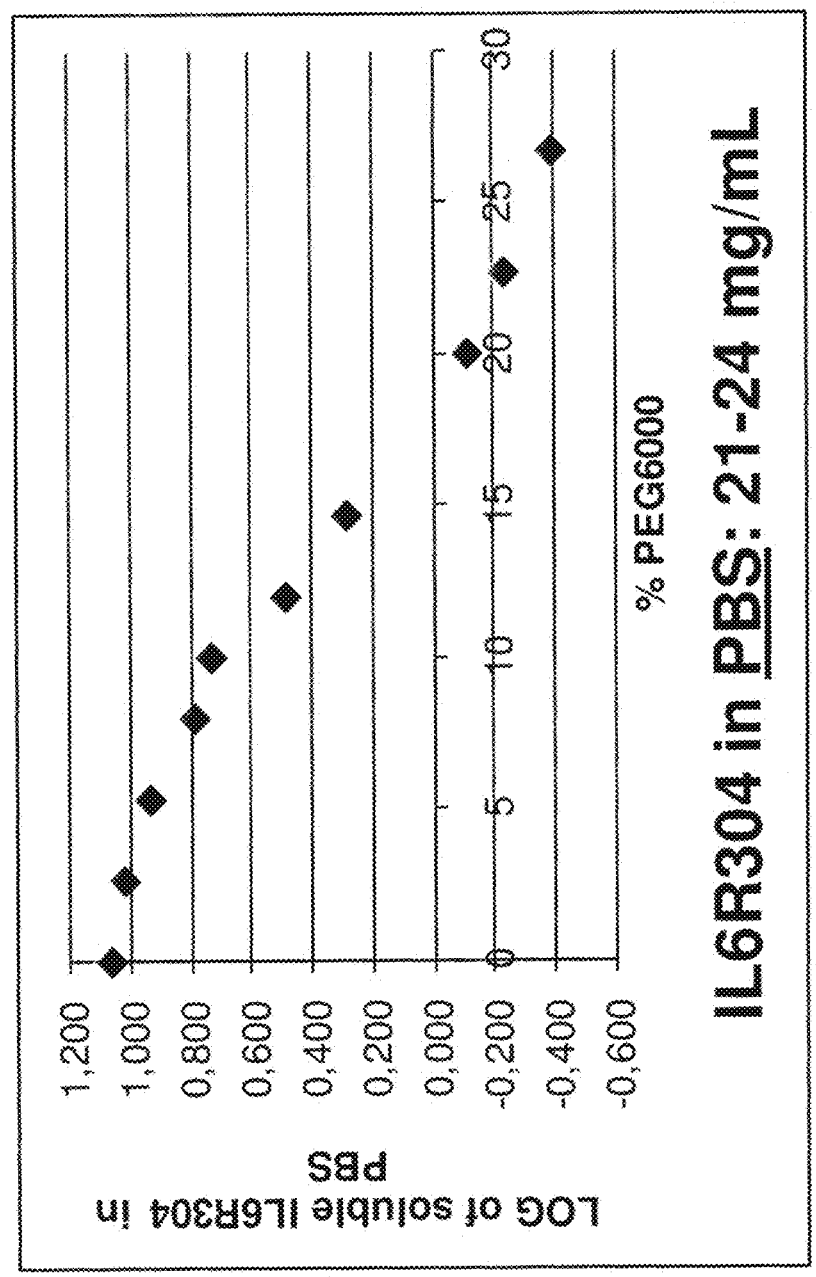
Figure 19:
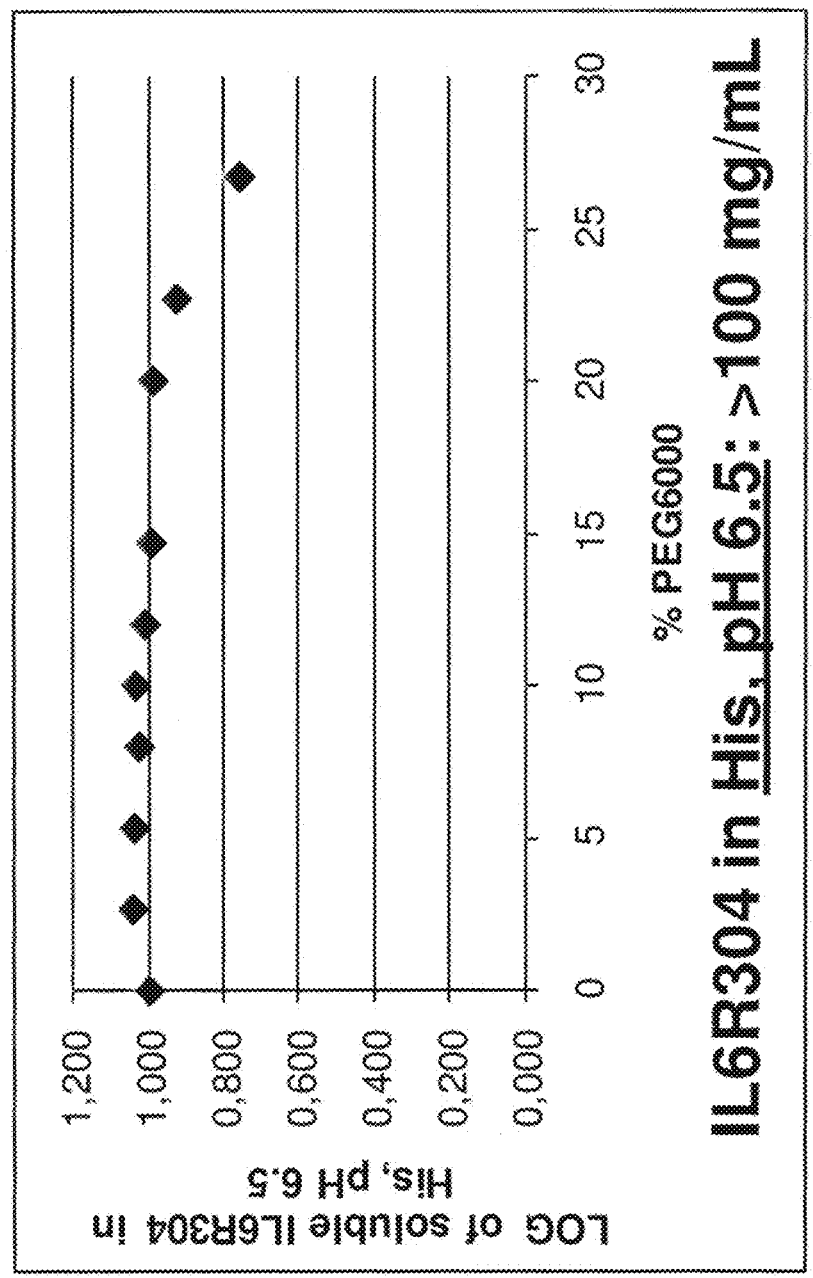
Figure 19:
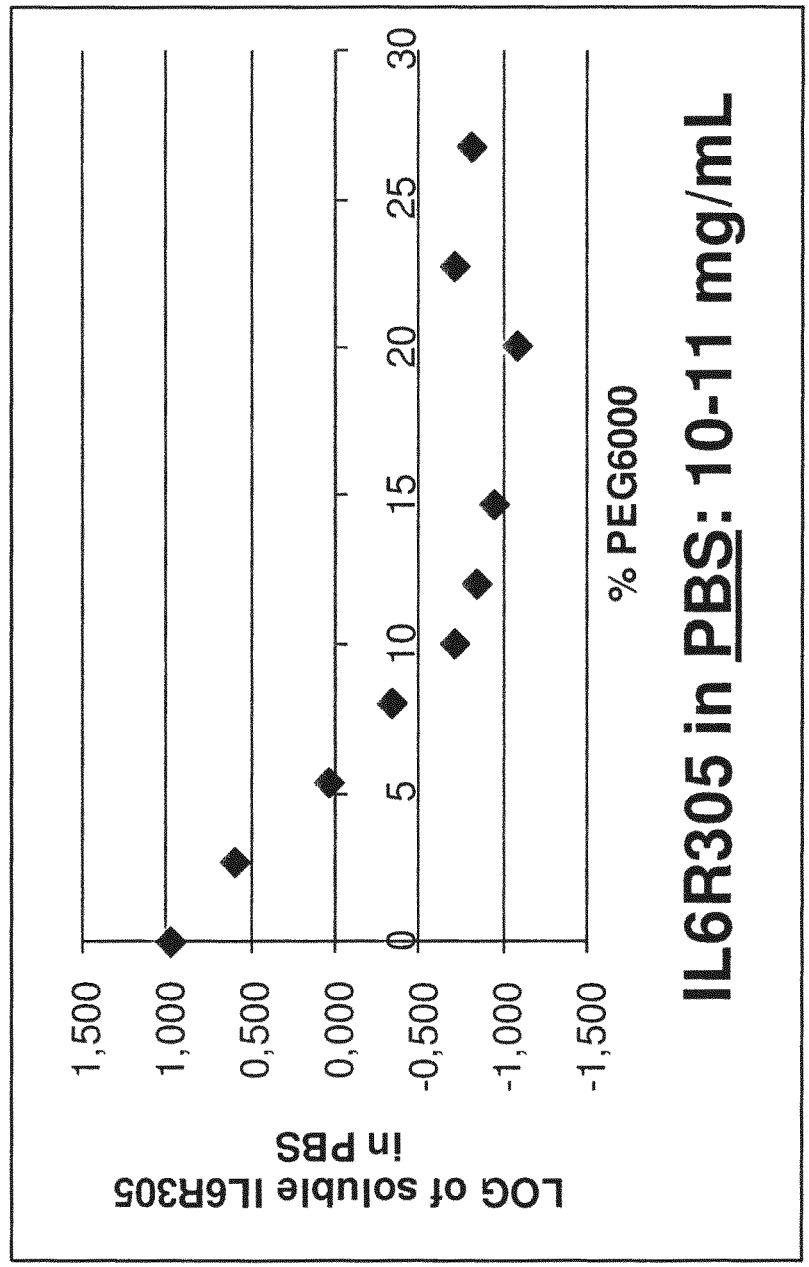
Figure 19:
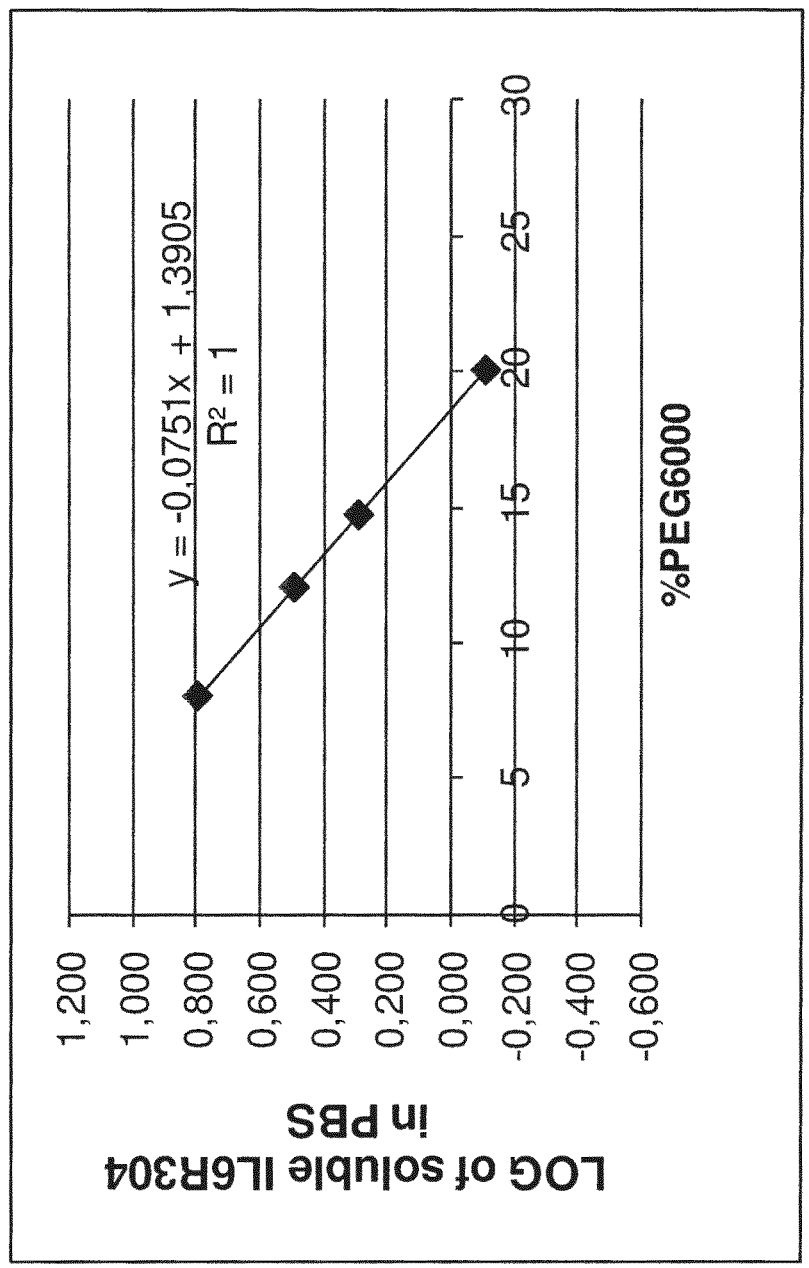

FIG. 19. (A)-(C): Log-values of the soluble IL-6R Nanobody concentration (Y-axis) vs. PEG6000 concentration (%) (X-axis), together with the calculated solubility values. (D) represents an example of how the linear regression analysis is performed on the obtained data points to determine the intercept with the X-axis (from which the theoretical solubility at zero % PEG6000 can be deduced).

Figure 20:
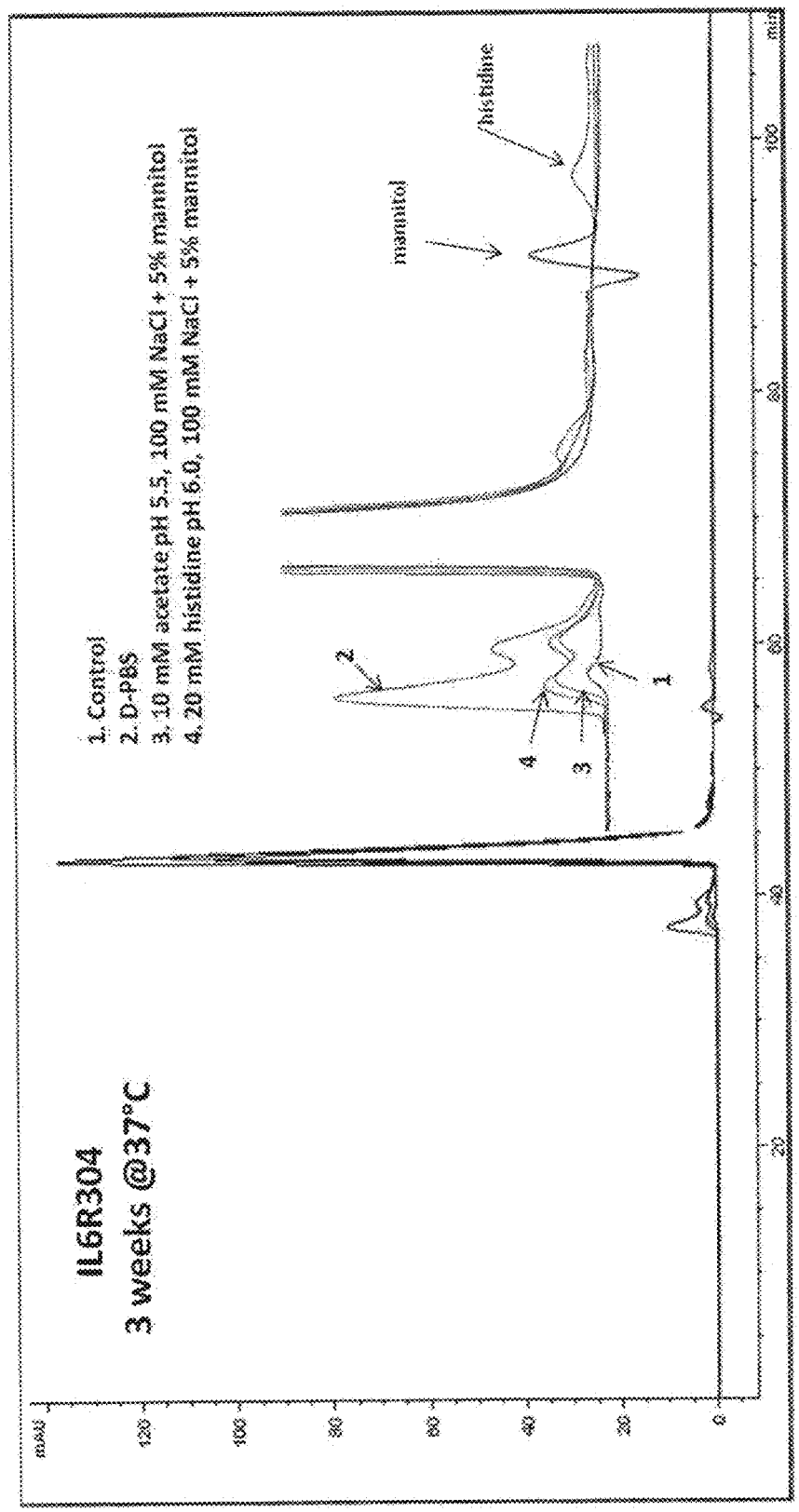

FIG. 20. Overlay of the SE-HPLC chromatograms of IL6R304 formulated at 10 mg/mL stored for 3 weeks at 37° C. Inset, zoom on the main peak to demonstrate the buffer-dependent differences in % aggregates.

Figure 21:
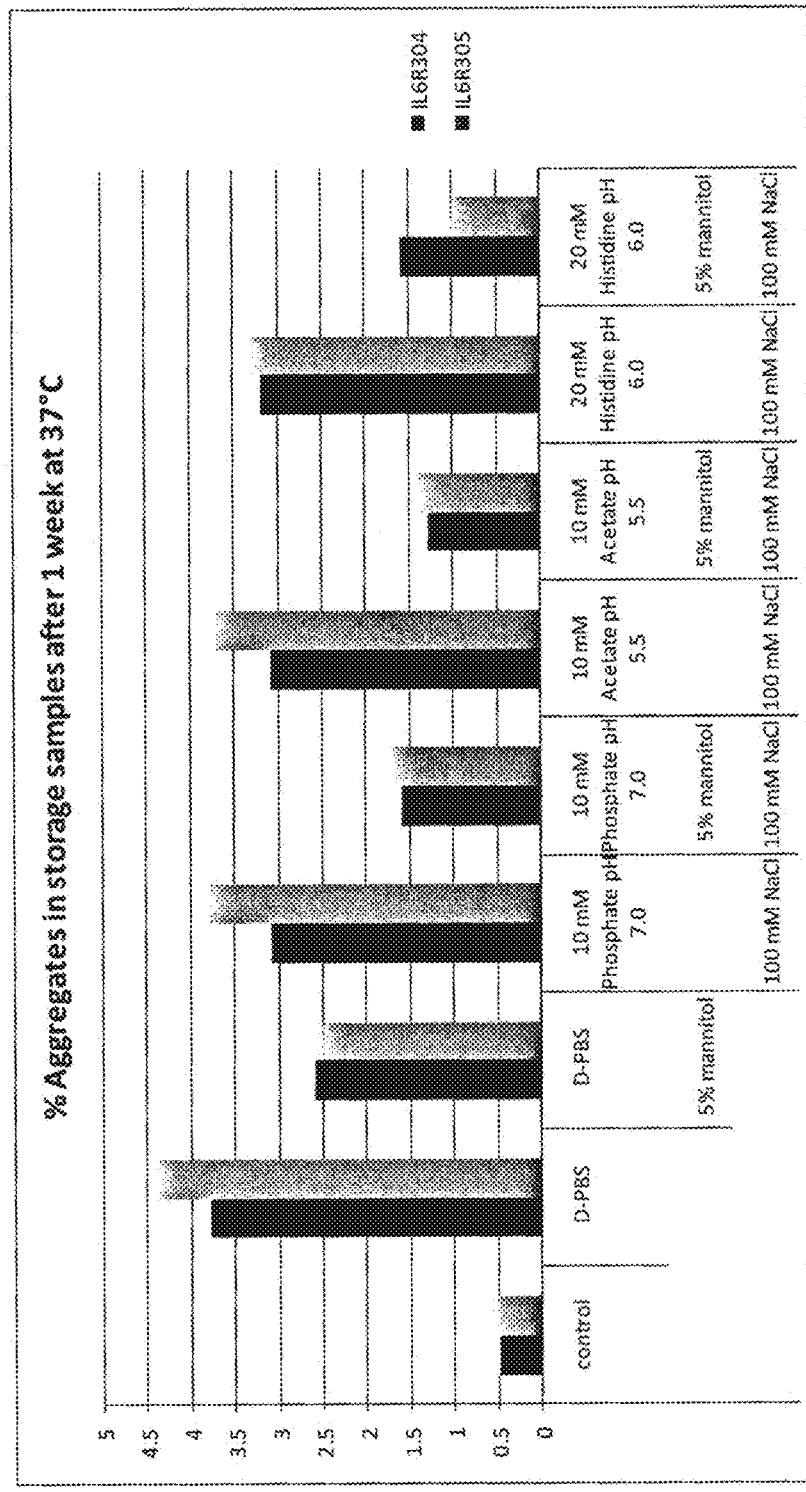

FIG. 21. Figure demonstrating the buffer-dependent differences in % aggregates (peak surface area in SE-HPLC) that were observed in the stability samples of IL6R304 and IL6R305 stored for 1 week at 37° C.

Figure 22:
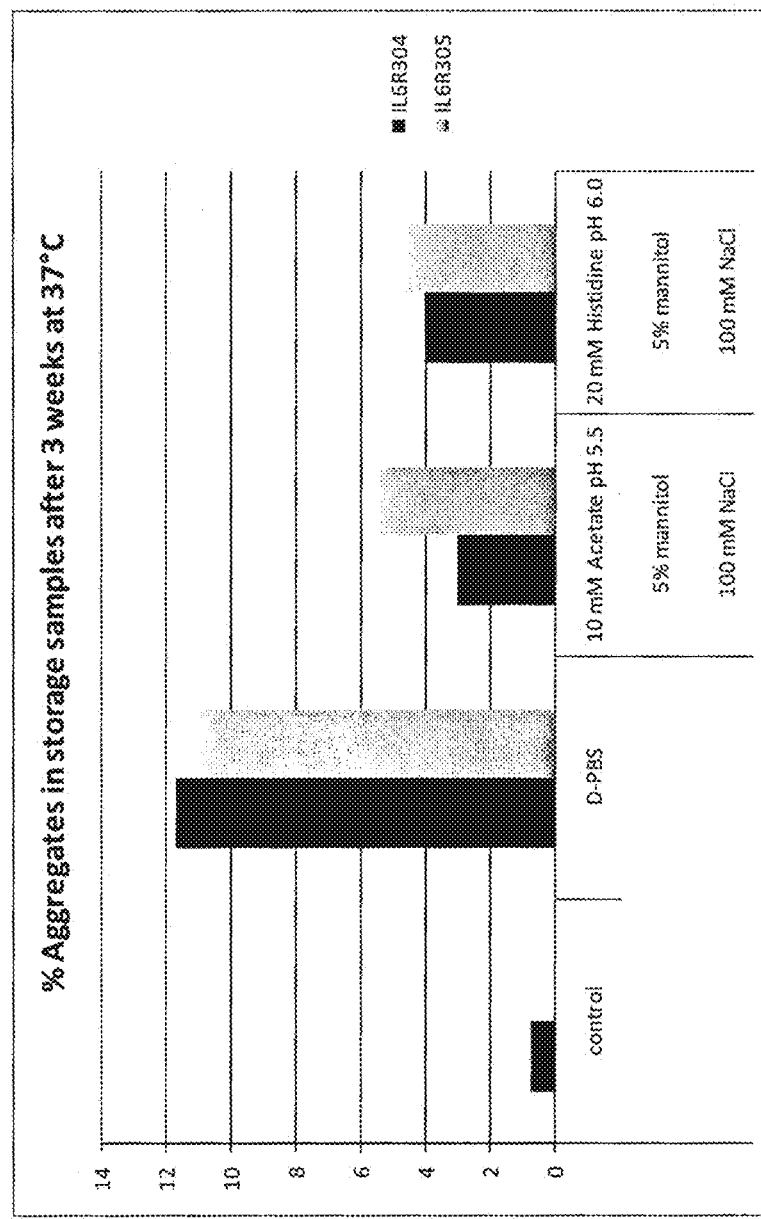

FIG. 22. Figure demonstrating the buffer-dependent differences in % aggregates (peak surface area in SE-HPLC) that were observed in the stability samples of IL6R304 and IL6R305 stored for 3 weeks at 37° C.

Figure 23:
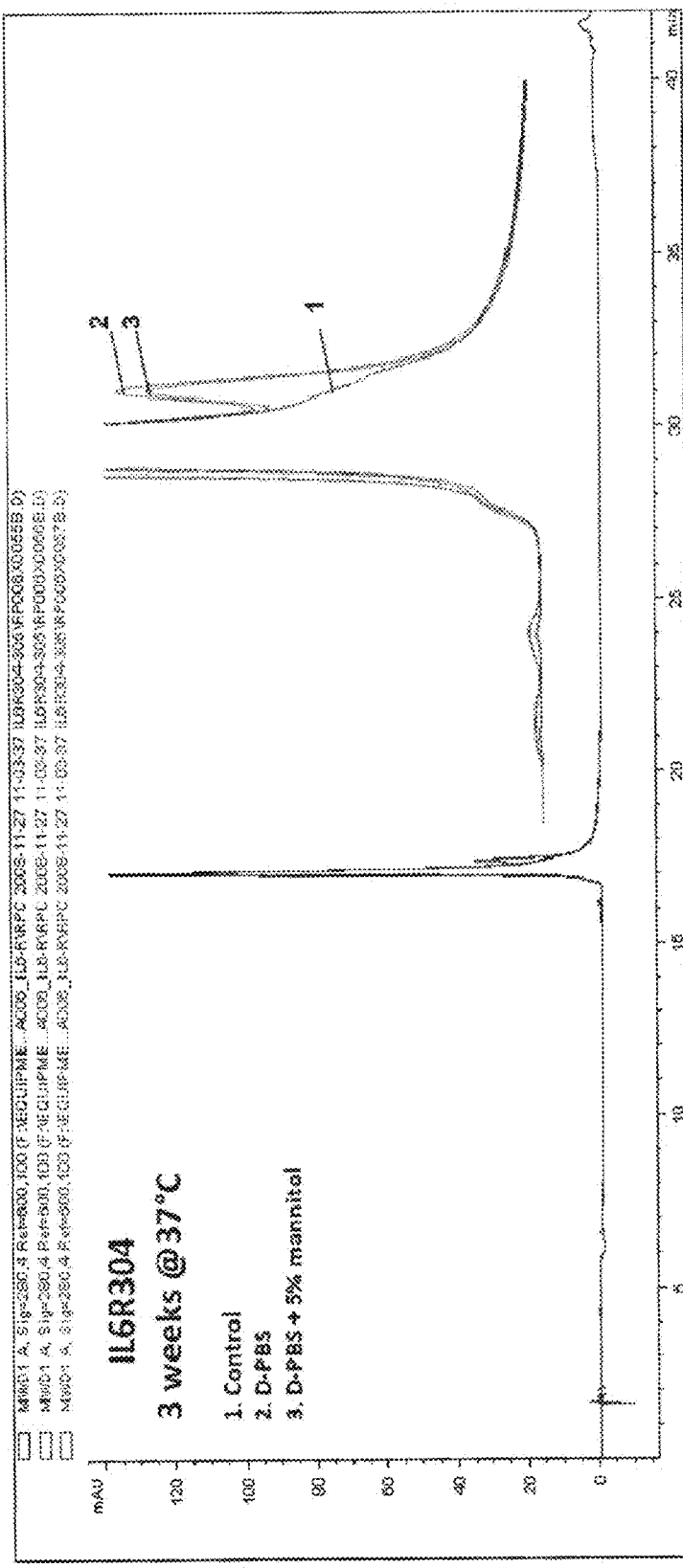
Figure 23B:
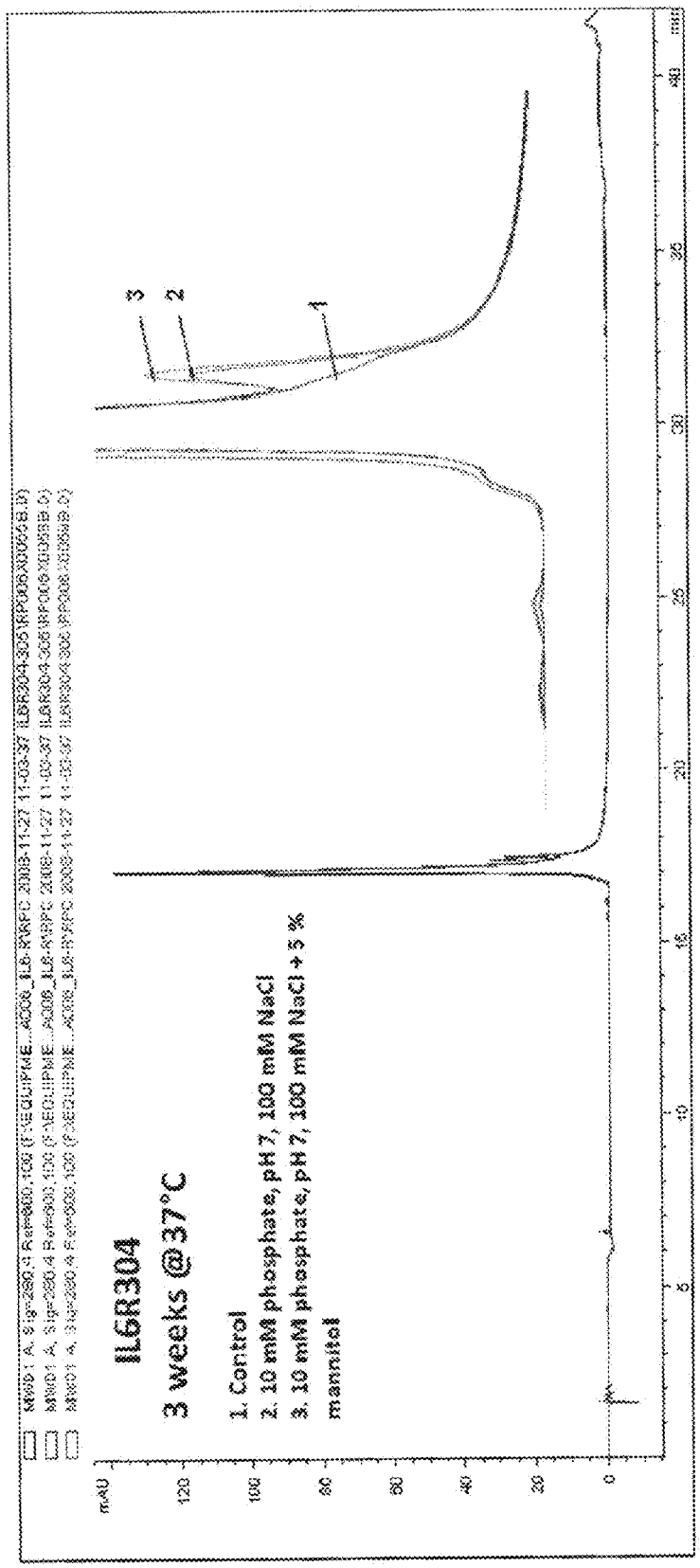
Figure 23:
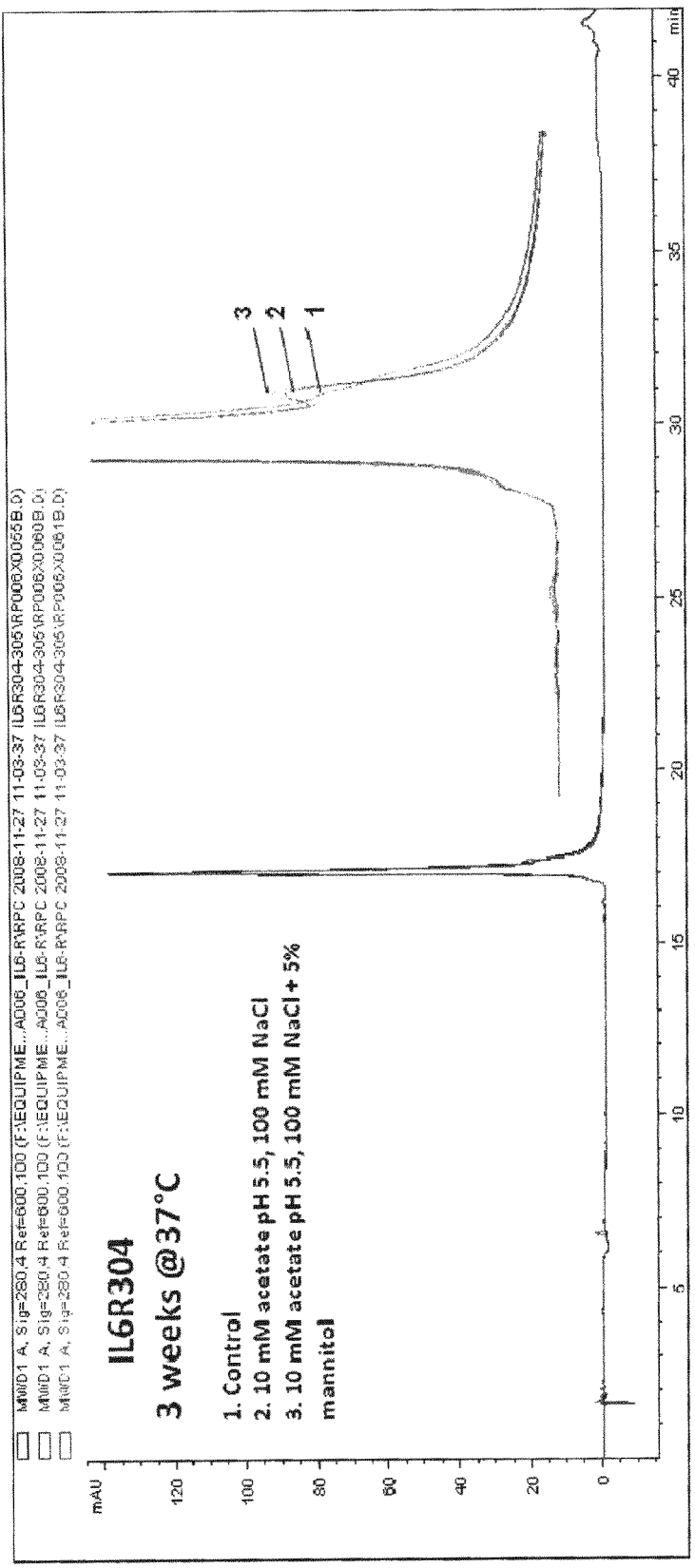
Figure 23D:
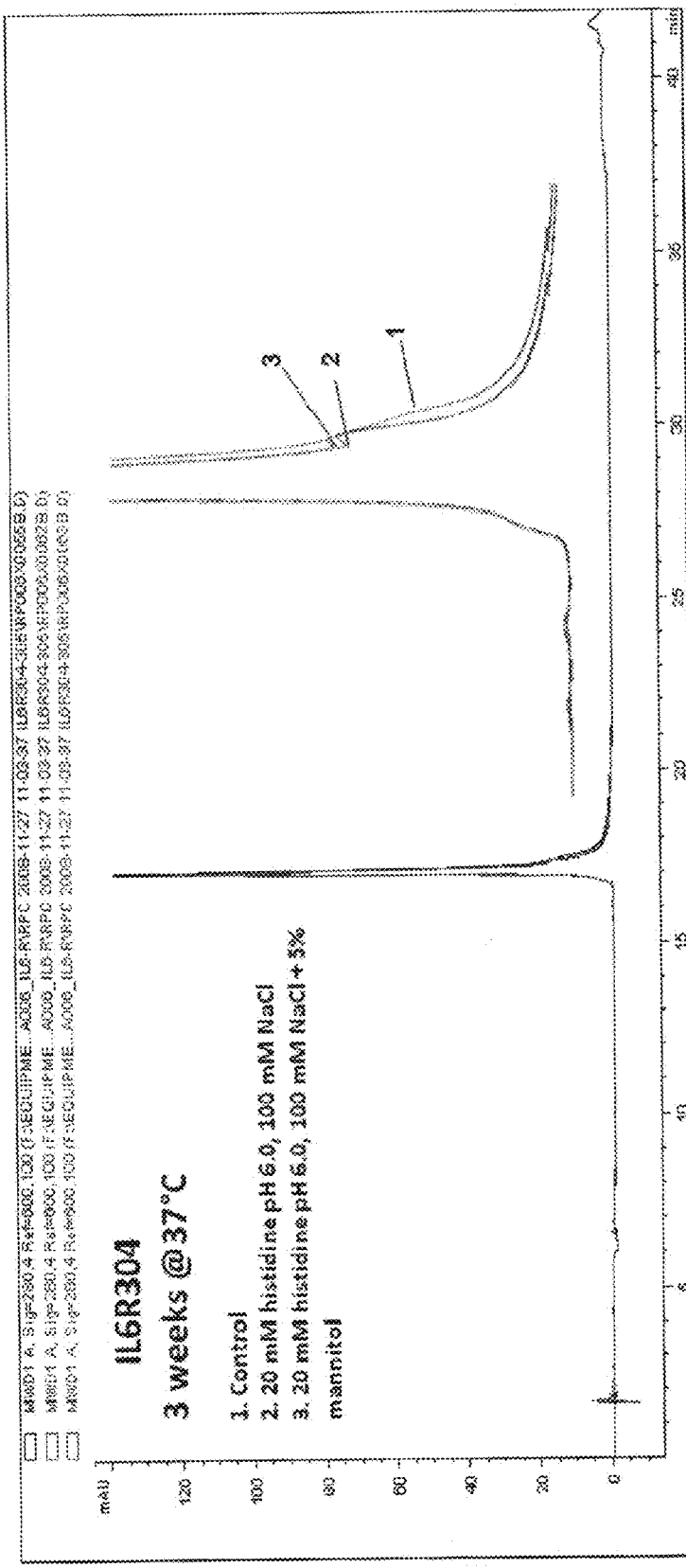

FIG. 23. Overlays of the RP-HPLC chromatograms from IL6R304 incubated for 3 weeks at 37° C. in different formulation buffers. A zoom on the main peak is shown as inset. Note the increase of two minor prepeaks and a postpeak in the IL6R304 samples stored for 3 weeks.

Figure 24:
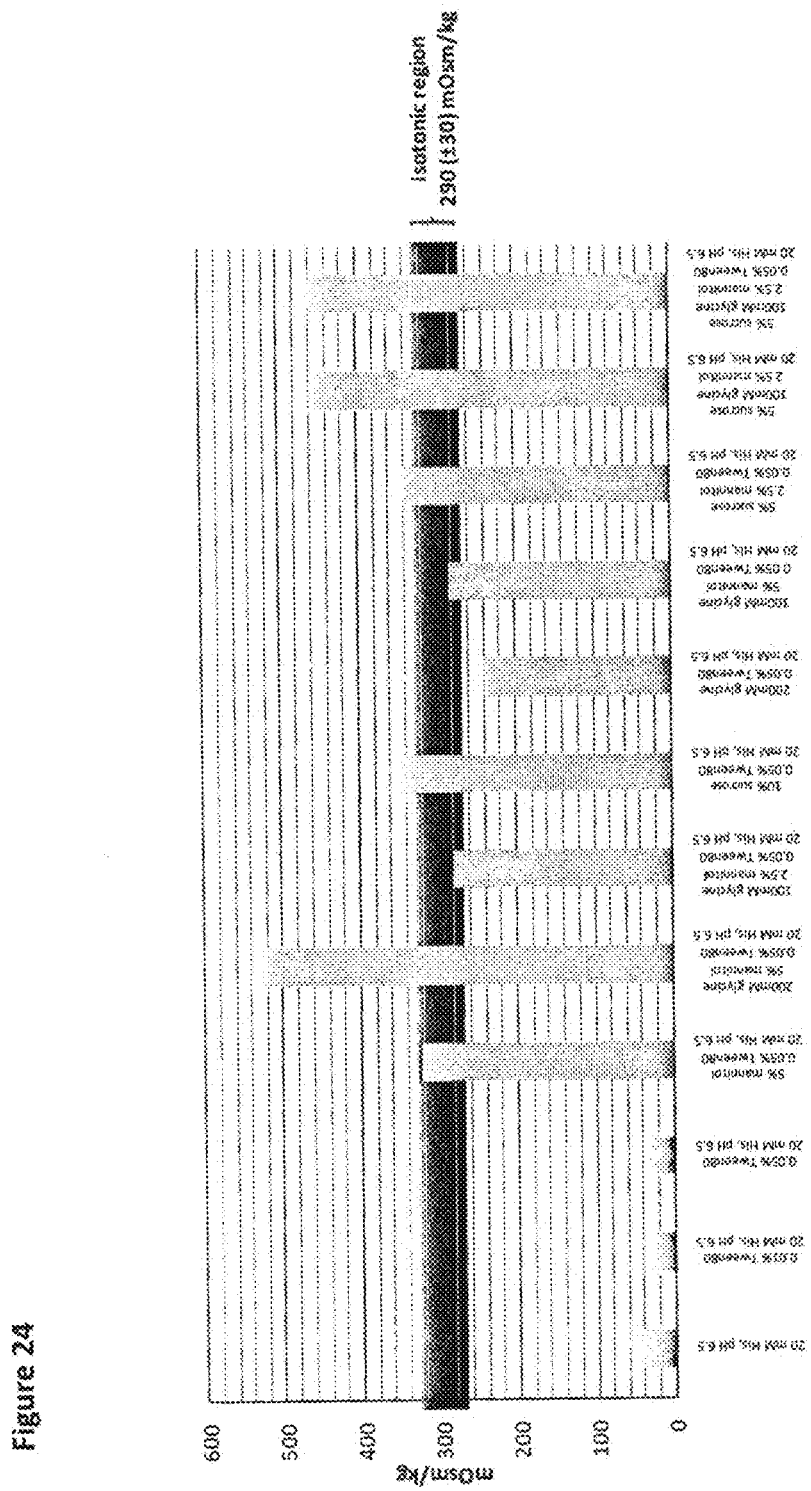

FIG. 24. Osmolality data of IL6R304 (10 mg/mL) in the 12 different buffer indicated in the graph. The horizontal bar defines the isotonic region.

Figure 25:
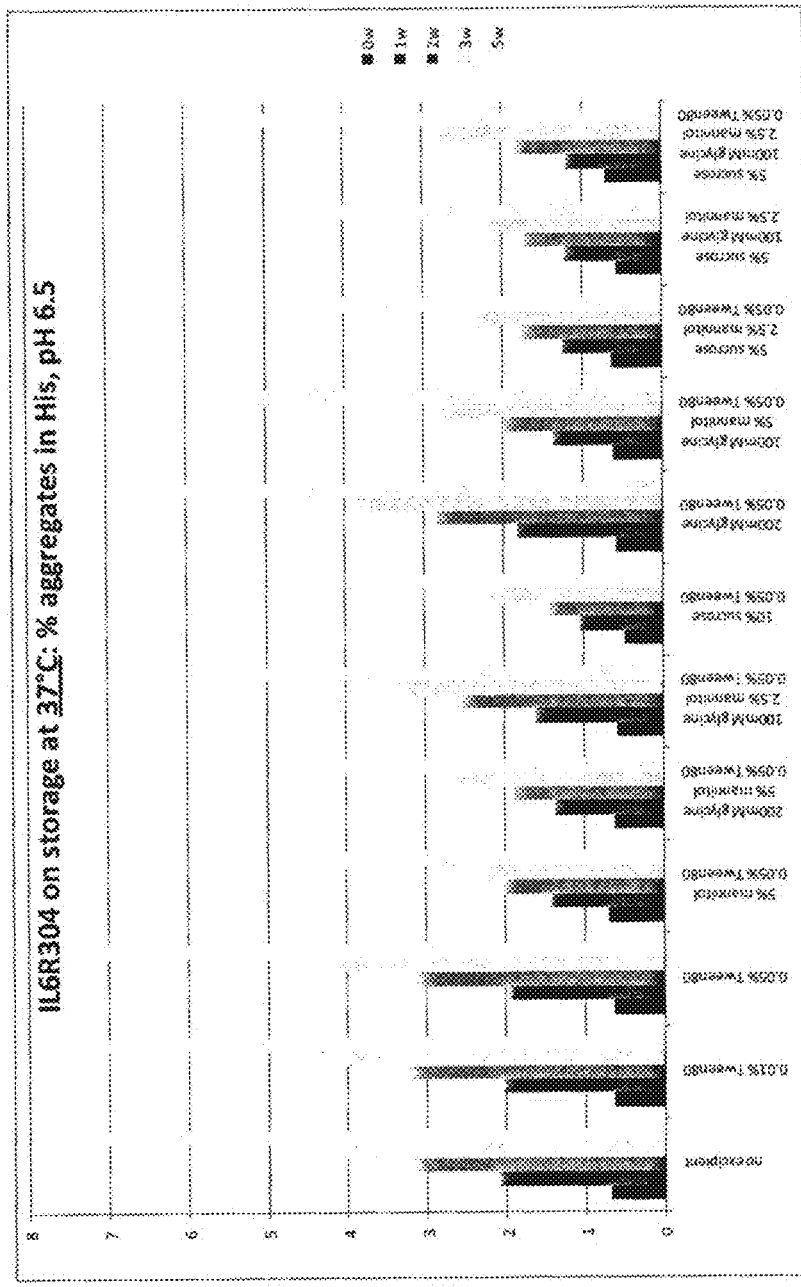
Figure 25:
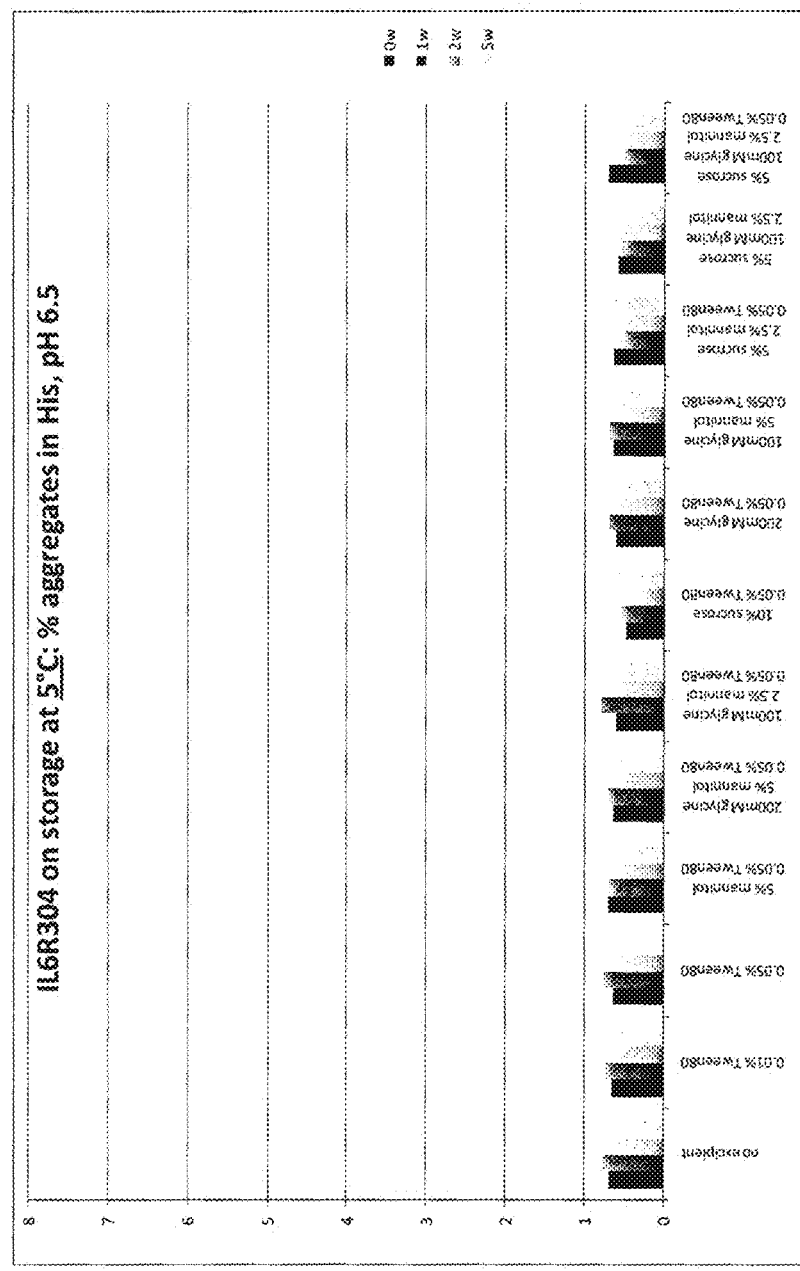

FIG. 25. Figure demonstrating the time-dependent increase of the % oligomers/aggregates (Y-axis) observed in SE-HPLC analysis of IL6R304 stored for up to 5 weeks at 37° C. (A) and 5° C. (B) in the buffers indicated in the graph. The % oligomers/aggregates is expressed as the sum of the % peak surface areas of prepeak 1a, prepeak 1b and prepeak 2 relative to the total peak surface area.

Figure 26:
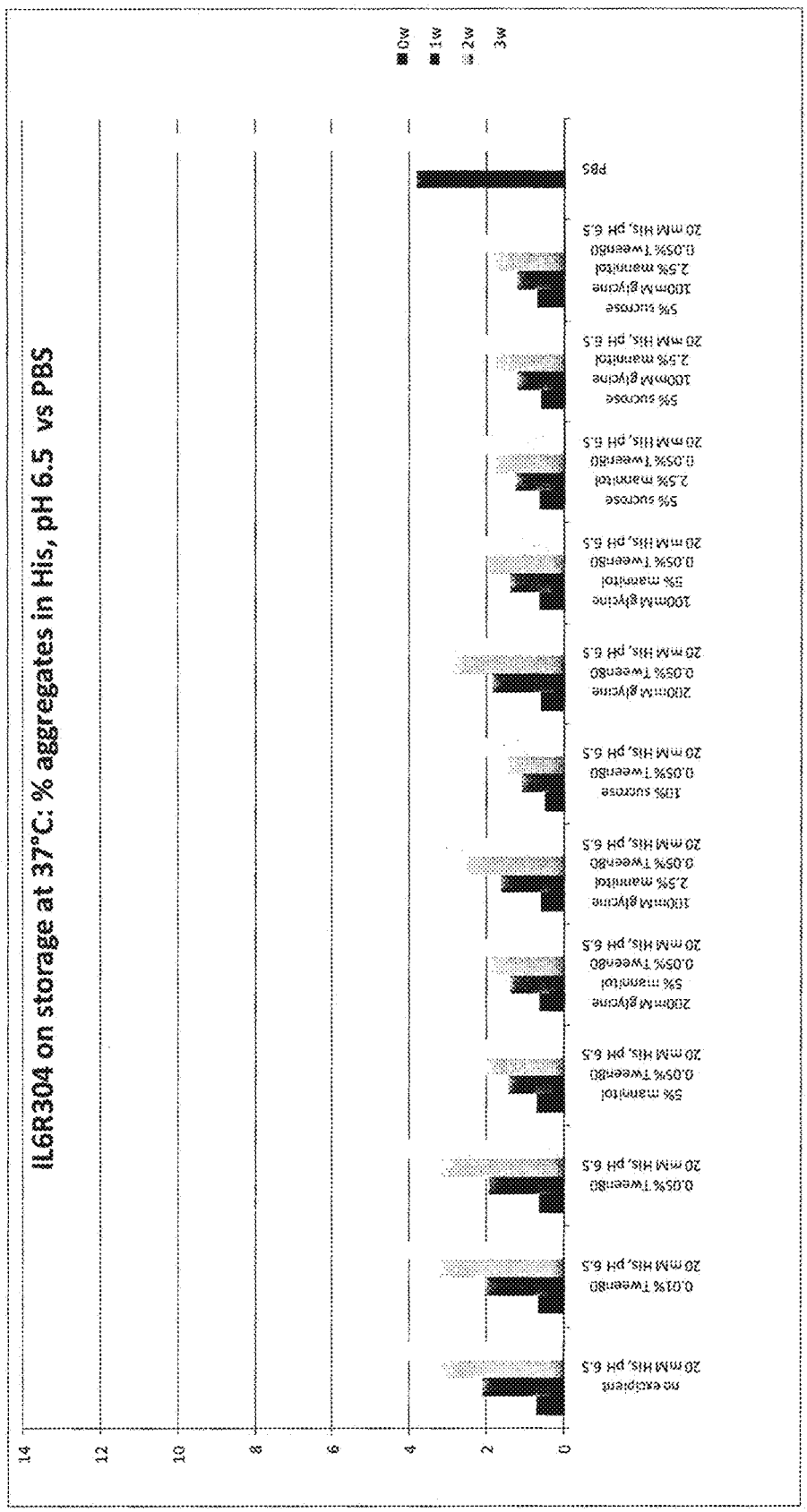
Figure 26B:
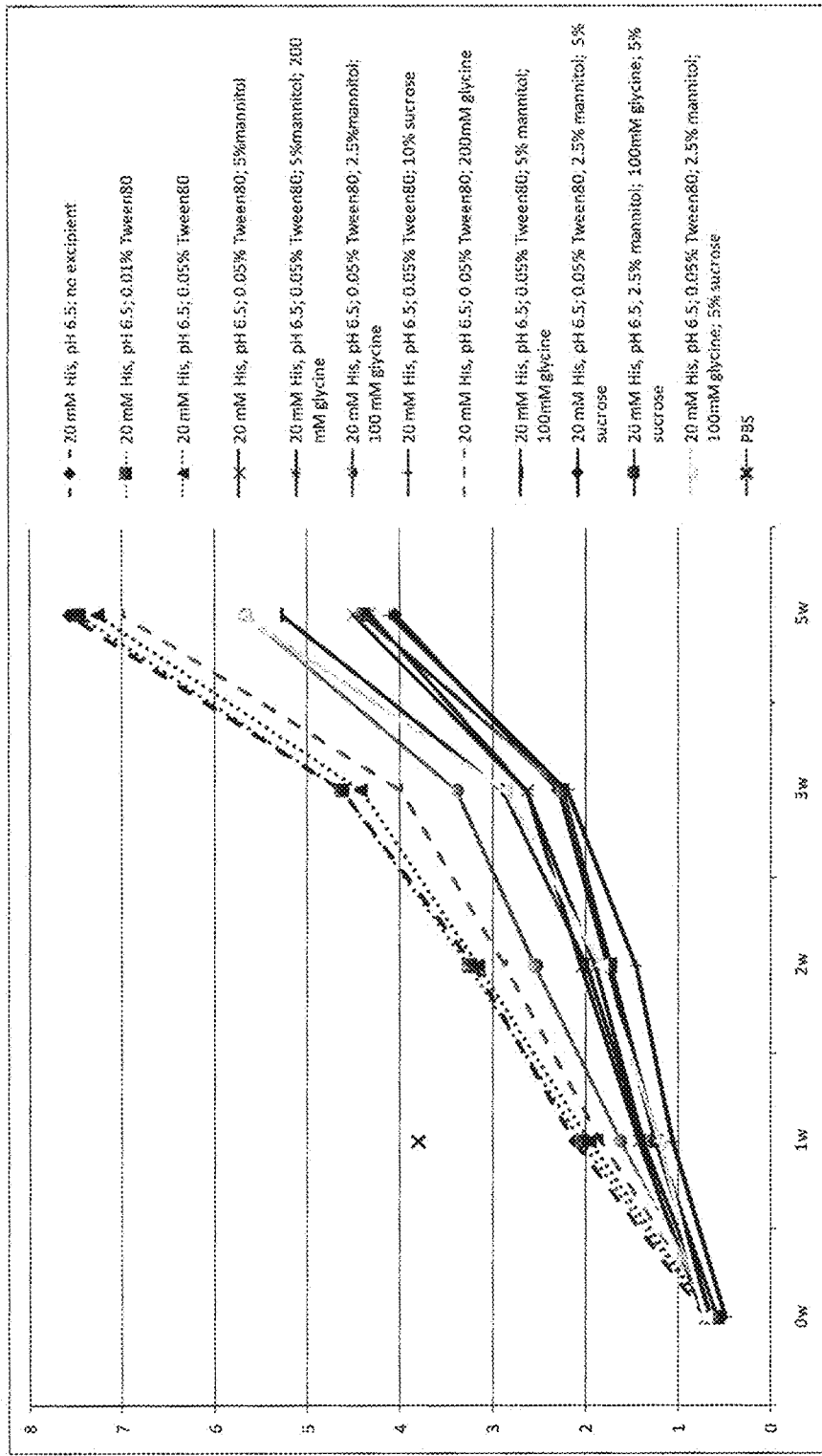

FIG. 26. (A): the % oligomers (% peak surface area) observed in the Histidine buffers after storage for 3 weeks at 37° C. compared to the equivalent sample in PBS buffer. (B): time-dependent and buffer-dependent increase in the % oligomers observed in the IL-6R stability samples stored for up to 5 weeks at 37° C., at a concentration of 10 mg/mL in the buffers indicated in the graph.

Figure 27:
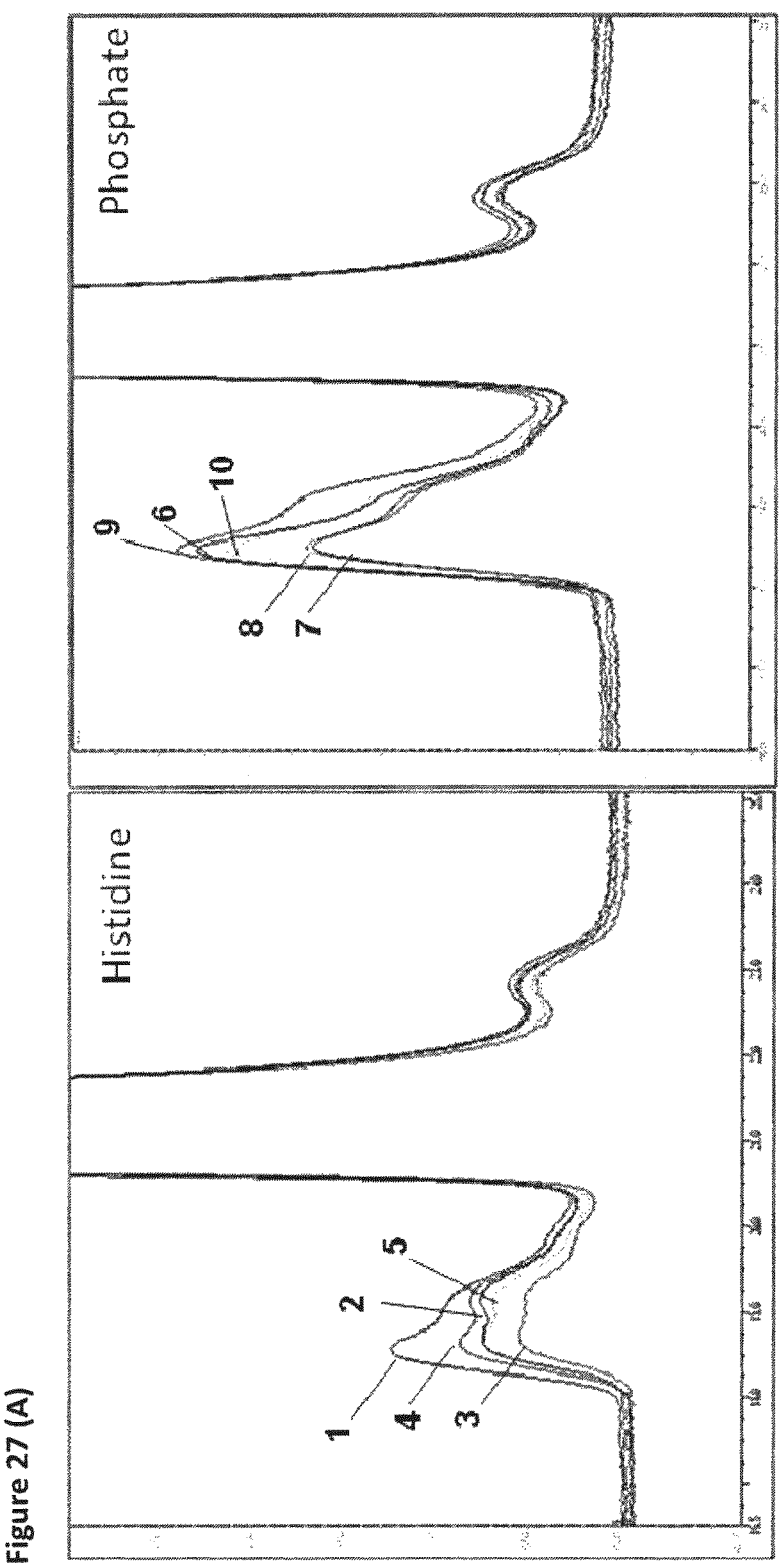
Figure 27:
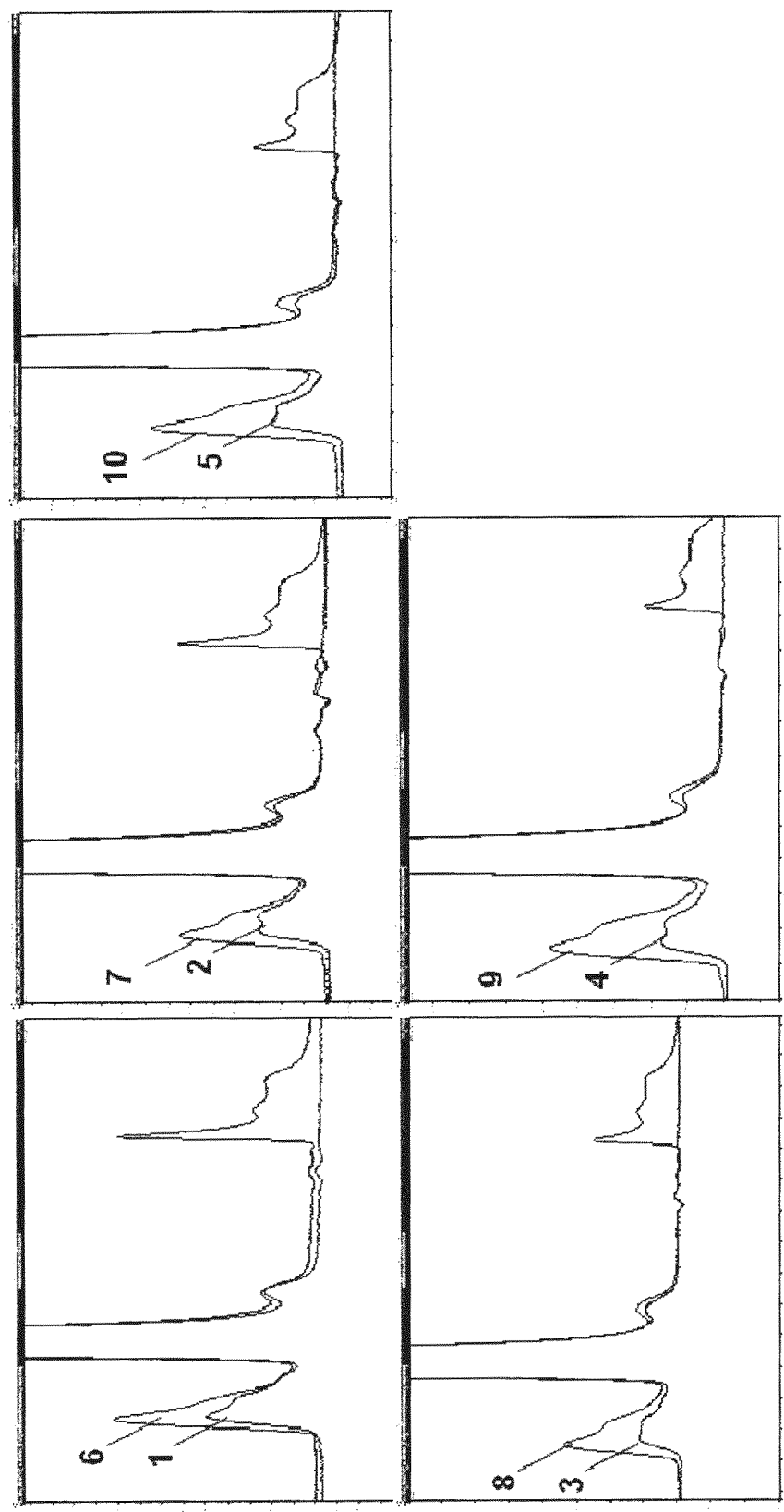

FIG. 27. SE-HPLC profile of IL6R304 in the different buffers as depicted in Table 21. IL6R304 was less prone to oligomerization in L-histidine buffer compared to phosphate buffer. (A) Less oligomers, which were seen as prepeaks during SE-HPLC analysis, were present in IL6R304 samples stored for 8 weeks at 37° C. in L-histidine buffer (buffers 1-5) compared to phosphate buffer (buffers 6-10). The amount of oligomers was lowest in buffer 3. (B) The effect of the different excipients on oligomerization in either L-histidine versus phosphate. Note that the surface area of the postpeak was higher in phosphate compared to L-histidine.

Figure 28:
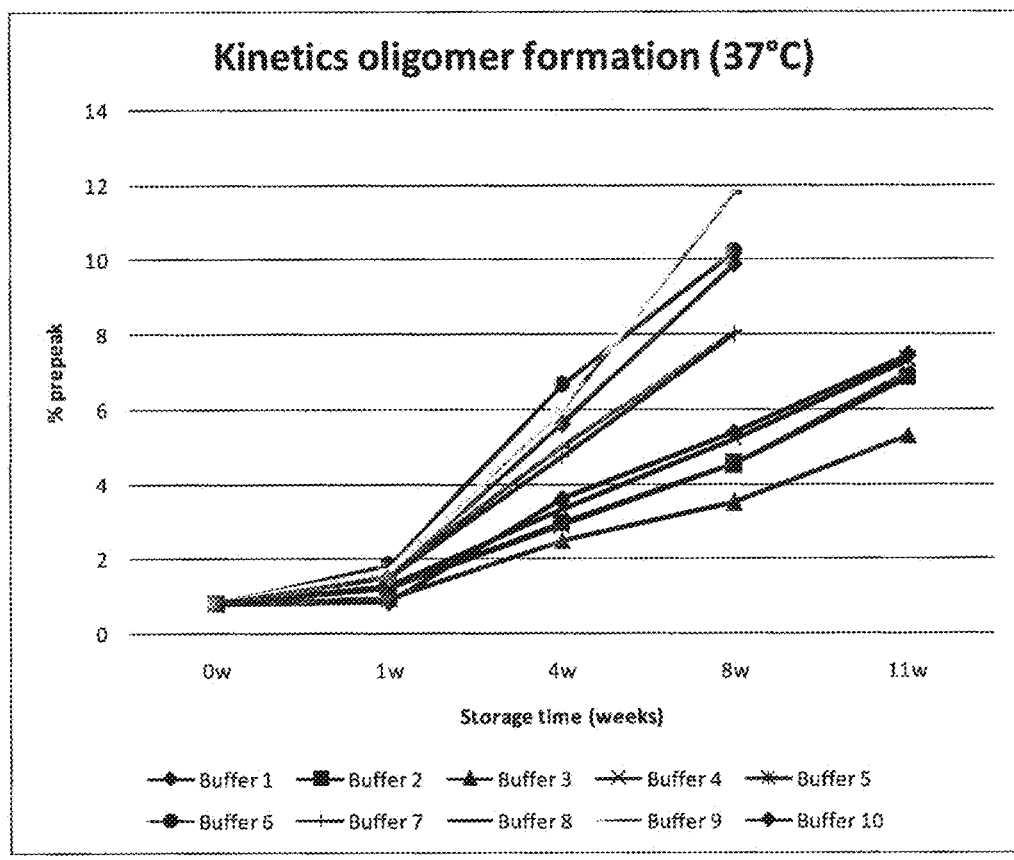

FIG. 28. Kinetics of oligomer formation upon storage of IL6R304 in the different buffers. Oligomerization was significantly slower in L-histidine (buffers 1-5) compared to phosphate buffer (buffers 6-10).

Figure 29:
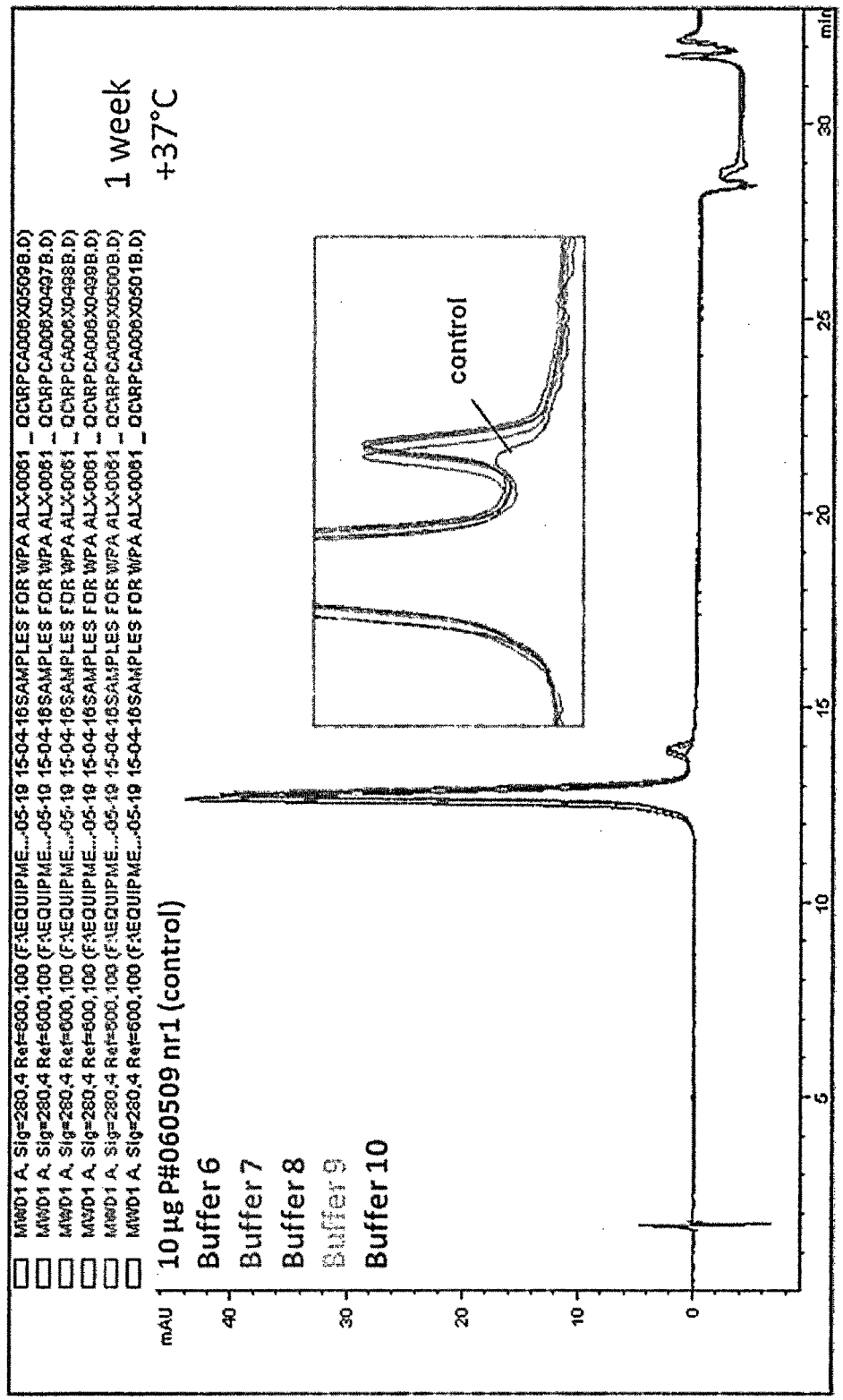
Figure 29:
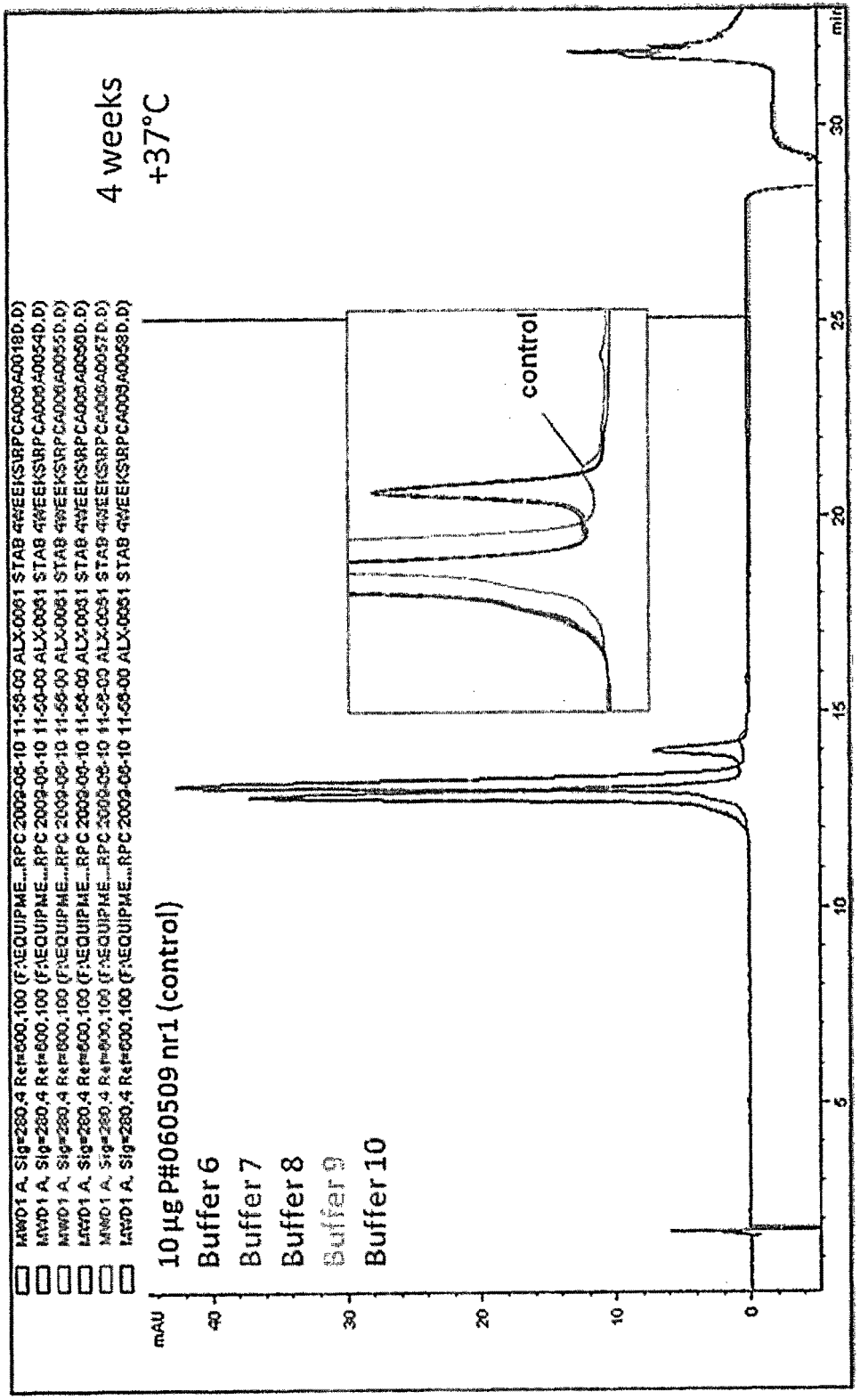
Figure 29:
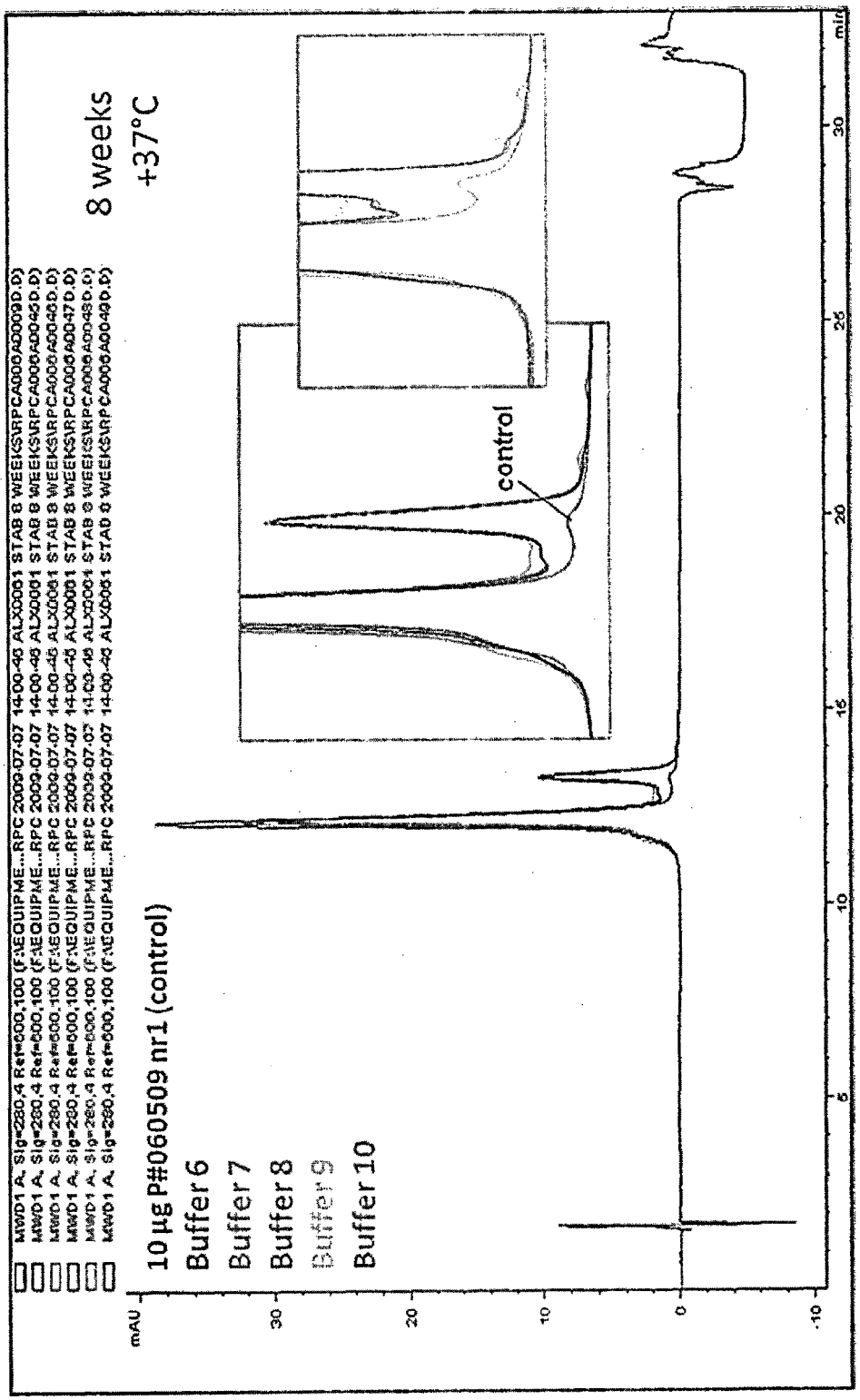

FIG. 29. Overlay of the RP-HPLC chromatograms from IL6R304 after storage for up to 8 weeks at +37° C. in 10 different formulation buffers. A zoom on the main peak and sidepeaks is shown as inset.

Figure 30:
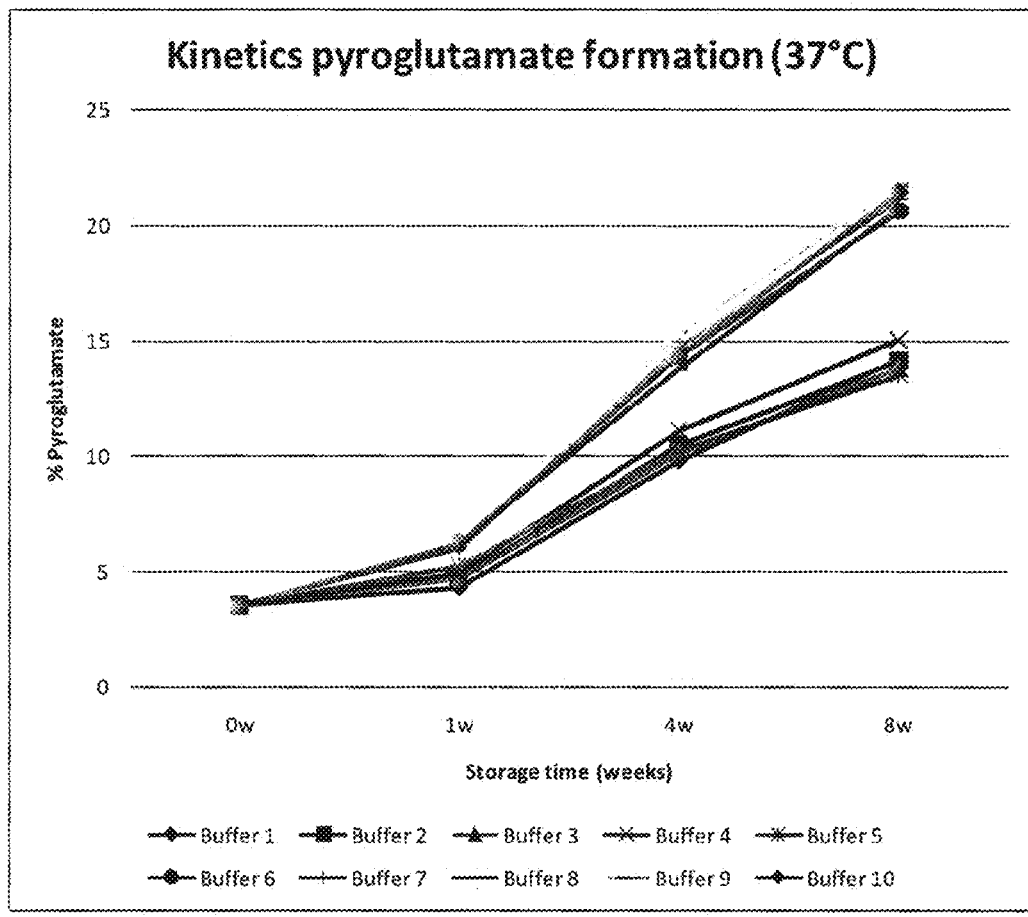

FIG. 30. Kinetics of the formation for the pyroglutamate variant of IL6R304 upon storage under stressed conditions in the different buffers. Less pyroglutamate is formed in L-histidine compared to phosphate buffer.

Figure 31:
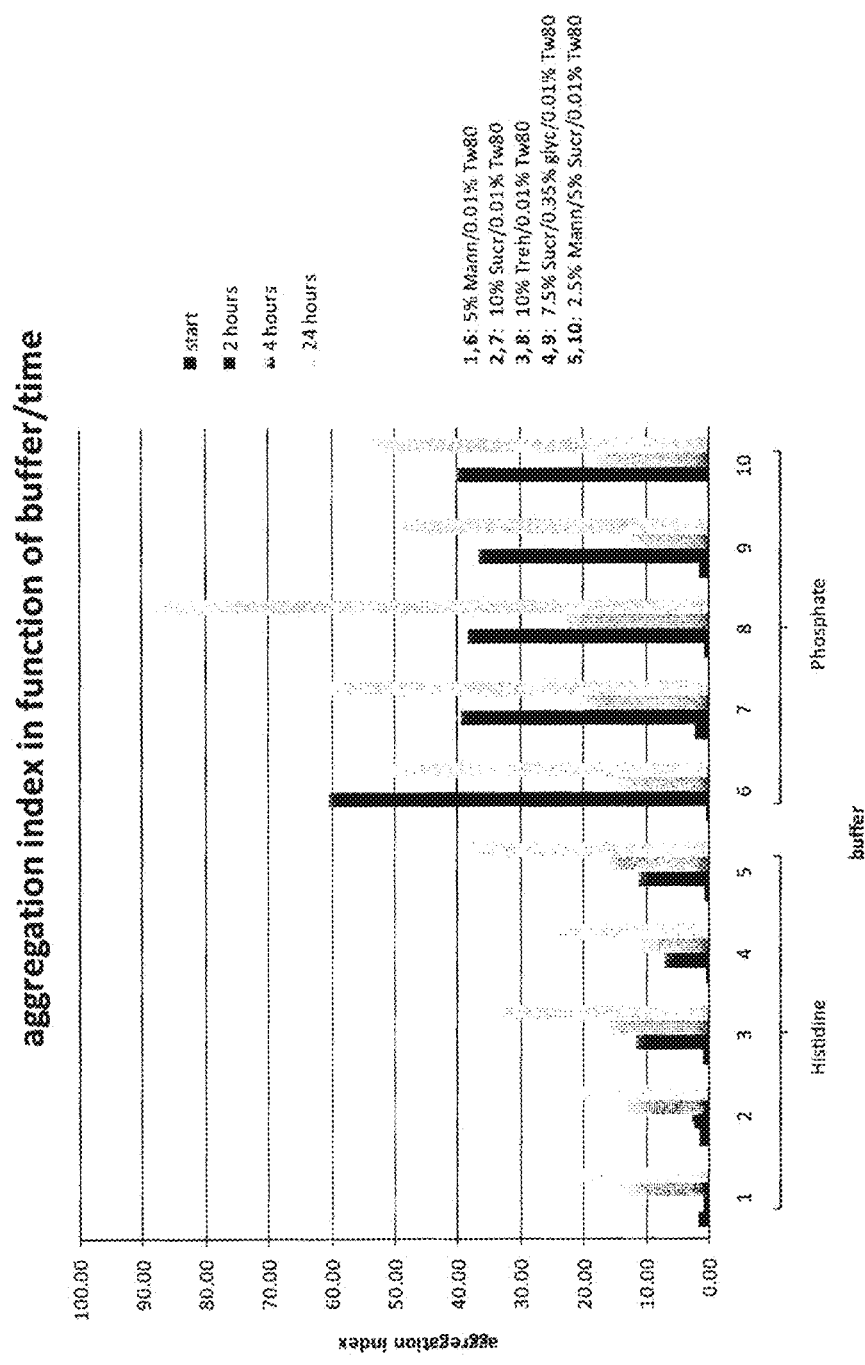

FIG. 31. Aggregation index before and after stirring of IL6R304.

Figure 32:
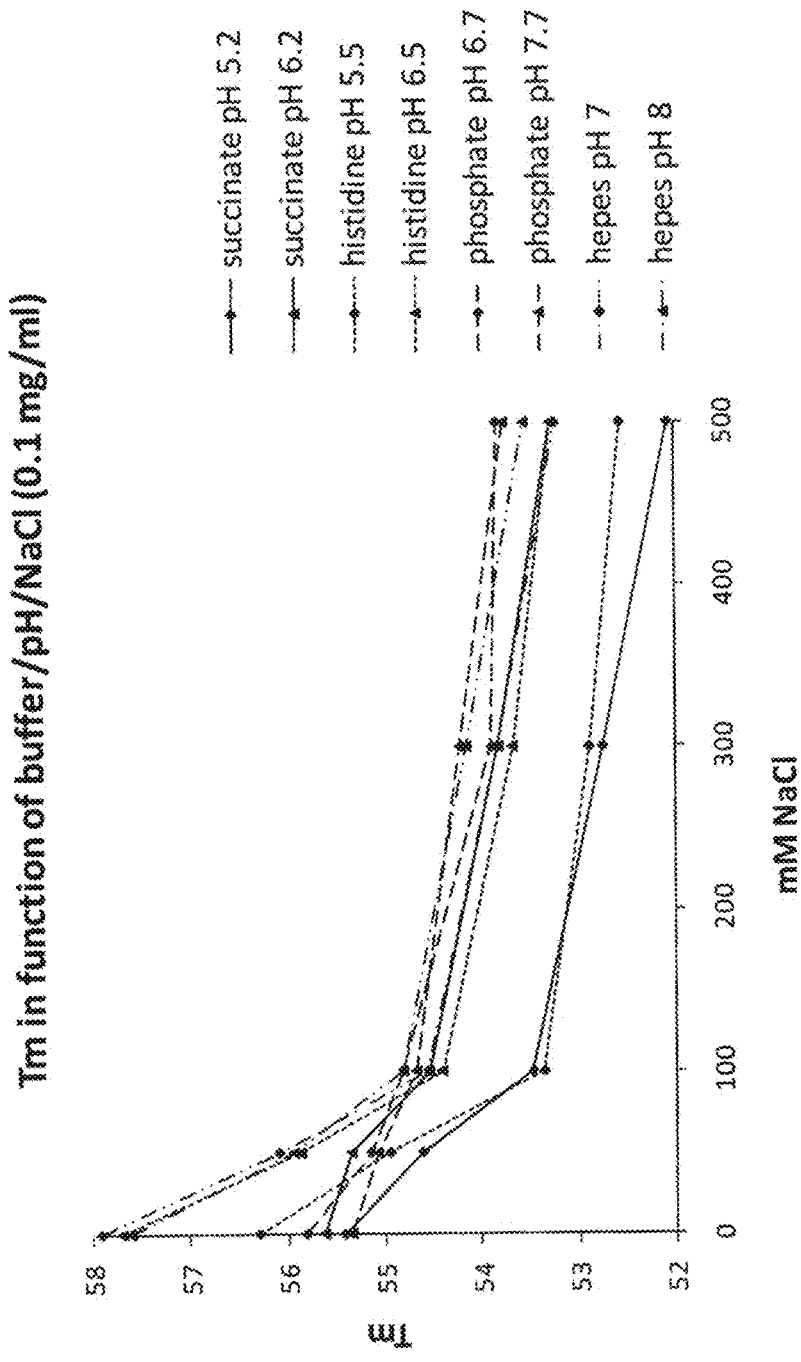
Figure 32:
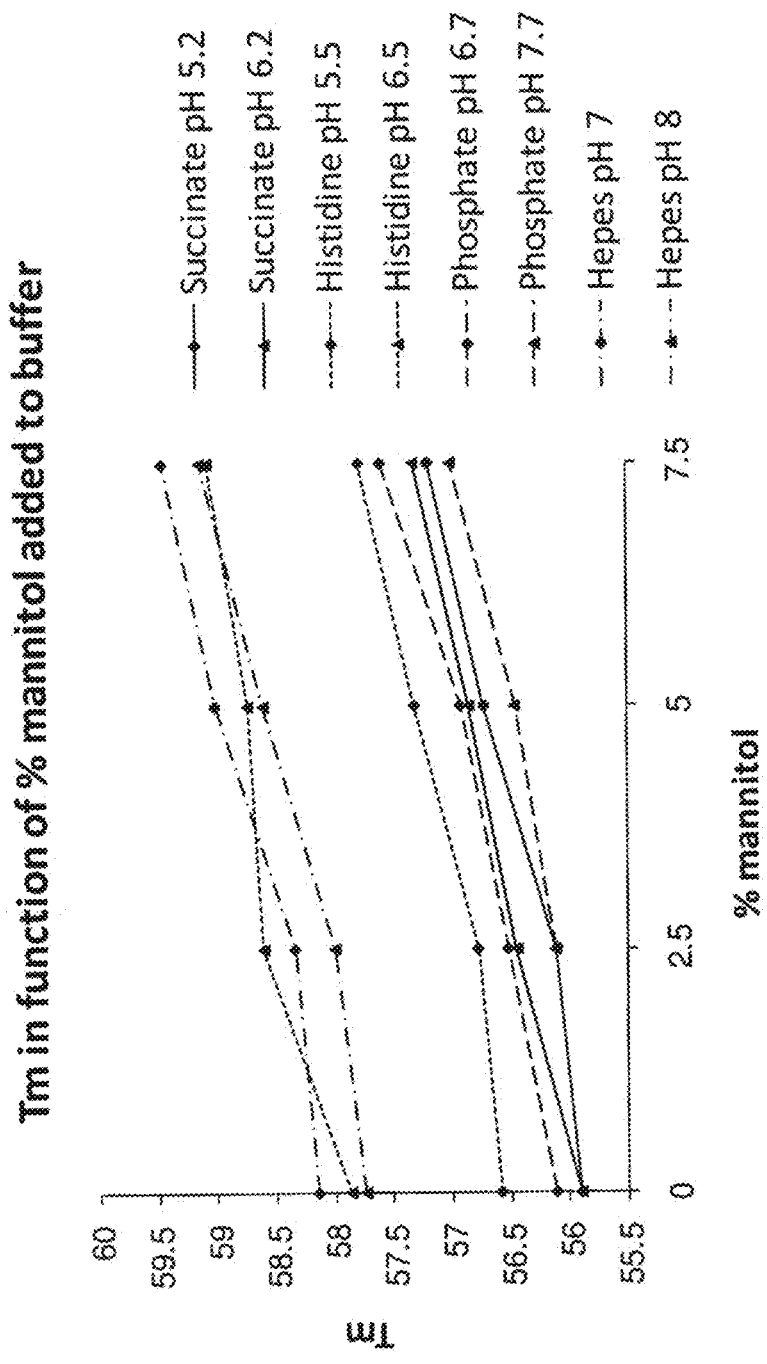

FIG. 32. Graphical presentation of Tm values for 23IL0064 as a function of NaCl concentration (A) and of mannitol concentration (B). Tm's were obtained in the thermal shift assay at 0.1 mg/mL.

Figure 33:
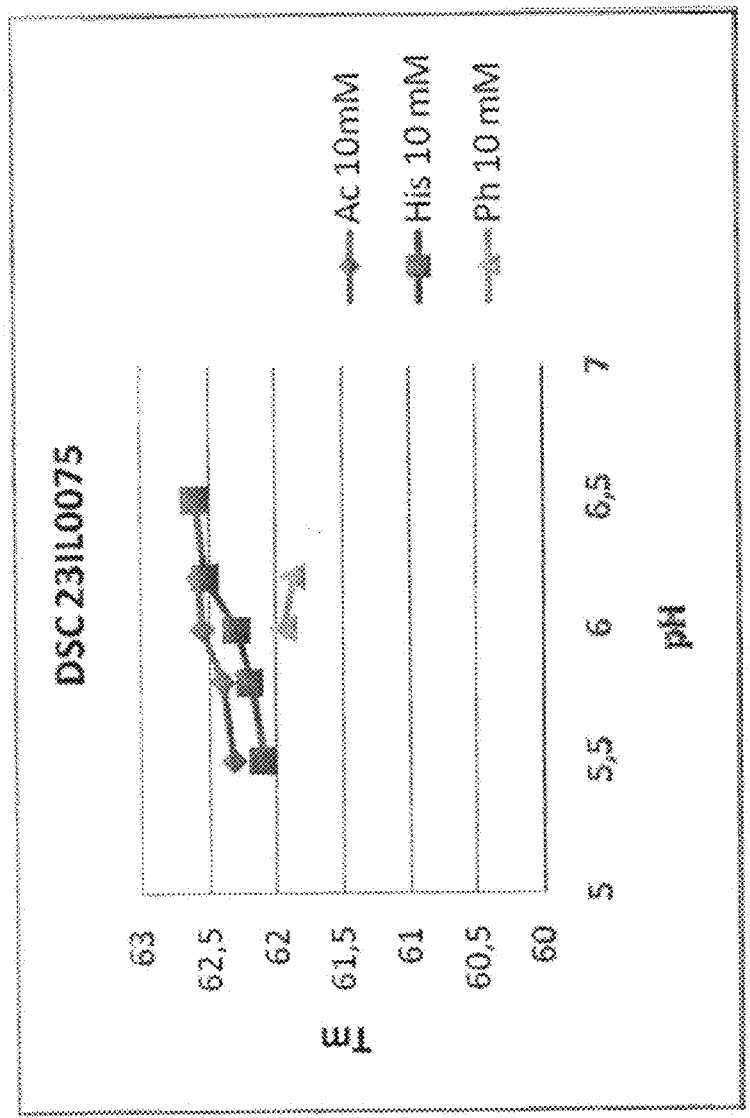

FIG. 33. Graphical representation of the melting temperatures measured for 23IL0075 as a function of the pH, in 10 mM acetate, in 10 mM histidine, and in 10 mM phosphate buffer. The protein concentration was 0.2 mg/mL. Scanning was performed at 1° C./min, starting at 30° C.

Figure 34:
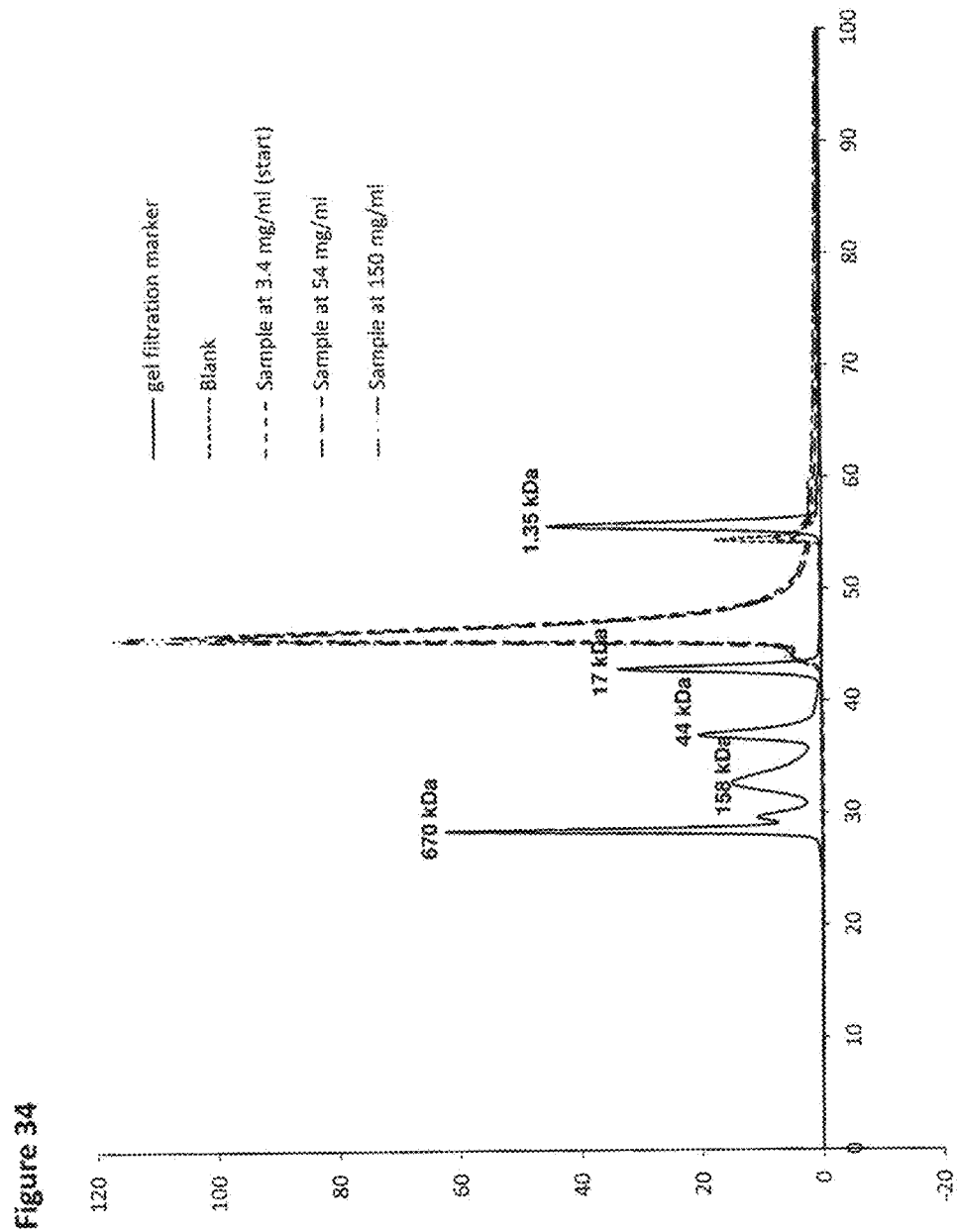

FIG. 34. SE-HPLC chromatograms (OD280) of 23IL0064 in 40 mM histidine (pH 6.0)/50 mM NaCl. The start sample was compared to samples after concentration. No aggregate formation due to concentration of the sample in the histidine buffer was observed. The SE-HPLC was run with a Phenomenex BIOSEP SEC S-2000 column, with D-PBS as mobile phase at 0.2 mL/min.

Figure 35:
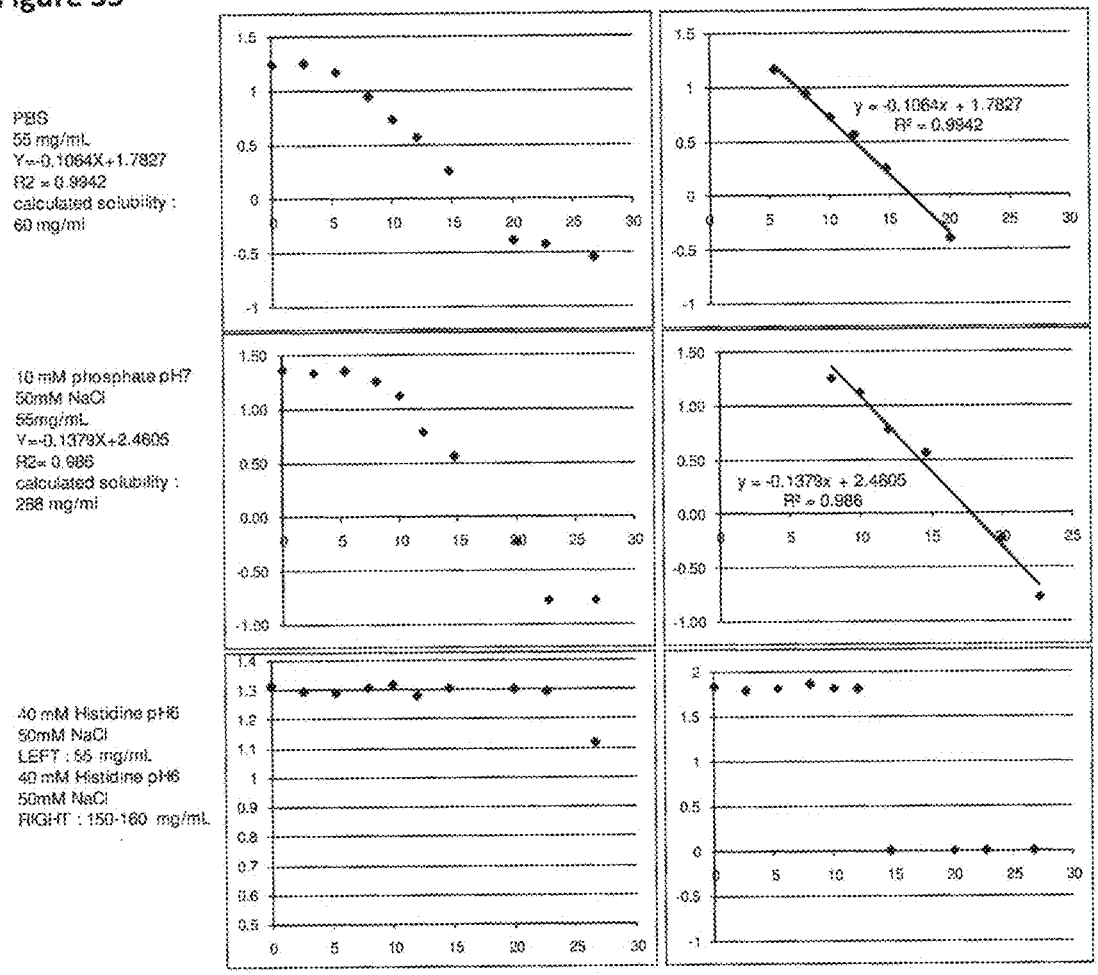

FIG. 35. Log-values of the soluble protein concentration (Y-axis) vs. PEG6000 concentration (%, X-axis). The right upper panel represents an example of how the linear regression analysis is performed on the obtained data points to determine the intercept with the X-axis (from which the theoretical solubility at zero % PEG6000 can be deduced). In the histidine buffer, the experiment was performed at two concentrations which are presented in the two bottom graphs. For these two graphs no regression was possible.

Figure 36:
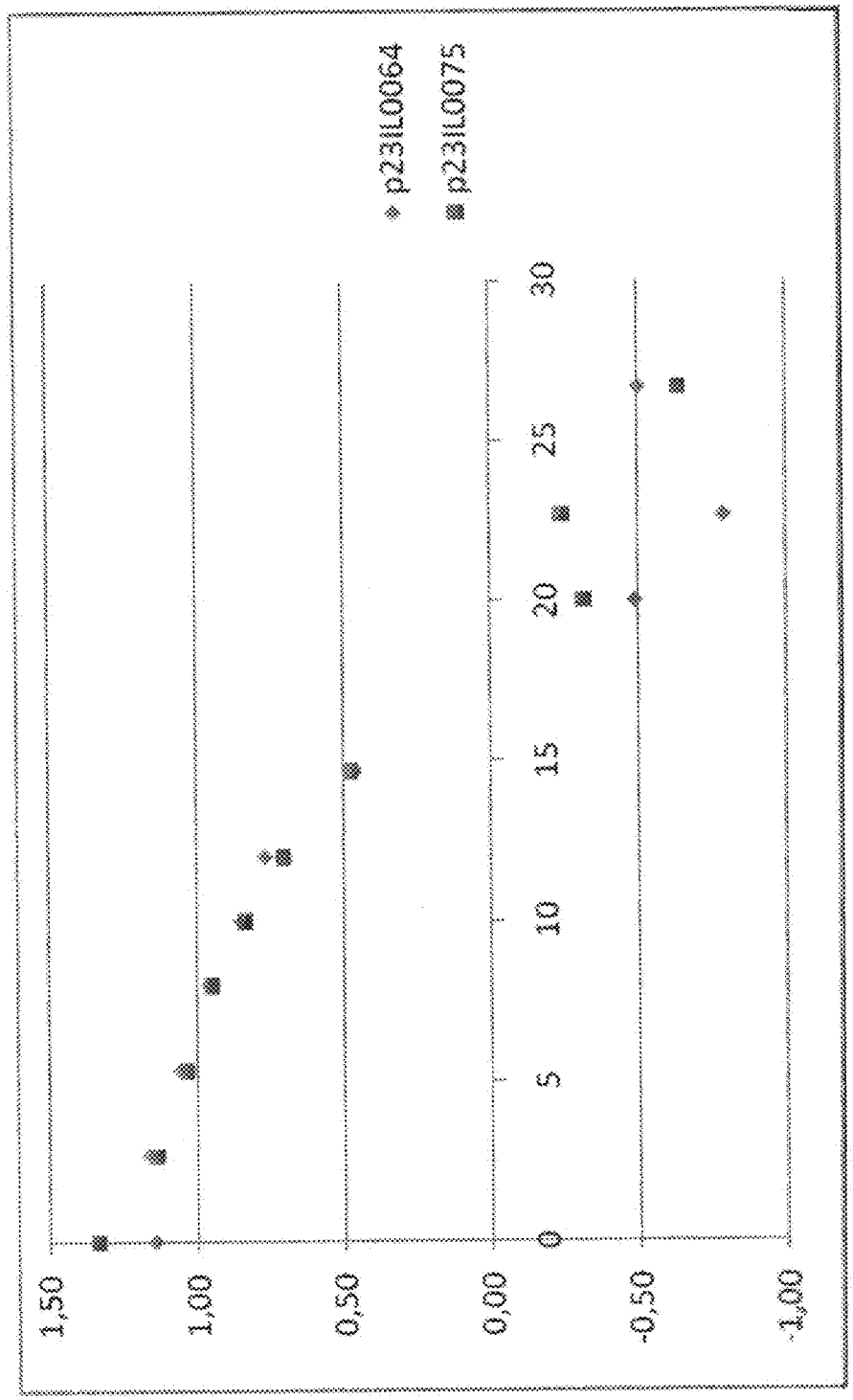

FIG. 36. Log-values of the soluble protein concentration (Y-axis) of p23IL0064 and 23IL0075 in 10 mM phosphate buffer pH 7 with 50 mM NaCl vs. PEG6000 concentration (X-axis). By regression analysis and extrapolation to a zero concentration of PEG6000, the theoretical maximum protein concentrations (apparent solubility values) were calculated and were for both proteins approximately 50 mg/mL. This number should only be used after confirmation with other techniques.

Figure 37:
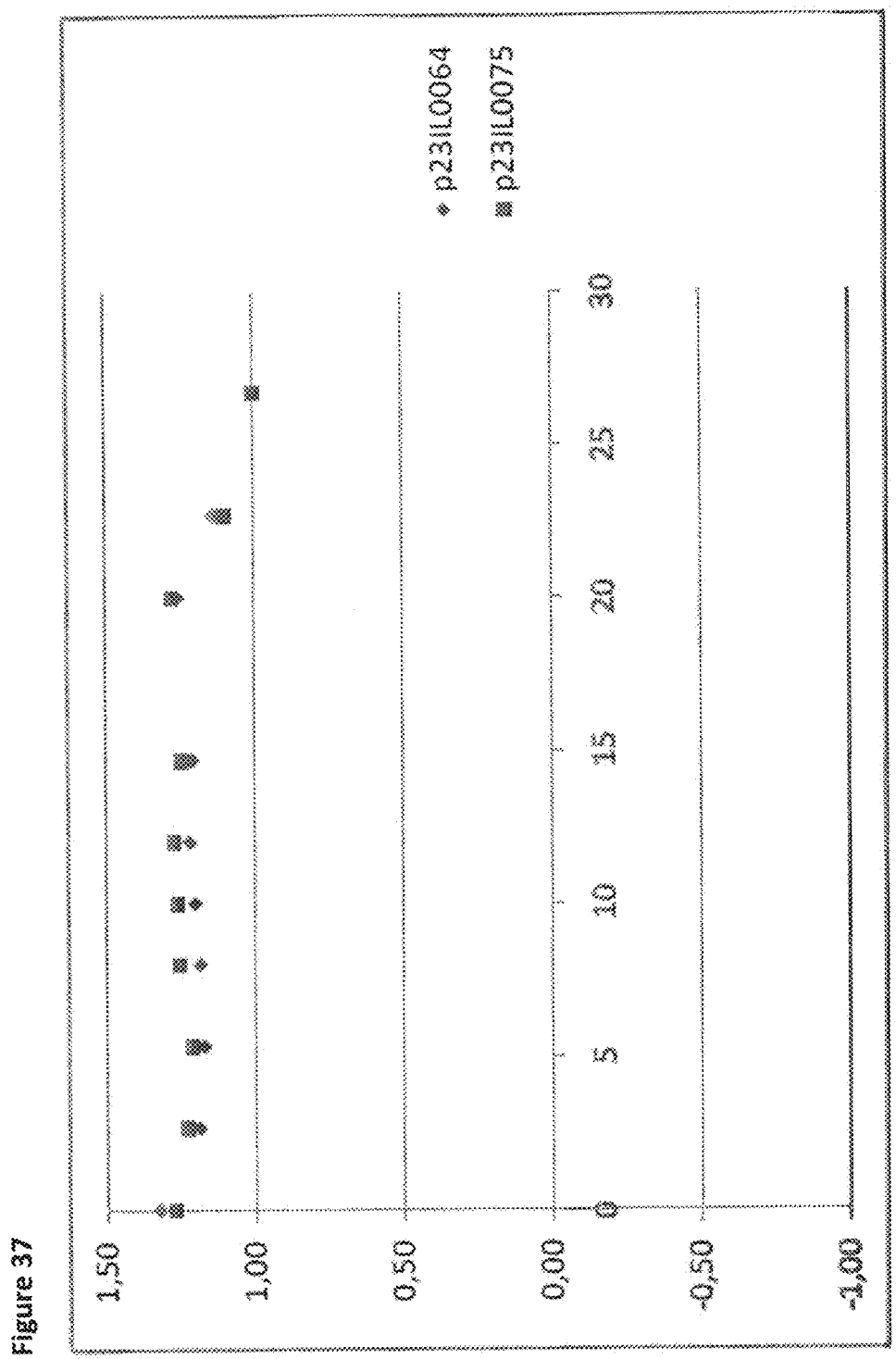

FIG. 37. Log-values of the soluble protein concentration (Y-axis) of p23IL0064 and p23IL0075 in 40 mM histidine pH 6.0 buffer with 50 mM NaCl vs. PEG6000 concentration (X-axis). In this graph regression was not possible since no precipitation occurred in the PEG % window explored.

Figure 38:
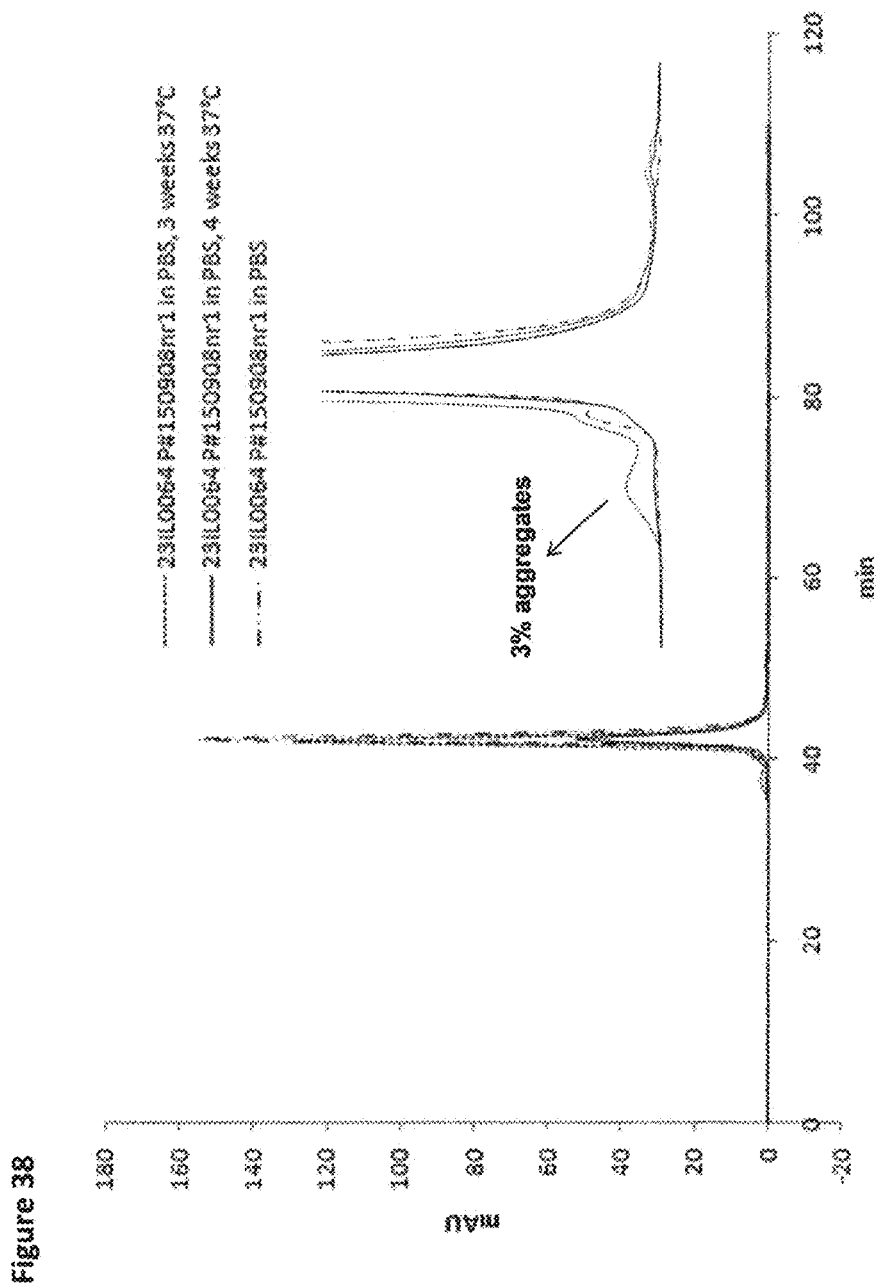

FIG. 38. SE-HPLC chromatograms (280 nm) of 25 μg 23IL0064 non-stressed and 37° C. (3w and 4w)-stressed samples in D-PBS. SE-HPLC was run on TSK-GEL G2000SWXL with D-PBS.

Figure 39:
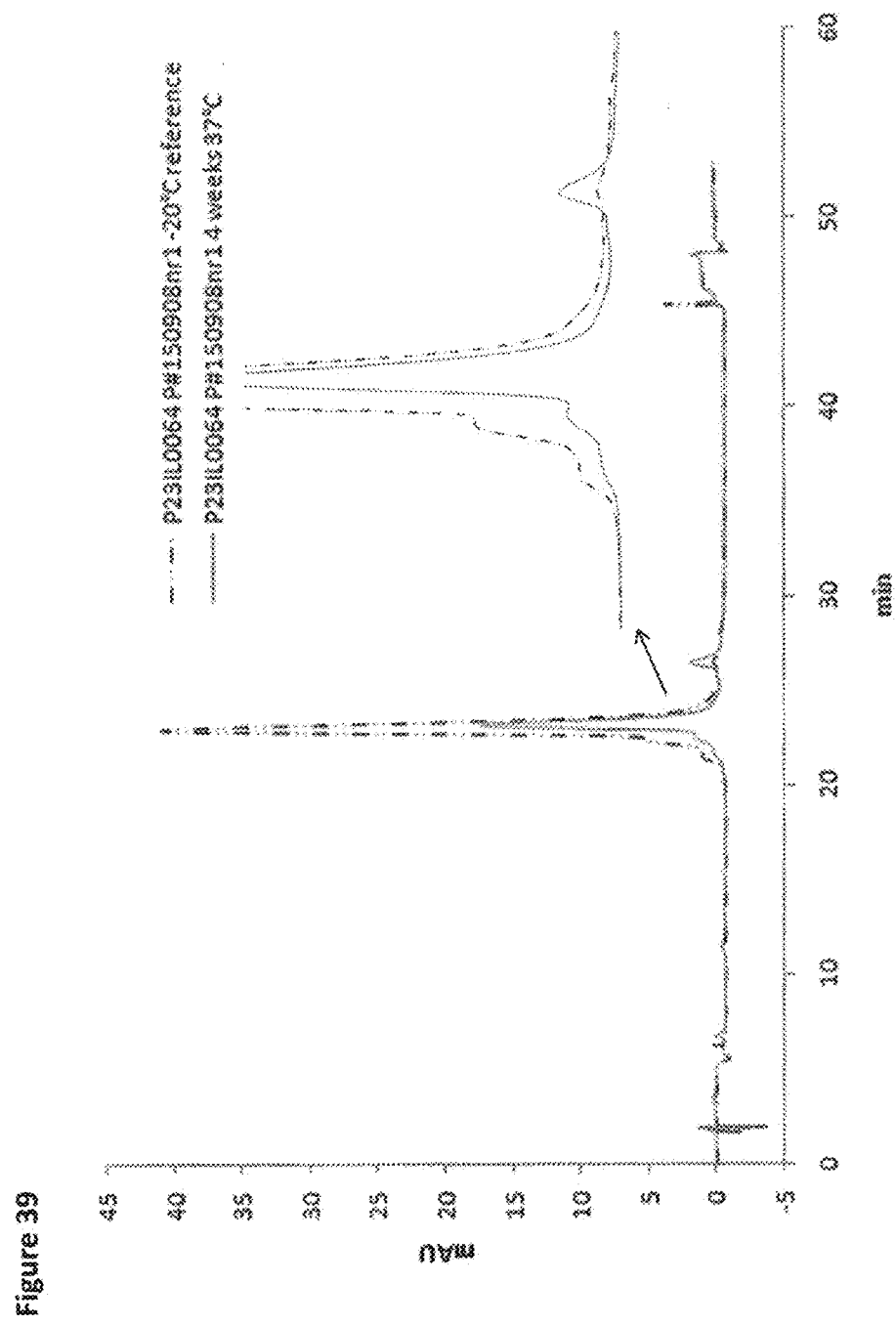

FIG. 39. RP-HPLC chromatograms (280 nm) of 25 μg 23IL0064 non-stressed and 37° C. (4w)-stressed sample in D-PBS. RP-HPLC was run on ZORBAX C-3 column with a water/acetonitrile 0.1% TFA gradient.

Figure 40:
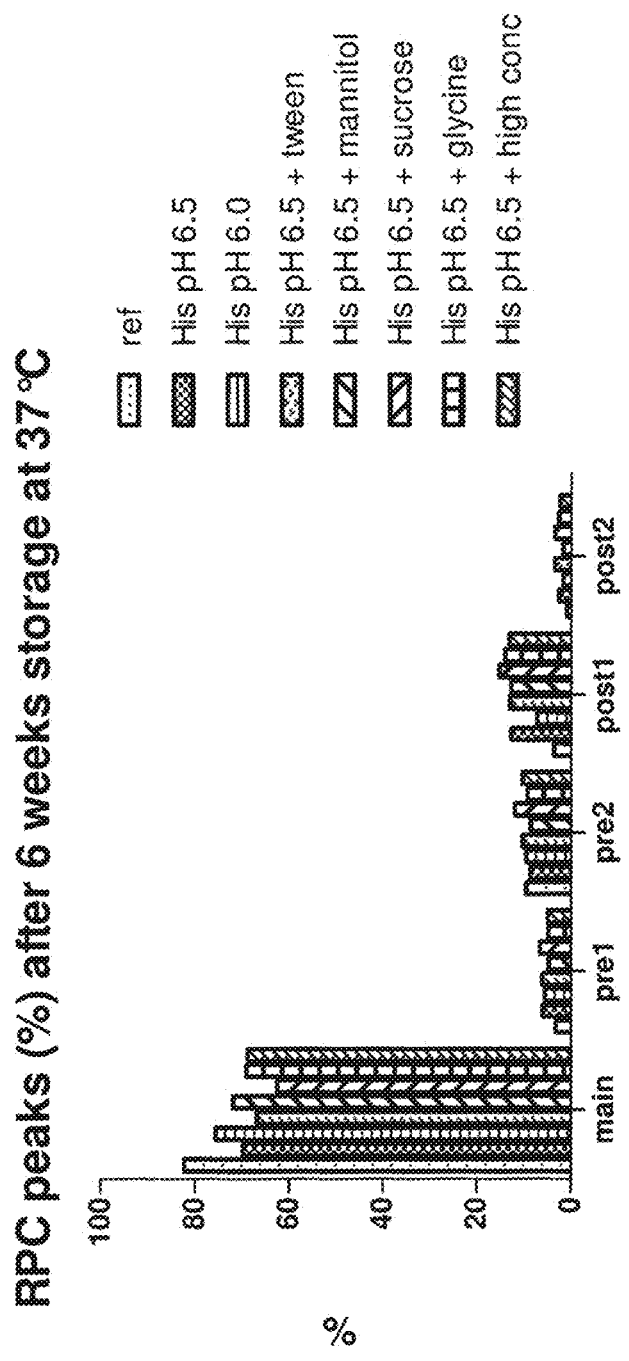

FIG. 40. Graphical representation of the % peak area of the different RP-HPLC peaks of 23IL0064 and product related substances after 6 weeks stress at 37° C. in different formulation buffers. The first bar represents the reference sample, stored at −80° C. until analysis. The pre-peak 2 was present in the start sample and did not increase during the storage at 37° C.

Figure 41:
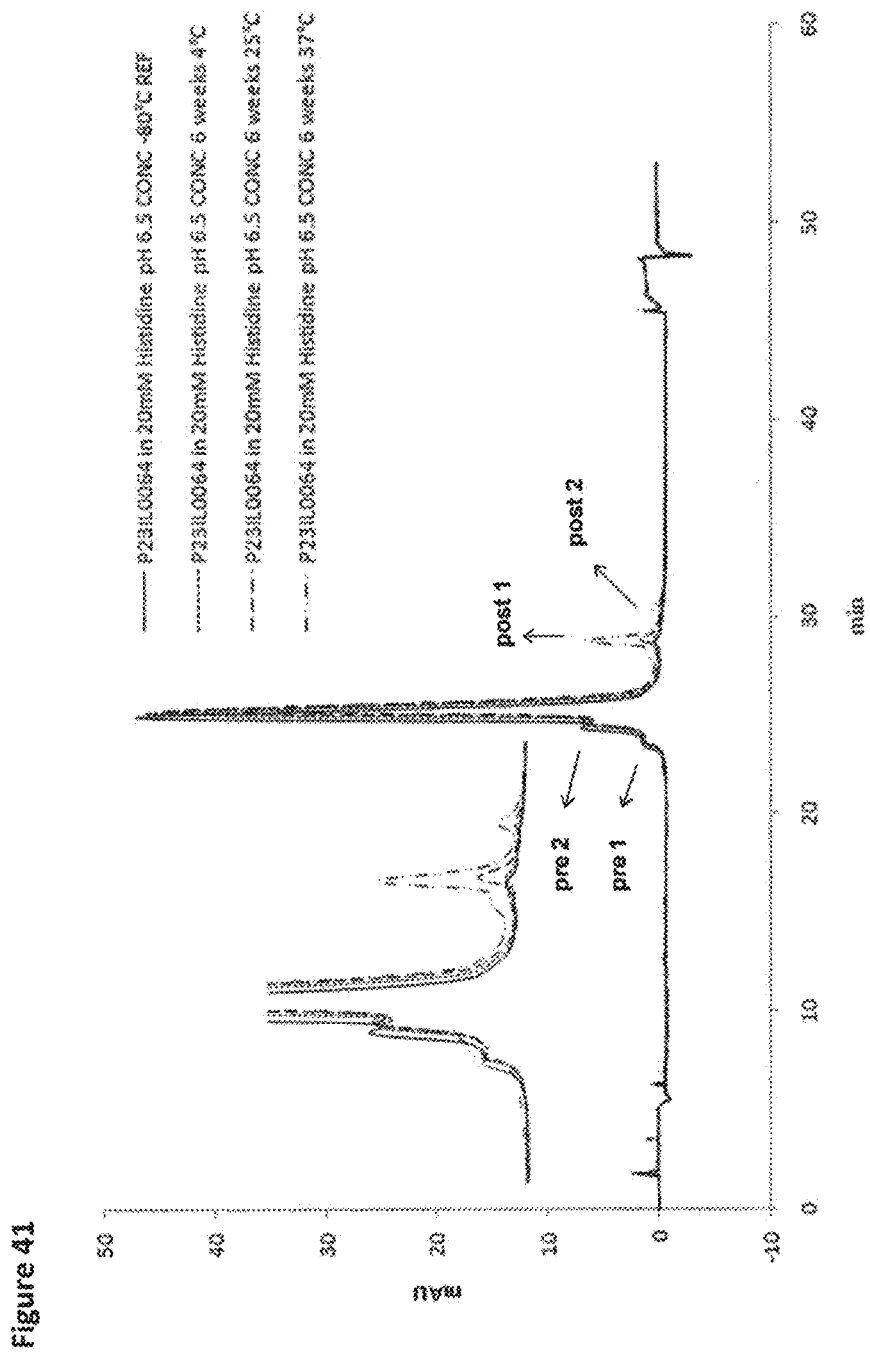

FIG. 41. Overlay of RP-HPLC chromatograms (280 nm) of 23IL0064 in 20 mM Histidine pH 6.5 (conc. 22.4 mg/mL). Comparison of 6 weeks 37° C., 6 weeks 25° C., 6 weeks 4° C., and −80° C. reference. RP-HPLC was run on ZORBAX 300SB-C3 column with a water/acetonitrile 0.1% TFA gradient 0.3%/min) at 75° C.

Figure 42:
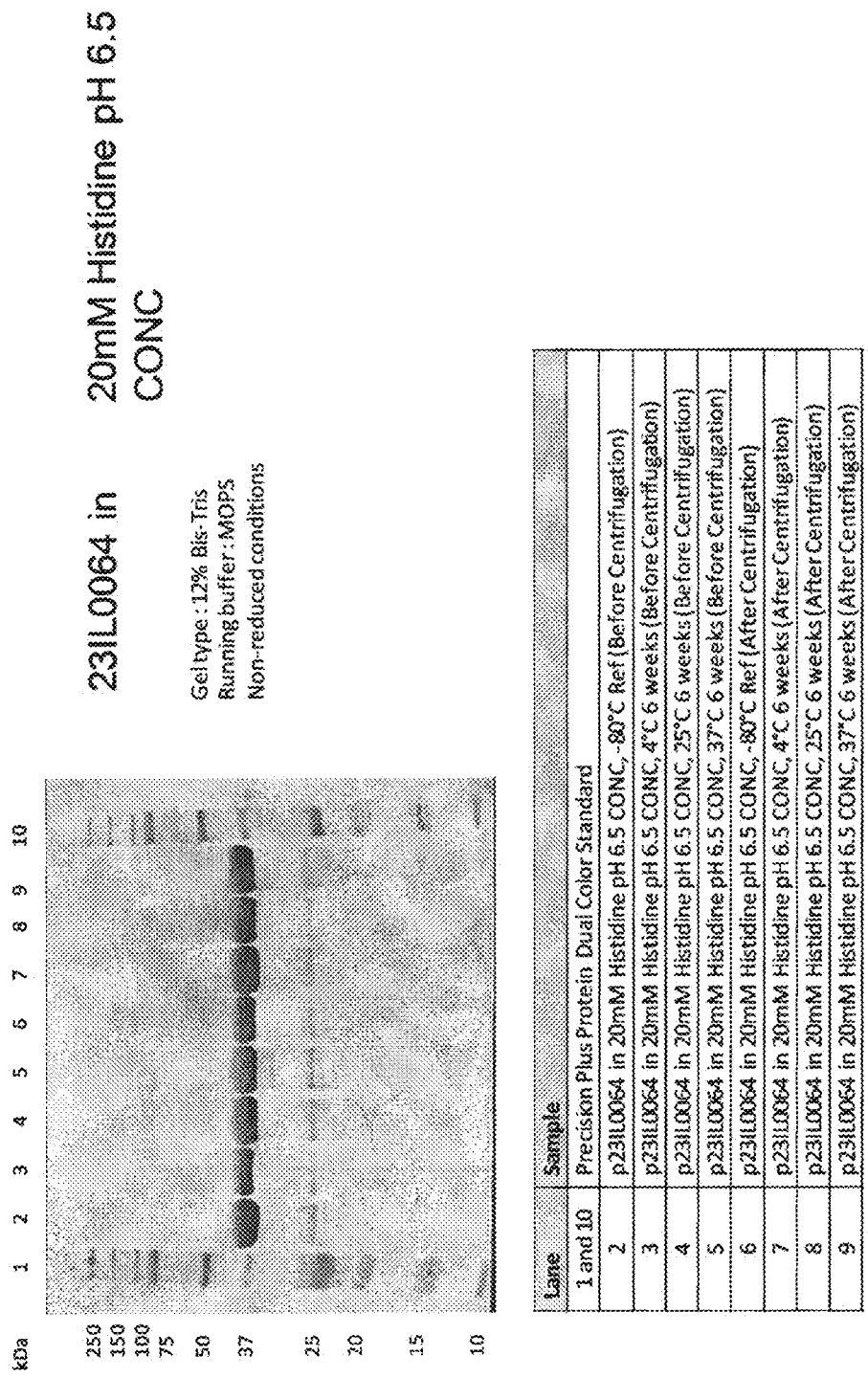

FIG. 42. SDS-PAGE of stability samples of 23IL0064 in 20 mM Histidine pH 6.5 CONC stressed for 6 weeks at 4° C., 25° C., 37° C. and its −80° C. Reference.

Figure 43:
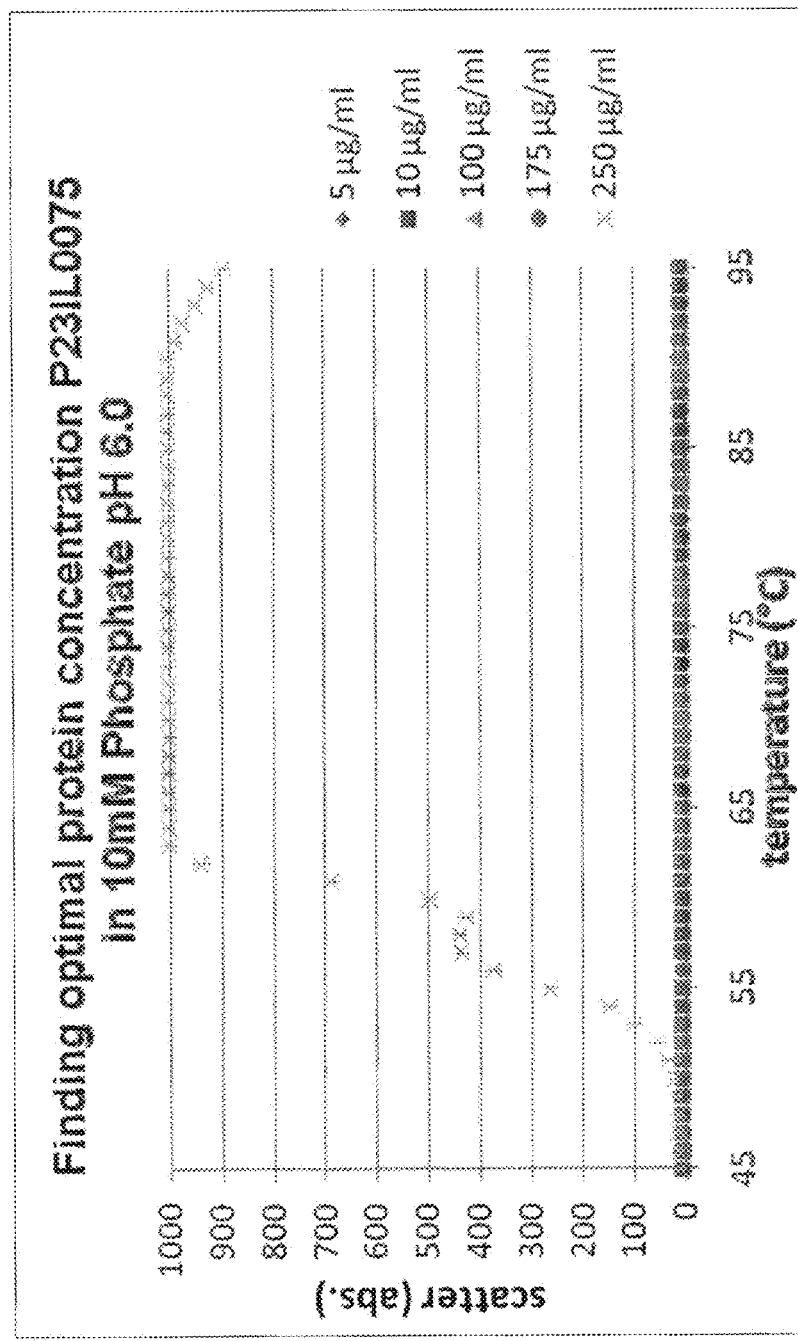

FIG. 43. Elastic light scattering as measured at 500 nm as a function of the temperature for 23IL0075 samples with different concentrations (as indicated in the legend).

Figure 44:
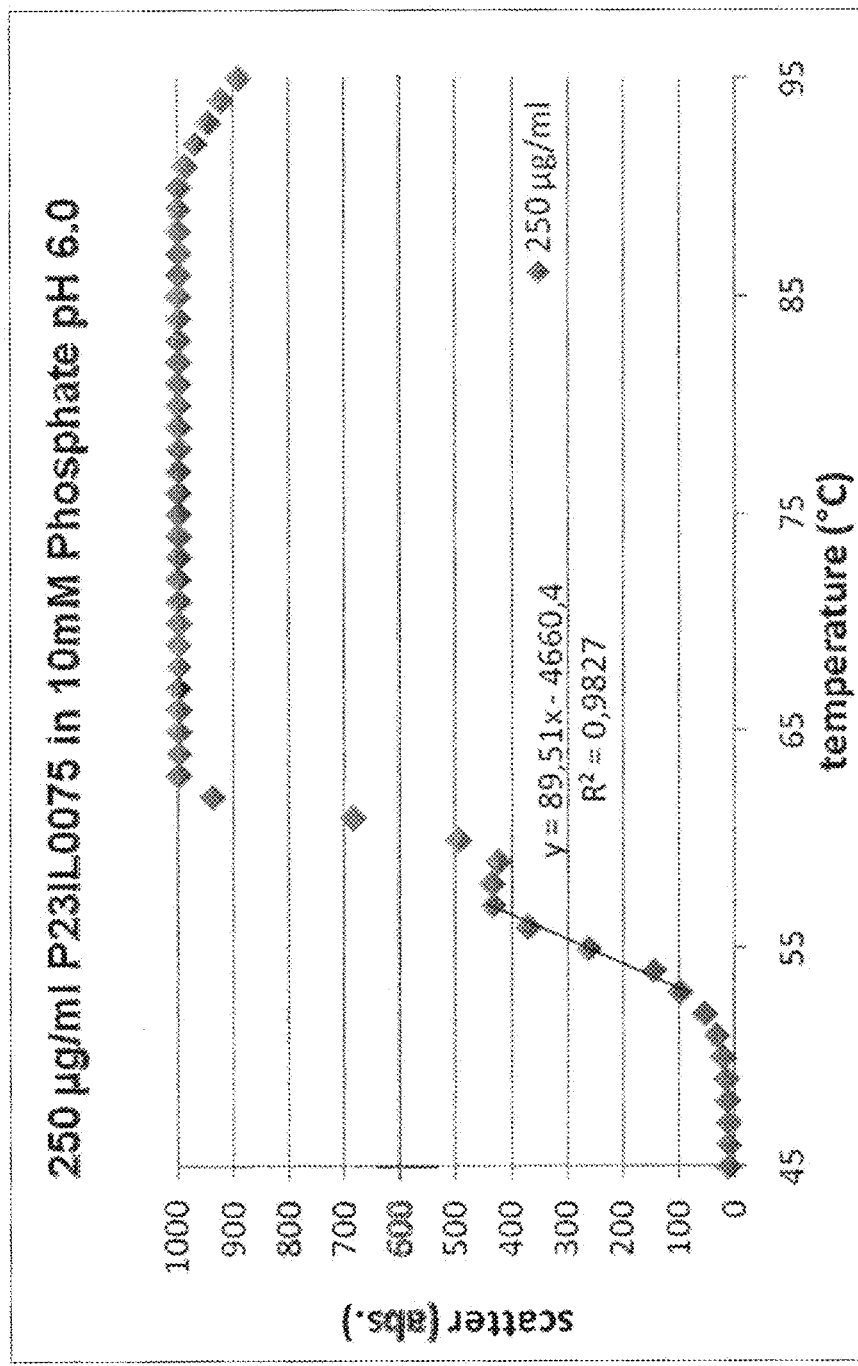

FIG. 44. Elastic light scattering as measured at 500 nm as a function of the temperature for 250 μg/mL 23IL0075 in 10 mM phosphate pH 6.0. The temperature of the onset of aggregate formation is determined by means of linear fit.

Figure 45:
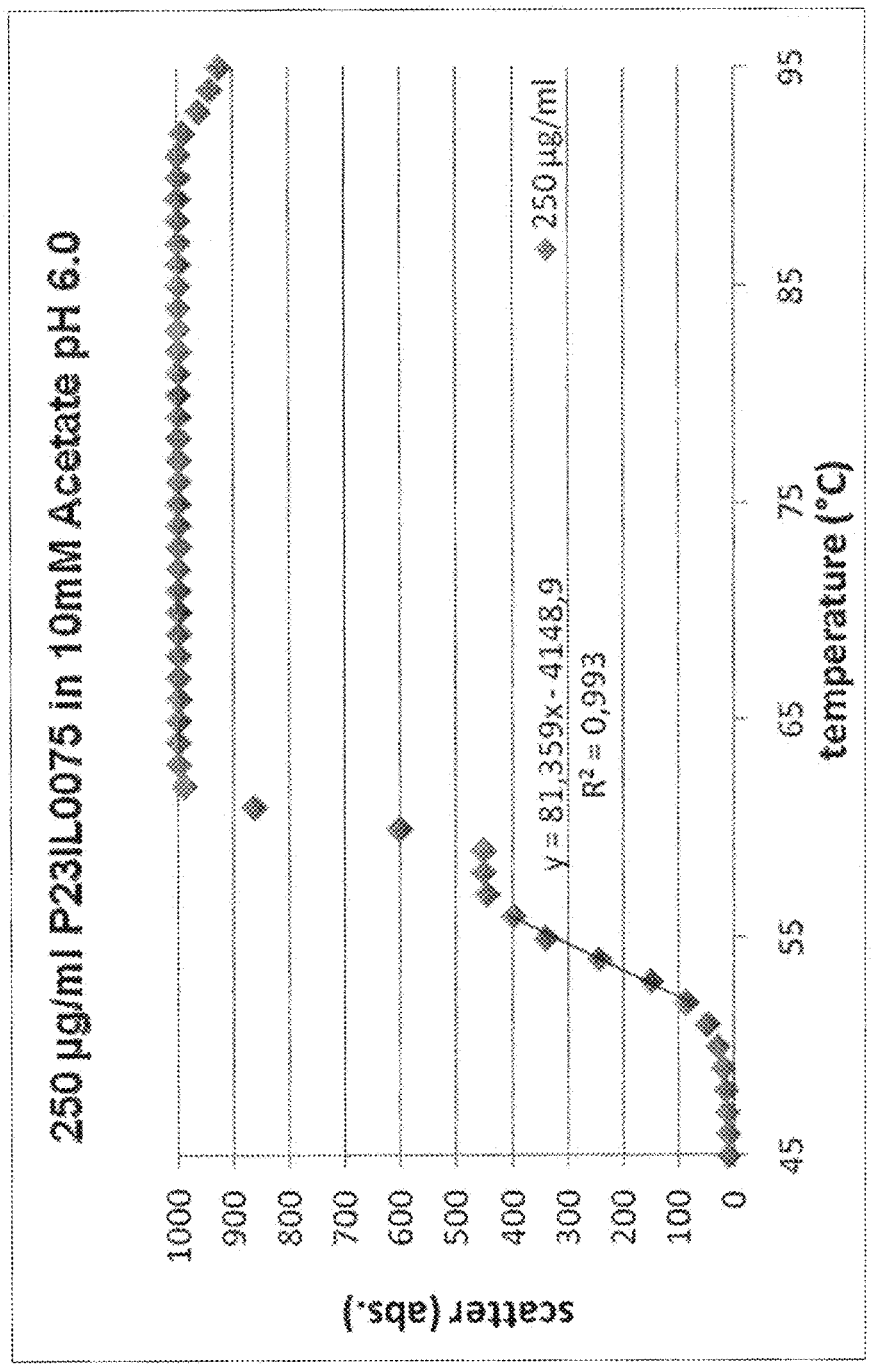

FIG. 45. Elastic light scattering as measured at 500 nm as a function of the temperature for 250 μg/mL 23IL0075 in 10 mM Acetate pH 6.0. The temperature of the onset of aggregate formation is determined by means of linear fit.

Figure 46:
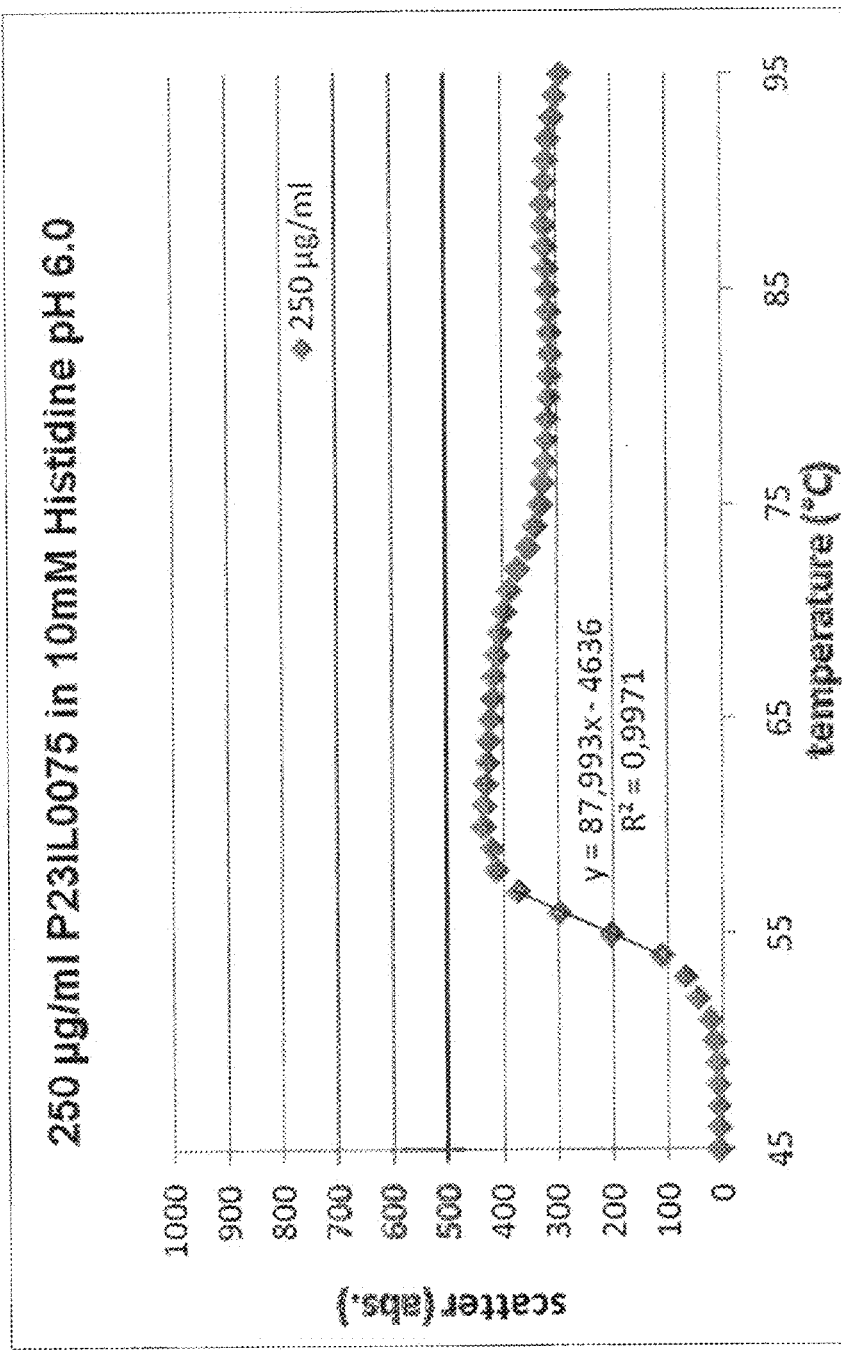

FIG. 46. Elastic light scattering as measured at 500 nm as a function of the temperature for 250 μg/mL 23IL0075 in 10 mM Histidine pH 6.0. The temperature of the onset of aggregate formation is determined by means of linear fit.

Figure 47:
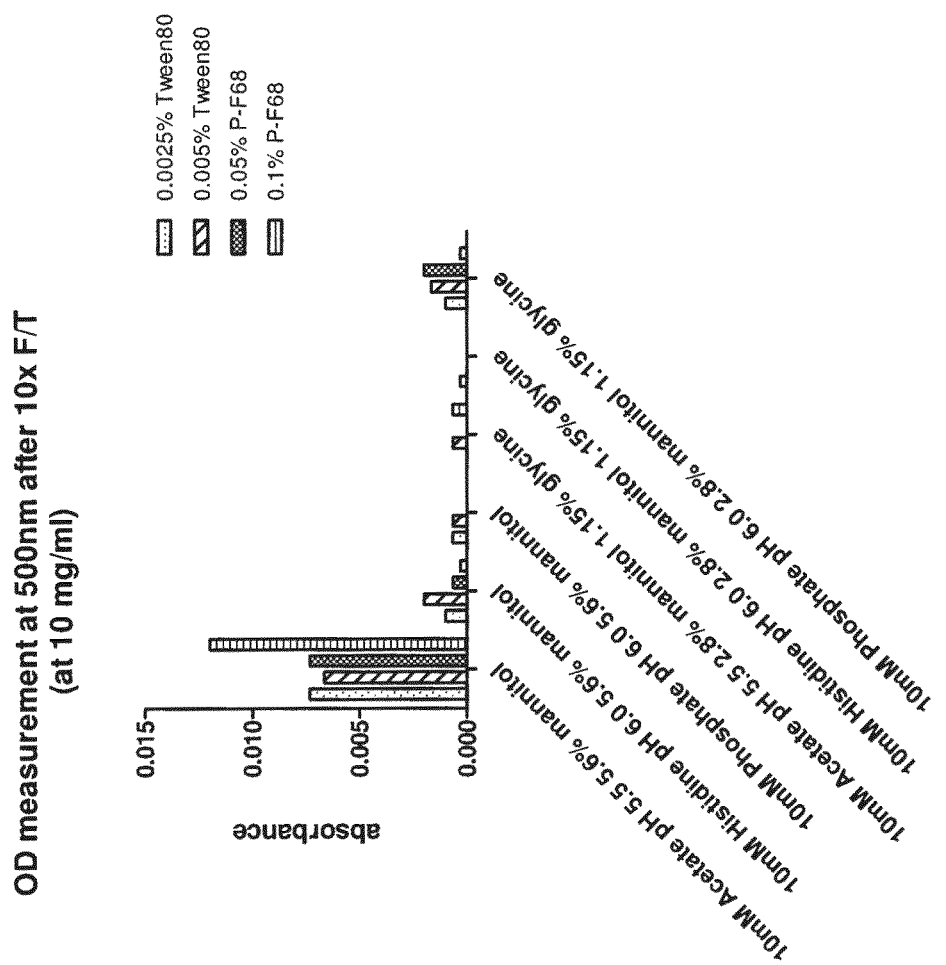
Figure 47:
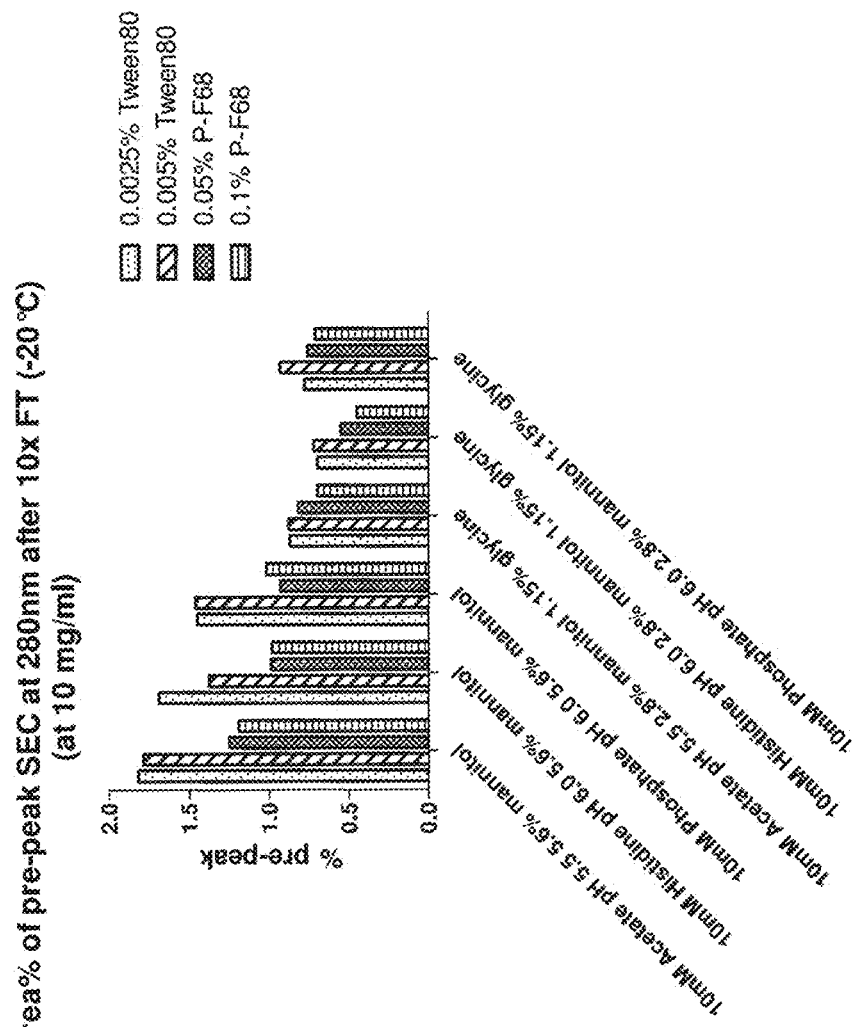

FIG. 47. Graphical representation of the opalescence (measured by OD500) (A) and the % oligomers (% pre-peak) detected in SE-HPLC (B) after freeze/thaw stress. The percentage of oligomers in the reference sample was approximately 0.4%. In this study, an acetate, a histidine and a phosphate buffer were compared, in combination with mannitol or a mixture of mannitol and glycine as excipients, and TWEEN (polysorbate) 80 or poloxamer in two different concentrations as surfactants.

Figure 48:
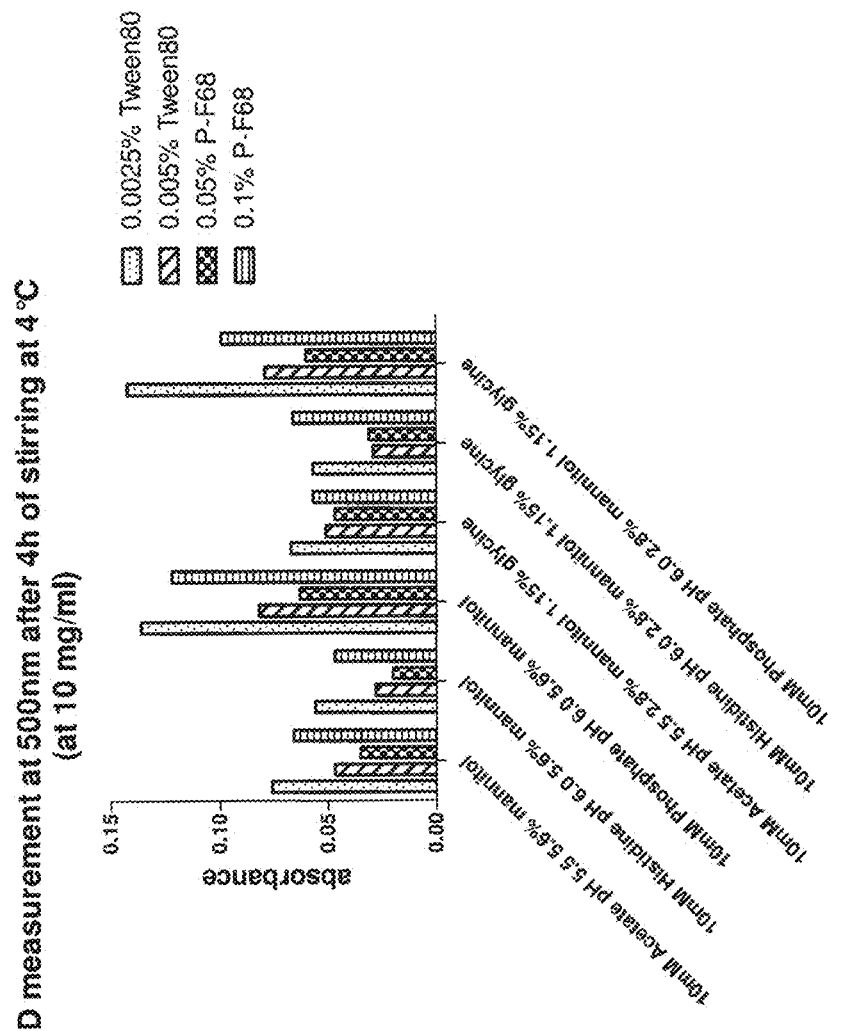
Figure 48:
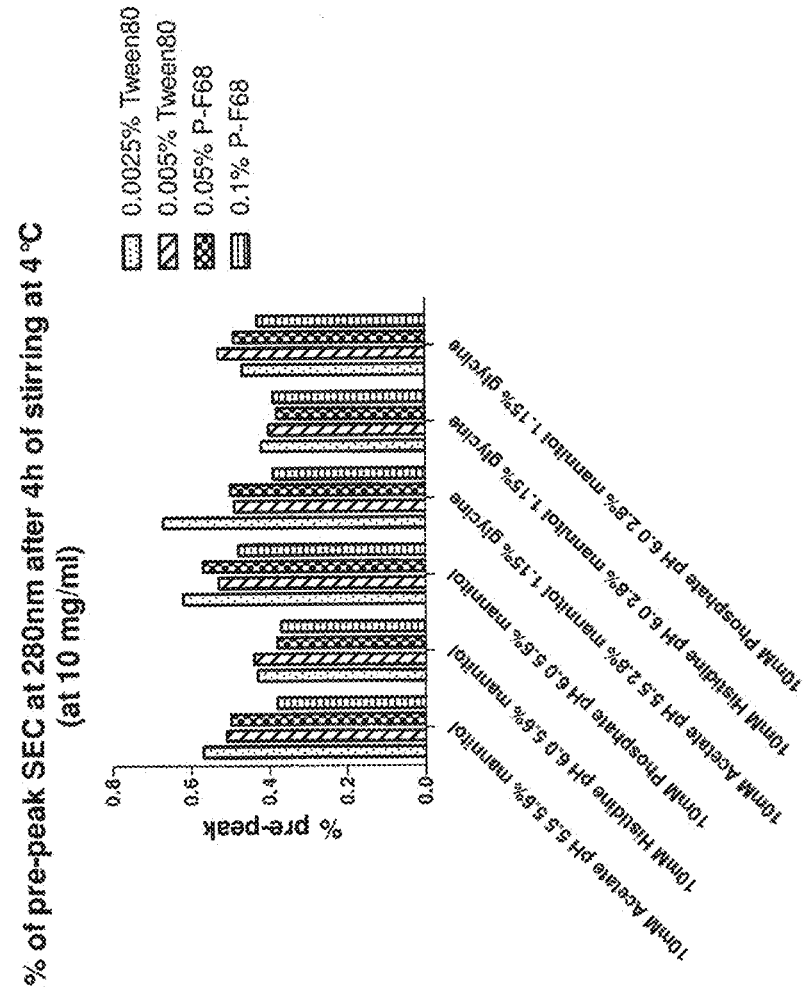

FIG. 48. Graphical representation of the opalescence (measured by OD500) (A) and the % oligomers detected in SE-HPLC (B) after shear stress. The percentage of oligomers in the reference sample was approximately 0.4%. In this study, an acetate, a histidine and a phosphate buffer were compared, in combination with mannitol or a mixture of mannitol and glycine as excipients, and TWEEN (polysorbate) 80 or poloxamer in two different concentrations as surfactants.

Figure 49:
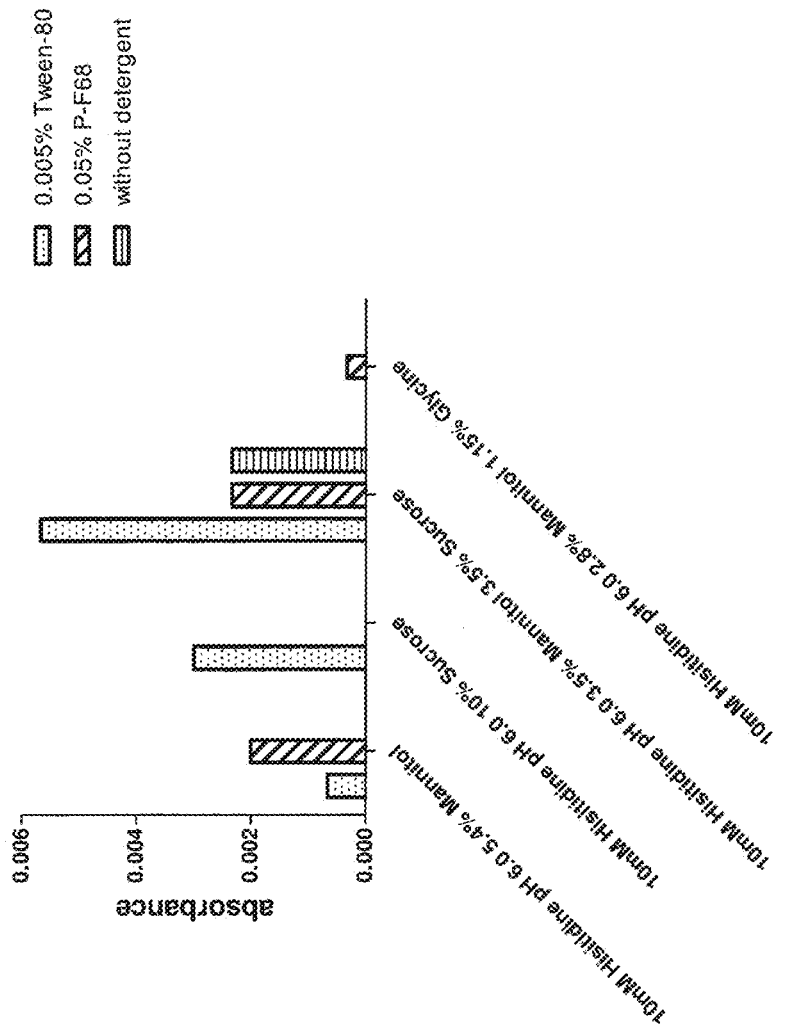
Figure 49:
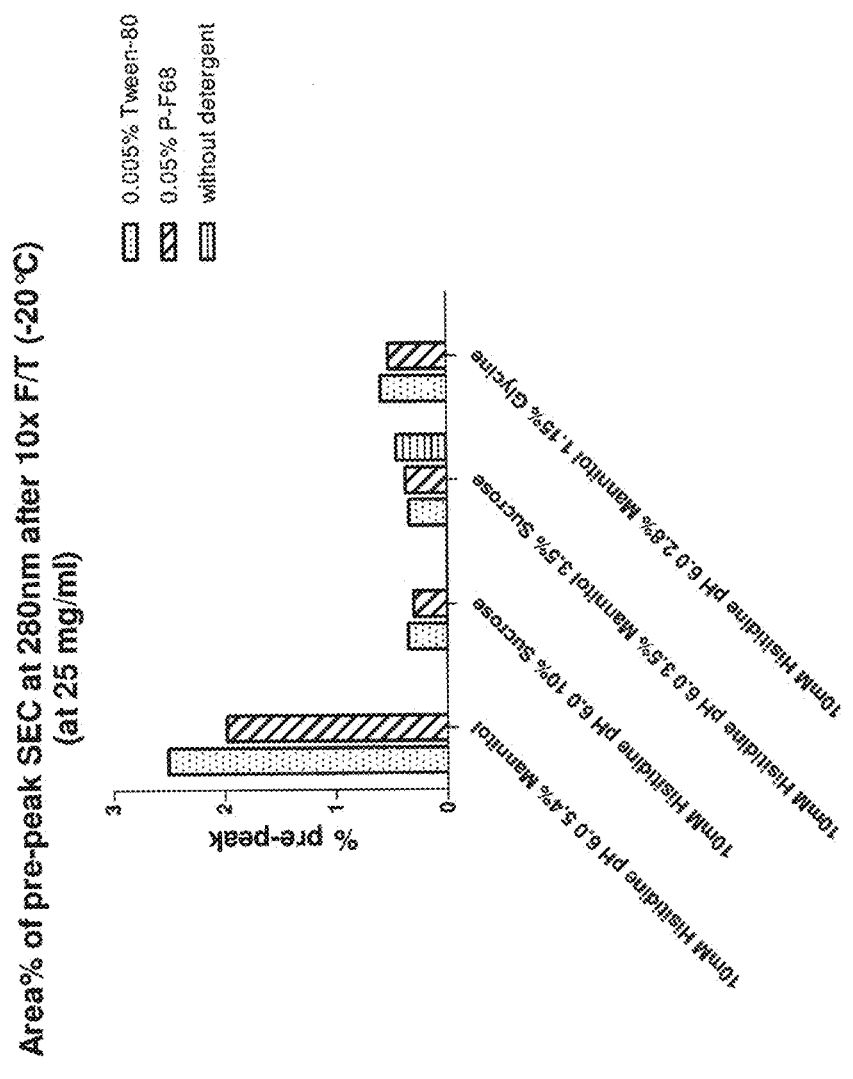

FIG. 49. Graphical representation of the opalescence (measured by OD500) (A), and the % oligomers detected in SE-HPLC (B) in different histidine buffers after freeze/thaw stress. The percentage of oligomers in the reference sample was approximately 0.4%.*For one sample the condition without detergent was included.

Figure 50:
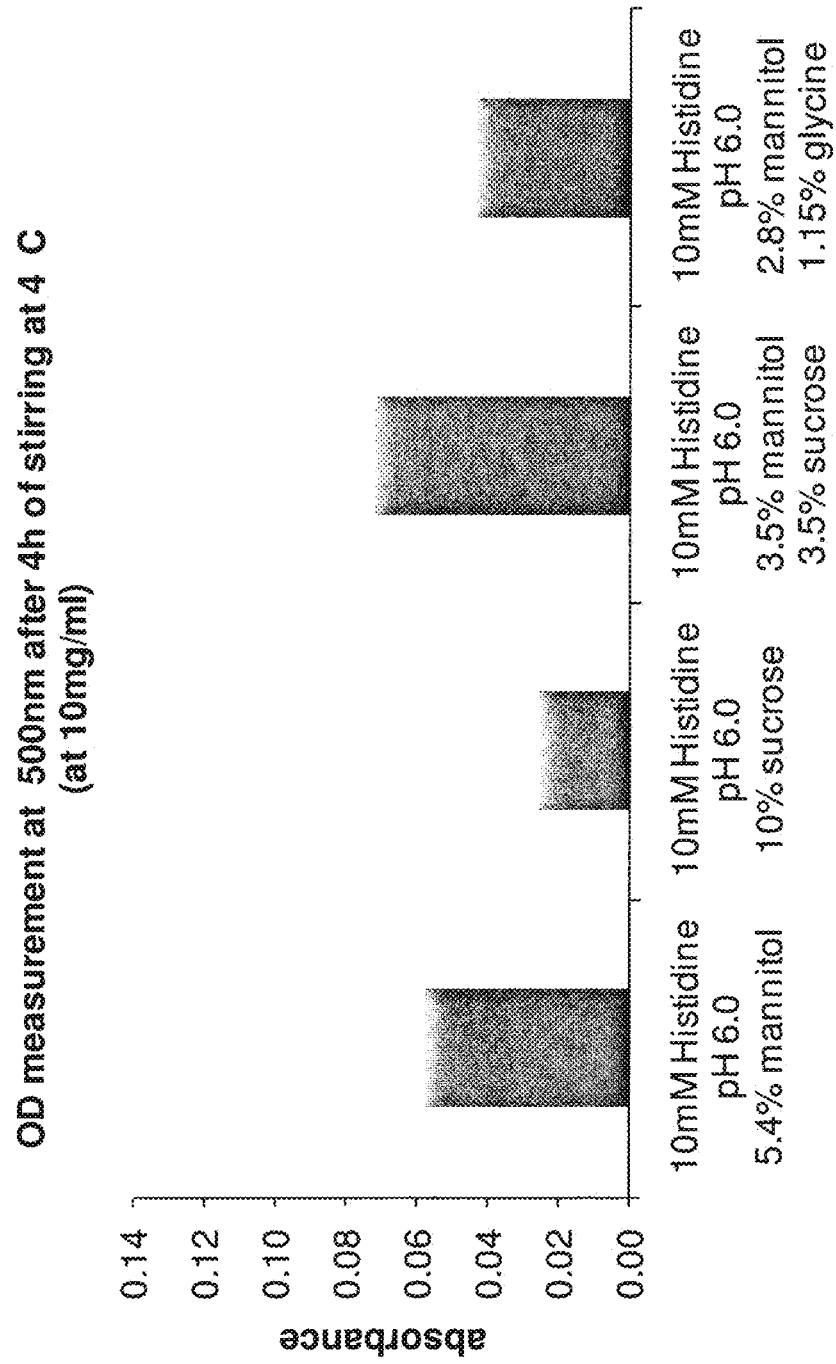
Figure 50:
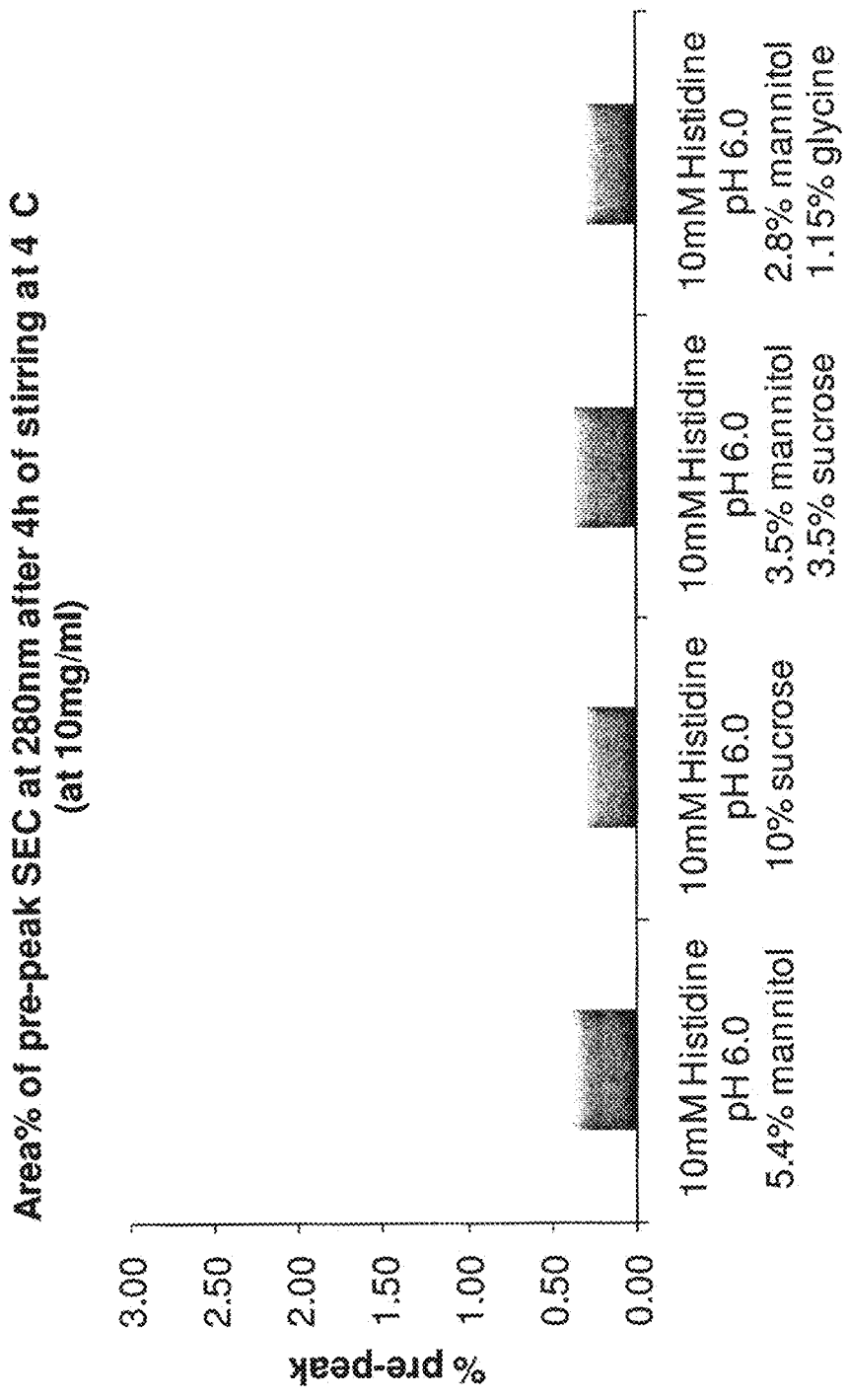
Figure 50:
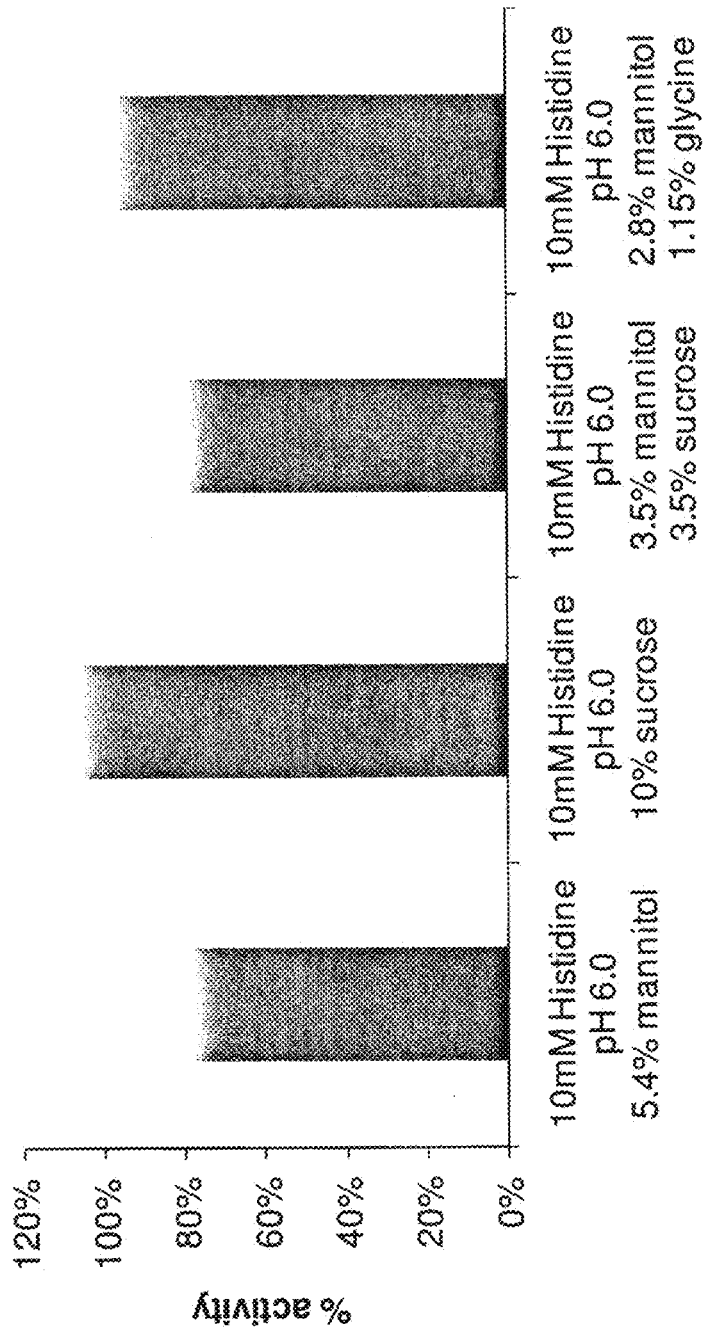

FIG. 50. Graphical representation of the opalescence (measured by OD500) (A), the % oligomers detected in SE-HPLC (B), and the % activity (albumin binding) of the Nanobody measured on BIACORE (C) after shear stress. The percentage of oligomers in the reference sample was approximately 0.4%. In this study no detergents were included, to mimic the situation during the final concentration step of the DSP process.

Figure 51:
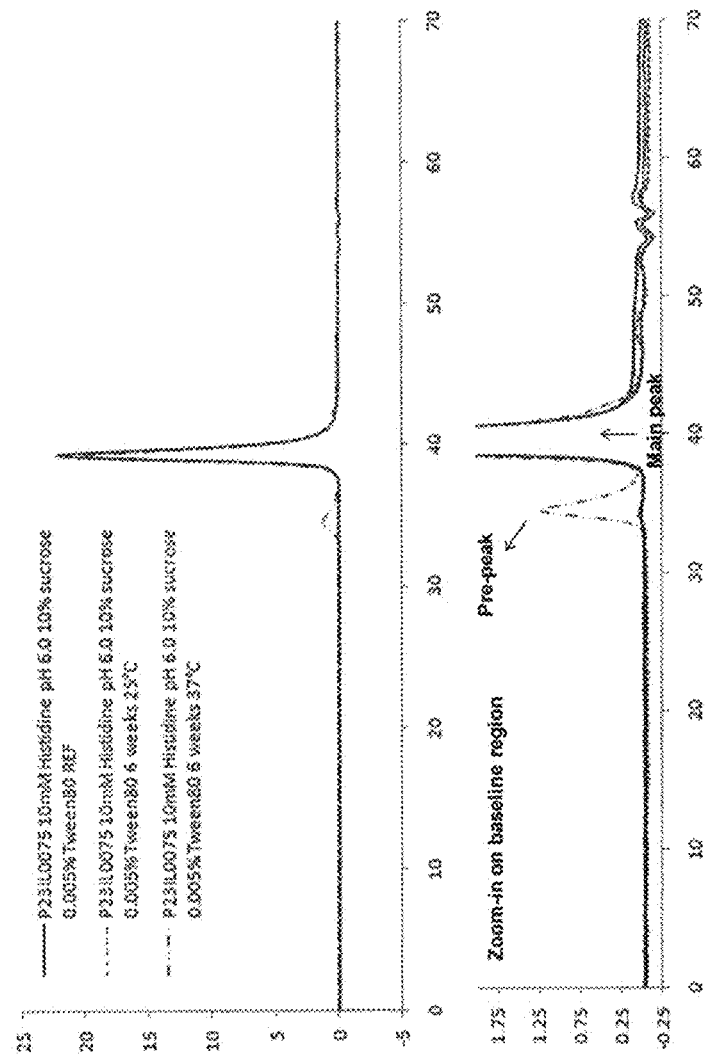

FIG. 51. SE-HPLC chromatograms (280 nm) of 23IL0075 at 25 mg/mL in 10 mM Histidine pH 6.0, 10% sucrose, 0.005% TWEEN (polysorbate) 80: the reference sample compared to 6 weeks storage at 25° C. and 37° C.

FIG. 52: Hallmark Residues in single variable domains.

Figure 53A:
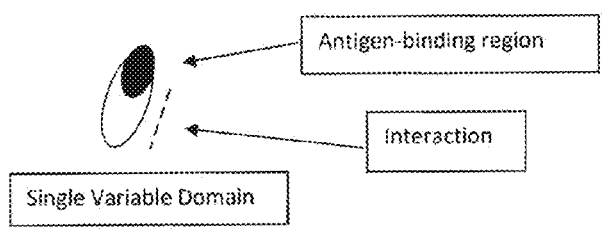

FIG. 53a+b: Illustration of various non-fused dimers (i.e. NFDs) and comparison with the conventional genetically fused molecules. Single Variable Domains in each construct or NFD may be different (53a+b) or identical (53a). The dashed line is a schematic interaction between the 2 VH domains that confer the NFD its stability (indicated here are surface interactions but these can also be other interaction as described in the invention herein).

Figure 54:
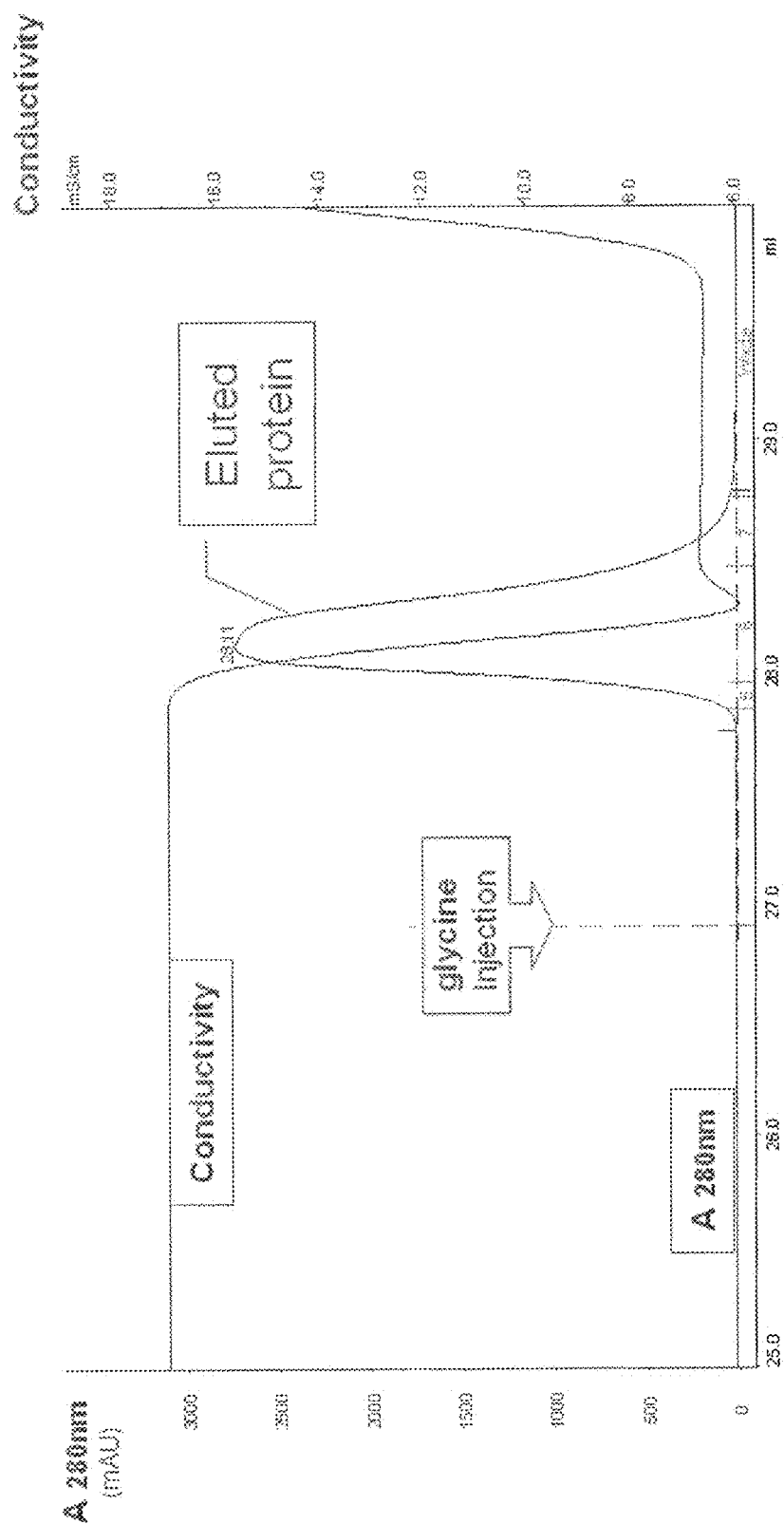

FIG. 54: Protein A affinity purification of polypeptide A (SEQ ID NO: 7) under conditions resulting in significant amounts of NFDs. The protein was loaded on a small column (400 µl resin MabSelectXtra, GE Healthcare) and eluted via injection of glycine [100 mM, pH=2.5]. The pH of the eluted Nanobody® solution was immediately neutralized using 1M Tris pH 8.8.

Figure 55:
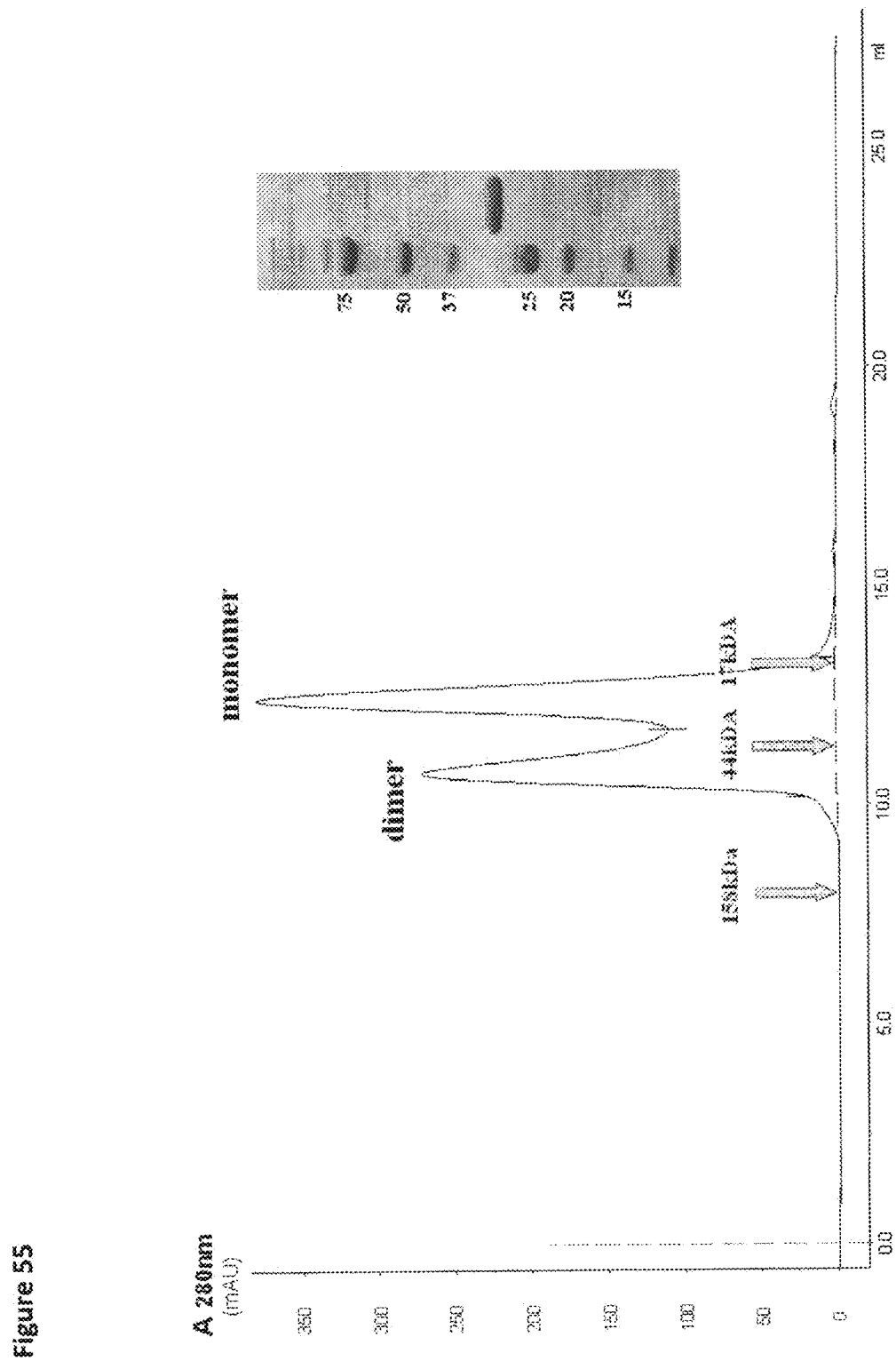

FIG. 55: Size exclusion chromatography of Protein A affinity purified polypeptide A. Separation of concentrated polypeptide A (fraction 6, see FIG. 54) on an analytical SUPERDEX 75 column (GE Healthcare). The Nanobody® fraction was resolved into two specific fractions corresponding to the molecular weight of monomeric and dimeric polypeptide A (position of molecular weight markers is indicated). Analysis via SDS-PAGE (right panel) did not reveal any difference between the two, indicating that under native conditions they behave as monomer and dimer. The latter is converted into a monomer conformation upon denaturation (SDS detergent and heat treatment).

Figure 56:
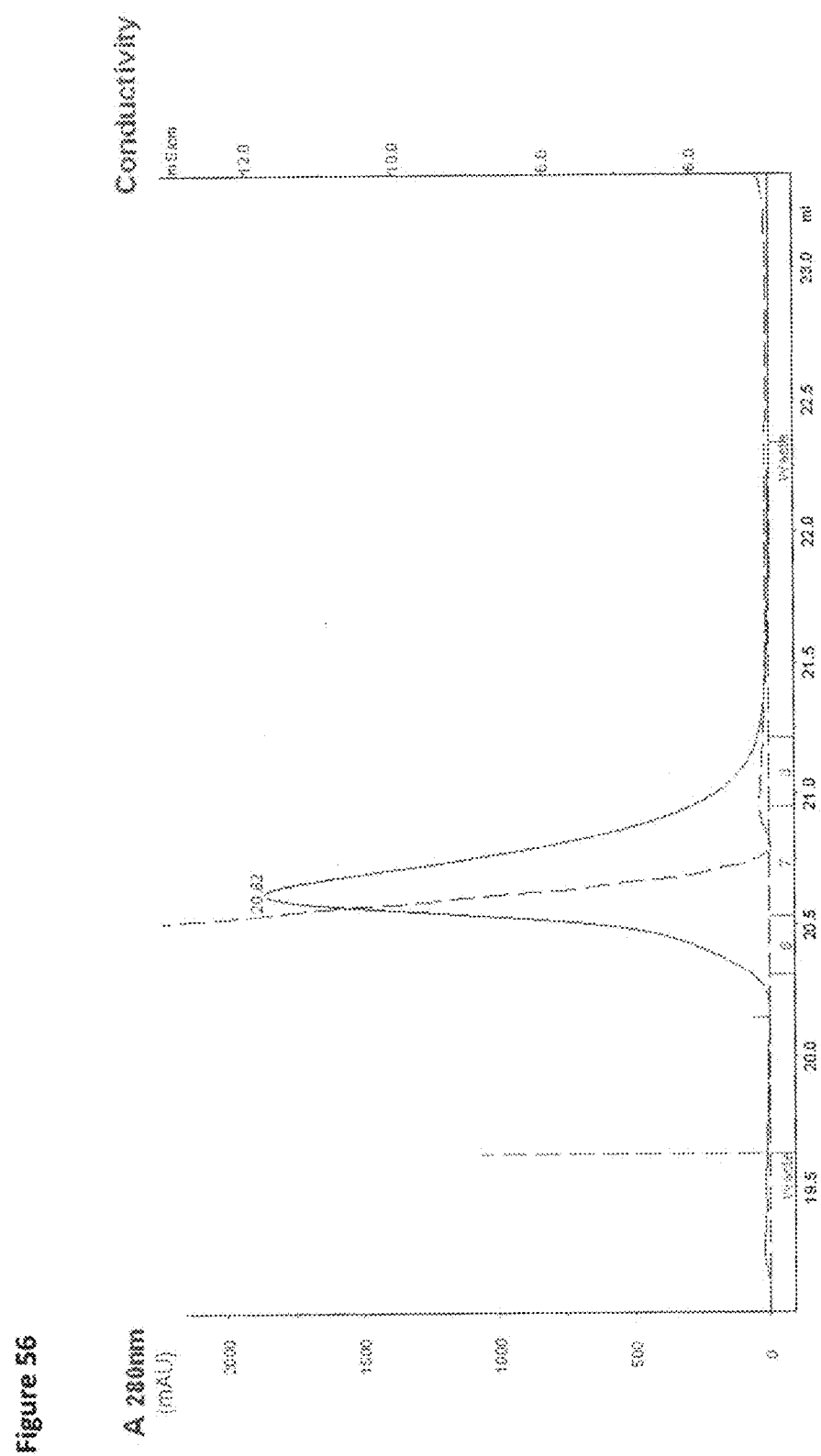

FIG. 56: Protein A affinity purification of polypeptide A at low column load. A limited amount of protein [approx. 2.5 mg/ml resin] was loaded on a small column (400 µl resin MabSelectXtra, GE Healthcare) and eluted via injection of glycine [100 mM, pH=2.5]. The pH of the eluted Nanobody® solution was immediately neutralized using 1M Tris pH 8.8.

Figure 57:
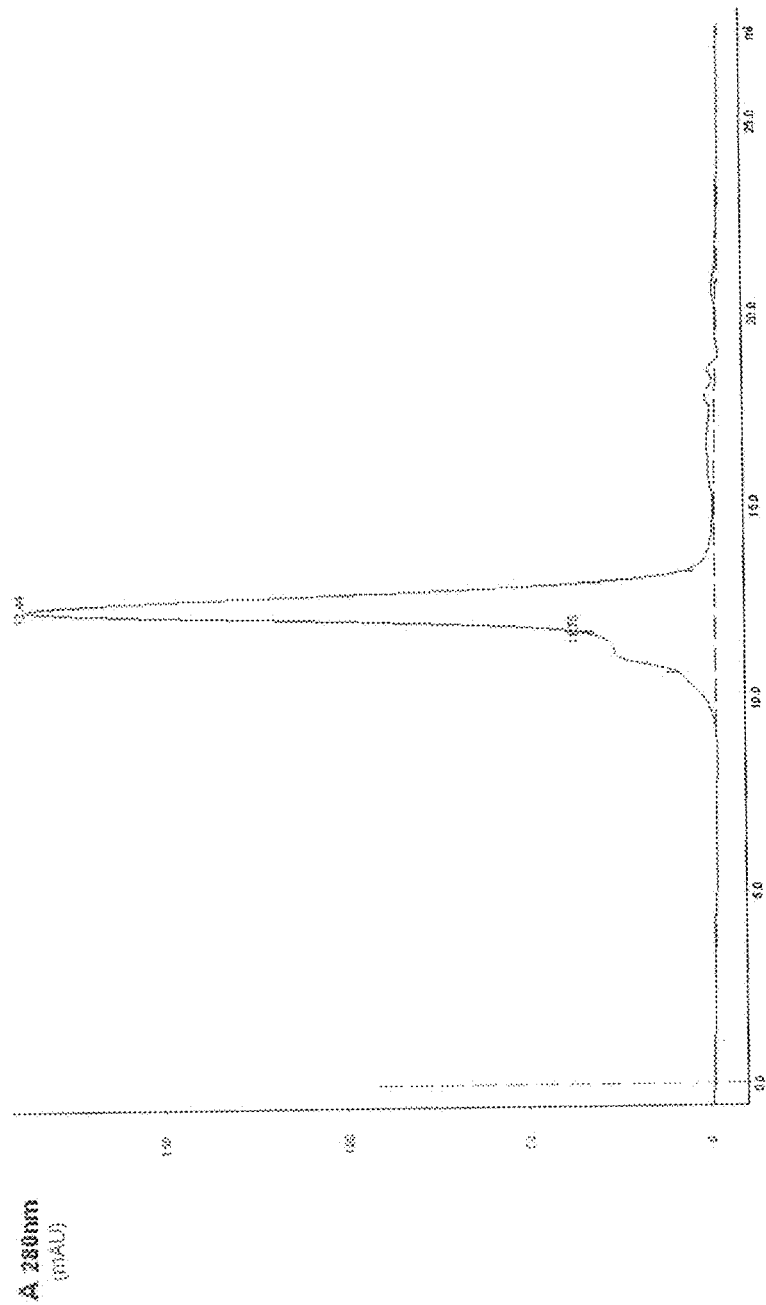

FIG. 57: Size exclusion chromatography of Protein A affinity purified polypeptide A. Separation of concentrated polypeptide A (fraction 7, see FIG. 56) on an analytical SUPERDEX 75 column (GE Healthcare). The Nanobody® fraction was resolved into a specific fraction corresponding to the molecular weight of monomeric polypeptide.

Figure 58:
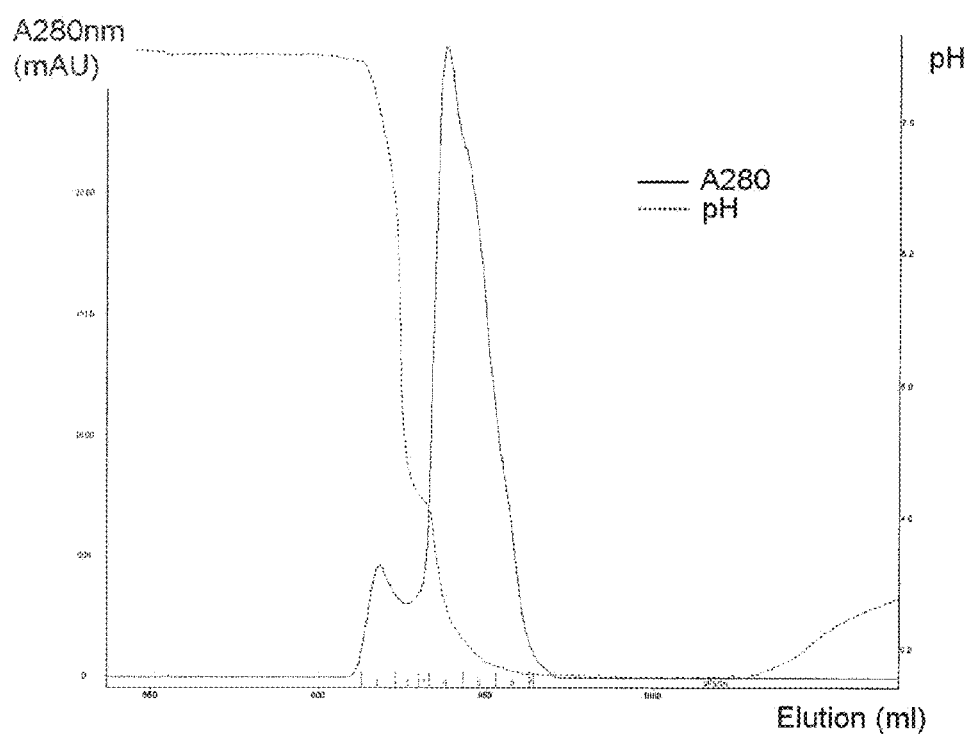

FIG. 58: Protein A elution of Polypeptide A. The pretreated periplasmic extract was loaded on a Protein A MabSelectXtra column, followed by a PBS wash until stable baseline. Elution was carried out via a pH shift using 100 mM glycine pH=2.5 (dotted line).

Figure 59:
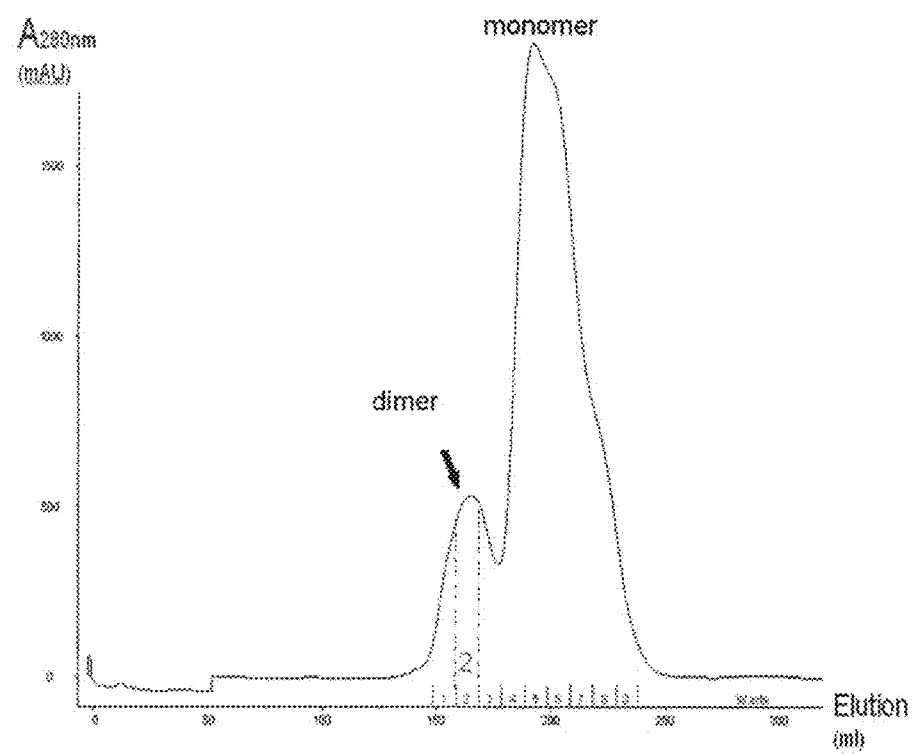

FIG. 59: Size Exclusion Chromatography of Polypeptide A monomer and dimer. The pre-peak (fraction 2) contains the dimeric Polypeptide A which was used in the stability studies.

Figure 60:
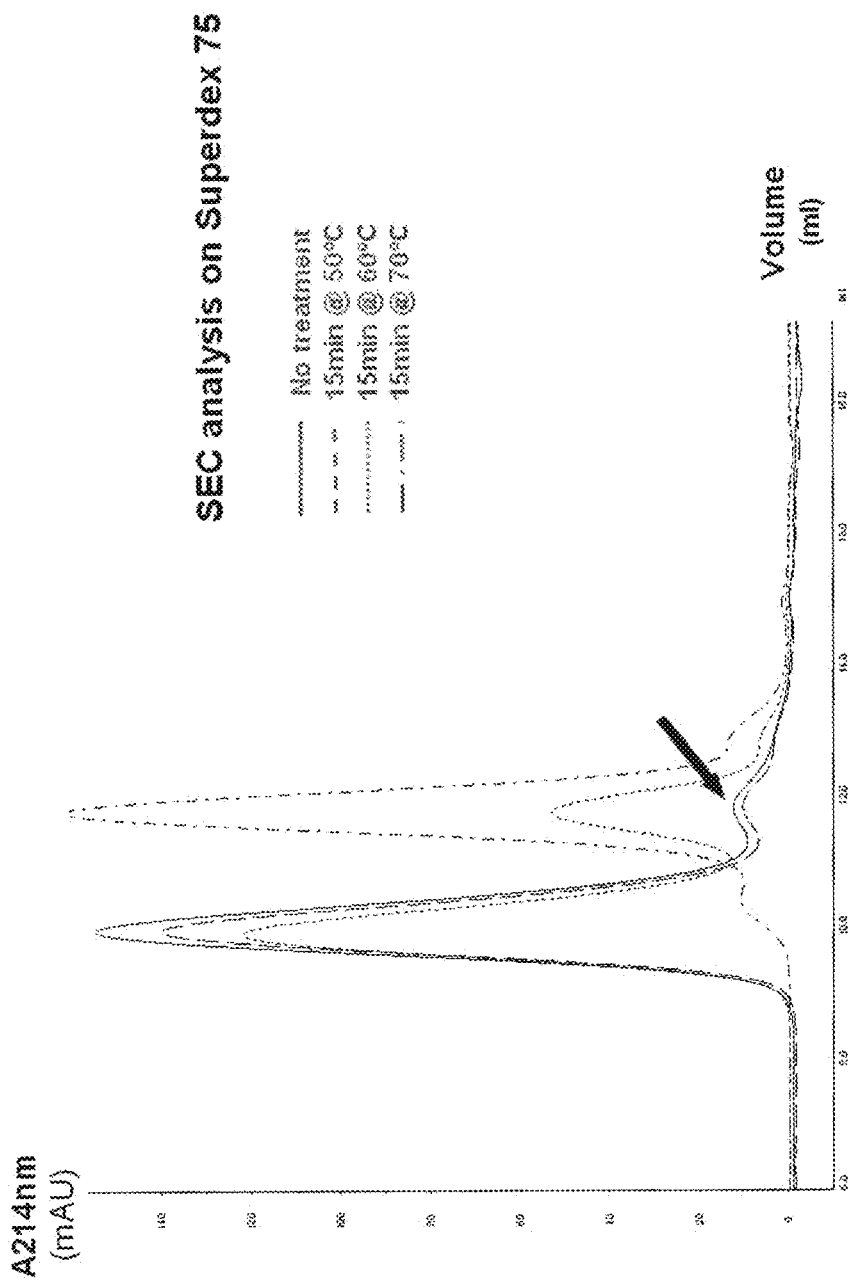

FIG. 60: Size exclusion chromatography of heat treated samples of dimeric Polypeptide A. Polypeptide A NFD (at 0.68 mg/ml) was used in several experiments: 20 µl dimer fractions were diluted with 90 µl D-PBS and incubated at different temperatures and 100 µl was analysed on a SUPERDEX 75™ 10/300GL column equilibrated in D-PBS.

Figure 61:
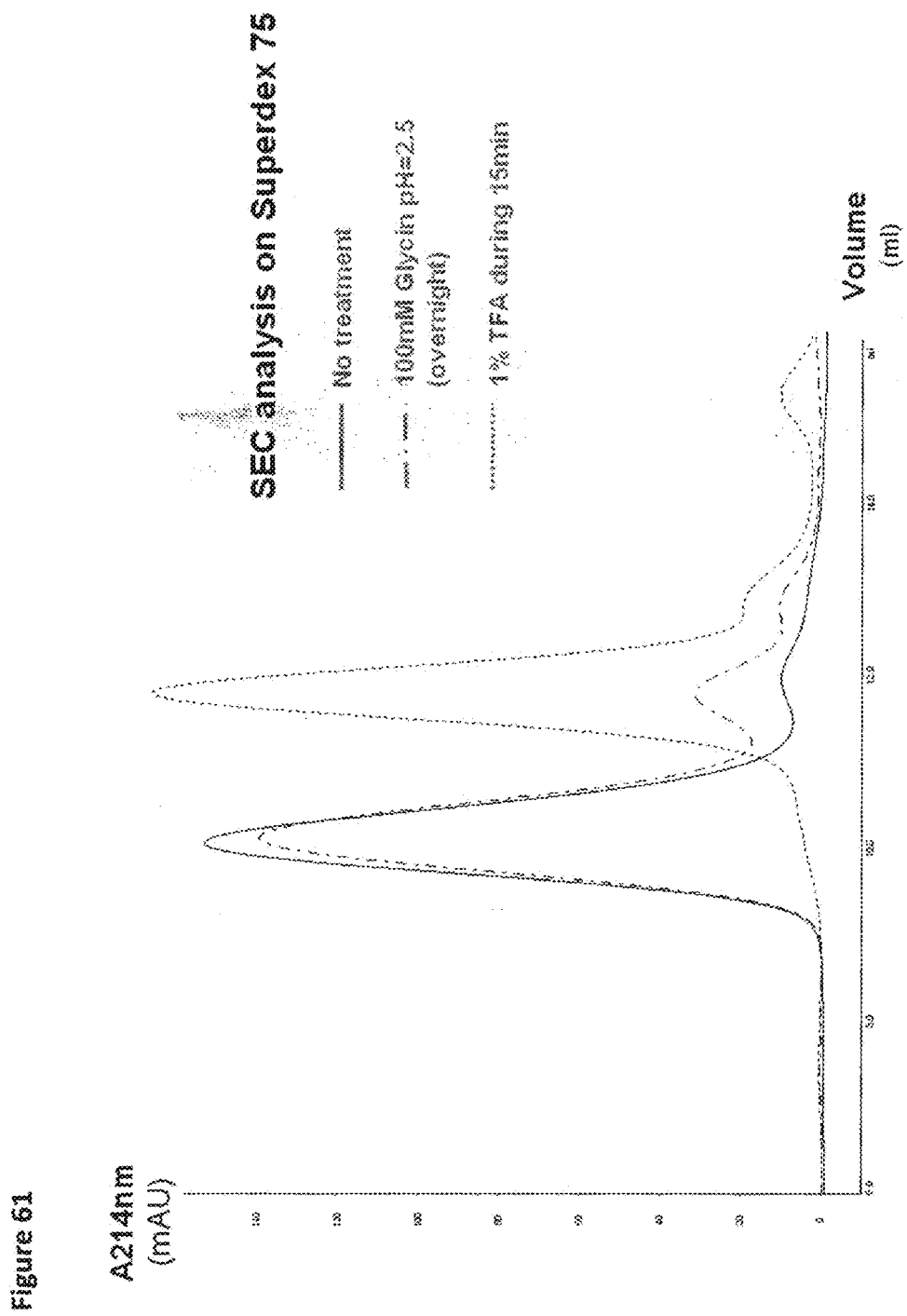

FIG. 61: Size exclusion chromatography of pH treated samples of Polypeptide A NFD. Polypeptide A NFD (at 0.68 mg/ml) was used in several experiments: 20 µl dimer samples were diluted with 90 µl [100 mM Piperazine pH=10.2] or 90 µl [100 mM Glycine, pH=2.5] and incubated overnight (ON) at 4° C. The control was incubated in D-PBS. Samples were analysed via SEC the next day. The incubation at elevated pH had no effect on the dissociation whereas low pH (glycine pH=2.5) resulted in approx 15% monomer. A more drastic incubation in 1% TFA during 15 min at room temperature resulted in almost 100% monomer.

Figure 62:
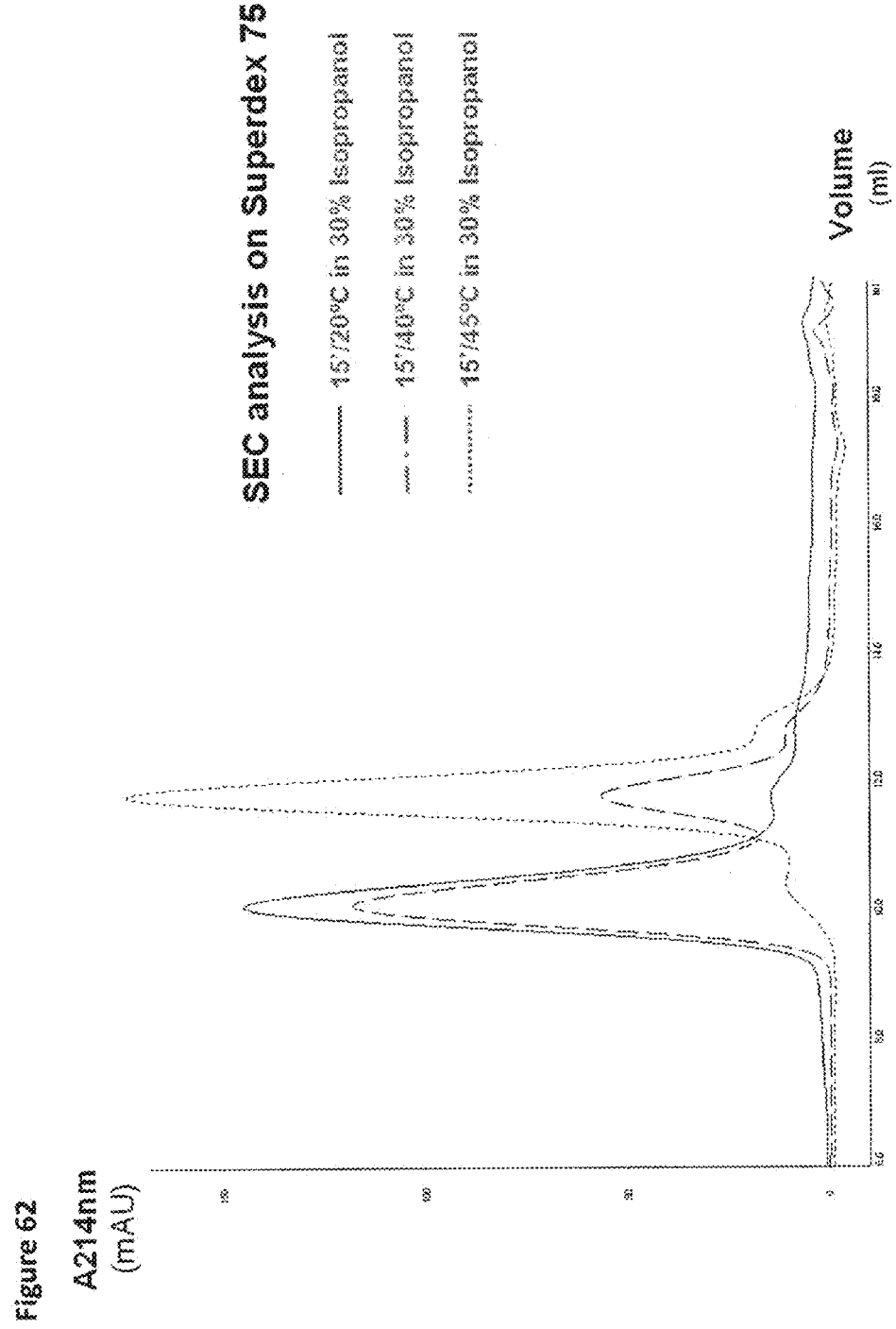

FIG. 62: Size exclusion chromatography of combined heat/organic solvent treated samples of Polypeptide A NFD. Polypeptide A NFD (at 0.68 mg/ml) was used in several experiments: 20 µl dimer fractions were diluted with 90 µl [10% Isopropanol] or 90 µl [30% Isopropanol] and incubated overnight (ON) at 4° C. or 15 minutes at 20° C. Combined treatments (heat and Isopropanol) were carried out during 15 minutes. The control was incubated in D-PBS. Samples were analysed via SEC. The incubation at elevated temperature with organic solvent resulted in accelerated dissociation into monomer.

Figure 63:
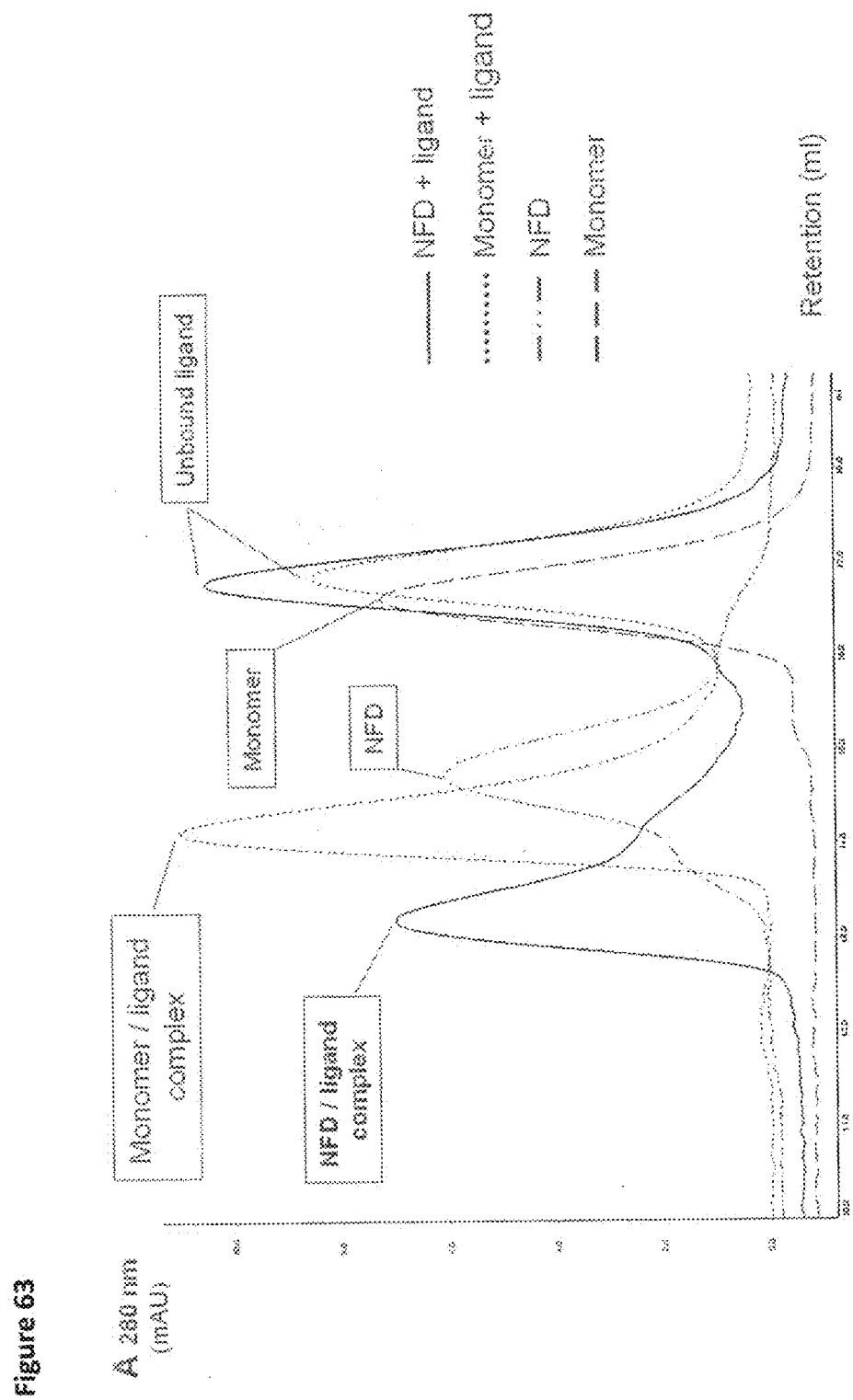

FIG. 63: Size exclusion chromatography of ligand-NFD complex formation: 20 µl samples of Ligand A (SEQ ID NO:13) was diluted in 90 µl [HBS-EP (BIACORE)+0.5M NaCl] and incubated for several hours at RT (ligand mix). Then NFD or Polypeptide A was added and after a short incubation (typically 30 min) the material was resolved via SEC. Polypeptide A [3.91 mg/ml]: 17 µl [1/10 diluted in HBS-EP] was added to the ligand mix and 100 µl was injected.

Figure 64:
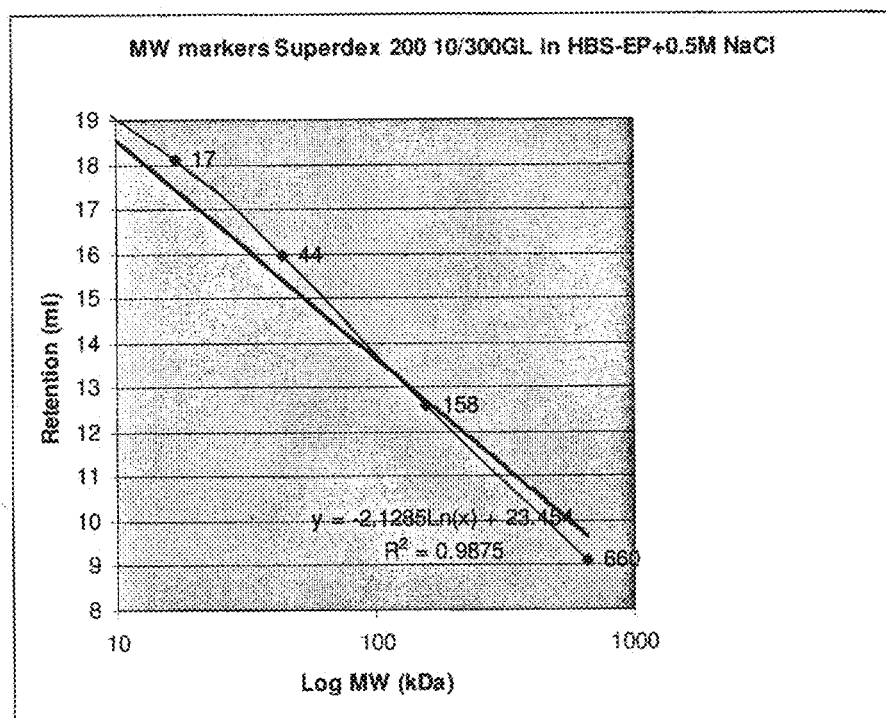

FIG. 64: The molecular weight (MW) of polypeptide A, Ligand A, Polypeptide A+Ligand A, NFD-Di of Polypeptide A, and NFD-Di of Polypeptide A+Ligand A was calculated (see Table 46 for read out from this figure) based on curve fitting of Molecular weight standards (Biorad #151-1901) run on the same column under same conditions.

FIG. 65: Monomer of Polypeptide B as present in the dimer (top) and an isolated monomer of polypeptide B (bottom).

Figure 66:
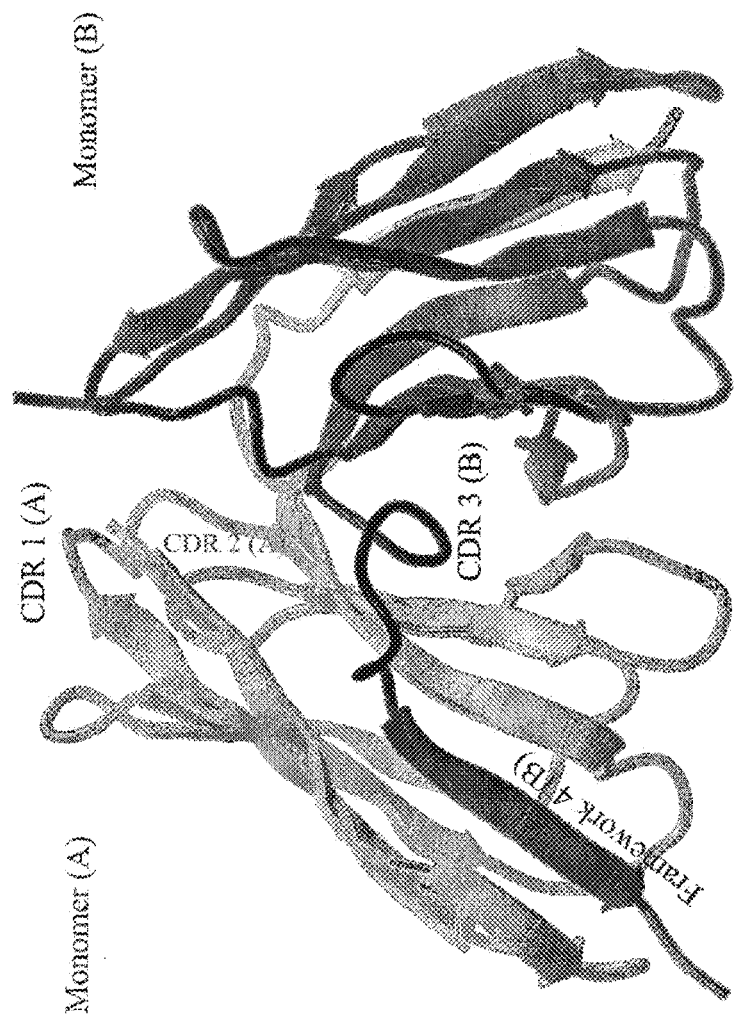

FIG. 66: Polypeptide B-dimer (an example of a NFD-Mo). Framework 4 of monomer A is replaced by framework 4 of monomer B and vice versa.

Figure 67:

FIG. 67: Electron-density of monomer B in black. Monomer A is shown in grey ribbon.

FIG. 68: Polypeptide B (top) and polypeptide F with Pro at position 45 (bottom).

Figure 69:
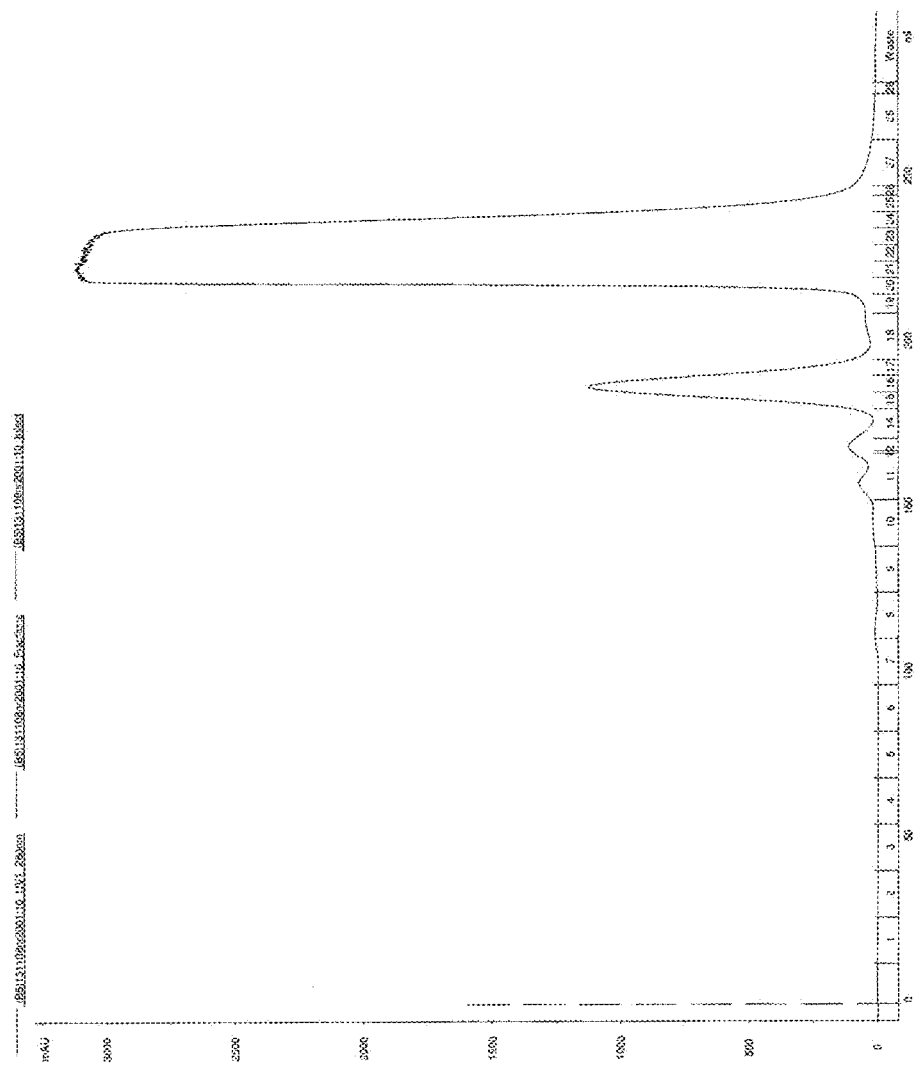

FIG. 69: Size exclusion chromatography of Polypeptide B material eluted from Protein A affinity column on SUPERDEX 75 XK 26/60 column.

Figure 70:
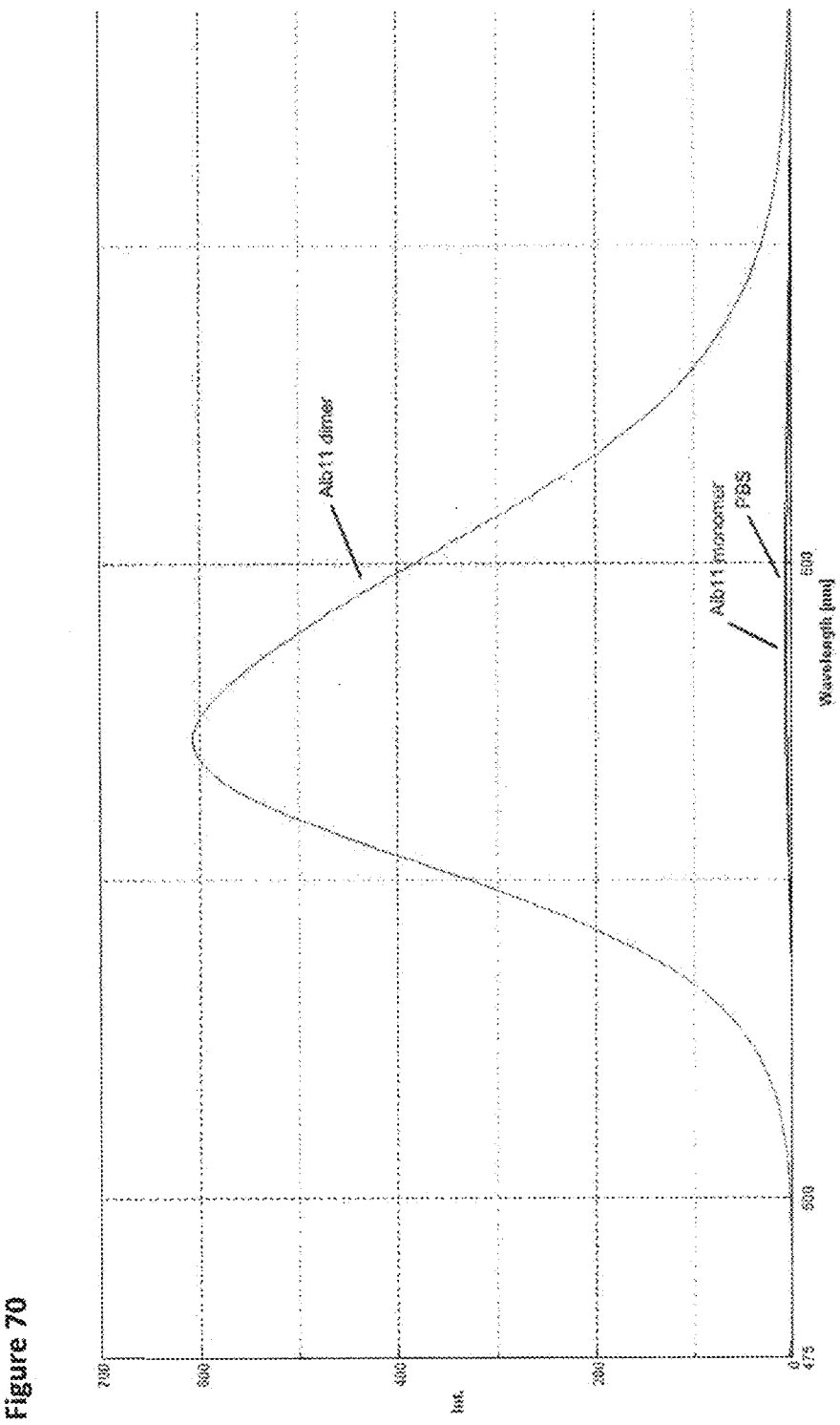

FIG. 70: Fluorescence emission SYPRO orange in the presence of polypeptide B and polypeptide B-dimer.

Figure 71:
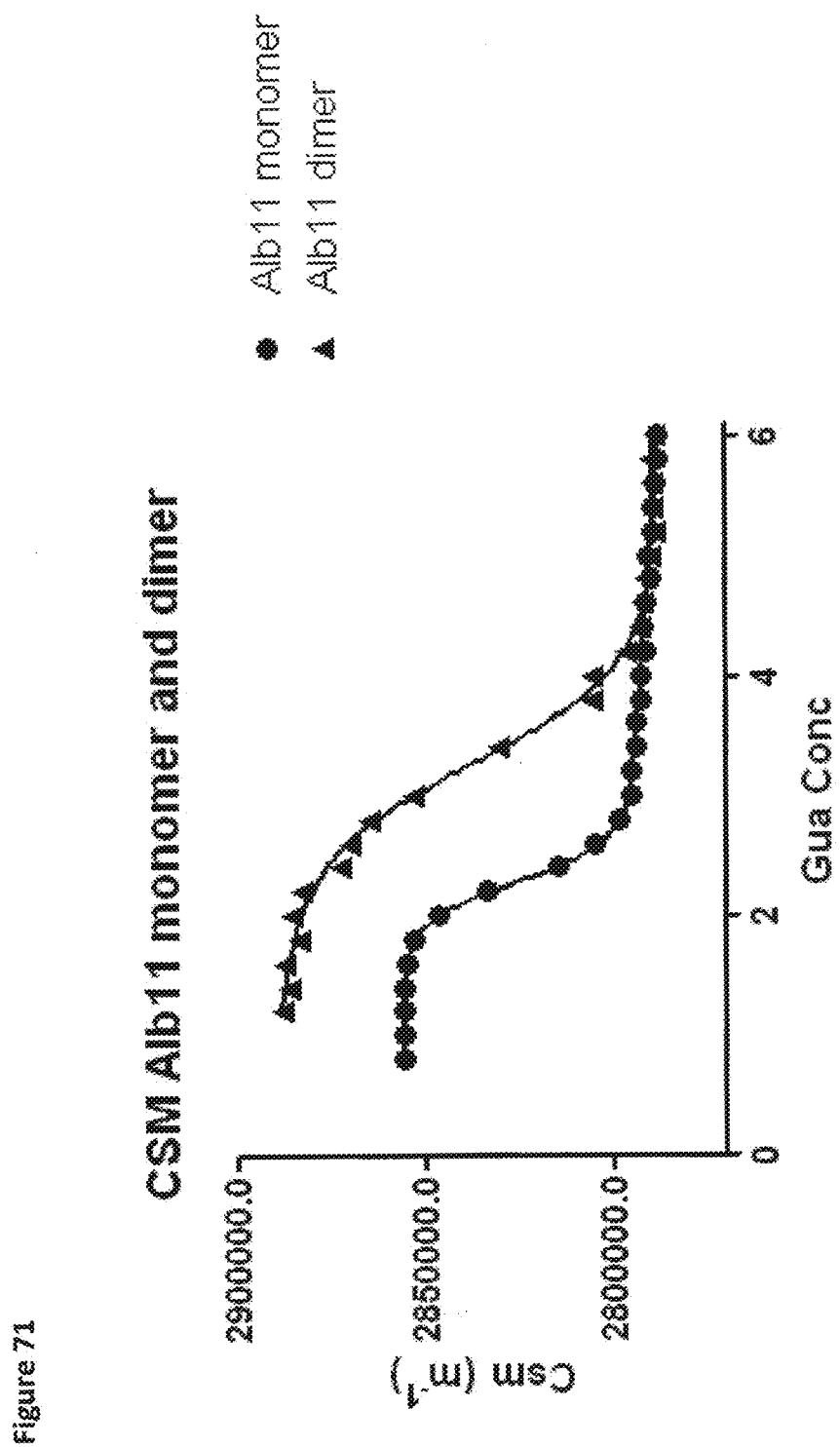

FIG. 71: Unfolding of Polypeptide B monomer and Polypeptide B-dimer in function of Guanidinium Hydrochloride concentration. Unfolding was monitored by intrinsic fluorescence measurements and thereby using center of spectral mass (CSM) as unfolding parameter.

Figure 72:
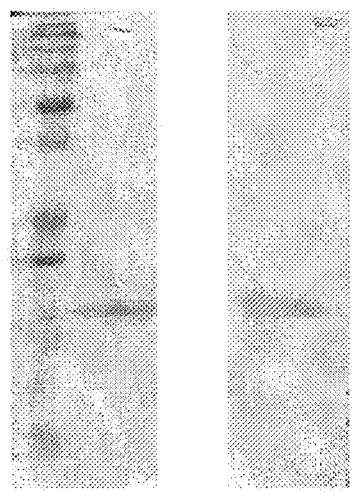

FIG. 72: Purity was analysed on a Coomassie stained gel (Panel A: Polypeptide G; Panel B: Polypeptide H).

Figure 73:
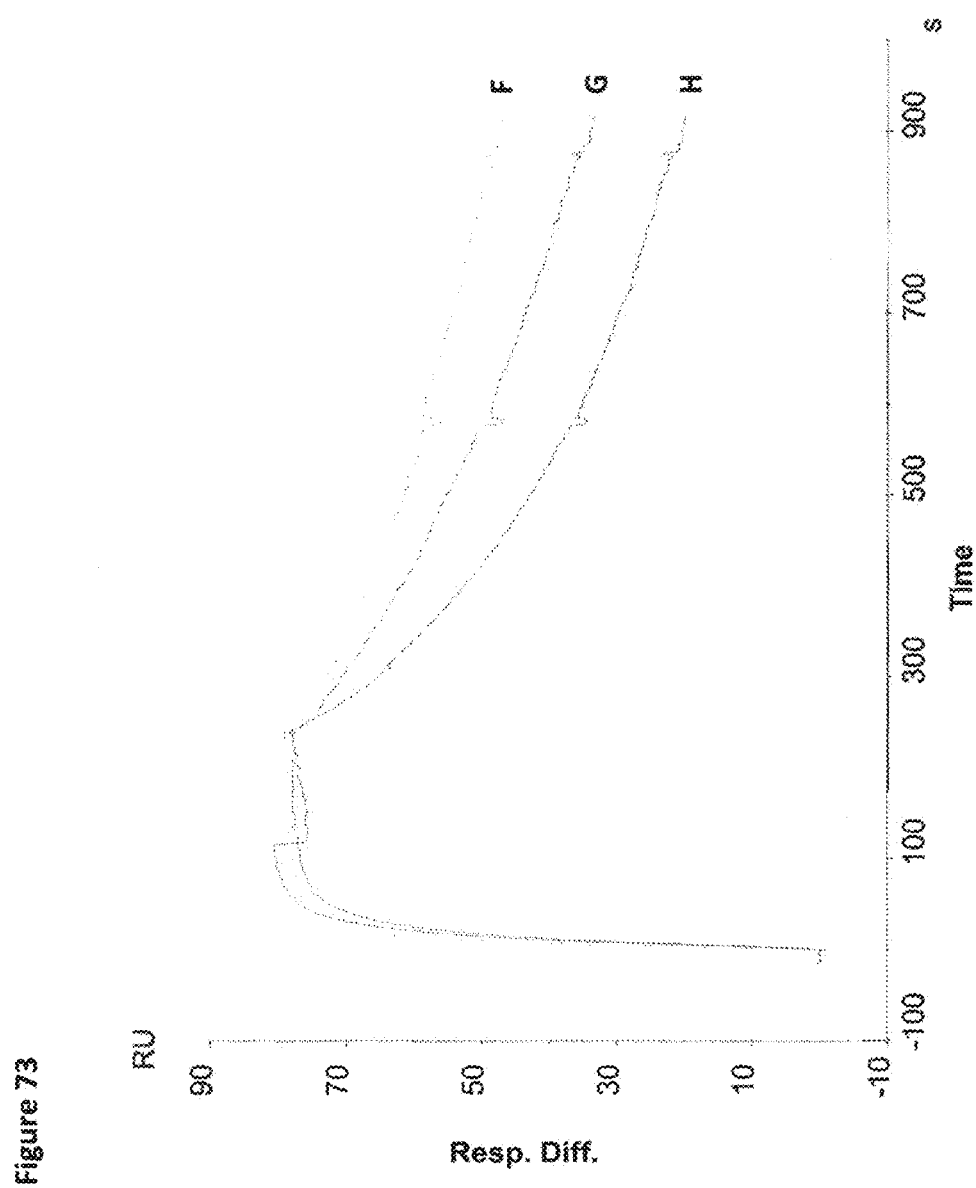

FIG. 73: Binding of polypeptide F, G, and H on HSA.

Figure 74:
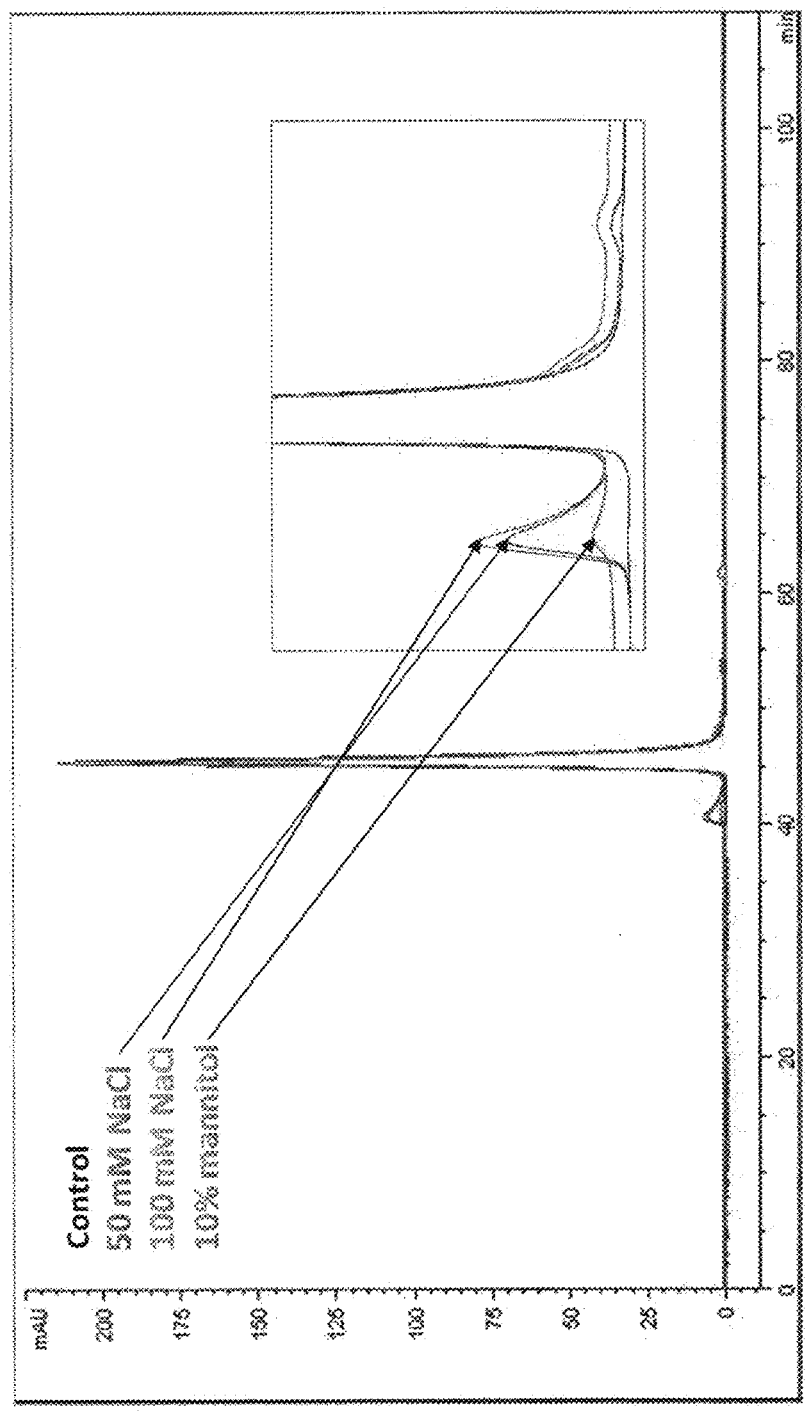

FIG. 74: The 280 nm SE-HPLC chromatograms of Polypeptide I formulated in phosphate buffer (2 weeks storage) with either 50 mM NaCl, 100 mM NaCl or 10% mannitol. A zoom on the main peak is shown as inset.

Figure 75:
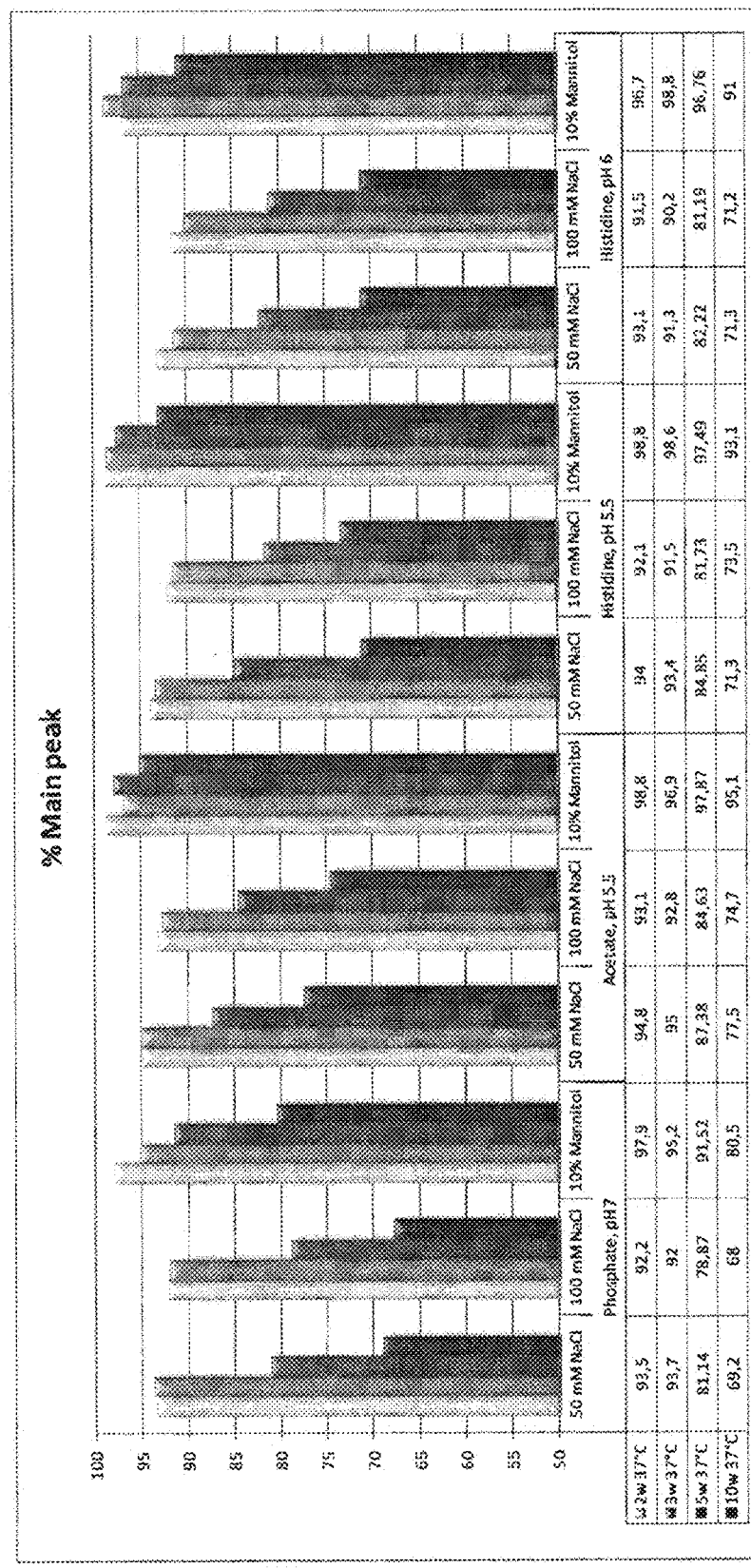
Figure 76:
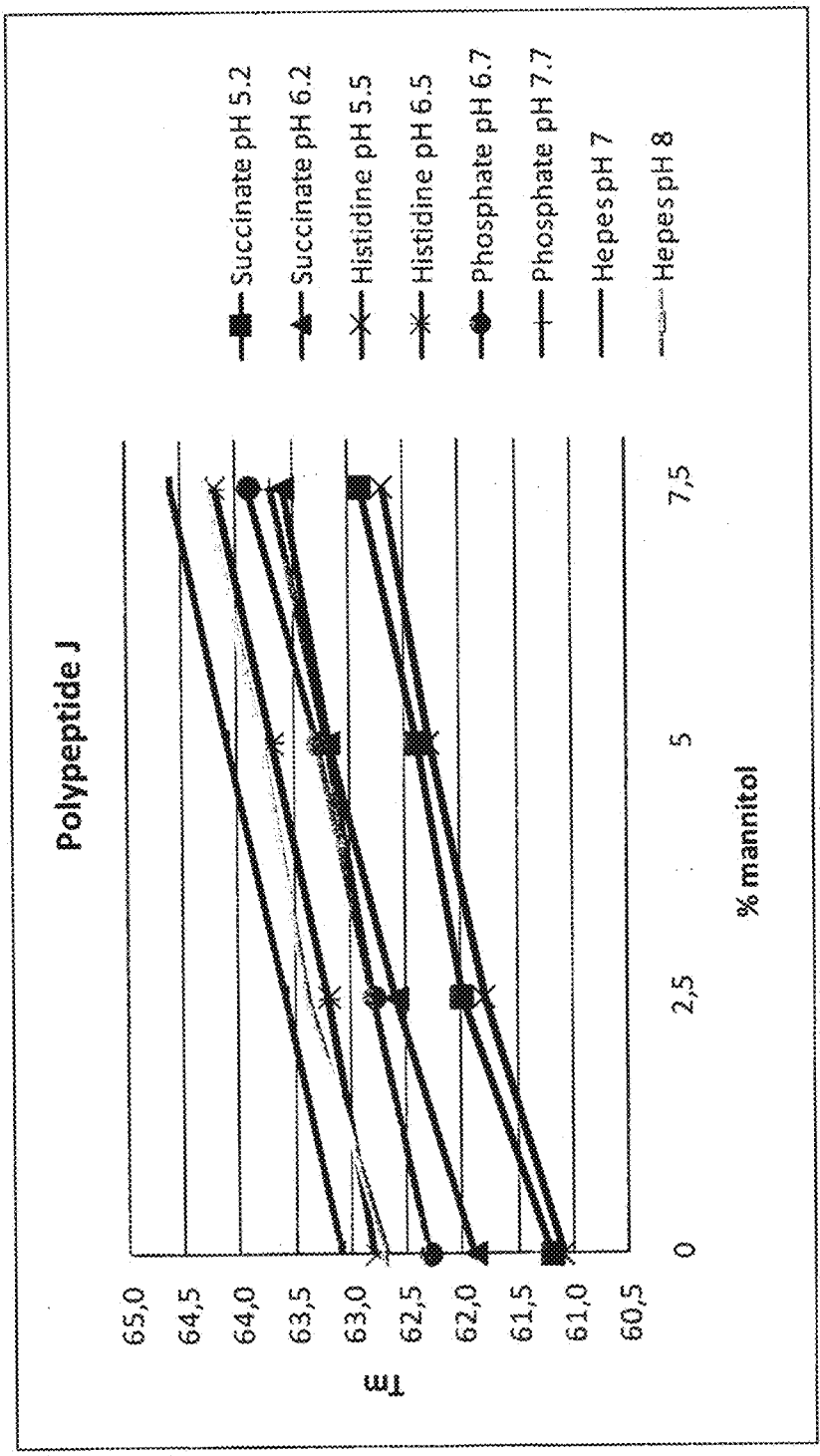
Figure 77:
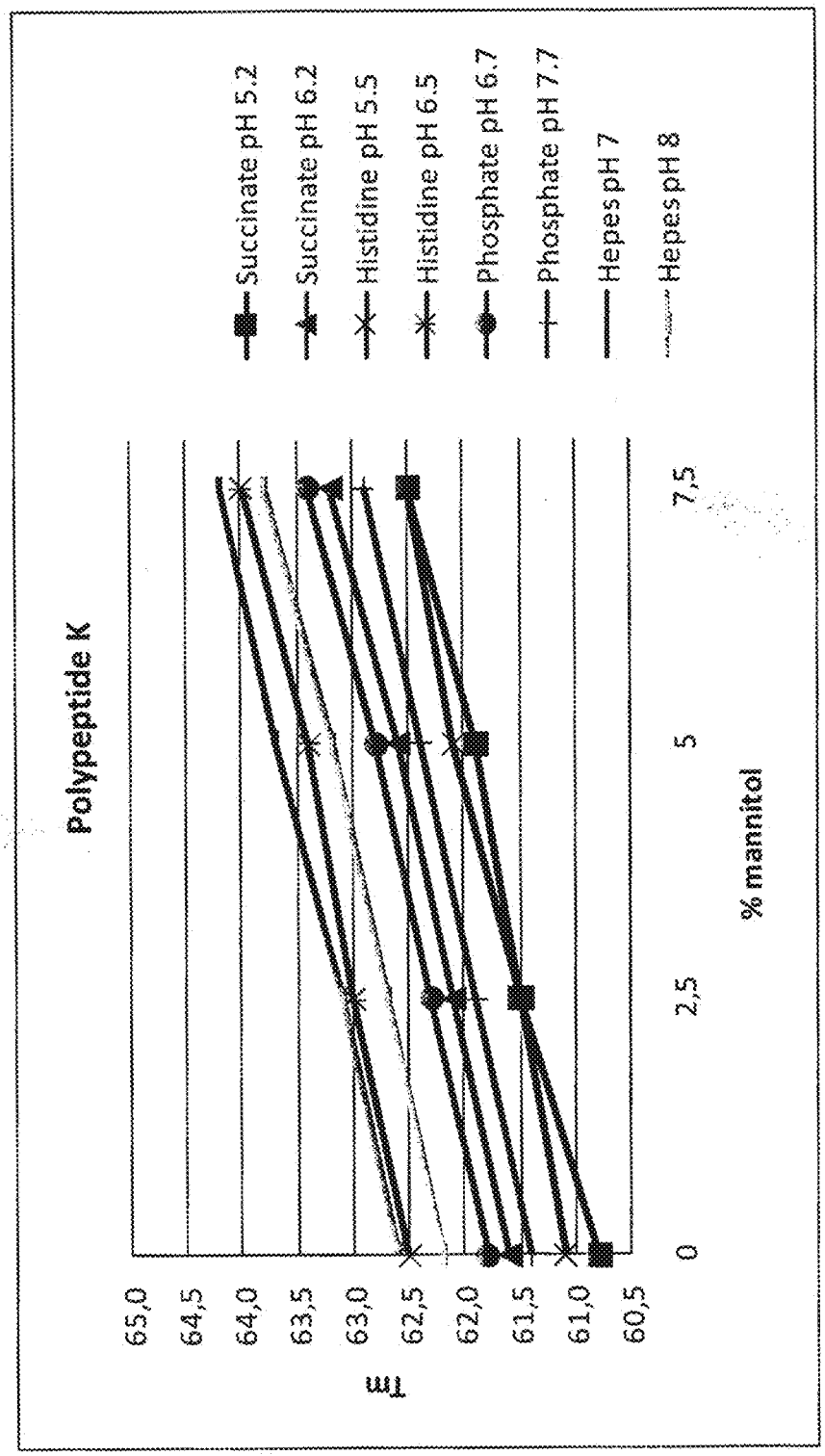
Figure 78:
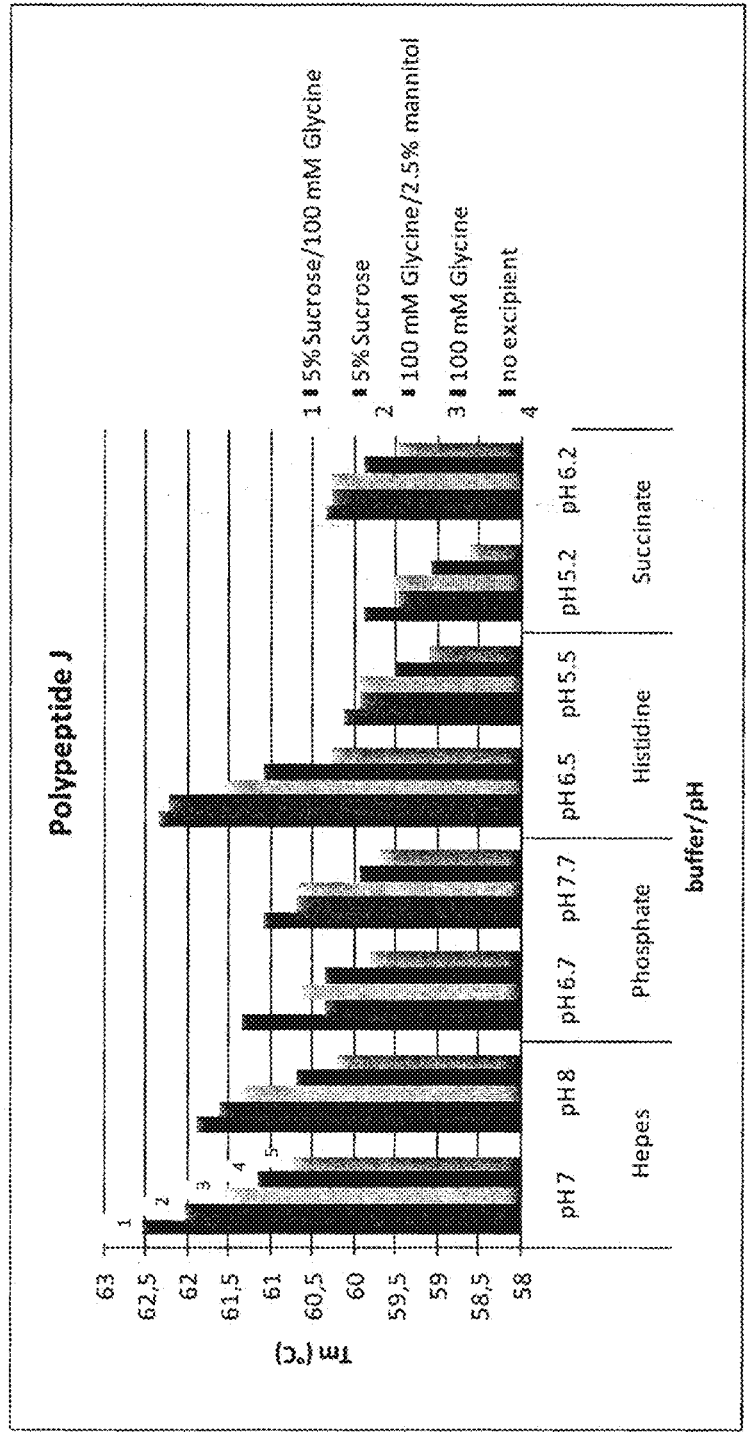
Figure 79:
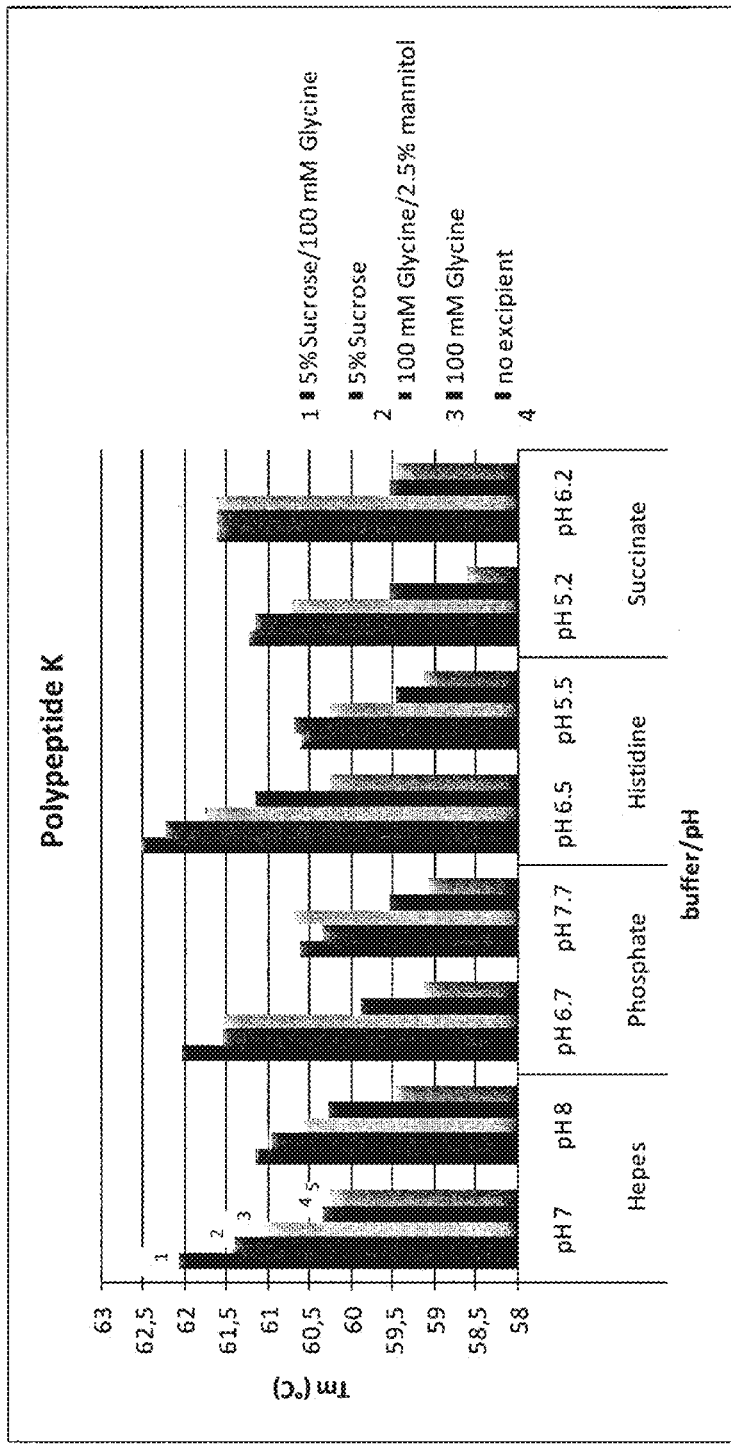

FIG. 75: Figure demonstrating the time-dependent decrease (A) and increase (B) of the surface area of, respectively, the main peak and % dimers observed in SE-HPLC analysis of Polypeptide I formulated in different buffers and stored for 10 weeks at 37° C.

FIGS. 76-79: Overview of the results obtained for thermal stability testing of Polypeptides J and K.

Figure 80:
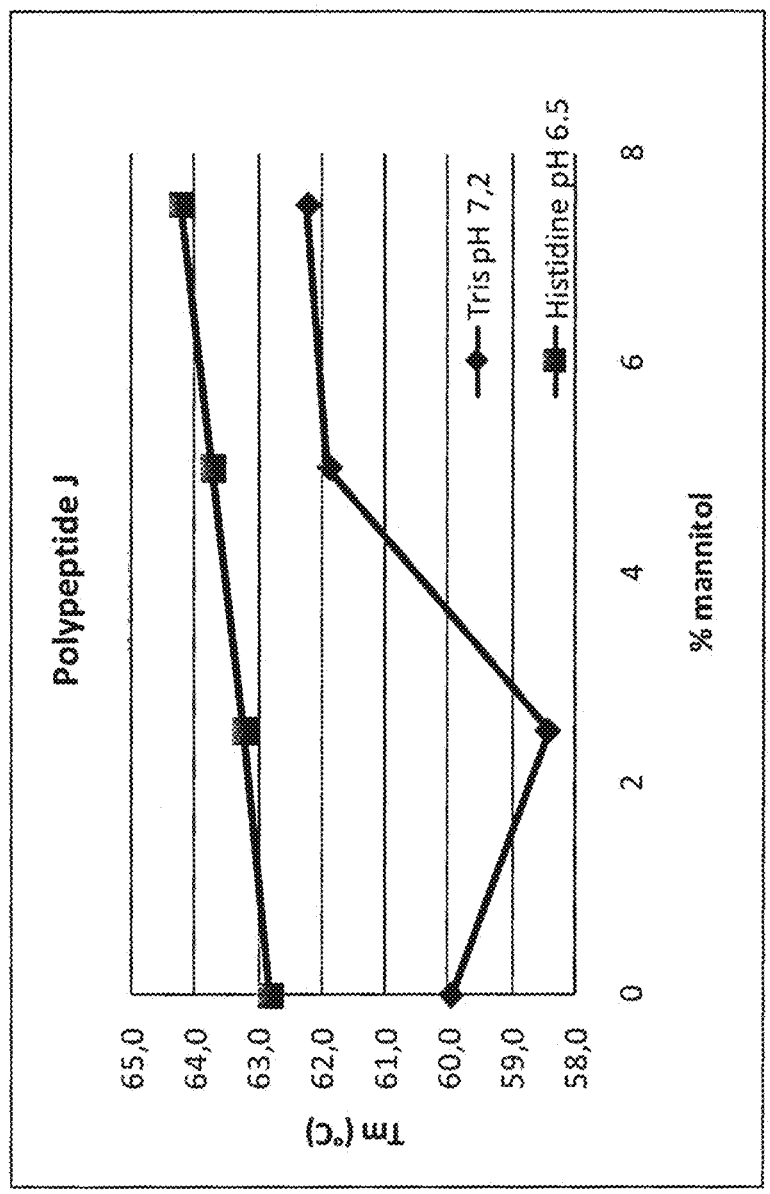

FIG. 80: Overview of the results obtained in thermal stability testing of Polypeptide J in Tris buffer pH 7.2 or Histidine pH 6.5, with sucrose, glycine or mannitol added as excipient.

Figure 81:
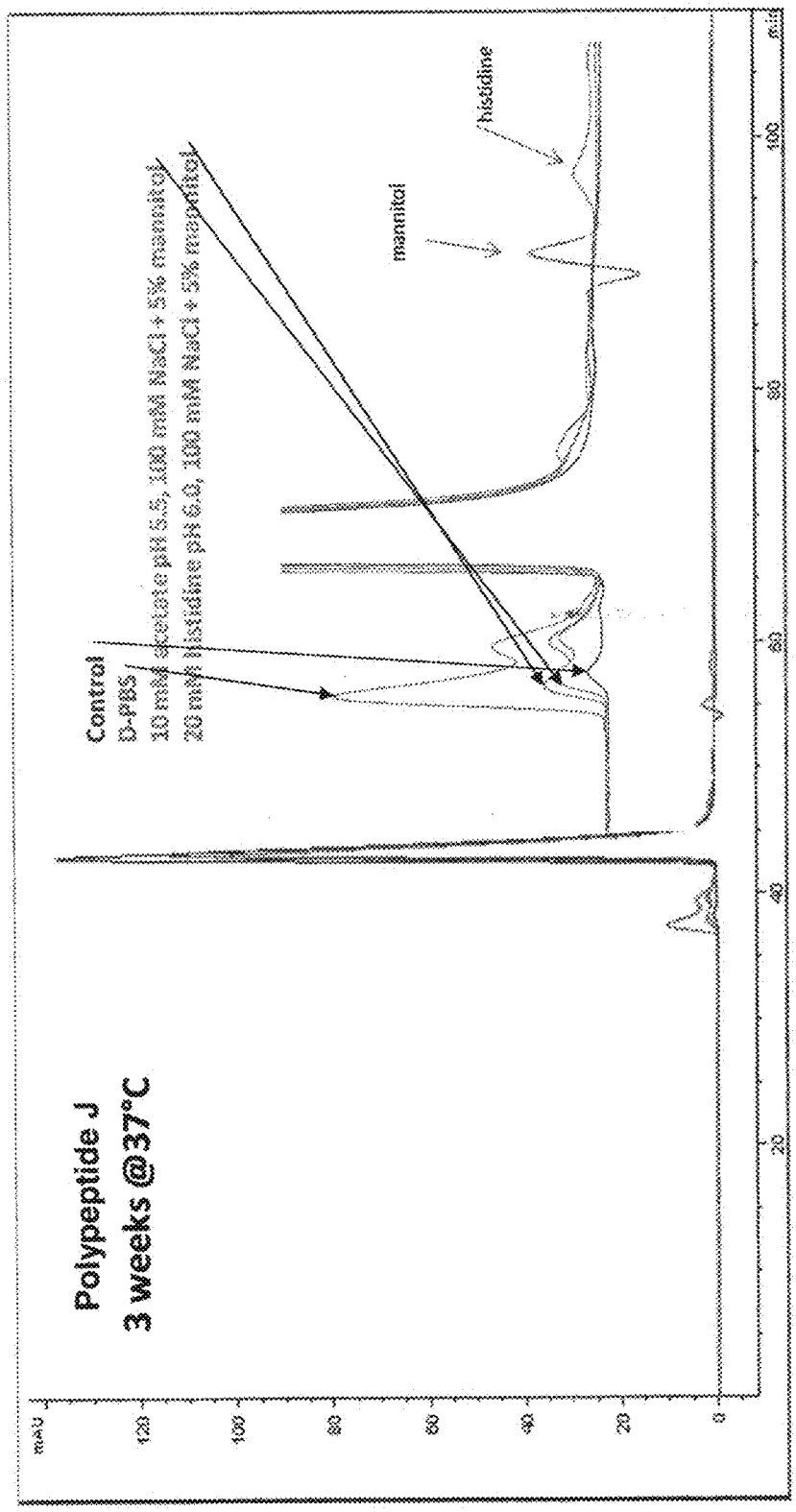

FIG. 81: Overlay of the SE-HPLC chromatograms of IL6R304 formulated at 10 mg/mL stored for 3 weeks at 37° C. Inset, zoom on the main peak to demonstrate the buffer-dependent differences in % aggregates.

Figure 82:
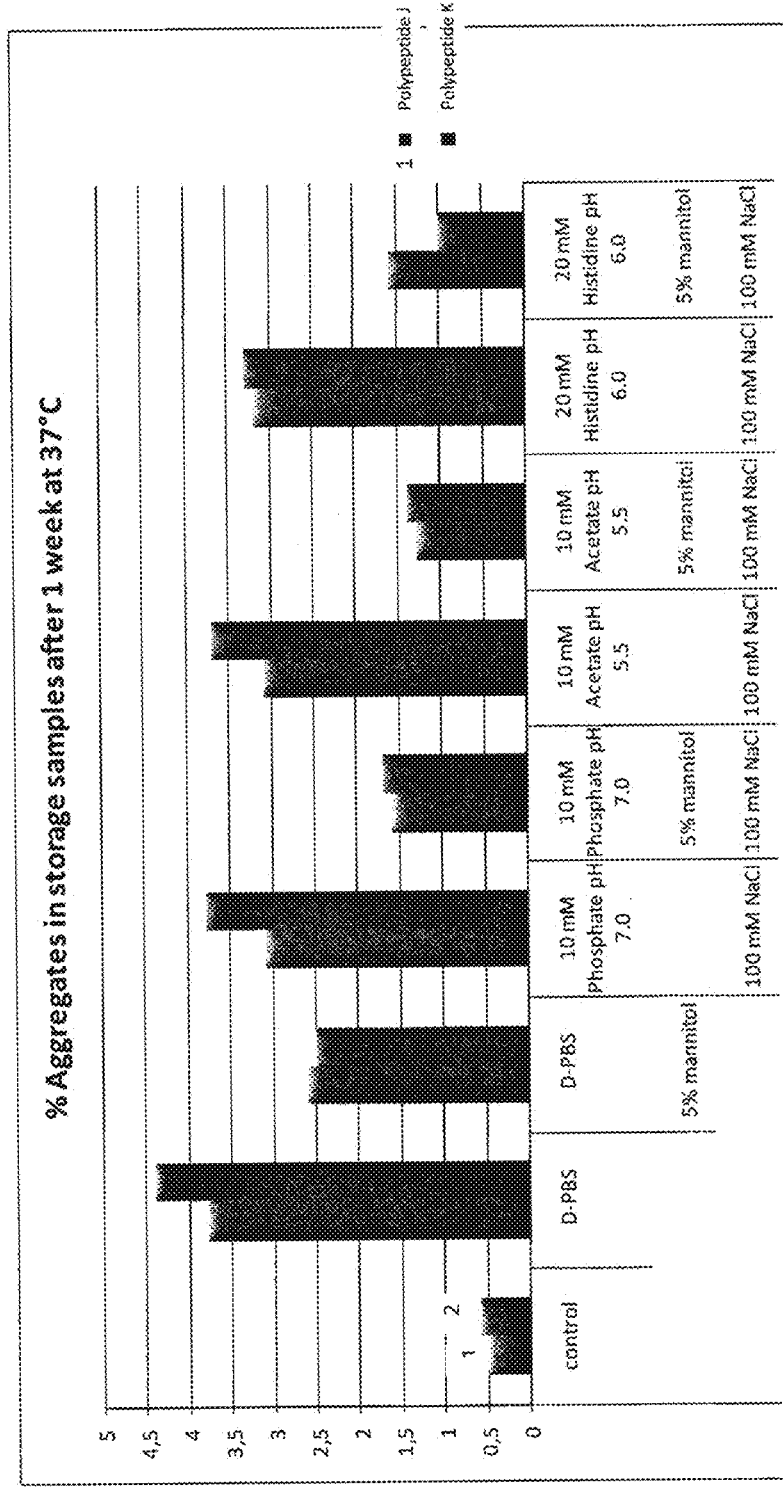

FIG. 82: Figure demonstrating the buffer-dependent differences in % aggregates (peak surface area in SE-HPLC) that were observed in the stability samples of Polypeptide J and Polypeptide K stored for 1 week at 37° C.

Figure 83:
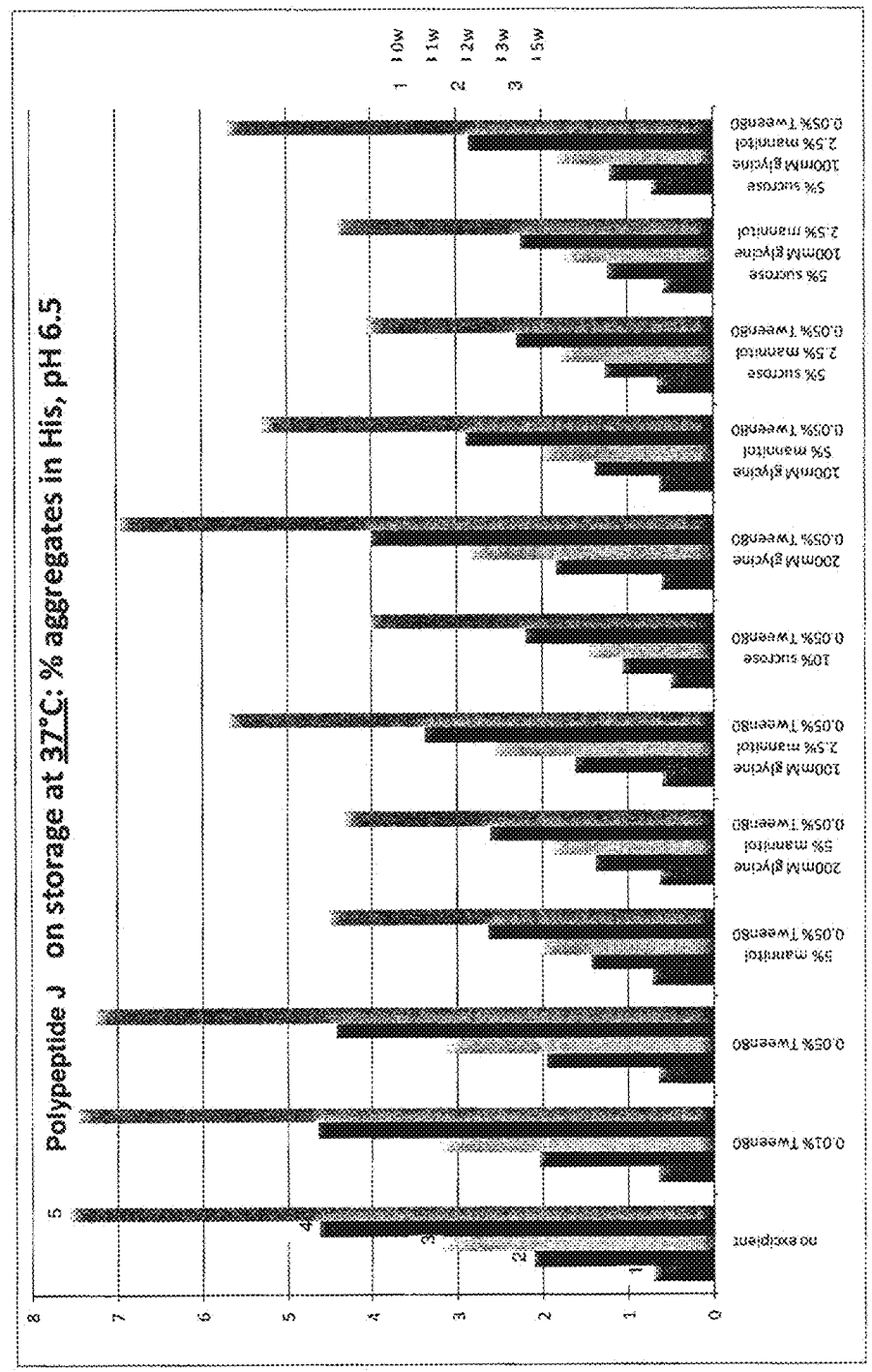

FIG. 83: Figure demonstrating the time-dependent increase of the % oligomers/aggregates (Y-axis) observed in SE-HPLC analysis of Polypeptide J stored for up to 5 weeks at 37° C. (A) in the buffers indicated in the graph. The % oligomers/aggregates is expressed as the sum of the % peak surface areas of prepeak 1a, prepeak 1b and prepeak 2 relative to the total peak surface area.

Figure 84:
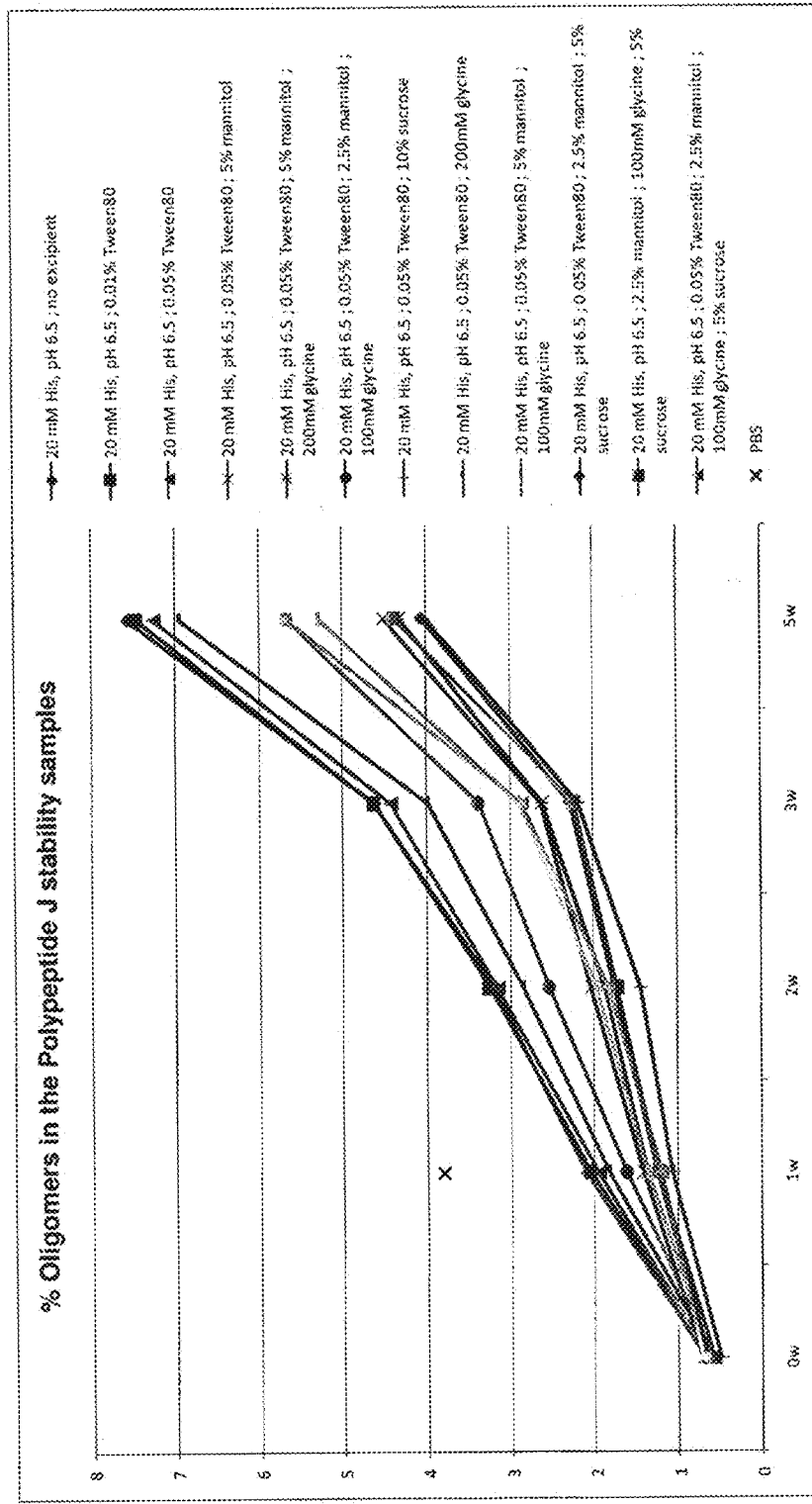

FIG. 84: Time-dependent and buffer-dependent increase in the % oligomers observed in the stability samples stored for up to 5 weeks at 37° C., at a concentration of 10 mg/mL in the buffers indicated in the graph.

Figure 85:
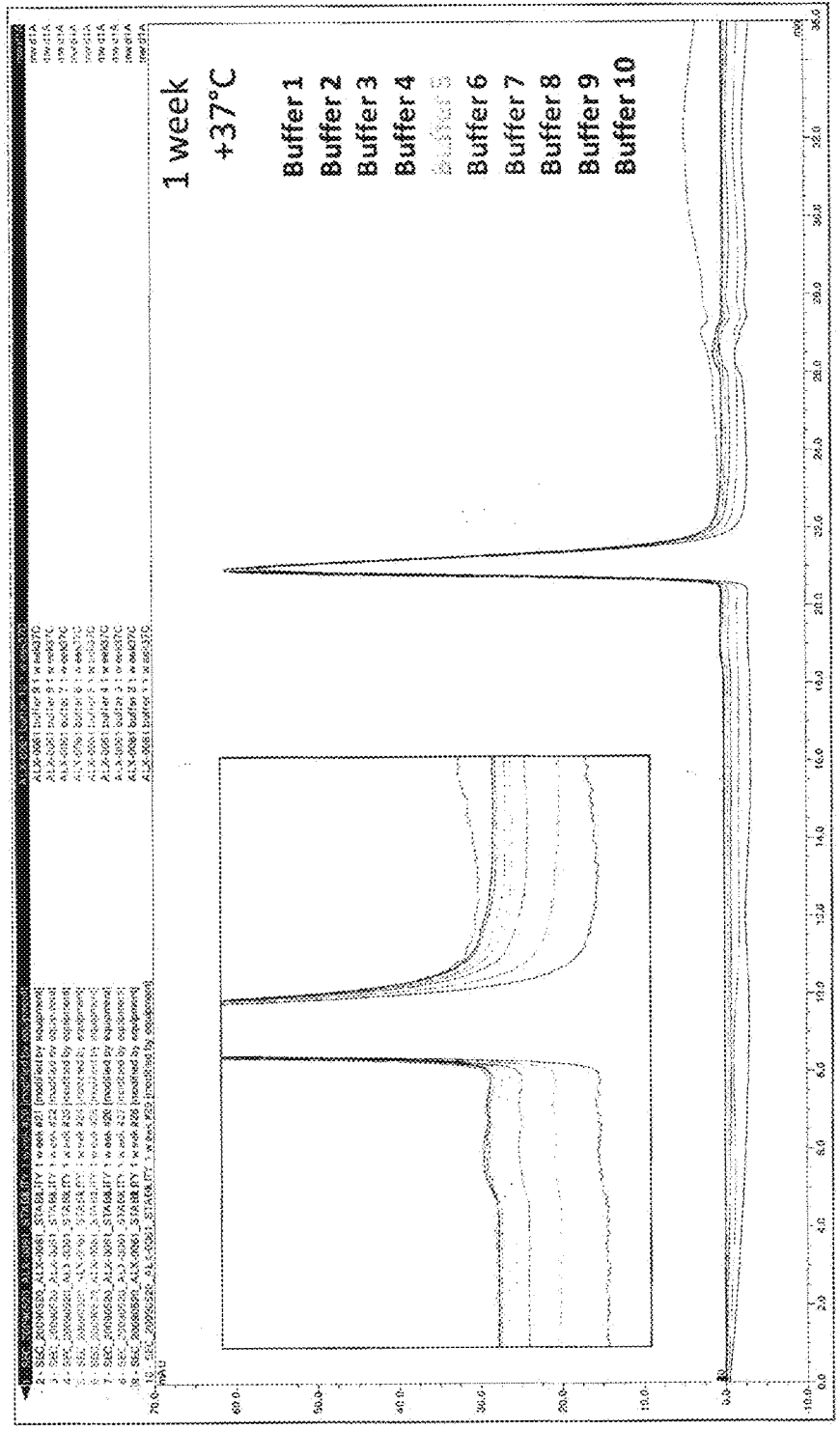
Figure 85:
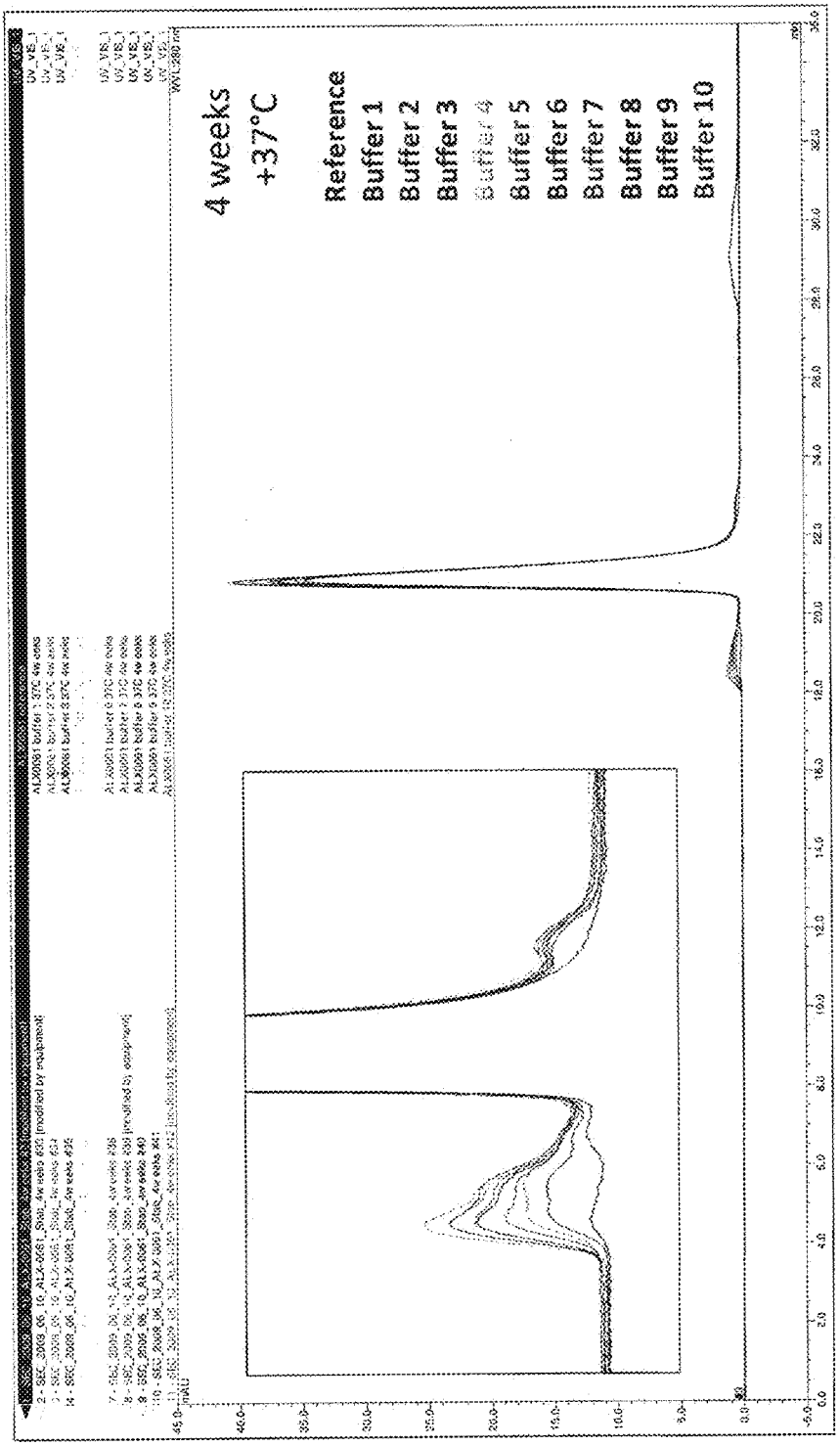
Figure 85:
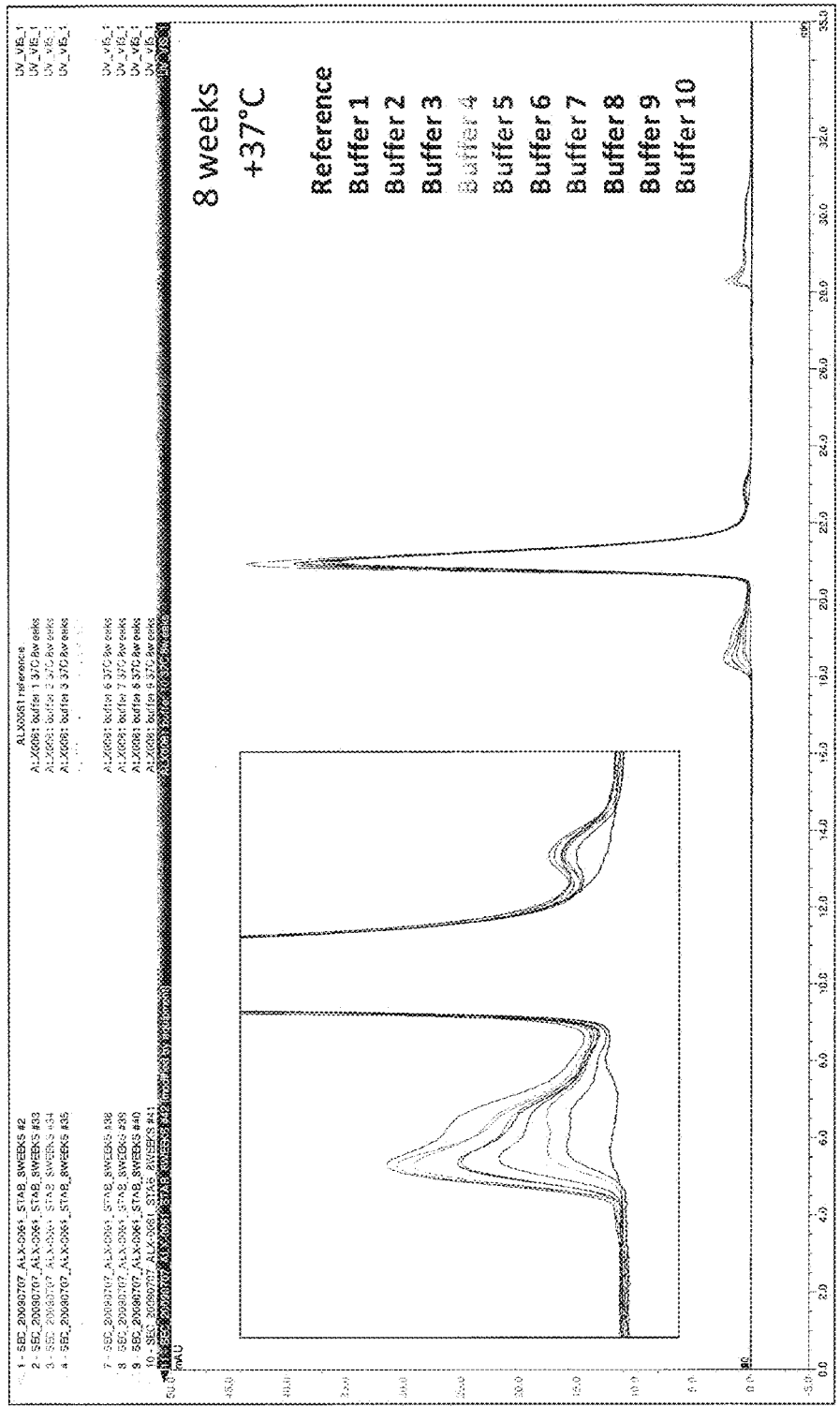

FIG. 85: Overlay of the SE-HPLC chromatograms from Polypeptide J after storage for up to 8 weeks at +37° C. in 10 different formulation buffers. A zoom on the main peak (inset) demonstrates the time-dependent increase of the surface area of prepeaks and postpeak.

Figure 86:
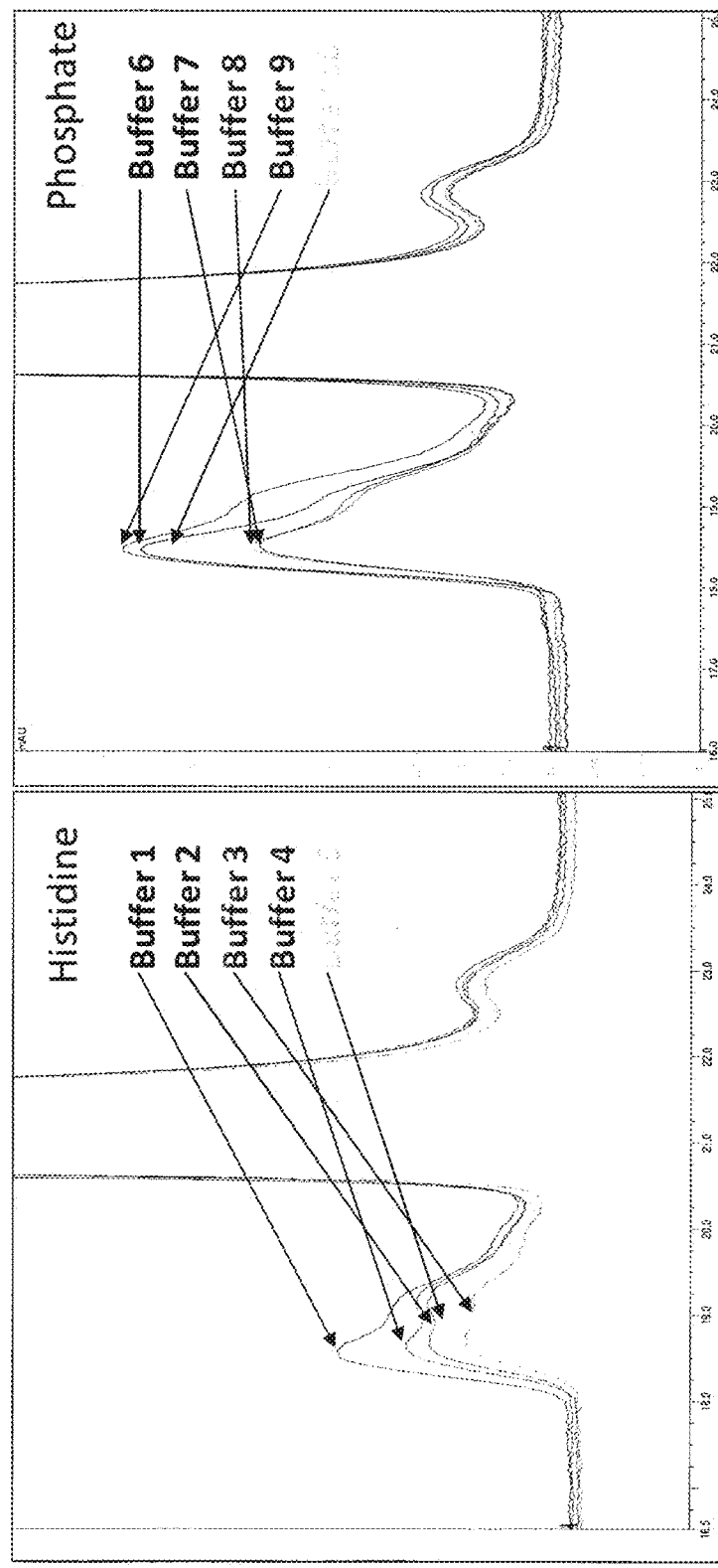

FIG. 86: SE-HPLC analysis of Polypeptide J samples stored for 8 weeks at 37° C. in L-histidine buffer (buffers 1-5) compared to phosphate buffer (buffers 6-10). The amount of oligomers was lowest in buffer 3.

Figure 87:
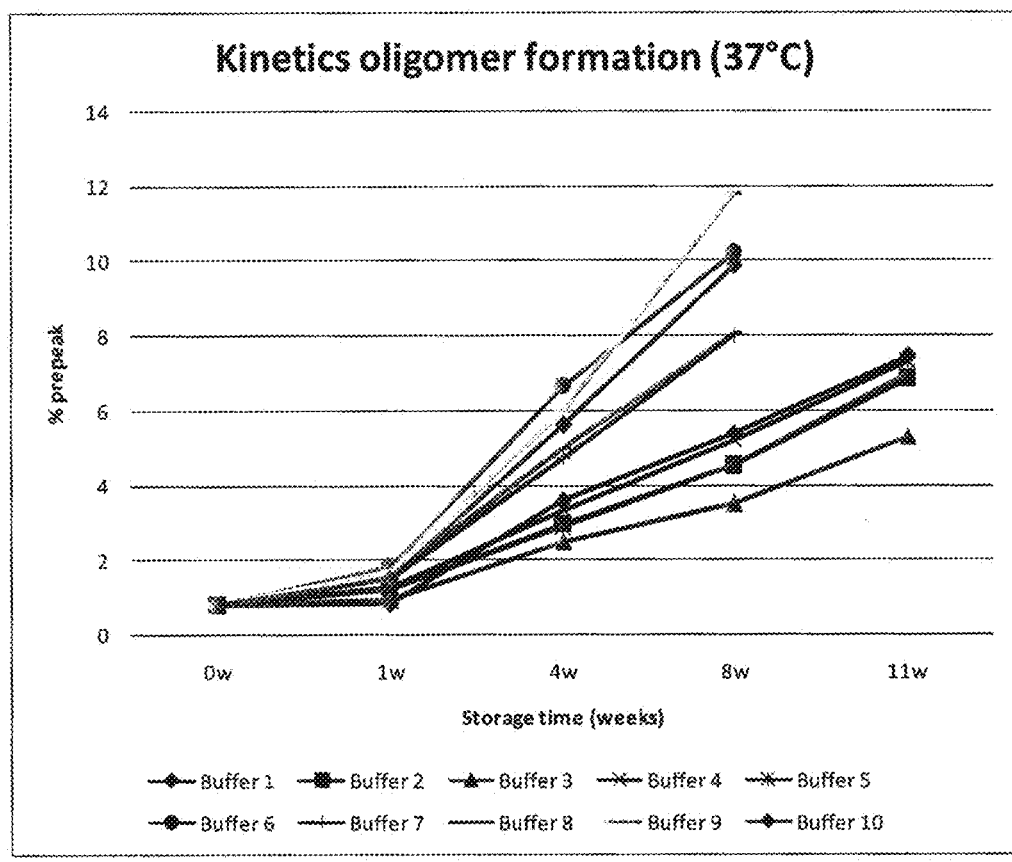

FIG. 87: Kinetics of oligomer formation upon storage of Polypeptide J in the different buffers.

DETAILED DESCRIPTION

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

As used herein, the term "isolated" in the context of a polypeptide refers to a polypeptide which is substantially free of cellular material or contaminating proteins from the cell or tissue source from which it is derived, or substantially free of chemical precursors or other chemicals when chemically synthesized. The language "substantially free of cellular material" includes preparations of a polypeptide in which the polypeptide is separated from cellular components of the cells from which it is isolated or recombinantly produced. Thus, a polypeptide that is substantially free of cellular material includes preparations of a polypeptide having less than about 30%, 20%, 10%, or 5% (by dry weight) of heterologous protein, polypeptide, peptide, or antibody (also referred to as a "contaminating protein"). When the polypeptide is recombinantly produced, it may also be substantially free of culture medium, i.e., culture medium represents less than about 20%, 10%, or 5% of the volume of the polypeptide preparation. When the polypeptide is produced by chemical synthesis, it is preferably substantially free of chemical precursors or other chemicals, i.e., it is separated from chemical precursors or other chemicals which are involved in the synthesis of the polypeptide. Accordingly, such preparations of a polypeptide have less than about 30%, 20%, 10%, 5% (by dry weight) of chemical precursors or compounds other than the polypeptide of interest. In a specific embodiment, an "isolated" polypeptide is purified by a multi-step purification process that comprises two chromatography steps (e.g. cation exchange and anion exchange), a 100K ultrafiltration step, followed by a buffer exchange and concentration step in Ultrafiltration/Diafiltration mode.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, such as a cynomolgus monkey, chimpanzee, baboon and a human), and more preferably a human. In a certain embodiment, the subject is a mammal, preferably a human, with one or more diseases or disorders. In another embodiment, the subject is a mammal, preferably a human, at risk of developing one or more diseases and/or disorders.

The terms "stability" and "stable" as used herein in the context of a formulation comprising a polypeptide comprising one or more single variable domains refer to the resistance of the polypeptide in the formulation to aggregation, to the formation of degradation products and/or to the formation of fragmentation products under given transportation and/or storage conditions. Apart from this and/or in addition, the "stable" formulations of the invention retain biological activity under given transportation and/or storage conditions. The stability of said polypeptide can be assessed by degrees of aggregation, degradation and/or fragmentation (as measured e.g. by SE-HPLC, RP-HPLC, IEX-HPLC, subvisible particle counting, analytical ultracentrifugation, dynamic light scattering, OD320/OD280 ratio measurement, elastic light scattering, etc.), and/or by % of biological activity (as measured e.g. by ELISA, BIACORE, etc.) compared to a reference formulation. For example, a reference formulation may be a reference standard frozen at −20° C. or below −65° C. (such as e.g. −80° C.) consisting of the same polypeptide at the same concentration in D-PBS or consisting of the same polypeptide at the same concentration and in the same buffer as the stressed samples but without applying the stress conditions, which reference formulation regularly gives a single peak by SE-HPLC, RP-HPLC and/or IEX-HPLC and/or keeps its biological activity in BIACORE and/or ELISA.

"Solubility" is often described as the maximum achievable protein concentration whereby all of the protein remains in solution. At this concentration the protein should still be monomeric and free of aggregates. For determining protein solubility only a limited number of (mostly empirical) techniques are currently available. A first and popular technique consists of concentrating the sample by using centrifugal ultrafiltration up to the point where an opalescent solution is formed. Subsequently, the insoluble fraction is removed and the protein content of the supernatant is measured. Centrifugal concentrating devices such as for example VIVASPIN concentrators with a molecular weight cut-off of 5 kDa can be used but require reasonable amounts of protein. Solubility can also be monitored using an inert macromolecule such as polyethylene glycol (PEG; Mr>6,000), which precipitates proteins primarily through an excluded volume effect, a process that can be generally understood in terms of a simple colloidal phase separation. A logarithmic linear relationship between protein solubility and weight percent polyethylene glycol can be obtained, and from this plot the intercept yields the solubility value. The term "good solubility" of the polypeptide of the invention, as used herein, means that no or little precipitation is observed of the polypeptide of the invention during downstream processing (DSP) and/or during storage for a short or longer time at 5° or −20° C. at concentrations ranging from 20-200 mg/mL or more. The formation of precipitates (oligomers or other particulates) can be measured e.g. by SE-HPLC, OD320/OD280 ratio measurement and/or elastic light scattering. Preferably, the polypeptides present in the formulations of the present invention have a solubility of at least 20 mg/mL, at least 30 mg/mL, at least 40 mg/mL, at least 50 mg/mL, at least 60 mg/mL, at least 65 mg/mL, at least 70 mg/mL, at least 80 mg/mL, at least 90 mg/mL, at least 100 mg/mL, at least 110 mg/mL, at least 120 mg/mL, at least 130 mg/mL, at least 140 mg/mL, at least 150 mg/mL, at least 200 mg/mL or even more. Preferably, the OD320/OD280 ratio of the formulations of the present invention is 0.05 or lower, such as 0.01 or lower or 0.005 or lower. The scattering in the formulation of the present invention should be within detection limit and preferably lower than 1000 abs, such as 750 abs or lower or 500 abs or lower.

The phrase "low to undetectable levels of aggregation" as used herein refers to samples containing no more than 5%, no more than 4%, no more than 3%, no more than 2%, no more than 1% or no more than 0.5% aggregation by weight of protein. Unless explicitly referred to differently, aggregation as used in the present invention means the development of high molecular weight aggregates, i.e. aggregates with an apparent molecular weight of more/higher than the apparent molecular weight observed in SE-HPLC analysis for dimers of the polypeptide of the invention (such as e.g. 44 kDa as observed for SEQ ID NO: 4; 36-38 kDa as observed for SEQ ID NO's 1-3; and 36 kDa as observed for SEQ ID NO: 5 in SE-HPLC) in comparison with molecular weight markers. Aggregation can be assessed by various methods known in the art. Without being limiting, examples include high performance size exclusion chromatography (SE-HPLC), sub-visible particle counting, analytical ultracentrifugation (AUC), dynamic light scattering (DLS), static light scattering (SLS), elastic light scattering, OD320/OD280 measurement, Fourier Transform Infrared Spectroscopy (FTIR), circular dichroism (CD), urea-induced protein unfolding techniques, intrinsic tryptophan fluorescence and/or differential scanning calorimetry techniques.

The term "low to undetectable levels of fragmentation and/or degradation" as used herein refers to samples containing equal to or more than 80%, 85%, 90%, 95%, 98% or 99% of the total protein, for example, in a single peak as determined by SE-HPLC, RP-HPLC and/or IEX-HPLC, representing the non-degraded polypeptide, and containing no other single peaks having more than 5%, more than 4%, more than 3%, more than 2%, more than 1%, or more than 0.5% of the total protein in each.

The term "very little to no loss of the biological activities" as used herein refers to single variable domain activities, including but not limited to, specific binding abilities of the single variable domain to the target of interest as measured by various immunological assays, including, but not limited to ELISAs and/or by Surface Plasmon Resonance (BIACORE). In one embodiment, the single variable domains of the formulations of the invention retain at least 50%, preferably at least 55%, 60%, 65%, 70%, 75%, 80%, 85%, 90%, 95%, 98% or even 99% or more of the ability to specifically bind to an antigen as compared to a reference formulation, as measured by an immunological assay known to one of skill in the art or described herein. For example, an ELISA based assay (e.g. as described in the Example section) may be used to compare the ability of the single variable domain to specifically bind to its target. A "reference formulation" as used herein refers to a formulation that is frozen at a temperature of −20±5° C. or at below −64° C. (such as e.g. at −80° C.) consisting of the same single variable domain at the same concentration in D-PBS or consisting of the same single variable domains at the same concentration in the same buffer/excipients as the stressed samples but without applying the stress conditions, which reference formulation regularly gives a single peak by SE-HPLC, RP-HPLC and/or IEX-HPLC and/or keeps its biological activity in BIACORE and/or ELISA.

The phrase "pharmaceutically acceptable" as used herein means approved by a regulatory agency of the Federal or a state government, or listed in the U.S. Pharmacopeia, European Pharmacopoeia or other generally recognized pharmacopeia for use in animals, and more particularly in humans. In this sense, it should be compatible with the other ingredients of the formulation and not eliciting an unacceptable deleterious effect in the subject.

According to the European Pharmacopoeia, a solution is considered isotonic if it has an osmolality of 290±30 mOsm/kg. Osmolality measurements were therefore performed on the different formulations used in the stability studies. Isotonicity can be measured by, for example, a vapor pressure or ice-freezing type osmometer.

As used herein, the term "effective amount" refers to the amount of an agent (e.g. a prophylactic or therapeutic agent) which is sufficient to reduce and/or ameliorate the severity and/or duration of one or more diseases and/or disorders.

The term "polyol" as used herein refers to sugars that contains many hydroxyl (—OH) groups compared to a normal saccharide. Polyols include alcohols and carbohydrates such as mannitol, sorbitol, maltitol, xylitol, isomalt, erythritol, lactitol, sucrose, glucose, galactose, fructose, fucose, ribose, lactose, maltose and cellubiose.

As used herein, the terms "therapeutic agent" and "therapeutic agents" refer to any agent(s) which can be used in the prevention, treatment and/or management of one ore more diseases and/or disorders. In the context of the present invention, the term "therapeutic agent" refers to a polypeptide comprising one or more single variable domains. In certain other embodiments, the term "therapeutic agent" refers to an agent other than the polypeptide of the invention which might be used in the formulation.

As used herein, the term "therapeutically effective amount" refers to the amount of a therapeutic agent (e.g. a polypeptide comprising one or more single variable domains), that is sufficient to reduce the severity of one or more diseases and/or disorders.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (e.g., serum albumin), amino acids (e.g., aspartic acid, glutamic acid, lysine, arginine, glycine), surfactants (e.g., SDS, TWEEN (polysorbate) 20, TWEEN (polysorbate) 80, poloxamers, polysorbate and nonionic surfactants), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., Mack Publishing Co., Easton, Pa.), which is incorporated herein in its entirety.

The term "variable domain" or "immunoglobulin variable domain" refers to the part or domain of an immunoglobulin molecule or antibody which is partially or fully responsible for antigen binding. The term "single variable domain" or "immunoglobulin single variable domain" (both terms are used interchangeably), defines molecules wherein the antigen binding site is present on, and formed by, a single immunoglobulin domain. This sets single variable domains apart from "conventional" immunoglobulins or their fragments, wherein two immunoglobulin domains, in particular two "variable domains" interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of a single variable domain is formed by a single VH or VL domain. Hence, the antigen binding site of a single variable domain is formed by no more than three CDRs. The term "single variable domain" does comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$ sequence) or a suitable fragment thereof; or a heavy chain variable domain sequence (e.g. a $V_H$ sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In one aspect of the invention, the single variable domains are light chain variable domain sequences (e.g. a $V_L$ sequence), or heavy chain variable domain sequences (e.g. a $V_H$ sequence); more specifically, the single variable domains can be heavy chain variable domain sequences that are derived from a conventional four-chain antibody or heavy chain variable domain sequences that are derived from a heavy chain antibody.

The single variable domain may be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody® (as defined herein, and including but not limited to a $V_{HH}$ sequence) [Note: Nanobody® and Nanobodies® are registered trademarks of Ablynx N.V.]; other single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-546), to Holt et al. 2003 (Trends Biotechnol. 21(11): 484-490); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the polypeptides of the invention may comprise one or more Nanobodies or a suitable fragment thereof. For a further description of $V_{HH}$'s and Nanobodies, reference is made to the review article by Muyldermans 2001 (Reviews in Molecular Biotechnology 74: 277-302); as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular $V_{HH}$ sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Thus, in the meaning of the present invention, the term "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

The term "single variable domain" also encompasses variable domains of different origin, comprising mouse, rat, rabbit, donkey, human and camelid variable domains; as well as fully human, humanized or chimeric variable domains. For example, the invention comprises camelid variable domains and humanized camelid variable domains, or camelized variable domains, e.g. camelized dAb as described by Ward et al (see for example WO 94/04678 and Davies and Riechmann (1994, FEBS Lett. 339(3): 285-290) and (1996, Protein Eng. 9(6): 531-537)). Moreover, the invention comprises fused variable domains, e.g. multivalent and/or multispecific constructs (for multivalent and multispecific polypeptides containing one or more $V_{HH}$ domains and their preparation, reference is also made to Conrath et al. 2001 (J. Biol. Chem. 276: 7346-7350) as well as to for example WO 96/34103 and WO 99/23221).

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

The single variable domains provided by the invention are preferably in essentially isolated form (as defined herein), or form part of a polypeptide of the invention (as defined herein), which may comprise or essentially consist of one or more single variable domains and which may optionally further comprise one or more further amino acid sequences (all optionally linked via one or more suitable linkers). For example, and without limitation, the one or more single variable domains may be used as a binding unit in such a polypeptide, which may optionally contain one or more further amino acid sequences that can serve as a binding unit (i.e. against one or more other targets), so as to provide a monovalent, multivalent or multispecific polypeptide of the invention, respectively as e.g. described in WO 08/101985, WO 08/142164, WO 09/068625, WO 09/068627 and WO 08/020079. Such a protein or polypeptide may also be in essentially isolated form (as defined herein) and the methods of the present invention for the expression and/or production of single variable domains equally apply to polypeptides comprising one or more single variable domains.

According to the invention, the term "single variable domain" may comprise constructs comprising two or more antigen binding units in the form of single variable domain, as outlined above. For example, two (or more) variable domains with the same or different antigen specificity can be linked to form e.g. a bivalent, trivalent or multivalent construct. By combining variable domains of two or more specificities, bispecific, trispecific etc. constructs can be formed. For example, a variable domain according to the invention may comprise two variable domains directed against target A, and one variable domain against target B. Such constructs and modifications thereof, which the skilled person can readily envisage, are all encompassed by the term variable domain as used herein and are also referred to as "polypeptide of the invention" or "polypeptides of the invention".

As further described in paragraph m) on page 53 of WO 08/020079, an amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The polypeptide comprising one or more single variable domains for use in the formulation of the invention may be therapeutic or prophylactic, and may be useful in the treatment and/or management of one or more diseases. In one specific aspect, the polypeptide has at least two single variable domains. In another specific aspect, the polypeptide has at least three single variable domains. Preferably, the polypeptide comprises at least one single variable domain directed against HSA. In another specific aspect, the polypeptide comprises at least a single variable domain against RANKL. In another specific aspect, the polypeptide comprises at least a single variable domain against IL-6R. In another specific aspect, the polypeptide comprises at least a single variable domain against IL-23. More preferably, the polypeptide is directed against and/or specifically binds RANKL and HSA, IL-6R and HSA and/or IL-23 and HSA. In yet another aspect, polypeptide comprises at least a single variable domain against RANKL and at least a single variable domain against HSA. In yet another aspect, polypeptide comprises at least a single variable domain against IL-6R and at least a single variable domain against HSA. In yet another aspect, polypeptide comprises at least a single variable domain against IL-23 and at least a single variable domain against HSA. In yet another aspect, polypeptide comprises at least two single variable domains against RANKL and at least a single variable domain against HSA. In yet another aspect, polypeptide comprises at least two single variable domains against IL-6R and at least a single variable domain against HSA. In yet another aspect, polypeptide comprises at least two single variable domains against IL-23 and at least a single variable domain against HSA. In a preferred aspect, the single variable domains used in the polypeptide of the invention are selected from WO 08/142164 (such as e.g. SEQ ID NO's: 745 and/or 791 of WO 08/142164), WO 08/020079, WO 09/068627 (such as e.g. SEQ ID NO's 2578, 2584 and/or 2585 of WO 09/068627), PCT application No. PCT/EP2010/054747 by Ablynx N.V., PCT application No. PCT/EP2010/054764 by Ablynx N.V. (such as e.g. SEQ ID NO's: 66 and/or 98 of PCT/EP2010/054764) and WO 08/028977 (such as e.g. SEQ ID NO: 62 of WO 08/028977). Preferred polypeptides of the invention are selected from SEQ ID NO's: 1 to 6.

The concentration of polypeptide of the invention present in the formulation can by any concentration of the polypeptide that provides the desired effect to the subject. In a preferred aspect, the concentration of the polypeptide of the invention is from 1 to 200 mg/mL such as about 1 mg/mL, about 2 mg/mL, about 5 mg/mL, about 10 mg/mL, about 15 mg/mL or about 20 mg/mL, about 30 mg/mL, about 40 mg/mL, about 50 mg/mL, about 60 mg/mL, about 65 mg/mL, about 70 mg/mL, about 80 mg/mL, about 90 mg/mL or about 100 mg/mL or more. In certain embodiments, the concentration of polypeptide of the invention can be 110 mg/mL or more, 120 mg/mL or more, 130 mg/mL or more, 140 mg/mL or more, 150 mg/mL or more or even 200 mg/mL or more. In a specific aspect, a formulation of the invention comprises about 10 mg/mL of polypeptide of the invention.

The formulation of the invention comprises an aqueous carrier having a pH of 5.5 to 8.0 and a polypeptide as defined above ("polypeptide of the invention") comprising one or more single variable domains at a concentration of 1 mg/mL to 200 mg/mL, said formulation being formulated for administration to a human subject, wherein said formulation further comprises one or more components selected from:
a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
b) An excipient at a concentration of 1% to 20%;
c) A surfactant at a concentration of 0.001% to 1% selected from TWEEN (polysorbate) 80, TWEEN (polysorbate) 20 or a poloxamer; and
wherein said formulation has an inorganic salt concentration of 150 mM or lower.

The stable formulations of the present invention comprise polypeptides of the invention that have a good solubility and a high stability even during transportation and/or long periods of storage and that exhibit little to no aggregation. In addition to the polypeptide of the invention, the formulations of the present invention comprise at least an aqueous carrier and a buffer. The carrier used in the formulation of the invention should be a liquid carrier. Preferably the carrier is an aqueous carrier such as e.g. distilled water, MILLI-Q water or Water for Injection (WFI).

The formulation should not contain inorganic salt at a concentration of more than 150 mM. Without being limiting, inorganic salts for use in the formulation of the invention can be selected from NaCl and KCl. Accordingly the formulation of the invention has an inorganic salt concentration of 150 mM or lower, preferably 120 mM or lower, or 100 mM or lower, more preferably 90 mM or lower, 80 mM or lower, 75 mM or lower, such as 50 mM or lower or even 40 mM or lower, 25 mM or lower, 10 mM or lower or 5 mM or lower. Most preferably, the formulation does not contain any inorganic salt.

The pH of the formulation of the invention generally should not be equal to the isoelectric point of the particular polypeptide of the invention present in the formulation and may range from about 5.5 to about 8.0, or from about 6.0 to about 7.5, preferably from about 6.2 to 7.5, from about 6.5 to 7.5, most preferably from about 6.5 to 7.0. In a specific aspect, the formulation of the invention has a pH of about 6.5. In another specific aspect, the formulation of the invention has a pH of about 7.0. In yet another specific aspect, the formulation of the invention has a pH of about 6.0.

The formulation may be buffered by a buffer selected from the group consisting of histidine pH 6.0-6.5, hepes pH 7.0-8.0, MES pH 6.0, succinate pH 6.0-6.5 and acetate pH 5.5-6.0, preferably hepes pH 7.0 or histidine pH 6.0-6.5, such as histidine pH 6.5 or histidine pH 6.0.

The concentration of the buffer present in the formulation of the invention may range from 1 mM to 100 mM, 5 mM to 100 mM, 5 mM to 75 mM, 5 mM to 50 mM, 10 mM to 50 mM, 10 mM to 25 mM, 10 mM to 20 mM. In a specific aspect, the concentration of buffer in the formulations of the invention is 1 mM, 2 mM, 5 mM, 10 mM, 15 mM, 20 mM, 25 mM, 50 mM, 75 mM, or 100 mM. Preferably, the concentration is between 10 and 20 mM, such as 10 mM or 15 mM.

Any form of histidine suitable for formulation and parenteral administration may be used in the formulation of the invention. The purity of histidine should be at least 98%, at least 99%, or at least 99.5%. In a specific aspect, a formulation of the invention comprises 15 mM histidine buffer pH 6.5. In another specific aspect, a formulation of the invention comprises 10 mM histidine buffer pH 6.0.

Apart from or in addition to histidine, hepes buffers pH7.0 may be used in the formulations of the present invention. Any form of hepes suitable for formulation and parenteral administration may be used in the formulation of the invention. The purity of hepes should be at least 98%, at least 99%, or at least 99.5%. In a specific aspect, a formulation of the invention comprises 15 mM hepes buffer pH7.0.

It will be understood by one skilled in the art that the formulation of the invention may be isotonic or slightly hypotonic with human blood, i.e. the formulation of the invention has essentially the same or a slightly lower osmotic pressure as human blood. Such isotonic or slightly hypotonic formulation generally has an osmotic pressure from about 240 mOSm/kg to about 320 mOSm/kg, such as about 240 mOSm/kg or higher, 250 mOSm/kg or higher or 260 mOSm/kg or higher.

Tonicity of a formulation is adjusted by the use of tonicity modifiers. "Tonicity modifiers" are those pharmaceutically acceptable inert substances that can be added to the formulation to provide an isotonicity of the formulation. A preferred tonicity modifier in the formulation of the invention are excipients. Preferred excipients for use in the formulation of the invention may be selected from sugars, polyols and surfactants.

Accordingly, in another aspect, the formulation of the invention comprises an excipient. Preferred excipients include polyols and/or sugars. The polyol and/or sugar may be a monosaccharide such as glucose or mannose, or a polysaccharide including disaccharides such as (without being limiting) sucrose and lactose, as well as sugar derivatives including sugar alcohols and sugar acids. Polyols and sugar alcohols include (without being limiting) mannitol, xylitol, erythritol, threitol, sorbitol and glycerol. A non-limiting example of a sugar acid is L-gluconate. Other exemplary sugars include (without being limiting) trehalose, glycine, maltose, raffinose, etc. The concentration of the excipient may range from about 1% to 10% (w:v), preferably from about 2.5% to 10% (w:v), more preferably from about 5% to 10% (w:v), such as e.g. 5% (w:v), 7.5% (w:v), 8% or 10% (w:v). Throughout the present invention the concentration of the excipient will be given as % (w:v). In a preferred aspect, the formulation comprises sucrose, preferably at a concentration of about 5% to 10% (w:v), such as about 8% (w:v).

In another aspect, the formulation of the invention comprises a surfactant. A surfactant refers to a surface-active agent comprising a hydrophobic portion and a hydrophilic portion. In a preferred aspect, the surfactant is non-ionic. Certain exemplary non-ionic surfactants include (without being limiting) PEG8000, and polysorbate, including without being limiting, polysorbate 80 (TWEEN 80) and polysorbate 20 (TWEEN 20), TRITON X-100, polyoxypropylene-polyoxyethylene esters (PLURONIC®), and NP-40. In a specific aspect, the surfactant is selected from TWEEN (polysorbate) 20, TWEEN (polysorbate) 80 or a poloxamer. The concentration of the surfactant may range from about 0.001% to 1% (v:v) (preferably from about 0.001% to 0.1% (v:v), or 0.01% to 0.1% (v:v) such as 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)). Throughout the present invention the concentration of the surfactant will be given as % (v:v). In a specific embodiment, the surfactant is TWEEN (polysorbate) 20 or TWEEN (polysorbate) 80, which is at a concentration of 0.001% (v:v), 0.005% (v:v), 0.01% (v:v), 0.02% (v:v), 0.05% (v:v), 0.08% (v:v), 0.1% (v:v), 0.5% (v:v) or 1% (v:v) of the formulation, preferably 0.01% (v:v).

In a preferred aspect, the formulation of the present invention comprises an aqueous carrier having a pH of 5.5 to 8.0 and a polypeptide as defined above ("polypeptide of the invention") comprising one or more single variable domains at a concentration of 1 mg/mL to 200 mg/mL, said formulation being formulated for administration to a human subject and said formulation further comprises at least two components selected from:
 a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
 b) An excipient at a concentration of 1% to 20%;
 c) A surfactant at a concentration of 0.001% to 1% selected from TWEEN (polysorbate) 80, TWEEN (polysorbate) 20 or poloxamers;
wherein said formulation has an inorganic salt concentration of 150 mM or lower.

In one aspect, in addition to the polypeptide of the invention, the formulation of the present invention may comprise at least an aqueous carrier having a pH of 5.5 to 8.0, a buffer selected from the group consisting of histidine pH 6.0-6.5, hepes pH 7.0-8.0, MES pH 6.0, succinate pH 6.0-6.5 and acetate pH 5.5-6.0, and an excipient. Preferably the buffer is histidine pH 6.0-6.5 or hepes pH 7.0. Most preferably the buffer is histidine pH 6.5 or histidine pH 6.0. The buffer preferably has a concentration ranging from 1 mM to 100 mM, 5 mM to 100 mM, 5 mM to 75 mM, 5 mM to 50 mM, 10 mM to 50 mM, 10 mM to 25 mM, 10 mM to 20 mM. In a specific aspect, the concentration of buffer in the formulations of the invention is 1 mM, 2 mM, 5 mM, 10 mM, 15 mM, 20 mM, 25 mM, 50 mM, 75 mM, or 100 mM. In a preferred aspect, the concentration is between 10 and 20 mM, such as 10 mM or 15 mM. In a specific aspect, a formulation of the invention comprises 15 mM histidine buffer pH 6.5. In another specific aspect, a formulation of the invention comprises 10 mM histidine buffer pH 6.0. Preferred excipients are polyols such as mannitol, sorbitol, etc., saccharides such as e.g. sucrose, mannose, trehalose, etc. The concentration of the excipient may range from about 1% to 20%, preferably from about 2.5% to 15%, more preferably from about 5% to 10%, such as e.g. 5%, 7.5%, 8% or 10%. In a preferred aspect, the formulation comprises sucrose, preferably at a concentration of about 5% to 10%, such as about 8% or about 10%. Accordingly, a preferred formulation of the invention may comprise 15 mM histidine pH 6.5 and 8% sucrose. Another preferred formulation of the invention may comprise 10 mM histidine pH 6.0 and 10% sucrose.

In another aspect, in addition to the polypeptide of the invention, the formulation of the present invention may comprise at least an aqueous carrier having a pH of 5.5 to 8.0, a buffer selected from the group consisting of histidine pH 6.0-6.5, hepes pH 7.0-8.0, MES pH 6.0, succinate pH 6.0-6.5 and acetate pH 5.5-6.0, and a surfactant. Preferably the buffer is selected from histidine pH 6.0-6.5 or hepes pH 7.0. Most preferably the buffer is histidine pH 6.5 or histidine pH 6.0. The buffer preferably has a concentration ranging from 1 mM to 100 mM, 5 mM to 100 mM, 5 mM to 75 mM, 5 mM to 50 mM, 10 mM to 50 mM, 10 mM to 25 mM, 10 mM to 20 mM. In a specific aspect, the concentration of buffer in the formulation of the invention is 1 mM, 2 mM, 5 mM, 10 mM, 15 mM, 20 mM, 25 mM, 50 mM, 75 mM, or 100 mM. In a preferred aspect, the concentration is between 10 and 20 mM, such as 10 mM or 15 mM. In a specific aspect, a formulation of the invention comprises 15 mM histidine buffer pH 6.5. In another specific aspect, a formulation of the invention comprises 10 mM histidine buffer pH 6.0. The surfactant may be selected from TWEEN (polysorbate) 20, TWEEN (polysorbate) 80 or poloxamers. The concentration of the surfactant may range from about 0.001% to 1% (preferably from about 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01%). In a specific embodiment, the surfactant is TWEEN (polysorbate) 20 or TWEEN (polysorbate) 80, which is at a concentration of 0.001%, 0.005%, 0.01%, 0.02%, 0.05%, 0.08%, 0.1%, 0.5% or 1% of the formulation, such as e.g. 0.01% TWEEN (polysorbate) 80 or 0.005% TWEEN (polysorbate) 80. Accordingly, a preferred formulation of the invention may comprise 15 mM histidine pH 6.5 and 0.01% TWEEN (polysorbate) 80. Another preferred formulation of the invention may comprise 10 mM histidine pH 6.0 and 0.005% TWEEN (polysorbate) 80.

In yet another aspect, in addition to the polypeptide of the invention, the formulation of the present invention may comprise at least an aqueous carrier having a pH of 5.5 to 8.0, an excipient and a surfactant. Preferred excipients are polyols such as mannitol, sorbitol, etc., saccharides such as e.g. sucrose, mannose, trehalose, etc. The concentration of the excipient may range from about 1% to 20%, preferably from about 2.5% to 15%, more preferably from about 5% to 10%, such as e.g. 5%, 7.5%, 8% or 10%. In a preferred aspect, the formulation comprises sucrose, preferably at a concentration of about 5% to 10%, such as about 8% or 10%. The surfactant may be selected from TWEEN (polysorbate) 20, TWEEN (polysorbate) 80 or a poloxamer. The concentration of the surfactant may range from about 0.001% to 1% (preferably from about 0.001% to 0.1%, or 0.01% to t 0.1% such as 0.001%, 0.005%, 0.01%, 0.02%, 0.05%, 0.08%, 0.1%, 0.5%, or 1% of the formulation, preferably 0.01%). In a specific embodiment, the surfactant is TWEEN (polysorbate) 20 or TWEEN (polysorbate) 80, which is at a concentration of 0.001%, 0.005%, 0.01%, 0.02%, 0.05%, 0.08%, 0.1%, 0.5% or 1% of the formulation, such as e.g. 0.01% TWEEN (polysorbate) 80 or 0.005% TWEEN (polysorbate) 80. Accordingly, a preferred formulation of the invention may comprise 8% sucrose and 0.01% TWEEN (polysorbate) 80. Another preferred formulation of the invention may comprise 10% sucrose and 0.005% TWEEN (polysorbate) 80.

Accordingly, a formulation of the invention may, in addition to the polypeptide of the invention, comprise for example:
 a) A buffer selected from a histidine buffer pH 6.5, histidine buffer pH 6.0 and hepes buffer pH 7.0 at a concentration of 10 mM to 100 mM; and
 b) An excipient selected from sucrose, sorbitol, trehalose and mannitol at a concentration of 1% to 20%.
 or
 a) A buffer selected from a histidine buffer pH 6.5, histidine buffer pH 6.0 and hepes buffer pH 7.0 at a concentration of 10 mM to 100 mM; and
 c) A surfactant selected from TWEEN (polysorbate) 80, TWEEN (polysorbate) 20 or a poloxamer at a concentration of 0.001% to 1%.
 or
 b) An excipient selected from sucrose, sorbitol, trehalose and mannitol at a concentration of 1% to 20%; and
 c) A surfactant selected from TWEEN (polysorbate) 80, TWEEN (polysorbate) 20 or a poloxamer at a concentration of 0.001% to 1%.
 or
 a) A buffer selected from a histidine buffer pH 6.5, and hepes buffer pH 7.0 at a concentration of 15 mM; and b) An excipient selected from sucrose, sorbitol, trehalose and mannitol at a concentration of 1% to 20%.
or
a) A buffer selected from a histidine buffer pH 6.5 and hepes buffer pH 7.0 at a concentration of 15 mM; and
c) A surfactant selected from TWEEN (polysorbate) 80, TWEEN (polysorbate) 20 or a poloxamer at a concentration of 0.001% to 1%.
or
a) A buffer selected from a histidine buffer pH 6.5 and hepes buffer pH 7.0 at a concentration of 10 mM to 100 mM; and
b) An excipient selected from sucrose, sorbitol, trehalose and mannitol at a concentration of 8%.
or
b) An excipient selected from sucrose, sorbitol, trehalose and mannitol at a concentration of 8%; and
c) A surfactant selected from TWEEN (polysorbate) 80, TWEEN (polysorbate) 20 or a poloxamer at a concentration of 0.001% to 1%.
or
a) A buffer selected from a histidine buffer pH 6.5 and hepes buffer pH 7.0 at a concentration of 10 mM to 100 mM; and
c) A surfactant selected from TWEEN (polysorbate) 80, TWEEN (polysorbate) 20 or a poloxamer at a concentration of 0.01%.
or
b) An excipient selected from sucrose, sorbitol, trehalose and mannitol at a concentration of 1% to 20%; and
c) A surfactant selected from TWEEN (polysorbate) 80, TWEEN (polysorbate) 20 or a poloxamer at a concentration of 0.01%.
or
a) A buffer selected from a histidine buffer pH 6.0 at a concentration of 10 mM; and
b) An excipient selected from sucrose, sorbitol, trehalose and mannitol at a concentration of 1% to 20%.
or
a) A buffer selected from a histidine buffer pH 6.0 at a concentration of 10 mM; and
c) A surfactant selected from TWEEN (polysorbate) 80, TWEEN (polysorbate) 20 or a poloxamer at a concentration of 0.001% to 1%.
or
a) A buffer selected from a histidine buffer pH 6.0 at a concentration of 10 mM to 100 mM; and
b) An excipient selected from sucrose, sorbitol, trehalose and mannitol at a concentration of 10%.
or
b) An excipient selected from sucrose, sorbitol, trehalose and mannitol at a concentration of 10%; and
c) A surfactant selected from TWEEN (polysorbate) 80, TWEEN (polysorbate) 20 or a poloxamer at a concentration of 0.001% to 1%.
or
a) A buffer selected from a histidine buffer pH 6.0 at a concentration of 10 mM to 100 mM; and
c) A surfactant selected from TWEEN (polysorbate) 80, TWEEN (polysorbate) 20 or a poloxamer at a concentration of 0.005%.
or
b) An excipient selected from sucrose, sorbitol, trehalose and mannitol at a concentration of 1% to 20%; and
c) A surfactant selected from TWEEN (polysorbate) 80, TWEEN (polysorbate) 20 or a poloxamer at a concentration of 0.005%.
or
a) Histidine buffer pH 6.5 or pH 6.0 at a concentration of 10 mM to 100 mM; and
b) Sucrose at a concentration of 1% to 20%.
or
a) Histidine buffer pH 6.5 or pH 6.0 at a concentration of 10 mM to 100 mM; and
c) TWEEN (polysorbate) 80 at a concentration of 0.001% to 1%.
or
b) Sucrose at a concentration of 1% to 20%; and
c) TWEEN (polysorbate) 80 at a concentration of 0.001% to 1%.
or
a) 15 mM histidine buffer pH 6.5; and
b) 8% sucrose.
or
a) 15 mM histidine buffer pH 6.5; and
c) 0.01% TWEEN (polysorbate) 80.
or
b) 8% sucrose; and
c) 0.01% TWEEN (polysorbate) 80.
or
a) 10 mM histidine buffer pH 6.0; and
b) 10% sucrose.
or
a) 10 mM histidine buffer pH 6.0; and
c) 0.005% TWEEN (polysorbate) 80.
or
b) 10% sucrose; and
c) 0.005% TWEEN (polysorbate) 80.

In a preferred aspect the formulation of the invention may comprise a polypeptide selected from SEQ ID NO's: 1 to 6. Accordingly the formulation of the invention may comprise:
a) 15 mM histidine buffer pH 6.5;
b) 8% sucrose; and
d) A polypeptide selected from SEQ ID NO's: 1 to 6 (e.g. at a concentration of 10 mg/ml).
or
a) 15 mM histidine buffer pH 6.5;
c) 0.01% TWEEN (polysorbate) 80; and
d) A polypeptide selected from SEQ ID NO's: 1 to 6 (e.g. at a concentration of 10 mg/ml).
or
b) 8% sucrose;
c) 0.01% TWEEN (polysorbate) 80; and
d) A polypeptide selected from SEQ ID NO's: 1 to 6 (e.g. at a concentration of 10 mg/ml).
or
a) 10 mM histidine buffer pH 6.0;
b) 10% sucrose; and
c) A polypeptide selected from SEQ ID NO's: 1 to 6 (e.g. at a concentration of 10 mg/ml).
or
a) 10 mM histidine buffer pH 6.0;
c) 0.005% TWEEN (polysorbate) 80; and
d) A polypeptide selected from SEQ ID NO's: 1 to 6 (e.g. at a concentration of 10 mg/ml).
or
b) 10% sucrose;
c) 0.005% TWEEN (polysorbate) 80; and
d) A polypeptide selected from SEQ ID NO's: 1 to 6 (e.g. at a concentration of 10 mg/ml).

In another preferred aspect, the formulation of the present invention comprises an aqueous carrier having a pH of 5.5 to 8.0 and a polypeptide as defined above ("polypeptide of the invention") comprising one or more single variable domains at a concentration of 1 mg/mL to 200 mg/mL, said formulation being formulated for administration to a human subject and comprises the components selected from:
- a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
- b) An excipient at a concentration of 1% to 20%; and
- c) A surfactant at a concentration of 0.001% to 1% selected from TWEEN (polysorbate) 80, TWEEN (polysorbate) 20 or a poloxamer;

wherein said formulation has an inorganic salt concentration of 150 mM or lower.

Accordingly in this preferred aspect, in addition to the polypeptide of the invention, the formulations of the present invention may comprise at least an aqueous carrier having a pH of 5.5 to 8.0, a buffer selected from the group consisting of histidine pH 6.0-6.5, hepes pH 7.0-8.0, MES pH 6.0, succinate pH 6.0-6.5 and acetate pH 5.5-6.0, an excipient and a surfactant. Preferably the buffer is selected from histidine pH 6.0-6.5 or hepes pH 7.0. Most preferably the buffer is histidine pH 6.5 or histidine pH 6.0. The buffer preferably has a concentration ranging from 1 mM to 100 mM, 5 mM to 100 mM, 5 mM to 75 mM, 5 mM to 50 mM, 10 mM to 50 mM, 10 mM to 25 mM, 10 mM to 20 mM. In a specific aspect, the concentration of buffer in the formulations of the invention is 1 mM, 2 mM, 5 mM, 10 mM, 15 mM, 20 mM, 25 mM, 50 mM, 75 mM, or 100 mM. In a preferred aspect, the concentration is between 10 and 20 mM, such as 10 mM or 15 mM. In a specific aspect, a formulation of the invention comprises 15 mM histidine buffer pH 6.5. In another specific aspect, a formulation of the invention comprises 10 mM histidine buffer pH 6.0. Preferred excipients are polyols such as mannitol, sorbitol, etc., saccharides such as e.g. sucrose, mannose, trehalose, etc. The concentration of the excipient may range from about 1% to 20%, preferably from about 2.5% to 15%, more preferably from about 5% to 10%, such as e.g. 5%, 7.5%, 8% or 10%. In a preferred aspect, the formulation comprises sucrose, preferably at a concentration of about 5% to 10%, such as about 8% or 10%. The surfactant may be selected from TWEEN (polysorbate) 20, TWEEN (polysorbate) 80 or a poloxamer. The concentration of the surfactant may range from about 0.001% to 1% (preferably from about 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01% or 0.005%). In a specific embodiment, the surfactant is TWEEN (polysorbate) 20 or TWEEN (polysorbate) 80, which is at a concentration of 0.001%, 0.005%, 0.01%, 0.02%, 0.05%, 0.08%, 0.1%, 0.5% or 1% of the formulation, such as e.g. 0.01% TWEEN (polysorbate) 80 or 0.005% TWEEN (polysorbate) 80. Accordingly, a preferred formulation of the invention may comprise 15 mM histidine pH 6.5, 8% sucrose and 0.01% TWEEN (polysorbate) 80. Another preferred formulation of the invention may comprise 10 mM histidine pH 6.0, 10% sucrose and 0.005% TWEEN (polysorbate) 80.

Accordingly, a formulation of the invention may, in addition to the polypeptide of the invention, comprise for example:
- a) A buffer selected from a histidine buffer pH 6.5, a histidine buffer pH 6.0 and hepes buffer pH 7.0 at a concentration of 10 mM to 100 mM;
- b) An excipient selected from sucrose, sorbitol, trehalose and mannitol at a concentration of 1% to 20%; and
- c) A surfactant selected from TWEEN (polysorbate) 80, TWEEN (polysorbate) 20 or a poloxamer at a concentration of 0.001% to 1%.

or
- a) A buffer selected from a histidine buffer pH 6.5 and hepes buffer pH 7.0 at a concentration of 15 mM;
- b) An excipient selected from sucrose, sorbitol, trehalose and mannitol at a concentration of 1% to 20%; and
- c) A surfactant selected from TWEEN (polysorbate) 80, TWEEN (polysorbate) 20 or a poloxamer at a concentration of 0.001% to 1%.

or
- a) A buffer selected from a histidine buffer pH 6.5 and hepes buffer pH 7.0 at a concentration of 10 mM to 100 mM;
- b) An excipient selected from sucrose, sorbitol, trehalose and mannitol at a concentration of 8%; and
- c) A surfactant selected from TWEEN (polysorbate) 80, TWEEN (polysorbate) 20 or a poloxamer at a concentration of 0.001% to 1%.

or
- a) A buffer selected from a histidine buffer pH 6.5 and hepes buffer pH 7.0 at a concentration of 10 mM to 100 mM;
- b) An excipient selected from sucrose, sorbitol, trehalose and mannitol at a concentration of 1% to 20%; and
- c) A surfactant selected from TWEEN (polysorbate) 80, TWEEN (polysorbate) 20 or a poloxamer at a concentration of 0.01%.

or
- a) A buffer selected from a histidine buffer pH 6.5 and hepes buffer pH 7.0 at a concentration of 15 mM;
- b) An excipient selected from sucrose, sorbitol, trehalose and mannitol at a concentration of 8%; and
- c) A surfactant selected from TWEEN (polysorbate) 80, TWEEN (polysorbate) 20 or a poloxamer at a concentration of 0.001% to 1%.

or
- a) A buffer selected from a histidine buffer pH 6.5 and hepes buffer pH 7.0 at a concentration of 10 mM to 100 mM;
- b) An excipient selected from sucrose, sorbitol, trehalose and mannitol at a concentration of 8%; and
- c) A surfactant selected from TWEEN (polysorbate) 80, TWEEN (polysorbate) 20 or a poloxamer at a concentration of 0.01%.

or
- a) A buffer selected from a histidine buffer pH 6.5 and hepes buffer pH 7.0 at a concentration of 15 mM;
- b) An excipient selected from sucrose, sorbitol, trehalose and mannitol at a concentration of 1% to 20%; and
- c) A surfactant selected from TWEEN (polysorbate) 80, TWEEN (polysorbate) 20 or a poloxamer at a concentration of 0.01%.

or
- a) A buffer selected from a histidine buffer pH 6.0 at a concentration of 10 mM;
- b) An excipient selected from sucrose, sorbitol, trehalose and mannitol at a concentration of 1% to 20%; and
- c) A surfactant selected from TWEEN (polysorbate) 80, TWEEN (polysorbate) 20 or a poloxamer at a concentration of 0.001% to 1%.

or
- a) A buffer selected from a histidine buffer pH 6.0 at a concentration of 10 mM to 100 mM;
- b) An excipient selected from sucrose, sorbitol, trehalose and mannitol at a concentration of 10%; and
- c) A surfactant selected from TWEEN (polysorbate) 80, TWEEN (polysorbate) 20 or a poloxamer at a concentration of 0.001% to 1%.

or
a) A buffer selected from a histidine buffer pH 6.0 at a concentration of 10 mM to 100 mM;
b) An excipient selected from sucrose, sorbitol, trehalose and mannitol at a concentration of 1% to 20%; and
c) A surfactant selected from TWEEN (polysorbate) 80, TWEEN (polysorbate) 20 or a poloxamer at a concentration of 0.005%.
or
a) A buffer selected from a histidine buffer pH 6.0 at a concentration of 10 mM;
b) An excipient selected from sucrose, sorbitol, trehalose and mannitol at a concentration of 10%; and
c) A surfactant selected from TWEEN (polysorbate) 80, TWEEN (polysorbate) 20 or a poloxamer at a concentration of 0.001% to 1%.
or
a) A buffer selected from a histidine buffer pH 6.0 at a concentration of 10 mM to 100 mM;
b) An excipient selected from sucrose, sorbitol, trehalose and mannitol at a concentration of 10%; and
c) A surfactant selected from TWEEN (polysorbate) 80, TWEEN (polysorbate) 20 or a poloxamer at a concentration of 0.005%.
or
a) A buffer selected from a histidine buffer pH 6.0 at a concentration of 15 mM;
b) An excipient selected from sucrose, sorbitol, trehalose and mannitol at a concentration of 1% to 20%; and
c) A surfactant selected from TWEEN (polysorbate) 80, TWEEN (polysorbate) 20 or a poloxamer at a concentration of 0.005%.
or
a) Histidine buffer pH 6.5 at a concentration of 10 mM to 100 mM;
b) Sucrose at a concentration of 1% to 20%; and
c) TWEEN (polysorbate) 80 at a concentration of 0.001% to 1%.
or
a) 15 mM histidine buffer pH 6.5;
b) 8% sucrose; and
c) 0.01% TWEEN (polysorbate) 80.
or
a) Histidine buffer pH 6.0 at a concentration of 10 mM to 100 mM;
b) Sucrose at a concentration of 1% to 20%; and
c) TWEEN (polysorbate) 80 at a concentration of 0.001% to 1%.
or
a) 10 mM histidine buffer pH 6.0;
b) 10% sucrose; and
c) 0.005% TWEEN (polysorbate) 80.

In a preferred aspect the formulation of the invention may comprise a polypeptide selected from SEQ ID NO's: 1 to 6. Accordingly the formulation of the invention may comprise:
a) 15 mM histidine buffer pH 6.5;
b) 8% sucrose;
c) 0.01% TWEEN (polysorbate) 80; and
d) A polypeptide selected from SEQ ID NO's: 1 to 6 (e.g. at a concentration of 10 mg/ml).
or
a) 10 mM histidine buffer pH 6.0;
b) 10% sucrose;
c) 0.005% TWEEN (polysorbate) 80; and
d) A polypeptide selected from SEQ ID NO's: 1 to 6 (e.g. at a concentration of 10 mg/ml).

The components present in the formulations of the invention have been selected such that the polypeptides of the invention have a good solubility (as defined herein). Preferably, the polypeptides present in the formulations of the present invention have a solubility of at least 0.7 mM, at least 0.8 mM, at least 0.9 mM, at least 1.0 mM, at least 1.1 mM, at least 1.2 mM, at least 1.3 mM, at least 1.4 mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.2 mM, at least 3.4 mM, at least 3.6 mM or more and/or at least 20 mg/ml, at least 30 mg/mL, at least 40 mg/mL, at least 50 mg/mL, at least 60 mg/mL, at least 65 mg/mL, at least 70 mg/mL, at least 80 mg/mL, at least 90 mg/mL, at least 100 mg/mL, at least 110 mg/mL, at least 120 mg/mL, at least 130 mg/mL, at least 140 mg/mL, at least 150 mg/mL or even 200 mg/mL or more as determined by the PEG exclusion method or by centrifugal ultrafiltration. A very good solubility of the polypeptides of the invention has been obtained with a formulation comprising a histidine buffer pH 6.5 or with a formulation comprising TWEEN (polysorbate) 80. Accordingly, the present invention relates to a formulation comprising an aqueous carrier and a polypeptide comprising one or more single variable domains, said formulation being formulated for administration to a human subject, wherein said formulation further comprises at least one of:
a) A histidine buffer pH 6.5 at a concentration of 10 mM to 100 mM (preferably 10 mM to 50 mM, more preferably 10 to 20 mM, such as 15 mM);
c) TWEEN (polysorbate) 80 at a concentration of 0.001% to 1% (preferably from about 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01%);
wherein said formulation has an inorganic salt concentration of 150 mM or lower; and
wherein the solubility of the polypeptide is at least at least 20 mg/mL, at least 50 mg/mL, preferably at least 90 mg/mL, at least 120 mg/mL, at least 150 mg/mL or even 200 mg/mL or more as determined by the PEG exclusion method or by centrifugal ultrafiltration. In a preferred aspect, the formulation comprises a histidine buffer pH 6.5 at a concentration of 10 mM to 100 mM (preferably 10 mM to 50 mM, more preferably 10 to 20 mM, such as 15 mM) and TWEEN (polysorbate) 80 at a concentration of 0.001% to 1% (preferably from about 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01%).

Apart from this and/or in addition, the polypeptides of the invention present in the formulation of the invention should preferably have a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

Without being limiting, melting point determination can be done by the fluorescence-based thermal shift assay which is based on the fact that upon thermal unfolding the hydrophobic regions of proteins, usually hidden in the core of the protein fold, become accessible for binding to a hydrophobic fluorescent dye. The fluorescence emission of this dye is quenched in aqueous solution, whereas upon binding to the hydrophobic patches of an unfolded protein a sharp increase in the fluorescence yield of the probe is observed. Temperature induced unfolding is typically a two-state process with a sharp transition between the folded and unfolded state, where the melting temperature (Tm) is defined as the temperature at which half of the protein is in the unfolded state, i.e. the first derivative of the fluorescence signal upon gradual heating of the sample is plotted and the observed peak (or peaks when multiple domains and/or variants of the same domain are present) represents the melting temperature. The thermal shift assay can be performed in a typical real-time PCR instrument where melting curves can be recorded accurately in high-throughput mode with only small quantities of protein required.

During a differential scanning calorimetry experiment the sample is heated at a constant rate in an adiabatic environment ($\Delta T=0$). The energy required to keep the temperature difference between a reference and the sample cell at zero is measured and yields the heat capacity as a function of temperature (Cp(T)). The temperature corresponding to the maximum heat capacity represents the melting temperature ($T_m$). If the temperature dependent unfolding process is reversible other thermodynamic parameters such as the unfolding enthalpy ($\Delta H_{unfolding}$) can be determined.

Increased melting temperatures have been observed for the polypeptides of the invention when present in a formulation with a pH of about 6.0 to 8.0, preferably 6.2 to 7.5, more preferably 6.5 to 7.5, most preferably 6.5-7.0. Increased melting temperature have also been obtained for the polypeptides of the invention when present in a formulation that comprise hepes pH 7.0, histidine pH 6.0-6.5, MES pH 6.0 or acetate pH 6.0, or a formulation that comprises an excipient, preferably a saccharides and/or polyol such as mannitol, trehalose, sorbitol or sucrose. Accordingly, the present invention relates to a formulation comprising an aqueous carrier at a pH of 6.0 to 8.0 and a polypeptide comprising one or more single variable domains, said formulation being formulated for administration to a human subject, wherein said formulation further comprises at least one of:

a) A buffer at a concentration of 10 mM to 100 mM (preferably 10 mM to 50 mM, more preferably 10 to 20 mM, such as 15 mM or 10 mM) selected from the group consisting of histidine pH 6.0-6.5, hepes pH 7.0-8.0, MES pH 6.0, succinate pH 6.0-6.5 and acetate pH 5.5-6.0;

b) An excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%).

wherein said formulation has an inorganic salt concentration of 150 mM or lower; and wherein the melting temperature of the polypeptide of the invention is at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

In a preferred aspect, the formulation comprises a buffer at a concentration of 10 mM to 100 mM (preferably 10 mM to 50 mM, more preferably 10 to 20 mM, such as 15 mM) selected from the group consisting of histidine pH 6.0-6.5, hepes pH 7.0-8.0, MES pH 6.0, succinate pH 6.0-6.5 and acetate pH 5.5-6.0, and an excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%).

Apart from this and/or in addition, the formulation of the present invention exhibits stability under at least one or more of the following stress conditions:

multiple (up to 10) freeze/thaw cycles;

storage at a temperature of 2-8° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

storage at a temperature of 25±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

mechanical stress.

Preferably the formulation of the invention is stable under one or more of the following forms of mechanical stress:

shaking the formulation during 10 s to 1 min;

pushing the formulation through a needle (25 G, preferably 26 G, more preferably 27 G, even more preferably 28 G, most preferably 29 G or more) with a syringe (the syringe used can be any commercially available syringe, such as e.g. a 1 mL, 2 mL, 3 mL, 4 mL, 5 mL, 10 mL, 20 mL, 30 mL, 40 mL up to 50 mL syringe);

rotating for two days at 10 rpm; and/or stirring for 1 hour at room temperature and/or 4-48 hours at 4° C. at at least 10 rpm (such as 50 rpm, 100 rpm or more).

Preferably, the formulation of the present invention is stable under more than one of the above stress conditions, such as at least two, at least three, at least four, at least five, at least six, at least seven or most preferably under all of the above stress conditions.

In one aspect, the formulation of the invention exhibits stability under one or more forms of mechanical and/or shear stress. Mechanical stress as used in the present invention can be any form of external force applied on the formulation that may affect the stability of the polypeptide present in the formulation. Without being limiting, the mechanical stress applied to the solution include shear stress, stir stress, shake stress, rotation stress, etc. The formulation of the invention may for example be shaken during at least 10 s, 20 s, 30 s, 40 s, 50 s up to 1 minute or more. The formulation of the invention may be pushed through a syringe (the syringe used can be any commercially available syringe, such as e.g. a 1 mL, 2 mL, 3 mL, 4 mL, 5 mL, 10 mL, 20 mL, 30 mL, 40 mL up to 50 mL syringe) with needle once, twice, three times, four times, five times up to 10 times or more. Preferably the needle has a size of 25 G (such as 26 G, 27 G, 28 G, 29 G, 30 G) or more. More preferably the size of the needles is 27 G or more. In addition or alternatively, the formulation of the invention may be rotated for 1 hour, 2 hours, 6 hours, 12 hours, 1 day up to two days or more at 10 rpm. The formulation of the invention may be stirred for 1 hour at room temperature and/or 4 hours, 8 hours, 12 hours, 24 hours or even 48 hours or more at 2-8° C. The speed of rotation is preferably above 10 rpm, such as e.g. 50 rpm, 100 rpm or more.

The stability of the formulation under mechanical stress can be assessed e.g. by visual inspection of the formulation or by measurement of the OD320/OD280 ratio. Preferably the OD320/OD280 ratio is 0.05 or lower, such as 0.01 or 0.005.

A good stability of the polypeptides of the invention under mechanical stress has been obtained with a formulation comprising an excipient, preferably a saccharide and/or polyol such as mannitol or sucrose or comprising TWEEN (polysorbate) 80. Accordingly, the present invention relates to a formulation comprising an aqueous carrier and a polypeptide comprising one or more single variable domains, said formulation being formulated for administration to a human subject, wherein said formulation further comprises at least one of:

b) An excipient, preferably a saccharide and/or polyol such as mannitol or sucrose at a concentration of 1% to 20% (preferably 2.5% to 10%, more preferably 5% to 10%, such as 5%, 7.5%, 8% or 10%);

c) A surfactant at a concentration of 0.001% to 1% (preferably from about 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01%) selected from TWEEN (polysorbate) 20, TWEEN (polysorbate) 80 or a poloxamer, wherein said formulation has an inorganic salt concentration of 150 mM or lower; and wherein the polypeptide is stable under mechanical stress as determined by OD320/OD280 ratio measurement. In a preferred aspect, the formulation comprises an excipient, preferably a saccharide and/or polyol such as mannitol or sucrose at a concentration of 1% to 20% (preferably 2.5% to 15%, more preferably 5% to 10%, such as 5%, 7.5%, 8% or 10%) and a surfactant at a concentration of 0.001% to 1% (preferably about 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01% or 0.005%) selected from TWEEN (polysorbate) 20 and TWEEN (polysorbate) 80. A preferred formulation comprises 8% sucrose and 0.01% TWEEN (polysorbate) 80. Another preferred formulation comprises 10% sucrose and 0.005% Tween 80.

In a specific aspect, the formulation of the invention comprises an excipient, preferably a saccharide and/or polyol such as mannitol or sucrose at a concentration of 1% to 20% (preferably 2.5% to 15%, more preferably 5% to 10%, such as 5%, 7.5%, 8% or 10%) and/or TWEEN (polysorbate) 20, TWEEN (polysorbate) 80 or a poloxamer (at a concentration ranging from about 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01%) and is characterized that the polypeptides present in the formulation are stable under mechanical stress.

In a preferred aspect, the formulation of the invention comprises an excipient, preferably a saccharide and/or polyol such as mannitol or sucrose at a concentration of 1% to 20% (preferably 2.5% to 15%, more preferably 5% to 10%, such as 5%, 7.5%, 8% or 10%) and/or TWEEN (polysorbate) 80 (at a concentration of 0.001%, 0.005%, 0.01%, 0.02%, 0.05%, 0.08%, 0.1%, 0.5%, or 1% of the formulation, preferably 0.01% or 0.005%) and is characterized that the polypeptides present in the formulation of the invention are stable when shaking the formulation during at least 10 s, 20 s, 30 s, 40 s, 50 s up to 1 minute of more. In another preferred aspect, the formulation of the invention comprises an excipient, preferably a saccharide and/or polyol such as mannitol or sucrose at a concentration of 1% to 20% (preferably 2.5% to 15%, more preferably 5% to 10%, such as 5%, 7.5%, 8% or 10%) and/or TWEEN (polysorbate) 80 (at a concentration of 0.001%, 0.005%, 0.01%, 0.02%, 0.05%, 0.08%, 0.1%, 0.5%, or 1% of the formulation, preferably 0.01% or 0.005%) and is characterized that the polypeptides present in the formulation of the invention are stable when pushing the formulation through a syringe (the syringe used can be any commercially available syringe, such as e.g. a 1 mL, 2 mL, 3 mL, 4 mL, 5 mL, 10 mL, 20 mL, 30 mL, 40 mL up to 50 mL syringe) with needle size of 25 G or more (such as 26 G, 27 G, 28 G, 29 G, 30 G or more, preferably 27 G or more) once, twice, three times, four times, five times up to 10 times or more. In another preferred aspect, the formulation of the invention comprises an excipient, preferably a saccharide and/or polyol such as mannitol or sucrose at a concentration of 1% to 20% (preferably 2.5% to 15%, more preferably 5% to 10%, such as 5%, 7.5%, 8% or 10%) and/or TWEEN (polysorbate) 80 (at a concentration of 0.001%, 0.005%, 0.01%, 0.02%, 0.05%, 0.08%, 0.1%, 0.5%, or 1% of the formulation, preferably 0.01% or 0.005%) and is characterized that the polypeptides present in the formulation of the invention are stable when rotating the formulation for 1 hour, 2 hours, 6 hours, 12 hours, 1 day up to two days or more at 10 rpm. In another preferred aspect, the formulation of the invention comprises an excipient, preferably a saccharide and/or polyol such as mannitol or sucrose at a concentration of 1% to 20% (preferably 2.5% to 15%, more preferably 5% to 10%, such as 5%, 7.5%, 8% or 10%) and/or TWEEN (polysorbate) 80 (at a concentration of 0.001%, 0.005%, 0.01%, 0.02%, 0.05%, 0.08%, 0.1%, 0.5%, or 1% of the formulation, preferably 0.01% or 0.005%) and is characterized that the polypeptides present in the formulation of the invention are stable when stirring the formulation for 1 hour at room temperature and/or 4 hours, 8 hours, 12 hours, 24 hours or even 48 hours or more at 2-8° C. at least 10 rpm (such as 50 rpm, 100 rpm or more).

A "freeze/thaw cycle" or "F/T cycle" is defined as the freezing of a sample in a freezer (−20±5° C.) or ultrafreezer (below −64° C. (such as e.g. at −80° C.)) until solid, followed by thawing at room temperature until all ice crystals have visually disappeared. In one aspect, the formulation of the invention exhibits stability under multiple (up to 10) freeze/thaw cycles. The formulation of the invention may exhibit stability under at least 1, at least 2, at least 3, at least 5 to up to at least 10 freeze/thaw cycles, such as e.g. 10 cycles at −20° C., 2 cycles at −80° C.+1 cycle at −20° C. or 2 cycles at −80° C.+6 cycles at −20° C.

In yet another aspect, the formulation of the invention exhibits stability when stored at a temperature of 5±5° C. The formulation of the invention may exhibit stability when stored at a temperature of 5±5° C. for at least 2 weeks, 3 weeks, 4 weeks, 8 weeks, 10 weeks, up to 3 months, 6 months, 11 months, 1 year, 1.5 year or even 2 years and more.

In yet another aspect, the formulation of the invention exhibits stability when stored at a temperature of 25±5° C. The formulation of the invention may exhibit stability when stored at a temperature of 25±5° C. for at least 2 weeks, 3 weeks, 4 weeks, at least 5 weeks, at least 8 weeks, at least 10 weeks, at least 3 months, at least 6 months, at least 1 year, 1.5 year or even 2 years or more.

In yet another aspect, the formulation of the invention exhibits stability when stored at a temperature of 37±5° C. The formulation of the invention may exhibit stability when stored at a temperature of 37±5° C. for at least 2 weeks, 3 weeks, 4 weeks, at least 5 weeks, at least 8 weeks, at least 10 weeks, at least 3 months, at least 6 months, at least 1 year, 1.5 year or even 2 years or more.

As is known to one skilled in the art, the temperatures indicated in this text can be subject to normal variations.

Preferably, in those formulations that are stable under one or more of the above stress conditions:

less than 10% (more preferably less than 5%, even more preferably less than 3%, most preferably less than 1%) of the polypeptide of the invention forms pyroglutamate at the N-terminal glutamic acid (e.g. as assessed by RP-HPLC) during storage under (one of the above) stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

less than 10% (more preferably less than 5%, even more preferably less than 3%, most preferably less than 1%) of the polypeptide of the invention forms dimers (e.g. as assessed by SE-HPLC) during storage under (one of the above) stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

at least 80% (at least 85%, at least 90%, at least 95%, at least 98%, at least 99%, or at least 99.5%) of the polypeptides of the invention retain their binding activity (e.g. as assessed by ELISA and/or BIACORE) to at least one of their (preferably to all of their) targets after storage under (one of the above) stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more) compared to the binding activity prior to the stress condition.

Stability of the formulations can be assessed by various analytical and/or immunological methods known in the art. The protein content of the polypeptides of the invention can, for example be detected by spectrophotometrical methods.

SDS-PAGE allows the visualization of the polypeptides in a given sample via direct staining. SDS-PAGE is used to separate proteins according to their size. Both reducing and non-reducing SDS-PAGE analysis can be performed.

The molecular size distribution and the relative amounts of polypeptide of the invention and protein impurities can be determined by Size Exclusion High Performance Liquid Chromatography (SE-HPLC). The relative amount of a specific protein impurity, expressed as area %, can be calculated by dividing the peak area corresponding to the impurity by the total integrated area. SE-HPLC methods are known to the skilled person and are also described in the Example section.

Reversed Phase High Performance Liquid chromatography (RP-HPLC) separates molecules with respect to differences in hydrophobicity and is based on the reversible interaction between the molecule and the hydrophobic stationary phase. In this assay a ZORBAX 300SB-C3 column (Agilent Technologies, Palo Alto, US) can be used. The relative amount of a specific protein impurity, expressed as area %, can be calculated by dividing the peak area corresponding to the impurity by the total integrated area. RP-HPLC methods are known to the skilled person and are also described in the Example section.

Polypeptides of the invention and their charge variants can be separated by Ion Exchange High Performance Liquid Chromatography (IEX-HPLC). Also potential impurities can be detected with this method. The relative amount of a specific protein impurity, expressed as area %, can be calculated by dividing the peak area corresponding to the impurity by the total integrated area. IEX-HPLC methods are known to the skilled person and are also described in the Example section.

The polypeptides present in the formulation of the invention preferably do not form pyroglutamate at the N-terminal glutamic acid. The formation of pyroglutamate in the sample can e.g. be measured by RP-HPLC. For example, analysis by RP-HPLC of a formulation containing SEQ ID NO: 4 after storage for 10 weeks at a temperature of 37° C., showed the formation of pyroglutamate as a separate peak at 18-19 minutes. Preferably in the formulation of the invention, less than 10% (more preferably less than 5%, even more preferably less than 3%, most preferably less than 1%) of the polypeptides form pyroglutamate at the N-terminal glutamic acid (e.g. as assessed by RP-HPLC) under one or more of the above stress conditions.

Little to no pyroglutamate formation of the polypeptides of the invention has been observed in formulations with a pH of 7.0 or lower, preferably 6.5 or lower, such as 6.5, 6.0 or 5.5, in e.g. histidine buffers and acetate buffers. Accordingly, the present invention relates to a formulation comprising an aqueous carrier at a pH of 7.0 or lower and a polypeptide comprising one or more single variable domains, said formulation being formulated for administration to a human subject, wherein said formulation further comprises:

a) A buffer at a concentration of 10 mM to 100 mM (preferably 10 mM to 50 mM, more preferably 10 to 20 mM, such as 15 mM or 10 mM) selected from the group consisting of histidine pH 6.0-6.5 and acetate pH 5.5-6.0, wherein said formulation has an inorganic salt concentration of 150 mM or lower; and wherein less than 10% (preferably less than 8%, more preferably less than 7%, most preferably less than 5%) of the polypeptides forms pyroglutamate at the N-terminal glutamic acid during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of pyroglutamate as measured by RP-HPLC. In a preferred aspect, the formulation comprises a histidine buffer pH 6.5 at 15 mM. In another preferred aspect, the formulation comprises a histidine buffer pH 6.0 at 10 mM.

The polypeptides present in the formulation of the invention also preferably do not form dimers. The formation of dimers in the sample can e.g. be measured by SE-HPLC. For example, analysis in SE-HPLC of a formulation containing SEQ ID NO: 4 after storage for 10 weeks at a temperature of 37° C., showed the formation of a separate peak eluting at an apparent molecular weight of 44 kDa in comparison with molecular weight markers, while the monomeric polypeptide eluted between the 44 and 17 kDa molecular weight markers. This separate peak at 44 kDa represented a dimeric form of SEQ ID NO: 4. Preferably in the formulation of the invention, less than 10% (more preferably less than 5%, even more preferably less than 3%, most preferably less than 1%) of the polypeptides forms dimers (e.g. as assessed by SE-HPLC) during storage under one or more of the above stress conditions.

Little to no dimer formation of the polypeptides of the invention has been observed in formulations with a histidine buffer or an acetate buffer and in formulations that comprise an excipient, preferably a saccharide and/or polyol such as mannitol, trehalose, sorbitol or sucrose. Accordingly, the present invention relates to a formulation comprising an aqueous carrier and a polypeptide comprising one or more single variable domains, said formulation being formulated for administration to a human subject, wherein said formulation further comprises at least one of:

a) A buffer at a concentration of 10 mM to 100 mM (preferably 10 mM to 50 mM, more preferably 10 to 20 mM, such as 15 mM or 10 mM) selected from the group consisting of histidine pH 6.0-6.5 and acetate pH 5.5-6.0;

b) An excipient, preferably a saccharide, a non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%), wherein said formulation has an inorganic salt concentration of 150 mM or lower; and wherein less than 10% (preferably less than 8%, more preferably less than 7%, most preferably less than 5%) of the polypeptides forms dimers during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of dimers as measured by SE-HPLC. In a preferred aspect, the formulation comprises a histidine buffer pH 6.5 at 15 mM. In another preferred aspect, the formulation comprises a histidine buffer pH 6.0 at 10 mM. In a preferred aspect, the formulation comprises a buffer at a concentration of 10 mM to 100 mM (preferably 10 mM to 50 mM, more preferably 10 to 20 mM, such as 15 mM or 10 mM) selected from the group consisting of histidine pH 6.0-6.5 and acetate pH 5.5-6.0 and an excipient, preferably a saccharide, non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%), such as e.g. 15 mM histidine pH 6.5 and 8% sucrose; or 10 mM histidine pH 6.0 and 10% sucrose.

Preferably in the formulation of the invention, less than 10% (more preferably less than 5%, even more preferably less than 3%, most preferably less than 1%) of the polypeptides forms pyroglutamate at the N-terminal glutamic acid (e.g. as assessed by RP-HPLC) and less than 10% (more preferably less than 5%, even more preferably less than 3%, most preferably less than 1%) of the polypeptides forms dimers (e.g. as assessed by SE-HPLC) during storage under one or more of the above stress conditions.

Apart from this and/or in addition, the formulation of the present invention should show only low to undetectable levels of aggregation even during storage under one or more of the above stress conditions. For example, in the formulation of the invention, no more than 5%, no more than 4%, no more than 3%, no more than 2%, no more than 1%, and most preferably no more than 0.5% of the polypeptides forms an aggregate after storage under one or more of the above stress conditions.

Aggregation as used in the present invention means the development of high molecular weight aggregates, i.e. aggregates with an apparent molecular weight in SE-HPLC analysis of more/higher than the molecular weight observed for dimers. As described above, 44 kDa is the apparent molecular weight observed in SE-HPLC analysis for dimers of SEQ ID NO: 4, 36-38 kDa is the apparent molecular weight observed in SE-HPLC analysis for dimers of SEQ ID NO's: 1-3 and 36 kDa is the apparent molecular weight observed in SE-HPLC analysis for dimers of SEQ ID NO: 5. Aggregation can be assessed by various methods known in the art. Without being limiting, examples include SE-HPLC, analytical ultracentrifugation, dynamic light scattering, subvisible particle counting and OD320/OD280 measurement.

In an analytical ultracentrifuge, a sample being spun can be monitored in real time through an optical detection system, using ultraviolet light absorption and/or interference optical refractive index sensitive system. This allows the operator to observe the evolution of the sample concentration versus the axis of rotation profile as a result of the applied centrifugal field. With modern instrumentation, these observations are electronically digitized and stored for further mathematical analysis. Two kinds of experiments are commonly performed on these instruments: sedimentation velocity experiments and sedimentation equilibrium experiments.

Sedimentation velocity experiments aim to interpret the entire time-course of sedimentation, and report on the shape and molar mass of the dissolved macromolecules, as well as their size-distribution (Perez-Ramirez and Steckert (2005) Therapeutic Proteins: Methods and Protocols. C. M. Smales and D. C. James, Eds. Vol. 308: 301-318. Humana Press Inc, Totowa, N.J., US.). The size resolution of this method scales approximately with the square of the particle radii, and by adjusting the rotor speed of the experiment size-ranges from 100 Da to 10 GDa can be covered. Sedimentation velocity experiments can also be used to study reversible chemical equilibria between macromolecular species, by either monitoring the number and molar mass of macromolecular complexes, by gaining information about the complex composition from multi-signal analysis exploiting differences in each components spectroscopic signal, or by following the composition dependence of the sedimentation rates of the macromolecular system, as described in Gilbert-Jenkins theory.

Sedimentation equilibrium experiments are concerned only with the final steady-state of the experiment, where sedimentation is balanced by diffusion opposing the concentration gradients, resulting in a time-independent concentration profile. Sedimentation equilibrium distributions in the centrifugal field are characterized by Boltzmann distributions. This experiment is insensitive to the shape of the macromolecule, and directly reports on the molar mass of the macromolecules and, for chemically reacting mixtures, on chemical equilibrium constants.

The kinds of information that can be obtained from an analytical ultracentrifuge include the gross shape of macromolecules, the conformational changes in macromolecules, and size distributions of macromolecular samples. For macromolecules, such as proteins, that exist in chemical equilibrium with different non-covalent complexes, the number and subunit stoichiometry of the complexes and equilibrium constant constants can be studied. (see also Scott D. J., Harding S. E. and Rowe A. J. Analytical Ultracentrifugation Techniques and Methods, RSC Publishing)

Dynamic light scattering (also known as Photon Correlation Spectroscopy or quasi-elastic light scattering) is a technique in physics, which can be used to determine the size distribution profile of small particles in solution. When a beam of light passes through a colloidal dispersion, the particles or droplets scatter some of the light in all directions. When the particles are very small compared with the wavelength of the light, the intensity of the scattered light is uniform in all directions (Rayleigh scattering); for larger particles (above approximately 250 nm diameter), the intensity is angle dependent (Mie scattering). If the light is coherent and monochromatic, as from a laser for example, it is possible to observe time-dependent fluctuations in the scattered intensity using a suitable detector such as a photomultiplier capable of operating in photon counting mode.

These fluctuations arise from the fact that the particles are small enough to undergo random thermal (Brownian) motion and the distance between them is therefore constantly varying. Constructive and destructive interference of light scattered by neighbouring particles within the illuminated zone gives rise to the intensity fluctuation at the detector plane which, as it arises from particle motion, contains information about this motion. Analysis of the time dependence of the intensity fluctuation can therefore yield the diffusion coefficient of the particles from which, via the Stokes Einstein equation, knowing the viscosity of the medium, the hydrodynamic radius or diameter of the particles can be calculated. (see also Berne B. J. and Pecora R. Dynamic Light Scattering With Applications to Chemistry, Biology and Physics, Dover Publications)

Aggregation can also be measured by the PAMAS SVSS-C(Small Volume Syringe System-C) instrument (PArtikelMess—and AnalyseSysteme GMBH), which is a particle size distribution analyzer for low viscous fluids. It uses the principle of light obscuration to detect sub-visible particles in the size range 1 µm-200 µm. The validation criteria/specified limits of the European Pharmacopoeia (EP<2.9.19 Particulate Contamination: sub-visible particles) for small and large volume parenterals are defined by the total counts per container:

For particles >10 µm, no more than 6000 counts per container

For particles >25 µm, no more than 600 counts per container

The OD320/OD280 ratio is also a measure for turbidity or the presence of particulates in the sample. In a preferred aspect, the OD320/OD280 ratio of the formulation of the invention should be 0.05 or lower, preferably 0.01 or lower, such as 0.005 or lower.

The tendency for aggregate formation of a polypeptide in a certain formulation can also be measured by elastic light scattering. Elastic light scattering can be measured in a spectrofluorometer (e.g. excitation and emission wavelength 500 nm) by temperature-induced denaturation as measured e.g. at an angle of 90°. Preferably the maximum scatter will stay within the absorption detection limit. The scatter should be 1000 abs. or lower, preferably 750 abs or lower, such as 500 abs or lower.

No particulate formation has been observed in formulations comprising a histidine buffer pH 6.0-6.5 under different stress conditions (such as e.g. storage at a temperature of 5±5° C. up to up to at least 2 weeks (preferably at least 3 weeks, at least 5 weeks, at least 8 weeks, at least 10 weeks, at least 3 months, at least 6 months, at least 1 year, 1.5 year or even 2 years or more) or storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)). Accordingly, the present invention relates to a formulation comprising an aqueous carrier and a polypeptide comprising one or more single variable domains, said formulation being formulated for administration to a human subject, wherein said formulation further comprises:

a) A histidine buffer pH 6.0-6.5 at a concentration of 10 mM to 100 mM (preferably 10 mM to 50 mM, more preferably 10 to 20 mM, such as 15 mM), wherein said formulation has an inorganic salt concentration of 150 mM or lower; and wherein no particulates are present under one or more of the above stress conditions (e.g. when stored at a temperature of 5±5° C. up to up to at least 2 weeks (preferably at least 3 weeks, at least 5 weeks, at least 8 weeks, at least 10 weeks, at least 3 months, at least 6 months, at least 1 year, 1.5 year or even 2 years or more) or when stored at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) as measured by OD320/OD280 ratio measurement and/or elastic light scattering. In a preferred aspect the formulation comprises a histidine buffer pH 6.5 at 15 mM. In another preferred aspect the formulation comprises a histidine buffer pH 6.0 at 10 mM.

Apart from this and/or in addition, the formulation of the present invention shows only low to undetectable levels of fragmentation and/or degradation even during storage under one ore more of the above stress conditions. Fragmentation and degradation can be measured e.g. by SE-HPLC and/or RP-HPLC. For example, analysis in SE-HPLC of a formulation containing SEQ ID NO: 4 after storage for 10 weeks at a temperature of 37° C., showed the formation of some minor postpeaks, representing degradation products of SEQ ID NO: 4. For example, analysis by RP-HPLC of a formulation containing SEQ ID NO: 4 after storage for 10 weeks at a temperature of 37° C., showed the formation of some minor peaks at 8-9 minutes, representing degradation products. Preferably in the formulation of the invention, no more than 5%, no more than 4%, no more than 3%, no more than 2%, no more than 1%, no more than 0.5%, no more than 0.1%, no more than 0.05%, and most preferably no more than 0.01% of the polypeptides shows degradation and/or fragmentation after storage under one or more of the above stress conditions.

The techniques of static light scattering (SLS), tangential flow filtration (TFF), Fourier Transform Infrared Spectroscopy (FTIR), circular dichroism (CD), urea-induced protein unfolding techniques, intrinsic tryptophan fluorescence and/or 1-anilino-8-naphthalenesulfonic acid (ANS) protein binding can also be used to assess the physical properties and stability of polypeptides.

Apart from this and/or in addition, the formulation of the present invention shows very little to no loss of potency and/or biological activity of their polypeptides, even during storage under one ore more of the above stress conditions.

The potency and/or biological activity of a biological describes the specific ability or capacity of said biological to achieve a defined biological effect. The potency and biological activities of the polypeptides of the invention can be assessed by various assays including any suitable in vitro assay, cell-based assay, in vivo assay and/or animal model known per se, or any combination thereof, depending on the specific disease or disorder involved. Suitable in vitro assays will be clear to the skilled person, and for example include ELISA; FACS binding assay; BIACORE; competition binding assay (AlphaScreen®, Perkin Elmer, Massachusetts, USA; FMAT); TRAP assay (osteoclast differentiation assay; Rissanen et al. 2005, J. Bone Miner. Res. 20, Suppl. 1: S256); NF-kappaB reporter gene assay (Mizukami et al. 2002, Mol. Cell. Biol. 22: 992-1000). For example, SEQ ID NO: 4 interacts with RANKL and blocks the interaction of this ligand with RANK, thereby preventing signalization through this receptor. SEQ ID NO's: 1 to 3 interact with IL-6R and block the interaction of this receptor with IL-6. SEQ ID NO's: 5 and 6 interact with IL-23 and block the interaction of this ligand with its receptor. The potency of SEQ ID NO's: 1 to 6 for blocking the respective ligand/receptor interaction can be determined, e.g. by ELISA, BIACORE, AlphaScreen®.

For example, in one embodiment, BIACORE kinetic analysis uses Surface Plasmon Resonance (SPR) technology to monitor macromolecular interactions in real time and is used to determine the binding on and off rates of polypeptides of the formulation of the invention to their target. BIACORE kinetic analysis comprises analyzing the binding and dissociation of the target from chips with immobilized polypeptides of the invention on their surface. A typical BIACORE kinetic study involves the injection of 250 µL of polypeptide reagent at varying concentration in HBS buffer containing 0.005% TWEEN (polysorbate) 20 over a sensor chip surface, onto which has been immobilized the antigen. In the BIACORE 3000 system, the ligand is immobilized on carboxymethylated dextran over a gold surface, while the second partner (analyte) is captured as it flows over the immobilized ligand surface. The immobilized ligands are remarkably resilient and maintain their biological activity. The bound analytes can be stripped from the immobilized ligand without affecting its activity to allow many cycles of binding and regeneration on the same immobilized surface. Interaction is detected in real time via SPR and at high sensitivity. Because the same affinity may reflect different on-rates and off-rates, this instrument excels over most other affinity measuring methods in that it measures on-rates (ka) and off-rates (kd). Concentration determination experiments are also feasible.

The formulation of the present invention exhibits almost no loss in biological activities of the polypeptide during the prolonged storage under the conditions described above, as assessed by various immunological assays including, for example, enzyme-linked immunosorbent assay (ELISA) and Surface Plasmon Resonance to measure the ability of the polypeptide to specifically bind to an antigen. The polypeptides present in the formulation of the present invention retain, even under the above defined stress conditions (such as storage under certain temperature stress for defined periods) more than 80%, more than 85%, more than 90%, more than 95%, more than 98%, more than 99%, or more than 99.5% of their initial biological activities (e.g., the ability to bind to RANKL, IL-6R, IL-23 and/or HSA) of the polypeptides prior to the storage. In some embodiments, the polypeptides in the formulation of the invention retain under the above defined stress conditions at least 80%, at least 85%, at least 90%, at least 95%, at least 98%, at least 99%, or at least 99.5% of the biological activity (e.g., the ability to bind to RANKL, IL-6R, IL-23 and/or HSA) compared to the polypeptides present in a reference formulation prior to the storage.

In one embodiment, the polypeptides of the invention binds HSA. In the formulations of the present invention, at least 80% (preferably at least 85%, at least 90%, at least 95%, at least 98%, at least 99%, or at least 99.5%) of said polypeptides retain their binding activity to HSA under one or more of the above stress conditions (such as storage under certain temperature stress for defined periods) compared to the binding activity prior to the stress condition. Without being limiting, the binding of the polypeptides to HSA can be determined e.g. by ELISA and/or BIACORE.

In another embodiment, the polypeptides of the invention bind RANKL. In the formulation of the present invention at least 80% (at least 85%, at least 90%, at least 95%, at least 98%, at least 99%, or at least 99.5%) of said polypeptides retain their binding activity to RANKL after storage under one or more of the above stress conditions compared to the binding activity prior to storage.

In another embodiment, the polypeptides of the invention bind IL-6R. In the formulation of the present invention at least 80% (at least 85%, at least 90%, at least 95%, at least 98%, at least 99%, or at least 99.5%) of said polypeptides retain their binding activity to IL-6R after storage under one or more of the above stress conditions compared to the binding activity prior to storage.

In another embodiment, the polypeptides of the invention bind IL-23. In the formulation of the present invention at least 80% (at least 85%, at least 90%, at least 95%, at least 98%, at least 99%, or at least 99.5%) of said polypeptides retain their binding activity to IL-23 after storage under one or more of the above stress conditions compared to the binding activity prior to storage.

In a preferred aspect, at least 80% (at least 85%, at least 90%, at least 95%, at least 98%, at least 99%, or at least 99.5%) of the polypeptides present in the formulation of the invention retain their binding activity to all of their targets (such as e.g. RANKL and HSA, IL-6R and HSA or IL-23 and HSA) after storage under one or more of the above stress conditions compared to the binding activity prior to storage.

Suitable animal models for determining the potency and/or biological activity of the polypeptides present in the formulations of the invention will be clear to the skilled person and will depend on the intended disease and/or disorder to be prevented and/or treated by the polypeptide of the invention. Suitable animal models for testing the potency and/or biological activity of SEQ ID NO's: 1 to 6 are e.g. described in WO 08/020079, WO 09/068627 and WO 08/142164.

Little to no loss of potency of the polypeptides of the invention has been observed in formulations with a histidine buffer and in formulations that comprise an excipient, preferably a saccharide, non-reducing sugar and/or polyol such as mannitol, sorbitol, trehalose or sucrose. Accordingly, the present invention relates to a formulation comprising an aqueous carrier and a polypeptide comprising one or more single variable domains, said formulation being formulated for administration to a human subject, wherein said formulation further comprises at least one of:
  a) A histidine buffer at a concentration of 10 mM to 100 mM (preferably 10 mM to 50 mM, more preferably 10 to 20 mM, such as 15 mM or 10 mM);
  b) An excipient, preferably a saccharide, non-reducing sugar and/or polyol such as mannitol, sorbitol, trehalose or sucrose at a concentration of 1% to 20% (preferably 2.5% to 15%, more preferably 5% to 10%, such as 5%, 7.5%, 8% or 10%),
wherein said formulation has an inorganic salt concentration of 150 mM or lower; and
wherein at least 80% (preferably at least 85%, at least 90%, at least 95%, at least 98%, at least 99%, or at least 99.5%) of the polypeptides retain their binding activity to at least one (preferably to all) of their targets under one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) compared to the binding activity prior to the stress conditions, said binding activity as measured by ELISA and/or BIACORE. In a preferred aspect, the formulation comprises a histidine buffer at a concentration of 10 mM to 100 mM (preferably 10 mM to 50 mM, more preferably 10 to 20 mM, such as 15 mM or 10 mM) and an excipient, preferably a saccharide, non-reducing sugar and/or polyol such as mannitol, sorbitol, trehalose or sucrose at a concentration of 1% to 20% (preferably 2.5% to 15%, more preferably 5% to 10%, such as 5%, 7.5%, 8% or 10%), such as e.g. 15 mM histidine pH 6.5 and 8% sucrose; or 10 mM histidine pH 6.0 and 10% sucrose.

Accordingly, in the stable formulations of the present invention preferably:
  the polypeptide of the invention has a solubility of at least 20 mg/mL, at least 50 mg/mL, preferably at least 90 mg/mL, at least 120 mg/mL, at least 150 mg/mL or even 200 mg/mL or more) (e.g. as assessed by PEG exclusion method or by centrifugal ultrafiltration);
  the polypeptide of the invention has a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) (e.g. as assessed by TSA or DSC);

less than 10% (more preferably less than 5%, even more preferably less than 3%, most preferably less than 1%) of the polypeptide of the invention forms pyroglutamate at the N-terminal glutamic acid (e.g. as assessed by RP-HPLC) during storage under one or more (of the above) stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

less than 10% (more preferably less than 5%, even more preferably less than 3%, most preferably less than 1%) of the polypeptide of the invention forms dimers (e.g. as assessed by SE-HPLC) during storage under one or more (of the above) stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);

at least 80% (at least 85%, at least 90%, at least 95%, at least 98%, at least 99%, or at least 99.5%) of the polypeptides of the invention retain their binding activity (e.g. as assessed by ELISA and/or BIACORE) to at least one (preferably to all) of their targets after storage under one or more (of the above) stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more) compared to the binding activity prior to the stress condition; and/or the polypeptide of the invention is stable under one or more of the following mechanical stress conditions:
shaking the formulation during 10 s to 1 min;
pushing the formulation through a needle (25 G, preferably 26 G, more preferably 27 G, even more preferably 28 G, most preferably 29 G or more) with a syringe (the syringe used can be any commercially available syringe, such as e.g. a 1 mL, 2 mL, 3 mL, 4 mL, 5 mL, 10 mL, 20 mL, 30 mL, 40 mL up to 50 mL syringe);
rotating for two days at 10 rpm; and/or
stirring for 1 hour at room temperature and/or 4-48 hours at 4° C. at least 10 rpm (such as 50 rpm, 100 rpm or more).

An example of a preferred formulation of the invention with these characteristics comprises 10 mg/mL of the polypeptide of the invention, 15 mM histidine pH 6.5, 8% sucrose and 0.01% TWEEN (polysorbate) 80. Another example of a preferred formulation of the invention with these characteristics comprises 10 mg/mL of the polypeptide of the invention, 10 mM histidine pH 6.0, 10% sucrose and 0.005% TWEEN (polysorbate) 80.

General methods for producing the single variable domains and/or polypeptides present in the formulation of the invention are known to the skilled person and/or have been described in the art. The single variable domains and/or polypeptides can be produced in any host known to the skilled person. For example but without being limiting, the single variable domains and/or polypeptides can be produced in prokaryotic hosts among which *E. coli* or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*. Production of Nanobodies in prokaryotes and lower eukaryotic hosts such as *Pichia pastoris* has e.g. been described in WO 94/04678, WO 94/25591 and WO 08/142164. The contents of these applications are explicitly referred to in the connection with general culturing techniques and methods, including suitable media and conditions. The contents of these documents are incorporated by reference. The skilled person can also devise suitable genetic constructs for expression of the polypeptides of the invention in different hosts on the basis of the present application and common general knowledge. The present invention also relates to conditions and genetic constructs described in the art, for example the general culturing methods, plasmids, promoters and leader sequences described in WO 94/25591, WO 08/020079, Gasser et al. 2006 (Biotechnol. Bioeng. 94: 535); Gasser et al. 2007 (Appl. Environ. Microbiol. 73: 6499); or Damasceno et al. 2007 (Microbiol. Biotechnol. 74: 381).

More particularly, the method for the expression and/or production of a polypeptide comprising one or more single variable domains at least comprising the steps of:
a) cultivating a host or host cell (as defined herein) under conditions that are such that said host or host cell will multiply;
b) maintaining said host or host cell under conditions that are such that said host or host cell expresses and/or produces the polypeptide;
c) isolating and/or purifying the secreted polypeptide from the medium.

To produce/obtain expression of the polypeptide, the transformed host cell or transformed host organism may generally be kept, maintained and/or cultured under conditions such that the (desired) polypeptide is expressed/produced. Suitable conditions will be clear to the skilled person and will usually depend upon the host cell/host organism used, as well as on the regulatory elements that control the expression of the (relevant) nucleotide sequence. Again, reference is made to the handbooks and patent applications mentioned above.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the polypeptide to be isolated).

In the present invention, the host can be removed from the culture medium by routine means. For example, the host can be removed by centrifugation or filtration. The solution obtained by removal of the host from the culture medium is also referred to as culture supernatant, or clarified culture supernatant. The polypeptides of the invention can be purified from the culture supernatant by standard methods. Standard methods include, but are not limited to chromatographic methods, including size exclusion chromatography, hydrophobic interaction chromatography, ion exchange chromatography, and affinity chromatography. These methods can be performed alone or in combination with other purification methods, e.g. precipitation or gel electrophoresis. The skilled person can devise suitable combinations of purification methods for the polypeptides of the invention on the basis of common general knowledge. For specific examples the art cited herein is referred to.

In one exemplary embodiment, the polypeptides of the invention can be purified from culture supernatant by a combination of affinity chromatography on Protein A, ion exchange chromatography and size exclusion chromatography. Reference to any "step of purification", includes, but is not limited to these particular methods.

More specifically, the polypeptides of the invention can be purified from culture supernatant using a process wherein the clarified supernatant (obtained by centrifugation) is captured on any combination of columns selected from (without being limiting) affinity chromatography resin such as Protein A resin, Cation Exchange Chromatography (CIEC) or an Anion Exchange Chromatography (AIEC) using for example Poros 50HS (POROS), SOURCE 30S or SOURCE 15S (GE Healthcare), SP SEPHAROSE (GE Healthcare), CAPTO S (GE Healthcare), CAPTO MMC (GE Healthcare) or Poros 50HQ (POROS), SOURCE 30Q or SOURCE 150 (GE Healthcare), Q SEPHAROSE (GE Healthcare), CAPTO Q and DEAE SEPHAROSE (GE Healthcare), Size exclusion chromatography (SE-HPLC) using for example SUPERDEX 75 or SUPERDEX 200 (GE Healthcare), hydrophobic interaction chromatography (HIC) using for example octyl, butyl SEPHAROSE or equivalents, optionally also including a tangential flow filtration (TFF) step. Any combination of columns can be used for the purification of the polypeptides of the invention, such as e.g. Protein A resin followed by Cation Exchange Chromatography or two Cation Exchange Chromatography steps.

The present invention also provides methods for preparing the stable formulations of the invention comprising the polypeptides of the invention. More particularly, the present invention provides methods for preparing stable formulations of such polypeptides, said methods comprising concentrating a fraction containing the purified polypeptide to the final polypeptide concentration using e.g. a semipermeable membrane with an appropriate molecular weight (MW) cutoff (e.g. a 5 kD cutoff for single variable domains; a 10 kD cutoff for bivalent polypeptides comprising two single variable domains; or a 15 kD cutoff for trivalent polypeptides comprising three single variable domains) and diafiltering and/or ultrafiltering to buffer exchange and further concentrate the polypeptide fraction into the formulation buffer using the same membrane. As extensively described above, the formulation buffer of the present invention may further comprise at least one of:

a) A buffer at a concentration of 10 mM to 100 mM selected from the group consisting of hepes pH 7.0-8.0, histidine pH 6.0-6.5, MES pH 6.0 and acetate pH 5.5-6.0;
b) An excipient at a concentration of 1% to 20%;
c) A surfactant at a concentration of 0.001% to 1% selected from TWEEN (polysorbate) 80, TWEEN (polysorbate) 20 or a poloxamer.

The pH of the formulation may range from about 5.5 to about 8.0, or may range from about 6.0 to about 7.5, preferably from about 6.2 to 7.5, from about 6.2 to 7.0, most preferably from about 6.5 to 7.0.

Surfactant (e.g. TWEEN (polysorbate) 20, TWEEN (polysorbate) 80 or poloxamer) will be added after the final diafiltration/ultrafiltration step at a concentration in the range of about 0% to 1%, preferably 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01% or 0.005%.

The formulation of the present invention may be sterilized by various sterilization methods, including sterile filtration, radiation, etc. In a specific embodiment, the polypeptide formulation is filter-sterilized with a presterilized 0.2 micron filter.

Preferably, the formulation of the present invention is supplied in a hermetically sealed container. Liquid formulations may comprise a quantity between 1 mL and 20 mL, preferably about 1 mL, 2 mL, 3 mL, 4 mL, 5 mL, 6 mL, 7 mL, 8 mL, 9 mL, 10 mL, 15 mL, or 20 mL.

The formulation of the present invention can be prepared as unit dosage forms by preparing a vial containing an aliquot of the formulation for a one time use. For example, a unit dosage of liquid formulation per vial may contain 1 mL, 2 mL, 3 mL, 4 mL, 5 mL, 6 mL, 7 mL, 8 mL, 9 mL, 10 mL, 15 mL, or 20 mL of the formulation. The pharmaceutical unit dosage forms can be made suitable for any form of delivery of the polypeptide of the invention including (without being limiting) parenteral delivery, topical delivery, pulmonary delivery, intranasal delivery, vaginal delivery, enteral delivery, rectal delivery, oral delivery and/or sublingual delivery. In one aspect, the present invention relates to a pharmaceutical unit dosage form suitable for parenteral (such as e.g. intravenous, intraarterial, intramuscular, intracerebral, intraosseous, intradermal, intrathecal, intraperitoneal, subcutaneous, etc.) administration to a subject, comprising a formulation of the invention in a suitable container. In another preferred aspect, the subject is a human. In a specific embodiment, the formulations of the present invention are formulated into single dose vials as a sterile liquid that contains 10 mg/mL of one of SEQ ID NO's: 1 to 6, 15 mM histidine buffer at pH 6.5, 8% sucrose and 0.01% TWEEN (polysorbate) 80. In another specific embodiment, the formulations of the present invention are formulated into single dose vials as a sterile liquid that contains 10 mg/mL of one of SEQ ID NO's: 1 to 6, 10 mM histidine buffer at pH 6.0, 10% sucrose and 0.005% TWEEN (polysorbate) 80.

The amount of a formulation of the present invention which will be effective in the prevention, treatment and/or management of a certain disease or disorder can be determined by standard clinical techniques well-known in the art or described herein. The precise dose to be employed in the formulation will also depend on the route of administration, and should be decided according to the judgment of the practitioner and each patient's circumstances. Effective doses may be extrapolated from dose-response curves derived from in vitro or animal model test systems. For formulations of the polypeptide, encompassed by the invention, the dosage administered to a patient may further be calculated using the patient's weight in kilograms (kg) multiplied by the dose to be administered in mg/kg.

The required volume (in mL) to be given is then determined by taking the mg dose required divided by the concentration of the polypeptide formulation. The final calculated required volume will be obtained by pooling the contents of as many vials as are necessary into syringe(s) to administer the polypeptide formulation of the invention.

The present invention also encompasses a finished packaged and labelled pharmaceutical product. This article of manufacture or kit includes the appropriate unit dosage form in an appropriate vessel or container such as a glass vial or other container that is hermetically sealed. In one embodiment, the unit dosage form is suitable for intravenous, intramuscular, intranasal, oral, topical or subcutaneous delivery. Thus, the invention encompasses formulations, preferably sterile, suitable for each delivery route. In the case of dosage forms suitable for parenteral administration (such as e.g. subcutaneous administration) the active ingredient, e.g., polypeptide of the invention, is sterile and suitable for administration as a particulate free solution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises the formulation containing the polypeptide. The packaging material includes instruction means which indicate that said polypeptide can be used to prevent, treat and/or manage one or more symptoms associated with the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide of interest, and wherein said packaging material includes instruction means which indicate that said agents can be used to prevent, treat and/or manage the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide, and wherein said packaging material includes instruction means which indicate that said agents can be used to prevent, treat and/or manage one or more symptoms associated with the disease or disorder by administering specific doses and using specific dosing regimens as described herein.

The formulations, containers, pharmaceutical unit dosages and kits of the present invention may be administered to a subject to prevent, treat and/or manage a specific disease and/or disorder. In a specific aspect, the formulations, containers, pharmaceutical unit dosages and kits of the present invention are administered to a subject to prevent, treat and/or manage a disease and/or disorder associated with or characterized by aberrant expression and/or activity of a certain target or one or more symptoms thereof. In another specific aspect, the formulations, containers, pharmaceutical unit dosages and kits of the present invention are administered to a subject to prevent, treat and/or manage diseases and/or disorders associated with aberrant expression and/or activity of RANKL, diseases and/or disorders associated with overexpression of IL-6, or diseases and disorders associated with heterodimeric cytokines and their receptors or one or more symptoms thereof.

Diseases and disorders associated with aberrant expression and/or activity of RANKL are for example bone diseases and disorders, and include (without being limiting) the following diseases and disorders: Osteoporosis (McClung 2006, Current Osteoporosis Reports 4: 28-33), including, but not limited to, primary osteoporosis, endocrine osteoporosis (including, but not limited to, hyperthyroidism, hyperparathyroidism (Anandarajah and Schwarz 2006, J. Cell Biochem. 97: 226-232), Cushing's syndrome, and acromegaly), hereditary and congenital forms of osteoporosis (including, but not limited to, osteogenesis imperfecta, homocystinuria, Menkes' syndrome, Riley-Day syndrome), osteoporosis due to immobilization of extremities, glucocorticoid-induced osteoporosis (Locklin et al. 2001, Bone 28 (Suppl.): S80; McClung 2006, Current Osteoporosis Reports 4: 28-33; Anandarajah and Schwarz 2006, J. Cell Biochem. 97: 226-232) and post-menopausal osteoporosis (McClung 2006, Current Osteoporosis Reports 4: 28-33); (Juvenile or Familial) Paget's disease (Cundy et al. 2002, Hum. Mol. Genet. 11: 2119-2127; Whyte et al. 2002, J. Bone Miner. Res. 17: 26-29; Whyte et al. 2002, N. Engl. J. Med. 347: 175-184; Johnson-Pais et al. 2003, J. Bone Miner Res. 18: 376-380; Anandarajah and Schwarz 2006, J. Cell Biochem. 97: 226-232; Anandarajah and Schwarz 2006, J. Cell Biochem. 97: 226-232); Osteomyelitis, i.e., an infectious lesion in bone, leading to bone loss; Hypercalcemia (Anandarajah and Schwarz 2006, J. Cell Biochem. 97: 226-232), including, but not limited to, hypercalcemia resulting from solid tumors (including, but not limited to, breast, lung and kidney) and hematologic malignancies (including, but not limited to, multiple myeloma (Sordillo and Pearse 2003, Cancer 97 (3 Suppl): 802-812; Vanderkerken et al. 2003, Cancer Res. 63: 287-289), lymphoma and leukemia), idiopathic hypercalcemia, and hypercalcemia associated with hyperthyroidism and renal function disorders; Bone loss, including but not limited to, osteopenia following surgery, osteopenia induced by steroid administration, osteopenia associated with disorders of the small and large intestine, and osteopenia associated with chronic hepatic and renal diseases; Osteonecrosis, i.e., bone cell death, including, but not limited to, osteonecrosis associated with traumatic injury, osteonecrosis associated with Gaucher's disease, osteonecrosis associated with sickle cell anemia, osteonecrosis associated with systemic lupus erythematosus, osteonecrosis associated with rheumatoid arthritis, osteonecrosis associated with periodontal disease, osteonecrosis associated with osteolytic metastasis, and osteonecrosis associated with other condition; Bone loss associated with arthritic disorders such as psoriatic arthritis, rheumatoid arthritis, loss of cartilage and joint erosion associated with rheumatoid arthritis (Bezerra et al. 2005, Brazilian Journal of Medical and Biological Research 38: 161-170; Anandarajah and Schwarz 2006, J. Cell Biochem. 97: 226-232); Arthritis (Bezerra et al. 2005, Brazilian Journal of Medical and Biological Research 38: 161-170), including inflammatory arthritis (McClung 2006, Current Osteoporosis Reports 4: 28-33), Collagen-induced arthritis (Bezerra et al. 2005, Brazilian Journal of Medical and Biological Research 38: 161-170); Periprosthetic osteolysis (McClung 2006, Current Osteoporosis Reports 4: 28-33; Anandarajah and Schwarz 2006, J. Cell Biochem. 97: 226-232); Cancer-related bone disease (McClung 2006, Current Osteoporosis Reports 4: 28-33); Bone loss associated with aromatase inhibitor therapy (Lewiecki 2006, Expert Opin. Biol. Ther. 6: 1041-1050); Bone loss associated with androgen deprivation therapy (Lewiecki 2006, Expert Opin. Biol. Ther. 6: 1041-1050); Bone loss associated bone metastasis; Bone loss associated with diseases having immune system involvement, such as adult and childhood leukaemias, cancer metastasis, autoimmunity, and various viral infections (Holstead Jones et al. 2002, Ann. Rheum. Dis. 61 (Suppl II): ii32-ii39); Osteopenic disorders such as adult and childhood leukaemia (Oliveri et al. 1999, Henry Ford Hosp. Med. 39: 45-48); chronic infections such as hepatitis C or HIV (Stellon et al. 1985, Gastroenterology 89: 1078-1083); autoimmune disorders such as diabetes mellitus (Piepkorn et al. 1997, Horm. Metab. Res. 29: 584-91), and lupus erythematosus (Seitz et al. 1985, Ann. Rheum Dis. 44: 438-445); allergic diseases such as asthma (Ebeling et al. 1998, J. Bone Min. Res. 13: 1283-1289); lytic bone metastases in multiple cancers such as breast cancer (Coleman 1998, Curr. Opin. Oncol. 10 (Suppl 1): 7-13); Prostate cancer; Myeloma bone disease (Anandarajah and Schwarz 2006, J. Cell Biochem. 97: 226-232); Periodontal infections (Anandarajah and Schwarz 2006, J. Cell Biochem. 97: 226-232); Expansile skeletal hyperphosphatasia (Anandarajah and Schwarz 2006, J. Cell Biochem. 97: 226-232); Bone metastases (Lewiecki 2006, Expert Opin. Biol. Ther. 6: 1041-1050; Anandarajah and Schwarz 2006, J. Cell Biochem. 97: 226-232).

Also encompassed within the scope of the present invention is the prevention and/or treatment with the formulations, containers, pharmaceutical unit dosages and kits of the invention of other diseases and disorders associated with an imbalance in the RANKL/RANK/OPG pathway. Such diseases and disorders include but are not limited to osteoporosis, inflammatory conditions, autoimmune conditions, asthma, rheumatoid arthritis, multiple sclerosis, Multiple myeloma (Sordillo and Pearse 2003, Cancer 97 (3 Suppl): 802-812; Vanderkerken et al. 2003, Cancer Res. 63: 287-289); Vascular diseases (Anandarajah and Schwarz 2006, J. Cell Biochem. 97: 226-232) and Cardiovascular disease (Lewiecki 2006, Expert Opin. Biol. Ther. 6: 1041-1050).

Also encompassed within the scope of the present invention is the prevention and/or treatment with the formulations, containers, pharmaceutical unit dosages and kits of the invention of diseases and disorders associated with osteopetrosis such as osteopetrosis tarda, osteopetrosis congenita and marble bone disease.

Disease and disorders caused by aberrant expression and/or activity, such as excessive IL-6 production or signaling include sepsis (Starnes et al., 1999) and various forms of cancer such as multiple myeloma disease (MM), renal cell carcinoma (RCC), plasma cell leukaemia (Klein et al., 1991), lymphoma, B-lymphoproliferative disorder (BLPD) and prostate cancer. Non-limiting examples of other diseases caused by aberrant expression and/or activity, such as excessive IL-6 production or signalling include bone resorption (osteoporosis) (Roodman et al., 1992; Jilka et al., 1992), cachexia (Strassman et al., 1992), psoriasis, mesangial proliferative glomerulonephritis, Kaposi's sarcoma, AIDS-related lymphoma (Emilie et al., 1994), inflammatory diseases and disorder such as rheumatoid arthritis, systemic onset juvenile idiopathic arthritis, hypergammaglobulinemia (Grau et al., 1990), Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al., 1991).

Diseases and disorders associated with heterodimeric cytokines and their receptors include inflammation and inflammatory disorders such as bowel diseases (colitis, Crohn's disease, IBD), infectious diseases, psoriasis, cancer, autoimmune diseases (such as MS), carcoidis, transplant rejection, cystic fibrosis, asthma, chronic obstructive pulmonary disease, rheumatoid arthritis, viral infection, common variable immunodeficiency.

The formulations, containers, pharmaceutical unit dosages and kits of the present invention may also be advantageously utilized in combination with one or more other therapies (e.g., one or more other prophylactic or therapeutic agents), preferably therapies useful in the prevention, treatment and/or management of the (same or another) disease or disorder. When one or more other therapies (e.g., prophylactic or therapeutic agents) are used, they can be administered separately, in any appropriate form and by any suitable route. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, other single variable domains, synthetic or natural inorganic molecules, mimetic agents, and synthetic or natural organic molecules. Any therapy (e.g., prophylactic or therapeutic agents) which is known to be useful, or which has been used or is currently being used for the prevention, treatment and/or management of one or more symptoms associated with a specific disease or disorder, can be used in combination with the formulations of the present invention in accordance with the invention described herein.

A formulation of the invention may be administered to a mammal, preferably a human, concurrently with one or more other therapies (e.g., one or more other prophylactic or therapeutic agents). The term "concurrently" is not limited to the administration of prophylactic or therapeutic agents/therapies at exactly the same time, but rather it is meant that the formulation of the invention and the other agent/therapy are administered to a mammal in a sequence and within a time interval such that the polypeptide contained in the formulation can act together with the other agent/therapy to provide an increased benefit than if they were administered otherwise. For example, the formulation of the invention and the one or more other prophylactic or therapeutic agents may be administered at the same time or sequentially in any order at different points in time; however, if not administered at the same time, they should be administered sufficiently close in time so as to provide the desired therapeutic or prophylactic effect.

When used in combination with other therapies (e.g., prophylactic and/or therapeutic agents), the formulations of the invention and the other therapy can act additively or synergistically. The invention contemplates administration of a formulation of the invention in combination with other therapies (e.g., prophylactic or therapeutic agents) by the same or different routes of administration, e.g., oral and parenteral.

Various delivery systems are known and can be used to administer the formulation of the present invention. Methods of administering formulations of the present invention include, but are not limited to, parenteral administration (e.g., intradermal, intramuscular, intraperitoneal, intravenous and, preferably subcutaneous), epidural administration, topical administration, and mucosal administration (e.g., intranasal and oral routes). In a specific embodiment, liquid formulations of the present invention are administered parenteral.

DEFINITIONS

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10$^{th}$ Ed. Blackwell Publishing, UK (2001); and Janeway et al., "Immunobiology" (6th Ed.), Garland Science Publishing/Churchill Livingstone, New York (2005), as well as to the general background art cited herein;

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

Amino acid residues will be indicated according to the standard three-letter or one-letter amino acid code, as mentioned in Table A-2.

TABLE A-2 one-letter and three-letter amino acid code

| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, uncharged (at pH 6.0-7.0) | Glycine[2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged (at pH 6.0-7.0) | Lysine | Lys | K |
| | Arginine | Arg | R |
| | Histidine[4] | His | H |
| | Aspartate | Asp | D |
| | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residu can generally be considered essentially uncharged at a pH of about 6.5.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).

Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a Nanobody® of the invention is said to comprise a CDR sequence, this may mean that said CDR sequence has been incorporated into the Nanobody® of the invention, but more usually this generally means that the Nanobody® of the invention contains within its sequence a stretch of amino acid residues with the same amino acid sequence as said CDR sequence, irrespective of how said Nanobody® of the invention has been generated or obtained. It should also be noted that when the latter amino acid sequence has a specific biological or structural function, it preferably has essentially the same, a similar or an equivalent biological or structural function in the first mentioned amino acid sequence (in other words, the first mentioned amino acid sequence is preferably such that the latter sequence is capable of performing essentially the same, a similar or an equivalent biological or structural function). For example, when a Nanobody® of the invention is said to comprise a CDR sequence or framework sequence, respectively, the CDR sequence and framework are preferably capable, in said Nanobody®, of functioning as a CDR sequence or framework sequence, respectively. Also, when a nucleotide sequence is said to comprise another nucleotide sequence, the first mentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleotide sequence).

A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis.

The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein).

The term "antigenic determinant" refers to the epitope on the antigen recognized by the antigen-binding molecule (such as a Nanobody® or a polypeptide of the invention) and more in particular by the antigen-binding site of said molecule. The terms "antigenic determinant" and "epitope" may also be used interchangeably herein.

As further described in paragraph m) on page 53 of WO 08/020079, an amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The term "specificity" refers to the number of different types of antigens or antigenic determinants to which a particular antigen-binding molecule or antigen-binding protein (such as a Nanobody® or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody® or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies® and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant ($K_A$), by means of the relationship $[K_D=1/K_A]$.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules (such as an amino acid sequence, Nanobody® or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation $DG=RT \cdot ln(K_D)$ (equivalently $DG=-RT \cdot ln(K_A)$), where R equals the gas constant, T equals the absolute temperature and ln denotes the natural logarithm. The $K_D$ for biological interactions which are considered meaningful (e.g. specific) are typically in the range of $10^{-10}$ M (0.1 nM) to $10^{-5}$M (10000 nM). The stronger an interaction is, the lower is its $K_D$. The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation of second). The on-rate $k_{on}$ has units $M^{-1}s^{-1}$. The on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2}=ln(2)/k_{off}$. The off-rate may vary between $10^{-6}$ $s^{-1}$ (near irreversible complex with a $t_{1/2}$ of multiple days) to 1 $s^{-1}$ ($t_{1/2}=0.69$ s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t½-alpha, t½-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t½-beta, either with or without an increase in the t½-alpha and/or the AUC or both.

In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to disassociate. Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner.

In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multi-merization (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10,000 times or more better than the affinity with which said amino acid sequence or polypeptide binds to the second target or polypeptide. For example, the first antigen may bind to the target or antigen with a $K_D$ value that is at least 10 times less, such as at least 100 times, and preferably at least 1000 times less, such as 10,000 times less or even less than that, than the $K_D$ with which said amino acid sequence or polypeptide binds to the second target or polypeptide. Preferably, when an amino acid sequence or polypeptide is "specific for" a first target or antigen compared to a second target or antigen, it is directed against (as defined herein) said first target or antigen, but not directed against said second target or antigen.

The terms "cross-block", "cross-blocked" and "cross-blocking" are used interchangeably herein to mean the ability of an amino acid sequence or other binding agents (such as a polypeptide of the invention) to interfere with the binding of other amino acid sequences or binding agents of the invention to a given target. The extend to which an amino acid sequence or other binding agents of the invention is able to interfere with the binding of another to a target, and therefore whether it can be said to cross-block according to the invention, can be determined using competition binding assays. One particularly suitable quantitative assay uses a BIACORE machine which can measure the extent of interactions using surface plasmon resonance technology. Another suitable quantitative cross-blocking assay uses an ELISA-based approach to measure competition between amino acid sequence or another binding agents in terms of their binding to the target.

The following generally describes a suitable BIACORE assay for determining whether an amino acid sequence or other binding agent cross-blocks or is capable of cross-blocking according to the invention. It will be appreciated that the assay can be used with any of the amino acid sequence or other binding agents described herein. The BIACORE machine (for example the BIACORE 3000) is operated in line with the manufacturer's recommendations. Thus in one cross-blocking assay, the target protein is coupled to a CM5 BIACORE chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the BIACORE chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated BIACORE chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above BIACORE cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The BIACORE assay described above is a primary assay used to determine if amino acid sequences or other binding agents cross-block each other according to the invention. On rare occasions particular amino acid sequences or other binding agents may not bind to target coupled via amine chemistry to a CM5 BIACORE chip (this usually occurs when the relevant binding site on target is masked or destroyed by the coupling to the chip). In such cases cross-blocking can be determined using a tagged version of the target, for example a N-terminal His-tagged version. In this particular format, an anti-His amino acid sequence would be coupled to the BIACORE chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an amino acid sequence or other binding agent directed against a target cross-blocks or is capable of cross-blocking as defined herein. It will be appreciated that the assay can be used with any of the amino acid sequences (or other binding agents such as polypeptides of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target amino acid sequence (in this case Ab-X). The background signal for the assay is defined as the signal obtained in wells with the coated amino acid sequence (in this case Ab-X), second solution phase amino acid sequence (in this case Ab-Y), target buffer only (i.e. without target) and target detection reagents. The positive control signal for the assay is defined as the signal obtained in wells with the coated amino acid sequence (in this case Ab-X), second solution phase amino acid sequence buffer only (i.e. without second solution phase amino acid sequence), target and target detection reagents. The ELISA assay may be run in such a manner so as to have the positive control signal be at least 6 times the background signal. To avoid any artefacts (e.g. significantly different affinities between Ab-X and Ab-Y for the target) resulting from the choice of which amino acid sequence to use as the coating amino acid sequence and which to use as the second (competitor) amino acid sequence, the cross-blocking assay may be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal {i.e. the amount of target bound by the coated amino acid sequence} as compared to the target detection signal obtained in the absence of the solution phase anti-target amino acid sequence (i.e. the positive control wells).

The amino acid residues of a Nanobody® are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication); or referred to herein. According to this numbering, FR1 of a Nanobody® comprises the amino acid residues at positions 1-30, CDR1 of a Nanobody® comprises the amino acid residues at positions 31-35, FR2 of a Nanobody® comprises the amino acids at positions 36-49, CDR2 of a Nanobody® comprises the amino acid residues at positions 50-65, FR3 of a Nanobody® comprises the amino acid residues at positions 66-94, CDR3 of a Nanobody® comprises the amino acid residues at positions 95-102, and FR4 of a Nanobody® comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.]. Alternative methods for numbering the amino acid residues of $V_H$ domains, which methods can also be applied in an analogous manner to $V_{HH}$ domains from Camelids and to Nanobodies®, are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise.

By the term "target molecule" or "target molecules" or "target" is meant a protein with a biological function in an organism including bacteria and virus, preferably animal, more preferably mammal most preferred human, wherein said biological function may be involved in the initiation or progression or maintenance of a disease.

The terms "stability" and "stable" as used herein in the context of a formulation comprising a polypeptide comprising one or more single variable domains refer to the resistance of the polypeptide in the formulation to aggregation (and particularly dimerization and/or oligomerization) under given storage conditions. Apart from this and/or in addition, the "stable" formulations of the invention retain biological activity under given storage conditions. The stability of said polypeptide can be assessed by degrees of aggregation (and particularly dimerization and/or oligomerization; as measured e.g. by SE-HPLC), and/or by % of biological activity (as measured e.g. by ELISA, BIACORE, etc.) compared to a reference formulation. For example, a reference formulation may be a reference standard frozen at −20° C. or <−65° C. (such as e.g. −80° C.) consisting of the same polypeptide at the same concentration in D-PBS or consisting of the same polypeptide at the same concentration and in the same buffer as the stressed samples but without applying the stress conditions, which reference formulation regularly gives a single peak by SE-HPLC and/or keeps its biological activity in BIACORE and/or ELISA.

The term "very little to no loss of the biological activities" as used herein refers to single variable domain activities, including but not limited to, specific binding abilities of the single variable domain to the target of interest as measured by various immunological assays, including, but not limited to ELISAs and/or by Surface Plasmon Resonance (BIACORE). In one embodiment, the single variable domains of the formulations of the invention retain at least 50%, preferably at least 55%, 60%, 65%, 70%, 75%, 80%, 85%, 90%, 95%, 98% or even 99% or more of the ability to specifically bind to an antigen as compared to a reference formulation, as measured by an immunological assay known to one of skill in the art or described herein. For example, an ELISA based assay (e.g. as described in the Example section) may be used to compare the ability of the single variable domain to specifically bind to its target. A "reference formulation" as used herein refers to a formulation that is frozen at a temperature of −20±5° C. or at <−64° C. (such as e.g. at −80° C.) consisting of the same single variable domain at the same concentration in D-PBS or consisting of the same single variable domains at the same concentration in the same buffer/excipients as the stressed samples but without applying the stress conditions, which reference formulation regularly gives a single peak by SE-HPLC and/or keeps its biological activity in BIACORE and/or ELISA.

The phrase "pharmaceutically acceptable" as used herein means approved by a regulatory agency of the Federal or a state government, or listed in the U.S. Pharmacopeia, European Pharmacopoeia or other generally recognized pharmacopeia for use in animals, and more particularly in humans. In this sense, it should be compatible with the other ingredients of the formulation and not eliciting an unacceptable deleterious effect in the subject.

As used herein, the term "effective amount" refers to the amount of an agent (e.g. a prophylactic or therapeutic agent) which is sufficient to reduce and/or ameliorate the severity and/or duration of one or more diseases and/or disorders.

The term "polyol" as used herein refers to sugars that contains many hydroxyl (—OH) groups compared to a normal saccharide. Polyols include alcohols and carbohydrates such as mannitol, sorbitol, maltitol, xylitol, isomalt, erythritol, lactitol, sucrose, glucose, galactose, fructose, fucose, ribose, lactose, maltose and cellubiose.

As used herein, the terms "therapeutic agent" and "therapeutic agents" refer to any agent(s) which can be used in the prevention, treatment and/or management of one ore more diseases and/or disorders. In the context of the present invention, the term "therapeutic agent" refers to a polypeptide comprising one or more single variable domains. In certain other embodiments, the term "therapeutic agent" refers to an agent other than the polypeptide of the invention which might be used in the formulation.

As used herein, the term "therapeutically effective amount" refers to the amount of a therapeutic agent (e.g. a polypeptide comprising one or more single variable domains), that is sufficient to reduce the severity of one or more diseases and/or disorders.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (e.g., serum albumin), amino acids (e.g., aspartic acid, glutamic acid, lysine, arginine, glycine), surfactants (e.g., SDS, TWEEN (polysorbate) 20, TWEEN (polysorbate) 80, poloxamers, polysorbate and nonionic surfactants), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., Mack Publishing Co., Easton, Pa.), which is incorporated herein in its entirety.

The term "variable domain" refers to the part or domain of an immunoglobulin molecule or antibody which is partially or fully responsible for antigen binding. The term "single variable domain" or "immunoglobulin single variable domain" (used interchangeably), defines molecules wherein the antigen binding site is present on, and formed by, a single immunoglobulin domain. This sets single variable domains apart from "conventional" immunoglobulins or their fragments, wherein two immunoglobulin domains, in particular two "variable domains" interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of a single variable domain is formed by a single VH or VL domain. Hence, the antigen binding site of a single variable domain is formed by no more than three CDRs. The term "single variable domain" does comprise fragments of conventional immunoglobulins wherein the antigen binding site is formed by a single variable domain.

The single variable domains that are present in the constructs of the invention may be any variable domain that forms a single antigen binding unit. Generally, such single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and ScFv fragments that need to interact with another variable domain—e.g. through a $V_H/V_L$ interaction—to form a functional antigen binding domain).

In one aspect of the invention, the single variable domains are light chain variable domain sequences (e.g. a $V_L$-sequence), or heavy chain variable domain sequences (e.g. a $V_H$-sequence); more specifically, the single variable domains can be heavy chain variable domain sequences that are derived from a conventional four-chain antibody or heavy chain variable domain sequences that are derived from a heavy chain antibody.

For example, the single variable domain may be a domain antibody (or an amino acid sequence that is suitable for use as a domain antibody), a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$ sequence); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 04/068820, WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a Nanobody® or a suitable fragment thereof. [Note: Nanobody®, Nanobodies® and Nanoclone® are trademarks of Ablynx N.V.] For a further description of $V_{HH}$'s and Nanobodies®, reference is made to the review article by Muyldermans in Reviews in Molecular Biotechnology 74(2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies® (in particular $V_{HH}$ sequences and partially humanized Nanobodies®) can in particular be characterized by the presence of one or more "Hallmark residues" in one or more of the framework sequences. A further description of the Nanobodies®, including humanization and/or camelization of Nanobodies®, as well as other modifications, parts or fragments, derivatives or "Nanobody® fusions", multivalent constructs (including some non-limiting examples of linker sequences) and different modifications to increase the half-life of the Nanobodies® and their preparations can be found e.g. in WO07/104529, WO 08/101985 and WO 08/142164.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Thus, in the meaning of the present invention, the term "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

In a specific aspect, the "single variable domain" is a "single variable VHH domain". The term "single variable VHH domain" indicates that the "single variable domain" is derived from a heavy chain antibody, preferably a camelid heavy chain antibody.

The term "single variable domain" also encompasses variable domains of different origin, comprising mouse, rat, rabbit, donkey, human and camelid variable domains; as well as fully human, humanized or chimeric variable domains. For example, the invention comprises camelid variable domains and humanized camelid variable domains, or camelized variable domains, e.g. camelized dAb as described by Ward et al (see for example WO 94/04678 and Davies and Riechmann (1994, FEBS Lett. 339(3): 285-290) and (1996, Protein Eng. 9(6): 531-537)). Moreover, the invention comprises fused variable domains, e.g. multivalent and/or multispecific constructs (for multivalent and multispecific polypeptides containing one or more $V_{HH}$ domains and their preparation, reference is also made to Conrath et al. 2001 (J. Biol. Chem. 276: 7346-7350) as well as to for example WO 96/34103 and WO 99/23221).

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

The single variable domains provided by the invention are preferably in essentially isolated form (as defined herein), or form part of a polypeptide of the invention (as defined herein), which may comprise or essentially consist of one or more single variable domains and which may optionally further comprise one or more further amino acid sequences (all optionally linked via one or more suitable linkers). For example, and without limitation, the one or more single variable domains may be used as a binding unit in such a polypeptide, which may optionally contain one or more further amino acid sequences that can serve as a binding unit (i.e. against one or more other targets), so as to provide a monovalent, multivalent or multispecific polypeptide of the invention, respectively as e.g. described in WO 08/101985, WO 08/142164, WO 09/068625, WO 09/068627 and WO 08/020079. Such a protein or polypeptide may also be in essentially isolated form (as defined herein) and the methods of the present invention for the expression and/or production of single variable domains equally apply to polypeptides comprising one or more single variable domains.

According to the invention, the term "single variable domain" may comprise constructs comprising two or more antigen binding units in the form of single variable domain, as outlined above. For example, two (or more) variable domains with the same or different antigen specificity can be linked to form e.g. a bivalent, trivalent or multivalent construct. By combining variable domains of two or more specificities, bispecific, trispecific etc. constructs can be formed. For example, a variable domain according to the invention may comprise two variable domains directed against target A, and one variable domain against target B. Such constructs and modifications thereof, which the skilled person can readily envisage, are all encompassed by the term variable domain as used herein and are also referred to as "polypeptide of the invention" or "polypeptides of the invention".

The polypeptide comprising one or more single variable domains for use in the formulation of the invention may be therapeutic or prophylactic, and may be useful in the treatment and/or management of one or more diseases. In one specific aspect, the polypeptide has at least one single variable domain. In another specific aspect, the polypeptide has at least two single variable domains. In yet another specific aspect, the polypeptide has at least three single variable domains. Preferably, the polypeptide comprises at least one single variable domain directed against HSA. In another specific aspect, the polypeptide comprises at least a single variable domain against RANKL. In another specific aspect, the polypeptide comprises at least a single variable domain against IL-6R. More preferably, the polypeptide is directed against and/or specifically binds HSA as well as another target such as RANKL or IL-6R. In yet another aspect, polypeptide comprises at least a single variable domain against RANKL and at least a single variable domain against HSA. In yet another aspect, polypeptide comprises at least a single variable domain against IL-6R and at least a single variable domain against HSA. In yet another aspect, polypeptide comprises at least two single variable domains against one target and at least a single variable domain against HSA. In yet another aspect, polypeptide comprises at least two single variable domains against RANKL and at least a single variable domain against HSA. In yet another aspect, polypeptide comprises at least two single variable domains against IL-6R and at least a single variable domain against HSA. In a preferred aspect, the single variable domains used in the polypeptide of the invention are selected from WO 08/142164 (such as e.g. SEQ ID NO's: 745 and/or 791 of WO 08/142164), WO 08/020079, WO 09/068627 (such as e.g. SEQ ID NO's 2578, 2584 and/or 2585 of WO 09/068627), U.S. provisional application No. 61/168,379 by Ablynx N.V., U.S. provisional application No. 61/168,410 by Ablynx N.V. (such as e.g. SEQ ID NO's: 77 and/or 109 of U.S. 61/168, 410) and WO 08/028977 (such as e.g. SEQ ID NO: 62 of WO 08/028977). Preferred polypeptides of the invention are selected from SEQ ID NO's: 7 to 12 and 17 to 20.

The term "non-fused" in the context of 'non-fused dimers' means every stable linkage (or also more specific conditions herein mentioned as "stable") existing under normal (e.g. storage and/or physiological) conditions which is not obtained via a direct genetic linkage or via a dedicated dimerization sequence as known in the literature (e.g. Jun-Fos interaction, interaction of CH2-CH3 domains of heavychains etc). Such linkage may be due to for example through chemical forces such as Van der Waal's forces, hydrogen bonds, and/or forces between peptides bearing opposite charges of amino acid residues. Furthermore, additional components such as structural changes may play a role. Such structural changes may e.g. be an exchange of framework regions, e.g. exchange of framework region 4 (a phenomenon also called "domain swapping pattern") beta strands derived from framework regions and may be prevented by stabilizing CDR3-FR4 region in the monomeric structure conformation. In contrast in a genetically linked or -fused construct, the fusion is forcing two entities to be expressed as a fusion protein, and the linkage is of a covalent nature (e.g. using peptide linkers between the two entities, linking the C-terminus of one with the N-terminus of the other protein domain). The term "stable" in the context of "stable dimer" or "stable NFD" ("stable NFDs") means that 50%, more preferably 60%, more preferably 70%, more preferably 80%, even more preferably 90%, even more preferably 95%, most preferred 99% are in the form of NFDs at the time point of measurement; wherein 100% represents the amount (e.g. molar amount per volume or weight per volume amount) of NFD and its corresponding monomer. Measurement of stability as defined herein, i.e. with regards to its dimeric nature, may be done by using size exclusion chromatography (using standard laboratory conditions such as PBS buffer at room temperature) and if required a pre-concentration step of the sample to be tested. The area under the peak in the size exclusion chromatogram of the identified dimeric and monomeric peak represents the relative amounts of the monomer and dimer, i.e. the NFD. NFD and/or NFDs are used herein interchangeably, thus wherever NFD is used NFDs are meant as well and vice versa.

A polypeptide or single variable domain that is "susceptible to dimerization", as used in the present invention, means that the respective polypeptide or single variable domain, under the specified conditions described in the present application (e.g. in a process called process-induced association and/or e.g. under stressful storage conditions, such as relative high temperature (e.g. 37° C.) over weeks (such as e.g. 4 weeks)), converts its otherwise stable monomeric single variable domains into stable dimeric molecules (i.e. NFDs as described herein).

Non-Fused-Dimers (NFDs)

Certain conditions or amino acid sequence alterations can convert otherwise stable monomeric single variable domains into stable dimeric and in certain instances multimeric molecules. Key in this process is to provide conditions in which two single variable domains are able to display an increased non-covalent interaction. NFDs are made e.g. in a process called process-induced association (hereinafter also "PIA"). This dimerization is among others a concentration driven event and can e.g. be enhanced by combining high protein concentrations (e.g. higher than 50 mg protein/ml), rapid pH shifts (e.g. pH shift of 2 units within 1 column volume) and/or rapid salt exchanges (e.g. salt exchange with 1 column volume) in the preparation process. The high concentration will enhance the likelihood of interactions of individual monomeric molecules while the pH and salt changes can induce transiently (partial) unfolding and/or promote hydrophobic interactions and/or rearrangement of the protein structure. Because these NFDs may ultimately be used in or as a therapeutic or prognostic agent, the term "NFD" or "NFDs" are meant to mean (or to be interchanged) that the NFD is in solution, e.g. in a physiological preparation, e.g. physiological buffer, comprising NFD or NFDs (unless the condition, e.g. a condition of special sorts, e.g. storage condition for up to 2.5 years for which a NFD is stable, is specifically described). Alternatively, NFDs can also be made under stressful storage conditions e.g. such as relative high temperature (e.g. 37° C.) over weeks such as e.g. 4 weeks. Furthermore, NFDs can be made (even with improved, i.e. faster, kinetics) by introducing destabilizing amino acid residues in the vicinity of the CDR3 and/or the framework region 4 of the single variable domain susceptible to dimerize (see experimental part, polypeptide F (=mutated polypeptide B) is forming NFDs more quickly than polypeptide B under the same conditions).

Attaining a high concentration of the components that have to dimerize can be obtained with a variety of procedures that include conditions that partially unfold the immunoglobulinic structure of the single variable domains, e.g. Nanobodies®, e.g. via chromatography (e.g. affinity chromatography such as Protein A, ion exchange, immobilized metal affinity chromatography or IMAC and Hydrophobic Interaction Chromatography or HIC), temperature exposure close to the Tm of the single variable domain, and solvents that are unfolding peptides such as 1 to 2 M Guanidinium Hydrochloride. E.g. for chromatography—during the process of elution of the proteins off the column using e.g. a pH shift or salt gradient (as explained later), the NFDs can be formed. Usually the required concentration and/or exact method to form NFDs has to be determined for each polypeptide of the invention and may not be possible for each polypeptide of the invention. It is our experience that there are certain single variable domains either alone (e.g. polypeptides B and F) and/or in a construct (e.g. polypeptides A, C, E, F) that form a NFD. Critical for dimerization may be a relative short CDR3 (e.g. 3 to 8 amino acids, more preferably 4 to 7 amino acids, even more preferably 5 to 6 amino acids, e.g. 6 amino acids) and destabilizing factors in the vicinity of the CDR3 and/or FR4. Furthermore, high concentration such as e.g. the maximum solubility of the polypeptides comprising single variable domain(s) at the concentration used (e.g. 5 mg polypeptide A per ml protein A resin—see experimental part), or storage at high temperature over weeks (e.g. 37° C. over 4 weeks), low pH (e.g. pH below pH 6), high concentration (higher than 50 mg/ml, e.g. 65 mg/ml) may be required to obtain a reasonable yield of NFD formation.

Next to column chromatography working at e.g. maximum column load, similar required high concentration to obtain NFDs can be achieved by concentration methods such as ultrafiltration and/or diafiltration, e.g. ultrafiltration in low ionic strength buffer.

The process is not linked to a specific number of single variable domains, as the formation of NFDs was observed with monovalent, bivalent and trivalent monomeric building blocks (=polypeptides comprising single variable domain(s)) and even with single variable domain-HSA fusions. In case the polypeptides comprises 2 different single variable domains, NFDs may form via only the identical or different (preferably the identical) single variable domain and usually only via one of the single variable domain(s), e.g. the one identified as susceptible to form NFDs (e.g. polypeptide B)(see also FIG. 53b).

It is an object of the present invention to provide soluble and stable (e.g. stable within a certain concentration range, buffer and/or temperature conditions) dimer-complexes called NFDs that may be used to target molecules and/or thus inhibit or promote cell responses. Herein described are NFDs comprising monomeric building blocks such as single variable domain—also called NFDs-Mo; NFDs comprising dimeric building blocks such as two covalently linked single variable domains—also called NFDs-Di; NFDs comprising trimeric building blocks such as three covalently linked single variable domains—also called NFDs-Tri; NFDs comprising tetrameric building blocks such as four covalently linked single variable domains—also called NFDs-Te; and NFDs comprising more than four (=multimeric) building blocks such as multimeric covalently linked single variable domains—also called NFDs-Mu (see FIG. 53a+b for schematic overview of such structures). The NFDs may contain identical single variable domains or different single variable domains (FIG. 53b). If the building blocks (polypeptide) consist of different single variable domains, e.g. Nanobodies®, it is our experience that preferably only one of the single variable domain in the polypeptide will dimerize. E.g. the dimerizing unit (single variable domain, e.g. Nanobody® such as e.g. polypeptide B or F) of a trivalent polypeptide (see FIG. 53b) may be in the middle, at the C-terminus or at the N-terminus of the construct.

It is another object of the invention to provide methods of making and uses of said NFDs.

It is still another object of the present invention to provide information on how to avoid such NFDs.

These above and other objectives are provided for by the present invention which, in a broad sense, is directed to methods, kits, non-fused-dimers that may be used in the treatment of neoplastic, immune or other disorders. To that end, the present invention provides for stable NFDs comprising a single variable domain or single variable domains such as e.g. Nanobody® or Nanobodies® (e.g. polypeptide B) that may be used to treat patients suffering from a variety of disorders. In this respect, the NFDs of the present invention have been surprisingly found to exhibit biochemical characteristics that make them particularly useful for the treatment of patients, for the diagnostic assessment of a disease in patients and/or disease monitoring assessment in patients in need thereof. More specifically, it was unexpectedly found that certain single variable domains, subgroups thereof (including humanized VHHs or truly camelized human VHs) and formatted versions thereof (and indeed this is also feasible for human VH and derivatives thereof), can be made to form stable dimers (i.e. NFD-Mo, NFD-Di, NFD-Tri, NFD-Te or NFD-Mu) that have beneficial properties with regard e.g. to manufacturability and efficacy. Single variable domains are known to not denature upon for example temperature shift but they reversibly refold upon cooling without aggregation (Ewert et al Biochemistry 2002, 41:3628-36), a hallmark which could contribute to efficient formation of antigen-binding dimers.

NFDs are of particular advantage in many applications. In therapeutic applications, NFDs-Mu, e.g. NDF-Di, binders may be advantageous in situation where oligomerization of the targeted receptors is needed such as e.g. for the death receptors (also referred to as TRAIL receptor). E.g. a NFD-Di due to their close interaction of the respective building blocks are assumed to have a different spatial alignment than "conventional" covalently linked corresponding tetramers and thus may provide positive or negative effect on the antigen-binding (see FIG. 53 for a schematic illustration of certain NFDs). Furthermore, a NFDs, e.g. a NFD-Mo, may bind a multimeric target molecule more effectively than a conventional covalently linked single variable domain dimer. Moreover, heteromeric NFDs may comprise target specific binders and binders to serum proteins, e.g. human serum albumin, with long half life. In addition, "conventional" covalently linked dimers (via e.g. amino acid sequence linkers) may have expression problems (by not having enough tRNA available for certain repetitive codons) and thus it may be advantageous to make the monomers first and than convert the monomers to a NFD in a post-expression process, e.g. by a process described herein. This may give yields that are higher for the NFD compared to the covalently linked dimer. Similarly, it may be expected that e.g. the overall yield of a NFD-Di or NFD-Tri will be higher compared to the relevant covalently linked tetramer or hexamer. The overall higher expression level may be the overriding factor in e.g. cost determination to select the NFD approach. E.g. it is reported that expression yields and secretion efficiency of recombinant proteins are a function of chain size (Skerra & Pluckthun, 1991, Protein Eng. 4, 971). Moreover, less linker regions could mean less protease susceptible linker regions on the overall protein. It could also be useful to test in vitro and/or in vivo the impact of multimerization of a single variable domain according to the methods described herein. All in all, it is expected that the finding of this invention may provide additional effective solutions in the drug development using formatted single variable domains as the underlying scaffold structure than with the hitherto known approaches, i.e. mainly covalently linked single variable domain formats.

The NFDs of the present invention can be stable in a desirable range of biological relevant conditions such as a wide range of concentration (i.e. usually low nM range), temperature (37 degrees Celsius), time (weeks, e.g. 3 to 4 weeks) and pH (neutral, pH5, pH6 or in stomach pH such as pH 1). In a further embodiment, NFDs of the present invention can be stable (at a rate of e.g. 95% wherein 100% is the amount of monomeric and dimeric form) in vivo, e.g. in a human body, over a prolonged period of time, e.g. 1 to 4 weeks or 1 to 3 months, and up to 6 to 12 months. Furthermore, the NFDs of the present invention can also be stable in a desirable range of storage relevant conditions such as a wide range of concentration (high concentration such as e.g. mg per ml range), temperature (−20 degrees Celsius, 4 degrees Celsius, 20 or 25 degrees Celsius), time (months, years), resistance to organic solvents and detergents (in formulations, processes of obtaining formulations). Furthermore, it has been surprisingly found that denaturation with guanidine HCl (GdnHCl) needs about 1 M more GdnHCl to denature the polypeptide B dimer than the polypeptide B monomer in otherwise same conditions (see experimental part). Additionally, the surprising finding that FR4 in the polypeptide B NFD-Mo is swapped (and possibly similarly for other NFDs according to the invention) indicates that indeed this dimers form stable complexes and can further stabilize single variable domain or Nanobody® structures. Furthermore, there is evidence that one of the humanisation sites (see experimental part: polypeptide E vs. polypeptide B) may have caused a weaker CDR3 interaction with the framework and thus a more extendable CDR3 is available that is more likely to trigger dimerization.

Thus, preferred NFDs of the invention are stable (with regards to the dimeric nature) within the following ranges (and wherein said ranges may further be combined, e.g. 2, 3, 4 or more ranges combined as described below, to form other useful embodiments):

Preferred embodiments of NFDs are stable (with regards to the dimeric nature) under physiological temperature conditions, i.e. temperature around 37 degrees Celsius, over a prolonged time period, e.g. a time up to 1 day, more preferably 1 week, more preferably 2 weeks, even more preferably 3 weeks, most preferred 4 weeks from the time point of delivery of the drug to the patient in need;

Preferred embodiments of NFDs are stable (with regards to the dimeric nature) under various storage temperature conditions, i.e. temperatures such as −20 degrees Celsius, more preferably 4 degrees Celsius, more preferably 20 degrees Celsius, most preferably 25 degrees Celsius, over a prolonged time period, e.g. up to 6 months, more preferably 1 year, most preferred 2 years;

Preferred embodiments of NFDs are stable (with regards to the dimeric nature) under various physiological pH conditions, i.e. pH ranges such as pH 6 to 8, more preferably pH 5 to 8, most preferred pH 1 to 8, over a prolonged time period, e.g. a time up to 1 week, more preferably 2 weeks, even more preferably 3 weeks, most preferred 4 weeks from the time point of delivery of the drug to the patient in need;

Preferred embodiments of NFDs are stable (with regards to the dimeric nature) under various physiological concentration conditions, i.e. concentration of NFDs below 200 ng NFD/ml solvents, e.g. in pH 7 buffer such as phosphate buffered solution and/or e.g. also serum, e.g. human serum; more preferably below 100 ng NFD/ml solvents, even preferably below 50 ng NFD/ml solvents, most preferred 10 ng NFD/ml solvents; in a further preferred embodiment NFDs are stable in above concentrations at 37 degrees Celsius up to 1 day and more, e.g. 1 week, more preferably 2 weeks, more preferably 3 weeks, and most preferred up to 4 weeks;

Preferred embodiments of NFDs are stable (with regards to the dimeric nature) under various physiological concentration conditions, i.e. concentration of NFDs of about 1 mg/ml, more preferably 5 mg/ml, more preferably 10 mg/ml, more preferably 15 mg/ml, more preferably 20 mg/ml, more preferably 30 mg/ml, more preferably 40 mg/ml, more preferably 50 mg/ml, more preferably 60 mg/ml, more preferably 70 mg/ml, and at temperature around 37 degrees Celsius, over a prolonged time period, e.g. a time up to 1 day, more preferably 1 week, more preferably 2 weeks, even more preferably 3 weeks, most preferred 4 weeks from the time point of delivery of the drug to the patient in need;

Preferred embodiments of NFDs are stable (with regards to the dimeric nature) under various storage concentration conditions, i.e. concentration of NFDs above 0.1 mg NFD/ml solvents, e.g. in pH 7 buffer such as phosphate buffered solution; more preferably above 1 mg NFD/ml solvents; more preferably above 5 mg NFD/ml solvents; more preferably above 10 mg NFD/ml solvents, and most preferred above 20 mg NFD/ml solvents; in a further preferred embodiment NFDs are stable in above concentrations at −20 degree Celsius up to 6 months and more, e.g. 1 year, more preferably 2 years, more preferably 3 years, and most preferred up to 4 years; in a further preferred embodiment NFDs are stable in above concentrations at 4 degrees Celsius up to 6 months and more, e.g. 1 year, more preferably 2 years, more preferably 3 years, and most preferred up to 4 years; in a further preferred embodiment NFDs are stable in above concentrations at 25 degrees Celsius up to 6 months and more, e.g. 1 year, more preferably 2 years, more preferably 3 years, and most preferred up to 4 years;

Preferred embodiments of NFDs are stable (with regards to the dimeric nature) in mixtures (e.g. pharmaceutical formulations or process intermediates) with organic solvents, e.g. alcohols such as ethanol, isopropyl alcohol, hexanol and/or others wherein alcohol (preferably ethanol) can be added up to 5%, more preferably 10%, even more preferably 15%, even more preferably 20%, most preferably 30%, for prolonged period of time at a particular temperature, e.g. over long storages, such as at −20 degrees Celsius up to 6 months and more, e.g. 1 year, more preferably 2 years, more preferably 3 years, and most preferred up to 4 years; in a further preferred embodiment NFDs are stable in above mixtures at 4 degrees Celsius up to 6 months and more, e.g. 1 year, more preferably 2 years, more preferably 3 years, and most preferred up to 4 years; in a further preferred embodiment NFDs are stable in above mixtures at 25 degrees Celsius up to 6 months and more, e.g. 1 year, more preferably 2 years, more preferably 3 years, and most preferred up to 4 years, wherein organic solvents such as e.g. alcohol (preferably ethanol) can be added up to 5%, more preferably 10%, even more preferably 15%, even more preferably 20%, most preferably 30%;

Preferred embodiments of NFDs are stable (with regards to the dimeric nature) in mixtures (e.g. pharmaceutical formulations or process intermediates) with detergents, e.g. nonionic detergents such as e.g. TRITON-X, up to 0.01%, more preferably 0.1%, most preferably 1%, for prolonged period of time at a particular temperature, e.g. over long storages, such as at −20 degrees Celsius up to 6 months and more, e.g. 1 year, more preferably 2 years, more preferably 3 years, and most preferred up to 4 years; in a further preferred embodiment NFDs are stable in above mixtures at 4 degrees Celsius up to 6 months and more, e.g. 1 year, more preferably 2 years, more preferably 3 years, and most preferred up to 4 years; in a further preferred embodiment NFDs are stable in above mixtures at 25 degrees Celsius up to 6 months and more, e.g. 1 year, more preferably 2 years, more preferably 3 years, and most preferred up to 4 years.

Another embodiment of the current invention is that the NFDs retain the binding affinity of at least one of the two components compared to the monomers, e.g. said affinity of the NFDs may be not less than 10%, more preferably not less than 50%, more preferably not less than 60%, more preferably not less than 70%, more preferably not less than 80%, or even more preferably not less than 90% of the binding affinity of the original monomeric polypeptide; or it has multiple functional binding components, with apparent affinity improved compared to the monomer, e.g. it may have a 2 fold, 3, 4, 5, 6, 7, 8, 9 or 10 fold, more preferably 50 fold, more preferably 100 fold more preferably 1000 fold improved affinity compared to the original monomeric polypeptide.

Another embodiment of the current invention is that the NFDs partially or fully lose the binding affinity of at least one of the two components compared to the monomers, e.g. said affinity of the NFDs may be not less than 90%, more preferably not less than 80%, more preferably not less than 70%, more preferably not less than 60%, more preferably not less than 50%, even more preferably not less than 30%, even more preferably not less than 20%, even more preferably not less than 10%, or even more preferably not less than 1% of the binding affinity of the original monomeric polypeptide or most preferred the binding affinity may not be detectable at all; or it has multiple functional binding components, with apparent affinity compared to the monomer that is decreased, e.g. it may have a 2 fold, 3, 4, 5, 6, 7, 8, 9 or 10 fold, more preferably 50 fold, more preferably 100 fold more preferably 1000 fold decreased affinity compared to the original monomeric polypeptide.

Furthermore, an embodiment of the current invention is a preparation comprising NFDs and their monomeric building blocks, e.g. preparations comprising more than 30% NFDs (e.g. the 2 identical monomeric building blocks that form said NFD), e.g. more preferably preparations comprising more than 35% NFDs, even more preferably preparations comprising more than 40% NFDs, even more preferably preparations comprising more than 50% NFDs, even more preferably preparations comprising more than 60% NFDs, even more preferably preparations comprising more than 70% NFDs, even more preferably preparations comprising more than 80% NFDs, even more preferably preparations comprising more than 90% NFDs, even more preferably preparations comprising more than 95% NFDs, and/or most preferred preparations comprising more than 99% NFDs (wherein 100% represents the total amount of NFDs and its corresponding monomeric unit). In a preferred embodiment, said ratios in a preparation can be determined as e.g. described herein for NFDs.

Moreover, another embodiment of the current invention is a pharmaceutical composition comprising NFDs, more preferably comprising more than 30% NFDs (e.g. the 2 identical monomeric building blocks form said NFD), e.g. more preferably a pharmaceutical composition comprising more than 35% NFDs, even more preferably a pharmaceutical composition comprising more than 40% NFDs, even more preferably a pharmaceutical composition comprising more than 50% NFDs, even more preferably a pharmaceutical composition comprising more than 60% NFDs, even more preferably a pharmaceutical composition comprising more than 70% NFDs, even more preferably a pharmaceutical composition comprising more than 80% NFDs, even more preferably a pharmaceutical composition comprising more than 90% NFDs, even more preferably a pharmaceutical composition comprising more than 95% NFDs, and/or most preferred a pharmaceutical composition comprising more than 99% NFDs (wherein 100% represents the total amount of NFDs and its corresponding monomeric unit).

Another embodiment of the present invention is a mixture comprising polypeptides in monomeric and dimeric form, i.e. the NFDs, wherein said preparation is stable for 1 months at 4 degrees Celsius in a neutral pH buffer in a 1 mM, more preferably 0.1 mM, more preferably 0.01 mM, more preferably 0.001 mM, or most preferably 100 nM overall concentration (=concentration of monomeric and dimeric form), and wherein said preparation comprises more than 25%, more preferably 30%, more preferably 40%, more preferably 50%, more preferably 60%, more preferably 70%, more preferably 80% or more preferably 90% dimer, i.e. NFD.

While the methodology described here is or may be in principle applicable to dimerize or multimerize either Fab fragments, Fv fragments, scFv fragments or single variable domains, it is the latter for which their use is most advantageous. In this case dimeric fragments, i.e. the NFDs, can be constructed that are stable, well defined and extend the applicability of said single variable domains beyond the current horizon. In a preferred embodiment, the NFDs are obtainable from naturally derived VHH, e.g. from llamas or camels, according to the methods described herein or from humanized versions thereof, or humanized versions wherein one or more of the so called hallmark residues, e.g. the ones forming the former light chain interface residues, also e.g. described in WO 2006/122825, or in FIG. 52 herein, are not changed and stay as derived from the naturally obtained single variable domains. In a further preferred embodiment, the NFDs are obtainable from polypeptides comprising at least a single domain antibody (or Nanobody®) with similar CDR3 and FR4 amino acid residues (SEQ ID NO: 14) as polypeptide B, e.g. NFDs obtainable from polypeptides comprising at least a Nanobody® having a CDR3 and FR4 region that has a 80%, more preferably 90%, even more preferably 95%, 96%, 97%, 98%, 99% sequence identity to SEQ ID NO: 14.

Previously, increasing the number of binding sites based on single variable domains meant the preparation of covalently linked domains at the genetic level or via other interaction domains (e.g. via fusion to Fc, Jun-Fos, CH2/CH3 constant domain of heavy chain interaction, VL-VH antibody domain interactions etc), whereas now it is possible to alternatively form such entities later, at the protein level. These non-fused dimers combine three main features: (a) possibility to combine one or more single variable domains of one or more specificities (e.g. against a target molecule and against a serum protein with long half life) into NFDs by biochemical methods (vs. genetic methods), (b) controlled dimeric interaction that retains or abolishes antigen binding (vs. "uncontrolled" aggregation), and (c) stability sufficient e.g. for long term storage (for practical and economic reasons) and application in vivo, i.e. for application over prolonged time at e.g. 37 degrees Celsius (important requirement for the commercial use of these NFDs).

Thus, it is a further object of the invention to create new individual and stable NFDs with bi- or even multifunctional binding sites. It has been found that antibody fragment fusion proteins containing single variable domains could be produced by biochemical methods which e.g. show the specified and improved properties as described herein. For example, a particular embodiment of the present invention is a NFD or NFDs comprising a first polypeptide comprising single variable domain(s), e.g. a Nanobody® or Nanobodies®, against a target molecule and a second polypeptide comprising single variable domain(s), e.g. a Nanobody® or Nanobodies®, against a serum protein, e.g. human serum albumin (see e.g. polypeptide C and E (each binding a receptor target and human serum albumin) in the experimental part, see also FIG. 53a+b). Other examples of using bispecificity can be found in Kufer et al, Trends in Immunology 22: 238 (2004). In the case in which two different antigen-binding single variable domains are used, the procedure to produce NFDs may be tweaked to promote the formation of heterodimers versus homodimers, or alternatively be followed by a procedure to separate these forms.

Moreover, it is an object of the invention, therefore, to provide (or select) in a first step a monomeric polypeptide essentially consisting of a single variable domain, wherein said polypeptide is capable to dimerize with itself by process-induced association (PIA) or other alternative methods described herein.

More specifically, we describe in this invention NFDs obtainable by e.g. a method that comprises the step of screening for preparations comprising antibody fragments or polypeptides comprising single variable domain(s) that form dimers by the processes as described herein. Hence said screening method comprising identifying said polypeptides may be a first step in the generation of NFDs. Multiple 'PIA' methods described herein can be used to force dimer formation in a starting preparation comprising its monomeric building block(s). An indication that dimers may be formed under suitable conditions, e.g. the process induced association (PIA) as described herein, is sufficient at this time and may simply mean that a small amount of e.g. the protein A purified fraction in the size exclusion chromatography is eluting as a presumable dimer in the standard purification protocol. Once the dimerization is suggested and later confirmed (e.g. by analytical SEC, dynamic light scattering and/or analytical ultracentrifugation) further improvement in order to favour dimerization (e.g. by higher column load, conditions favouring partial unfolding, conditions favouring hydrophobic interactions, high temperature such as e.g. 37° C. exposure of some time, e.g. weeks such as e.g. 4 weeks, introduction of CDR3 destabilizing amino acid residues etc) or in order to minimize dimerization (opposite strategy) can be initiated (in order to e.g. increase the yield).

The invention relates, furthermore, to a process of selection of a monomeric polypeptide that comprises at least one single variable domain, preferably at least one Nanobody®, capable of forming a NFD according to the invention and as defined herein, characterized in that the NFD is stable and preferably has a similar or better apparent affinity to the target molecule than the monomeric polypeptide showing that the binding site is active or at least is partially active. Said affinity may be not less than 10%, more preferably 50%, more preferably not less than 60%, more preferably not less than 70%, more preferably not less than 80%, or even more preferably not less than 90% of the binding affinity of the original monomeric polypeptide, e.g. may have a 2 fold, 3, 4, 5, 6, 7, 8, 9 or 10 fold, more preferably 50 fold, more preferably 100 fold more preferably 1000 fold improved apparent affinity compared to original monomeric polypeptide. Said affinity may be expressed by features known in the art, e.g. by dissociation constants, i.e. Kd, affinity constants, i.e. Ka, koff and/or kon values—these and others can reasonably describe the binding strength of a NFD to its target molecule.

Moreover, the invention relates, furthermore, to a process of selection of a monomeric polypeptide that comprises at least one single variable domain, preferably at least one Nanobody®, capable of forming a NFD according to the invention and as defined herein, characterized in that the NFD is stable and preferably has no apparent affinity to the target molecule, e.g. human serum albumin.

Said selection may comprise the step of concentrating the preparation comprising the monomeric starting material, i.e. the polypeptide comprising or essentially consisting of at least one single variable domain, to high concentration, e.g. concentration above 5 mg/ml resin, by methods known by the skilled person in the art, e.g. by loading said polypeptide to a column, e.g. protein A column, to the near overload of the column capacity (e.g. up to 2 to 5 mg polypeptide per ml resin protein A) and then optionally eluting said polypeptide with a "steep" pH shift ("steep" meaning e.g. a particular pH shift or change (e.g. a decrease or increase of 10, more preferably 100 or more preferably 1000 fold of the H+ concentration) in one step (i.e. immediate buffer change) or within one, two or three (more preferably one or immediate buffer change) column volume(s)). Furthermore, the "steep" pH shift may be combined with a selected pH change, i.e. the pH can start above or below the pI of the polypeptide and then change into a pH below or above the pI of said polypeptide. Alternatively, concentration of said polypeptides leading to NFD formation is obtainable by other means such as e.g. immobilized metal ion affinity chromatography (IMAC), or ultra-filtration. Preferably conditions are used wherein the polypeptides of the invention are likely to unfold (extremes in pH and high temperature) and/or combinations of conditions favouring hydrophobic interaction such as e.g. pH changes around the pI of the polypeptide and low salt concentration. Furthermore, the conditions used to drive these dimers apart may be also useful to explore when determining further methods for producing these dimers, i.e. combining these procedures (e.g. 15 minutes of exposure to a temperature of about 70 degrees Celsius for Polypeptide A with a high polypeptide concentration and subsequent cooling).

Examples of methods to obtain NFDs are further described in a non limiting manner in the experimental part of this invention.

Another object of the invention is the process to obtain a NFD characterized in that the genes coding for the complete monomeric polypeptide comprising at least one single variable domain (e.g. one, two, three or four single variable domain(s)) or functional parts of the single variable domain(s) (e.g. as obtained by the screening method described herein) are cloned at least into one expression plasmid, a host cell is transformed with said expression plasmid(s) and cultivated in a nutrient solution, and said monomeric polypeptide is expressed in the cell or into the medium, and in the case that only parts of the fusion proteins were cloned, protein engineering steps are additionally performed according to standard techniques.

Furthermore, another object of the invention is the process of associating two monomeric identical polypeptides comprising at least one single variable domain (e.g. one, two, three or four single variable domain(s)) or functional parts of the single variable domain(s) to form a NFD, wherein said process comprises the step of creating an environment where hydrophobic interactions and/or partial refolding of said polypeptides are favoured e.g. by up-concentrating a preparation comprising the monomeric polypeptides, salting-out, adding detergents or organic solvents, neutralizing the overall charge of said polypeptide (i.e. pH of polypeptide solution around the pI of said polypeptide or polypeptides) and/or high temperature close to the melting temperature of the polypeptide or the single variable domain susceptible to dimerization, e.g. at temperature around 37° C. or higher e.g. 40° C., 45° C. or 50° C. or higher over a prolonged time, e.g. weeks such as e.g. 1, 2 3, 4 or more weeks, preferably 4 weeks during dimerization process thus allowing close interaction between the polypeptides. Interestingly and surprisingly said conditions do not have to be upheld in order to stabilize the NFDs once the dimer is formed, i.e. the NFDs in solution are surprisingly stable in a wide range of biological relevant conditions such as mentioned herein.

The NFDs according to the invention may show a high avidity against corresponding antigens and a satisfying stability. These novel NFD structures can e.g. easily be prepared during the purification process from the mixture of polypeptides and other proteins and/or peptides obtained by the genetically modified prokaryotic or eukaryotic host cell such as e.g. *E. coli* and *Pichia pastoris*.

Furthermore, the monomeric building blocks capable of forming NFDs may be pre-selected before doing a process for selection or screening as above and further herein described by taking into consideration primary amino acid sequences and crystal structure information if available. Moreover, in order to understand the potential interactions in these non-fused protein domains, it may be advisable to analyze different X-ray or NMR structures of non-fused single variable domains, i.e. NFDs. This then exemplifies how possibly in solution interactions in NFDs can occur but this is by no means then a complete explanation for the likely area of interaction between the NFD components.

Furthermore, further stabilization of the dimer may be beneficial and may be done by suitable linker linking the ends of the polypeptides and/or cysteines at the interaction sites. E.g. a covalent attachment of the two domains may be possible by introducing 2 cysteines in each of the two building blocks at spatially opposite positions to force formation of a disulphide bridge at the new site of interaction, or at N- or C-terminal region of the NFD as has e.g. been done with diabodies (Holliger & Hudson, Nat Biotech 2004, 23 (9): 1126). Furthermore, it may be advantageous to introduce a flexible peptide between the ends of the two monomeric building blocks. As an example, the upper hinge region of mouse IgG3 may be used. However, a variety of hinges or other linkers may be used. It is not required for dimerization per se, but provides a locking of the two building blocks. The naturally occurring hinges of antibodies are reasonable embodiments of hinges. In such case, the polypeptides of the invention need to be present first under reducing conditions, to allow the NFDs to form during purification after which oxidation can lead to the cysteine pairings, locking the NFDs into a fixed state. In the case of NFDs, the hinges or linkers may be shorter than in conventional covalently linked single variable domain containing polypeptides. This is not to disturb the expected close interaction of the monomeric building blocks, and flexibility of the dimer is not necessary. The choice of the hinge is governed by the desired residue sequence length (Argos, 1990, J. Mol. Biol. 211, 943-958), compatibility with folding and stability of the dimers (Richardson & Richardson, 1988, Science 240, 1648-1652), secretion and resistance against proteases, and can be determined or optimized experimentally if needed.

Furthermore, further stabilization of the monomers may be beneficial (i.e. avoidance of the dimerization or in certain instances possible multimerizations) and may be done by choosing suitable linkers linking the ends of the polypeptides and/or cysteines at or close to the CDR3 and/or FR4 region that prevent the single variable domain from dimerisation. E.g. a covalent stabilization of the CDR3 and/or FR4 may be possible by introducing 2 cysteines close to or/and within the CDR3 and/or FR4 region at spatially opposite positions to force formation of a disulphide bridge as has e.g. been done with cystatin that was stabilized against three-dimensional domain swapping by engineered disulfide bonds (Wahlbom et al., J. of Biological Chemistry Vol. 282, No. 25, pp. 18318-18326, Jun. 22, 2007). Furthermore, it may be advantageous to introduce a flexible peptide that is then engineered to have one cysteine that than forms a disulfide bond to e.g. a cysteine before the CDR3 region. In such case, the polypeptides of the invention need to be present first under reducing conditions, to allow the monomers to form after which oxidation can lead to the cysteine pairings, locking the monomers into a fixed, stabilized state.

Furthermore, further stabilization of the monomers may be beneficial (i.e. avoidance of the dimerization or in certain instances possible multimerizations) and may be done by replacing a destabilizing amino acid residue or residues (e.g. identified by screening of mutants, e.g. by affinity maturation methods—see e.g. WO2009/004065) by a stabilizing amino acid residue or residues in the vicinity of CDR3 and/or FR4.

In another aspect of the invention, further stabilization of the monomers can be achieved (i.e. avoidance of the dimerization or in certain instances possible multimerizations) by suitable formulation. In particular, the present invention provides a method for suppressing the dimerization and multimerization of (human serum) albumin-binding Nanobodies® (e.g. polypeptide B) and other polypeptides comprising Nanobodies® by providing mannitol or other polyols to a liquid formulation. Mannitol is generally used for maintaining the stability and isotonicity of liquid protein formulations. It is also a common bulking agent for lyophilization of the formulation. Surprisingly, the present invention discovered that mannitol can specifically inhibit the formation of dimers observed during storage (at elevated temperature) of several albumin-binding Nanobodies®. As a result, mannitol-containing formulations increase protein stability and sustain biological activity, thereby prolonging the shelf-life of the drug product. The stabilizing effect of mannitol is supported by data that demonstrate higher Tm (melting temperature) values in protein formulations with increasing mannitol concentrations.

This invention will also cover the use of other polyols, non-reducing sugars, NaCl or amino acids.

The dimers formed by e.g. the serum albumin-binding Nanobody® "polypeptide B" of the invention (SEQ ID NO: 8) was shown to be completely inactive for binding to HSA (BIACORE analysis), suggesting that the albumin binding site in the dimer interface is blocked by dimer formation. The addition of mannitol to the liquid formulation as proposed by this invention will therefore not only suppress the dimerization process but, importantly, will also preserve the HSA-binding activity of Nanobody® and slow down the inactivation. In general, the mannitol containing formulations according to the inventions prolong the shelf-life of the formulated protein/drug product. The invention is believed to be applicable to any albumin-binding Nanobody® and may be applicable to all Nanobodies® that have a tendency to form dimers in general. Thus, the mannitol formulations of the invention are indicated for the formulation of any Nanobody®, as process intermediate, drug substance or drug product. This invention may be used in a wide variety of liquid formulations which may consist of any buffering agent, a biologically effective amount of protein, a concentration of mannitol that is no greater than approximately 0.6M and other excipients including polyols, non-reducing sugars, NaCl or amino acids. The liquid formulations may be stored directly for later use or may be prepared in a dried form, e.g. by lyophilization. Mannitol may be used in any formulation to inhibit the formation of high molecular weight species such as the observed dimers during storage, freezing, thawing and reconstitution after lyophilization.

Thus, the present invention also relates to a formulation that comprises a polypeptide comprising one or more single variable domains, said formulation being formulated for administration to a human subject, and said formulation further comprising an excipient at a concentration of 1% to 20% (w:v).

Preferred excipients include polyols and/or sugars. The polyol and/or sugar may be a monosaccharide such as glucose or mannose, or a polysaccharide including disaccharides such as (without being limiting) sucrose and lactose, as well as sugar derivatives including sugar alcohols and sugar acids. Polyols and sugar alcohols include (without being limiting) mannitol, xylitol, erythritol, threitol, sorbitol and glycerol. A non-limiting example of a sugar acid is L-gluconate. Other exemplary sugars include (without being limiting) trehalose, glycine, maltose, raffinose, etc. The concentration of the excipient may range from about 1% to 20% (w:v), preferably from about 2.5% to 10% (w:v), more preferably from about 5% to 10% (w:v), such as e.g. 5% (w:v), 7.5% (w:v), 8% or 10% (w:v). Throughout the present invention the concentration of the excipient will be given as % (w:v). In a preferred aspect, the formulation comprises sucrose, preferably at a concentration of about 5% to 10% (w:v), such as about 8% (w:v).

In one aspect, the formulation of the present invention comprises an aqueous carrier with a pH of 5.5 to 8.0 and a polypeptide comprising one or more single variable domains at a concentration of 1 mg/ml to 200 mg/ml, said formulation being formulated for administration to a human subject, and said formulation further comprising an excipient at a concentration of 1% to 20% (w:v).

In another aspect, the formulation of the present invention comprises an aqueous carrier with a pH of 5.5 to 8.0 and a polypeptide comprising one or more single variable domains at a concentration of 1 mg/ml to 200 mg/ml, said formulation being formulated for administration to a human subject, and said formulation further comprising an excipient at a concentration of 1% to 20% (w:v), wherein said formulation has an inorganic salt concentration of 150 mM or lower.

The stable formulations of the present invention comprise polypeptides of the invention that have a high stability even during transportation and/or long periods of storage and that exhibit little to no aggregation (particularly dimerization and/or oligomerization). In addition to the polypeptide of the invention, the formulations of the present invention comprise at least an aqueous carrier and a buffer. The carrier used in the formulation of the invention should be a liquid carrier. Preferably the carrier is an aqueous carrier such as e.g. distilled water, MILLI-Q water or Water for Injection (WFI).

The pH of the formulation of the invention generally should not be equal to the isoelectric point of the particular polypeptide and may range from about 5.5 to about 8.0, or from about 6.0 to about 7.5, preferably from about 6.2 to 7.5, from about 6.5 to 7.5, most preferably from about 6.5 to 7.0.

The buffer can be any pharmaceutically acceptable buffer and can (without being limiting) be e.g. selected from the group consisting of histidine pH 6.0-6.5, hepes pH 7.0-8.0, MES pH 6.0, succinate pH 6.0-6.5 and acetate pH 5.5-6.0. The concentration of the buffer present in the formulation of the invention may range from 1 mM to 100 mM, 5 mM to 100 mM, 5 mM to 75 mM, 5 mM to 50 mM, 10 mM to 50 mM, 10 mM to 25 mM, 10 mM to 20 mM. In a specific aspect, the concentration of buffer in the formulations of the invention is 1 mM, 2 mM, 5 mM, 10 mM, 15 mM, 20 mM, 25 mM, 50 mM, 75 mM, or 100 mM. Preferably, the concentration is between 10 and 20 mM, such as 10 mM or 15 mM.

It will be understood by one skilled in the art that the formulation of the invention may be isotonic or slightly hypotonic with human blood, i.e. the formulation of the invention has essentially the same or a slightly lower osmotic pressure as human blood. Such isotonic or slightly hypotonic formulation generally has an osmotic pressure from about 240 mOSm/kg to about 320 mOSm/kg, such as about 240 mOSm/kg or higher, 250 mOSm/kg or higher or 260 mOSm/kg or higher.

Tonicity of a formulation is adjusted by the use of tonicity modifiers. "Tonicity modifiers" are those pharmaceutically acceptable inert substances that can be added to the formulation to provide an isotonicity of the formulation. Preferred tonicity modifier in the formulation of the invention are salts and/or excipients.

The formulation of the invention may additionally comprise a surfactant. A surfactant refers to a surface-active agent comprising a hydrophobic portion and a hydrophilic portion. In a preferred aspect, the surfactant is non-ionic. Certain exemplary non-ionic surfactants include (without being limiting) PEG8000, and polysorbate, including without being limiting, polysorbate 80 (TWEEN 80) and polysorbate 20 (TWEEN 20), TRITON X-100, polyoxypropylene-polyoxyethylene esters (PLURONIC®), and NP-40. In a specific aspect, the surfactant is selected from TWEEN (polysorbate) 20, TWEEN (polysorbate) 80 or a poloxamer. The concentration of the surfactant may range from about 0.001% to 1% (v:v) (preferably from about 0.001% to 0.1% (v:v), or 0.01% to 0.1% (v:v) such as 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)). Throughout the present invention the concentration of the surfactant will be given as % (v:v).

The formulation of the invention may also comprise one or more inorganic salts. In one aspect, the concentration of inorganic salt should not be more than 150 mM. Without being limiting, inorganic salts for use in the formulation of the invention can be selected from NaCl and KCl. Accordingly the formulation of the invention has an inorganic salt concentration of 150 mM or lower, preferably 120 mM or lower, or 100 mM or lower, more preferably 90 mM or lower, 80 mM or lower, 75 mM or lower, such as 50 mM or lower or even 40 mM or lower, 25 mM or lower, 10 mM or lower or 5 mM or lower. In one aspect, the formulation does not contain any inorganic salt.

The polypeptides of the invention present in the formulation of the invention should preferably have a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

Without being limiting, melting point determination can be done by the fluorescence-based thermal shift assay which is based on the fact that upon thermal unfolding the hydrophobic regions of proteins, usually hidden in the core of the protein fold, become accessible for binding to a hydrophobic fluorescent dye. The fluorescence emission of this dye is quenched in aqueous solution, whereas upon binding to the hydrophobic patches of an unfolded protein a sharp increase in the fluorescence yield of the probe is observed. Temperature induced unfolding is typically a two-state process with a sharp transition between the folded and unfolded state, where the melting temperature (Tm) is defined as the temperature at which half of the protein is in the unfolded state, i.e. the first derivative of the fluorescence signal upon gradual heating of the sample is plotted and the observed peak (or peaks when multiple domains and/or variants of the same domain are present) represents the melting temperature. The thermal shift assay can be performed in a typical real-time PCR instrument where melting curves can be recorded accurately in high-throughput mode with only small quantities of protein required.

During a differential scanning calorimetry experiment the sample is heated at a constant rate in an adiabatic environment ($\Delta T=0$). The energy required to keep the temperature difference between a reference and the sample cell at zero is measured and yields the heat capacity as a function of temperature (Cp(T)). The temperature corresponding to the maximum heat capacity represents the melting temperature ($T_m$). If the temperature dependent unfolding process is reversible other thermodynamic parameters such as the unfolding enthalpy ($\Delta H_{unfolding}$) can be determined.

Increased melting temperatures have been observed for the polypeptides of the invention when present in a formulation that comprises an excipient, preferably a saccharides and/or polyol such as mannitol, trehalose, sorbitol or sucrose. Accordingly, the present invention relates to a formulation comprising a polypeptide comprising one or more single variable domains, said formulation being formulated for administration to a human subject, wherein said formulation further comprises at least an excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%); and wherein the melting temperature of the polypeptide of the invention is at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

Accordingly, the present invention relates to a formulation comprising an aqueous carrier at a pH of 6.0 to 8.0 and a polypeptide comprising one or more single variable domains, said formulation being formulated for administration to a human subject, wherein said formulation further comprises at least an excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%); wherein the melting temperature of the polypeptide of the invention is at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

Accordingly, the present invention relates to a formulation comprising an aqueous carrier at a pH of 6.0 to 8.0 and a polypeptide comprising one or more single variable domains, said formulation being formulated for administration to a human subject, wherein said formulation further comprises at least an excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%), wherein said formulation has an inorganic salt concentration of 150 mM or lower; and wherein the melting temperature of the polypeptide of the invention is at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

The formulation of the present invention exhibit stability when stored at a temperature of 37±5° C. The formulation of the invention may exhibit stability when stored at a temperature of 37±5° C. for at least 2 weeks, 3 weeks, 4 weeks, at least 5 weeks, at least 8 weeks, at least 10 weeks, at least 3 months, at least 6 months, at least 1 year, 1.5 year or even 2 years or more.

As is known to one skilled in the art, the temperatures indicated in this text can be subject to normal variations.

Preferably, in those formulations that are stable under one or more of the above stress conditions:

less than 10% (more preferably less than 5%, even more preferably less than 3%, most preferably less than 1%) of the polypeptide of the invention forms dimers (e.g. as assessed by SE-HPLC) during storage under stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more); and/or at least 80% (at least 85%, at least 90%, at least 95%, at least 98%, at least 99%, or at least 99.5%) of the polypeptide of the invention retains its binding activity (e.g. as assessed by ELISA and/or BIACORE) to at least one of its (preferably to all of its) targets after storage under stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more) compared to the binding activity prior to the stress condition.

As indicated above, the polypeptides present in the formulation of the invention preferably do not form dimers. The formation of dimers in the sample can e.g. be measured by SE-HPLC. For example, analysis in SE-HPLC of a formulation containing SEQ ID NO: 17 after storage for 10 weeks at a temperature of 37° C., showed the formation of a separate peak eluting at an apparent molecular weight of 44 kDa in comparison with molecular weight markers, while the monomeric polypeptide eluted between the 44 and 17 kDa molecular weight markers. This separate peak at 44 kDa represented a dimeric form of SEQ ID NO: 17. Preferably in the formulation of the invention, less than 10% (more preferably less than 5%, even more preferably less than 3%, most preferably less than 1%) of the polypeptides forms dimers (e.g. as assessed by SE-HPLC) during storage under one or more of the above stress conditions.

Little to no dimer formation of the polypeptides of the invention has been observed in formulations that comprise an excipient, preferably a saccharide and/or polyol such as mannitol, trehalose, sorbitol or sucrose. Accordingly, the present invention relates to a formulation comprising a polypeptide comprising one or more single variable domains, said formulation being formulated for administration to a human subject, wherein said formulation further comprises at least an excipient, preferably a saccharide, a non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%); wherein less than 10% (preferably less than 8%, more preferably less than 7%, most preferably less than 5%) of the polypeptides forms dimers during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of dimers as measured by SE-HPLC.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, a non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%); wherein less than 10% (preferably less than 8%, more preferably less than 7%, most preferably less than 5%) of the polypeptides forms dimers during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of dimers as measured by SE-HPLC.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, a non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%); wherein said formulation has an inorganic salt concentration of 150 mM or lower; and wherein less than 10% (preferably less than 8%, more preferably less than 7%, most preferably less than 5%) of the polypeptides forms dimers during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of dimers as measured by SE-HPLC.

Apart from this and/or in addition, the formulation of the present invention shows very little to no loss of potency and/or biological activity of their polypeptides, even during storage under one or more of the above stress conditions.

The potency and/or biological activity of a biological describes the specific ability or capacity of said biological to achieve a defined biological effect. The potency and biological activities of the polypeptides of the invention can be assessed by various assays including any suitable in vitro assay, cell-based assay, in vivo assay and/or animal model known per se, or any combination thereof, depending on the specific disease or disorder involved. Suitable in vitro assays will be clear to the skilled person, and for example include ELISA; FACS binding assay; BIACORE; competition binding assay (AlphaScreen®, Perkin Elmer, Massachusetts, USA; FMAT); TRAP assay (osteoclast differentiation assay; Rissanen et al. 2005, J. Bone Miner. Res. 20, Suppl. 1: S256); NF-kappaB reporter gene assay (Mizukami et al. 2002, Mol. Cell. Biol. 22: 992-1000). For example, SEQ ID NO: 17 interacts with RANKL and blocks the interaction of this ligand with RANK, thereby preventing signalization through this receptor. SEQ ID NO's: 18 to 20 interact with IL-6R and block the interaction of this receptor with IL-6. The potency of the polypeptides of the invention for blocking the respective ligand/receptor interaction can be determined, e.g. by ELISA, BIACORE, AlphaScreen®.

For example, in one embodiment, BIACORE kinetic analysis uses Surface Plasmon Resonance (SPR) technology to monitor macromolecular interactions in real time and is used to determine the binding on and off rates of polypeptides of the formulation of the invention to their target. BIACORE kinetic analysis comprises analyzing the binding and dissociation of the target from chips with immobilized polypeptides of the invention on their surface. A typical BIACORE kinetic study involves the injection of 250 µL of polypeptide reagent at varying concentration in HBS buffer containing 0.005% TWEEN (polysorbate) 20 over a sensor chip surface, onto which has been immobilized the antigen. In the BIACORE 3000 system, the ligand is immobilized on carboxymethylated dextran over a gold surface, while the second partner (analyte) is captured as it flows over the immobilized ligand surface. The immobilized ligands are remarkably resilient and maintain their biological activity. The bound analytes can be stripped from the immobilized ligand without affecting its activity to allow many cycles of binding and regeneration on the same immobilized surface. Interaction is detected in real time via SPR and at high sensitivity. Because the same affinity may reflect different on-rates and off-rates, this instrument excels over most other affinity measuring methods in that it measures on-rates (ka) and off-rates (kd). Concentration determination experiments are also feasible.

The formulation of the present invention exhibits almost no loss in biological activities of the polypeptide during the prolonged storage under the conditions described above, as assessed by various immunological assays including, for example, enzyme-linked immunosorbent assay (ELISA) and Surface Plasmon Resonance to measure the ability of the polypeptide to specifically bind to an antigen. The polypeptides present in the formulation of the present invention retain, even under the above defined stress conditions (such as storage under certain temperature stress for defined periods) more than 80%, more than 85%, more than 90%, more than 95%, more than 98%, more than 99%, or more than 99.5% of their initial biological activities (e.g., the ability to bind to vWF, RANKL, IL-6R and/or HSA) of the polypeptides prior to the storage. In some embodiments, the polypeptides in the formulation of the invention retain under the above defined stress conditions at least 80%, at least 85%, at least 90%, at least 95%, at least 98%, at least 99%, or at least 99.5% of the biological activity (e.g., the ability to bind to vWF, RANKL, IL-6R and/or HSA) compared to the polypeptides present in a reference formulation prior to the storage.

In one embodiment, the polypeptides of the invention bind HSA. In the formulations of the present invention, at least 80% (preferably at least 85%, at least 90%, at least 95%, at least 98%, at least 99%, or at least 99.5%) of said polypeptides retain their binding activity to HSA under one or more of the above stress conditions (such as storage under certain temperature stress for defined periods) compared to the binding activity prior to the stress condition. Without being limiting, the binding of the polypeptides to HSA can be determined e.g. by ELISA and/or BIACORE.

In a preferred aspect, at least 80% (at least 85%, at least 90%, at least 95%, at least 98%, at least 99%, or at least 99.5%) of the polypeptides present in the formulation of the invention retain their binding activity to all of their targets (such as e.g. RANKL and HSA, IL-6R and HSA or IL-23 and HSA) after storage under one or more of the above stress conditions compared to the binding activity prior to storage.

Suitable animal models for determining the potency and/or biological activity of the polypeptides present in the formulations of the invention will be clear to the skilled person and will depend on the intended disease and/or disorder to be prevented and/or treated. Suitable animal models for testing the potency and/or biological activity of the polypeptides of the invention are e.g. described in WO 08/020079, WO 09/068627 and WO 08/142164.

Little to no loss of potency of the polypeptides of the invention has been observed in formulations that comprise an excipient, preferably a saccharide, non-reducing sugar and/or polyol such as mannitol, sorbitol, trehalose or sucrose. Accordingly, the present invention relates to a formulation comprising a polypeptide comprising one or more single variable domains, said formulation being formulated for administration to a human subject, wherein said formulation further comprises at least an excipient, preferably a saccharide, non-reducing sugar and/or polyol such as mannitol, sorbitol, trehalose or sucrose, at a concentration of 1% to 20% (preferably 2.5% to 15%, more preferably 5% to 10%, such as 5%, 7.5%, 8% or 10%); wherein at least 80% (preferably at least 85%, at least 90%, at least 95%, at least 98%, at least 99%, or at least 99.5%) of the polypeptides retain their binding activity to at least one (preferably to all) of their targets under one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) compared to the binding activity prior to the stress conditions, said binding activity as measured by ELISA and/or BIACORE.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, non-reducing sugar and/or polyol such as mannitol, sorbitol, trehalose or sucrose, at a concentration of 1% to 20% (preferably 2.5% to 15%, more preferably 5% to 10%, such as 5%, 7.5%, 8% or 10%); wherein at least 80% (preferably at least 85%, at least 90%, at least 95%, at least 98%, at least 99%, or at least 99.5%) of the polypeptides retain their binding activity to at least one (preferably to all) of their targets under one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) compared to the binding activity prior to the stress conditions, said binding activity as measured by ELISA and/or BIACORE.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, non-reducing sugar and/or polyol such as mannitol, sorbitol, trehalose or sucrose, at a concentration of 1% to 20% (preferably 2.5% to 15%, more preferably 5% to 10%, such as 5%, 7.5%, 8% or 10%); wherein said formulation has an inorganic salt concentration of 150 mM or lower; and wherein at least 80% (preferably at least 85%, at least 90%, at least 95%, at least 98%, at least 99%, or at least 99.5%) of the polypeptides retain their binding activity to at least one (preferably to all) of their targets under one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) compared to the binding activity prior to the stress conditions, said binding activity as measured by ELISA and/or BIACORE.

Accordingly, in the stable formulations of the present invention preferably:

the polypeptide of the invention has a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) (e.g. as assessed by TSA or DSC);

less than 10% (more preferably less than 5%, even more preferably less than 3%, most preferably less than 1%) of the polypeptide of the invention forms dimers (e.g. as assessed by SE-HPLC) during storage under one or more stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more); and/or at least 80% (at least 85%, at least 90%, at least 95%, at least 98%, at least 99%, or at least 99.5%) of the polypeptide of the invention retains its binding activity (e.g. as assessed by ELISA and/or BIACORE) to at least one (preferably to all) of its targets after storage under one or more stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more) compared to the binding activity prior to the stress condition.

General methods for producing the single variable domains and/or polypeptides present in the formulation of the invention are known to the skilled person and/or have been described in the art. The single variable domains and/or polypeptides can be produced in any host known to the skilled person. For example but without being limiting, the single variable domains and/or polypeptides can be produced in prokaryotic hosts among which *E. coli* or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*. Production of Nanobodies in prokaryotes and lower eukaryotic hosts such as *Pichia pastoris* has e.g. been described in WO 94/04678, WO 94/25591 and WO 08/142164. The contents of these applications are explicitly referred to in the connection with general culturing techniques and methods, including suitable media and conditions. The contents of these documents are incorporated by reference. The skilled person can also devise suitable genetic constructs for expression of the polypeptides of the invention in different hosts on the basis of the present application and common general knowledge. The present invention also relates to conditions and genetic constructs described in the art, for example the general culturing methods, plasmids, promoters and leader sequences described in WO 94/25591, WO 08/020079, Gasser et al. 2006 (Biotechnol. Bioeng. 94: 535); Gasser et al. 2007 (Appl. Environ. Microbiol. 73: 6499); or Damasceno et al. 2007 (Microbiol. Biotechnol. 74: 381).

More particularly, the method for the expression and/or production of a polypeptide comprising one or more single variable domains at least comprising the steps of:
  d) cultivating a host or host cell (as defined herein) under conditions that are such that said host or host cell will multiply;
  e) maintaining said host or host cell under conditions that are such that said host or host cell expresses and/or produces the polypeptide;
  f) isolating and/or purifying the secreted polypeptide from the medium.

To produce/obtain expression of the polypeptide, the transformed host cell or transformed host organism may generally be kept, maintained and/or cultured under conditions such that the (desired) polypeptide is expressed/produced. Suitable conditions will be clear to the skilled person and will usually depend upon the host cell/host organism used, as well as on the regulatory elements that control the expression of the (relevant) nucleotide sequence. Again, reference is made to the handbooks and patent applications mentioned above.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the polypeptide to be isolated).

In the present invention, the host can be removed from the culture medium by routine means. For example, the host can be removed by centrifugation or filtration. The solution obtained by removal of the host from the culture medium is also referred to as culture supernatant, or clarified culture supernatant. The polypeptides of the invention can be purified from the culture supernatant by standard methods. Standard methods include, but are not limited to chromatographic methods, including size exclusion chromatography, hydrophobic interaction chromatography, ion exchange chromatography, and affinity chromatography. These methods can be performed alone or in combination with other purification methods, e.g. precipitation or gel electrophoresis. The skilled person can devise suitable combinations of purification methods for the polypeptides of the invention on the basis of common general knowledge. For specific examples the art cited herein is referred to.

In one exemplary embodiment, the polypeptides of the invention can be purified from culture supernatant by a combination of affinity chromatography on Protein A, ion exchange chromatography and size exclusion chromatography. Reference to any "step of purification", includes, but is not limited to these particular methods.

More specifically, the polypeptides of the invention can be purified from culture supernatant using a process wherein the clarified supernatant (obtained by centrifugation) is captured on any combination of columns selected from (without being limiting) affinity chromatography resin such as Protein A resin, Cation Exchange Chromatography (CIEC) or an Anion Exchange Chromatography (AIEC) using for example Poros 50HS (POROS), SOURCE 30S or SOURCE 15S (GE Healthcare), SP SEPHAROSE (GE Healthcare), CAPTO S (GE Healthcare), CAPTO MMC (GE Healthcare) or Poros 50HQ (POROS), SOURCE 30Q or SOURCE 150 (GE Healthcare), Q SEPHAROSE (GE Healthcare), CAPTO Q and DEAE SEPHAROSE e (GE Healthcare), Size exclusion chromatography (SE-HPLC) using for example SUPERDEX 75 or SUPERDEX 200 (GE Healthcare), hydrophobic interaction chromatography (HIC) using for example octyl, butyl SEPHAROSE or equivalents, optionally also including a tangential flow filtration (TFF) step. Any combination of columns can be used for the purification of the polypeptides of the invention, such as e.g. Protein A resin followed by Cation Exchange Chromatography or two Cation Exchange Chromatography steps.

The present invention also provides methods for preparing the stable formulations of the invention comprising the polypeptides of the invention. More particularly, the present invention provides methods for preparing stable formulations of such polypeptides, said methods comprising concentrating a fraction containing the purified polypeptide to the final polypeptide concentration using e.g. a semipermeable membrane with an appropriate molecular weight (MW) cutoff (e.g. a 5 kD cutoff for single variable domains; a 10 kD cutoff for bivalent polypeptides comprising two single variable domains; or a 15 kD cutoff for trivalent polypeptides comprising three single variable domains) and diafiltering and/or ultrafiltering to buffer exchange and further concentrate the polypeptide fraction into the formulation buffer using the same membrane. As extensively described above, the formulation buffer of the present invention may further comprise an excipient at a concentration of 1% to 20%.

The pH of the formulation may range from about 5.5 to about 8.0, or may range from about 6.0 to about 7.5, preferably from about 6.2 to 7.5, from about 6.2 to 7.0, most preferably from about 6.5 to 7.0.

Surfactant (e.g. TWEEN (polysorbate) 20, TWEEN (polysorbate) 80 or poloxamer) may be added after the final diafiltration/ultrafiltration step at a concentration in the range of about 0% to 1%, preferably 0.001% to 0.1%, or 0.01% to 0.1% such as 0.001%, 0.005%, 0.01%, 0.02%, 0.05%, 0.08%, 0.1%, 0.5%, or 1% of the formulation, preferably 0.01% or 0.005%.

The formulation of the present invention may be sterilized by various sterilization methods, including sterile filtration, radiation, etc. In a specific embodiment, the polypeptide formulation is filter-sterilized with a presterilized 0.2 micron filter.

Preferably, the formulation of the present invention is supplied in a hermetically sealed container. Liquid formulations may comprise a quantity between 1 mL and 20 mL, preferably about 1 mL, 2 mL, 3 mL, 4 mL, 5 mL, 6 mL, 7 mL, 8 mL, 9 mL, 10 mL, 15 mL, or 20 mL.

The formulation of the present invention can be prepared as unit dosage forms by preparing a vial containing an aliquot of the formulation for a one time use. For example, a unit dosage of liquid formulation per vial may contain 1 mL, 2 mL, 3 mL, 4 mL, 5 mL, 6 mL, 7 mL, 8 mL, 9 mL, 10 mL, 15 mL, or 20 mL of the formulation. The pharmaceutical unit dosage forms can be made suitable for any form of delivery of the polypeptide of the invention including (without being limiting) parenteral delivery, topical delivery, pulmonary delivery, intranasal delivery, vaginal delivery, enteral delivery, rectal delivery, oral delivery and/or sublingual delivery. In one aspect, the present invention relates to a pharmaceutical unit dosage form suitable for parenteral (such as e.g. intravenous, intraarterial, intramuscular, intracerebral, intraosseous, intradermal, intrathecal, intraperitoneal, subcutaneous, etc) administration to a subject, comprising a formulation of the invention in a suitable container. In another preferred aspect, the subject is a human. In another specific embodiment, the formulations of the present invention are formulated into single dose vials as a sterile liquid that contains 10 mg/mL of one of SEQ ID NO's: 7 to 12, 10 mM histidine buffer at pH 6.0, 10% sucrose and 0.0005% TWEEN (polysorbate) 80.

The amount of a formulation of the present invention which will be effective in the prevention, treatment and/or management of a certain disease or disorder can be determined by standard clinical techniques well-known in the art or described herein. The precise dose to be employed in the formulation will also depend on the route of administration, and should be decided according to the judgment of the practitioner and each patient's circumstances. Effective doses may be extrapolated from dose-response curves derived from in vitro or animal model test systems. For formulations of the polypeptide, encompassed by the invention, the dosage administered to a patient may further be calculated using the patient's weight in kilograms (kg) multiplied by the dose to be administered in mg/kg.

The required volume (in mL) to be given is then determined by taking the mg dose required divided by the concentration of the polypeptide formulation. The final calculated required volume will be obtained by pooling the contents of as many vials as are necessary into syringe(s) to administer the polypeptide formulation of the invention.

The present invention also encompasses a finished packaged and labelled pharmaceutical product. This article of manufacture or kit includes the appropriate unit dosage form in an appropriate vessel or container such as a glass vial or other container that is hermetically sealed. In one embodiment, the unit dosage form is suitable for intravenous, intramuscular, intranasal, oral, topical or subcutaneous delivery. Thus, the invention encompasses formulations, preferably sterile, suitable for each delivery route. In the case of dosage forms suitable for parenteral administration (such as e.g. subcutaneous administration) the active ingredient, e.g., polypeptide of the invention, is sterile and suitable for administration as a particulate free solution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises the formulation containing the polypeptide. The packaging material includes instruction means which indicate that said polypeptide can be used to prevent, treat and/or manage one or more symptoms associated with the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide of interest, and wherein said packaging material includes instruction means which indicate that said agents can be used to prevent, treat and/or manage the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide, and wherein said packaging material includes instruction means which indicate that said agents can be used to prevent, treat and/or manage one or more symptoms associated with the disease or disorder by administering specific doses and using specific dosing regimens as described herein.

The formulations, containers, pharmaceutical unit dosages and kits of the present invention may be administered to a subject to prevent, treat and/or manage a specific disease and/or disorder. In a specific aspect, the formulations, containers, pharmaceutical unit dosages and kits of the present invention are administered to a subject to prevent, treat and/or manage a disease and/or disorder associated with or characterized by aberrant expression and/or activity of a certain target or one or more symptoms thereof. In another specific aspect, the formulations, containers, pharmaceutical unit dosages and kits of the present invention are administered to a subject to prevent, treat and/or manage diseases and/or disorders associated with aberrant expression and/or activity of RANKL, diseases and/or disorders associated with overexpression of IL-6, or vascular diseases and/or disorders or one or more symptoms thereof.

Diseases and disorders associated with aberrant expression and/or activity of RANKL are for example bone diseases and disorders, and include (without being limiting) the following diseases and disorders: Osteoporosis (McClung 2006, Current Osteoporosis Reports 4: 28-33), including, but not limited to, primary osteoporosis, endocrine osteoporosis (including, but not limited to, hyperthyroidism, hyperparathyroidism (Anandarajah and Schwarz 2006, J. Cell Biochem. 97: 226-232), Cushing's syndrome, and acromegaly), hereditary and congenital forms of osteoporosis (including, but not limited to, osteogenesis imperfecta, homocystinuria, Menkes' syndrome, Riley-Day syndrome), osteoporosis due to immobilization of extremities, glucocorticoid-induced osteoporosis (Locklin et al. 2001, Bone 28 (Suppl.): S80; McClung 2006, Current Osteoporosis Reports 4: 28-33; Anandarajah and Schwarz 2006, J. Cell Biochem. 97: 226-232) and post-menopausal osteoporosis (McClung 2006, Current Osteoporosis Reports 4: 28-33); (Juvenile or Familial) Paget's disease (Cundy et al. 2002, Hum. Mol. Genet. 11: 2119-2127; Whyte et al. 2002, J. Bone Miner. Res. 17: 26-29; Whyte et al. 2002, N. Engl. J. Med. 347: 175-184; Johnson-Pais et al. 2003, J. Bone Miner Res. 18: 376-380; Anandarajah and Schwarz 2006, J. Cell Biochem. 97: 226-232; Anandarajah and Schwarz 2006, J. Cell Biochem. 97: 226-232); Osteomyelitis, i.e., an infectious lesion in bone, leading to bone loss; Hypercalcemia (Anandarajah and Schwarz 2006, J. Cell Biochem. 97: 226-232), including, but not limited to, hypercalcemia resulting from solid tumors (including, but not limited to, breast, lung and kidney) and hematologic malignancies (including, but not limited to, multiple myeloma (Sordillo and Pearse 2003, Cancer 97 (3 Suppl): 802-812; Vanderkerken et al. 2003, Cancer Res. 63: 287-289), lymphoma and leukemia), idiopathic hypercalcemia, and hypercalcemia associated with hyperthyroidism and renal function disorders; Bone loss, including but not limited to, osteopenia following surgery, osteopenia induced by steroid administration, osteopenia associated with disorders of the small and large intestine, and osteopenia associated with chronic hepatic and renal diseases; Osteonecrosis, i.e., bone cell death, including, but not limited to, osteonecrosis associated with traumatic injury, osteonecrosis associated with Gaucher's disease, osteonecrosis associated with sickle cell anemia, osteonecrosis associated with systemic lupus erythematosus, osteonecrosis associated with rheumatoid arthritis, osteonecrosis associated with periodontal disease, osteonecrosis associated with osteolytic metastasis, and osteonecrosis associated with other condition; Bone loss associated with arthritic disorders such as psoriatic arthritis, rheumatoid arthritis, loss of cartilage and joint erosion associated with rheumatoid arthritis (Bezerra et al. 2005, Brazilian Journal of Medical and Biological Research 38: 161-170; Anandarajah and Schwarz 2006, J. Cell Biochem. 97: 226-232); Arthritis (Bezerra et al. 2005, Brazilian Journal of Medical and Biological Research 38: 161-170), including inflammatory arthritis (McClung 2006, Current Osteoporosis Reports 4: 28-33), Collagen-induced arthritis (Bezerra et al. 2005, Brazilian Journal of Medical and Biological Research 38: 161-170); Periprosthetic osteolysis (McClung 2006, Current Osteoporosis Reports 4: 28-33; Anandarajah and Schwarz 2006, J. Cell Biochem. 97: 226-232); Cancer-related bone disease (McClung 2006, Current Osteoporosis Reports 4: 28-33); Bone loss associated with aromatase inhibitor therapy (Lewiecki 2006, Expert Opin. Biol. Ther. 6: 1041-1050); Bone loss associated with androgen deprivation therapy (Lewiecki 2006, Expert Opin. Biol. Ther. 6: 1041-1050); Bone loss associated bone metastasis; Bone loss associated with diseases having immune system involvement, such as adult and childhood leukaemias, cancer metastasis, autoimmunity, and various viral infections (Holstead Jones et al. 2002, Ann. Rheum. Dis. 61 (Suppl II): ii32-ii39) Osteopenic disorders such as adult and childhood leukaemia (Oliveri et al. 1999, Henry Ford Hosp. Med. 39: 45-48), chronic infections such as hepatitis C or HIV (Stellon et al. 1985, Gastroenterology 89: 1078-1083), autoimmune disorders such as diabetes mellitus (Piepkorn et al. 1997, Horm. Metab. Res. 29: 584-91), and lupus erythematosus (Seitz et al. 1985, Ann. Rheum Dis. 44: 438-445), allergic diseases such as asthma (Ebeling et al. 1998, J. Bone Min. Res. 13: 1283-1289), lytic bone metastases in multiple cancers such as breast cancer (Coleman 1998, Curr. Opin. Oncol. 10 (Suppl 1): 7-13); Prostate cancer; Myeloma bone disease (Anandarajah and Schwarz 2006, J. Cell Biochem. 97: 226-232); Periodontal infections (Anandarajah and Schwarz 2006, J. Cell Biochem. 97: 226-232); Expansile skeletal hyperphosphatasia (Anandarajah and Schwarz 2006, J. Cell Biochem. 97: 226-232); Bone metastases (Lewiecki 2006, Expert Opin. Biol. Ther. 6: 1041-1050; Anandarajah and Schwarz 2006, J. Cell Biochem. 97: 226-232).

Also encompassed within the scope of the present invention is the prevention and/or treatment with the formulations, containers, pharmaceutical unit dosages and kits of the invention of other diseases and disorders associated with an imbalance in the RANKL/RANK/OPG pathway. Such diseases and disorders include but are not limited to osteoporosis, inflammatory conditions, autoimmune conditions, asthma, rheumatoid arthritis, multiple sclerosis, Multiple myeloma (Sordillo and Pearse 2003, Cancer 97 (3 Suppl): 802-812; Vanderkerken et al. 2003, Cancer Res. 63: 287-289); Vascular diseases (Anandarajah and Schwarz 2006, J. Cell Biochem. 97: 226-232) and Cardiovascular disease (Lewiecki 2006, Expert Opin. Biol. Ther. 6: 1041-1050).

Also encompassed within the scope of the present invention is the prevention and/or treatment with the formulations, containers, pharmaceutical unit dosages and kits of the invention of diseases and disorders associated with osteopetrosis such as osteopetrosis tarda, osteopetrosis congenita and marble bone disease.

Disease and disorders caused by excessive IL-6 production include sepsis (Starnes et al., 1999) and various forms of cancer such as multiple myeloma disease (MM), renal cell carcinoma (RCC), plasma cell leukaemia (Klein et al., 1991), lymphoma, B-lymphoproliferative disorder (BLPD) and prostate cancer. Non-limiting examples of other diseases caused by excessive IL-6 production or signalling include bone resorption (osteoporosis) (Roodman et al., 1992; Jilka et al., 1992), cachexia (Strassman et al., 1992), psoriasis, mesangial proliferative glomerulonephritis, Kaposi's sarcoma, AIDS-related lymphoma (Emilie et al., 1994), inflammatory diseases and disorder such as rheumatoid arthritis, systemic onset juvenile idiopathic arthritis, hypergammaglobulinemia (Grau et al., 1990); Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al., 1991).

Vascular diseases and/or disorders include acute coronary syndrome (ACS), myocardial infarction, thrombotic thrombocytopenic purpura (TTP) or Moschcowitz syndrome, vascular surgery and stroke.

The formulations, containers, pharmaceutical unit dosages and kits of the present invention may also be advantageously utilized in combination with one or more other therapies (e.g., one or more other prophylactic or therapeutic agents), preferably therapies useful in the prevention, treatment and/or management of the (same or another) disease or disorder. When one or more other therapies (e.g., prophylactic or therapeutic agents) are used, they can be administered separately, in any appropriate form and by any suitable route. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, other single variable domains, synthetic or natural inorganic molecules, mimetic agents, and synthetic or natural organic molecules. Any therapy (e.g., prophylactic or therapeutic agents) which is known to be useful, or which has been used or is currently being used for the prevention, treatment and/or management of one or more symptoms associated with a specific disease or disorder, can be used in combination with the formulations of the present invention in accordance with the invention described herein.

A formulation of the invention may be administered to a mammal, preferably a human, concurrently with one or more other therapies (e.g., one or more other prophylactic or therapeutic agents). The term "concurrently" is not limited to the administration of prophylactic or therapeutic agents/therapies at exactly the same time, but rather it is meant that the formulation of the invention and the other agent/therapy are administered to a mammal in a sequence and within a time interval such that the polypeptide contained in the formulation can act together with the other agent/therapy to provide an increased benefit than if they were administered otherwise. For example, the formulation of the invention and the one or more other prophylactic or therapeutic agents may be administered at the same time or sequentially in any order at different points in time; however, if not administered at the same time, they should be administered sufficiently close in time so as to provide the desired therapeutic or prophylactic effect.

When used in combination with other therapies (e.g., prophylactic and/or therapeutic agents), the formulations of the invention and the other therapy can act additively or synergistically. The invention contemplates administration of a formulation of the invention in combination with other therapies (e.g., prophylactic or therapeutic agents) by the same or different routes of administration, e.g., oral and parenteral.

Various delivery systems are known and can be used to administer the formulation of the present invention. Methods of administering formulations of the present invention include, but are not limited to, parenteral administration (e.g., intradermal, intramuscular, intraperitoneal, intravenous and, preferably subcutaneous), epidural administration, topical administration, and mucosal administration (e.g., intranasal and oral routes). In a specific embodiment, liquid formulations of the present invention are administered parenteral.

A particular advantage of the NFDs described in this invention is the ability to assemble functionally or partly functionally during e.g. the manufacturing process (e.g. purification step etc) in a controllable manner. A dimerization principle is used which allows the formation of homodimers. Examples described herein include NFDs-Mo, NFDs-Di, and NFDs-Tri. In these cases, the monomeric building blocks are expressed in a bacterial system and then bound in high concentration to a separation chromatographic device, e.g. Protein A or IMAC, and eluted swiftly to retain the desired dimeric complexes, i.e. the NFDs, in substantial yield. Under these conditions, the homodimeric proteins form by themselves and can directly be isolated in the dimeric form by said separation step and/or further isolated by size exclusion chromatography.

The present invention is further illustrated by the following preferred aspects and examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

PREFERRED ASPECTS

1. A formulation, such as a pharmaceutical formulation, comprising an aqueous carrier having a pH of 5.5 to 8.0 and a polypeptide comprising one or more single variable domains at a concentration of 1 mg/mL to 200 mg/mL, said formulation being formulated for administration to a human subject and said formulation further comprising one or more components selected from:
   a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
   b) An excipient at a concentration of 1% to 20%;
   c) A surfactant at a concentration of 0.001% to 1% selected from TWEEN (polysorbate) 80, TWEEN (polysorbate) 20 or a poloxamer,
   wherein said formulation has an inorganic salt concentration of 150 mM or lower.
2. The formulation of aspect 1, wherein the inorganic salt concentration is from 50 mM to 100 mM or lower.
3. The formulation of aspect 2, that does not contain any inorganic salt.
4. The formulation of any of aspects 1 to 3, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
5. The formulation of aspect 4, wherein the formulation comprises a histidine buffer pH 6.5.
6. The formulation of aspect 4, wherein the formulation comprises a histidine buffer pH 6.0.
7. The formulation of any of aspects 4 to 6, wherein the buffer has a concentration of 10 to 50 mM, preferably 10 to 20 mM, such as 10 mM or 15 mM.
8. The formulation of any of aspects 1 to 7, wherein the formulation comprises a surfactant at a concentration of 0.001% to 1% selected from TWEEN (polysorbate) 80, TWEEN (polysorbate) 20 or a poloxamer.
9. The formulation of aspect 8, wherein the formulation comprises TWEEN (polysorbate) 80.
10. The formulation of any of aspects 8 or 9, wherein the surfactant has a concentration of 0.001% to about 0.1%, or about 0.01% to about 0.1% such as 0.001%, 0.005%, 0.01%, 0.02%, 0.05%, 0.08%, 0.1%, 0.5%, or 1% of the formulation, preferably 0.01%.
11. The formulation of any of aspects 1 to 3, wherein the formulation comprises an excipient at a concentration of 1% to 20%.
12. The formulation of aspect 11, wherein the excipient is a dissaccharide and/or a polyol.
13. The formulation of aspect 11, wherein the excipient is selected from sucrose, mannitol, sorbitol and trehalose.
14. The formulation of any of aspects 11 to 13, wherein the excipient has a concentration of 2.5% to 15%, preferably 5% to 10%, such as 5%, 7.5%, 8% or 10%.
15. The formulation of any of aspects 1 to 14, wherein the polypeptide has a solubility of at least 20 mg/mL as determined by the PEG exclusion method or by centrifugal ultrafiltration.
16. The formulation of aspect 15, wherein the polypeptide has a solubility of at least 50 mg/mL as determined by the PEG exclusion method or by centrifugal ultrafiltration.
17. The formulation of aspect 16, wherein the polypeptide has a solubility of at least 90 mg/mL as determined by the PEG exclusion method or by centrifugal ultrafiltration.
18. The formulation of aspect 17, wherein the polypeptide has a solubility of at least 120 mg/mL as determined by the PEG exclusion method or by centrifugal ultrafiltration.
19. The formulation of aspect 18, wherein the polypeptide has a solubility of at least 150 mg/mL as determined by the PEG exclusion method or by centrifugal ultrafiltration.

20. The formulation of aspect 19, wherein the polypeptide has a solubility of at least 200 mg/mL as determined by the PEG exclusion method or by a concentration experiment.
21. The formulation of any of aspects 1 to 20, wherein the formulation at least comprises one or more components selected from:
  a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
  c) A surfactant at a concentration of 0.001% to 1% selected from TWEEN (polysorbate) 80, TWEEN (polysorbate) 20 or a poloxamer.
22. The formulation of aspect 21, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
23. The formulation of aspect 22, wherein the formulation comprises a histidine buffer pH 6.5.
24. The formulation of aspect 22, wherein the formulation comprises a histidine buffer pH 6.0.
25. The formulation of any of aspects 22 to 24, wherein the buffer has a concentration of 10 to 50 mM, preferably 10 to 20 mM, such as 10 mM or 15 mM.
26. The formulation of any of aspects 21 to 25, wherein the formulation comprises a surfactant at a concentration of 0.001% to 1% selected from TWEEN (polysorbate) 80, TWEEN (polysorbate) 20 or a poloxamer.
27. The formulation of aspect 26, wherein the formulation comprises TWEEN (polysorbate) 80.
28. The formulation of any of aspects 26 or 27, wherein the surfactant has a concentration of 0.001% to about 0.1%, or about 0.01% to about 0.1% such as 0.001%, 0.005%, 0.01%, 0.02%, 0.05%, 0.08%, 0.1%, 0.5%, or 1% of the formulation, preferably 0.01%.
29. The formulation of any of aspect 1 to 28, wherein the polypeptide has a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).
30. The formulation of aspect 29, which has a pH of 6.2 to 7.5.
31. The formulation of aspect 30, which has a pH of 6.5 to 7.5.
32. The formulation of aspect 31, which has a pH of 6.5 to 7.0.
33. The formulation of any of aspects 29 to 32, wherein the formulation at least comprises one or more components.
  a) A buffer at a concentration of 10 mM to 100 mM selected from the group consisting of histidine pH 6.0-6.5, hepes pH 7.0-8.0, MES pH6.0, succinate pH 6.0-6.5 and acetate pH 5.5-6.0;
  b) An excipient at a concentration of 1% to 20%.
34. The formulation of aspect 33, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
35. The formulation of aspect 34, wherein the formulation comprises a histidine buffer pH 6.0-6.5 or a hepes buffer pH 7.0.
36. The formulation of any of aspects 34 or 35, wherein the buffer has a concentration of 10 to 50 mM, preferably 10 to 20 mM, such as 10 mM or 15 mM.
37. The formulation of any of aspects 33 to 36, wherein the formulation comprises an excipient at a concentration of 1% to 20%.
38. The formulation of aspect 37, wherein the excipient is a dissaccharide and/or a polyol.
39. The formulation of aspect 38, wherein the excipient is selected from sucrose, mannitol, sorbitol and trehalose.
40. The formulation of any of aspects 37 to 39, wherein the excipient has a concentration of 2.5% to 15%, preferably 5% to 10%, such as 5%, 7.5%, 8% or 10%.
41. The formulation of any of aspects 1 to 40, wherein the polypeptide is stable after multiple (up to 10) freeze/thaw cycles, said stability as determined by SE-HPLC, IEX-HPLC, RP-HPLC, BIACORE analysis and/or potency assay.
42. The formulation of any of aspects 1 to 41, wherein the polypeptide is stable during storage at a temperature of 2-8° C. up to up to at least 2 weeks (preferably at least 3 weeks, at least 5 weeks, at least 8 weeks, at least 10 weeks, at least 3 months, at least 6 months, at least 1 year, 1.5 year or even 2 years or more), said stability as determined by OD320/OD280 measurement, elastic light scattering, SE-HPLC and/or RP-HPLC.
43. The formulation of aspects 42, wherein no particulates are present as measured by OD320/OD280 measurement and/or elastic light scattering.
44. The formulation of any of aspects 42 or 43, in which the OD320/OD280 is 0.05 or less.
45. The formulation of any of aspects 42 or 43, in which the scattering in elastic light scattering stays within the detection range, and/or preferably is 1000 abs or less.
46. The formulation of any of aspects 42 to 45, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
47. The formulation of aspect 46, wherein the formulation comprises a histidine buffer pH 6.0-6.5 or a hepes buffer pH 7.0.
48. The formulation of any of aspects 46 or 47, wherein the buffer has a concentration of 10 to 50 mM, preferably 10 to 20 mM, such as 10 mM or 15 mM.
49. The formulation of any of aspects 1 to 48, wherein the polypeptide is stable during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more), said stability as determined by OD320/OD280 measurement, elastic light scattering, SE-HPLC, RP-HPLC, IEX-HPLC, potency assay (such as BIACORE or ELISA) and/or SDS-PAGE.
50. The formulation of aspect 49, wherein less than 10% (preferably less than 8%, more preferably less than 7%, most preferably less than 5%) of the polypeptides forms pyroglutamate at the N-terminal glutamic acid during storage, the % of pyroglutamate as measured by RP-HPLC.
51. The formulation of aspect 50, which has a pH of 7.0 or less.
52. The formulation of any of aspects 50 or 51, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
53. The formulation of aspect 52, wherein the formulation comprises a histidine buffer or an acetate buffer.

54. The formulation of any of aspects 52 or 53, wherein the buffer has a concentration of 10 to 50 mM, preferably 10 to 20 mM, such as 10 mM or 15 mM.
55. The formulation of any of aspects 49 to 54, wherein less than 10% (preferably less than 7.5%, more preferably less than 5%, most preferably less than 2%) of the polypeptides forms dimers during storage, the % of dimers as measured by SE-HPLC.
56. The formulation of aspect 55, wherein the formulation at least comprises one or more components selected from:
a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
b) An excipient at a concentration of 1% to 20%.
57. The formulation of aspect 56, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
58. The formulation of aspect 57, wherein the formulation comprises a histidine buffer or an acetate buffer.
59. The formulation of any of aspects 57 or 58, wherein the buffer has a concentration of 10 to 50 mM, preferably 10 to 20 mM, such as 10 mM or 15 mM.
60. The formulation of any of aspects 55 to 59, wherein the formulation comprises an excipient at a concentration of 1% to 20%.
61. The formulation of aspect 60, wherein the excipient is a disaccharide and/or a polyol.
62. The formulation of aspect 60, wherein the excipient is a non-reducing sugar.
63. The formulation of aspect 61 or 62, wherein the excipient is selected from trehalose, mannitol and sucrose.
64. The formulation of any of aspects 60 to 63, wherein the excipient has a concentration of 2.5% to 15%, preferably 5% to 10%, such as 5%, 7.5%, 8% or 10%.
65. The formulation of any of aspects 49 to 64, wherein no particulates are present as measured by OD320/OD280 measurement and/or elastic light scattering.
66. The formulation of aspect 65, in which the OD320/OD280 is 0.05 or less.
67. The formulation of aspect 65, in which the scattering in elastic light scattering stays within the detection range, and/or preferably is 1000 abs or less.
68. The formulation of any of aspects 65 to 67, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
69. The formulation of aspect 68, wherein the formulation comprises a histidine buffer.
70. The formulation of any of aspects 68 or 69, wherein the buffer has a concentration of 10 to 50 mM, preferably 10 to 20 mM, such as 10 mM or 15 mM.
71. The formulation of any of aspects 49 to 70, wherein at least 80% (preferably at least 90%, more preferably at least 95% or even at least 99%) of the polypeptides retain their binding activity to at least one of their targets after storage compared to the binding activity prior to storage, said binding activity as measured by ELISA and/or BIACORE.
72. The formulation of aspect 71, wherein the formulation at least comprises one or more components selected from:
a) A buffer at a concentration of 10 mM to 100 mM selected from the group consisting of hepes pH 7.0-8.0, histidine pH 6.0-6.5, MES pH 6.0 and acetate pH 5.5-6.0;
b) An excipient at a concentration of 1% to 20%.
73. The formulation of aspect 72, wherein the formulation comprises a buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0.
74. The formulation of aspect 73, wherein the formulation comprises a histidine buffer.
75. The formulation of any of aspects 73 or 74, wherein the buffer has a concentration of 10 to 50 mM, preferably 10 to 20 mM, such as 10 mM or 15 mM.
76. The formulation of any of aspects 71 to 75, wherein the formulation comprises an excipient at a concentration of 1% to 20%.
77. The formulation of aspect 76, wherein the excipient is a disaccharide and/or a polyol.
78. The formulation of aspect 76, wherein the excipient is a non-reducing sugar.
79. The formulation of aspect 77 or 78, wherein the excipient is selected from mannitol, trehalose and sucrose.
80. The formulation of any of aspects 76 to 79, wherein the excipient has a concentration of 2.5% to 15%, preferably 5% to 10%, such as 5%, 7.5%, 8% or 10%.
81. The formulation of any of aspects 1 to 80, wherein the single variable domain is stable under mechanical stress as determined by visual inspection and/or OD320/OD280 measurement.
82. The formulation of aspect 81, in which the OD320/OD280 is 0.05 or less.
83. The formulation of any of aspects 81 or 82, wherein the mechanical stress is selected from shaking during 105 to 1 min, pushing through a needle (25 G, preferably 26 G, more preferably 27 G, even more preferably 28 G, most preferably 29 G or more) with a syringe, rotation for two days at 10 rpm, and stirring for 1 hour at room temperature and/or 4-48 hours at 4° C. at at least 10 rpm (such as 50 rpm, 100 rpm or more).
84. The formulation of any of aspects 81 to 83, wherein the formulation at least comprises one or more components selected from:
b) An excipient at a concentration of 1% to 20%;
c) A surfactant at a concentration of 0.001% to 1% selected from TWEEN (polysorbate) 80, TWEEN (polysorbate) 20 or a poloxamer.
85. The formulation of any of aspects 81 to 84, wherein the formulation comprises an excipient at a concentration of 1% to 20%.
86. The formulation of aspect 85, wherein the excipient is a sugar and/or polyol.
87. The formulation of aspect 85, wherein the excipient is selected from mannitol, glycine and sucrose, such as sucrose, or mannitol and glycine.
88. The formulation of any of aspects 85 to 87, wherein the excipient has a concentration of 2.5% to 15%, preferably 5% to 10%, such as 5%, 7.5%, 8% or 10%.
89. The formulation of any of aspects 84 to 88, wherein the formulation comprises a surfactant at a concentration of 0.001% to 1% selected from TWEEN (polysorbate) 80, TWEEN (polysorbate) 20 or a poloxamer.
90. The formulation of aspect 89, wherein the formulation comprises TWEEN (polysorbate) 80.
91. The formulation of any of aspects 89 or 90, wherein the surfactant has a concentration of 0.001% to about 0.1%, or about 0.01% to about 0.1% such as 0.001%, 0.005%, 0.01%, 0.02%, 0.05%, 0.08%, 0.1%, 0.5%, or 1% of the formulation, preferably 0.01%.
92. The formulation of any of aspects 1 to 91, wherein the concentration of polypeptide is about 1 to 200 mg/ml or more, preferably about 5 to 100 mg/mL or more, more preferably about 5 to 50 mg/mL or more, most preferably about 5 to 30 mg/mL or more, such as around 5 mg/mL, around 10 mg/mL, around 20 mg/mL, around 30 mg/mL, around 40 mg/mL, around 50 mg/mL, around 60 mg/mL, around 70 mg/mL, around 80 mg/mL, around 90 mg/mL, around 100 mg/mL, around 150 mg/mL or even more.
93. The formulation of any of aspects 1 to 92, wherein the aqueous carrier is distilled water.
94. The formulation of any of aspects 1 to 93, wherein the aqueous carrier is MILLI-Q grade water or Water for Injection (WFI).
95. The formulation according to any of aspects 1 to 94, which is isotonic or slightly hypotonic.
96. The formulation according to aspect 95, which has an osmolality of 290±60 mOsm/kg.
97. The formulation of any of aspects 1 to 96, wherein the polypeptide comprises two or more single variable domains, such as two or three.
98. The formulation of any of aspects 1 to 97, wherein the polypeptide specifically binds RANKL, IL-6R or IL-23.
99. The formulation of aspect 98, wherein the polypeptide is selected from one of SEQ ID NO's: 1 to 6.
100. The formulation of any of aspects 1 to 99, wherein
   the polypeptide has a solubility of at least 20 mg/mL, preferably 50 mg/mL or more, more preferably 90 mg/mL or more or 120 mg/mL or more, most preferably 150 mg/mL or more, or even 200 mg/mL or more, as determined by the PEG exclusion method or by a concentration experiment;
   the polypeptide has a melting temperature of at least 59° C. or more, preferably at least 60° C. or more, more preferably at least 61° C. or more or at least 62° C. or more, most preferably at least 63° C. or more as measured by the thermal shift assay (TSA) and/or differential scanning calorimetry (DSC);
   no particulates are present as measured by OD320/OD280 and/or elastic light scattering;
   less than 10% of the polypeptide forms pyroglutamate at the N-terminal glutamic acid during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more), the % of pyroglutamate as measured by RP-HPLC;
   less than 10% of the polypeptide forms dimers during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more), the % of dimers as measured by SE-HPLC;
   at least 80% of the polypeptide retains its binding activity to at least one of its targets after storage at 37±5° C. up to at least 2 weeks (preferably at least 3 weeks, at least 5 weeks, at least 2 months, at least 6 months, at least 1 year, 1.5 year or even 2 years or more) compared to the binding activity prior to storage, said binding activity as measured by ELISA and/or BIACORE; and/or
   the polypeptide is stable during mechanical stress.
101. The formulation of any of aspects 1 to 100, wherein said formulation comprises at least two components selected from:
a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
b) An excipient at a concentration of 1% to 20%;
c) A surfactant at a concentration of 0.001% to 1% selected from TWEEN (polysorbate) 80, TWEEN (polysorbate) 20 or a poloxamer.
102. The formulation of any of aspects 1 to 101, wherein said formulation comprises the following components:
a) A buffer at a concentration of 10 mM to 100 mM selected from the group consisting of histidine pH 6.0-6.5, hepes pH 7.0-8.0, MES pH 6.0, succinate pH 6.0-6.5 and acetate pH 5.5-6.0;
b) An excipient at a concentration of 1% to 20%;
c) A surfactant at a concentration of 0.001% to 1% selected from TWEEN (polysorbate) 80, TWEEN (polysorbate) 20 or a poloxamer.
103. The formulation of any of aspects 1, 101 and/or 102, wherein the pH is between 6.0 and 8, preferably between 6.2 and 7.5, more preferably between 6.5 and 7.5 or 6.5 and 7.0, such as 6.5 or 7.0.
104. The formulation of any of aspects 1, 101 to 103, wherein the buffer is a histidine buffer.
105. The formulation of aspect 104, wherein the buffer is a histidine pH 6.5 or histidine pH 6.0 buffer.
106. The formulation of any of aspects 104 or 105, wherein the histidine buffer has a concentration of 10 to 50 mM, more preferably 10 to 20 mM.
107. The formulation of any of aspects 104 to 106, wherein the histidine buffer has a concentration of about 10 mM or about 15 mM.
108. The formulation of any of aspects 1, 101 and/or 102 to 107, wherein the excipient is a saccharide and/or polyol.
109. The formulation of aspect 108, wherein the excipient is a non-reducing sugar.
110. The formulation of aspect 108, wherein the excipient is selected from mannitol, trehalose, sorbitol and sucrose.
111. The formulation of any of aspect 108 to 110, wherein the excipient has a concentration of 2.5% to 15%, more preferably 5% to 10%.
112. The formulation of aspect 111, wherein the excipient has a concentration selected from about 5%, 7.5%, 8% and 10%.
113. The formulation of any of aspects 1, 101 and/or 102 to 112, wherein the surfactant is TWEEN (polysorbate) 80.
114. The formulation of aspect 113, wherein the surfactant has a concentration of 0.01% to 0.1%, preferably 0.01% to 0.05%.
115. The formulation of aspect 114, wherein the surfactant has a concentration of about 0.01% or 0.005%.
116. The formulation of any of aspects 1 to 115, comprising:
a) A histidine pH 6.5 buffer at a concentration of 10 mM to 100 mM;
b) Sucrose at a concentration of 1% to 20%; and
c) TWEEN (polysorbate) 80 at a concentration of 0.001% to 1%.
117. The formulation of aspect 116, comprising:
a) 15 mM histidine pH 6.5;
b) 8% sucrose; and
c) 0.01% TWEEN (polysorbate) 80.
118. The formulation of aspect 117, comprising:
a) 15 mM histidine pH 6.5;
b) 8% sucrose;
c) 0.01% TWEEN (polysorbate) 80; and
d) A polypeptide selected from SEQ ID NO's: 1 to 6.
119. The formulation of any of aspects 1 to 115, comprising:
a) A histidine pH 6.0 buffer at a concentration of 10 mM to 100 mM;
b) Sucrose at a concentration of 1% to 20%; and
c) TWEEN (polysorbate) 80 at a concentration of 0.001% to 1%.

120. The formulation of aspect 119, comprising:
a) 10 mM histidine pH 6.0;
b) 10% sucrose; and
c) 0.005% TWEEN (polysorbate) 80.
121. The formulation of aspect 120, comprising:
a) 10 mM histidine pH 6.0;
b) 10% sucrose;
c) 0.005% TWEEN (polysorbate) 80; and
d) A polypeptide selected from SEQ ID NO's: 1 to 6.
122. A method for the preparation of a formulation of any of aspects 1 to 121, at least comprising the step of concentrating the polypeptide and exchanging it with the selected buffer and/or excipient.
123. A sealed container containing a formulation according to any of aspects 1 to 121.
124. A pharmaceutical unit dosage form suitable for parenteral administration to a human, comprising a formulation according to any of aspects 1 to 121 in a suitable container.
125. A kit comprising one or more of the sealed containers according to aspect 123 and/or pharmaceutical unit dosage forms according to aspect 124, and instructions for use of the formulation.
126. The formulation, container, pharmaceutical unit dosage or kit according to any of the preceding aspects for use in therapy.
127. Method for prevention and/or treatment of one or more diseases and/or disorders, comprising administering to a subject in need thereof a formulation according to any of aspects 1 to 121.
128. Method of aspect 127, wherein the disease is a disease and/or disorder associated with aberrant expression and/or activity of RANKL, disease and/or disorder associated with aberrant expression and/or activity, such as overexpression of IL-6, or disease and disorder associated with heterodimeric cytokines and their receptors.
129. Method of aspect 128, wherein the disease is selected from osteoporosis, cancer induced bone loss and/or bone loss associated with autoimmunity and/or viral infection.
130. Method of aspect 128, wherein the disease is selected from rheumatoid arthritis, abnormal synovial cell growth, plasmocytosis induced Castleman's disease, tumor, muscle protein proteolysis, multiple sclerosis, systemic lupus erythematosus, inflammatory bowel disease, pancreatitis, psoriasis, angiogenesis, systemic-onset type juvenile rheumatoid arthritis, spinal cord injury, endothelial injury or destruction, mesothelioma, vasculitis, osteoarthritis, inner ear disorder, cancer, rejection after transplantation, pancreatic islet transplantation, myocardial infraction, prostate cancer, choroidal neovascularization, muscle regeneration, inflammatory myopathy, chronic rejection in cardiac transplant, delayed graft function
131. Method of aspect 128, wherein the disease is selected from inflammation and inflammatory disorders such as bowel diseases (colitis, Crohn's disease, IBD), infectious diseases, psoriasis, cancer, autoimmune diseases (such as MS), carcoidis, transplant rejection, cystic fibrosis, asthma, chronic obstructive pulmonary disease, rheumatoid arthritis, viral infection, common variable immunodeficiency.
A-1. A stable NFD.
A-2. A stable NFD in solution.
A-3. A stable NFD obtainable by a process comprising the step of concentrating a polypeptide comprising at least one single variable domain and/or by a process comprising the step of storage of a polypeptide comprising at least one single variable domain at elevated temperature, e.g. at a temperature close to the melting temperature or e.g. at 37° C. over a prolonged time period, e.g. such as 1 to 4 weeks, e.g. 4 weeks.
A-4. A stable NFD obtainable by a process comprising the step of concentrating a polypeptide comprising and/or consisting of one or more single variable domain(s) and one or more linkers.
A-5. A stable NFD according to any of aspects A-3 or A-4, wherein the step of concentrating is done by affinity- and/or ion exchange chromatography.
A-6. A stable NFD according to any of the aspects A-3 to A-5, wherein the step of concentrating is done on a Protein A column, and wherein high amounts of polypeptide are loaded on the column, e.g. 2 to 5 mg per ml resin Protein A.
A-7. A stable NFD according to any of the aspects 5 or 6, wherein the polypeptide is eluted by a steep pH gradient, e.g. a one step pH change of 2.
A-8. A stable NFD according to the previous aspects, wherein the NFD is stable over a period of up to 2 years at −20 degrees Celcius.
A-9. A stable NFD according to the aspects above, wherein the NFD is stable over a period of up to 2 weeks at 4 degrees Celcius.
A-10. A stable NFD according to the previous aspects, wherein the NFD is stable over a period of up to 15 minutes at 50 degrees Celcius.
A-11. A stable NFD according to the previous aspects, wherein the NFD is stable at acidic pH.
A-12. A stable NFD according to the previous aspects, wherein the NFD is stable at acidic pH over a prolonged period of time, e.g. a time up to 1 day, more preferably 1 week, more preferably 2 weeks, even more preferably 3 weeks, most preferred 4 weeks.
A-13. A stable NFD according to the previous aspects, wherein the NFD is stable at basic pH over a prolonged period of time, e.g. a time up to 1 day, more preferably 1 week, more preferably 2 weeks, even more preferably 3 weeks, most preferred 4 weeks.
A-14. A stable NFD according to the previous aspects, wherein the NFD is stable between pH 3 and pH 8.
A-15. A stable NFD according to the previous aspects, wherein the NFD is stable between pH 2.5 and pH 8.
A-16. A stable NFD according to the previous aspects, wherein the NFD is stable between pH 3 and pH 8 for 4 weeks at 4 degrees Celcius.
A-17. A stable NFD according to the previous aspects, wherein the NFD is stable when mixing with organic solvents.
A-18. A stable NFD according to the previous aspects, wherein the NFD is stable when mixing with an alcohol, e.g. isopropanol.
A-19. A stable NFD according to the previous aspects, wherein the NFD is stable when mixing with 30% v/v of an alcohol, e.g. isopropanol.
A-20. A stable NFD according to the previous aspects, wherein the dissociation constant of the binding of the NFD to its target molecule is about the same as the dissociation constant of the binding of its corresponding monomeric building block to said target molecule.
A-21. A stable NFD according to the previous aspects, wherein there is no specific binding to its target molecule.
A-22. A stable NFD according to the previous aspects, wherein the dissociation constant of the binding of the NFD to its target molecule is 30% or less, preferably 20% or less, more preferably 10% or less, of the dissociation constant of the binding of its corresponding monomeric building block to said target molecule.

A-23. A stable NFD according to the previous aspects, wherein the dissociation constant of the binding of the NFD to its target molecule is 100 nM or less, preferably 10 nM or less, more preferably 1 nM or less.

A-24. A stable NFD according to the previous aspects, wherein the koff value for the binding of the NFD to its target molecule is about the same as the koff value for the binding of its corresponding monomeric building block.

A-25. A stable NFD according to the previous aspects, wherein the koff value for the binding of the NFD to its target molecule is not more than 90%, more preferably not more than 50%, even more preferably not more than 40%, even more preferably not more than 30%, even more preferably not more than 20%, most preferably not more than 10% higher than the koff value for the binding of its corresponding monomeric building block.

A-26. A stable NFD according to the previous aspects, wherein the koff value for the binding of the NFD to its target molecule is not more than 50% higher than the koff value for the binding of its corresponding monomeric building block.

A-27. A stable NFD according to the previous aspects, wherein the koff value for the binding of the NFD to its target molecule is not more than 10% higher than the koff value for the binding of its corresponding monomeric building block.

A-28. A stable NFD according to the previous aspects, wherein the single variable domain is a Nanobody® such as a VHH, a humanized VHH, an affinity-matured, stabilized, sequence optimized or otherwise altered VHH or a construct thereof.

A-29. A stable NFD according to the previous aspects, wherein the single variable domain is selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19 and SEQ ID NO: 20, preferably SEQ ID NO: 8.

A-30. A stable NFD according to the previous aspects, wherein the single variable domain is selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19 and SEQ ID NO: 20, preferably SEQ ID NO: 8 and of a functional sequence that is at least 70%, more preferably at least 80%, even more preferably at least 90%, most preferably at least 95% identical to any of SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19 and SEQ ID NO: 20, preferably SEQ ID NO: 8

A-31. A stable NFD according to the previous aspects, wherein the single variable domain is selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19 and SEQ ID NO: 20, preferably SEQ ID NO: 8 and of a functional sequence that is at least 70%, more preferably at least 80%, even more preferably at least 90%, most preferably at least 95% identical to any of SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19 and SEQ ID NO: 20, preferably SEQ ID NO: 8 2; and wherein said polypeptide specifically binds to its target molecule(s), more preferably has a dissociation constant to at least one of its target molecules (if bi- or multispecific), of 100 nM or less, even more preferably of 10 nM or less, most preferably of 1 nM or less.

A-32. A NFD of any of the previous aspects (e.g. as described herein) wherein the single variable domain is not VHH-R9 as described in Spinelli et al, FEBS Letters 564 (2004) 35-40.

A-33. A functional fragment of a NFD as described in any of aspects A-1 to A-32.

A-34. A polypeptide comprising at least one single variable domain, wherein said at least one single variable domains can form a NFD as e.g. described in any of aspects A-1 to A-32.

B-1. A preparation comprising a NFD as described in any of aspects A-1 to A-32, a functional fragment of aspect A-33, or a polypeptide of aspect A-34.

B-2. A preparation comprising a NFD as described in any of aspects A-1 to A-32, a functional fragment of aspect A-33 or a polypeptide of aspect A-34, wherein the ratio of NFD and its corresponding monomeric building block is about 1 part NFD/1 part corresponding monomeric building block to about 1 part NFD/2 parts corresponding monomeric building block.

B-3. A preparation comprising a NFD as described in any of aspects A-1 to A-32, a functional fragment of aspect A-33 or a polypeptide of aspect A-34, wherein the ratio of NFD and its corresponding monomeric building block is about 1 part NFD/1 part corresponding monomeric building block to about 2 parts NFD/1 part corresponding monomeric building block.

B-4. A preparation comprising a NFD as described in any of claims A-1 to A-32, a functional fragment of aspect A-33 or a polypeptide of aspect A-34, wherein the ratio of NFD and its corresponding monomeric building block is 25% NFD/75% monomeric building block.

B-5. A preparation comprising a NFD as described in aspects A-1 to A-32, a functional fragment of aspect A-33 or a polypeptide of aspect A-34, wherein the ratio of NFD and its corresponding monomeric building block is 75% NFD/25% monomeric building block.

C-1. A process of making a NFD according to any of aspects A-1 to A-32, a functional fragment of aspect A-33 or a polypeptide of aspect A-34, comprising a process step that has a condition that favors hydrophobic interactions.

C-2. A process of making a NFD according to aspect C-1, wherein said process step is a purification step.

C-3. A process of making a NFD according to aspect C-1, wherein within said process step, the condition is such that it promotes partial protein unfolding.

C-4. A process of making a NFD according to aspect C-3, wherein said process step is a purification step.

C-5. A process of making a NFD according to any of aspects A-1 to A-32, a functional fragment of aspect A-33 or a polypeptide of aspect A-34, comprising the step of up-concentrating the monomeric building blocks of said NFD, e.g. by binding the polypeptides comprising one or more single variable domain(s) on an affinity chromatography column, e.g. Protein A or IMAC.

C-6. A process of making a NFD according to any of aspects A-1 to A-32, a functional fragment of aspect A-33 or a polypeptide of aspect A-34, comprising the step of binding polypeptides comprising one or more single variable domain(s) on a affinity chromatography column, e.g. Protein A or IMAC, and eluting with a pH step which allows release of said polypeptide.

C-7. A process of making a NFD according to any of aspects A-1 to A-32, a functional fragment of aspect A-33 or a polypeptide of aspect A-34, comprising the step of binding polypeptides comprising one or more single variable domain(s) on a affinity chromatography column, e.g. Protein A, and eluting with a pH step which allows release of said polypeptide within 1 column volume.

C-8. A process of making a NFD according to any of aspects A-1 to A-32, a functional fragment of aspect A-33 or a polypeptide of aspect A-34, comprising the step of ultrafiltration.

C-9. A process according to aspect C-8, wherein the ultrafiltration is done under conditions of low salt.

C-10. A process of making a NFD according to any of aspects A-1 to A-32, a functional fragment of aspect A-33 or a polypeptide of aspect A-34, comprising the process step of storing the appropriate polypeptide comprising one or more single variable domain(s) at elevated temperature over a prolonged time.

C-11. A process of making a NFD according to aspect C-10, wherein said elevated temperature is 37° C. and time is 1, 2, 3, 4, 5, or 6, preferably 4 weeks.

C-12. A process of making a NFD according to any of aspect C-10 or C-11, wherein said elevated temperature is such that it promotes partial protein unfolding and exposure is over 1, 2, 3, 4, 5, or 6, preferably 4 weeks.

C-13. A process of making a NFD according to any of aspect C-10 to C-12, wherein said elevated temperature is close to the melting temperature of the polypeptide and exposure is over 1, 2, 3, 4, 5, or 6, preferably 4 weeks.

C-14. A process of making a NFD according to any of aspect C-9 to C-13, wherein the CDR3 of said single variable domain is destabilized.

C-15. A process of making a NFD according to any of aspects C-10 to C-14, wherein the single variable domain is a Nanobody®, such as e.g. a VHH, a humanized VHH, an affinity-matured, stabilized, sequence optimized or otherwise altered VHH.

D-1. A process of making monomeric polypeptides comprising one or more single variable domain(s), e.g. Nanobody® such as a VHH, a humanized VHH, an affinity-matured, stabilized, sequence optimized or otherwise altered VHH, wherein each of the steps in the making of said polypeptide does not generate more than 10%, more preferably not more than 5%, even more preferably not more than 4%, even more preferably not more than 3%, even more preferably not more than 2%, even more preferably not more than 1%, most preferred not more than 0.1% w/w corresponding NFD.

D-2. A process according to aspect D-1, wherein each of the steps in said process avoids conditions favoring hydrophobic interactions.

D-3. A process according to any of aspects D-1 or D-2, wherein said conditions favoring hydrophobic interactions is a high concentration of the polypeptides, i.e. a concentration of the polypeptides e.g. more than 10 mg polypeptide per ml resin column material; and thus a process avoiding said interactions is avoiding such conditions in each step of its making.

D-4. A process according to aspect D-3, wherein column loads, e.g. of an affinity column, are carefully evaluated and overload of the column is avoided, i.e. a column load maximum should be determined wherein not more than 10%, more preferably not more than 5%, even more preferably not more than 4%, even more preferably not more than 3%, even more preferably not more than 2%, even more preferably not more than 1%, most preferred not more than 0.1% w/w NFD is generated.

D-5. A process according to any of aspects D1 to D-4 of making monomeric polypeptides comprising one or more single variable domain(s), e.g. Nanobody® such as a VHH, a humanized VHH, an affinity-matured, stabilized, sequence optimized or otherwise altered VHH devoid of NFD or with no more than 50%, more preferably no more than 40%, even more preferably no more than 30%, even more preferably no more than 20%, most preferred no more than 10% NFD, wherein each of the steps in said process avoids conditions favoring hydrophobic interactions, e.g. wherein the process does not consist of a protein A step and/or wherein said process avoids conditions wherein the one or more single variable domain is partially unfolded, e.g. CDR3 is destabilized and/or partially unfolded by e.g. elevated temperature such as a temperature close to the melting temperature of the polypeptide or e.g. 37° C., over a prolonged time, e.g. weeks such as e.g. 4 weeks.

E-1. A pharmaceutical formulation comprising a polypeptide susceptible to dimerization (i.e. the formation of NFDs), e.g. a polypeptide as described in any of aspects A-1 to A-31, e.g. a polypeptide that comprises at least one of SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19, SEQ ID NO: 20, e.g. a polypeptide that comprises polypeptide B, and polyol.

E-2. The pharmaceutical formulation according to aspect E-1, wherein the polyol is in a concentration of e.g. not more than 0.6M.

E-3. The pharmaceutical formulation according to any of aspects E-1 or E-2, wherein the polyol is one or more selected from sorbitol, mannitol, xylitol, ribitol, and erythritol.

E-4. The pharmaceutical formulation according to any of aspects E-1 to E-3, wherein the polyol is mannitol, and e.g. in a concentration of not more than 0.6 M mannitol.

E-5. The pharmaceutical formulation according to any of aspects E-1 to E-4, wherein the polypeptide comprises a single variable domain that binds serum albumin, preferably human serum albumin.

E-6. The pharmaceutical formulation according to any of aspects E-1 to E-5, wherein the polypeptide comprises polypeptide B.

E-7. The pharmaceutical formulation according to any of aspects E-1 to E-6, additionally comprising a non-reducing sugar such as e.g. sucrose and/or trehalose and optionally NaCl and/or amino acids.

E-8. The pharmaceutical formulation according to any of aspects E-1 to E-7, that is a liquid formulation.

E-9. The pharmaceutical formulation according to any of aspects E-1 to E-8, that is prepared in a dried form, e.g. by lyophilization.

E-10. The pharmaceutical formulation according to any of aspects E-1 to E-9, that is used as an injectable.

E-11. The pharmaceutical formulation according to any of aspects E-1 to E-10, that is used as a subcutaneous formulation.

F-1 A formulation, such as a pharmaceutical formulation, comprising a polypeptide comprising one or more single variable domains, said formulation being formulated for administration to a human subject, further comprising an excipient at a concentration of 1% to 20%.

F-2. A formulation comprising an aqueous carrier having a pH of 5.5 to 8.0 and a polypeptide comprising one or more single variable domains at a concentration of 1 mg/mL to 200 mg/mL, said formulation being formulated for administration to a human subject, and said formulation further comprising an excipient at a concentration of 1% to 20%.

F-3. A formulation comprising an aqueous carrier having a pH of 5.5 to 8.0 and a polypeptide comprising one or more single variable domains at a concentration of 1 mg/mL to 200 mg/mL, said formulation being formulated for administration to a human subject, and said formulation further comprising an excipient at a concentration of 1% to 20%, wherein said formulation has an inorganic salt concentration of 150 mM or lower.

F-4. The formulation of any of aspect F-1 to F-3, wherein said single variable domain is susceptible to dimerization.

F-5. The formulation of aspect F-4, wherein the inorganic salt concentration is from 50 mM to 100 mM or lower.

F-6. The formulation of aspect F-5, that does not contain any inorganic salt.

F-7. The formulation of any of aspect F-1 to F-6, wherein the polypeptide has a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

F-8. The formulation of aspect F-7, wherein the formulation at least comprises an excipient at a concentration of 1% to 20%.

F-9. The formulation of aspect F-7, wherein the excipient is a dissaccharide and/or a polyol.

F-10. The formulation of aspect F-9, wherein the excipient is selected from sucrose, mannitol, sorbitol and trehalose.

F-11. The formulation of any of aspects F-8 to F-10, wherein the excipient has a concentration of 2.5% to 15%, preferably 5% to 10%, such as 5%, 7.5%, 8% or 10%.

F-12. The formulation of any of aspects F-1 to F-11, wherein the polypeptide is stable during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more), said stability as determined by SE-HPLC.

F-13. The formulation of aspect F-12, wherein less than 10% (preferably less than 7.5%, more preferably less than 5%, most preferably less than 2%) of the polypeptides forms dimers during storage, the % of dimers as measured by SE-HPLC.

F-14. The formulation of aspect F-13, wherein the formulation at least comprises an excipient at a concentration of 1% to 20%.

F-15. The formulation of aspect F-14, wherein the excipient is a disaccharide and/or a polyol.

F-16. The formulation of aspect F-14, wherein the excipient is a non-reducing sugar.

F-17. The formulation of aspect F-15 or F-16, wherein the excipient is selected from trehalose, mannitol and sucrose.

F-18. The formulation of any of aspects F-14 to F-17, wherein the excipient has a concentration of 2.5% to 15%, preferably 5% to 10%, such as 5%, 7.5%, 8% or 10%.

F-19. The formulation of any of aspects F-12 to F-18, wherein at least 80% (preferably at least 90%, more preferably at least 95% or even at least 99%) of the polypeptides retain their binding activity to at least one of their targets after storage compared to the binding activity prior to storage, said binding activity as measured by ELISA and/or BIA-CORE.

F-20. The formulation of aspect F-19, wherein the formulation at least comprises an excipient at a concentration of 1% to 20%.

F-21. The formulation of aspect F-20, wherein the excipient is a disaccharide and/or a polyol.

F-22. The formulation of aspect F-20, wherein the excipient is a non-reducing sugar.

F-23. The formulation of aspect F-21 or F-22, wherein the excipient is selected from mannitol, trehalose and sucrose.

F-24. The formulation of any of aspects F-20 to F-23, wherein the excipient has a concentration of 2.5% to 15%, preferably 5% to 10%, such as 5%, 7.5%, 8% or 10%.

F-25. The formulation of any of aspects F-1 to F-24, wherein the aqueous carrier is distilled water.

F-26. The formulation of any of aspects F-1 to F-24, wherein the aqueous carrier is MILLI-Q grade water or Water for Injection (WFI).

F-27. The formulation according to any of aspects F-1 to F-26, which is isotonic or slightly hypotonic.

F-28. The formulation according to aspect F-27, which has an osmolality of 290±60 mOsm/kg.

F-29. The formulation of any of aspects F-1 to F-28, wherein the polypeptide comprises two or more single variable domains, such as two or three.

F-30. The formulation of any of aspects F-1 to F-29, wherein the polypeptide specifically binds serum albumin (preferably human serum albumin), vWF, RANKL or IL-6R.

F-31. The formulation of any of aspects F-1 to F-30, wherein the polypeptide comprises at least a single variable domain that binds serum albumin, preferably human serum albumin.

F-32. The formulation of aspect F-31, wherein the polypeptide is selected from one of SEQ ID NO's: 7 to 12 and 15 to 20.

F-33. A method for the preparation of a formulation of any of aspects F-1 to F-32, at least comprising the step of concentrating the polypeptide and exchanging it with the selected buffer and excipient.

F-34. A sealed container containing a formulation according to any of aspects F-1 to F-32.

F-35. A pharmaceutical unit dosage form suitable for parenteral administration to a human, comprising a formulation according to any of aspects F-1 to F-32 in a suitable container.

F-36. A kit comprising one or more of the sealed containers according to aspect F-34 and/or pharmaceutical unit dosage forms according to aspect F-35, and instructions for use of the formulation.

F-37. The formulation, container, pharmaceutical unit dosage or kit according to any of the preceding aspects for use in therapy.

F-38. Method for prevention and/or treatment of one or more diseases and/or disorders, comprising administering to a subject in need thereof a formulation according to any of aspects F-1 to F-32.

F-39. Method of aspect F-38, wherein the disease and/or disorder is a disease and/or disorder associated with aberrant expression and/or activity of RANKL, disease and/or disorder associated with overexpression of IL-6, or vascular disease and/or disorder.

F-40. Method of aspect F-39, wherein the disease and/or disorder is selected from osteoporosis, cancer induced bone loss and/or bone loss associated with autoimmunity and/or viral infection.

F41. Method of aspect F-39, wherein the disease and/disorder is selected from rheumatoid arthritis, abnormal synovial cell growth, plasmocytosis induced Castleman's disease, tumor, muscle protein proteolysis, multiple sclerosis, systemic lupus erythematosus, inflammatory bowel disease, pancreatitis, psoriasis, angiogenesis, systemic-onset type juvenile rheumatoid arthritis, spinal cord injury, endothelial injury or destruction, mesothelioma, vasculitis, osteoarthritis, inner ear disorder, cancer, rejection after transplantation, pancreatic islet transplantation, myocardial infarction, prostate cancer, choroidal neovascularization, muscle regeneration, inflammatory myopathy, chronic rejection in cardiac transplant, delayed graft function.

F-42. Method of aspect F-39, wherein the disease and/or disorder is selected from acute coronary syndrome (ACS), myocardial infarction, thrombotic thrombocytopenic purpura (TTP) or Moschcowitz syndrome, vascular surgery and stroke.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All of the references described herein are incorporated by reference, in particular for the teaching that is referenced hereinabove.

EXAMPLES

Example 1

Formulation and Stability Studies with RANKL008a

Example 1.1

Materials and Methods Used in the Study 1.1.1 Single Variable Domains

RANKL008a (SEQ ID NO: 4; EVQLVESGGGLVQPGGSLRLSCAASG-FTFSSYPMGWFRQAPGKGREFVS SITGSGGSTYY-ADSVKGRFTISRDNAKNTLYLQMNSL-RPEDTAVYYCAAYIRPDTYLSRDYRKYDYWGQGTL-VTVSS GGGGSGGGSEVQLVESGGGLVQPGNSL-RLSCAASGFTFSSFGMSWVRQAPGK-GLEWVSSISGSGSDTLYADSVKG RFTISRDNAKT-TLYLQMNSLRPEDTAVYYCTIGGSLSRSSQGTLVTVS-SGGGGSGGGSEVQLVESGGGLVQPGGSLR LSCAAS-GFTFSSYPMGWFRQAPGKGREFVS-SITGSGGSTYYADSVKGRFTISRD-NAKNTLYLQMNSLRPEDTAVYYC AAYIRPDTYLSRDYRKYDYWGQGTLVTVSS) has been described as SEQ ID NO: 759 in WO 2008/142164. RANKL008a is a trivalent bispecific Nanobody consisting of three humanized variable domains of a heavy-chain llama antibody, of which two identical subunits are specific for binding to RANKL while the remaining subunit binds to HSA. The subunits are fused head-to-tail with a G/S linker in the following format: RANKL13H5-9GS-Alb8-9GS-RANKL13H5.

RANKL008a was expressed in *Pichia pastoris* and purified on SP SEPHAROSE as a capturing step and a Q filter as a polishing step or on SP SEPHAROSE as a capturing step and CAPTO MMC as a polishing step or alternatively by using a ProtA capture step followed by and SP SEPHAROSE polishing step. Concentration of the Nanobody and buffer switch to PBS, 10 mM phosphate+100 mM NaCl, 10 mM phosphate+5% mannitol or 10 mM phosphate+115 mM NaCl or others buffers was done via UF/DF or by dialysis. A final filtration on a 0.22 µm filter was performed. The different batches of RANKL008a ranged in concentration from 143 to 62.8 mg/mL. Most batches were prepared at concentrations of about 60-85 mg/mL.

1.1.2 Other Reagents

All reagents used in the study are standard chemical reagents of highest purity. The complete composition of D-PBS was 137 mM NaCl, 2.7 mM KCl, 10 mM Sodium Phosphate dibasic, 2 mM Potassium Phosphate monobasic.

1.1.3 Equipment and Columns for Testing

HPLC experiments were carried out on an Agilent 1200 series instrument from Agilent Technologies (Palo Alto, USA). The columns used were:
RP-HPLC: ZORBAX 300SB-C3 5-micron;
SE-HPLC: TSK-GEL G2000SW$_{XL}$ (Tosoh Bioscience, Japan);
IEX-HPLC: Dionex PROPAC $_H$CX-10 column;

The concentration of the purified RANKL008a batches was determined by spectroscopy at 280 nm either using a NANODROP ND-1000 (Thermoscientific), or a Uvikon 943 Spectrophotometer (Kontron Instruments) or an Eppendorf Biophotometer 613.

Particle size distribution was measured on a PAMAS SVSS-C particle counter (PArtikelMess-und AnalyseSysteme GMBH).

For potency measurements a BIACORE 3000 (GE Healthcare) was used. Elisa based potency assays were performed using standard laboratory equipment and plate reader instrumentation.

Osmolality measurement was done with an osmometer Model 3320 from Advanced instruments.

1.1.4 Inhibition ELISA for RANKL Potency Measurement

RANKL008a interacts with human (soluble) receptor activator of nuclear factor-kappaB ligand (RANKL) and blocks the interaction of this ligand with its human receptor activator of nuclear factor-kappaB (RANK), thereby preventing signalization through this receptor. The potency of RANKL008a was measured by an ELISA-based inhibition assay that allows assessment of the relative potency of the RANKL binding moieties of an unknown batch of RANKL008a relative to that of a reference batch.

For the reference, the control and the test samples, different dilutions of Nanobodies were prepared. These dilutions were pre-incubated with a constant amount of 5 ng/mL soluble RANKL and a constant amount of 200 ng/mL RANK-Fc. Subsequently, this mixture was transferred to a microtiter plate coated with a non-blocking anti-Fc Nanobody. After washing, residual bound RANKL was detected with a polyclonal biotinylated anti-human RANKL antibody, followed by hors radish peroxidase (HRP)-labeled streptavidin detection.

The relative potency of the test samples compared to the reference samples was analysed by use of PLA 2.0 Software (Stegmann Systems).

1.1.5 ELISA for HSA Binding

The relative potency of the HSA binding moiety in RANKL008a was measured by an ELISA. Briefly, HSA was coated onto a plastic multiwell MAXISORP ELISA plate by adsorption. After blocking excess binding sites on the plates with Superblock T20, a dilution series of references, control and test samples was applied on the plate. Bound Nanobody was subsequently detected using a bivalent anti-Nanobody Nanobody, directly conjugated to horseradish peroxidase (HRP).

The relative potency of the test samples compared to the reference samples was analysed by use of PLA 2.0 Software (Stegmann Systems).

1.1.6 Purity Assay of RANKL008a by Size Exclusion High Performance Liquid Chromatography (SE-HPLC)

The SE-HPLC assay consisted of a pre-packed silica gel TSK-GEL G2000SW$_{XL}$ column, a mobile phase consisting of KCl, NaCl and phosphate buffer pH 7.2 (D-PBS) and UV detection at 280 nm. The relative amount of the specific protein, variant, or impurities expressed as area %, was calculated by dividing the peak area corresponding to the specific protein or to any protein impurity by the total area of all integrated peaks.

1.1.7 Purity Assay of RANKL008a by Reverses Phase High Performance Liquid Chromatography (RP-HPLC)

In the RP-HPLC assay a ZORBAX 300SB-C3 column (Agilent Technologies, Palo Alto, US) was used. The relative amount of a specific protein impurity was determined by measuring the light absorbance of the components eluting from the RP-HPLC column. The relative amount of the specific protein, variant, or impurities expressed as area %, was calculated by dividing the peak area corresponding to the specific protein or to any protein impurity by the total area of all integrated peaks.

1.1.8 Purity Assay of RANKL008a by Ion Exchange High Performance Liquid Chromatography (IEX-HPLC)

The IEX-HPLC assay combined the use of a pre-packed Dionex PROPAC WCX-10 weak cation exchange column, a mobile phase consisting of citrate buffer pH 5.5 and UV detection at 280 nm. After loading the protein(s) on the column, bound materials were eluted by a sodium chloride gradient. The relative amount of the specific protein, variant, or impurities expressed as area %, was calculated by dividing the peak area corresponding to the specific protein or to any protein impurity by the total area of all integrated peaks.

1.1.9 Relative Potency Determination on BIACORE

RANKL or HSA was immobilized on the BIACORE chip (amine coupling using the BIACORE amine coupling kit). After a preconditioning step of 5 injections of RANKL008a, all samples were diluted to 2.5 nM in triplicate and analyzed on the chip. Slopes were determined using the general fit method and the linear fit model (BIAevaluation software). To determine the initial binding rate (IBR), the slope between 5 s and 30 s was selected. The values of these slopes were transferred in excel and the percentage activity/potency compared to the RANKL008a reference material was determined. BIACORE potency is thus expressed as relative potency compared to the reference materials.

Example 1.2

Stability of the Nanobody in Different Buffers after Different Freeze/Thaw Cycles A freeze/thaw stability study was performed to determine the effect of repetitive freeze and thawing on the recovery, physical stability and chemical stability of RANKL008a. Aliquots of batch RANKL008a formulated at ~60-85 mg/mL in the buffers 1-12 given in Table 1 were subjected to 10 freeze/thaw (F/T) cycles at −20° C. One F/T cycle is defined by freezing the sample for 1 hour in a freezer at −20° C. followed by thawing at room temperature for 30 minutes. The stressed samples were compared with reference material (stored at 4° C.) using SE-HPLC (FIG. 1 (A); representative figure of the experiments performed in phosphate buffer), RP-HPLC (FIG. 2; representative figure of the experiments performed in phosphate buffer) and the ELISA potency assays (Table 2). All other data of the freeze thaw experiments demonstrate similar patterns as given in FIGS. 1 and 2 (except FIG. 1 (B) see below).

Subjecting RANKL008a to 10 F/T cycles had no significant effect on its stability: the SE-HPLC- and RP-HPLC profiles were comparable between the reference batches and material subjected to multiple freeze/thaw cycles. There was no decrease in the total surface area and no new peaks were being formed, except in 20 mM L-histidine, pH 5.5+10% mannitol and 20 mM L-histidine, pH 6+10% mannitol, where the main peak had a very small shoulder in the SE-HPLC chromatograms (FIG. 1 (B) showing the data at pH 5.5 and where the minor shoulder on the main peak is indicated by an arrow). In Table 3 and Table 4 data are included for the integration of the different peaks (expressed as % surface area) in the SE-HPLC and RP-HPLC analysis respectively. These data demonstrate that no changes occur in the profiles after 10 freeze thaw cycles.

Analysis by the ELISA potency assays indicated no loss of activity after repetitive freezing and thawing in all formulations, except in 20 mM Histidine, pH 5.5+10% mannitol where there appeared to be a lower RANKL and HSA binding potency.

Example 1.3

Stability of the Nanobody in Different Buffers when Stored at 37° C. Up to 10 Weeks RANKL008a was formulated in different buffers at ~60-85 mg/mL (buffers 1-12 given in Table 1). The stability of the different samples was assessed in accelerated stress conditions at 37° C.±3° C. Samples were taken after 2, 3, 5 and 10 weeks storage at this temperature and were analyzed using SE-HPLC, RP-HPLC and IEX-HPLC. BIACORE was performed on the samples stored for 10 weeks to evaluate loss in potency.

1.3.1 SE-HPLC Analysis

The results of the analysis of a sample by SE-HPLC is given in FIG. 3 where an example is shown for the sample stored during two weeks at 37° C. in the presence of 50 or 100 mM salt or 10% mannitol phosphate buffer. Storage at 37° C. resulted in the formation of a clear prepeak eluting at about 40 minutes and some minor postpeaks close to the main peak; at the 60 minutes elution time (see insert in FIG. 3) some degradation fragments could be observed. In Table 3 the integration data for all samples analysed is summarized for the different peaks observed (except peaks after 60 minutes elution time). The peak area of the prepeak increased over time but was reduced by the addition of mannitol to the buffer (Table 3). The postpeaks after 60 minutes elution time corresponded to degradation products (due to remaining proteolytic activity in sample). The relative area (%) of these peaks increased only slightly, implying that degradation was restricted to a minimum.

The prepeak represented the dimeric form of RANKL008a. The peak surface area of the prepeak increased with storage time (Table 3) and was accompanied by a concomitant decrease in surface area of the main peak (Table 3). The propensity to form dimers was significantly lower in the formulations containing 10% mannitol, which seemed to have a positive effect in suppressing the dimerization process. Note the significant lower amounts of dimers observed in the Acetate and Histidine buffers (pH 5.5) containing 10% mannitol (Table 1 and FIG. 4). FIG. 4(A) summarizes the % surface area for the main peak in the different buffers and at different time points when stored at 37° C. FIG. 4(B) summarizes the data for the % prepeak (dimer).

1.3.2 RP-HPLC Analysis

A representative RP-HPLC is given in FIG. 5 where the RP-HPLC chromatogram of a RANKL008a sample stored in phosphate buffer with different concentrations salt or 10% mannitol is represented. The RP-HPLC profiles of RANKL008a formulated in the 12 different buffers were comparable to this Figure. In Table 4 integration data for the different peaks detected is summarized. In FIG. 5 the inset shows a zoom on the main peak where the two pre-peaks can be discriminated, while the post peak that is fully base line resolved from the main peak is the pyro-glutamate variant of the RANKL008a where the N-terminal glutamic acid has been converted to the pyroglutamate form.

There were two differences between the RP-HPLC profiles of the reference batch and the storage samples. Firstly, the pyroglutamate peak increased with increased incubation time and was more apparent in phosphate buffer at pH 7 than at pH 5.5 or pH 6. Secondly, a prepeak was being formed in function of storage time. The surface area of this peak was higher in the phosphate buffer.

There were no differences in the RP-HPLC profiles of the samples without or with mannitol.

1.3.3 IEX-HPLC Analysis

A representative IEX-HPLC chromatogram of the RANKL008a stored for 2 weeks in phosphate buffer with different salt concentrations or 10% mannitol is depicted in FIG. 6. The inset shows a zoom in on the main peak where a minor post peak 1 and a more significant post-peak 2 is observed. Results of the analysis of the different samples by IEX-HPLC are given in Table 5 and FIG. 7.

The first postpeak constituted maximally 4.5% of the total peak surface area. The surface area of this peak was the highest in phosphate buffer and the lowest or even absent in the mannitol-containing buffers. The peak area of the second peak on the other hand was substantial, yet significantly lower in the buffers containing 10% mannitol (FIG. 7). The material eluting in the post-peak was collected by fraction collection and re-chromatographed on the SE-HPLC column described above. This post-peak 2 elutes in the SE-HPLC chromatogram at the dimer position demonstrating that i) this dimer does not dissociate under these conditions and that ii) this dimer elutes later on the IEX-HPLC column. Therefore we can conclude that the post-peak 2 is the dimerized form of the RANKL008a.

1.3.4 BIACORE Potency Analysis of the RANKL008a Stored at 37° C.

The RANKL and HSA binding of RANKL008a in stability samples stored for 10 weeks at 37° C. was compared with the activity of the unstressed reference batch using BIACORE analysis. The relative potencies are given in Table 6 and are expressed as % activity compared to reference batch.

After 10 weeks of storage at 37° C. the relative potency of RANKL008a for binding RANKL had dropped to 70-80% in the different buffers (Table 6). In histidine, pH 6+10% mannitol, the activity remained the highest (87.4%). The higher the NaCl concentration in the buffer, the lower the relative potency in the sample (compare the values obtained in buffers with 50 mM NaCl and 100 mM NaCl in Table 6).

The relative potency for HSA binding had dropped more compared to the activity for RANKL binding after 10 weeks storage at 37° C. This decrease in activity however was less significant in the mannitol-containing buffers than in the NaCl-containing buffers. As observed for RANKL binding, the percentage activity on HSA decreased with increasing concentrations of NaCl in the different buffers.

Example 1.4

Osmolality Measurement for the Nanobodies in the Different Buffers

Osmolality measurements were performed on the different formulations used in the stability studies:
RANKL008a in 10 mM Phosphate/10% mannitol: 635 mOsm/kg
RANKL008a in 10 mM Acetate/10% mannitol: 643 mOsm/kg
RANKL008a in 20 mM L-histidine pH 5.5/10% mannitol: 712 mOsm/kg
RANKL008a in 20 mM L-histidine pH 6.0/10% mannitol: 667 mOsm/kg
RANKL008a in 10 mM acetate buffer pH 5.5/100 mM NaCl: 272 mOsm/kg
RANKL008a in 10 mM phosphate/5% mannitol: 389 mOsm/kg
Formulations containing 10% mannitol were hypertonic.

Example 1.5

Stability of the Nanobodies During Mechanical Stress

Mechanical stress experiments were performed on RANKL008a (62.2 mg/mL) in 10 mM phosphate buffer pH 7.0 with 115 mM NaCl. The RANKL008a sample was diluted (in the 10 mM phosphate buffer pH 7.0 with 115 mM) or undiluted with and without 0.01% TWEEN (polysorbate) 80. The samples were shaken, stirred, rotated and pushed through a needle with a syringe (the syringe used can be any commercially available syringe, such as e.g. a 1 mL, 2 mL, 3 mL, 4 mL, 5 mL, 10 mL, 20 mL, 30 mL, 40 mL up to 50 mL syringe) as follows:
Diluted to 5 mg/mL or undiluted and shaken (10 s-1 min);
Pushed through a syringe (3 mL) with needle 25 G (undiluted) (10×);
Rotated (10 rpm) on an end over end mixer for 2 days at room temperature (undiluted)
Stirred 1 hour at room temperature for 2 days at 5° C. (diluted to 5 mg/mL)

The different samples were compared visually for any differences in appearance.

Strong shaking for a short time (10 s) caused strong foaming of the samples in the absence of TWEEN (polysorbate) 80, the diluted sample got very opaque (FIG. 8) while this was less pronounced for the undiluted sample. In the presence of the TWEEN (polysorbate) 80 this opacity was not observed.

The undiluted RANKL008a sample with and without 0.01% TWEEN (polysorbate) 80 was pushed 10 times through a needle (25 G) with a 3 mL syringe. The sample without TWEEN (polysorbate) 80 got opaque, there was also formation of foam and tiny air bubbles were visible when tapping the vial, in the vial with 0.01% TWEEN (polysorbate) 80 opacity was limited.

The undiluted RANKL008a sample with or without 0.01% TWEEN (polysorbate) 80 was rotated for 2 days at 10 rpm. Both samples stayed clear.

The diluted (to 5 mg/mL) RANKL008a sample with or without 0.01% TWEEN (polysorbate) 80 was stirred for 1 hour at room temperature and further for 2 days at 5° C. The visual observations are as follows: stirring during 1 h at room temperature induced an opacity which was not observed in the presence of 0.01% TWEEN (polysorbate) 80. After stirring 1 hour at room temperature, the sample without TWEEN (polysorbate) 80 was slightly opaque while the sample with TWEEN (polysorbate) 80 stayed clear. After 2 days stirring at 5° C., both sample were opaque but the opacity in the sample without TWEEN (polysorbate) 80 was higher.

With the addition of 0.01% TWEEN (polysorbate) 80, the RANKL008a sample was less or not opaque after mechanical stress and there was less foam formation. This indicates that the sample is less susceptible to denaturation at the air-water interface if TWEEN (polysorbate) 80 is added.

Example 1.6

Syringeability of the Different Nanobody Formulations

The effect of using different diluents—i.e. saline solution, phosphate buffer without TWEEN (polysorbate) 80 or phosphate buffer with TWEEN (polysorbate) 80—on content, visual appearance and potency of RANKL008a at low concentration (0.28 mg/mL) was determined after passage through different syringes and needles. RANKL008a was diluted in different diluents followed by passage or 24 h storage in syringes (Becton Dickinson) (FIG. 9). FIG. 9 contains the legends to the different samples generated during this experiment where the following codes are applied:

S25/0: storage at 25° C. for 0 minute
S25/24: storage at 25° C. for 24 h
−TW: buffer minus TWEEN (polysorbate) 80
+TW: buffer+TWEEN (polysorbate) 80
PLACEBO refers to the following buffer: 10 mM $Na_2HPO_4$ pH 7.0+115 mM NaCl
TUB: sample stored in a polystyrene tube Visual inspection and content determination of RANKL008a after dilution in different diluents and passage/storage in syringes is given in Table 7. Data on turbidity measurement at 320 and 350 nm are given in FIG. 10. The relative HSA and RANKL potency of RANKL008a after dilution in different diluents and passage/storage in syringes is shown in FIG. 11.

Passage through a syringe slightly increased turbidity when using 10 mM $Na_2HPO_4$, 115 mM NaCl (pH 7.0). Dilution in saline solution caused a drop in RANKL/HSA binding activity of 18-34.0%. A similar effect was observed using 10 mM $Na_2HPO_4$, 115 mM NaCl (pH 7.0) without TWEEN (polysorbate) 80, i.e. a drop of 15-27%. In contrast, dilution in 10 mM $Na_2HPO_4$, 115 mM NaCl (pH 7.0) with TWEEN (polysorbate) 80 did not appear to have a dramatic effect confirming the beneficial role of TWEEN (polysorbate) 80 in the buffer.

Example 1.7

Stability of Nanobody Formulations During Syringe Passage with Different Needle Size The effect of syringe passage on visual appearance of the RANKL008a using different needle sizes and needle size combinations was evaluated. RANKL008a was diluted in an Eppendorf tube (TUB) in 10 mM $Na_2HPO_4$, 115 mM NaCl, 0.01% TWEEN (polysorbate) 80 (v:v), (pH 7.0) to a final concentration of 0.28 mg/mL followed by single passage through a 1 mL Becton Dickinson syringe equipped with different needles (i.e. Terumo 18 G, 23 G, 27 G and 30 G) (FIG. 12). In this Figure and Table 8 the following codes apply:

+TW: buffer+TWEEN (polysorbate) 80
PLACEBO refers to the following buffer: 10 mM $Na_2HPO_4$ pH 7.0+115 mM NaCl
TUB: sample stored in a polystyrene tube
18 G/18 G: sample drawn up with a 18 G needle and expelled through a 18 G needle
18 G/27 G: drawn up with a 18 G needle and expelled through a 27 G needle
All other coding is similar to the two examples given above.

Turbidity was determined by visual inspection and by measurement of the absorption at wavelengths of 320 nm, 340 nm, 350 nm and/or 500 nm, and determining the ratio of the obtained value over the absorption at A278 nm (mostly 320/278 and 350/278). A ratio of >0.05 was considered significant. Visual inspection, content and turbidity of RANKL008a before (TUB) and after passage through syringes with different needle size is shown in Table 8.

In a further experiment, RANKL008a was subjected to single passage through a 1 mL syringe equipped with different needle sizes (i.e. 27 G and 29 G) both undiluted (65 mg/mL) and diluted in 10 mM $Na_2HPO_4$, 115 mM NaCl, 0.01% TWEEN (polysorbate) 80 (v:v), (pH 7.0) to a final concentration of 0.28 mg/mL (FIG. 13). Visual inspection, content and turbidity of RANKL008a before (TUB) and after passage through syringes with different needle size is shown in Table 9.

In Table 9 and FIG. 13 the following codes are used:
+TW: buffer+TWEEN (polysorbate) 80
PLACEBO refers to the following buffer: 10 mM $Na_2HPO_4$ pH 7.0+115 mM NaCl
TUB: sample stored in a polystyrene tube
27 G/27 G: sample drawn up with a 27 G needle and expelled through a 27 G needle
29 G/29 G: drawn up with a 29 G needle and expelled through a 29 G needle
T: Terumo needle, B Becton Dickinson needle
0028 refers to concentration at 0.28 mg/mL, 6500 to about 65 mg/mL Different combinations of needle sizes did not have a significant effect on RANKL008a recovery or sample turbidity both at low (0.28 mg/mL) and high (62.8 mg/mL) concentration (up to gauge sizes 29 and 27 respectively). In both experiments turbidity values were low (<0.05).

Example 2

Formulation and Stability Studies with Nanobodies that Bind IL-6R

Example 2.1

Materials and Methods Used in the Study 2.1.1 Single Variable Domains

Three Nanobodies that were used in this study have been described in PCT application No. PCT/EP2010/054764 to Ablynx N.V. IL6R304 is a bispecific Nanobody consisting of two humanized variable domains of a heavy-chain llama antibody, one binding to IL-6R, the other one (Alb8) binding to HSA. The trivalent bispecific Nanobodies IL6R305 and IL6R306 consist of two identical subunits that are specific for IL-6R while the third subunit binds to HSA. The build-up of the subunits differs in IL6R305 and IL6R306 (see Table C-27 of PCT/EP2010/054764). The subunits in all three Nanobodies are fused head to-tail with a 9 G/S linker. The sequences and characteristics of the three Nanobodies are given in Table 10.

The Nanobodies were expressed in *Pichia pastoris*. Concentration of the Nanobody and buffer switch to PBS or other formulation buffer was done via UF/DF (Sartorius Hydrosart SARTOCON Slice 200, 10 kDa). A final filtration was carried out at 0.22 µm. An overview of the different IL-6R Nanobody batches is given in Table 11.

Unstressed samples in PBS or other formulations were used as reference material for analyzing the storage stability samples.

2.1.2 Other Reagents

Reagents used in the study are given in Table 12. The complete composition of D-PBS was 137 mM NaCl, 2.7 mM KCl, 10 mM Sodium Phosphate dibasic, 2 mM Potassium Phosphate monobasic.

2.1.3 Equipment and Methods for Measurements

HPLC experiments were carried out on an Agilent 1200 series instrument from Agilent Technologies (Palo Alto, USA) or on a Dionex Ultimate 3000 instrument. The columns used were:
RP-HPLC: ZORBAX 300SB-C3 5-micron, 4.6×150 mm (Agilent, Cat. No. 883995-909) or ZORBAX 300SB-C8 5-micron, 4.6×150 mm (Agilent, Cat. No. 883995-906);
SE-HPLC: Phenomenex BIOSEP SEC S2000 (00H-2145-KD)

Concentration determinations of the Nanobodies were done with NANODROP ND-1000 (Thermoscientific), with a Uvikon 943 Spectrophotometer (Kontron Instruments) or with an Eppendorf Biophotometer 6131 at 280 nm.

Particle size distribution was measured on a PAMAS SVSS-C particle counter (PArtikelMess-und AnalyseSysteme GMBH).

Osmolality measurement was done with an osmometer Model 3320 from Advanced instruments.

For measurement of binding activity BIACORE 3000 (GE Healthcare) was used.

The thermal shift assay (TSA) was performed on a Light-Cycler480 Q-PCR device (Roche).

For determination of the Tm, an automated VP-capillary Differential Scanning calorimeter (DSC, MicroCal) was used.

2.1.4 Purity Assay of the IL-6R Nanobodies by Size Exclusion High Performance Liquid Chromatography (SE-HPLC)

The SE-HPLC assay consisted of a pre-packed Phenomenex BIOSEP SEC S2000 column, a mobile phase consisting of KCl, NaCl and phosphate buffer pH 7.2 (D-PBS) and UV detection at 280 nm. The relative amount of specific protein impurity was expressed as area %, and was calculated by dividing the peak area corresponding to the protein impurity by the total integrated area.

The method can resolve and quantify the relative amounts of intact material and product related impurities such as aggregates and degradation fragments.

2.1.5 Purity Assay of the IL-6R Nanobodies by Reverses Phase High Performance Liquid Chromatography (RP-HPLC)

In the RP-HPLC assay a ZORBAX 300SB-C3 or ZORBAX 300SB-C8 column (Agilent Technologies, Palo Alto, US) at elevated temperatures were used. With the C3 column, mobile phase A consisted of 0.1% TFA and mobile phase B consisted of 0.1% TFA in ACN/isopropanol. With the C8 column, mobile phase A consisted of 0.1% TFA and mobile phase B consisted of 0.1% TFA in 1-propanol. The relative amount of a specific protein impurity was determined by measuring the light absorbance (280 nm) of the components eluting from the RP-HPLC column. The relative amount of a specific protein impurity, expressed as area %, was calculated by dividing the peak area corresponding to the impurity by the total integrated area.

2.1.6 Measurement of Particle Size Distribution (PAMAS)

The measurements on the PAMAS SVSS-C particle counter were performed as follows: 100 µl sample was diluted 1/10 in 1 mL MILLI-Q water and 10 consecutive measurements were performed in all 16 channels (diameter set 1, 2, 3, 4, 5, 6, 7, 8, 9, 10, 15, 25, 50, 100, 150 and 200 µm). For calculation of the average value, the first 2 measurements were excluded and the dilution factor was taken into account. The results are given as cumulative data (total particle counts >x µm) or differential data (total particle counts between diameter x and y µm). Only the cumulative data are presented.

2.1.7 Affinity Measurement on BIACORE

A chip was first immobilized with HSA (amine coupling using the BIACORE amine coupling kit). After a preconditioning step of 5 injections of the Nanobody, all samples were diluted to 2.5 nM in triplicate and analyzed on the chip. Quality control of the chips using the reference sample was included in the experiment to detect any loss of activity or decrease in response (deterioration of the chip). Slopes were determined using the general fit method and the linear fit model (BIAevaluation software). To determine the initial binding rate (IBR), the slope between 5 s and 30 s was selected. The values of these slopes were transferred in excel and the percentage activity compared to the reference was determined.

2.1.8 ELISA Based Potency Assay for HSA Binding

Human Serum Albumin (HSA) was immobilized onto a multiwell MAXISORP ELISA plate by adsorption. After blocking excess binding sites on the plates with Superblock T20 (PBS) blocking buffer, a dilution series of test and reference samples was applied on the plate. Bound Nanobody was subsequently detected using a bivalent anti-Nanobody Nanobody directly conjugated to horseradish peroxidase (HRP). In the presence of $H_2O_2$ HRP catalyzes a chemical reaction with Tetramethylbenzidine (es TMB) which results in the formation of a color. The reaction was stopped by adding 1N HCl. The optical density of the color was measured at 450 nm.

2.1.9 ELIAS Based Potency Assay for IL-6R Binding

For the reference, control and test samples, different dilutions of the Nanobodies were prepared. These dilutions were pre-incubated with a constant amount of 100 ng/mL IL-6, followed by the addition of 4 ng/mL soluble IL-6R. Subsequently, this mixture was transferred to a microtiter plate coated with a non neutralizing anti-IL-6R Nanobody. After washing, residual bound IL-6 was detected with biotinylated anti-human IL-6 monoclonal antibody, followed by HRP-labeled streptavidin detection. In the presence of $H_2O_2$ HRP catalyzes a chemical reaction with Tetramethylbenzidine (es TMB) which results in the formation of a color. The reaction was stopped by adding 1N HCl. The optical density of the color was measured at 450 nm. The relative potency of the test samples compared to the reference sample was analyzed by use of PLA 2.0 Software.

2.1.10 Capillary Isoelectric Focusing (cIEF)

Capillary Isoelectric Focusing (cIEF) is an analysis/separation technique that differentiates proteins with respect to charge, i.e., it separates proteins according to their isoelectric points (pI). The separation principle is similar to gel-based/flatbed IEF but differs mainly in its format, that is, the separation takes place in an open tube of narrow format (capillary) eliminating the need for any anticonvective matrix support. Also, cIEF is a fully automated instrument with online detection and data acquisition. A drawback of traditional cIEF in a conventional CE instrument is that the focused (stationary)

zones must be mobilized past the single-point detection area in order to record the signal. During mobilization the zones may become broadened with contaminant loss of resolution and decreased detectability. Moreover, the analysis time and risk of protein aggregation/precipitation will increase. By imaging cIEF the focusing process is followed in real-time over the whole-column/capillary by a CCD camera excluding the mobilization step. As soon as the focusing process is completed the analysis run is finished.

Example 2.2

Tm Determination

The melting temperature (Tm) in different buffers was determined using the fluorescence-based thermal shift assay (TSA, for IL6R304 and IL6R305) and by differential scanning calorimetry (DSC, for IL6R304).

2.2.1 Thermal Shift Assay

The thermal shift assay or TSA can be performed in 96-well plate in a Q-PCR device to evaluate the effect of buffer couple, ionic strength, pH and excipients on the thermal stability of proteins. The assay results in a Tm value that is indicative for the thermal stability in the tested buffers. Briefly, the assay follows the signal changes of a fluorescence dye, such as SYPRO Orange, while the protein undergoes thermal unfolding. When SYPRO Orange is added to a properly folded protein solution, it is exposed in an aqueous environment and its fluorescence signal is quenched. When the temperature rises, the protein undergoes thermal unfolding and exposes its hydrophobic core region. SYPRO Orange then binds to the hydrophobic regions, unquenches which results in the increase of the fluorescence signal.

In a first experiment, the Tm was assessed for IL6R304 and IL6R305 in different buffers, excipients and combinations thereof using the TSA assay. The obtained Tm values are displayed graphically in FIG. 14 and FIG. 15.

In all conditions tested, the Tm values were slightly higher for IL6R304 than for IL6R305. The buffers and excipients tested had a similar effect on the Tm values of IL6R304 and IL6R305:

Effect of buffer pH: the highest melting points were obtained in Hepes buffer (pH 7 and pH 8) and L-histidine pH 6.5, followed by phosphate buffer (pH 6.7 and 7.7), Tris pH 7.2 and succinate buffer pH 6.2. The lowest melting points were obtained in PBS (58.82° C. for IL6R304) and in the buffers with the lowest pH, i.e. succinate pH 5.2 and L-histidine pH 5.5. The higher melting point in L-histidine pH 6.5 correlates well with the higher solubility of IL6R304 in this buffer (see Example 2.3).

Effect of [NaCl] concentration: the highest melting temperatures were measured when no sodium chloride was added to the buffers. Tm values decreased gradually with increasing NaCl concentration; the effect plateaus at 300 mM NaCl.

Effect of the excipients mannitol, sucrose and glycine: all excipients tested appeared to have a stabilizing effect on IL6R304 and IL6R305, since the melting temperatures increased with increasing excipient concentration. The highest Tm values were obtained in buffers containing 7.5% mannitol or 5% sucrose.

In summary, IL6R304 and IL6R305 seemed to be more stable in buffers that had a neutral pH and which contained a low NaCl concentration and significant amounts of mannitol or sucrose. This is represented schematically in Table 13. L-histidine pH 6.5 appeared to be a good buffer to take forward in further stability testing and formulation work. Another important argument for proceeding with a L-histidine buffer is that the solubility of IL6R304 was shown to increase dramatically in this buffer compared to PBS (see Example 2.3). Buffers containing high NaCl concentration should be avoided, while Hepes buffers at neutral pH could preferably be used.

2.2.2 Differential Scanning Calorimetry

To identify other suitable buffers to be used in purification protocols, i.e. in which the protein displays acceptable stability, differential scanning calorimetry (DSC) was used to determine the melting temperature of IL6R304 in different candidate buffers.

FIG. 16 shows the results of a DSC experiment performed on IL6R304 formulated in different buffers. The highest melting temperatures were observed in MES (pH 6.0) and Hepes (pH 7.0), whereas acetate, Tris-HCl and phosphate indicate a slightly lower thermal stability. The Tm value obtained in citrate (pH 3.5) was on average 10° C. lower than in the other buffers. All heat capacity (Cp) melting peaks were sharp and rather symmetrical in all buffers. The restoration of a baseline after the transition indicated that no precipitation had occurred.

An overview of all Tm values obtained in the DSC experiments is shown in Table 14. From these results we can conclude that adding more NaCl lead to a gradual decrease in melting temperature, as was also observed in the TSA.

2.2.3 TSA Experiment Using Experimental Design

A second TSA experiment was performed on IL6R304 using experimental design (DOE). The DOE consisted of different steps. The outcome of each step was used to define the DOE for the next step. Briefly, the experimental set-ups and obtained results were the following:

Step 1: L-histidine, succinate, phosphate and Tris were tested at different pH (6-7) and buffer strength (10-40 mM). The most promising formulation was found to be low ionic strength L-histidine and Phosphate buffers with a pH of 7 and 6, respectively.

Step 2: the effect of adding NaCl and different excipients to 15 mM L-histidine pH 6.5 and 7 and 15 mM Phosphate pH 6 and 6.5 was tested. One representative of three excipient families was included: mannitol (polyol), sucrose (non-reducing sugar) and arginine (amino acid). It was concluded that Arginine and/or NaCl decrease the Tm of IL6R304. A maximal melting temperature was reached in sucrose or a mix of sucrose/mannitol (10% in total). Furthermore, a higher Tm was obtained in L-histidine than in phosphate. For both buffers, best results were obtained at pH 6.5.

Step 3: other representatives, i.e. sorbitol, xylitol, ribitol, trehalose and glycine, from the three excipient families were tested in 15 mM L-histidine and 15 mM phosphate, both at pH 6.5. Again, the Tm of IL6R304 was higher in L-histidine buffer than in phosphate for all excipients and excipient combinations. The best buffer formulation contained 10% sorbitol or trehalose.

(Table 15)

In a fourth step, the outcome of the statistical analysis of the DOE was confirmed by a repeat of the TSA and by differential scanning calorimetry.

Example 2.3

Solubility of the Nanobodies in Different Buffers 2.3.1 Solubility in PBS and the Effect of Tween 80

During downstream processing and storage of the IL6R304, IL6R305 and IL6R306 Nanobodies in D-PBS buffer, precipitation occurred. Precipitates were already formed during storage overnight at 5° C. or −20° C., even in samples that were filtered (0.22 μm) before storage. This not only resulted in significant product loss, but also made it inconvenient to perform subsequent experiments since filtration steps needed to be incorporated constantly. From these observations it was clear that PBS is not a suitable formulation buffer for any of the IL-6R Nanobodies and that alternative storage buffers needed to be identified. In an initial experiment, it was assessed whether TWEEN (polysorbate) 80 could prevent this precipitation (aggregation) from occurring.

Briefly, IL6R304 (P#051108nr1) was diluted to 2 mg/mL in PBS buffer, PBS buffer+0.1% (v:v) TWEEN (polysorbate) 80 or PBS buffer+0.2% (v:v) TWEEN (polysorbate) 80. The three samples were stored for 4 days at 5° C. and subsequently analyzed for visible particulates (appearance testing by visual inspection; Table 16), sub-visible particle counts (PAMAS; FIG. 17), via UV spectroscopy (A320/A280 ratio, i.e. measure for the presence of particulates; Table 16) and SE-HPLC (FIG. 18). Significantly more and larger particles were present in the IL6R304 sample formulated in PBS compared to the IL6R304 sample formulated in PBS+TWEEN (polysorbate) 80.

2.3.2 Concentration Experiments to Determine the Solubility of IL6R304 and IL6R305

IL6R304 and IL6R305, both formulated in PBS, were concentrated stepwise with a Vivascience concentrator (VIVASPIN 500 5,000 MWCO, 500 μl concentrator). During the concentration experiment, the retentate was mixed gently regularly and was analyzed visually for particulates/precipitation. The presence of insoluble aggregates in the retentate was verified by checking the protein concentration before and after centrifugation at maximum speed. Based on the results from the thermal shift assay (see Example 2.2.1), the solubility of IL6R304 was also analyzed in 20 mM Histidine, pH 6.5.

In conclusion, the solubility of IL6R304 and IL6R305 in PBS was limited, with estimated values of 20 mg/mL and 15 mg/mL, respectively (concentration at which protein precipitation occurred). No precipitation of IL6R304 was observed at a concentration between 20-90 mg/mL in L-histidine buffer suggesting that the solubility can be increased significantly by changing the formulation buffer. Note that no significant protein loss has been observed.

2.3.3 Determination of the Theoretical Solubility

The theoretical solubility of IL6R304 and IL6R305 was determined using the PEG exclusion method in PBS buffer (IL6R304, IL6R305) or in 20 mM L-histidine, pH 6.5 (IL6R304). Briefly, a concentrated Nanobody solution (30-80 mg/mL) in the respective buffer was incubated for 15 minutes at room temperature in the presence of increasing concentrations of PEG6000. After centrifugation at 20000×g for 3 minutes, log values of the [soluble protein concentration] were plotted versus PEG6000 concentration (FIG. 19). By regression analysis and extrapolation to a zero concentration of PEG6000, the theoretical maximum protein concentration (and thus solubility values) could be obtained for the Nanobodies in the buffers tested. The obtained solubility values correlated well with the values obtained experimentally using the stepwise concentration experiments with the VIVASPIN centrifugal concentrators. When comparing the solubility of IL6R304 in PBS and L-histidine pH 6.5, it could be concluded that the solubility of IL6R304 increased significantly in the L-histidine buffer.

Example 2.4

Storage Stability Study of the Nanobodies at 37° C.

An initial storage stability study was performed to get a general understanding of the stability of the IL-6R Nanobodies and to determine if adding mannitol in the formulation buffer has a beneficial effect in minimizing the formation of potential dimers, as was observed for RANKL008a (see Example 1.3).

The three IL-6R Nanobodies were formulated in different buffers (Table 17) at a concentration of 10 mg/mL (IL6R304), 7.1 mg/mL (IL6R305) and 10.3 mg/mL (IL6R306). The stability of the different samples was assessed in accelerated stress conditions at 37° C. Samples were analyzed after 1 week using SE-HPLC and RP-HPLC. Selected samples of IL6R304 and IL6R305 were also analyzed after 3 weeks of storage.

2.4.1 SE-HPLC Analysis

For all three IL-6R Nanobodies, prolonged storage at 37° C. resulted in the formation of prepeaks and some minor postpeaks. The postpeaks probably corresponded to degradation products (due to remaining proteolytic activity in sample). The surface area of these postpeaks remained very low, suggesting only minimal degradation after 3 weeks at 37° C.

All three IL-6R Nanobodies had a strong tendency to form dimers/oligomers (aggregates), which were visible as prepeak(s) in the chromatograms of the SE-HPLC analysis. An example chromatogram is shown in FIG. 20. The peak area of the prepeak increased significantly over time (represented as % aggregates in FIG. 21 and FIG. 22) and was accompanied by a concomitant decrease in surface area of the main peak. The propensity to form dimmers/oligomers appeared to be somewhat higher for IL6R305 than for IL6R304. Also, more dimmers/oligomers were being formed in PBS compared to the other buffers that were tested. Importantly, the lowest amounts of oligomers were observed in the mannitol-containing formulations.

2.4.2 RP-HPLC Analysis

The RP-HPLC profile of IL6R304 at time point 0 weeks included a main peak with a shoulder eluting before the main material and a postpeak that was not well resolved from the main peak. This postpeak most likely corresponded to the pyroglutamate-containing variant of IL6R304. The surface area of this peak increased with storage time and was highest in PBS and phosphate buffer compared to the acetate and histidine buffers. After 3 weeks of storage, the surface areas of two thus far unidentified prepeaks increased (FIG. 23).

The RP-HPLC profile of IL6R305 at time point 0 weeks included a main peak with some minor prepeaks. The resolving power of the RP-HPLC method used was insufficient to separate the pyroglutamate-containing variant from the main material.

Example 2.5

Osmolality Measurement

According to the European Pharmacopoeia, a solution is considered isotonic if it has an osmolality of 290±30 mOsm/kg. Osmolality measurements on 20 mM L-histidine pH 6.5 containing different concentrations of excipients were therefore performed to define the range of excipient concentration that would be acceptable for an isotonic liquid formulation of IL6R304.

IL6R304 (10 mg/mL) was formulated in the different buffers of Table 18. The results from osmolality measurement of these formulations are shown in FIG. 24.

Example 2.6

Storage Stability Study of IL6R304 at 5° C. And 37° C.

An overview of the different formulation buffers and methods used in stability testing of IL6R304 batch P#051108nr1 is given in Table 18 and Table 19, respectively. Because IL6R304 was found to be prone to aggregation and precipitation, TWEEN (polysorbate) 80 was added to most formulations.

2.6.1 Appearance and OD280

No turbidity was observed in the samples stored for 5 weeks at 5° C., indicating that 20 mM L-histidine pH 6.5 is a much better storage buffer for IL6R304 than PBS.

After storage for 1 week at 37° C., a slight turbidity was observed in all 12 samples. In the IL6R304 samples in buffers 1, 2, 3, 7, 8 and 9 more opalescence was observed compared to IL6R304 in the buffers 4, 5, 6, 10, 11 and 12, which all contained mannitol. After storage for 2 weeks at 37° C., slightly more turbidity was observed compared to the 1 week samples. However, the trend observed for the 1 week samples continued: the IL6R304 samples in buffers 1, 2, 3, 7, 8 and 9 showed more opalescence compared to the mannitol-containing buffers. After storage for 5 weeks at 37° C., turbidity was still present and slightly less in the samples containing mannitol. However, it seemed like the turbidity had not increased compared to the 2 weeks samples.

Despite the opacity observed in the stressed samples, the protein concentration in the samples has not decreased significantly (data not shown) although there was a slight trend to a lower concentration due to a higher turbidity. Also, the OD320/OD280 ratio, which is a measure for turbidity or the presence of particulates, was <0.05 in all buffer conditions. In fact, the ratio was 2-10 fold lower than observed in the unstressed sample in PBS, again showing that the L-histidine pH 6.5 buffer has a stabilizing effect on IL6R304.

2.6.2 SE-HPLC Analysis

Samples of the reference material (0 weeks) and samples stored for up to 6 months at 5° C. and 37° C. were analyzed using SE-HPLC.

No differences were observed between the SE-HPLC profiles of the reference samples (at 0 weeks) and the samples stored for up to 5 weeks at 5° C. In addition, there were no significant differences between the different buffers. The small amounts of aggregates already present in the start material were not increasing with prolonged storage time (FIG. 25(B)), indicating that the Histidine buffer had a stabilizing effect on ILR304, even in the absence of excipients such as TWEEN (polysorbate) 80, mannitol or sucrose. Note that IL6R304 formed aggregates when stored for a short time (hours-days) at 5° C. in D-PBS buffer.

SE-HPLC analysis of the samples stored for 6 months at 5° C. also did not show increase in area % of the prepeaks, meaning that no oligomers were formed under these storage conditions, not even in the formulation containing only 20 mM L-histidine, pH 6.5 i.e. without TWEEN (polysorbate) −80 or any excipient (data not shown).

Prolonged storage at 37° C. resulted in the formation of prepeaks and some minor postpeaks. The postpeaks probably corresponded to degradation products (due to remaining proteolytic activity in sample). The relative area (%) of these peaks increased only slightly, implying that degradation was restricted to a minimum. The other peaks visible in the chromatograms were background peaks arising from the buffer components.

The peak area of the prepeaks increased significantly over time (FIG. 25 (A) and FIG. 26 (B)). Given the relative position of the prepeaks to the main peak, the prepeaks most likely represented dimeric or oligomeric forms (aggregates) of IL6R304. The peak surface area of the prepeak increased with storage time and was accompanied by a concomitant decrease in surface area of the main peak.

An important observation was that the propensity to form dimers/oligomers was buffer-dependent: the propensity to oligomerize was significantly lower in the mannitol- and sucrose-containing formulations. Glycine appeared not to have such a positive effect in preventing the oligomerization process. TWEEN (polysorbate) 80 had no inhibitory effect on the formation of oligomers.

Importantly, the % oligomers observed in all 12 L-histidine buffers after storage for 3 weeks at 37° C. was significantly lower than the equivalent sample in D-PBS buffer, i.e. 2.2-4.6% in L-histidine, pH 6.5 compared to 11.7% PBS (FIG. 26(A)). This buffer-dependent effect on the physical stability of IL6R304 correlated very well with the buffer-dependent differences observed in thermal stability testing of IL6R304 (Example 2.2): the melting temperature of IL6R304 was found to be only 58.8° C. in PBS but is 62.8° C. in 20 mM L-histidine, pH 6.5. Increasing the intrinsic stability of IL6R304 by changing the formulation buffer from PBS to L-histidine proved to have a clear beneficial effect on its stability upon storage.

In the samples stored for 6 months at 37° C., the lowest % of oligomers was found in the formulation containing 10% sucrose, again corroborating the stabilizing effect of sucrose on IL6R304 (Table 20).

2.6.3 RP-HPLC Analysis

Samples of the reference material (0 weeks) and samples stored for up to 5 weeks at 5° C. and 37° C. were analyzed using RP-HPLC.

The RP-HPLC profiles at time point 0 weeks included a main peak, two pre-peaks and a badly resolved postpeak. This post-peak most probably corresponded to the pyroglutamate-containing variant of IL6R304.

The RP-HPLC profiles of the reference batch and the stability samples stored for up to 5 weeks at 5° C. were found to be comparable.

In the stability samples stored at 37° C., the peak surface area of the pyroglutamate peak increased with storage time while the surface area of the main peak decreased. The total area remained unchanged.

After 5 weeks of storage at 37° C., the surface area of the two prepeaks had increased in all buffer conditions. The identity of these variants is unknown at the moment, but could correspond to degradation fragments.

There were no significant buffer-dependent differences in the RP-HPLC profiles of the different samples suggesting that chemical modifications, such as pyroglutamate formation and oxidation which are typically detected by RP-HPLC, were limited and at present unaffected by the buffer.

Example 2.7

Storage Stability Study of IL6R304 at −70° C., −20° C., 5° C., 25° C. and 37° C.

IL6R304 was formulated at 10 mg/mL in the 10 different buffers shown in Table 21, stored at −70° C., −20° C., +5° C. and +37° C. for 8 weeks and for 1 week+25° C. Stability samples were analyzed using SE-HPLC, RP-HPLC, OD280 and visual inspection. Selected samples were also analyzed using BIACORE (HSA binding) and potency assays (HSA and IL-6R).

2.7.1. Storage for 8 Weeks at −70° C., −20° C., 5° C. and 1 Week at 25° C.

IL6R304 was shown to be stable after storage for 8 weeks at −70° C., −20° C., 5° C. and for 1 week at 25° C. in all 10 buffers tested. No significant differences were observed in potency, turbidity, SE-HPLC and RP-HPLC profiles between the reference material and the 10 different storage samples.

2.7.2. Storage for 8 Weeks at 37° C.

Appearance and OD280

Compared to the samples stored at −70° C., −20° C. and 5° C., turbidity was observed in the samples stored at 37° C. The absorbance values at 350 nm had increased accordingly to >0.01 AU in most buffers, although the A350/A280 ratio was still <0.05 in all buffer conditions. Despite the opacity observed in the stressed samples, the protein concentration in the samples had not decreased significantly.

SE-HPLC

Prolonged storage at 37° C. resulted in the time-dependent formation of a postpeak and prepeak. The postpeak has a retention time between 22 and 23 minutes and most likely corresponded to IL6R304 degradation fragments. The surface area of this peak however remained low (approximately 2%), suggesting only minimal degradation after 8 weeks at 37° C. The other postpeaks visible in the chromatograms were background peaks arising from the buffer components.

The SE-HPLC profile of IL6R304 at time point 0 weeks included a main peak and two minor prepeaks, which were not completely baseline-resolved. The surface area of the prepeaks increased over time and was accompanied by a concomitant decrease in surface area of the main peak. Given the relative position and heterogeneity of the prepeaks, they most likely represented dimeric and/or oligomeric forms of IL6R304. Because of this heterogeneity and the decreasing resolution between the prepeaks over time, the peaks were for simplicity integrated as a single peak.

An important observation was that the propensity to form dimers/oligomers was buffer-dependent: about 2-fold less oligomers were being formed in L-histidine buffer compared to phosphate buffer (FIG. 27, FIG. 28). The lowest amount of oligomers was observed in the trehalose-containing formulation, followed by the sucrose-containing formulation. Overall, after storage of IL6R304 at 37° C. for several weeks, the amount of oligomers present in these buffers was significantly less than observed previously in D-PBS or in L-histidine pH 6.5 devoid of any excipient.

The presence of a non-reducing sugar suppressed the extent of IL6R304 oligomerization considerably.

RP-HPLC

The RP-HPLC chromatograms from the ILR304 stability samples stored for up to 8 weeks at 37° C. are shown in FIG. 29.

The RP-HPLC profile of ILR304 at time point 0 weeks included a main peak, with 2 badly resolved shoulders eluting before the main material, a first postpeak corresponding to the pyroglutamate-containing variant of ILR304 and a second postpeak, corresponding to the ILR304 variant missing one disulphide bridge. The identity of both variants has been confirmed by LC-MS.

After storage during 1 week, the surface area of the second postpeak had decreased to a relative area % of 0, most likely due to spontaneous oxidation into the correctly folded molecule.

The surface area of the pyroglutamate peak increased with storage time while the surface area of the main peak decreased. The total surface area was not changing significantly over time or among the different buffers. FIG. 30 clearly demonstrates that the kinetics of pyroglutamate formation was different in L-histidine, pH 6.5 versus phosphate, pH 6.5. At all time points, less pyroglutamate was present in the L-histidine buffer. On the other hand, there was no correlation between the type of excipient present in the buffer and the amount of pyroglutamate being observed.

After storage for 8 weeks, two new postpeaks were being formed. The first postpeak was situated between the main peak and the pyroglutamate peak, while the second postpeak eluted just after the pyroglutamate peak. The identity of these variants is currently not known.

Capillary Isoelectric Focusing (cIEF)

cIEF integration data of IL6R304 stored for 8 weeks at 37° C. in the different buffers are shown in Table 22. The samples formulated in 15 mM L-histidine, pH 6.5 contain less charge variants compared to the phosphate buffer.

Potency Assay and BIACORE

The potency of the samples stored for 8 weeks at 37° C. in buffers 1-5 was determined relative to an unstressed reference batch using the HSA-binding ELISA and the inhibition ELISA for IL-6R as described in Examples 2.1.8 and 2.1.9 (Table 23). The HSA binding functionality of the samples stored in buffers 1-10 was also analyzed using BIACORE (Table 24). Samples formulated in the same buffers and stored at −70° C. were included as the reference molecules.

Whereas the potency assays showed comparable HSA and IL-6R binding potencies between the stability samples and the reference material, BIACORE analysis demonstrated some differences in HSA binding activities.

Overall, the activities of the samples formulated in phosphate buffer (buffers 6-10) were lower than in L-histidine (buffers 1-5). A functionality loss of approximately 16% was observed in the buffers containing a combination of sucrose and glycine (buffer 4 and 9). The combination of sucrose and mannitol (buffer 5 and 10) showed no loss of functionality of IL6R304 in the L-histidine buffer, while a decrease of 10% was observed in the phosphate buffer. Formulations containing either mannitol, sucrose or trehalose showed an activity between 90 and 100% after storage for 8 weeks at 37° C.

General Conclusion about the Storage Stability Study at 37° C.

Storage for up to 8 weeks of IL6R304 in different formulation buffers under temperature stress conditions (37° C.) resulted in the following observations:

The propensity of IL6R304 to form oligomers was dependent on the buffer and excipient: about 2-fold less oligomers were being formed in L-histidine buffer compared to phosphate buffer, while the presence of a non-reducing sugar suppressed the extent of IL6R304 oligomerization even further;

The chemical stability of IL6R304 was better in L-histidine buffer compared to phosphate buffer;

The HSA binding activity was maintained longer in L-histidine buffer compared to phosphate buffer.

Example 2.8

Stability Under Stir Stress

IL6R304 was formulated at 1 mg/mL in the 10 different buffers shown in Table 21. Aliquots of 5 mL were stirred at maximum speed for up to 24 hours at 2-8° C. Samples were analyzed after 2, 4 and 24 hours of stirring.

All solutions remained clear after 2 hours of stirring (Table 25). An increase in turbidity was observed in six out of ten buffers after 4 hours. The highest opalescence was present in buffer 10. Overall, the increase in turbidity was more pronounced in the phosphate buffers (buffer 6-10). These observations were confirmed after determination of the aggregation index, defined as $100*OD350/(OD280-OD350)$ (FIG. 31). No soluble aggregates were observed during SE-HPLC of the different samples.

In conclusion, the stir stress data suggest a somewhat better stir stress stability of IL6R304 in L-histidine, pH 6.5 compared to phosphate buffer, pH 6.5. No significant differences were observed between the various excipients, although a slightly higher turbidity was observed in the presence of 10% trehalose and 2.5% mannitol/5% sucrose.

Example 2.9

Long-Term Stability Study at −70° C., +5° C. and +25° C.

IL6R304 batch CMC-D-0048, formulated in 15 mM L-Histidine, 8% sucrose, 0.01% TWEEN (polysorbate) 80 (pH6.5) at 10.52 mg/mL, was stored for 6 months at −70° C., +5° C. and +25° C. Samples were analysed after 3 and 6 months of storage by visual inspection (appearance), A280 (content), SEC-HPLC, cIEF, RP-HPLC and potency assays (IL6R inhibition assay and HSA binding assay). The results are summarized in Table 42, Table 43 and Table 44 for storage at −70° C., +5° C., and +25° C., respectively.

There were no significant changes in appearance, content, potency, cIEF and HPLC profiles between the control sample (timepoint 0 months) and all test samples stored at −70° C. or 5° C. indicating that IL6R304 is stable for at least 6 months under these conditions.
Regarding the sample stored at +25° C., the following observations were made when comparing the results of the stressed samples and the control sample:
  SE-HPLC: there is a small, yet gradual increase in the surface area of the pre peak (oligomers) and post peak (degradation fragments).
  cIEF: a post peak is being formed which is believed to correspond to the pyroglutamate variant.
  RP-HPLC: three new peaks are being formed, i.e. a pre peak, most likely corresponding to degradation fragments that are present in the samples (see also SEC-HPLC data) and two yet unidentified post peaks. The surface area of pre peak 2 and post peak 2 (pyroglutamate) are gradually increasing with prolonged incubation time.
No potency loss is observed in the samples stored for up to 6 months at +25° C.

Example 3

Formulation and Stability Studies with Nanobodies that Bind I123

Example 3.1

Materials and Methods Used in the Study 3.1.1 Single Variable Domains
23IL0064 (SEQ ID NO: 5; EVQLLESGGGLVQPGGSL-RLSCAASGRIFSLPASGNIFNLLTIAWYRQAPGKG RELVATINSGSRTYYADSVKGRFTIS-RDNSKKTLYLQMNSLRPEDTAVYYC-QTSGSGSPNFWGQGTLVTVSSGGGGS GGGSEVQLVESGGGLVQPGNSL-RLSCAASGFTFSSFGMSWVRQAPGK-GLEWVSSISGSGSDTLYADSVKGRFTISR DNAKT-TLYLQMNSLRPEDTAVYYCTIGGSLSRSSQGTLVTVS-SGGGGSGGGSEVQLLESGGGLVQPGGSLRLSCAAS GRTLSSYAMGWFRQAPGKGREFVSRIS-QGGTAIYYADSVKGRFTISRDNSKNT-LYLQMNSLRPEDTAVYYCAKDPS PYYRGSAYLLSG-SYDSWGQGTLVTVSS) has been described as SEQ ID NO: 2616 in WO 2009/068627. 23IL0064 consists of three humanized variable domains of a heavy-chain llama antibody: 119A3v16 and 81A12v4, binding different epitopes of IL23 p19, and the ALB8 binding HSA. 23IL0075 (SEQ ID NO: 6; EVQLLESGGGLVQPGGSLRLSCAAS-GRIFSLPASGNIFNLLTIAW-YRQAPGKGRELVATINSGSRTYYADSVK GRFTIS-RDNSKKTLYLQMNSLRPEDTAVYYCQTSGSGSPNFW-GQGTLVTVSSGGGGSGGGSEVQLVESGGGLVQP GNSLRLSCAASGFTFSSFGM-SWVRQAPGKGLEWVSSISGSGSDTLY-ADSVKGRFTISRDNAKTTLYLQMNSLRPED TAVYYC-TIGGSLSRSSQGTLVTVSSGGGGSGGGSEVQLLESGG-GLVQPGGSLRLSCAASGRTLSSYAMGWFRQAPG KGREFVARISQGGTAIYYADSVKGRFT-ISRDNSKNTLYLQMNSLRPEDTAVYY-CAKDPSPYYRGSAYLLSGSYDSWG QGTLVTVSS) has been described as SEQ ID NO: 2622 in WO 2009/068627. 23IL0075 consists of three humanized variable domains of a heavy-chain llama antibody: 119A3v16 and 81A12v5, binding different epitopes of IL23 p19, and the ALB8 binding HSA. The subunits in both Nanobodies are fused head-to-tail with a 9G/S linker.

23IL0064 (3.79 mg/mL in D-PBS) and 23IL0075 (4.21 mg/mL in D-PBS) were expressed in *Pichia pastoris*. After clarifying the fermentation broth via a centrifugation step, followed by a TFF step, the Nanobodies were captured on MABCAPTURE A (Poros), followed by an elution at pH 2.6 using 100 mM glycine. A buffer switch to 1/10 D-PBS was performed, and the Nanobodies were further polished on Poros 50HS (Poros). Finally, a treatment with 50 mM OGP for LPS-removal was performed, followed by a final size exclusion step using SUPERDEX 75 pg (GE Healthcare).

Unstressed samples in D-PBS or other formulations were used as reference material for analyzing the storage stability samples.

3.1.2 Other Critical Reagents
Reagents used in the study are given in Table 26. The complete composition of D-PBS was 137 mM NaCl, 2.7 mM KCl, 10 mM Sodium Phosphate dibasic, 2 mM Potassium Phosphate monobasic.

3.1.3 Equipment and Methods for Measurements
HPLC experiments were carried out on an Agilent 1200 series instrument from Agilent Technologies (Palo Alto, USA). The columns used were:
  RP-HPLC: ZORBAX 300SB-C3 5-micron, 4.6×150 mm (Agilent, Cat. No. 883995-909) and ZORBAX 300SB-C8 5-micron, 4.6×150 mm (Agilent, Cat. No. 883995-906)
  SE-HPLC: TSK-GEL G2000SW$_{XL}$ (Tosoh Bioscience, Japan; Part#08540)
  IEX-HPLC: PROPAC WCX-10, 4×250 mm, 10 μm (Dionex)

Concentration determinations of the Nanobodies was done with NANODROP ND-1000 (Thermoscientific), with a Uvikon 943 Spectrophotometer (Kontron Instruments) or an Eppendorf Biophotometer 6131 at 280 nm.

Particle size distribution was measured on a PAMAS SVSS-C particle counter (PArtikelMess-und AnalyseSysteme GMBH).

Osmolality measurement was done with an osmometer Model 3320 from Advanced instruments.

The thermal shift assay was performed on a LightCycler480 Q-PCR device (Roche).

For determination of the Tm, an automated VP-capillary Differential Scanning calorimeter (DSC, MicroCal) was used.

Elastic light scattering was measured in a Jasco Spectrofluorometer (FP-6500).

3.1.4 Purity Assay of the Nanobodies by Size Exclusion High Performance Liquid Chromatography (SE-HPLC)

The SE-HPLC assay consisted of a pre-packed silica gel TSK-GEL G2000SW$_{XL}$ column equipped with a guard column pre-column filter, a mobile phase consisting of KCl, NaCl and phosphate buffer pH 7.2 (D-PBS) and UV detection at 280 nm. The relative amount of specific protein impurity was expressed as area %, and was calculated by dividing the peak area corresponding to the specific protein impurity by the total integrated area.

3.1.5 Purity Assay of the Nanobodies by Reverses Phase High Performance Liquid Chromatography (RP-HPLC)

In the RP-HPLC assay a ZORBAX 300SB-C3 column or ZORBAX 300SB-C8 column (Agilent Technologies, Palo Alto, US) was used. The relative amount of a specific protein impurity was determined by measuring the light absorbance of the components eluting from the RP-HPLC column. The relative amount of a specific protein impurity, expressed as area %, was calculated by dividing the peak area corresponding to the impurity by the total integrated area.

3.1.6 Purity Assay of the Nanobodies by Ion Exchange High Performance Liquid Chromatography (IEX-HPLC)

The IEX-HPLC assay combined the use of a pre-packed Dionex PROPAC WCX-10 weak cation exchange column, a mobile phase consisting of citrate buffer pH5.5 and UV detection at 280 nm. After loading the protein(s) on the column, bound materials were eluted by a sodium chloride gradient. The relative amount of the specific protein, variant, or impurities expressed as area %, was calculated by dividing the peak area corresponding to the specific protein or to any protein impurity by the total area of all integrated peaks.

3.1.7 Measurement of Particle Size Distribution (PAMAS)

The measurements on the PAMAS SVSS-C particle counter were performed as follows: 100 µl sample was diluted 1/10 in 1 mL MILLI-Q water and 10 consecutive measurements were performed in all 16 channels (diameter set 1, 2, 3, 4, 5, 6, 7, 8, 9, 10, 15, 25, 50, 100, 150 and 200 µm). For calculation of the average value, the first 2 measurements were excluded and the dilution factor was taken into account. The results are given as cumulative data (total particle counts >x µm) or differential data (total particle counts between diameter x and y µm). Only the cumulative data are presented.

3.1.8 Capillary Isoelectric Focusing (cIEF)

Capillary Isoelectric Focusing (cIEF) is an analysis/separation technique that differentiates proteins with respect to charge, i.e., it separates proteins according to their isoelectric points (pI). The separation principle is similar to gel-based/flatbed IEF but differs mainly in its format, that is, the separation takes place in an open tube of narrow format (capillary) eliminating the need for any anticonvective matrix support. Also, cIEF is a fully automated instrument with online detection and data acquisition. A drawback of traditional cIEF in a conventional CE instrument is that the focused (stationary) zones must be mobilized past the single-point detection area in order to record the signal. During mobilization the zones may become broadened with contaminant loss of resolution and decreased detectability. Moreover, the analysis time and risk of protein aggregation/precipitation will increase. By imaging cIEF the focusing process is followed in real-time over the whole-column/capillary by a CCD camera excluding the mobilization step. As soon as the focusing process is completed the analysis run is finished.

Example 3.2

Melting Temperature of the Nanobodies

The measurement of the melting temperature of a protein in different buffers is a faster way to screen for buffers in which the protein has the highest physical stability. It is generally accepted that this will be predictive for the long term stability at lower temperatures. The melting temperature can be determined using many different techniques.

3.2.1 Melting Temperature of 23IL0064 in Different Formulation Buffers Measured by Thermal Shift Assay We used the thermal shift assay (TSA), which measures the change in fluorescence intensity when the SYPRO orange binds the hydrophobic parts of the protein that is undergoing thermal unfolding. The thermal shift assay was performed on the LightCycler480 Q-PCR device (Roche) making use of 96-well plates.

In a first study, the effect of buffer couple, ionic strength and pH on the thermodynamic stability of 23IL0064 was evaluated in a thermal shift analysis experiment. The tested buffers used are presented in Table 28. Each buffer was tested at a pH interval spanning 1 pH unit around their pKa. An overview of the results is presented in FIG. 32. The melting temperatures decreased with increasing salt concentration. Further pH 5.2 and pH 5.5 seemed less favorable compared to pH 6.2 and above. The best buffers were Hepes (pH 7 and 8) and Histidine pH 6.5. In all buffers, the addition of mannitol slightly increased the melting temperatures.

3.2.2 Melting Temperature of 23IL0064 and 23IL0075 in Different Formulation Buffers Measured by Thermal Shift Assay and Differential Scanning Calorimetry (DSC)

23IL0064 and 23IL0075 were analyzed in parallel in different formulation and purification buffers by the thermal shift assay (TSA) (Tables 34) and DSC (Table 33). For both molecules and in all tested buffers (acetate, MES, Hepes, TRIS, and Histidine), the melting temperatures decreased with increasing NaCl concentration, and the melting temperatures were highest in the presence of mannitol.

3.2.3 Melting Temperature of 23IL0075 in a Wide Range of Formulation Buffers Measured by Thermal Shift Assay The melting temperature for 23IL0075 in another range of buffers and a lower pH range was screened by TSA. For this, a design of experiments was set up to investigate the Tm of 23IL0075 varying the following parameters: pH range between 5 and 6, buffer concentration between 10 and 50 mM, and 4 different buffers: histidine, acetate, phosphate and succinate. A full factorial design+central composite design was performed, in total 22 different buffers were tested in 84 experiments. The experiments were divided over two 96-well plates, on the second plate the pH range was expanded to 4.8 and 6.2, and the buffer concentration to 7 and 65 mM. The phosphate buffer was only tested at pH 6 and 6.2. From the experimental results, for each buffer a model was built that was used to predict Tm's as a function of the buffer concentration and the pH. The results are shown in Table 35.

Succinate clearly had overall the lowest predicted Tm values. For acetate and histidine at low concentrations and high pH the largest predicted Tm values were obtained. In fact the model showed for all buffers highest predicted Tm values for lowest buffer concentrations. According to the Design-Expert Numerical Optimization of the model the best buffer was histidine buffer pH 6.2 (desirability 1), followed closely by acetate pH 6 (desirability 0.96) and phosphate pH 6 (desirability 0.90).

3.2.4 Confirmation of Tm by Differential Scanning Calorimetry

We confirmed the Tm determination by differential scanning calorimetry in the buffers selected in Example 3.2.3. The results are shown in the graph in FIG. 33. The trends were identical to what was observed in the TSA though the absolute values of the Tm were higher: around 62° C. in DSC compared to around 59° C. in the TSA.

3.2.5 Melting Temperature of 23IL0075 in a Range of Formulation Buffers to Explore a Wide Range of Excipients Measured by Thermal Shift Assay A second design of experiments (DOE) was prepared to study the influence of some combinations of excipients on the thermodynamic stability of 23IL0075. The combination of a sugar or a polyol (mannitol, sucrose or sorbitol), with an amino acid (Glycine or arginine/glutamic acid mixture), and a non-ionic detergent (TWEEN (polysorbate) 80, TWEEN (polysorbate) 20 or P-F68) were studied. These combinations were tested in three buffers (10 mM Acetate pH 5.5, 10 mM Histidine pH 6.0 and 10 mM Phosphate pH 6.0) (see Table 35). Based on the measured melting temperatures, the optimal buffer compositions were calculated (see Table 36). Highest melting temperatures were predicted for the histidine buffer, the lowest melting temperatures for the phosphate buffer. For all three buffers sucrose came out as the best excipient, the mixture of arginine and glutamic acid as the worst. Mannitol and sorbitol, alone or in combination with glycine were also good as excipient, though always gave a little bit lower Tm than sucrose. Glycine alone was not so efficient.

Example 3.3

Solubility of the Nanobodies 3.3.1 Concentration Experiments to Determine the Solubility of 23IL0064

The IL23 Nanobody 23IL0064, respectively in D-PBS buffer, in NaPhosphate 10 mM pH 7 with 50 mM NaCl, and in L-histidine 40 mM pH 6 with 50 mM NaCl, was concentrated stepwise with a VIVASPIN concentrator (Vivascience 5,000 MWCO 0.5-mL and 5-mL concentrators). During the concentration experiment, the retentate was regularly gently mixed and the concentration determined by OD280 measurements. The presence of insoluble aggregates in the retentate was verified by checking the protein concentration before and after centrifugation at maximum speed in a benchtop Eppendorf centrifuge. In all three buffers a concentration of 50 mg/mL could be reached without visual precipitation. Then the protein solution was transferred from the 5 mL to the 0.5 mL VIVASPIN® concentrator and concentrated at a much higher centrifugal force (15000×g instead of 1500×g). This caused rapid further concentration, and local concentrations close to the membrane were even much higher than the average concentration measured after recovery of the retentate. In Table 27, the final concentrations achieved are summarized, obtained after pipetting up and down the retentate, and centrifugation to remove precipitate.

All samples were also analyzed by SE-HPLC. Concentrating in D-PBS buffer resulted in an increase in % pre-peak. In the 10 mM phosphate buffer and in the 40 mM Histidine buffer, both with 50 mM NaCl, the SE-HPLC profile remained exactly the same at 83 and 150 mg/mL compared to the starting material (FIG. 34). A generic SE-HPLC method was used on a Phenomenex BIOSEP SEC S-2000 column, with D-PBS as mobile phase at 0.2 mL/min.

A sample of the concentrated 23IL0064 protein solutions was diluted to 55 mg/mL using the respective buffers for further use in the PEG precipitation method.

3.3.2 Determination of the Theoretical Solubility of 23IL0064

The theoretical solubility of 23IL0064 was determined using the PEG exclusion method in D-PBS buffer, in NaPhosphate 10 mM pH 7, NaCl 50 mM, and in L-histidine 40 mM pH 6, NaCl 50 mM. Briefly, a concentrated Nanobody solution (55 mg/mL) in the respective buffer was incubated for 15 minutes at room temperature in the presence of increasing concentrations of PEG6000. After centrifugation at 20000×g for 3 minutes, log values of the [soluble protein concentration] were plotted versus PEG6000 concentration (FIG. 35). By regression analysis and extrapolation to a zero concentration of PEG6000, the theoretical maximum protein concentration (and thus solubility values) could be obtained for the Nanobody in the buffers tested.

When extrapolating from the regression plots to a zero concentration of PEG6000, a theoretical solubility value of 60 mg/mL and of 288 mg/mL was calculated for 23IL0064 in D-PBS and in 10 mM phosphate buffer/50 mM NaCl respectively. 23IL0064 showed extremely good solubility in the histidine buffer: in the experiment starting from 55 mg/mL only at a PEG concentration of 27% the protein started to precipitate slightly. Therefore the experiment was repeated with the protein dissolved at 150 mg/mL. There only at 10% PEG precipitation occurred, but then no volume was left for OD measurements. So the solubility was actually too high to obtain a value in this assay.

In conclusion highest solubility was obtained in 40 mM Histidine pH 6 with 50 mM NaCl. In phosphate buffer with 50 mM NaCl, the solubility was better than in D-PBS (with 137 mM NaCl).

3.3.3 Determination of the Theoretical Solubility of 23IL0064 and 23IL0075

The theoretical solubility was determined for 23IL0064 and 23IL0075 using the PEG exclusion method in NaPhosphate 10 mM pH7, NaCl 50 mM, and in L-histidine 40 mM pH 6, NaCl 50 mM (the same buffers as used in the previous solubility study for 23IL0064 described above). The graphs (FIG. 36 and FIG. 37) representing the protein concentration in the supernatant as a function of the % PEG concentration were very similar as obtained in the previous experiment. Again the apparent solubility in histidine was higher than in the phosphate buffer, and could not be calculated due to minimal precipitation under the protein (5 mg/mL) and PEG concentrations (26.7%) used. The calculated solubility in phosphate buffer pH 7 for 23IL0064 and 23IL0075 were lower than in the previous experiment, i.e. 55 and 42 mg/mL respectively, while we observed up to 288 mg/mL in the earlier experiment. We must stress though that these experiments were performed pipetting extremely low volumes of highly viscous solutions, and therefore the absolute numbers of solubility should be confirmed with other techniques.

Example 3.4

Stressed Stability Studies for 23IL0064 in D-PBS

An initial 37° C. stressed stability study was performed in D-PBS. The original batch was sterilized through a 0.22 μm filter and 500 μl was stored at 37° C. in 1.5 mL-eppendorf vials for each time point (4, 8, 12, 16, 20 and 24 weeks). Additionally approximately 9×100 μl was stored at −20° C. (reference). A first sample was already analyzed after 3 weeks using SE-HPLC and a pre-peak of aggregates was detected (3%) (FIG. 38). After 4 weeks at 37° C., the total peak area on SE-HPLC and on RP-HPLC was reduced to only half of the reference sample (FIGS. 38 and 39). We therefore decided to prematurely terminate the stability study. In some of the remaining samples the content was still measured by OD280 after centrifugation. The loss of material in the 4w-37° C.-sample through precipitation (all samples were centrifuged before analysis) was confirmed in the additional 3 samples stressed for 6 weeks at 37° C.: in 2 of the 3 samples half of the material was lost (Table 29).

It can be concluded that 23IL0064 in D-PBS easily formed aggregates which precipitate following storage for 4 weeks on at 37° C. In the RP-HPLC analysis of the 37° C.-stressed sample also 12% post-peak was observed corresponding to N-terminal pyro-glutamate formation (FIG. 41).

Example 3.5

Stressed Stability Study for 23IL0064 in Histidine Buffer

From the results described in previous Examples on the solubility, the thermal shift assay, and the 37° C.-stressed stability in D-PBS for 23IL0064, it was concluded that phosphate was not the optimal buffer for formulation of 23IL0064. In the TSA described in Example 3.2.2, we explored some potential formulation buffers and the highest Tm's were obtained in histidine pH 6.5, Hepes pH 7, and Hepes pH 8. In the solubility experiment (see Example 3.3) the solubility in a 40 mM histidine pH 6, with 50 mM NaCl was very high. We therefore decided to test the storage stability in histidine buffer. In Table 30 a list of tested formulation buffers is given. The goal of this set-up was to compare histidine pH 6.5 with histidine pH 6, investigate the influence of some commonly used excipients, and the influence of a higher concentration on the stability (difference between 5 mg/mL and 22 mg/mL). One sample in Hepes pH 8 was also included, only to be tested after 3 weeks at 37° C.

For this study, 3.2 mL of the original batch was dialyzed to the 20 mM Hepes buffer pH 8 and approximately 65 mL (approx. 246 g) was dialyzed to the 20 mM Histidine buffer pH 6.5. The excipients were added in concentrated solutions (2×), and the sample at pH 6 was prepared by adding HCl. The samples were then concentrated to approximately 5 mg/mL, sterilized through a 0.22 μm filter and aliquoted in 1.5 mL-eppendorfs (500 μL/eppendorf) for storage under the different conditions.

3.5.1 Stability During Freeze Thaw

One sample of each of above formulations in histidine was subjected to 10 freeze/thaw cycles. The samples were analyzed by RP-HPLC and OD280 content. No difference with the reference sample (one freeze/thaw) was observed.

3.5.2 Shear Stress

Two samples of each of above formulations in histidine were subjected to shear stress. The test was conducted in a cold room (4-8° C.) in small glass tubes with 300 μl of protein solution, stirred through a magnetic bar for 4 and 8 hours at a medium rotation speed.

In all samples stressed with 4 and 8 hours of shearing clear opalescence was present. This was quantified by OD280 content analysis after centrifugation of the samples. Analysis by SE-HPLC did not reveal any aggregates. RP-HPLC analysis after 4 hours of shear stress showed no degradation, but after 8 hours of stress some increase of the non-resolved pre-peak appeared, especially in the concentrated sample. Also on SDS-PAGE generally no degradation was detected. In Table 31 a crude ranking based on the opalescence and material loss in the content analysis is given.

3.5.3 Storage at 4° C., 25° C. and 37° C. for 6 Weeks

The first analysis was performed after 2.5 weeks at 25° C. and 37° C. storage. The samples were analyzed on RP-HPLC (see also Table 32), SE-HPLC, SDS-PAGE and OD 280/350. Very little degradation was observed after 2.5 weeks (data not shown). The results after 6 weeks of storage at 37° C. are discussed below (for the sample in Hepes pH 8, the 2.5 weeks 37° C. results are discussed).

RP-HPLC Analysis

RP-HPLC analysis was performed mainly to detect chemical degradation. Stress at 25° C. and at 37° C. typically caused increase of the post-peak corresponding to the N-terminal pyroglutamate. This post-peak increased less in the histidine buffer pH 6 than in pH 6.5, and fastest in the Hepes buffer pH 8: e.g. after 2.5 weeks at 37° C. there was 11% pyroglutamate post peak in Hepes pH 8, 7% in histidine pH 6.5, and 5% in histidine pH 6 (data not shown).

Further a second unknown post-peak appeared. In FIG. 40 an overview of the integration data is given. In FIG. 41 an overlay between the chromatograms obtained for the different storage temperatures of 23IL0064 in histidine buffer pH 6.5 at 22 mg/mL is given.

SE-HPLC Analysis

For the samples at 5 mg/mL stressed for 6 weeks at 37° C., small amounts of aggregates (between 0.5 and 1%) were observed. The peaks were integrated. The separated pre- and postpeaks were never higher than 1 percent.

For the sample at 22.4 mg/mL however, 3% aggregates were detected in the sample stored at 37° C.

SDS-PAGE Analysis

Analysis by SDS-PAGE showed little degradation. For the samples stressed at 37° C. for 6 weeks, a slight increase in intensity of a degradation band at a Mw of approximately 27 kDa was observed and some thin bands under the main band were present (FIG. 42). No difference between the different formulation buffers was observed.

Analysis of OD280, OD350 and Subvisible Particles

All samples in the storage stability study were further analyzed for their Nanobody content (by OD280), for their opacity (by OD350), and to detect subvisible particles (by PAMAS). Very similar results were obtained between the reference and the different temperature storage samples (data not shown).

Example 3.6

Elastic Light Scattering

The tendency for aggregate formation of 23IL0075 in the different formulation buffers was determined using elastic light scattering measured at an angle of 90° by temperature-induced denaturation as measured in the Jasco Spectrofluorometer (excitation and emission wavelength 500 nm). First we looked for the optimal protein concentration, using the 10 mM phosphate buffer pH 6.0. At concentrations of 175 μg/mL 23IL0075 or lower no increase in scatter intensity was seen in the tested temperature interval: (45-95° C.). Only at 250 μg/mL scatter was observed. The curve seemed to display two transitions, which could indicate the formation of two different types of aggregates (see FIG. 43).

The experiment was repeated for the acetate and the histidine buffers, both at pH 6.0. The aggregation onset temperatures in the three buffers were very similar (Table 37). The main difference between the three buffers was the maximum scatter: it stayed within detector range (around 435 abs) for histidine while it went out of range in the phosphate as well as in the acetate buffers (FIGS. 44 and 45). In histidine the second transition was absent (FIG. 46). As the scatter is proportional to the level of aggregates formed, this indicated that the 10 mM histidine would be a more optimal formulation buffer than 10 mM acetate and 10 mM phosphate pH 6.

Example 3.7

Freeze/Thaw and Shear Stress Study on 23IL0075 in a Histidine, Acetate and Phosphate Formulation Buffer with Mannitol or a Mixture of a Mannitol and Glycine as Excipients, and a Non-Ionic Detergent as Surfactant The sensitivity of 23IL0075 to freeze/thawing and to shear or stirring has been investigated in different candidate formulation buffers (see Table 38). The freeze/thaw stress study consisted of 10 cycles: 100 µL sample in an eppendorf tube was frozen at −20° C. until completely frozen, and thawed at room temperature for 30 minutes followed by gentle mixing. The shear stress test was conducted in a cold room (4-8° C.) in small glass tubes with 150 µl of protein solution; the protein solution was stirred through a magnetic bar for 4 hours at a medium rotation speed. All samples were analyzed by RP-HPLC, SE-HPLC and OD500, some samples also by BIACORE. On RP-HPLC, no influence of shear or freeze/thaw was detected.

On SE-HPLC, dependent on the formulation buffer, freeze/thaw stress caused an increase in % pre-peak up to 2.5% (FIG. 47 (B)). A mixture of mannitol and glycine protected better against freeze/thaw stress than only mannitol as excipient (FIG. 47).

In the shear stressed samples hardly any increase in % pre-peak on SE-HPLC was detected but up to 10 times more opalescence (OD500) was measured than in the freeze/thaw samples. Optical density at 500 nm (OD500) increased in the stirred samples and correlated with the opalescence in the samples. We conclude that in the histidine buffer with 0.05% Poloxamer or with 0.005% TWEEN (polysorbate) 80 the opalescence remained lowest (FIG. 48).

Example 3.8

Freeze/Thaw, Shear Stress and Temperature Stress (37° C.) Stability Study for 23IL0075 in a Histidine Formulation Buffer with Different Combinations of Excipients Based on the conclusions of Example 3.7, we further tested freeze/thaw, shear stress and temperature stress (37° C.) stability in different histidine formulation buffers (FIG. 49 and FIG. 50). Different excipients were tested in a formulation with 25 mg/mL of protein. An overview of the formulation buffers tested in F/T and storage stability is presented in Table 39. In FIG. 49 the results of OD500 measurements and SE-HPLC after freeze/thaw stress are presented. A negligible increase of OD500 was observed. In SE-HPLC, we saw an increase of oligomers only for the sample with 5.4% mannitol as excipient. Table 40 presents the tested buffers for shear stress. Here no detergents were included, to mimic the situation during the final concentration step of the DSP process. In FIG. 50 the OD500, SE-HPLC and BIACORE results obtained after 4 hours of stirring of the formulation are presented. Stirring of the sample caused increase in OD500 absorption, but no influence on the % soluble oligomers as measured by SE-HPLC. These samples were also tested for albumin binding on BIACORE. We conclude that the protein was best protected against the shear stress by 10% sucrose, followed by a mixture of mannitol and glycine as excipients. By comparison of the values with the values of Example 3.7, we see that the results were reproducible, and that for the shear stress the addition of some detergent was beneficial.

The accelerated stability samples at 25 mg/mL in the different candidate formulation buffers were analyzed by OD500, SE-HPLC and RP-HPLC after 3 and 6 weeks storage. In SE-HPLC, the increase of oligomers was only seen at 37° C. (FIG. 51). In RP-HPLC the post-peak corresponding to the pyroglutamate increased from 3% to 4% after 6 weeks storage at 25° C., but to on average 9% after 6 weeks at 37° C. In Table 41 the RP-HPLC and SE-HPLC results after 3 and 6 weeks storage at 37° C. and 6 weeks at 25° C. are shown. The OD500 values remained for all buffers (except one outlier) below 0.01.

Tables

TABLE 1

Overview of the different formulation buffers of RANKL008a used in stability testing.

| Buffer | Concentration RANKL008a (mg/mL) | Buffer | [NaCl] (mM) | Mannitol % (w:v) |
|---|---|---|---|---|
| 1 | 60 | 10 mM NaH$_2$PO$_4$•2H$_2$O, pH 7 | 50 | 0 |
| 2 | 60 | 10 mM NaH$_2$PO$_4$•2H$_2$O, pH 7 | 100 | 0 |
| 3 | 60 | 10 mM NaH$_2$PO$_4$•2H$_2$O, pH 7 | 0 | 10 |
| 4 | 59 | 10 mM Na-acetate, pH 5.5 | 50 | 0 |
| 5 | 59 | 10 mM Na-acetate, pH 5.5 | 100 | 0 |
| 6 | 59 | 10 mM Na-acetate, pH 5.5 | 0 | 10 |
| 7 | 60 | 20 mM L-histidine, pH 5.5 | 50 | 0 |
| 8 | 60 | 20 mM L-histidine, pH 5.5 | 100 | 0 |
| 9 | 60 | 20 mM L-histidine, pH 5.5 | 0 | 10 |
| 10 | 58 | 20 mM L-histidine, pH 6 | 50 | 0 |
| 11 | 58 | 20 mM L-histidine, pH 6 | 100 | 0 |
| 12 | 58 | 20 mM L-histidine, pH 6 | 0 | 10 |
| 13 | 84.3 | 10 mM NaH$_2$PO$_4$•2H$_2$O, pH 7 | 100 | 0 |
| 14 | 70 | 10 mM NaH$_2$PO$_4$•2H$_2$O, pH 7 | 0 | 5 |

TABLE 2

Relative potencies of HSA and RANKL binding moieties of RANKL008a after 10 F/T cycles as determined by the ELISA potency assays (inhibition and HSA binding).

| Buffer | Relative potency (relative to reference material) | |
|---|---|---|
| | RANKL | HSA |
| Phosphate + 50 mM NaCl, pH 7 | 0.904 | 0.767 |
| Phosphate + 100 mM NaCl, pH 7 | 0.966 | 0.672 |
| Phosphate + 10% Mannitol, pH 7 | 0.956 | 0.715 |
| Acetate + 50 mM NaCl, pH 5.5 | 1.033 | 0.747 |
| Acetate + 100 mM NaCl, pH 5.5 | 0.905 | 0.705 |
| Acetate + 10% Mannitol, pH 5.5 | 0.878 | 0.737 |
| Histidine + 50 mM NaCl, pH 5.5 | 0.724 | 0.723 |
| Histidine + 100 mM NaCl, pH 5.5 | 0.719 | 0.670 |
| Histidine + 10% Mannitol, pH 5.5 | 0.692 | 0.572 |
| Histidine + 50 mM NaCl, pH 6 | 0.927 | 0.768 |
| Histidine + 100 mM NaCl, pH 6 | 0.923 | 0.680 |
| Histidine + 10% Mannitol, pH 6 | 0.882 | 0.754 |

TABLE 3

Integration data (% of total surface area) of the different peaks observed in the SE-HPLC chromatograms of RANKL008a after 10 F/T cycles or stored at 37° C. in different formulation buffers at all time points tested and in comparison with each control sample (each buffer).

| SE-HPLC | Sample | Phosphate pH 7 50 mM NaCl 60 mg/ml | Phosphate pH 7 100 mM NaCl 60 mg/ml | Phosphate pH 7 10% Mannitol 60 mg/ml | Acetate pH 5.5 50 mM NaCl | Acetate pH 5.5 100 mM NaCl | Acetate pH 5.5 10% Mannitol 59 mg/ml | Histidine pH 5.5 50 mM NaCl |
|---|---|---|---|---|---|---|---|---|
| % Prepeak | control | 0 | 0 | 0 | 0 | 0 | 0 | 0 |
|  | 10 F/T cycles | 0 | 0 | 0 | 0 | 0 | 0 | 0 |
|  | 2 w 37° C. | 5.6 | 6.9 | 1.3 | 4.6 | 6.3 | 2.3 | 5.5 |
|  | 3 w 37° C. | 4.4 | 6.2 | 0.65 | 3.9 | 5.9 | 0.18 | 5.6 |
|  | 5 w 37° C. | 13.7 | 15.8 | 3.9 | 11.5 | 14.2 | 1.22 | 14.0 |
|  | 10 w 37° C. | 23.8 | 25.3 | 11.1 | 21.0 | 23.9 | 3.4 | 27.2 |
| % Main peak | control | 100 | 100 | 100 | 100 | 100 | 100 | 100 |
|  | 10 F/T cycles | 100 | 100 | 100 | 100 | 100 | 100 | 100 |
|  | 2 w 37° C. | 93.5 | 92.2 | 97.9 | 94.8 | 93.1 | 98.8 | 94.0 |
|  | 3 w 37° C. | 93.7 | 92.0 | 95.2 | 95.0 | 92.8 | 96.9 | 93.4 |
|  | 5 w 37° C. | 81.14 | 78.87 | 91.52 | 87.38 | 84.63 | 97.87 | 84.85 |
|  | 10 w 37° C. | 69.2 | 68.0 | 80.5 | 77.5 | 74.7 | 95.1 | 71.3 |
| % Postpeak1 | control | 0 | 0 | 0 | 0 | 0 | 0 | 0 |
|  | 10 F/T cycles | 0 | 0 | 0 | 0 | 0 | 0 | 0 |
|  | 2 w 37° C. | 0 | 0 | 0 | 0 | 0 | 0 | 0 |
|  | 3 w 37° C. | 0 | 0 | 0 | 0 | 0 | 0 | 0 |
|  | 5 w 37° C. | 3.16 | 3.36 | 3.12 | 0 | 0 | 0 | 0 |
|  | 10 w 37° C. | 3.7 | 3.5 | 5.0 | 0 | 0 | 0 | 0 |
| % Postpeak2 | control | 0 | 0 | 0 | 0 | 0 | 0 | 0 |
|  | 10 F/T cycles | 0 | 0 | 0 | 0 | 0 | 0 | 0 |
|  | 2 w 37° C. | 0.23 | 0.27 | 0.19 | 0.23 | 0.26 | 0.19 | 0.19 |
|  | 3 w 37° C. | 0.57 | 0.58 | 0.31 | 0.49 | 0.53 | 0.27 | 0.48 |
|  | 5 w 37° C. | 0.41 | 0.47 | 0.27 | 0.37 | 0.39 | 0.25 | 0.45 |
|  | 10 w 37° C. | 0.5 | 0.5 | 0.3 | 0.4 | 0.4 | 0.2 | 0.4 |
| % Postpeak3 | control | 0 | 0 | 0 | 0 | 0 | 0 | 0 |
|  | 10 F/T cycles | 0 | 0 | 0 | 0 | 0 | 0 | 0 |
|  | 2 w 37° C. | 0.62 | 0.64 | 0.60 | 0.37 | 0.41 | 0.46 | 0.31 |
|  | 3 w 37° C. | 1.15 | 1.25 | 1.07 | 0.52 | 0.64 | 0.61 | 0.49 |
|  | 5 w 37° C. | 1.59 | 1.50 | 1.49 | 0.75 | 0.78 | 0.66 | 0.70 |
|  | 10 w 37° C. | 2.7 | 2.6 | 3.1 | 1.1 | 1.0 | 1.3 | 1.1 |

| SE-HPLC | Sample | Histidine pH 5.5 100 mM NaCl | Histidine pH 5.5 10% Mannitol 60 mg/ml | Histidine pH 6 50 mM NaCl | Histidine pH 6 100 mM NaCl | Histidine pH 6 10% Mannitol 58 mg/ml |
|---|---|---|---|---|---|---|
| % Prepeak | control | 0 | 0 | 0 | 0 | 0 |
|  | 10 F/T cycles | 0 | 0 | 0 | 0 | 0 |
|  | 2 w 37° C. | 7.5 | 0.54 | 6.3 | 7.7 | 0.63 |
|  | 3 w 37° C. | 7.9 | 0.34 | 7.0 | 8.6 | 0.39 |
|  | 5 w 37° C. | 17.1 | 1.5 | 16.2 | 17.4 | 2.0 |
|  | 10 w 37° C. | 27.8 | 5.4 | 26.8 | 27.0 | 7.3 |
| % Main peak | control | 100 | 100* | 100 | 100 | 100* |
|  | 10 F/T cycles | 100 | 100 | 100 | 100 | 100 |
|  | 2 w 37° C. | 92.1 | 98.8 | 93.1 | 91.5 | 96.7 |
|  | 3 w 37° C. | 91.5 | 98.6 | 91.3 | 90.2 | 98.8 |
|  | 5 w 37° C. | 81.73 | 97.49 | 82.22 | 81.19 | 96.76 |
|  | 10 w 37° C. | 73.5 | 93.1 | 71.3 | 71.2 | 91.0 |
| % Postpeak1 | control | 0 | 0 | 0 | 0 | 0 |
|  | 10 F/T cycles | 0 | 0 | 0 | 0 | 0 |
|  | 2 w 37° C. | 0 | 0 | 0 | 0 | 0 |
|  | 3 w 37° C. | 0 | 0 | 0 | 0 | 0 |
|  | 5 w 37° C. | 0 | 0 | 0 | 0 | 0 |
|  | 10 w 37° C. | 0 | 0 | 0 | 0 | 0 |
| % Postpeak2 | control | 0 | 0 | 0 | 0 | 0 |
|  | 10 F/T cycles | 0 | 0 | 0 | 0 | 0 |
|  | 2 w 37° C. | 0.17 | 0.19 | 0.20 | 0.23 | 0.18 |
|  | 3 w 37° C. | 0.55 | 0.27 | 0.54 | 0.5 | 0.27 |
|  | 5 w 37° C. | 0.29 | 0.23 | 0.52 | 0.42 | 0.37 |
|  | 10 w 37° C. | 0.5 | 0.2 | 0.4 | 0.4 | 0.3 |
| % Postpeak3 | control | 0 | 0 | 0 | 0 | 0 |
|  | 10 F/T cycles | 0 | 0 | 0 | 0 | 0 |
|  | 2 w 37° C. | 0.26 | 0.37 | 0.40 | 0.58 | 0.53 |
|  | 3 w 37° C. | 0.55 | 0.57 | 1.12 | 0.71 | 0.56 |
|  | 5 w 37° C. | 0.88 | 0.78 | 1.06 | 0.99 | 0.87 |
|  | 10 w 37° C. | 1.3 | 1.3 | 1.5 | 1.4 | 1.5 |

TABLE 4

Integration data (% of total surface area) of the different peaks observed in the RP-HPLC chromatograms of RANKL008a after 10 F/T cycles or stored at 37° C. in different formulation buffers at all time points tested and in comparison with each control sample (each buffer)

| RP-HPLC | Sample | Phosphate pH 7 50 mM NaCl 60 mg/ml | Phosphate pH 7 100 mM NaCl 60 mg/ml | Phosphate pH 7 10% Mannitol 60 mg/ml | Acetate pH 5.5 50 mM NaCl | Acetate pH 5.5 100 mM NaCl | Acetate pH 5.5 10% Mannitol 59 mg/ml | Histidine pH 5.5 50 mM NaCl |
|---|---|---|---|---|---|---|---|---|
| % Prepeak 1 | control | 0.25 | 0.14 | 0 | 0 | 0 | ND | 0 |
| | 10 F/T cycles | 0.20 | 0.08 | 0 | 0 | 0 | 0 | 0 |
| | 2 w 37° C. | 0 | 0 | 0 | 0 | 0 | 0 | 0 |
| | 3 w 37° C. | 0 | 0 | 0 | 0 | 0 | 0 | 0 |
| | 5 w 37° C. | 0 | 0 | 0 | 0 | 0 | 0 | 0 |
| | 10 w 37° C. | 0 | 0 | 0 | 0 | 0 | 0 | 0 |
| % Prepeak 2 | Control | 0 | 0 | 0 | 0 | 0 | ND | 0 |
| | 10 F/T cycles | 0 | 0 | 0 | 0 | 0 | 0 | 0 |
| | 2 w 37° C. | 1.10 | 1.00 | 1.10 | 0.78 | 0.82 | 0.78 | 0.82 |
| | 3 w 37° C. | 1.6 | 1.4 | 1.8 | 0.7 | 0.8 | 0.9 | 0.7 |
| | 5 w 37° C. | 2.1 | 2.0 | 2.3 | 1.0 | 0.9 | 1.1 | 1.1 |
| | 10 w 37° C. | 3.4 | 2.9 | 3.7 | 1.5 | 1.5 | 1.9 | 1.6 |
| % Main peak | Control | 96.6 | 96.7 | 96.7 | 96.8 | 97.0 | ND | 96.5 |
| | 10 F/T cycles | 96.7 | 96.6 | 95.9 | 97.0 | 96.7 | 96.6 | 97.0 |
| | 2 w 37° C. | 93.7 | 94.0 | 93.5 | 95.8 | 96.0 | 95.6 | 96.0 |
| | 3 w 37° C. | 92.3 | 92.7 | 91.9 | 95.7 | 95.5 | 95.4 | 95.6 |
| | 5 w 37° C. | 90.2 | 90.3 | 89.1 | 94.8 | 95.1 | 94.7 | 94.7 |
| | 10 w 37° C. | 84.1 | 85.4 | 83.4 | 93.5 | 93.3 | 92.7 | 93.3 |
| % Pyroglut. | Control | 3.2 | 3.1 | 3.3 | 3.2 | 2.9 | ND | 3.5 |
| | 10 F/T cycles | 3.1 | 3.3 | 4.0 | 3.3 | 3.2 | 3.4 | 3.0 |
| | 2 w 37° C. | 5.1 | 4.7 | 5.4 | 3.4 | 3.2 | 3.6 | 3.2 |
| | 3 w 37° C. | 6.1 | 6.0 | 6.3 | 3.6 | 3.7 | 3.7 | 3.7 |
| | 5 w 37° C. | 7.7 | 7.7 | 8.6 | 4.1 | 3.9 | 4.2 | 4.2 |
| | 10 w 37° C. | 12.5 | 11.7 | 12.9 | 5.0 | 5.2 | 5.5 | 5.2 |

| RP-HPLC | Sample | Histidine pH 5.5 100 mM NaCl | Histidine pH 5.5 10% Mannitol 60 mg/ml | Histidine pH 6 50 mM NaCl | Histidine pH 6 100 mM NaCl | Histidine pH 6 10% Mannitol 58 mg/ml |
|---|---|---|---|---|---|---|
| % Prepeak 1 | control | 0 | 0 | 0 | 0 | 0 |
| | 10 F/T cycles | 0 | 0 | 0 | 0 | 0 |
| | 2 w 37° C. | 0 | 0 | 0 | 0 | 0 |
| | 3 w 37° C. | 0 | 0 | 0 | 0 | 0 |
| | 5 w 37° C. | 0 | 0 | 0 | 0 | 0 |
| | 10 w 37° C. | 0 | 0 | 0 | 0 | 0 |
| % Prepeak 2 | Control | 0 | 0 | 0 | 0 | 0 |
| | 10 F/T cycles | 0 | 0 | 0 | 0 | 0 |
| | 2 w 37° C. | 0.72 | 0.76 | 0.76 | 0.79 | 0.87 |
| | 3 w 37° C. | 0.9 | 0.9 | 0.7 | 0.9 | 0.9 |
| | 5 w 37° C. | 1.2 | 1.2 | 1.2 | 1.1 | 1.5 |
| | 10 w 37° C. | 1.7 | 2.0 | 2.0 | 1.9 | 2.1 |
| % Main peak | Control | 96.6 | 96.4 | 96.7 | 96.8 | 96.8 |
| | 10 F/T cycles | 95.8 | 96.5 | 96.4 | 96.8 | 96.8 |
| | 2 w 37° C. | 95.7 | 95.9 | 95.6 | 95.7 | 95.5 |
| | 3 w 37° C. | 95.4 | 95.3 | 95.6 | 95.5 | 95.5 |
| | 5 w 37° C. | 94.6 | 94.8 | 94.4 | 94.7 | 94.0 |
| | 10 w 37° C. | 93.3 | 92.4 | 93.1 | 92.3 | 92.0 |
| % Pyroglut. | Control | 3.0 | 3.6 | 3.3 | 3.2 | 3.2 |
| | 10 F/T cycles | 3.3 | 3.5 | 3.6 | 3.2 | 3.2 |
| | 2 w 37° C. | 3.5 | 3.4 | 3.6 | 3.5 | 3.6 |
| | 3 w 37° C. | 3.7 | 3.7 | 3.6 | 3.6 | 3.6 |
| | 5 w 37° C. | 4.3 | 4.1 | 4.4 | 4.1 | 4.4 |
| | 10 w 37° C. | 5.1 | 5.5 | 4.8 | 5.8 | 5.9 |

TABLE 5

Integration data (% of total surface area) of the different peaks observed in the IEX-HPLC chromatograms of RANKL008a stored for 10 weeks at 37° C. in different formulation buffers.

| Buffer | % Main peak | % Post peak 1 | % Post peak 2 |
|---|---|---|---|
| Phosphate + 50 mM NaCl, pH 7 | 69.6 | 4.4 | 26.0 |
| Phosphate + 100 mM NaCl, pH 7 | 67.0 | 4.5 | 28.1 |
| Phosphate + 10% Mannitol, pH 7 | 84.6 | 3.2 | 12.1 |
| Acetate + 50 mM NaCl, pH 5.5 | 72.8 | 2.7 | 24.4 |
| Acetate + 100 mM NaCl, pH 5.5 | 69.6 | 2.8 | 27.6 |
| Acetate + 10% Mannitol, pH 5.5 | 95.4 | 0 | 4.6 |
| Histidine + 50 mM NaCl, pH 5.5 | 66.0 | 2.8 | 31.2 |
| Histidine + 100 mM NaCl, pH 5.5 | 68.1 | 2.8 | 29.0 |
| Histidine + 10% Mannitol, pH 5.5 | 92.8 | 0 | 7.2 |
| Histidine + 50 mM NaCl, pH 6 | 67.4 | 2.6 | 30.1 |
| Histidine + 100 mM NaCl, pH 6 | 67.0 | 2.6 | 30.4 |
| Histidine + 10% Mannitol, pH 6 | 88.8 | 2.6 | 9.0 |

TABLE 6

Relative potencies of the HSA and RANKL binding moieties of RANKL008a after 10 weeks at 37° C. as measured by Biacore analysis.

| Buffer | Relative potency RANKL | Relative potency HSA |
|---|---|---|
| Phosphate + 50 mM NaCl, pH 7 | 81.0 | 57.4 |
| Phosphate + 100 mM NaCl, pH 7 | 78.6 | 56.6 |
| Phosphate + 10% Mannitol, pH 7 | 76.3 | 66.8 |
| Acetate + 50 mM NaCl, pH 5.5 | 80.1 | 63.0 |
| Acetate + 100 mM NaCl, pH 5.5 | 78.0 | 59.0 |
| Acetate + 10% Mannitol, pH 5.5 | 80.9 | 79.4 |
| Histidine + 50 mM NaCl, pH 5.5 | 80.2 | 59.7 |
| Histidine + 100 mM NaCl, pH 5.5 | 73.1 | 55.0 |
| Histidine + 10% Mannitol, pH 5.5 | 75.2 | 73.6 |
| Histidine + 50 mM NaCl, pH 6 | 79.1 | 59.3 |
| Histidine + 100 mM NaCl, pH 6 | 78.3 | 57.5 |
| Histidine + 10% Mannitol, pH 6 | 87.4 | 83.4 |

TABLE 7

Visual inspection and content determination of RANKL008a after dilution to 0.28 mg/mL in different diluents and passage/storage in syringes (refer to FIG. 9).

| Sample* | visual inspection | content (mg/mL)(95% confidence interval) |
|---|---|---|
| 0028 SALINE TUB | small precipitates | 0.265 (0.261-0.270) |
| 0028 SALINE SYR S25/0 | small precipitates | 0.263 (0.261-0.265) |
| 0028 SALINE SYR S25/24 | small precipitates | 0.259 (0.256-0.262) |
| 0028 PLACEBO-TW TUB | small precipitates | 0.272 (0.271-0.273) |
| 0028 PLACEBO-TW SYR S25/0 | small precipitates | 0.268 (0.267-0.269) |
| 0028 PLACEBO-TW SYR S25/24 | small precipitates | 0.268 (0.259-0.276) |
| 0028 PLACEBO + TW TUB | clear | 0.281 (0.281-0.281) |
| 0028 PLACEBO + TW SYR S25/0 | slightly turbid | 0.280 (0.278-0.282) |
| 0028 PLACEBO + TW SYR S25/24 | slightly turbid | 0.279 (0.277-0.281) |

*S25/0: storage at 25° C. for 0 minute
S25/24: storage at 25° C. for 24 h
−TW: buffer minus Tween 80
+TW: buffer + Tween 80
PLACEBO refers to the following buffer: 10 mM Na2HPO4 pH 7.0 + 115 mM NaCl
TUB: sample stored in a polystyrene tube

TABLE 8

Visual inspection, content (confidence interval) and turbidity of RANKL008a diluted to 0.28 mg/mL before (TUB) and after passage through syringes with different needle size as described in Example 1.8.

| Sample* | visual inspection | content (mg/mL) (95% confidence interval) | OD 320/278 ratio | OD 350/278 ratio |
|---|---|---|---|---|
| 0028 PLACEBO + TW TUB | clear | 0.288 (0.275-0.301) | 0.0010 | 0.0019 |
| 0028 PLACEBO + TW 18 G/18 G | clear | 0.285 (0.284-0.286) | 0.0003 | 0.0000 |
| 0028 PLACEBO + TW 18 G/23 G | clear | 0.288 (0.271-0.307) | 0.0000 | 0.0000 |
| 0028 PLACEBO + TW 18 G/27 G | clear | 0.285 (0.279-0.290) | 0.0000 | 0.0002 |
| 0028 PLACEBO + TW 18 G/30 G | clear | 0.286 (0.285-0.287) | 0.0005 | 0.0002 |
| 0028 PLACEBO + TW 23 G/23 G | clear | 0.287 (0.285-0.289) | 0.0005 | 0.0007 |
| 0028 PLACEBO + TW 27 G/27 G | clear | 0.285 (0.284-0.286) | 0.0001 | 0.0005 |
| 0028 PLACEBO + TW 30 G/30 G | clear | 0.287 (0.280-0.294) | 0.0007 | 0.0019 |

*+TW: buffer + Tween 80
PLACEBO refers to the following buffer: 10 mM Na2HPO4 pH 7.0 + 115 mM NaCl
TUB: sample stored in a polystyrene tube
18 G/18 G: sample drawn up with a 18 G needle and expelled through a 18 G needle
18 G/27 G: drawn up with a 18 G needle and expelled through a 27 G needle
All other coding is similar to the two examples given above

TABLE 9

Visual inspection, content (with 95% confidence interval) and turbidity of RANKL008a before (TUB) and after passage through syringes with different needle size as described in Example 1.7 at a concentration of 0.28 mg/mL or about 65 mg/mL.

| Sample* | visual inspection | content (mg/mL) (95% confidence interval) | OD 320/278 ratio | OD 350/278 ratio |
|---|---|---|---|---|
| 0028 PLACEBO + TW TUB | clear | 0.284 (0.283-0.285) | 0.0014 | 0.0010 |
| 0028 PLACEBO + TW 27 G/27 G (3x) | clear | 0.284 (0.283-0.285) | 0.0031 | 0.0021 |
| 0028 PLACEBO + TW 29 G/29 G B | clear | 0.282 (0.280-0.284) | 0.0024 | 0.0010 |

TABLE 9-continued

Visual inspection, content (with 95% confidence interval) and turbidity of RANKL008a before (TUB) and after passage through syringes with different needle size as described in Example 1.7 at a concentration of 0.28 mg/mL or about 65 mg/mL.

| Sample* | visual inspection | content (mg/mL) (95% confidence interval) | OD 320/278 ratio | OD 350/278 ratio |
|---|---|---|---|---|
| 0028 PLACEBO + TW 29 G/29 G T | clear | 0.283 (0.282-0.284) | 0.0041 | 0.0033 |
| 6500 PLACEBO + TW TUB | clear | 63.5 (62.4-64.6) | 0.0019 | 0.0006 |
| 6500 PLACEBO + TW 27 G/27 G (3x) | clear | 62.9 (62.7-63.1) | 0.0015 | 0.0008 |

*+TW: buffer + Tween 80
PLACEBO refers to the following buffer: 10 mM Na2HPO4 pH 7.0 + 115 mM NaCl
TUB: sample stored in a polystyrene tube
27 G/27 G: sample drawn up with a 27 G needle and expelled through a 27 G needle
29 G/29 G: drawn up with a 29 G needle and expelled through a 29 G needle
T: Terumo needle, B Becton Dickinson needle
0028 refers to concentration at 0.28 mg/mL, 6500 to 65 mg/mL

TABLE 10

Protein sequences of Nanobodies used in Example 2

IL6R304, SEQ ID NO: 1
EVQLVESGGGLVQPGGSLRLSCAASGSVFKINVMAWYRQAPGKGRELVAGIISGGSTSYADSVKGRFTISRDNA
KNTLYLQMNSLRPEDTAVYYCAFITTESDYDLGRRYWGQGTLVTVSSGGGGSGGGSEVQLVESGGGLVQPGNSL
RLSCAASGFTFSSFGNSWVRQAPGKGLEWVSSISGSGSDTLYADSVKGRFTISRDNAKTTLYLQMNSLRPEDTA
VYYCTIGGSLSRSSQGTLVTVSS

IL6R305, SEQ ID NO: 2
EVQLVESGGGLVQPGGSLRLSCAASGSVFKINVMAWYRQAPGKGRELVAGIISGGSTSYADSVKGRFTISRDNA
KNTLYLQMNSLRPEDTAVYYCAFITTESDYDLGRRYWGQGTLVTVSSGGGGSGGGSEVQLVESGGGLVQPGGSL
RLSCAASGSVFKINVMAWYRQAPGKGRELVAGIISGGSTSYADSVKGRFTISRDNAKNTLYLQMNSLRPEDTAV
YYCAFITTESDYDLGRRYWGQGTLVTVSSGGGGSGGGSEVQLVESGGGLVQPGNSLRLSCAASGFTFSSFGNSW
VRQAPGKGLEWVSSISGSGSDTLYADSVKGRFTISRDNAKTTLYLQMNSLRPEDTAVYYCTIGGSLSRSSQGTL
VTVSS

IL6R306, SEQ ID NO: 3
EVQLVESGGGLVQPGGSLRLSCAASGSVFKINVMAWYRQAPGKGRELVAGIISGGSTSYADSVKGRFTISRDNA
KNTLYLQMNSLRPEDTAVYYCAFITTESDYDLGRRYWGQGTLVTVSSGGGGSGGGSEVQLVESGGGLVQPGNSL
RLSCAASGFTFSSFGMSWVRGAPGKGLEWVSSISGSGSDTLYADSVKGRFIISRDNAKTTLYLQMNSLRPEDTA
VYYCTIGGSLSRSSQGTLVTVSSGGGGSGGGSEVQLVESGGGLVQPGGSLRLSCAASGSVFKINVMAWYRQAPG
KGRELVAGIISGGSTSYADSVKGRFTISRDNAKNTLYLQMNSLRPEDTAVYYCAFITTESDYDLGRRYWGQGTL
VTVSS

TABLE 11

Overview of the IL6R batches used in the formulation and stability studies described in Example 2.

| Batch no. | Nanobody | Buffer | Concentration |
|---|---|---|---|
| P#051108nr1 | IL6R304 | PBS | 4.58 mg/mL |
| P#051108nr2 | IL6R305 | PBS | 3.46 mg/mL |
| P#051108nr2 | IL6R306 | PBS | 5.65 mg/mL |
| B5#030309nr1.5-9 | IL6R304 | 25 mM hepes, pH 7.5, 100 mM NaCl | 3.79 mg/mL |
| B5#060509nr1 | IL6R304 | 25 mM hepes, pH 7.5, 100 mM NaCl | 4.6 mg/mL |

TABLE 12

Reagents used in the formulation and stability study described in Example 2

| Reagent | Provider | Cat No. |
|---|---|---|
| ACN, HPLC grade | Biosolve | Cat. No. 012007 |
| TFA | Biosolve | Cat. No. 20234131 |
| Isopropanol, HPLC grade | Biosolve | Cat. No. 162606 |
| MilliQ grade water | | |
| D-PBS | Gibco | Cat. No. 14190-094 |
| NaCl | Merck | Cat. No. 1.06404.1000 |
| Gel filtration standard | Bio-Rad | Cat. No. 151-1901 |
| HSA | Sigma | Cat. No. A3782 |
| L-histidine | Fluka | Cat. No. 53319 |
| D-Mannitol | Fluka | Cat. No. 17311 |

TABLE 12-continued

Reagents used in the formulation and stability study described in Example 2

| Reagent | Provider | Cat No. |
|---|---|---|
| Sucrose | Fluka | Cat. No. 18219 |
| Glycine | Fluka | Cat. No. 50058 |
| Tween-80 | Merck | Cat. No. 1051 65661 609 |
| L-histidine-HCl monohydrate | Sigma | Cat. No. 53369 |
| Succinic acid disodium hexahydrate | Fluka | Cat. No. 14158 |
| Trizma base | Sigma | Cat. No. T6066-5 |
| Sorbitol | Fluka | Cat. No. 85529 |
| Xylitol | Sigma | Cat. No. X3375-100g |
| Ribitol | Fluka | Cat. No. 02240 |
| L-Arginine | Fluka | Cat. No. 11009 |
| MES | Sigma | Cat. No. M3671 |
| Sodium dihydrogenphosphate | Merck | Cat. No. 1.06345.1000 |
| Disodium hydrogenphosphate | Merck | Cat. No. 1.06576.1000 |

TABLE 13

Summary of the results from the TSA assay.

| Buffer/pH | Histidine pH 6.5 Hepes pH 7 | Hepes pH 8 Phos. pH 6.7 | Phos. pH 7.7 | Succinate pH 6.2 | Histidine pH 5.5 Succinate pH 5.2 | Tris pH 7 PBS |
|---|---|---|---|---|---|---|
| NaCl | 0 | 100 | 200 | 300 | 400 | 500 |
| Mannitol | 7.5% | 5% | 2.5% | 0 | | |
| Sucrose | 10% | 5% | | | | |
| Glycine | 200 mM | 100 mM | | | | |

The Tm values obtained in the different buffer are coded from white to dark grey, i.e. from higher to lower Tm values.

TABLE 14

Overview of the Tm values obtained by DSC using IL6R304.

| Buffer | Tm (° C.) in 0 mM NaCl | Tm (° C.) in 25 mM NaCl | Tm (° C.) in 100 mM NaCl | Tm (° C.) in 500 mM NaCl |
|---|---|---|---|---|
| 25 mM citrate pH 3.5 | 50.21 | — | — | — |
| 25 mM acetate pH 5.5 | 61.30 | 61.21 | 60.19 | 58.59 |
| 25 mM MES pH 6.0 | 62.52 | 61.83 | 60.60 | 58.66 |
| 25 mM hepes pH 7.0 | 62.48 | 62.27 | 61.13 | 59.24 |
| 25 mM phosphate pH 7.0 | 60.70 | — | — | — |
| 25 mM Tris pH 7.5 | 61.82 | 61.82 | 60.91 | 59.43 |

TABLE 15

Overview of the Tm results obtained by DSC and TSA using IL6R304 formulated in different buffers.

| Excipient(s) | DSC | | TSA | |
|---|---|---|---|---|
| | Tm (° C.) in 15 mM L-histidine, pH 6.5 | Tm (° C.) 15 mM phosphate, pH 6.5 | Tm (° C.) in 15 mM L-histidine, pH 6.5 | Tm (° C.) 15 mM phosphate, pH 6.5 |
| — | ND | ND | 61.09*/61.11** | 60.48/60.48 |
| 5% mannitol | 64.74 | 63.81 | 61.91/61.87 | 61.34/61.31 |
| 10% sucrose | 65.40 | 64.35 | 62.78/63.20 | 62.34/62.78 |
| 10% trehalose | 65.28 | 64.51 | 62.78/63.59 | 63.17/63.61 |
| 2.5% mannitol + 2.5% sucrose | 64.37 | 63.83 | 61.52/61.91 | 61.53/61.30 |
| 2.5% sorbitol + 2.5% trehalose | 64.65 | 63.85 | 62.34/62.34 | 62.77/62.77 |
| 2.5% sorbitol + 2.5% trehalose + 1.5 mM Glycine | 64.83 | 64.33 | 62.33/62.35 | 63.19/62.96 |
| 10% trehalose + 0.01% Tween-80 | Run failure | 63.77 | ND | ND |

*measurement 1, **measurement 2

TABLE 16

Visual appearance, UV spectroscopy and PAMAS data demonstrating a higher solubility for IL6R304 in the presence of Tween 80.

| | IL6R304 (2 mg/mL) stored for 4 days at 5° C. | | |
|---|---|---|---|
| | PBS | PBS + 0.1 % Tween 80 | PBS + 0.2 % Tween 80 |
| Appearance | Turbid, opaque | Clear, colorless | Clear, colorless |
| A320/A280 | 0.014 | 0.012 | 0.009 |

TABLE 16-continued

Visual appearance, UV spectroscopy and PAMAS data demonstrating a higher solubility for IL6R304 in the presence of Tween 80.

IL6R304 (2 mg/mL) stored for 4 days at 5° C.

|  | PBS | PBS + 0.1 % Tween 80 | PBS + 0.2 % Tween 80 |
|---|---|---|---|
| Sub-visible particle counts/100 µl | | | |
| >1 µm | 157.557 | 42.243 | 52.157 |
| >2 µm | 69.471 | 19.514 | 21.429 |
| >3 µm | 43.371 | 12.043 | 12.743 |
| >4 µm | 29.757 | 8.329 | 8.600 |
| >5 µm | 18.300 | 4.971 | 4.800 |
| >6 µm | 11.814 | 3.114 | 3.143 |
| >7 µm | 8.300 | 2.300 | 2.186 |
| >8 µm | 5.900 | 1.671 | 1.500 |
| >9 µm | 4.543 | 1.214 | 1.086 |
| >10 µm | 3.400 | 971 | 800 |
| >15 µm | 800 | 271 | 300 |
| >25 µm | 200 | 100 | 86 |
| >50 µm | 114 | 29 | 14 |
| >100 µm | 86 | 0 | 14 |
| >150 µm | 71 | 0 | 14 |
| >200 µm | 71 | 0 | 14 |

TABLE 17

Overview of the different formulation buffers used in initial stability testing of IL6R304, IL6R305 and IL6R306.

| Condition | Buffer | [NaCl] | Mannitol |
|---|---|---|---|
| 1 | PBS | 0 mM | 0 % |
| 2 | PBS | 0 mM | 5 % |
| 3 | 10 mM NaH$_2$PO$_4$ · 2H$_2$O, pH 7 | 100 mM | 0 % |
| 4 | 10 mM NaH$_2$PO$_4$ · 2H$_2$O, pH 7 | 100 mM | 5 % |
| 5 | 10 mM Na-acetate, pH 5.5 | 100 mM | 0 % |
| 6 | 10 mM Na-acetate, pH 5.5 | 100 mM | 5 % |
| 7 | 20 mM L-histidine, pH 6 | 100 mM | 0 % |
| 8 | 20 mM L-histidine, pH 6 | 100 mM | 5 % |

TABLE 18

Overview of the different formulation buffers used in stability testing of IL6R304.

| Buffer | Concentration IL6R304 | Buffer | % Tween 80 | % Mannitol | % Sucrose | mM Glycine |
|---|---|---|---|---|---|---|
| 1 | 10 mg/mL | 20 mM L-histidine | / | / | / | / |
| 2 | 10 mg/mL | 20 mM L-histidine | 0.01 | / | / | / |
| 3 | 10 mg/mL | 20 mM L-histidine | 0.05 | / | / | / |
| 4 | 10 mg/mL | 20 mM L-histidine | 0.05 | 5 | / | / |
| 5 | 10 mg/mL | 20 mM L-histidine | 0.05 | 5 | / | 200 |
| 6 | 10 mg/mL | 20 mM L-histidine | 0.05 | 2.5 | / | 100 |
| 7 | 10 mg/mL | 20 mM L-histidine | 0.05 | / | 10 | / |
| 8 | 10 mg/mL | 20 mM L-histidine | 0.05 | / | / | 200 |
| 9 | 10 mg/mL | 20 mM L-histidine | 0.05 | / | 5 | 100 |
| 10 | 10 mg/mL | 20 mM L-histidine | 0.05 | 2.5 | 5 | / |
| 11 | 10 mg/mL | 20 mM L-histidine | / | 2.5 | 5 | 100 |
| 12 | 10 mg/mL | 20 mM L-histidine | 0.05 | 2.5 | 5 | 100 |

TABLE 19

Methods used for assessing the stability of IL6R304 at different time points (represented as x weeks or w) after storage at 5° C. and 37° C.

| | | | Stress condition | |
|---|---|---|---|---|
| Method | Purpose | Ref. material | 5° C. | 37° C. |
| A280 | Content | 0w | 1, 2 and 5w | 1, 2, 3 and 5w |
| Appearance | Precipitation | 0w | 1, 2 and 5w | 1, 2, 3 and 5w |
| RP-HPLC | Purity/variants | 0w | 1, 2 and 5w | 1, 2, 3 and 5w |
| SE-HPLC | Purity/aggregation/hydrolysis | 0w | 1, 2 and 5w | 1, 2, 3 and 5w |
| Biacore | Potency (HSA binding) | 0w | 5w | 5w |
| Osmolality | Characteristic | 0w | — | — |

TABLE 20

Overview of the SE-HPLC integration results after storage for 6 months at 37° C.

| Buffer | % pre peak 1 | % pre peak 2 | % main peak | % post peak |
|---|---|---|---|---|
| Ref | 0.52 | 0.17 | 99.3 | 0 |
| Buffer 1 | ND | ND | ND | ND |
| Buffer 2 | 20.4 | 2.1 | 73.4 | 4.1 |

TABLE 20-continued

Overview of the SE-HPLC integration results after storage for 6 months at 37° C.

| Buffer | % pre peak 1 | % pre peak 2 | % main peak | % post peak |
|---|---|---|---|---|
| Buffer 3 | ND | ND | ND | ND |
| Buffer 4 | 18.1 | 1.7 | 76.0 | 4.2 |
| Buffer 5 | 22.2 | 2.0 | 71.4 | 4.4 |
| Buffer 6 | 21.4 | 1.7 | 72.7 | 4.2 |
| Buffer 7 | 15.1 | 0 | 80.5 | 4.4 |
| Buffer 8 | 21.1 | 2.4 | 72.0 | 4.5 |
| Buffer 9 | 16.7 | 2.7 | 76.3 | 4.3 |
| Buffer 10 | 15.8 | 1.9 | 77.9 | 4.4 |
| Buffer 11 | 17.5 | 2.0 | 76.4 | 4.2 |
| Buffer 12 | 16.8 | 3.3 | 75.7 | 4.2 |

TABLE 21

Overview of the different formulation buffers tested in the stability study.

| Nr. | Conc. | Buffer | Mannitol | Sucrose | Trehalose | Glycine | Tween-80 |
|---|---|---|---|---|---|---|---|
| 1 | 10 mg/mL | 15 mM L-histidine, pH 6.5 | 5% | | | | 0.01% |
| 2 | 10 mg/mL | 15 mM L-histidine, pH 6.5 | | 10% | | | 0.01% |
| 3 | 10 mg/mL | 15 mM L-histidine, pH 6.5 | | | 10% | | 0.01% |
| 4 | 10 mg/mL | 15 mM L-histidine, pH 6.5 | | 7.5% | | 0.35% | 0.01% |
| 5 | 10 mg/mL | 15 mM L-histidine, pH 6.5 | 2.5% | 5% | | | 0.01% |
| 6 | 10 mg/mL | 15 mM phosphate, pH 6.5 | 5% | | | | 0.01% |
| 7 | 10 mg/mL | 15 mM phosphate, pH 6.5 | | 10% | | | 0.01% |
| 8 | 10 mg/mL | 15 mM phosphate, pH 6.5 | | | 10% | | 0.01% |
| 9 | 10 mg/mL | 15 mM phosphate, pH 6.5 | | 7.5% | | 0.35% | 0.01% |
| 10 | 10 mg/mL | 15 mM phosphate, pH 6.5 | 2.5% | 5% | | | 0.01% |

TABLE 22 cIEF integration data of IL6R304 stored for 8 weeks at 37° C. in the different buffers

| Buffer | % prepeak (acidic variants) | % main peak | % postpeak (basic variants) |
|---|---|---|---|
| 1 | 5.5 | 81.3 | 13.0 |
| 2 | 5.0 | 81.5 | 13.5 |
| 3 | 6.1 | 79.7 | 14.2 |
| 4 | 5.7 | 81.2 | 13.2 |
| 5 | 5.1 | 81.2 | 13.7 |
| 6 | 9.0 | 71.6 | 19.3 |
| 7 | 9.9 | 70.5 | 19.6 |
| 8 | 8.3 | 71.8 | 19.9 |
| 9 | 11.7 | 68.5 | 19.8 |
| 10 | 8.7 | 70.5 | 20.2 |

TABLE 23

Relative potency of IL6R304 after 8 weeks at +37° C. compared to B5#030309nr2.3-5.

| Buffer | HSA | IL-6R |
|---|---|---|
| 1 | 1.080 (0.954-1.223) | 1.153 (0.957-1.389) |
| 2 | 0.975 (0.887-1.072) | 0.980 (0.760-1.263) |
| 3 | 1.038 (0.952-1.132) | 1.117 (0.910-1.372) |
| 4 | 1.182 (1.074-1.300) | 1.061 (0.908-1.240) |
| 5 | 1.080 (1.004-1.161) | 1.082 (0.925-1.266) |

TABLE 24

Summary of the Biacore results for HSA binding of the stability samples stored for 8 weeks at 37° C., expressed as % activity compared to the equivalent sample stored at −70° C.

| Buffer | % activity compared to reference |
|---|---|
| 1 | 97.5 |
| 2 | 93.2 |
| 3 | 92.5 |
| 4 | 83.9 |
| 5 | 101.9 |
| 6 | 92.2 |
| 7 | 89.4 |
| 8 | 99.0 |
| 9 | 84.3 |
| 10 | 89.6 |

TABLE 25

Appearance of IL6R304 after 0, 2, 4 and 24 hours of stirring at 2-8° C.

| Buffer | 0 hrs | 2 hrs | 4 hrs | 24 hrs |
|---|---|---|---|---|
| 1 | clear | clear | clear | clear/slightly opalescent |
| 2 | clear | clear | clear | clear/slightly opalescent |
| 3 | clear | clear | slightly opalescent | slightly opalescent |
| 4 | clear | clear | clear | clear/slightly opalescent |
| 5 | clear | clear | slightly opalescent | slightly opalescent |
| 6 | clear | clear | slightly opalescent | opalescent |
| 7 | clear | clear | slightly opalescent | opalescent |
| 8 | clear | clear | slightly opalescent | highly opalescent |
| 9 | clear | clear | clear | opalescent |
| 10 | clear | clear | opalescent | opalescent |

TABLE 26

Reagents used in the formulation and stability study described in Examples 3.

| Reagent | Provider | Cat No. |
|---|---|---|
| ACN, HPLC grade | Biosolve | Cat. No. 012007 |
| TFA | Biosolve | Cat. No. 20234131 |
| N-propanol, HPLC grade | Sigma-Aldrich | Cat. No. 34871 |
| MilliQ grade water | | |
| D-PBS | Invitrogen | Cat. No. 14190 |
| NaCl | Merck | Cat. No. 1.06404.1000 |
| Gel filtration standard | Bio-Rad | Cat. No. 151-1901 |
| HSA | Sigma | Cat. No. A3782 |
| L-histidine | Fluka | Cat. No. 53319 |
| D-Mannitol | Fluka | Cat. No. 17311 |
| Sucrose | Fluka | Cat. No. 18219 |
| Glycine | Fluka | Cat. No. 50058 |
| Tween 80 | Merck | Cat. No. K351 65661 609 |

TABLE 27

Final concentrations obtained after concentration of 23IL0064 using Vivaspin filters. The filtration was stopped at the moment the final volume became limited (100 to 200 μL) and protein loss occurred. All samples were analyzed by SE-HPLC: the percent pre-peak (% of total surface area) represent aggregates in the sample.

| buffer condition | start conditions | | after ULTRAFILTRATION | | |
|---|---|---|---|---|---|
| | concentration | % pre-peak in SE-HPLC | concentration | % pre-peak in SE-HPLC | % recovery |
| D-PBS | 3.8 mg/mL | 2.80% | 110 mg/mL | 6.30% | 42% [1] |
| 50 mM NaCl, 10 mM Phosphate pH 7 | 3.4 mg/mL | 2.70% | 83 mg/mL | 2.80% | 66% [1] |
| 50 mM NaCl, 40 mM Histidine pH 6 | 3.4 mg/mL | 2.70% | 150 mg/mL | 2.70% | 59% [1] |

[1] Low recoveries can be due to local concentration effects obtained during the dead-end ultrafiltration set-up.

TABLE 28

Buffers tested in a thermal shift assay for 23IL0064.

| Buffer | pKa | pH | Concentration (mM) | mM NaCl | % mannitol |
|---|---|---|---|---|---|
| Succinate | 5.64 | 5.2 | 20 | 0 | 0-2.5-5-7.5 |
| | (pK2) | 6.2 | | 50-150-300-500 | 0 |
| Histidine | 6.04 | 5.5 | 20 | 0 | 0-2.5-5-7.5 |
| | (pK2) | 6.5 | | 50-150-300-500 | 0 |
| Phosphate | 7.20 | 6.7 | 20 | 0 | 0-2.5-5-7.5 |
| | (pK2) | 7.7 | | 50-150-300-500 | 0 |
| hepes | 7.48 | 7.0 | 20 | 0 | 0-2.5-5-7.5 |
| | | 8.0 | | 50-150-300-500 | 0 |

TABLE 29

Concentrations measured by Nanodrop (average of 2 measurements) in the samples stressed at 37° C. The concentration was determined after a short high speed spin (1 min at 15000xg)

| P23IL0064 Samples (4 mg/mL in D-PBS) | Concentration (mg/mL) |
|---|---|
| Reference (−20° C.) | 4.05 |
| 3 weeks 37° C. (label 24 w) | 3.99 |
| 4 weeks 37° C. (label 4 w) | 2.0 |
| 6 weeks 37° C. (label 8 w) | 2.30 |
| 6 weeks 37° C. (label 12 w) | 4.11 |
| 6 weeks 37° C. (label 16 w) | 2.33 |

TABLE 30

Buffers tested in stressed stability for 23IL0064.

| Buffer | pH | Concentration* | Excipient/surfactant | Time point analyzed | Storage Temp. |
|---|---|---|---|---|---|
| Hepes 20 mM | 8 | 5 mg/mL | | 2.5 w | 37° C. |
| His 20 mM | 6.5 | 5 mg/mL | | 2.5 w/6 w | 4-25-37° C. |
| His 20 mM | 6.5 | 22 mg/mL** | | 2.5 w/6 w | 4-25-37° C. |
| His 20 mM | 6 | 5 mg/mL | | 2.5 w/6 w | 4-25-37° C. |
| His 20 mM | 6.5 | 5 mg/mL | 0.02% Tween 80 | 2.5 w/6 w | 4-25-37° C. |
| His 20 mM | 6.5 | 5 mg/mL | 8% mannitol | 2.5 w/6 w | 4-25-37° C. |
| His 20 mM | 6.5 | 5 mg/mL | 8% sucrose | 2.5 w/6 w | 4-25-37° C. |
| His 20 mM | 6.5 | 5 mg/mL | 1.5% glycine | 2.5 w/6 w | 4-25-37° C. |

*The exact concentrations used in the study ranged between 4.9 and 5.1 mg/mL
**Labeled as 'HIGH CONC' in figures, actual conc. was 22.36 mg/mL.

TABLE 31

Crude ranking of the degree of opalescence and material loss induced by shear stress for 23IL0064 in different formulation buffers.

| 5 mg/mL | 20 mM Histidine pH 6.5 + 8% sucrose | Lower |
|---|---|---|
| | 20 mM Histidine pH 6.5 + 8% mannitol | ↓ |
| | 20 mM Histidine pH 6.0 | |
| | 20 mM Histidine pH 6.5 + 1.5% glycine | |
| | 20 mM Histidine pH 6.5 + 0.02% Tween 80 | |
| | 20 mM Histidine pH 6.5 | |
| | 20 mM Histidine pH 6.5 CONC (22.36 mg/ml) | Higher opalescence |

TABLE 32

Integration data of the RP-HPLC analysis of the stability samples of 23IL0064 in different buffer conditions (comparison of 6 weeks 37° C., 6 weeks 25° C., 6 weeks 4° C. and −80° C. Ref).

| p23IL0064 in | Stress condition | pre 1 22.4 | pre 2 23.3 | main peak 23.9 | post 1 27.5 | post 2 29.0 | Total peak area (%)* |
|---|---|---|---|---|---|---|---|
| 20 mM Histidine pH 6.5 | −80° C. Ref | 68 | 195 | 1671 | 76 | 20 | 2029 |
| | % | 3% | 10% | 82% | 4% | 1% | 100% |
| | 6 weeks 4° C. | 77 | 201 | 1791 | 85 | 29 | 2182 |
| | % | 4% | 9% | 82% | 4% | 1% | 108% |
| | 6 weeks 25° C. | 77 | 196 | 1696 | 125 | 33 | 2127 |
| | % | 4% | 9% | 80% | 6% | 2% | 105% |
| | 6 weeks 37° C. | 130 | 186 | 1499 | 274 | 57 | 2146 |
| | % | 6% | 9% | 70% | 13% | 3% | 106% |
| 20 mM Histidine pH 6.0 | −80° C. Ref | 68 | 199 | 1807 | 66 | 20 | 2159 |
| | % | 3% | 9% | 84% | 3% | 1% | 100% |
| | 6 weeks 4° C. | 69 | 195 | 1751 | 71 | 17 | 2104 |
| | % | 3% | 9% | 83% | 3% | 1% | 97% |
| | 6 weeks 25° C. | 67 | 206 | 1696 | 90 | 22 | 2080 |
| | % | 3% | 10% | 82% | 4% | 1% | 96% |
| | 6 weeks 37° C. | 117 | 200 | 1573 | 152 | 37 | 2079 |
| | % | 6% | 10% | 76% | 7% | 2% | 96% |
| 20 mM Histidine pH 6.5 + 0.02% Tween80 | −80° C. Ref | 66 | 175 | 1564 | 49 | 14 | 1867 |
| | % | 4% | 9% | 84% | 3% | 1% | 100% |
| | 6 weeks 4° C. | 74 | 196 | 1749 | 85 | 29 | 2133 |
| | % | 3% | 9% | 82% | 4% | 1% | 114% |
| | 6 weeks 25° C. | 86 | 196 | 1556 | 117 | 37 | 1992 |
| | % | 4% | 10% | 78% | 6% | 2% | 107% |
| | 6 weeks 37° C. | 116 | 195 | 1258 | 245 | 66 | 1881 |
| | % | 6% | 10% | 67% | 13% | 4% | 101% |
| 20 mM Histidine pH 6.5 + 8% mannitol | −80° C. Ref | 70 | 201 | 1770 | 66 | 19 | 2128 |
| | % | 3% | 9% | 83% | 3% | 1% | 100% |
| | 6 weeks 4° C. | 68 | 193 | 1739 | 80 | 14 | 2093 |
| | % | 3% | 9% | 83% | 4% | 1% | 98% |
| | 6 weeks 25° C. | 82 | 192 | 1665 | 123 | 32 | 2094 |
| | % | 4% | 9% | 80% | 6% | 2% | 98% |
| | 6 weeks 37° C. | 95 | 173 | 1438 | 256 | 35 | 1998 |
| | % | 5% | 9% | 72% | 13% | 2% | 94% |
| 20 mM Histidine pH 6.5 + 8% sucrose | −80° C. Ref | 56 | 193 | 1685 | 70 | 16 | 2019 |
| | % | 3% | 10% | 83% | 3% | 1% | 100% |
| | 6 weeks 4° C. | 61 | 198 | 1691 | 62 | 17 | 2029 |
| | % | 3% | 10% | 83% | 3% | 1% | 100% |
| | 6 weeks 25° C. | 80 | 202 | 1591 | 123 | 29 | 2026 |
| | % | 4% | 10% | 79% | 6% | 1% | 100% |
| | 6 weeks 37° C. | 139 | 246 | 1292 | 316 | 73 | 2065 |
| | % | 7% | 12% | 63% | 15% | 4% | 102% |
| 20 mM Histidine pH 6.5 + 1.5% glycine | −80° C. Ref | 53 | 167 | 1413 | 51 | 15 | 1698 |
| | % | 3% | 10% | 83% | 3% | 1% | 100% |
| | 6 weeks 4° C. | 68 | 197 | 1669 | 67 | 18 | 2019 |
| | % | 3% | 10% | 83% | 3% | 1% | 119% |
| | 6 weeks 25° C. | 74 | 189 | 1596 | 124 | 31 | 2014 |
| | % | 4% | 9% | 79% | 6% | 2% | 119% |
| | 6 weeks 37° C. | 95 | 185 | 1359 | 278 | 52 | 1968 |
| | % | 5% | 9% | 69% | 14% | 3% | 116% |
| 20 mM Histidine pH 6.5 CONC | −80° C. Ref | 72 | 233 | 1984 | 81 | 15 | 2385 |
| | % | 3% | 10% | 83% | 3% | 1% | 100% |
| | 6 weeks 4° C. | 90 | 218 | 1880 | 88 | 21 | 2297 |
| | % | 4% | 9% | 82% | 4% | 1% | 96% |
| | 6 weeks 25° C. | 96 | 235 | 1848 | 143 | 33 | 2355 |
| | % | 4% | 10% | 78% | 6% | 1% | 99% |
| | 6 weeks 37° C. | 126 | 261 | 1725 | 332 | 62 | 2505 |
| | % | 5% | 10% | 69% | 13% | 2% | 105% |

(%)* recovery calculated by using the total area compared to the −80° C. Ref of the same condition.

TABLE 33

Melting temperatures for 23IL0064 and 23IL0075 in different buffers as determined by differential scanning calorimetry (at 1 mg/mL). Scanning was performed at 1° C./min, starting at 30° C.

| Buffer | 23IL0064 | 23IL0075 |
|---|---|---|
| 25 mM acetate; pH 5.5; 50 mM NaCl | 55.5 | 58.0 |
| 25 mM acetate; pH 5.5; 250 mM NaCl | 52.9 | 55.5 |
| 25 mM MES; pH 6.0; 50 mM NaCl | 56.2 | 58.8 |
| 25 mM MES; pH 6.0; 250 mM NaCl | 53.2 | 55.7 |
| 25 mM hepes; pH 7.0; 50 mM NaCl | 56.7 | 59.3 |
| 25 mM hepes; pH 7.0; 250 mM NaCl | 53.7 | 56.2 |

TABLE 33-continued

Melting temperatures for 23IL0064 and 23IL0075 in different buffers as determined by differential scanning calorimetry (at 1 mg/mL). Scanning was performed at 1° C./min, starting at 30° C.

| Buffer | 23IL0064 | 23IL0075 |
|---|---|---|
| 25 mM Tris; pH 7.5; 50 mM NaCl | 56.3 | 58.7 |
| 25 mM Tris; pH 7.5; 250 mM NaCl | 53.5 | 56.1 |

TABLE 34

Melting temperatures for 23IL0064 and 23IL0075 in buffers as determined by thermal shift assay (at 0.1 mg/mL).

| Buffer | 23IL0064 | 23IL0075* | 23IL0075* |
|---|---|---|---|
| 20 mM Histidine pH 6.5; 50 mM NaCl | 54.5 | 57.0 | 57.0 |
| 20 mM Histidine pH 6.5 | 56.6 | 59.2 | 59.3 |
| 20 mM Histidine pH 6.5; 7 5% mannitol | 57.9 | 60.7 | 60.6 |
| 20 mM hepes pH 7; 50 mM NaCl | 54.8 | 57.4 | 57.5 |
| 20 mM hepes pH 7 | 56.8 | 59.8 | 59.9 |
| 20 mM hepes pH 7; 7.5% mannitol | 58.2 | 61.1 | 61.2 |
| 20 mM hepes pH 8; 50 mM NaCl | 55.0 | 57.6 | 57.8 |
| 20 mM hepes pH 8 | 56.4 | 59.5 | 59.4 |
| 20 mM hepes pH 8; 7.5% mannitol | 57.6 | 60.3 | 60.3 |

*Measurements were performed on the 2 batches

TABLE 35

Design-Expert Numerical Optimization of the model. The larger the Desirability coefficient the better the proposal of the optimum.

Solutions for phosphate

| Number | Conc(log10) (mM) | PH | Buffer | Tm (° C.) | Desirability |
|---|---|---|---|---|---|
| 1 | 1.00 | 6.00 | Phosphate | 59.0012 | 0.895 |
| 2 | 1.04 | 6.00 | Phosphate | 58.9419 | 0.881 |

Solutions for Acetate

| Number | Conc(log10) (mM) | PH | Buffer | Tm (° C.) | Desirability |
|---|---|---|---|---|---|
| 1 | 1.00 | 6.00 | Acetate | 59.2759 | 0.959 |
| 2 | 1.01 | 6.08 | Acetate | 59.2615 | 0.956 |
| 3 | 1.11 | 5.88 | Acetate | 59.1489 | 0.929 |
| 4 | 1.10 | 5.80 | Acetate | 59.1345 | 0.926 |
| 5 | 1.15 | 5.72 | Acetate | 59.0452 | 0.905 |
| 6 | 1.16 | 5.68 | Acetate | 59.0036 | 0.895 |
| 7 | 1.32 | 6.09 | Acetate | 58.9476 | 0.882 |
| 8 | 1.33 | 6.15 | Acetate | 58.9406 | 0.881 |
| 9 | 1.35 | 6.21 | Acetate | 58.9317 | 0.879 |
| 10 | 1.19 | 5.56 | Acetate | 58.8937 | 0.870 |
| 11 | 1.32 | 5.89 | Acetate | 58.8726 | 0.865 |
| 12 | 1.00 | 5.00 | Acetate | 58.77 | 0.841 |
| 13 | 1.35 | 5.69 | Acetate | 58.7182 | 0.829 |
| 14 | 1.50 | 6.12 | Acetate | 58.7181 | 0.829 |
| 15 | 1.10 | 5.10 | Acetate | 58.682 | 0.820 |
| 16 | 1.16 | 5.19 | Acetate | 58.6346 | 0.809 |
| 17 | 1.57 | 6.08 | Acetate | 58.5857 | 0.798 |
| 18 | 1.44 | 5.71 | Acetate | 58.5814 | 0.797 |
| 19 | 1.35 | 5.50 | Acetate | 58.5692 | 0.794 |
| 20 | 1.55 | 5.96 | Acetate | 58.5672 | 0.793 |
| 21 | 1.6 | 6.18 | Acetate | 58.5354 | 0.786 |
| 22 | 1.70 | 6.00 | Acetate | 58.3294 | 0.738 |
| 23 | 1.62 | 5.68 | Acetate | 58.215 | 0.711 |
| 24 | 1.34 | 5.01 | Acetate | 58.0486 | 0.672 |
| 25 | 1.47 | 5.20 | Acetate | 57.9981 | 0.660 |
| 26 | 1.33 | 4.96 | Acetate | 57.9943 | 0.659 |
| 27 | 1.56 | 5.35 | Acetate | 57.9714 | 0.654 |
| 28 | 1.27 | 4.83 | Acetate | 57.9579 | 0.651 |
| 29 | 1.62 | 5.41 | Acetate | 57.9098 | 0.639 |
| 30 | 1.53 | 5.16 | Acetate | 57.8061 | 0.615 |
| 31 | 1.61 | 5.29 | Acetate | 57.7715 | 0.607 |
| 32 | 1.57 | 5.20 | Acetate | 57.7583 | 0.604 |
| 33 | 1.56 | 5.18 | Acetate | 57.7496 | 0.602 |
| 34 | 1.35 | 4.79 | Acetate | 57.7035 | 0.591 |
| 35 | 1.65 | 5.24 | Acetate | 57.61 | 0.569 |
| 36 | 1.65 | 5.17 | Acetate | 57.5141 | 0.547 |
| 37 | 1.70 | 5.00 | Acetate | 57.0985 | 0.449 |

37 Solutions found

Solutions for Histidine

| Number | Conc(log10) (mM) | PH | Buffer | Tm (° C.) | Desirability |
|---|---|---|---|---|---|
| 1 | 1.01 | 6.19 | Histidine | 59.4631 | 1.000 |
| 2 | 1.00 | 6.18 | Histidine | 59.4654 | 1.000 |
| 3 | 1.02 | 6.20 | Histidine | 59.4617 | 1.000 |
| 4 | 1.01 | 6.20 | Histidine | 59.4767 | 1.000 |
| 5 | 1.01 | 6.20 | Histidine | 59.4702 | 1.000 |
| 6 | 1.01 | 6.18 | Histidine | 59.4525 | 1.000 |
| 7 | 1.01 | 6.18 | Histidine | 59.4554 | 1.000 |
| 8 | 1.00 | 6.19 | Histidine | 59.4736 | 1.000 |
| 9 | 1.02 | 6.19 | Histidine | 59.4524 | 1.000 |
| 10 | 1.02 | 6.19 | Histidine | 59.4537 | 1.000 |
| 11 | 1.01 | 6.20 | Histidine | 59.4644 | 1.000 |
| 12 | 1.02 | 6.20 | Histidine | 59.4559 | 1.000 |
| 13 | 1.01 | 6.18 | Histidine | 59.4608 | 1.000 |
| 14 | 1.02 | 6.19 | Histidine | 59.4556 | 1.000 |
| 15 | 1.00 | 6.21 | Histidine | 59.485 | 1.000 |
| 16 | 1.01 | 6.18 | Histidine | 59.4505 | 1.000 |
| 17 | 1.02 | 6.19 | Histidine | 59.4579 | 1.000 |
| 18 | 1.03 | 6.21 | Histidine | 59.4523 | 1.000 |
| 19 | 1.01 | 6.18 | Histidine | 59.4562 | 1.000 |
| 20 | 1.01 | 6.21 | Histidine | 59.4702 | 1.000 |
| 21 | 1.00 | 6.19 | Histidine | 59.4689 | 1.000 |
| 22 | 1.01 | 6.20 | Histidine | 59.4711 | 1.000 |
| 23 | 1.05 | 6.21 | Histidine | 59.4363 | 0.997 |

23 Solutions found

Solutions for Succinate

| Number | Conc(log10) (mM) | PH | Buffer | Tm (° C.) | Desirability |
|---|---|---|---|---|---|
| 1 | 1.00 | 5.94 | Succinate | 57.8819 | 0.633 |
| 2 | 1.00 | 5.94 | Succinate | 57.8819 | 0.633 |
| 3 | 1.00 | 5.94 | Succinate | 57.8819 | 0.633 |
| 4 | 1.00 | 5.93 | Succinate | 57.8819 | 0.633 |
| 5 | 1.00 | 5.95 | Succinate | 57.8818 | 0.633 |
| 6 | 1.00 | 5.92 | Succinate | 57.8818 | 0.633 |
| 7 | 1.00 | 5.96 | Succinate | 57.8817 | 0.633 |

7 Solutions found

TABLE 36

Optimization results based on obtained melting temperatures in the screening of a wide range of excipients in a histidine, acetate or phosphate buffer for the formulation of 23IL0075. The results were ordered from high to low Tm value. The formulation composition has to be read combining the identity of the excipients in columns 2 to 4 and the amount of each excipient in columns 5 to 7.

| Combination number | Sugar/ polyol | Detergent | Amino acid | Buffer | % sugar/ polyol | % amino acid | % Detergent | Tm value (° C.) |
|---|---|---|---|---|---|---|---|---|
| 47 | Sucrose | Tween 20 | Glycine | HistidinePH6 | 10.5 | 0 | 0 | 62.97 |
| 44 | Sucrose | Tween 20 | Arg/Glu | HistidinePH6 | 10.5 | 0 | 0 | 62.5 |
| 5 | Mannitol | P-F68 | Glycine | HistidinePH6 | 5.6 | 0 | 0 | 62.22 |
| 41 | Sucrose | P-F68 | Glycine | HistidinePH6 | 10.5 | 0 | 0 | 62.22 |
| 11 | Mannitol | Tween 20 | Glycine | HistidinePH6 | 5.6 | 0 | 0 | 62.18 |
| 46 | Sucrose | Tween 20 | Glycine | AcetatePH5.5 | 10.5 | 0 | 0 | 62.16 |
| 42 | Sucrose | P-F68 | Glycine | PhosphatePH6 | 6.3 | 0.91 | 0 | 62.13 |
| 38 | Sucrose | P-F68 | Arg/Glu | HistidinePH6 | 10.5 | 0 | 0 | 61.9 |
| 6 | Mannitol | P-F68 | Glycine | PhosphatePH6 | 3.7 | 0.77 | 0 | 61.86 |
| 43 | Sucrose | Tween 20 | Arg/Glu | AcetatePH5.5 | 10.5 | 0 | 0 | 61.77 |
| 40 | Sucrose | P-F68 | Glycine | AcetatePH5.5 | 8.8 | 0.37 | 0 | 61.74 |
| 22 | Sorbitol | P-F68 | Glycine | AcetatePH5.5 | 3.9 | 0.69 | 0 | 61.7 |
| 48 | Sucrose | Tween 20 | Glycine | PhosphatePH6 | 9.2 | 0.28 | 0 | 61.67 |
| 4 | Mannitol | P-F68 | Glycine | AcetatePH5.5 | 4.7 | 0.37 | 0 | 61.58 |
| 53 | Sucrose | Tween 80 | Glycine | HistidinePH6 | 10.5 | 0 | 0 | 61.58 |
| 54 | Sucrose | Tween 80 | Glycine | PhosphatePH6 | 6.4 | 0.90 | 0 | 61.52 |
| 17 | Mannitol | Tween 80 | Glycine | HistidinePH6 | 5.6 | 0 | 0 | 61.44 |
| 37 | Sucrose | P-F68 | Arg/Glu | AcetatePH5.5 | 10.5 | 0 | 0 | 61.43 |
| 23 | Sorbitol | P-F68 | Glycine | HistidinePH6 | 5.6 | 0 | 0 | 61.39 |
| 12 | Mannitol | Tween 20 | Glycine | PhosphatePH6 | 5.6 | 0 | 0 | 61.33 |
| 10 | Mannitol | Tween 20 | Glycine | AcetatePH5.5 | 5.6 | 0 | 0 | 61.2 |
| 30 | Sorbitol | Tween 20 | Glycine | PhosphatePH6 | 0.0 | 2.3 | 0.0021 | 61.2 |
| 29 | Sorbitol | Tween 20 | Glycine | HistidinePH6 | 5.6 | 0 | 0 | 61.19 |
| 50 | Sucrose | Tween 80 | Arg/Glu | HistidinePH6 | 10.5 | 0 | 0 | 61.14 |
| 52 | Sucrose | Tween 80 | Glycine | AcetatePH5.5 | 8.4 | 0.46 | 0 | 61.1 |
| 2 | Mannitol | P-F68 | Arg/Glu | HistidinePH6 | 5.6 | 0 | 0 | 61.07 |
| 45 | Sucrose | Tween 20 | Arg/Glu | PhosphatePH6 | 10.5 | 0 | 0 | 61.01 |
| 18 | Mannitol | Tween 80 | Glycine | PhosphatePH6 | 5.6 | 0 | 0 | 60.93 |
| 8 | Mannitol | Tween 20 | Arg/Glu | HistidinePH6 | 5.6 | 0 | 0 | 60.88 |
| 28 | Sorbitol | Tween 20 | Glycine | AcetatePH5.5 | 5.6 | 0 | 0 | 60.86 |
| 24 | Sorbitol | P-F68 | Glycine | PhosphatePH6 | 3.2 | 1.00 | 0 | 60.84 |
| 16 | Mannitol | Tween 80 | Glycine | AcetatePH5.5 | 5.6 | 0 | 0 | 60.73 |
| 19 | Sorbitol | P-F68 | Arg/Glu | AcetatePH5.5 | 5.6 | 0 | 0.062 | 60.71 |
| 49 | Sucrose | Tween 80 | Arg/Glu | AcetatePH5.5 | 10.5 | 0 | 0 | 60.68 |
| 20 | Sorbitol | P-F68 | Arg/Glu | HistidinePH6 | 5.6 | 0 | 0.036 | 60.65 |
| 39 | Sucrose | P-F68 | Arg/Glu | PhosphatePH6 | 10.5 | 0 | 0 | 60.5 |
| 1 | Mannitol | P-F68 | Arg/Glu | AcetatePH5.5 | 5.6 | 0 | 0 | 60.43 |
| 34 | Sorbitol | Tween 80 | Glycine | AcetatePH5.5 | 3.9 | 0.69 | 0 | 60.29 |
| 26 | Sorbitol | Tween 20 | Arg/Glu | HistidinePH6 | 5.6 | 0 | 0.0004 | 60.27 |
| 35 | Sorbitol | Tween 80 | Glycine | HistidinePH6 | 5.6 | 0 | 0 | 60.18 |
| 14 | Mannitol | Tween 80 | Arg/Glu | HistidinePH6 | 5.6 | 0 | 0 | 60.17 |
| 3 | Mannitol | P-F68 | Arg/Glu | PhosphatePH6 | 5.5 | 0.06 + 0.05 | 0 | 60.15 |
| 25 | Sorbitol | Tween 20 | Arg/Glu | AcetatePH5.5 | 5.6 | 0 | 0.0017 | 60.04 |
| 7 | Mannitol | Tween 20 | Arg/Glu | AcetatePH5.5 | 5.6 | 0 | 0 | 59.98 |
| 51 | Sucrose | Tween 80 | Arg/Glu | PhosphatePH6 | 10.5 | 0 | 0 | 59.98 |
| 9 | Mannitol | Tween 20 | Arg/Glu | PhosphatePH6 | 5.6 | 0 | 0 | 59.86 |
| 21 | Sorbitol | P-F68 | Arg/Glu | PhosphatePH6 | 5.6 | 0 | 0.106 | 59.73 |
| 13 | Mannitol | Tween 80 | Arg/Glu | AcetatePH5.5 | 5.6 | 0 | 0 | 59.54 |
| 15 | Mannitol | Tween 80 | Arg/Glu | PhosphatePH6 | 5.6 | 0 | 0 | 59.49 |
| 36 | Sorbitol | Tween 80 | Glycine | PhosphatePH6 | 5.6 | 0 | 0 | 59.46 |
| 31 | Sorbitol | Tween 80 | Arg/Glu | AcetatePH5.5 | 5.6 | 0 | 0.0027 | 59.36 |
| 32 | Sorbitol | Tween 80 | Arg/Glu | HistidinePH6 | 4.9 | 0.34 + 0.29 | 0.0009 | 59.34 |
| 27 | Sorbitol | Tween 20 | Arg/Glu | PhosphatePH6 | 5.6 | 0 | 0.0039 | 59.17 |
| 33 | Sorbitol | Tween 80 | Arg/Glu | PhosphatePH6 | 5.6 | 0 | 0.0049 | 58.59 |

TABLE 37

Comparison of the aggregation onset temperatures and maximum scatter reached for 23IL0075 in 3 buffers (250 μg/mL), as measured by elastic light scattering. (Temperature interval: 45-95° C., temperature gradient: 2° C./min, data pitch: 1° C., wavelength (ex/em): 500 nm, band width (ex/em): 3 nm.)

|  | Aggregation onset temperature | Maximum scatter reached |
| --- | --- | --- |
| 10 mM phosphate pH 6 | 52.1° C. | Out of scale |
| 10 mM acetate pH 6 | 51.0° C. | Out of scale |
| 10 mM histidine pH 6 | 52.7° C. | 435 abs |

TABLE 38

List of buffers tested in freeze/thaw and stir stress study of 23IL0075 (10 mg/mL)

| No. | Buffer | | |
| --- | --- | --- | --- |
| 1 | 10 mM Acetate pH 5.5 | 5.6% mannitol | 0.0025% Tween 80 |
| 2 | 10 mM Acetate pH 5.5 | 5.6% mannitol | 0.005% Tween 80 |
| 3 | 10 mM Acetate pH 5.5 | 5.6% mannitol | 0.05% P-F68 |
| 4 | 10 mM Acetate pH 5.5 | 5.6% mannitol | 0.1% P-F68 |
| 5 | 10 mM Histidine pH 6.0 | 5.6% mannitol | 0.0025% Tween 80 |
| 6 | 10 mM Histidine pH 6.0 | 5.6% mannitol | 0.005% Tween 80 |
| 7 | 10 mM Histidine pH 6.0 | 5.6% mannitol | 0.05% P-F68 |
| 8 | 10 mM Histidine pH 6.0 | 5.6% mannitol | 0.1% P-F68 |
| 9 | 10 mM Phosphate pH 6.0 | 5.6% mannitol | 0.0025% Tween 80 |
| 10 | 10 mM Phosphate pH 6.0 | 5.6% mannitol | 0.005% Tween 80 |
| 11 | 10 mM Phosphate pH 6.0 | 5.6% mannitol | 0.05% P-F68 |
| 12 | 10 mM Phosphate pH 6.0 | 5.6% mannitol | 0.1% P-F68 |
| 13 | 10 mM Acetate pH 5.5 | 2.8% mannitol 1.15% glycine | 0.0025% Tween 80 |
| 14 | 10 mM Acetate pH 5.5 | 2.8% mannitol 1.15% glycine | 0.005% Tween 80 |
| 15 | 10 mM Acetate pH 5.5 | 2.8% mannitol 1.15% glycine | 0.05% P-F68 |
| 16 | 10 mM Acetate pH 5.5 | 2.8% mannitol 1.15% glycine | 0.1% P-F68 |
| 17 | 10 mM Histidine pH 6.0 | 2.8% mannitol 1.15% glycine | 0.0025% Tween 80 |
| 18 | 10 mM Histidine pH 6.0 | 2.8% mannitol 1.15% glycine | 0.005% Tween 80 |
| 19 | 10 mM Histidine pH 6.0 | 2.8% mannitol 1.15% glycine | 0.05% P-F68 |
| 20 | 10 mM Histidine pH 6.0 | 2.8% mannitol 1.15% glycine | 0.1% P-F68 |
| 21 | 10 mM Phosphate pH 6.0 | 2.8% mannitol 1.15% glycine | 0.0025% Tween 80 |
| 22 | 10 mM Phosphate pH 6.0 | 2.8% mannitol 1.15% glycine | 0.005% Tween 80 |
| 23 | 10 mM Phosphate pH 6.0 | 2.8% mannitol 1.15% glycine | 0.05% P-F68 |
| 24 | 10 mM Phosphate pH 6.0 | 2.8% mannitol 1.15% glycine | 0.1% P-F68 |

TABLE 39

Stability study of 23IL0075 in 10 mM Histidine pH 6.0 with different excipients. The samples were stressed by 10Xfreeze/thaw, and were stored at different temperatures (−70° C., 5° C., 25° C. and 37° C.) for a stability study. The stressed and stability samples were analyzed using OD measurement, RP-HPLC and SE-HPLC.

| No. | Conc. (mg/mL) | Buffer | Mannitol | Sucrose | Glycine | Poloxamer 188 | Tween-80 |
| --- | --- | --- | --- | --- | --- | --- | --- |
| 1 | 25 | 10 mM L-histidine, pH 6 | 5.4% | | | | 0.005% |
| 2 | 25 | 10 mM L-histidine, pH 6 | | 10.0% | | | 0.005% |
| 3 | 25 | 10 mM L-histidine, pH 6 | 3.5% | 3.5% | | | 0.005% |
| 4 | 25 | 10 mM L-histidine, pH 6 | 2.8% | | 1.15% | | 0.005% |
| 5 | 25 | 10 mM L-histidine, pH 6 | 5.4% | | | 0.05% | |
| 6 | 25 | 10 mM L-histidine, pH 6 | | 10.0% | | 0.05% | |
| 7 | 25 | 10 mM L-histidine, pH 6 | 3.5% | 3.5% | | 0.05% | |
| 8 | 25 | 10 mM L-histidine, pH 6 | 2.8% | | 1.15% | 0.05% | |
| 9 | 25 | 10 mM L-histidine, pH 6 | 3.5% | 3.5% | | | |

TABLE 40

Samples subjected to shear stress by stirring. The samples were afterwards analyzed by OD measurements, RP-HPLC, SE-HPLC and Biacore.

| No. | Conc. | Buffer | Mannitol | Sucrose | Glycine |
|---|---|---|---|---|---|
| 1 | 10 mg/mL | 10 mM L-histidine, pH 6 | 5.4% | | |
| 2 | 10 mg/mL | 10 mM L-histidine, pH 6 | | 10.0% | |
| 3 | 10 mg/mL | 10 mM L-histidine, pH 6 | 3.5% | 3.5% | |
| 4 | 10 mg/mL | 10 mM L-histidine, pH 6 | 2.8% | | 1.15% |

TABLE 41

Results of SE-HPLC and RP-HPLC chromatography of 23IL0075 at 25 mg/mL in different candidate formulation buffers (details see table above) in accelerated stability study at 25 and 37° C.

| | 3 weeks 37° C. | | 6 weeks 37° C. | | 6 weeks 25° C. | |
|---|---|---|---|---|---|---|
| Excipients | % pre-peak in SE-HPLC (oligomers)* | % postpeak in RP-HPLC (N-terminal pyroglutamate)** | % pre-peak* in SE-HPLC | % postpeak** in RP-HPLC | % pre-peak* in SE-HPLC | % postpeak** in RP-HPLC |
| Mannitol/Tween 80 | 4.8 | 6.7 | 6.9 | 9.5 | 0.7 | 4.9 |
| Sucrose/Tween 80 | 4.0 | 6.0 | 7.1 | 9.2 | 0.6 | 4.1 |
| Mannitol/sucrose/Tween 80 | 5.3 | 5.6 | 9.5 | 8.5 | 0.6 | 3.8 |
| Mannitol/Glycine/Tween 80 | 7.2 | 5.6 | 12 | 8.8 | 0.7 | 3.9 |
| Mannitol/PF | 5.0 | 6.2 | 12*** | 14.7*** | 0.8 | 5.6 |
| Sucrose/PF | 3.7 | 5.8 | 7.9 | 9.4 | 0.6 | 4.1 |
| Mannitol/Sucrose/PF | 4.3 | 5.4 | 8.5 | 8.3 | 0.7 | 4.1 |
| Mannitol/Glycine/PF | 5.4 | 5.4 | 11 | 8.6 | 0.8 | 3.9 |
| Mannitol/Sucrose | 3.5 | 5.2 | 7.5 | 8.3 | 0.8 | 3.8 |

*In the reference sample 0.3 to 0.4% pre-peak in SE-HPLC;

**% post-peak in RP-HPLC was present;

***The sample stressed for 6 weeks at 37° C. in mannitol and Poloxamer 188 was an outlier also based on the OD500 value that was 0.1 compared to OD500 values always below 0.01 for all other samples.

TABLE 42

Stability data of IL6R304 batch CMC-D-0048, stored at −70° C.

| | Time point (months) | | |
|---|---|---|---|
| Test Method | Initial (0) | 3 | 6 |
| Appearance | Clear, colorless solution | Clear, colorless solution | Clear, colorless solution |
| A280 | 10.52 mg/mL | 10.38 mg/mL | 10.45 mg/mL |
| SEC-HPLC | Purity = 99.20% | Purity = 98.67% | Purity = 98.76% |
| | Pre peaks = 0.80% | Pre peaks = 1.33% | Pre peaks = 1.24% |
| | Post peaks = 0.00% | Post peaks = 0.00% | Post peaks = 0.00% |
| cIEF | Purity = 100.00% | Purity = 100.00% | Purity = 99.30% |
| | Post peak = 0.00% | Post peak = 0.00% | Post peak = 0.70% |
| RP-HPLC | Purity = 93.90% | Purity = 91.93% | Purity = 92.8% |
| | Pre peak 1 = 0.00% | Pre peak 1 = 0.14% | Pre peak 1 = 0.12% |
| | Pre peak 2 = 3.20% | Pre peak 2 = 3.41% | Pre peak 2 = 3.00% |
| | Post peak 1 = 0.00% | Post peak 1 = 0.00% | Post peak 1 = 0.00% |
| | Post peak 2 = 2.60% | Post peak 2 = 4.10% | Post peak 2 = 3.60% |
| | Post peak 3 = 0.00% | Post peak 3 = 0.00% | Post peak 3 = 0.00% |
| | Post peak 4 = 0.20% | Post peak 4 = 0.29% | Post peak 4 = 0.32% |
| | Post peak 5 = 0.00% | Post peak 5 = 0.14% | Post peak 5 = 0.15% |
| Potency (IL-6R inhibition) | 1.256 ± 0.084 | 0.973 ± 0.072 | 1.049 ± 0.090 |
| Potency (HSA binding) | 1.044 ± 0.094 | 0.955 ± 0.085 | 0.985 ± 0.069 |

TABLE 43

Stability data of IL6R304 batch CMC-D-0048, stored at +5° C.

| | Time point (months) | | |
|---|---|---|---|
| Test Method | Initial (0) | 3 | 6 |
| Appearance | Clear, colorless solution | Clear, colorless solution | Clear, colorless solution |
| A280 | 10.52 mg/mL | 10.29 mg/mL | 10.33 mg/mL |
| SEC-HPLC | Purity = 99.20% | Purity = 98.50% | Purity = 98.62% |
| | Pre peaks = 0.80% | Pre peaks = 1.50% | Pre peaks = 1.38% |
| | Post peaks = 0.00% | Post peaks = 0.00% | Post peaks = 0.00% |
| cIEF | Purity = 100.00% | Purity = 100.00% | Purity = 99.30% |
| | Post peak = 0.00% | Post peak = 0.00% | Post peak = 0.70% |
| RP-HPLC | Purity = 93.90% | Purity = 91.71% | Purity = 92.30% |
| | Pre peak 1 = 0.00% | Pre peak 1 = 0.15% | Pre peak 1 = 0.11% |
| | Pre peak 2 = 3.20% | Pre peak 2 = 3.53% | Pre peak 2 = 3.20% |
| | Post peak 1 = 0.00% | Post peak 1 = 0.00% | Post peak 1 = 0.00% |
| | Post peak 2 = 2.60% | Post peak 2 = 4.16% | Post peak 2 = 3.90% |
| | Post peak 3 = 0.00% | Post peak 3 = 0.00% | Post peak 3 = 0.00% |
| | Post peak 4 = 0.20% | Post peak 4 = 0.29% | Post peak 4 = 0.35% |
| | Post peak 5 = 0.00% | Post peak 5 = 0.15% | Post peak 5 = 0.12% |
| Potency (IL6R inhibition) | 1.256 ± 0.084 | 0.959 ± 0.061 | 1.015 ± 0.076 |
| Potency (HSA binding) | 1.044 ± 0.094 | 0.930 ± 0.103 | 0.983 ± 0.078 |

TABLE 44

Stability data of IL6R304 batch CMC-D-0048, stored at +25° C.

| | Time point (months) | | |
|---|---|---|---|
| Test Method | Initial (0) | 3 | 6 |
| Appearance | Clear, colorless solution | Clear, colorless solution | Clear, colorless solution |
| A280 | 10.52 mg/mL | 10.29 mg/mL | 10.48 mg/mL |
| SEC-HPLC | Purity = 99.20% | Purity = 97.81% | Purity = 97.13% |
| | Pre peaks = 0.80% | Pre peaks = 1.57% | Pre peaks = 1.87% |
| | Post peaks = 0.00% | Post peaks = 0.62% | Post peaks = 1.00% |
| cIEF | Purity = 100.00% | Purity = 96.40% | Purity = 92.30% |
| | Post peak = 0.00% | Post peak = 3.60% | Post peak = 7.70% |
| RP-HPLC | Purity = 93.90% | Purity = 87.77% | Purity = 82.30% |
| | Pre peak 1 = 0.00% | Pre peak 1 = 0.44% | Pre peak 1 = 0.87% |
| | Pre peak 2 = 3.20% | Pre peak 2 = 4.56% | Pre peak 2 = 6.40% |
| | Post peak 1 = 0.00% | Post peak 1 = 0.00% | Post peak 1 = 1.10% |
| | Post peak 2 = 2.60% | Post peak 2 = 6.26% | Post peak 2 = 8.80% |
| | Post peak 3 = 0.00% | Post peak 3 = 0.54% | Post peak 3 = 0.86% |
| | Post peak 4 = 0.20% | Post peak 4 = 0.30% | Post peak 4 = 0.32% |
| | Post peak 5 = 0.00% | Post peak 5 = 0.13% | Post peak 5 = 0.16% |
| Potency (IL6R inhibition) | 1.256 ± 0.084 | 0.945 ± 0.065 | 0.949 ± 0.066 |
| Potency (HSA binding) | 1.044 ± 0.094 | 0.967 ± 0.095 | 0.926 ± 0.065 |

Example 4

Generation of NFDs 4.1 Fermentation of Polypeptide a (SEQ ID NO: 7) Producing *E. coli* Clone Fermentation of Polypeptide A (SEQ ID NO: 7) clone 1 (identified as disclosed in WO 2006/122825) was carried out at 10 liter scale in Terrific Broth (Biostat Bplus, Sartorius) with 100 µg/ml carbenicillin. A two percent inoculum of the preculture (grown overnight in TB, 2% glucose, 100 µg/ml carbenicillin) was used to start the production culture (22° C./1 vvm). Induction (using 1 mm IPTG) was started at an $OD_{600}$ of 8.0. After a short induction at 22° C., the cell paste was collected via centrifugation (Sigma 8K, rotor 12510; 7000 rpm for 30 min) and frozen at −20° C.

4.2 Purification of Polypeptide A

Purified Polypeptide A (monomer and dimer) was generated via a process consisting of 6 steps:

4.2.1 Extraction from Cell Pellet

The frozen cell pellet was thawed, the cells were resuspended in cold PBS using an Ultra Turrax Oka Works; S25N-25G probe, 11.000 rpm.) and agitated for 1 h at 4° C. This first periplasmic extract was collected via centrifugation; a second extraction was carried out in a similar way on the obtained cell pellet. Both extractions did account for more than 90% of the periplasmic Polypeptide A content (the $2^{nd}$ extraction did yield about 25%).

4.2.2 Removal of Major Contaminants Via Acidification

The periplasmic extract was acidified to pH=3.5 using 1M citric acid (VWR (Merck) #1.00244.0500) 10 mM molar final pH=3.5 and further pH adjusted with 1M HCl. The solution was agitated overnight at 4° C. The precipitated proteins and debris was pelleted down via centrifugation.

4.2.3 Micro-Filtration and Concentration of the Extract

The supernatant was made particle free using a SARTOCON Slice Crossflow system (17521-101, Sartorius) equipped with Hydrosart 0.20 μm membrane (305186070 10—SG, Sartorius) and further prepared for Cation Exchange Chromatography (CEX) via Ultra filtration. The volume that needed to be applied to CEX was brought down to approx 2 liter via ultra filtration using a SARTOCON Slice Crossflow system equipped with Hydrosart 10,000 MWCO membranes (305144390 1E—SG, Sartorius). At that point the conductivity (<5 mS/cm) and pH (=3.5) were checked.

4.2.4. Capture and Purification Via CEX

The cleared and acidified supernatant was applied to a Source 30S column (17-1273-01, GE Healthcare) equilibrated in buffer A (10 mM Citric acid pH=3.5) and the bound proteins were eluted with a 10CV linear gradient to 100% B (1M NaCl in PBS). The Polypeptide A fraction was collected and stored at 4° C.

4.2.5. Affinity Purification on Protein A Column

Polypeptide A (amount=well below column capacity) was further purified via Protein A affinity chromatography (MabSelect Xtra™, 17-5269-07, GE Healthcare). A one step elution was carried out using 100 mM Glycine pH 2.5. The collected sample was immediately neutralized using 1M Tris pH7.5 (see FIG. 58).

4.2.6. Size Exclusion Chromatography (Optional e.g. in Order to Isolate NFDs and/or Determine Amount of NFDs)

The purified Nanobody® fraction was further separated and transferred to D-PBS (Gibco#14190-169) via SEC using a Hiload™ XK26/60 SUPERDEX 75 column (17-1070-01, GE Healthcare) equilibrated in D-PBS. Fraction 2 contained the dimeric Polypeptide A (see FIG. 59).

In a further experiment, Polypeptide A (SEQ ID NO: 7) was accumulated on a Protein A column, its concentration well above 5 mg polypeptide A/ml resin, and eluted via a steep pH shift (one step buffer change to 100 mM Glycine pH 2.5). During elution of the polypeptide A from the column it was 'stacked' into an elution front, consisting of 'locally' very high concentrations (actual value after elution >5 mg/ml), and combination with the pH shift led to the isolation of about 50% stable dimer (see FIG. 54).

The shift from monomer to dimer is demonstrated via size exclusion chromatography (SEC), allowing determination of the percentage of dimerization (see FIG. 55). When loading less polypeptide A on Protein A (i.e. 2 mg/ml resin under otherwise same conditions as above, i.e. one step elution with 100 mM Glycine pH 2.5), almost no dimers (<5%) were detected during SEC (see FIG. 56 and FIG. 57). Similarly, NFDs of a polypeptide comprising one singe variable domain (NFD-Mo), a polypeptide comprising three single variable domains (NFD-Tri), and a polypeptide comprising a HSA (human serum albumin) and a single variable domain fusion were obtained (see Table 45).

TABLE 45

Examples of obtained NFDs

| Code for Monomeric polypeptide | SEQ ID NO of monomeric building block | Obtained by | Isolated stable NFD type | Monomeric polypeptide comprising |
|---|---|---|---|---|
| Polypeptide A | 7 | Protein A + SEC | NFD-Di | Two identical single variable domains |
| Polypeptide B, also referred to as Alb11 | 8 | IMAC + AEX + SEC; Protein A + SEC | NFD-Mo | One single variable domain binding to human serum albumin |
| Polypeptide C | 9 | Protein A + SEC | NFD-Tri | Three single variable domains of which one binds to human serum albumin and the two other single variable domains bind to a receptor target |
| Polypeptide D | 10 | Protein A + SEC | NFD-Mo | Singe variable domain and HSA |
| Polypeptide E | 11 | Protein A + SEC | NFD-Di | Two single variable domains of which one binds to human serum albumin and the other single variable domain binds to a receptor target |
| Polypeptide F | 12 | Protein A + SEC | NFD-Mo | One single variable domain binding to human serum albumin |

Example 5

Stability of NFDs

During purification of Polypeptide A stable non fused dimers (NFDs) were generated (see above). In order to get more insight into the stability and nature of this non-covalent interaction, stable Polypeptide A NFDs were subjected to distinctive conditions aiming to dissociate the dimer into monomer. The stability of the complex was evaluated via 3 criteria: heat-stability, pH-stability, organic solvent resistance and combinations thereof.

51 Experimental Set Up

The Polypeptide A NFD was generated during a Polypeptide A preparation (see above) and was stored at −20° C. for 2.5 years. This dimeric material was obtained via Protein A chromatography and Size Exclusion Chromatography (SEC) in PBS. In the latter, monomeric and dimeric material were separated to a preparation of >95% pure dimer. Upon thawing about 5% monomeric material was detected (see arrow in FIG. 60). The concentration of dimeric material was 0.68 mg/ml.

Analytic Size Exclusion Chromatography

The stability of the Polypeptide A NFD dimer was analysed via analytic SEC on a SUPERDEX 75 10/300GL column (17-5174-01, GE Healthcare) using an Äkta Purifier10 workstation (GE Healthcare). The column was equilibrated in D-PBS at room temperature (20° C.). A flow rate of 1 ml/min was used. Proteins were detected via absorption at 214 nm. 12 µg samples of Polypeptide A NFD were injected.

Overview Analytic SEC Runs:
20 µl POLYPEPTIDE A NFD+90 µl D-PBS→15'/50° C.→100 µl analyzed
20 µl POLYPEPTIDE A NFD+90 µl D-PBS→15'/20° C.→100 µl analyzed
20 µl POLYPEPTIDE A NFD+90 µl D-PBS→30'/45° C.→100 µl analyzed
20 µl POLYPEPTIDE A NFD+90 µl D-PBS→15'/60° C.→100 µl analyzed
20 µl POLYPEPTIDE A NFD+90 µl D-PBS→15'/70° C.→100 µl analyzed
20 µl POLYPEPTIDE A NFD+90 µl [100 mM Piperazin pH=10.2]→ON/4° C.→100 µl analyzed
20 µl POLYPEPTIDE A NFD+90 µl [100 mM Glycin pH=2.5]→ON/4° C.→100 µl analyzed
20 µl POLYPEPTIDE A NFD+90 µl [10% Isopropanol]→ON/4° C.→100 µl analyzed
20 µl POLYPEPTIDE A NFD+90 µl [30% Isopropanol]→ON/4° C.→100 µl analyzed
20 µl POLYPEPTIDE A NFD+90 µl [1% TFA]→15'/20° C.→100 µl analyzed
20 µl POLYPEPTIDE A NFD+90 µl [30% Isopropanol]→15'/50° C.→100 µl analyzed
20 µl POLYPEPTIDE A NFD+90 µl [30% Isopropanol]→15'/20° C.→100 µl analyzed
20 µl POLYPEPTIDE A NFD+90 µl [30% Isopropanol]→15'/40° C.→100 µl analyzed
20 µl POLYPEPTIDE A NFD+90 µl [30% Isopropanol]→15'/45° C.→100 µl analyzed This material was used in several experiments: 20 µl dimer fractions were diluted with 90 µl D-PBS or other solvents, incubated under different conditions and 100 µl samples were analysed via analytic SEC.

5.2 Tests

In a first set of experiments incubation during 15 minutes at increasing temperatures was carried out (45, 50, 60 and 70° C.), followed by analytic SEC (SUPERDEX 75™ 10/300GL). An incubation at 70° C. during 15 min resulted in an almost complete shift to monomeric Polypeptide A, whereas lower temperatures (e.g. 50° C.) did not result in such a drastic effect. After 15 minutes at 60° C. about 25% dissociated material was detected (see FIG. 60).

In a second set of experiments the effect of pH on the stability of Polypeptide A NFD was explored. 20 µl NFD was mixed with 90 µl [100 mM Piperazin pH=10.2] or 90 µl [100 mM Glycine, pH=2.5] and incubated overnight (ON) at 4° C. 20 µl NFD was mixed with 90 µl [1% TFA] at room temperature for 15 minutes and then immediately analysed via SEC. The control was incubated in D-PBS. Samples were analysed via SEC the next day (see FIG. 61).

A third set of experiments consisted of a combined treatment: Temperature and organic solvent (Isopropanol). Neither incubation in 10 or 30% Isopropanol overnight at 4° C., nor incubation in 10 or 30% Isopropanol during 15 minutes at room temperature resulted in any significant dissociation. However, combining increased temperatures and organic solvent resulted in a much faster dissociation into monomer. Whereas incubation at 45° C. or 30% Isopropanol had no effect alone, combining both (during 15 minutes) resulted in an almost full dissociation into monomer. Isopropanol treatment at 40° C. yielded only 30% dissociation (see FIG. 62).

5.3 Discussion

The concentration independent character of the dimer/monomer equilibrium was further substantiated by the near irreversibility of the interaction under physiological conditions. In addition, the rather drastic measures that needed to be applied to (partly) dissociate the dimer into monomer point to an intrinsic strong interaction. Dissociation is only obtained by changing the conditions drastically (e.g. applying a pH below 2.0) or subjecting the molecule to high energy conditions. Temperature stability studies (data not shown) indicate that the Tm of Polypeptide A NFD is 73° C., so the observed dissociation into monomer might be indeed linked to (partial) unfolding.

The solubilizing properties of TFA combined with protonation at extreme low pH, increasing the hydrophilicity, also results in dissociation.

The combination of elevated temperature and organic solvent dissociation indicates that the interaction is mainly based on e.g. hydrophobicity (e.g. Van der Waals force), hydrogen bonds, and/or ionic interactions.

The conditions used to drive these dimers apart may be also useful to explore when determining further methods for producing these dimers, i.e. combining these procedures (e.g. temperature of higher than 75 degrees Celsius) with a high polypeptide concentration.

Example 6

Ligand Binding of NFDs

The binding of Ligand A (SEQ ID NO: 13) to Polypeptide A and Polypeptide A NFD-Di was studied via analytic size exclusion.

6.1 Ligand A Production

Ligand A is known to be the binding domain of Polypeptide A, i.e. it comprises the epitope of Polypeptide A (i.e. Ligand A represents the A1 domain of vWF).

Ligand A [1.46 mg/ml] was produced via *Pichia* in shaker flasks. Biomass was produced in BGCM medium. For induction a standard medium switch to methanol containing medium (BMCM) was done. The secreted protein was captured from the medium via IMAC, further purified on a Heparin affinity column and finally formulated in 350 mM NaCl in 50 mM Hepes via Size Exclusion Chromatography (SEC) (SUPERDEX 75 HiLoad 26/60).

6.2 Analytic SEC on SUPERDEX 200 10/300GL

Polypeptide A (with 2 expected binding sites) and its corresponding NFD (with 4 expected binding sites) were obtained as disclosed in example 4 and added to 5× excess of the Ligand A. The resulting shift in molecular weight was studied via size exclusion chromatography (SEC) (FIG. 63). The shift in retention approximately indicates the number of Ligand A molecules binding to the Polypeptide A or corresponding NFD. Ligand A has a molecular weight of about 20 kDa. The molecular weight shift of the NFD/Ligand A complex compared to NFD alone or Polypeptide/Ligand A complex to Polypeptide A indicates the number of Ligand A per NFD or per Polypeptide A bound (see Table 46).

TABLE 46

Molecular weight shift of the NFD/Ligand A complex compared to NFD alone or Polypeptide/Ligand A complex to Polypeptide A

| Material | Retention (ml) | Measured MW (KDa)* | Theoretical MW (Da) | Measured MW shift with ligand A exposure | Estimated Number of Ligand A bound |
|---|---|---|---|---|---|
| NFD + Ligand A | 13.2 | 123.6 | 153940 (assuming 4 Ligand A bindings) | 62.5 | 3 |
| Polypeptide A + ligand A | 14.1 | 79.1 | 76970 (assuming 2 Ligand A bindings) | 54.1 | 2 |
| NFD | 14.7 | 61.1 | (55752) | Not applicable | Not applicable |
| Polypeptide A | 16.6 | 25.0 | (27876) | Not applicable | Not applicable |
| Ligand A | 16.8 | 22.8 | (24547) | Not applicable | Not applicable |

*MW was calculated based on curve fitting of Molecular weight standards (Biorad #151-1901) run on the same column under same conditions (see FIG. 64).

6.3 Overview Analytic SEC Runs on SUPERDEX 75 10/300GL (B7)040308.1: Complex ligand-NFD 5 µl mix (ON stored at 4° C.)+80 µl A buffer
(B7)040308.2: 20 µl Molecular weight marker+80 µl A buffer
(B7)040308.3: Complex 20 µl ligand+90 µl A buffer, 4 h at RT+Polypeptide A [17 µl 1/10], 30 min at RT before analysis
(B7)040308.4: Polypeptide A [17 µl in 90 µl A buffer]
(B7)040308.5: Ligand in A buffer (1 h at RT)+Polypeptide A, 15 min at RT before analysis.
(B7)040308.6: Ligand+Buffer A+NFD
(B7)040308.7: rest sample #6 after 1 h at RT
(B7)040308.8: Buffer A+NFD The correlation of the expected MW shows that more than 2 ligands (likely 3 and possibly 4 due to the atypical behaviour of Ligand A complexes on the SEC) are bound by the NFD.

Example 7

Further Characterization of a NFD with Polypeptide B

Example 7.1

Crystal Structure of a Non-Fused Dimer: Polypeptide B 7.1.1 Crystallization

The protein was first concentrated to a concentration of about 30 mg/mL. The purified protein was used in crystallization trials with approximately 1200 different conditions. Conditions initially obtained have been optimized using standard strategies, systematically varying parameters critically influencing crystallization, such as temperature, protein concentration, drop ratio and others. These conditions were also refined by systematically varying pH or precipitant concentrations.

7.1.2 Data Collection and Processing

Crystals have been flash-frozen and measured at a temperature of 100K. The X-ray diffraction data have been collected from the crystals at the SWISS LIGHT SOURCE (SLS, Villingen, Switzerland) using cryogenic conditions.

The crystals belong to the space group P $2_1$ with 2 molecules in the asymmetric unit. Data were processed using the program XDS and XSCALE. Data collection statistics are summarized in Table 47.

TABLE 47

Statistics of data collection and processing

| | |
|---|---|
| X-ray source | PX-3 (SLS[1]) |
| Wavelength (Å) | 0.97800 |
| Detector | MARCCD |
| Temperature (K) | 100 |
| Space group | P $2_1$ |
| Cell dimensions: | |
| a; b; c (Å) | 37.00; 67.06; 41.14 |
| α; β; γ (°) | 90.0; 97.7; 90.0 |
| Resolution (Å)[2] | 1.20 (1.30-1.26) |
| Unique reflections[2] | 60716 (4632) |
| Multiplicity[2] | 4.1 (4.1) |
| Completeness (%)[2] | 97.7 (96.7) |
| $R_{sym}$ (%)[2,3] | 7.2 (41.4) |
| $R_{meas}$ (%)[2,4] | 8.3 (47.6) |
| I/σ[2] | — (—) |
| Mean(I)/sigma[2,5] | 12.83 (4.01) |

[1]SWISS LIGHT SOURCE (SLS, Villingen, Switzerland)
[2]Numbers in brackets corresponds to the resolution bin with $R_{sym}$ = 41.4%

$$^3R_{sym} = \frac{\sum_h \sum_i^{n_h} |\hat{I}_h - I_{h,i}|}{\sum_h \sum_i^{n_h} I_{h,i}} \text{ with } \hat{I}_h = \frac{1}{n}\sum_i^{n_h} I_{h,i}, \text{ where } I_{h,i} \text{ is the intensity}$$

value of the ith measurement of h $$^4R_{sym} = \frac{\sum_h \sqrt{\frac{n_h}{n_h - 1}} \sum_i^{n_h} |\hat{I}_h - I_{h,i}|}{\sum_h \sum_i^{n_h} I_{h,i}} \text{ with } \hat{I}_h = \frac{1}{n}\sum_i^{n_h} I_{h,i}, \text{ where } I_{h,i} \text{ is the}$$

intensity value of the ith measurement of h
[5]Calculated from independent reflections 7.1.3 Structure Modelling and Refinement The phase information necessary to determine and analyze the structure was obtained by molecular replacement.

Subsequent model building and refinement was performed according to standard protocols with the software packages CCP4 and COOT. For the calculation of the R-factor, a measure to cross-validate the correctness of the final model, 1.6% of measured reflections were excluded from the refinement procedure (Table 48). The ligand parameterisation was carried out with the program CHEMSKETCH. LIBCHECK (CCP4) was used for generation of the corresponding library files.

Statistics of the final structure and the refinement process are listed in Table 48.

TABLE 48

Refinement statistics[1]

| | |
|---|---|
| Resolution (Å) | 20.0-1.20 |
| Number of reflections (working/test) | 59743/972 |
| $R_{cryst}$ (%) | 14.8 |
| $R_{free}$ (%) | 16.9 |
| Total number of atoms in protein | 1759 |
| Deviation from ideal geometry[2] | |
| Bond lengths (Å) | 0.006 |
| Bond angles (°) | 1.17 |

[1]Values as defined in REFMAC5, without sigma cut-off
[2]Root mean square deviations from geometric target values 7.1.4 Overall Structure The asymmetric unit of crystals is comprised of 2 monomers. The Nanobody® is well resolved by electron density maps.

7.1.5 Structure

The 2 polypeptide B-monomers that form the polypeptide B dimer (NFD-Mo) have a properly folded CDR1 and CDR2 and framework 1-3. The framework 4 residues (residues 103-113 according to the Kabat numbering scheme) are exchanged between the 2 monomers. This results in an unfolded CDR3 of both monomers that are present in the dimer (see FIG. 65). Dimer formation is mediated by the exchange of a β-strand from C1105 to Ser113 between both monomers (see FIG. 66). Strand exchange is completely defined by electron density (see FIG. 67).

The residues of framework 1-3 and CDR1 and CDR2 of the monomer that form the dimer have a classical VHH fold and are almost perfectly superimposable on a correctly folded polypeptide B VHH domain (backbone rmsd <0.6 Å). A decreased stabilization of CDR3 in polypeptide B compared to the structures of VHH's with similar sequences to polypeptide B can be one of the causes of the framework 4 exchanged dimerization. A slightly modified form of polypeptide B with a Proline at position 45 shows a hydrogen-bond between Y91 and the main-chain of L98. This hydrogen-bond has a stabilizing effect on the CDR3 conformation.

Due to the leucine at position 45 in polypeptide B, the tyrosine 91 can not longer form the hydrogen-bond with the main-chain of leucine-98. This leads to a decreased stabilization of the CDR3 conformation in polypeptide B (FIG. 68).

Example 7.2

Stability and Various Other Studies of the NFD with Polypeptide B

7.2.1 Production and Isolation of Polypeptide B

Tagless polypeptide B was over-expressed in *E. coli* TOP10 strain at 28° C. after overnight induction with 1 mM IPTG. After harvesting, the cultures were centrifuged for 30 minutes at 4500 rpm and cell pellets were frozen at −20° C. Afterward the pellets were thawed and re-suspended in 50 mM phosphate buffer containing 300 mM NaCl and shaken for 2 hours at room temperature. The suspension was centrifuged at 4500 rpm for 60 minutes to clear the cell debris from the extract. The supernatant containing polypeptide B, was subsequently loaded on Poros MABCAPTURE A column mounted on Akta chromatographic system. After washing the affinity column extensively with D-PBS, bound polypeptide B protein was eluted with 100 mM Glycine pH 2.7 buffer. Fractions eluted from column with acid were immediately neutralized by adding 1.5M TRIS pH8.5 buffer. At this stage the protein was already very pure as only a single band of the expected molecular weight was observed on Coomassie-stained SDS-PAGE gels. The fractions containing the polypeptide B were pooled and subsequently concentrated by ultrafiltration on a stirred cell with a polyethersulphone membrane with a cut-off of 5 kDa (MILLIPORE). The concentrated protein solution was afterwards loaded on a SUPERDEX 75 XK 26/60 column. On the chromatogram (see FIG. 69), besides the main peak eluting between 210 mL and 240 mL, a minor peak eluting between 180 mL and 195 ml was present.

Analysis on SDS-PAGE uncovered that both major peaks contain a single polypeptide with the same mobility (data not shown). This observation was the first indication that the peak eluting between 180 mL and 195 mL is a dimeric species, whereas the material eluting between 210 mL and 240 mL is a monomer. Further analysis on reversed phase chromatography and LC/MS of the dimeric and monomer species uncovered that both contain the same polypeptide with a molecular weight of about 12110 dalton. In this way from a 10 L fermentor run, in total 30 mg of the dimeric species and 1200 mg of the monomeric form of polypeptide B was isolated.

7.2.2 Antigen Binding Properties

The binding of the polypeptide B monomer and Polypeptide B dimer to human serum albumin was tested by surface plasmon resonance in a BIACORE 3000 instrument. In these experiments human serum albumin was immobilized on CM5 chip via standard amine coupling method. The binding of both monomeric polypeptide B and dimeric polypeptide B at a concentration of 10 nanomolar were tested. Only for the monomer, binding was observed whereas no increase in signal was observed for the dimeric polypeptide B.

7.2.3 Difference in Physicochemical Properties Between Monomeric and Dimeric Polypeptide B The fluorescent dye SYPRO orange (5000× Molecular Probes) can be used to monitor the thermal unfolding of proteins or to detect the presence of hydrophobic patches on proteins. In the experiment, monomeric and dimeric Polypeptide B at a concentration of 150 microgram/mL were mixed with SYPRO orange (final concentration 10×). The solution was afterwards transferred to quartz cuvette, and fluorescence spectra were recorded on A Jasco FP6500 instrument. Excitation was at 465 nm whereas the emission was monitored from 475 to 700 nm. As shown in FIG. 70, only a strong signal for the dimeric polypeptide B was observed, whereas no increase in fluorescence emission intensity was observed for the polypeptide B monomeric species. This observation strongly suggests that monomeric and dimeric forms of polypeptide B have a distinct conformation.

7.2.4 AUC-EQ—Sedimentation-Diffusion Equilibrium

Material and Methods

Experiments were performed with an Analytical ultracentrifuge XL-I from Beckman-Coulter using the interference optics of the instrument. Data were collected at a temperature of 20° C. and rotational speeds of 25000 rpm and 40000 rpm. 150 μL were filled in the sample sector of 12 mm two sector titanium centerpieces. Samples were diluted with standard PBS, which was also used for optical referencing. Attainment of apparent chemical and sedimentation equilibrium was verified by comparing consecutive scans until no change in concentration with time was observed. Data were evaluated with the model-independent M*-function and various explicit models using NONLIN. Standard values for the $\overline{v}$ of the protein and the density of the solvent were used. Where appropriate, 95% confidence limits are given in brackets.

Result

Polypeptide B was found to have a molar mass of 11.92 kg/mole (11.86-11.97) kg/mole from a fit assuming a single, monodisperse component. This agrees well with the result from the model-free analysis which is 12.25 kg/mole at zero concentration. Attempts to describe the data assuming self-association, non-ideality or polydispersity did not improve the global rmsd of the fit.

Polypeptide B was equally well-defined, having a molar mass of 23.06 kg/mole (22.56-23.44) kg/mole based on a direct fit assuming a single, monodisperse component. The model-free analysis revealed a molar mass of 22.69 kg/mole. A small contribution from thermodynamic non-ideality improved the fit slightly but did not alter the molar mass. No evidence for a reversible self-association could be found.

The ratio of the M(Polypeptide B-dimer)/M(Polypeptide B) was 1.93. The small deviation from the expected factor of 2 can be explained by a different $\overline{v}$ of Polypeptide B Dimer compared to Polypeptide B, slight density differences for the different dilutions due to the slightly different Polypeptide B, slight density differences for the dilutions due to the slightly different buffers used (PBS for dilution and D-PBS for the stock solutions) and a contribution from non ideality too small to be reliably described with the data available.

7.2.5 Stability Study of Polypeptide F and Polypeptide B at 4° C., 25° C. and 37° C.

Solutions of monomeric polypeptide F and polypeptide B, formulated in D-PBS, were concentrated to 20 mg/mL and put on storage at 4° C., 25° C. and 37° C. After 3 and 6 weeks samples were analyzed by size exclusion chromatography on a Phenomenex BIOSEP SEC S-2000 column. In the SEC chromatograms of both polypeptide F and Polypeptide B, the presence of a pre-peak was only observed in the chromatograms of the samples stored at 37° C. The pre-peak corresponding to a dimer, was not observed in samples stored at 4° C., 25° C. or in a reference material stored at −20° C.

In the Table 49 below the percentage of dimer present in the samples stored at 37° C. (expressed as percentage of area of dimer versus total area) for both polypeptide F and polypeptide B are compiled. As can be observed in this table, it appears that polypeptide B is more susceptible to dimer formation than polypeptide F.

TABLE 49

| Nanobody ® | % dimer-3 weeks | % dimer-6 weeks |
|---|---|---|
| Polypeptide F | 3.1 | 5.8 |
| Polypeptide B | 20.9 | 37.1 |

In a separate experiment the effect of mannitol as excipient in the formulation buffer was evaluated. In this case monomeric polypeptide B was formulated at a protein concentration of 18 mg/mL respectively in D-PBS or D-PBS containing 5% mannitol. Samples were stored at 37° C. and analyzed by size exclusion chromatography on a Phenomenex BIOSEP SEC S-2000 column after 2, 4, 6 and 8 weeks.

In the table 50 below, the percentage of dimer present in the samples stored at 37° C. (expressed as percentage of area of dimer versus total area) for Polypeptide B stored in D-PBS and in D-PBS/5% mannitol were compiled. As shown in this table, the presence of mannitol in the buffer had a clear effect on the kinetics of dimer formation of polypeptide B at 37° C.

TABLE 50

| | % dimer after 2 weeks | % dimer after 4 weeks | % dimer after 6 weeks | % dimer after 8 weeks |
|---|---|---|---|---|
| Polypeptide B | 13.5 | 22.1 | 30.0 | 41.8 |
| Polypeptide B with 5% mannitol | 5.3 | 11.7 | 16.8 | 23.7 |

In another experiment, solutions of both monomeric polypeptide F and polypeptide B at concentrations of 5 mg/ml, 10 mg/mL and 20 mg/mL in D-PBS were stored at 37° C. After 6 weeks, samples were analyzed by size exclusion chromatography on a Phenomenex BIOSEP SEC S-2000 column. In the table below the percentage of dimer present in the samples stored at 37° C. (expressed as percentage of area of dimer versus total area) for polypeptide F and polypeptide B stored at 5 mg/mL, 10 mg/mL and 20 mg/mL are compiled. From this experiment we learned, as observed earlier, that dimer formation proceeds faster for the polypeptide B than for polypeptide F, but also that the kinetics of dimer formation are largely dependent on the protein concentration.

TABLE 51

| | % dimer (5 mg/mL) | % dimer (10 mg/mL) | % dimer (20 mg/mL) |
|---|---|---|---|
| Polypeptide F | 1.2 | 3.1 | 5.7 |
| Polypeptide B | 13.0 | 20.6 | 36.9 |

Similarly, dimer and possibly multimer formation was observed for polypeptides comprising polypeptide B and other single variable domains, e.g. polypeptides comprising one polypeptide B and 2 Nanobodies® binding to a therapeutic target (e.g. 2 identical Nanobody® directed against a therapeutic target). The dimer/multimer formation of said polypeptides comprising e.g. polypeptide B and other Nanobodies® could be slowed down or in some instances almost avoided if they were formulated in a mannitol containing liquid formulation.

Other polyols and/or sugars that are believed to be beneficial to reduce or avoid the formation of dimers (NFDs) and other possibly higher multimers are listed in Table 52. A wide variety of liquid formulations may be useful which may consist of or comprise any buffering agent, a biologically effective amount of polypeptide of the invention, a concentration of mannitol that is no greater than approximately 0.6M and other excipients including polyols, non-reducing sugars, NaCl or amino acids.

TABLE 52

| Polyols | sorbitol, mannitol, xylitol, ribitol, erythritol |
|---|---|
| Non-reducing sugars | sucrose, trehalose |

7.2.6 Chaotrope Induced Unfolding of Polypeptide B and Polypeptide B Dimer

Chaotrope induced unfolding is a technique frequently used to assess the stability of proteins. To monitor chaotrope induced unfolding intrinsic fluorescence of tryptophan or tyrosine residue can be used. As unfolding parameter the 'center of spectral mass' (CSM=Σ(fluorescence intensity× wavenumber)/Σ(fluorescence intensity) can be used. Unfolding experiments with Polypeptide B monomer and Polypeptide B dimer were performed at 25 μg/mL in Guanidinium Hydrochloride solution in the concentration range 0-6M. After overnight incubation of these solutions fluorescence spectra were recorded using a Jasco FP-6500 instrument. Excitation was at 295 nm and spectra were recorded between 310 to 440 nm. Using the spectral data the CSM-value was calculated using the formula above. In the FIG. 71, the CSM as a function of Guanidinium Hydrochloride concentration is shown. As can be observed in FIG. 71, polypeptide B dimer unfolds at higher concentrations of Guanidinium Hydrochloride, and allows us to conclude that the monomer is less stable than the Polypeptide B-dimer.

Example 8

Further Characterization of a NFD with Polypeptide G and H

Different mutants of polypeptide F have been constructed, expressed and purified. Sequence information is provided below. Purity was analysed on a Coomassie stained gel (FIG. 72) and western blot.

8.1 Binding to Serum Albumin in BIACORE

Binding of Nanobodies® to human serum albumin (HSA) is characterized by surface plasmon resonance in a BIACORE 3000 instrument, and an equilibrium constant $K_D$ was determined. In brief, HSA was covalently bound to CM5 sensor chips surface via amine coupling until an increase of 500 response units was reached. Remaining reactive groups were inactivated. Nanobody® binding was assessed using series of different concentrations. Each Nanobody® concentration was injected for 4 min at a flow rate of 45 µl/min to allow for binding to chip-bound antigen. Next, binding buffer without Nanobody® was sent over the chip at the same flow rate to allow dissociation of bound Nanobody®. After 15 minutes, remaining bound analyte was removed by injection of the regeneration solution (50 mM NaOH).

From the sensorgrams obtained (FIG. 73) for the different concentrations of each analyte. $K_D$ values were calculated via kinetic data analysis. Polypeptide H (with introduction of GL instead of EP, in particular P is replaced by L, see also FIG. 68 and examples above) had a greater koff rate.

TABLE 53

$k_{off}$ values of Polypeptide F and the humanized derivatives Polypeptide G and Polypeptide H as determined in Biacore for binding to HSA.

| Nanobody® | $K_{off}$ (1/s) |
|---|---|
| Polypeptide F | 6.83E−4 |
| Polypeptide G | 1.18E−3 |
| Polypeptide H | 1.97E−3 |

8.2 Stability on Storage

Solutions of monomeric Polypeptide G and Polypeptide H, formulated in D-PBS, are concentrated to 20 mg/mL and put on storage at 4° C., 25° C. and 37° C. After 3 and 6 weeks samples are analyzed by size exclusion chromatography on a Phenomenex BIOSEP SEC S-2000 column.

Example 9

Stability of the Polypeptide I in Different Buffers when Stored at 37° C. Up to 10 Weeks Polypeptide I (SEQ ID NO: 17) is a trivalent bispecific Nanobody consisting of three humanized variable domains of a heavy-chain llama antibody, of which two identical subunits are specific for binding to RANKL while the remaining subunit binds to HSA.

Polypeptide I was expressed in *Pichia pastoris* and purified on SP SEPHAROSE as a capturing step and a Q filter as a polishing step or on SP SEPHAROSE as a capturing step and CAPTO MMC as a polishing step or alternatively by using a ProtA capture step followed by and SP SEPHAROSE polishing step. Concentration of the Polypeptide I and buffer switch to PBS, 10 mM phosphate+100 mM NaCl, 10 mM phosphate+10% mannitol or 10 mM phosphate+50 mM NaCl or others buffers was done via UF/DF or by dialysis. A final filtration on a 0.22 µm filter was performed. Polypeptide I was formulated in different buffers at ~60 mg/mL (buffers 1-12 given in Table 53-A)

TABLE 53-A

Overview of the different formulation buffers of Polypeptide I used in stability testing.

| Buffer | Concentration Polypeptide I (mg/mL) | Buffer | [NaCl] (mM) | Mannitol % (w:v) |
|---|---|---|---|---|
| 1 | 60 | 10 mM $NaH_2PO_4 \cdot 2H_2O$, pH 7 | 50 | 0 |
| 2 | 60 | 10 mM $NaH_2PO_4 \cdot 2H_2O$, pH 7 | 100 | 0 |
| 3 | 60 | 10 mM $NaH_2PO_4 \cdot 2H_2O$, pH 7 | 0 | 10 |
| 4 | 59 | 10 mM Na-acetate, pH 5.5 | 50 | 0 |
| 5 | 59 | 10 mM Na-acetate, pH 5.5 | 100 | 0 |
| 6 | 59 | 10 mM Na-acetate, pH 5.5 | 0 | 10 |
| 7 | 60 | 20 mM L-histidine, pH 5.5 | 50 | 0 |
| 8 | 60 | 20 mM L-histidine, pH 5.5 | 100 | 0 |
| 9 | 60 | 20 mM L-histidine, pH 5.5 | 0 | 10 |
| 10 | 58 | 20 mM L-histidine, pH 6 | 50 | 0 |
| 11 | 58 | 20 mM L-histidine, pH 6 | 100 | 0 |
| 12 | 58 | 20 mM L-histidine. pH 6 | 0 | 10 |

The stability of the different samples was assessed in accelerated stress conditions at 37° C.±3° C. Samples were taken after 2, 3, 5 and 10 weeks storage at this temperature and were analyzed using SE-HPLC. BIACORE was performed on the samples stored for 10 weeks to evaluate loss in potency.

9.1 SE-HPLC Analysis

The SE-HPLC assay consisted of a pre-packed silica gel TSK-GEL G2000SW$_{XL}$ column, a mobile phase consisting of KCl, NaCl and phosphate buffer pH 7.2 (D-PBS) and UV detection at 280 nm. The relative amount of specific protein impurity was expressed as area %, and was calculated by dividing the peak area corresponding to the specific protein or protein impurity by the total integrated area.

The results of the analysis of a sample by SE-HPLC is given in FIG. 74 where an example is shown for the sample stored during two weeks at 37° C. in the presence of 50 or 100 mM salt or 10% mannitol-containing phosphate buffer. Storage at 37° C. resulted in the formation of a clear prepeak eluting at about 40 minutes and some minor postpeaks close to the main peak; these postpeaks elute between 48-55 minutes (see insert in FIG. 74) and represent some degradation fragments. In Table 54 the integration data for all samples analysed is summarized for the different peaks observed (except buffer peaks after 60 minutes elution time)

TABLE 54

Integration data (% of total surface area) of the different peaks observed in the SE-HPLC chromatograms of Polypeptide I stored at 37° C. in different formulation buffers at all time points tested and in comparison with each control sample (each buffer).

| SE-HPLC | Sample | Phosphate pH 7 50 mM NaCl | Phosphate pH 7 100 mM NaCl | Phosphate pH 7 | Acetate pH 5.5 50 mM NaCl | Acetate pH 5.5 100 mM NaCl | Acetate pH 5.5 10% Mannitol | Histidine pH 5.5 50 mM NaCl |
|---|---|---|---|---|---|---|---|---|
| % Prepeak | control | 0 | 0 | 0 | 0 | 0 | 0 | 0 |
| | 2 w 37° C. | 5.6 | 6.9 | 1.3 | 4.6 | 6.3 | 2.3 | 5.5 |
| | 3 w 37° C. | 4.4 | 6.2 | 0.65 | 3.9 | 5.9 | 0.18 | 5.6 |
| | 5 w 37° C. | 13.7 | 15.8 | 3.9 | 11.5 | 14.2 | 1.22 | 14.0 |
| | 10 w 37° C. | 23.8 | 25.3 | 11.1 | 21.0 | 23.9 | 3.4 | 27.2 |
| % Main peak | control | 100 | 100 | 100 | 100 | 100 | 100 | 100 |
| | 2 w 37° C. | 93.5 | 92.2 | 97.9 | 94.8 | 93.1 | 98.8 | 94.0 |
| | 3 w 37° C. | 93.7 | 92.0 | 95.2 | 95.0 | 92.8 | 96.9 | 93.4 |
| | 5 w 37° C. | 81.14 | 78.87 | 91.52 | 87.38 | 84.63 | 97.87 | 84.85 |
| | 10 w 37° C. | 69.2 | 68.0 | 80.5 | 77.5 | 74.7 | 95.1 | 71.3 |

TABLE 54-continued

Integration data (% of total surface area) of the different peaks observed in the SE-HPLC chromatograms of Polypeptide I stored at 37° C. in different formulation buffers at all time points tested and in comparison with each control sample (each buffer).

| | | | | | | | | |
|---|---|---|---|---|---|---|---|---|
| % Postpeak1 | control | 0 | 0 | 0 | 0 | 0 | 0 | 0 |
| | 2 w 37° C. | 0 | 0 | | 0 | 0 | 0 | 0 |
| | 3 w 37° C. | 0 | 0 | | 0 | 0 | 0 | 0 |
| | 5 w 37° C. | 3.16 | 3.36 | | 0 | 0 | 0 | 0 |
| | 10 w 37° C. | 3.7 | 3.5 | | 0 | 0 | 0 | 0 |
| % Postpeak2 | control | 0 | 0 | | 0 | 0 | 0 | 0 |
| | 2 w 37° C. | 0.23 | 0.27 | 0.19 | 0.23 | 0.26 | 0.19 | 0.19 |
| | 3 w 37° C. | 0.57 | 0.58 | 0.31 | 0.49 | 0.53 | 0.27 | 0.48 |
| | 5 w 37° C. | 0.41 | 0.47 | 0.27 | 0.37 | 0.39 | 0.25 | 0.45 |
| | 10 w 37° C. | 0.5 | 0.5 | 0.3 | 0.4 | 0.4 | 0.2 | 0.4 |
| % Postpeak3 | control | 0 | 0 | 0 | 0 | 0 | 0 | 0 |
| | 2 w 37° C. | 0.62 | 0.64 | 0.60 | 0.37 | 0.41 | 0.46 | 0.31 |
| | 3 w 37° C. | 1.15 | 1.25 | 1.07 | 0.52 | 0.64 | 0.61 | 0.49 |
| | 5 w 37° C. | 1.59 | 1.50 | 1.49 | 0.75 | 0.78 | 0.66 | 0.70 |
| | 10 w 37° C. | 2.7 | 2.6 | 3.1 | 1.1 | 1.0 | 1.3 | 1.1 |

| SE-HPLC | Sample | Histidine pH 5.5 100 mM NaCl | Histidine pH 5.5 10% Mannitol | Histidine pH 6 50 mM NaCl | Histidine pH 6 100 mM NaCl | Histidine pH 6 10% Mannitol |
|---|---|---|---|---|---|---|
| % Prepeak | control | 0 | 0 | 0 | 0 | 0 |
| | 2 w 37° C. | 7.5 | 0.54 | 6.3 | 7.7 | 0.63 |
| | 3 w 37° C. | 7.9 | 0.34 | 7.0 | 8.6 | 0.39 |
| | 5 w 37° C. | 17.1 | 1.5 | 16.2 | 17.4 | 2.0 |
| | 10 w 37° C. | 27.8 | 5.4 | 26.8 | 27.0 | 7.3 |
| % Main peak | control | 100 | 100* | 100 | 100 | 100* |
| | 2 w 37° C. | 92.1 | 98.8 | 93.1 | 91.5 | 96.7 |
| | 3 w 37° C. | 91.5 | 98.6 | 91.3 | 90.2 | 98.8 |
| | 5 w 37° C. | 81.73 | 97.49 | 82.22 | 81.19 | 96.76 |
| | 10 w 37° C. | 73.5 | 93.1 | 71.3 | 71.2 | 91.0 |
| % Postpeak1 | control | 0 | 0 | 0 | 0 | 0 |
| | 2 w 37° C. | 0 | 0 | 0 | 0 | 0 |
| | 3 w 37° C. | 0 | 0 | 0 | 0 | 0 |
| | 5 w 37° C. | 0 | 0 | 0 | 0 | 0 |
| | 10 w 37° C. | 0 | 0 | 0 | 0 | 0 |
| % Postpeak2 | control | 0 | 0 | 0 | 0 | 0 |
| | 2 w 37° C. | 0.17 | 0.19 | 0.20 | 0.23 | 0.18 |
| | 3 w 37° C. | 0.55 | 0.27 | 0.54 | 0.5 | 0.27 |
| | 5 w 37° C. | 0.29 | 0.23 | 0.52 | 0.42 | 0.37 |
| | 10 w 37° C. | 0.5 | 0.2 | 0.4 | 0.4 | 0.3 |
| % Postpeak3 | control | 0 | 0 | 0 | 0 | 0 |
| | 2 w 37° C. | 0.26 | 0.37 | 0.40 | 0.58 | 0.53 |
| | 3 w 37° C. | 0.55 | 0.57 | 1.12 | 0.71 | 0.56 |
| | 5 w 37° C. | 0.88 | 0.78 | 1.06 | 0.99 | 0.87 |
| | 10 w 37° C. | 1.3 | 1.3 | 1.5 | 1.4 | 1.5 |

The peak area of the prepeak increased over time but was reduced by the addition of mannitol to the buffer (Table 54). The postpeaks between 48-55 minutes elution time corresponded to degradation products (due to remaining proteolytic activity in sample). The relative area (%) of these peaks increased only slightly, implying that degradation was restricted to a minimum.

The prepeak represented the dimeric form of Polypeptide I. The peak surface area of the prepeak increased with storage time (Table 54) and was accompanied by a concomitant decrease in surface area of the main peak (Table 54). The propensity to form dimers was significantly lower in the formulations containing 10% mannitol, which seemed to have a positive effect in suppressing the dimerization process. Note the significant lower amounts of dimers observed in the Acetate and Histidine buffers (pH 5.5) containing 10% mannitol (Table 54 and FIG. 75). FIG. 75(A) summarizes the % surface area for the main peak in the different buffers and at different time points when stored at 37° C. FIG. 75(B) summarizes the data for the % prepeak (dimer).

9.2 BIACORE Potency Analysis of the Polypeptide I Stored at 37° C.

The RANKL and HSA binding of Polypeptide I in stability samples stored for 10 weeks at 37° C. was compared with the activity of the unstressed reference batch using BIACORE analysis. RANKL or HSA was immobilized on the BIACORE chip (amine coupling using the BIACORE amine coupling kit). After a preconditioning step of 5 injections of Polypeptide I, all samples were diluted to 2.5 nM in triplicate and analyzed on the chip. Slopes were determined using the general fit method and the linear fit model (BIAevaluation software). To determine the initial binding rate (IBR), the slope between 5 s and 30 s was selected. The values of these slopes were transferred in excel and the percentage activity/potency compared to the Polypeptide I reference material was determined. BIACORE potency is thus expressed as relative potency compared to the reference materials. The relative potencies are given in Table 55 and are expressed as % activity compared to reference batch.

After 10 weeks of storage at 37° C. the relative potency of Polypeptide I for binding RANKL had dropped to 70-80% in the different buffers (Table 55). In histidine, pH 6+10% mannitol, the activity remained the highest (87.4%). The higher the NaCl concentration in the buffer, the lower the relative potency in the sample (compare the values obtained in buffers with 50 mM NaCl and 100 mM NaCl in Table 55).

TABLE 55

Relative potencies of the HSA and RANKL binding moieties of Polypeptide I after 10 weeks at 37° C. as measured by Biacore analysis.

| Buffer | Relative potency | |
|---|---|---|
| | RANKL | HSA |
| Phosphate + 50 mM NaCl, pH 7 | 81.0 | 57.4 |
| Phosphate + 100 mM NaCl, pH 7 | 78.6 | 56.6 |
| Phosphate + 10% Mannitol, pH 7 | 76.3 | 66.8 |
| Acetate + 50 mM NaCl, pH 5.5 | 80.1 | 63.0 |
| Acetate + 100 mM NaCl, pH 5.5 | 78.0 | 59.0 |
| Acetate + 10% Mannitol, pH 5.5 | 80.9 | 79.4 |
| Histidine + 50 mM NaCl, pH 5.5 | 80.2 | 59.7 |
| Histidine + 100 mM NaCl, pH 5.5 | 73.1 | 55.0 |
| Histidine + 10% Mannitol, pH 5.5 | 75.2 | 73.6 |
| Histidine + 50 mM NaCl, pH 6 | 79.1 | 59.3 |
| Histidine + 100 mM NaCl, pH 6 | 78.3 | 57.5 |
| Histidine + 10% Mannitol, pH 6 | 87.4 | 83.4 |

The relative potency for HSA binding had dropped more compared to the activity for RANKL binding after 10 weeks storage at 37° C. This decrease in activity however was less significant in the mannitol-containing buffers than in the NaCl-containing buffers. As observed for RANKL binding, the percentage activity on HSA decreased with increasing concentrations of NaCl in the different buffers.

Example 10

Tm Determination of Polypeptides J and K

Polypeptide J (SEQ ID NO: 18) is a bispecific Nanobody consisting of two humanized variable domains of a heavy-chain llama antibody, one binding to IL-6R, the other one (Alb11) binding to HSA. The trivalent bispecific Polypeptide K (SEQ ID NO: 19) consists of two identical subunits that are specific for IL-6R while the third subunit binds to HSA.

The polypeptides were expressed in *Pichia pastoris*. Concentration of the polypeptide and buffer switch to PBS or other formulation buffer was done via UF/DF (Sartorius Hydrosart SARTOCON Slice 200, 10 kDa) or dialysis. A final filtration was carried out at 0.22 µm.

The melting temperature (Tm) in different buffers was determined using the fluorescence-based thermal shift assay. The thermal shift assay or TSA can be performed in 96-well plate in a Q-PCR device to evaluate the effect of buffer couple, ionic strength, pH and excipients on the thermal stability of proteins. The assay results in a Tm value that is indicative for the thermal stability in the tested buffers. Briefly, the assay follows the signal changes of a fluorescence dye, such as SYPRO Orange, while the protein undergoes thermal unfolding. When SYPRO Orange is added to a properly folded protein solution, it is exposed in an aqueous environment and its fluorescence signal is quenched. When the temperature rises, the protein undergoes thermal unfolding and exposes its hydrophobic core region. SYPRO Orange then binds to the hydrophobic regions, unquenches which results in the increase of the fluorescence signal.

The Tm was assessed for Polypeptide J and Polypeptide K in different buffers, excipients and combinations thereof using the TSA assay. The obtained Tm values are displayed graphically in FIGS. 76 to 80. In all conditions tested, the Tm values were slightly higher for Polypeptide J than Polypeptide K. The excipients tested (mannitol, sucrose and glycine) had a similar effect on the Tm values of Polypeptide J and Polypeptide K. All excipients tested appeared to have a sta- bilizing effect on Polypeptide J and Polypeptide K, since the melting temperatures increased with increasing excipient concentration. The highest Tm values were obtained in buffers containing 7.5% mannitol or 5% sucrose.

Example 11

Storage Stability Study of Polypeptides J and K at 37° C.

An initial storage stability study was performed to get a general understanding of the stability of Polypeptides J, K and L and to determine if adding mannitol in the formulation buffer has a beneficial effect in minimizing the formation of potential dimers, as was observed for Polypeptide I (see Example 9). The trivalent bispecific Polypeptide L (SEQ ID NO: 20) consists of two identical subunits that are specific for IL-6R while the third subunit binds to HSA.

The three Polypeptides were formulated in different buffers (Table 56) at a concentration of 10 mg/mL (Polypeptide J), 7.1 mg/mL (Polypeptide K) and 10.3 mg/mL (Polypeptide L).

TABLE 56

Overview of the different formulation buffers used in initial stability testing of Polypeptide J, Polypeptide K and Polypeptide L.

| Condition | Buffer | [NaCl] | Mannitol |
|---|---|---|---|
| 1 | PBS | 0 mM | 0% |
| 2 | PBS | 0 mM | 5% |
| 3 | 10 mM NaH$_2$PO$_4$•2H$_2$O, pH | 100 mM | 0% |
| 4 | 10 mM NaH$_2$PO$_4$•2H$_2$O, pH | 100 mM | 5% |
| 5 | 10 mM Na-acetate, pH 5.5 | 100 mM | 0% |
| 6 | 10 mM Na-acetate, pH 5.5 | 100 mM | 5% |
| 7 | 20 mM L-histidine, pH 6 | 100 mM | 0% |
| 8 | 20 mM L-histidine, pH 6 | 100 mM | 5% |

The stability of the different samples was assessed in accelerated stress conditions at 37° C. Samples were analyzed after 1 week using SE-HPLC. Selected samples of Polypeptides J and K were also analyzed after 3 weeks of storage. The SE-HPLC assay consisted of a pre-packed Phenomenex BIOSEP SEC S2000 column, a mobile phase consisting of KCl, NaCl and phosphate buffer pH 7.2 (D-PBS) and UV detection at 280 nm. The relative amount of specific protein impurity was expressed as area %, and was calculated by dividing the peak area corresponding to the specific protein or protein impurity by the total integrated area. The method can resolve and quantify the relative amounts of intact material and product related impurities such as aggregates and degradation fragments.

For both Polypeptides, prolonged storage at 37° C. resulted in the formation of prepeaks and some minor postpeaks. The postpeaks probably corresponded to degradation products (due to remaining proteolytic activity in sample). The surface area of these postpeaks remained very low, suggesting only minimal degradation after 3 weeks at 37° C.

Both Polypeptides had a strong tendency to form dimers/oligomers (aggregates), which were visible as prepeak(s) in the chromatograms of the SE-HPLC analysis. An example chromatogram is shown in FIG. 81. The peak area of the prepeak increased significantly over time (represented as % aggregates in FIG. 82) and was accompanied by a concomitant decrease in surface area of the main peak. The lowest amounts of oligomers were observed in the mannitol-containing formulations.

Example 12

Storage Stability Study of Polypeptide J at 5° C. And 37° C.

An overview of the different formulation buffers and methods used in stability testing of Polypeptide J is given in Table 57 and Table 58, respectively.

TABLE 57

Overview of the different formulation buffers used in stability testing of Polypeptide J.

| Buffer | Concentration Polypeptide J | Buffer | % Tween 80 | % Mannitol | % Sucrose | mM Glycine |
|---|---|---|---|---|---|---|
| 1  | 10 mg/mL | 20 mM L-histidine | /    | /   | /  | /   |
| 2  | 10 mg/mL | 20 mM L-histidine | 0.01 | /   | /  | /   |
| 3  | 10 mg/mL | 20 mM L-histidine | 0.05 | /   | /  | /   |
| 4  | 10 mg/mL | 20 mM L-histidine | 0.05 | 5   | /  | /   |
| 5  | 10 mg/mL | 20 mM L-histidine | 0.05 | 5   | /  | 200 |
| 6  | 10 mg/mL | 20 mM L-histidine | 0.05 | 2.5 | /  | 100 |
| 7  | 10 mg/mL | 20 mM L-histidine | 0.05 | /   | 10 | /   |
| 8  | 10 mg/mL | 20 mM L-histidine | 0.05 | /   | /  | 200 |
| 9  | 10 mg/mL | 20 mM L-histidine | 0.05 | /   | 5  | 100 |
| 10 | 10 mg/mL | 20 mM L-histidine | 0.05 | 2.5 | 5  | /   |
| 11 | 10 mg/mL | 20 mM L-histidine | /    | 2.5 | 5  | 100 |
| 12 | 10 mg/mL | 20 mM L-histidine | 0.05 | 2.5 | 5  | 100 |

TABLE 58

Methods used for assessing the stability of Polypeptide J at different time points (represented as x weeks or w) after storage at 5° C. and 37° C.

| Method | Purpose | Ref. material | Stress condition 5° C. | Stress condition 37° C. |
|---|---|---|---|---|
| A280 | Content | 0 w | 1, 2 and 5 w | 1, 2, 3 and 5 w |
| Appearance | Precipitation | 0 w | 1, 2 and 5 w | 1, 2, 3 and 5 w |
| RPC | Purity/variants | 0 w | 1, 2 and 5 w | 1, 2, 3 and 5 w |
| SEC | Purity/aggregation/hydrolysis | 0 w | 1, 2 and 5 w 6 months | 1, 2, 3 and 5 w 6 months |
| BIACORE | Potency (HSA binding) | 0 w | 5 w | 5 w |
| Osmolality | Characteristic | 0 w | / | / |

Samples of the reference material (0 weeks) and samples stored for up to 6 months at 5° C. and 37° C. were analyzed using SE-HPLC. No differences were observed between the SE-HPLC profiles of the reference samples (at 0 weeks) and the samples stored for up to 5 weeks at 5° C. SE-HPLC analysis of the samples stored for 6 months at 5° C. did not show increase in area % of the prepeaks, meaning that no oligomers were formed under these storage conditions, not even in the formulation containing only 20 mM L-histidine, pH 6.5 i.e. without TWEEN (polysorbate) 80 or any excipient (data not shown).

Prolonged storage at 37° C. resulted in the formation of prepeaks and some minor postpeaks. The postpeaks probably corresponded to degradation products (due to remaining proteolytic activity in sample). The relative area (%) of these peaks increased only slightly, implying that degradation was restricted to a minimum. The other peaks visible in the chromatograms were background peaks arising from the buffer components.

The peak area of the prepeaks increased significantly over time (FIG. 83 and FIG. 84). Given the relative position of the prepeaks to the main peak, the prepeaks most likely represented dimeric or oligomeric forms (aggregates) of Polypeptide J. The peak surface area of the prepeak increased with storage time and was accompanied by a concomitant decrease in surface area of the main peak.

An important observation was that the propensity to form dimers/oligomers was buffer-dependent: the propensity to oligomerize was significantly lower in the mannitol- and sucrose-containing formulations. Glycine appeared not to have such a positive effect in preventing the oligomerization process. TWEEN (polysorbate) 80 had no inhibitory effect on the formation of oligomers.

In the samples stored for 6 months at 37° C., the lowest % of oligomers was found in the formulation containing 10% sucrose, again corroborating the stabilizing effect of sucrose on Polypeptide J (Table 59).

Example 13

Storage Stability Study of Polypeptide J at −70° C., −20° C., 5° C., 25° C. and 37° C.

Polypeptide J was formulated at 10 mg/mL in the 10 different buffers shown in Table 60, stored at −70° C., −20° C., +5° C. and 37° C. for 8 weeks and for 1 week+25° C. Stability samples were analyzed using SE-HPLC. Selected samples were also analyzed using BIACORE (HSA binding) and potency assays (HSA and IL-6R).

TABLE 59

Overview of the SE-HPLC integration results after storage for 6 months at 37° C.

| Buffer | % pre peak 1 | % pre peak 2 | % main peak | % post peak |
|---|---|---|---|---|
| Ref | 0.52 | 0.17 | 99.3 | 0 |
| Buffer 1 | ND | ND | ND | ND |
| Buffer 2 | 20.4 | 2.1 | 73.4 | 4.1 |
| Buffer 3 | ND | ND | ND | ND |
| Buffer 4 | 18.1 | 1.7 | 76.0 | 4.2 |
| Buffer 5 | 22.2 | 2.0 | 71.4 | 4.4 |
| Buffer 6 | 21.4 | 1.7 | 72.7 | 4.2 |
| Buffer 7 | 15.1 | 0 | 80.5 | 4.4 |
| Buffer 8 | 21.1 | 2.4 | 72.0 | 4.5 |
| Buffer 9 | 16.7 | 2.7 | 76.3 | 4.3 |
| Buffer 10 | 15.8 | 1.9 | 77.9 | 4.4 |
| Buffer 11 | 17.5 | 2.0 | 76.4 | 4.2 |
| Buffer 12 | 16.8 | 3.3 | 75.7 | 4.2 |

TABLE 60

Overview of the different formulation buffers tested in the stability study.

| Nr. | Conc. | Buffer | Mannitol | Sucrose | Trehalose | Glycine | Tween-80 |
|---|---|---|---|---|---|---|---|
| 1 | 10 mg/mL | 15 mM L-histidine, pH 6.5 | 5% |  |  |  | 0.01% |
| 2 | 10 mg/mL | 15 mM L-histidine, pH 6.5 |  | 10% |  |  | 0.01% |
| 3 | 10 mg/mL | 15 mM L-histidine, pH 6.5 |  |  | 10% |  | 0.01% |

TABLE 60-continued

Overview of the different formulation buffers tested in the stability study.

| Nr. | Conc. | Buffer | Mannitol | Sucrose | Trehalose | Glycine | Tween-80 |
|---|---|---|---|---|---|---|---|
| 4 | 10 mg/mL | 15 mM L-histidine, pH 6.5 | | 7.5% | | 0.35% | 0.01% |
| 5 | 10 mg/mL | 15 mM L-histidine, pH 6.5 | 2.5% | 5% | | | 0.01% |
| 6 | 10 mg/mL | 15 mM phosphate, pH 6.5 | 5% | | | | 0.01% |
| 7 | 10 mg/mL | 15 mM phosphate, pH 6.5 | | 10% | | | 0.01% |
| 8 | 10 mg/mL | 15 mM phosphate, pH 6.5 | | | 10% | | 0.01% |
| 9 | 10 mg/mL | 15 mM phosphate, pH 6.5 | | 7.5% | | 0.35% | 0.01% |
| 10 | 10 mg/mL | 15 mM phosphate, pH 6.5 | 2.5% | 5% | | | 0.01% |

13.1 Storage for 8 Weeks at −70° C., −20° C., 5° C. and 1 Week at 25° C.

Polypeptide J was shown to be stable after storage for 8 weeks at −70° C., −20° C., 5° C. and for 1 week at 25° C. in all 10 buffers tested. No significant differences were observed in potency, and SE-HPLC profiles between the reference material and the 10 different storage samples (data not shown).

132. Storage for 8 Weeks at 37° C.

SE-HPLC

Prolonged storage at 37° C. resulted in the time-dependent formation of a postpeak and prepeak. The postpeak has a retention time between 22 and 23 minutes and most likely corresponded to Polypeptide J degradation fragments. The surface area of this peak however remained low (approximately 2%), suggesting only minimal degradation after 8 weeks at 37° C. The other postpeaks visible in the chromatograms were background peaks arising from the buffer components.

The SE-HPLC profile of Polypeptide J at time point 0 weeks included a main peak and two minor prepeaks, which were not completely baseline-resolved. The surface area of the prepeaks increased over time (FIG. 85) and was accompanied by a concomitant decrease in surface area of the main peak. Given the relative position and heterogeneity of the prepeaks, they most likely represented dimeric and/or oligomeric forms of Polypeptide J. Because of this heterogeneity and the decreasing resolution between the prepeaks over time, the peaks were for simplicity integrated as a single peak.

An important observation was that the propensity to form dimers/oligomers was buffer-dependent: about 2-fold less oligomers were being formed in L-histidine buffer compared to phosphate buffer (FIG. 86, FIG. 87). The lowest amount of oligomers was observed in the trehalose-containing formulation, followed by the sucrose-containing formulation. The presence of a non-reducing sugar suppressed the extent of Polypeptide J oligomerization considerably.

Potency Assay and BIACORE

The potency of the samples stored for 8 weeks at 37° C. in buffers 1-5 was determined relative to an unstressed reference batch using an HSA-binding ELISA and an inhibition ELISA for IL-6R (Table 61).

In the ELISA based potency assay for HSA binding, human serum albumin (HSA) was immobilized onto a multiwell MAXISORP ELISA plate by adsorption. After blocking excess binding sites on the plates with Superblock T20 (PBS) blocking buffer, a dilution series of test and reference samples was applied on the plate. Bound Polypeptide was subsequently detected using a bivalent anti-Nanobody Nanobody directly conjugated to horseradish peroxidase (HRP). In the presence of $H_2O_2$ HRP catalyzes a chemical reaction with Tetramethylbenzidine (es TMB) which results in the formation of a color. The reaction was stopped by adding 1N HCl. The optical density of the color was measured at 450 nm.

In the ELISA based potency assay for IL-6R binding, for the reference, control and test samples, different dilutions of the Polypeptides were prepared. These dilutions were pre-incubated with a constant amount of 100 ng/mL IL-6, followed by the addition of 4 ng/mL soluble IL-6R. Subsequently, this mixture was transferred to a microtiter plate coated with a non neutralizing anti-IL-6R Nanobody. After washing, residual bound IL-6 was detected with biotinylated anti-human IL-6 monoclonal antibody, followed by HRP-labeled streptavidin detection. In the presence of $H_2O_2$ HRP catalyzes a chemical reaction with Tetramethylbenzidine (es TMB) which results in the formation of a color. The reaction was stopped by adding 1N HCl. The optical density of the color was measured at 450 nm. The relative potency of the test samples compared to the reference sample was analyzed by use of PLA 2.0 Software.

The HSA binding functionality of the samples stored in buffers 1-10 was also analyzed using BIACORE (Table 62). For the affinity measurement on BIACORE, a chip was first immobilized with HSA (amine coupling using the BIACORE amine coupling kit). After a preconditioning step of 5 injections of the Polypeptide J, all samples were diluted to 2.5 nM in triplicate and analyzed on the chip. Quality control of the chips using the reference sample was included in the experiment to detect any loss of activity or decrease in response (deterioration of the chip). Slopes were determined using the general fit method and the linear fit model (BIAevaluation software). To determine the initial binding rate (IBR), the slope between 5 s and 30 s was selected. The values of these slopes were transferred in excel and the percentage activity compared to the reference was determined.

Samples formulated in the same buffers and stored at −70° C. were included as the reference molecules.

TABLE 61

Relative potency of Polypeptide J after 8 weeks at +37° C. compared to a reference sample.

| Buffer | HSA | IL-6R |
|---|---|---|
| 1 | 1.080 (0.954-1.223) | 1.153 (0.957-1.389) |
| 2 | 0.975 (0.887-1.072) | 0.980 (0.760-1.263) |
| 3 | 1.038 (0.952-1.132) | 1.117 (0.910-1.372) |
| 4 | 1.182 (1.074-1.300) | 1.061 (0.908-1.240) |
| 5 | 1.080 (1.004-1.161) | 1.082 (0.925-1.266) |

TABLE 62

Summary of the Biacore results for HSA binding of the stability samples stored for 8 weeks at 37° C., expressed as % activity compared to the equivalent sample stored at −70° C.

| Buffer | % activity compared to reference |
|---|---|
| 1 | 97.5 |
| 2 | 93.2 |
| 3 | 92.5 |
| 4 | 83.9 |
| 5 | 101.9 |
| 6 | 92.2 |
| 7 | 89.4 |
| 8 | 99.0 |
| 9 | 84.3 |
| 10 | 89.6 |

Whereas the potency assays showed comparable HSA and IL-6R binding potencies between the stability samples and the reference material, BIACORE analysis demonstrated some differences in HSA binding activities. A functionality loss of approximately 16% was observed in the buffers containing a combination of sucrose and glycine (buffer 4 and 9). Formulations containing either mannitol, sucrose or trehalose showed an activity between 90 and 100% after storage for 8 weeks at 37° C.

TABLE A

Sequence Listings

| Code | SEQ ID NO: | Sequence |
|---|---|---|
| Polypeptide A | 7 | EVQLVESGGGLVQPGGSLRLSCAASGRTFSYNPMGWFRQAPGKGRELVAAISRT GGSTYYPDSVEGRFTISRDNAKRMVYLQMNSLRAEDTAVYYCAAAGVRAEDGRV RTLPSEYTFWGQGTQVTVSSAAAEVQLVESGGGLVQPGGSLRLSCAASGRTFSYN PMGWFRQAPGKGRELVAAISRTGGSTYYPDSVEGRFTISRDNAKRMVYLQMNS LRAEDTAVYYCAAAGVRAEDGRVRTLPSEYTFWGQGTQVTVSS |
| Polypeptide B | 8 | EVQLVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTL VTVSS |
| Polypeptide C | 9 | EVQLVESGGGLVQPGGSLRLSCAASGFTFSDYDIGWFRQAPGKGREGVSGISSSD GNTYYADSVKGRFTISRDNAKNTLYLQMNSLRPEDTAVYYCAAEPPDSSWYLDGS PEFFKYWGQGTLVTVSSGGGGSGGGGSEVQLVESGGGLVQPGNSLRLSCAASGFT FSSFGMSWVRQAPGKGLEWVSSISGSGSDTLYADSVKGRFTISRDNAKTTLYLQ MNSLRPEDTAVYYCTIGGSLSRSSQGTLVTVSSGGGGSGGGGSEVQLVESGGGLVQ PGGSLRLSCAASGFTFSDYDIGWFRQAPGKGREGVSGISSSDGNTYYADSVKGRF TISRDNAKNTLYLQMNSLRPEDTAVYYCAAEPPDSSWYLDGSPEFFKYWGQGTL VTVSS |
| Polypeptide D | 10 | EVQLVESGGGLVQPGGSLRLSCAASGFTFSDYDIGWFRQAPGKGREGVSGISSSD GNTYYADSVKGRFTISRDNAKNTLYLQMNSLRPEDTAVYYCAAEPPDSSWYLDGS PEFFKYWGQGTLVTVSSDAHKSEVAHRFKDLGEENFKALVLIAFAQYLQQCPFED HVKLVNEVTEFAKTCVADESAENCDKSLHTLFGDKLCTVATLRETYGEMADCCAK QEPERNECFLQHKDDNPNLPRLVRPEVDVMCTAFHDNEETFLKKYLYEIARRHPY FYAPELLFFAKRYKAAFTECCQAADKAACLLPKLDELRDEGKASSAKQRLKCASLQK FGERAFKAWAVARLSQRFPKAEFAEVSKLVTDLTKVHTECCHGDLLECADDRADL AKYICENQDSISSKLKECCEKPLLEKSHCIAEVENDEMPADLPSLAADFVESKDVCK NYAEAKDVFLGMFLYEYARRHPDYSVVLLLRLAKTYETTLEKCCAAADPHECYAKV FDEFKPLVEEPQNLIKQNCELFEQLGEYKFQNALLVRYTKKVPQVSTPTLVEVSRNL GKVGSKCCKHPEAKRMPCAEDYLSVVLNQLCVLHEKTPVSDRVTKCCTESLVNRR PCFSALEVDETYVPKEFNAETFTFHADICTLSEKERQIKKQTALVELVKHKPKATKE QLKAVMDDFAAFVEKCCKADDKETCFAEEGKKLVAASQAALGL |
| Polypeptide E | 11 | EVQLVESGGGLVQPGGSLRLSCAASGFTFSDYDIGWFRQAPGKGREGVSGISSSD GNTYYADSVKGRFTISRDNAKNTLYLQMNSLRPEDTAVYYCAAEPPDSSWYLDGS PEFFKYWGQGTLVTVSSGGGGSGGGGSEVQLVESGGGLVQPGNSLRLSCAASGFT FSSFGMSWVRQAPGKGLEWVSSISGSGSDTLYADSVKGRFTISRDNAKTTLYLQ MNSLRPEDTAVYYCTIGGSLSRSSQGTLVTVSS |
| Polypeptide F | 12 | AVQLVESGGGLVQPGNSLRLSCAASGFTFRSFGMSWVRQAPGKEPEWVSSISGS GSDTLYADSVKGRFTISRDNAKTTLYLQMNSLKPEDTAVYYCTIGGSLSRSSQGTQ VTVSS |
| Ligand A | 13 | DISEPPLHDFYCSRLLDLVFLLDGSSRLSEAEFEVLKAFVVDMMERLRISQKWVRV AVVEYHDGSHAYIGLKDRKRPSELRRIASQVKYAGSQVASTSEVLKYTLFQIFSKIDR PEASRIALLLMASQEPQRMSRNFVRYVQGLKKKKVIVIPVGIGPHANLKQIRLIEKQ APENKAFVLSSVDELEQQRDEIVSYLCDLAPEAPPPTHHHHHH |

TABLE A-continued

Sequence Listings

| Code | SEQ ID NO: | Sequence |
|---|---|---|
| CDR3 and FR4 of polypeptide B | 14 | GGSLSRSSQGTLVTVSS |
| Polypeptide G | 15 | EVQLVESGGGLVQPGGSLRLSCAASGFTFRSFGMSWVRQAPGKEPEWVSSISGSGSDTLYADSVKGRFTISRDNAKTTLYLQMNSLKPEDTAVYYCTIGGSLSRSSQGTQVTVSS |
| Polypeptide H | 16 | EVQLVESGGGLVQPGGSLRLSCAASGFTFRSFGMSWVRQAPGKGLEWVSSISGSGSDTLYADSVKGRFTISRDNAKTTLYLQMNSLKPEDTAVYYCTIGGSLSRSSQGTQVTVSS |
| Polypeptide I | 17 | EVQLVESGGGLVQPGGSLRLSCAASGFTFSSYPMGWFRQAPGKGREFVSSITGSGGSTYYADSVKGRFTISRDNAKNTLYLQMNSLRPEDTAVYYCAAYIRPDTYLSRDYRKYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAASGFIFSSYPMGWFRQAPGKGREFVSSITGSGGSTYYADSVKGRFTISRDNAKNTLYLQMNSLRPEDTAVYYCAAYIRPDTYLSRDYRKYDYWGQGTLVTVSS |
| Polypeptide J | 18 | EVQLVESGGGLVQPGGSLRLSCAASGSVFKINVMAWYRQAPGKGRELVAGIISGGSTSYADSVKGRFTISRDNAKNTLYLQMNSLRPEDTAVYYCAFITTESDYDLGRRYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Polypeptide K | 19 | EVQLVESGGGLVQPGGSLRLSCAASGSVFKINVMAWYRQAPGKGRELVAGIISGGSTSYADSVKGRFTISRDNAKNTLYLQMNSLRPEDTAVYYCAFITTESDYDLGRRYWGQGTLVTVSSGGGGSGGGSEVQLVESGGGLVQPGGSLRLSCAASGSVFKINVMAWYRQAPGKGRELVAGIISGGSTSYADSVKGRFTISRDNAKNTLYLQMNSLRPEDTAVYYCAFITTESDYDLGRRYWGQGTLVIVSSGGGGSGGGSEVQLVESGGGLVQPGNSLRLSCAASGFIFSSFGMSWVRQAPGKGLEWVSSISGSGSDTLYADSVKGRFTISRDNAKTTLYLQMNSLRPEDTAVYYCTIGGSLSRSSQGTLVIVSS |
| Polypeptide L | 20 | EVQLVESGGGLVQPGGSLRLSCAASGSVFKINVMAWYRQAPGKGRELVAGIISGGSTSYADSVKGRFTISRDNAKNTLYLQMNSLRPEDTAVYYCAFITTESDYDLGRRYWGQGTLVIVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAASGSVFKINVMAWYRQAPGKGRELVAGIISGGSTSYADSVKGRFTISRDNAKNTLYLQMNSLRPEDTAVYYCAFITTESDYDLGRRYWGQGTLVTVSS |

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All of the references described herein are incorporated by reference, in particular for the teaching that is referenced hereinabove.

The invention claimed is:

1. A formulation comprising an aqueous carrier having a pH of 5.5 to 8.0 and a polypeptide comprising one or more single variable domains at a concentration of 1 mg/mL to 200 mg/mL, said formulation being formulated for administration to a human subject and said formulation further comprising one or more components selected from:
   a) A buffer at a concentration of 10 mM to 100 mM selected from the group consisting of histidine pH 6.0-6.5, 4-(2-hydroxyethyl)-1-piperazineethanesulfonic acid (hepes) pH 7.0-8.0, 2-(N-morpholino)ethanesulfonic acid (MES) pH 6.0, succinate pH 6.0-6.5 and acetate pH 5.5-6.0;
   b) An excipient at a concentration of 1% to 20% (w:v);
   c) A surfactant at a concentration of 0.001% to 1% (v:v) selected from the group consisting of polysorbate 80, polysorbate 20 and a poloxamer;
   wherein said formulation has an inorganic salt concentration of 150 mM or lower and wherein the polypeptide is selected from the group consisting of SEQ ID NOs: 1 to 4.

2. The formulation of claim 1, that does not contain any inorganic salt.

3. The formulation of claim 1, wherein the concentration of polypeptide is about 5 to 100 mg/mL.

4. The formulation of claim 1, wherein the polypeptide comprises two or more single variable domains, or two or three single variable domains.

5. The formulation of claim 1, wherein
   the polypeptide has a solubility at room temperature of at least 20 mg/mL, as determined by the polyethylene glycol (PEG) exclusion method or by a concentration experiment;
   the polypeptide has a melting temperature of at least 59° C. as measured by the thermal shift assay (TSA) and/or differential scanning calorimetry (DSC);
   no particulates are present as measured by OD320/OD280 and/or elastic light scattering;
   less than 10% of the polypeptide forms pyroglutamate at an N-terminal glutamic acid during storage at a temperature of 37±5° C. up to at least 2 weeks, the % of pyroglutamate as measured by Reversed Phase High Performance Liquid Chromatography (RP-HPLC;

less than 10% of the polypeptide forms dimers during storage at a temperature of 37±5° C. up to at least 2 weeks, the % of dimers as measured by Size Exclusion High Performance Liquid Chromatography (SE-HPLC);

at least 80% of the polypeptide retains its binding activity to at least one of its targets after storage at 37±5° C. up to at least 2 weeks, compared to the binding activity prior to storage, said binding activity as measured by enzyme-linked immunosorbent assay (ELISA) and/or Surface Plasmon Resonance; and/or the polypeptide is stable during mechanical stress.

6. The formulation of claim 1, wherein the pH is between 6.0 and 8.0, between 6.2 and 7.5, between 6.5 and 7.5, between 6.5 and 7.0, 6.5 or 7.0.

7. The formulation of claim 1, wherein the buffer is a histidine buffer.

8. The formulation of claim 7, wherein the buffer is a histidine pH 6.5 or histidine pH 6.0 buffer.

9. The formulation of claim 7, wherein the histidine buffer has a concentration of 10 to 50 mM, 10 to 20 mM, 10 mM or 15 mM.

10. The formulation of claim 1, wherein the excipient is a saccharide, a nonreducing sugar or polyol.

11. The formulation of claim 10, wherein the excipient is selected from the group consisting of mannitol, trehalose, sorbitol and sucrose.

12. The formulation of claim 10, wherein the excipient has a concentration of 2.5% to 15% (w:v), 5% to 10% (w:v), 5% (w:v), 7.5% (w:v), 8% (w:v) or 10% (w:v).

13. The formulation of claim 1, wherein the surfactant is polysorbate 80.

14. The formulation of claim 13, wherein the surfactant has a concentration of 0.01% to 0.1% (v:v), 0.01% to 0.05% (v:v), 0.01% or 0.005% (v:v).

15. The formulation of claim 1, comprising:
a) A histidine pH 6.5 or pH 6.0 buffer at a concentration of 10 mM to 100 mM;
b) Sucrose at a concentration of 1% to 20% (w:v); and
c) Polysorbate 80 at a concentration of 0.001% to 1% (v:v).

16. The formulation of claim 15, comprising:
a) 15 mM histidine pH 6.5;
b) 8% (w:v) sucrose; and
c) 0.01% (v:v) Polysorbate 80.

17. The formulation of claim 15, comprising:
a) 10 mM histidine pH 6.0;
b) 10% (w:v) sucrose; and
c) 0.005% (v:v) Polysorbate 80.

18. The formulation of claim 16, comprising:
a) 15 mM histidine pH 6.5;
b) 8% (w:v) sucrose;
c) 0.01% (v:v) Polysorbate 80; and
d) A polypeptide selected from SEQ ID NOs: 1 to 4.

19. The formulation of claim 17, comprising:
a) 10 mM histidine pH 6.0;
b) 10% (w:v) sucrose;
c) 0.005% (v:v) Polysorbate 80; and
d) A polypeptide selected from SEQ ID NOs: 1 to 4.

20. The formulation of claim 1, for use in therapy.

21. The formulation of claim 1, wherein the concentration of polypeptide is about 150 mg/mL.

22. A sealed container containing a formulation according to claim 1.

23. A kit comprising one or more of the sealed containers according to claim 22 and instructions for use of the formulation.

24. A pharmaceutical unit dosage form suitable for parenteral administration to a human, comprising a formulation according to claim 1 in a suitable container.

25. A kit comprising one or more of the pharmaceutical unit dosage forms according to claim 24, and instructions for use of the formulation.

* * * * *